US012685777B2

(12) United States Patent
Crabtree et al.

(10) Patent No.: US 12,685,777 B2
(45) Date of Patent: Jul. 21, 2026

(54) COMPOSITIONS, SYSTEMS, AND METHODS FOR MODULATING A TARGET GENE

(71) Applicant: The Board of Trustees of the Leland Stanford Junior University, Stanford, CA (US)

(72) Inventors: Gerald R. Crabtree, Stanford, CA (US); Nathanael Gray, Stanford, CA (US); Sai Gourisankar, Stanford, CA (US); Andrey Krokhotin, Stanford, CA (US); Wenzhi Ji, Stanford, CA (US); Tinghu Zhang, Stanford, CA (US); Samuel H. Kim, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/927,508

(22) Filed: Oct. 25, 2024

(65) Prior Publication Data

US 2025/0127909 A1 Apr. 24, 2025

Related U.S. Application Data

(63) Continuation of application No. PCT/US2023/020719, filed on May 2, 2023.

(Continued)

(51) Int. Cl.
*A61K 47/55* (2017.01)
*A61P 35/00* (2006.01)

(52) U.S. Cl.
CPC .............. *A61K 47/55* (2017.08); *A61P 35/00* (2018.01)

(58) Field of Classification Search
CPC ................................ A61K 47/55; A61P 35/00
See application file for complete search history.

(56) References Cited

U.S. PATENT DOCUMENTS 4,166,452 A 9/1979 Generales
4,256,108 A 3/1981 Theeuwes (Continued)

FOREIGN PATENT DOCUMENTS

EP 0590267 B1 5/2002
EP 1391213 A1 2/2004

(Continued)

OTHER PUBLICATIONS

Liu at al., Bioessays. Dec. 2015; 37(12): 1277-1286 (Year: 2015).*

(Continued)

*Primary Examiner* — Clinton A Brooks
*Assistant Examiner* — Izabela Schmidt
(74) *Attorney, Agent, or Firm* — Bret E. Field; Bozicevic, Field & Francis LLP

(57) ABSTRACT

Methods of regulating expression of a target gene in a cell are provided. Aspects of the methods contacting the cell with a compound having a first moiety covalently linked to a second moiety, wherein: (i) the first moiety exhibits specific binding to a first endogenous protein; (ii) the second moiety exhibits specific binding to a second endogenous protein distinct from the first endogenous protein; and (iii) upon contacting the cell, the first endogenous protein and the second endogenous protein are spatially complexed to each other via the compound to yield a gain-of-function in the cell and thereby activate a process not normally controlled by either of the first and second endogenous proteins. Embodiments of the methods provide one or more beneficial features, including but not limited to: utilization of less than about 50% of an amount of the second endogenous protein present in the cell; mediation of the gain-of-function with an EC50 of less than about 1 micromolar; modulation of expression of the target gene in less than or equal to about (Continued)

16 hours; etc. Also provided are compositions that find use in practicing methods of the disclosure.

23 Claims, 48 Drawing Sheets

Related U.S. Application Data

(60) Provisional application No. 63/406,602, filed on Sep. 14, 2022, provisional application No. 63/406,570, filed on Sep. 14, 2022, provisional application No. 63/406,128, filed on Sep. 13, 2022, provisional application No. 63/388,386, filed on Jul. 12, 2022, provisional application No. 63/337,330, filed on May 2, 2022.

(56) References Cited

U.S. PATENT DOCUMENTS 4,265,874 A 5/1981 Bonsen et al.
5,023,252 A 6/1991 Hseih
5,200,534 A 4/1993 Rao
5,202,448 A 4/1993 Carver et al.
5,229,529 A 7/1993 Ueno et al.
5,274,137 A 12/1993 Nicolaou et al.
5,279,949 A 1/1994 Nair
5,283,253 A 2/1994 Holton et al.
5,294,637 A 3/1994 Chen et al.
5,415,869 A 5/1995 Straubinger et al.
5,639,592 A 6/1997 Evans et al.
5,677,336 A 10/1997 Jones et al.
5,821,263 A 10/1998 Scola et al.
5,824,701 A 10/1998 Greenwald et al.
5,869,680 A 2/1999 Mas et al.
5,985,310 A 11/1999 Castillo et al.
6,017,924 A 1/2000 Edwards et al.
6,323,315 B1 11/2001 Pettit et al.
6,462,038 B1 10/2002 Higuchi et al.
6,534,516 B1 3/2003 Edwards et al.
6,808,710 B1 10/2004 Wood et al.
6,960,474 B2 11/2005 Salvati et al.
7,026,484 B2 4/2006 Zhi et al.
7,029,674 B2 4/2006 Carreno et al.
7,101,550 B2 9/2006 Wood et al.
7,214,690 B2 5/2007 Higuchi et al.
7,288,553 B2 10/2007 Lanter et al.
7,365,202 B2 4/2008 Tan et al.
7,488,802 B2 2/2009 Collins et al.
7,521,051 B2 4/2009 Collins et al.
7,722,868 B2 5/2010 Freeman et al.
7,727,980 B2 6/2010 Zhi et al.
7,794,710 B2 9/2010 Chen et al.
7,816,372 B2 10/2010 Zhi et al.
7,892,540 B2 2/2011 Chen et al.
7,919,578 B2 4/2011 Melnick et al.
7,943,743 B2 5/2011 Korman et al.
8,008,449 B2 8/2011 Korman et al.
8,088,905 B2 1/2012 Collins et al.
8,168,179 B2 5/2012 Honjo et al.
8,168,757 B2 5/2012 Finnefrock et al.
8,183,388 B2 5/2012 Jadhav et al.
8,193,357 B2 6/2012 Pedram et al.
8,217,149 B2 7/2012 Irving et al.
8,338,464 B2 12/2012 Melnick et al.
8,354,509 B2 1/2013 Carven et al.
8,383,796 B2 2/2013 Korman et al.
8,420,694 B2 4/2013 Hasuoka
8,445,507 B2 5/2013 Jung et al.
8,460,886 B2 6/2013 Shibayama et al.
8,460,927 B2 6/2013 Chen
8,519,158 B2 8/2013 Zhi et al.
8,552,154 B2 10/2013 Freeman et al.
8,580,811 B2 11/2013 Pedram et al.
8,703,503 B2 4/2014 Melnick et al.
8,709,416 B2 4/2014 Langermann et al.
8,741,295 B2 6/2014 Olive
8,747,833 B2 6/2014 Chen et al.
8,779,108 B2 7/2014 Queva et al.
8,791,075 B2 7/2014 Melnick et al.
8,802,689 B2 8/2014 Jung et al.
8,865,918 B2 10/2014 Zhi et al.
8,951,518 B2 2/2015 Honjo et al.
8,952,136 B2 2/2015 Carven et al.
8,981,063 B2 3/2015 Chen
8,993,731 B2 3/2015 Tyson
9,045,545 B1 6/2015 Clube
9,067,998 B1 6/2015 Clube
9,084,776 B2 7/2015 Korman et al.
9,085,539 B2 7/2015 Ivachtchenko et al.
9,102,725 B2 8/2015 Korman et al.
9,102,727 B2 8/2015 Freeman et al.
9,102,728 B2 8/2015 Tyson
9,108,953 B2 8/2015 Babaoglu et al.
9,109,034 B1 8/2015 Clube
9,175,082 B2 11/2015 Zhou et al.
9,181,342 B2 11/2015 Davis
9,205,148 B2 12/2015 Langermann et al.
9,212,224 B2 12/2015 Cogswell et al.
9,217,034 B2 12/2015 Li et al.
9,220,776 B2 12/2015 Sharma et al.
9,249,161 B2 2/2016 Albrecht et al.
9,255,089 B2 2/2016 Aktoudianakis et al.
9,266,891 B2 2/2016 Engelhardt et al.
9,273,135 B2 3/2016 Korman et al.
9,308,253 B2 4/2016 Kim et al.
9,340,524 B2 5/2016 Chen et al.
9,358,289 B2 6/2016 Korman et al.
9,359,285 B2 6/2016 Zhi et al.
9,387,231 B2 7/2016 Finkel et al.
9,387,247 B2 7/2016 Korman et al.
9,402,888 B2 8/2016 Ertl et al.
9,402,899 B2 8/2016 Honjo et al.
9,481,663 B2 11/2016 Dilhas et al.
9,604,916 B2 3/2017 Dalton et al.
9,610,332 B2 4/2017 Yaffe et al.
9,611,225 B2 4/2017 Dwivedi et al.
9,622,992 B2 4/2017 Dalton et al.
9,744,149 B2 8/2017 Dalton et al.
9,809,583 B2 11/2017 Choi et al.
9,814,728 B2 11/2017 Sverdrup et al.
9,840,526 B1 12/2017 Leung et al.
9,884,038 B2 2/2018 Dalton et al.
9,889,110 B2 2/2018 Dalton et al.
9,943,506 B2 4/2018 Melnick et al.
9,963,433 B2 5/2018 Qin
9,969,683 B2 5/2018 Dalton et al.
9,994,545 B2 6/2018 Dilhas et al.
10,053,418 B2 8/2018 Dalton et al.
10,071,129 B2 9/2018 Young et al.
10,106,507 B2 10/2018 Shönbrunn et al.
10,150,739 B2 12/2018 Wu et al.
10,300,073 B2 5/2019 Haudenschild et al.
10,308,630 B2 6/2019 Dilhas et al.
10,328,074 B2 6/2019 Engelhardt et al.
10,434,075 B2 10/2019 Cox et al.
10,526,291 B2 1/2020 Schönbrunn et al.
10,526,310 B2 1/2020 Dilhas et al.
10,532,103 B2 1/2020 Gray et al.
10,556,882 B2 2/2020 Dilhas et al.
10,662,148 B2 5/2020 Narayanan et al.
10,689,395 B2 6/2020 Vadivelu et al.
10,738,016 B2 8/2020 Schönbrunn et al.
10,766,875 B2 9/2020 Dihas et al.
10,815,221 B2 10/2020 Chen et al.
10,934,271 B2 3/2021 Dihas et al.
10,975,059 B2 4/2021 Hu et al.
11,001,570 B2 5/2021 Steurer et al.
11,020,404 B2 6/2021 Haudenschild et al.
11,117,865 B2 9/2021 Zhou et al.
11,161,839 B2 11/2021 Bellenie et al.
11,185,549 B2 11/2021 Haendler
11,192,880 B2 12/2021 Isaac et al.
11,242,324 B2 2/2022 Zhou et al.

(56) References Cited

U.S. PATENT DOCUMENTS

| | | | |
|---|---|---|---|
| 11,242,351 | B2 | 2/2022 | Al-Awar et al. |
| 11,267,820 | B2 | 3/2022 | Vadivelu et al. |
| 11,279,703 | B2 | 3/2022 | Upadhayaya et al. |
| 11,332,465 | B2 | 5/2022 | Shen et al. |
| 11,358,938 | B2 | 6/2022 | Zhou et al. |
| 2005/0214738 | A1 | 9/2005 | Stankunas et al. |
| 2009/0018083 | A1 | 1/2009 | Melnick et al. |
| 2010/0130564 | A1 | 5/2010 | Melnick et al. |
| 2012/0014979 | A1 | 1/2012 | Dent |
| 2012/0157428 | A1 | 6/2012 | Albrecht et al. |
| 2012/0208800 | A1 | 8/2012 | Chung et al. |
| 2014/0005169 | A1 | 1/2014 | Albrecht et al. |
| 2014/0044770 | A1 | 2/2014 | Yaffe et al. |
| 2014/0080137 | A1 | 3/2014 | Espinosa et al. |
| 2014/0243286 | A1 | 8/2014 | Arnold et al. |
| 2014/0243322 | A1 | 8/2014 | Arnold et al. |
| 2014/0296243 | A1 | 10/2014 | Albrecht et al. |
| 2014/0296246 | A1 | 10/2014 | Aktoudianakis et al. |
| 2014/0336190 | A1 | 11/2014 | Aktoudianakis et al. |
| 2014/0371157 | A1 | 12/2014 | Young et al. |
| 2015/0087636 | A1 | 3/2015 | Sverdrup |
| 2015/0133436 | A1 | 5/2015 | Chung et al. |
| 2015/0148333 | A1 | 5/2015 | Albrecht et al. |
| 2015/0148344 | A1 | 5/2015 | Babaoglu et al. |
| 2016/0031868 | A1 | 2/2016 | Aktoudianakis et al. |
| 2016/0060260 | A1 | 3/2016 | Palmer et al. |
| 2016/0075695 | A1 | 3/2016 | Aktoudianakis et al. |
| 2016/0129001 | A1 | 5/2016 | Engelhardt et al. |
| 2016/0166549 | A1 | 6/2016 | Melnick et al. |
| 2016/0362410 | A1 | 12/2016 | Bondke et al. |
| 2017/0226065 | A1 | 8/2017 | Schönbrunn et al. |
| 2017/0304315 | A1 | 10/2017 | Haudenschild et al. |
| 2018/0050043 | A1 | 2/2018 | Sverdrup |
| 2018/0237453 | A1 | 8/2018 | Vadivelu et al. |
| 2018/0282316 | A1 | 10/2018 | Aktoudianakis et al. |
| 2018/0290984 | A1 | 10/2018 | Schönbrunn et al. |
| 2018/0305424 | A1 | 10/2018 | Crabtree et al. |
| 2019/0055203 | A1 | 2/2019 | Schönbrunn et al. |
| 2019/0111143 | A1 | 4/2019 | Gray et al. |
| 2019/0262355 | A1 | 8/2019 | Sdelci et al. |
| 2019/0292168 | A1 | 9/2019 | Hu et al. |
| 2019/0359573 | A1 | 11/2019 | Zhou et al. |
| 2019/0367530 | A1 | 12/2019 | Morales et al. |
| 2019/0381013 | A1 | 12/2019 | Brasier et al. |
| 2020/0046726 | A1 | 2/2020 | Haudenschild et al. |
| 2020/0071297 | A1 | 3/2020 | Steurer et al. |
| 2020/0095252 | A1 | 3/2020 | Upadhayaya et al. |
| 2020/0255450 | A1 | 8/2020 | Fan et al. |
| 2020/0308147 | A1 | 10/2020 | Isaac et al. |
| 2020/0325119 | A1 | 10/2020 | Isaac et al. |
| 2020/0331921 | A1 | 10/2020 | Al-Awar et al. |
| 2020/0338065 | A1 | 10/2020 | Betancort et al. |
| 2020/0339595 | A1 | 10/2020 | Vadivelu et al. |
| 2020/0385408 | A1 | 12/2020 | Xu et al. |
| 2020/0405809 | A1 | 12/2020 | Anders et al. |
| 2020/0407328 | A1 | 12/2020 | Schönbrunn et al. |
| 2021/0053978 | A1 | 2/2021 | Al-Awar et al. |
| 2021/0147382 | A1 | 5/2021 | Bellenie et al. |
| 2021/0147419 | A1 | 5/2021 | Fan et al. |
| 2021/0163497 | A1 | 6/2021 | Bellenie et al. |
| 2021/0206756 | A1 | 7/2021 | Bellenie et al. |
| 2021/0221821 | A1 | 7/2021 | Blake et al. |
| 2021/0330672 | A1 | 10/2021 | Franken et al. |
| 2021/0355088 | A1 | 11/2021 | Schönbrunn et al. |
| 2022/0047596 | A1 | 2/2022 | Mills et al. |
| 2022/0119370 | A1 | 4/2022 | Schönbrunn et al. |
| 2022/0177459 | A1 | 6/2022 | Du et al. |
| 2022/0185820 | A1 | 6/2022 | Shen et al. |

FOREIGN PATENT DOCUMENTS

| | | | |
|---|---|---|---|
| WO | WO-9310076 | A1 | 5/1993 |
| WO | WO-9323555 | A1 | 11/1993 |
| WO | WO-9407876 | A1 | 4/1994 |
| WO | WO-9407880 | A1 | 4/1994 |
| WO | WO-9407881 | A1 | 4/1994 |
| WO | WO-9407882 | A1 | 4/1994 |
| WO | WO-9614856 | A1 | 5/1996 |
| WO | WO-9633212 | A1 | 10/1996 |
| WO | WO-9813059 | A1 | 4/1998 |
| WO | WO-9822451 | A1 | 5/1998 |
| WO | WO-9828288 | A1 | 7/1998 |
| WO | WO-9858927 | A1 | 12/1998 |
| WO | WO-9909021 | A1 | 2/1999 |
| WO | WO-9914209 | A1 | 3/1999 |
| WO | WO-9918113 | A1 | 4/1999 |
| WO | WO-2004002226 | A1 | 1/2004 |
| WO | WO-2005027902 | A1 | 3/2005 |
| WO | WO-2007117653 | A2 | 10/2007 |
| WO | WO-2011001266 | A2 | 1/2011 |
| WO | WO-2012101062 | A1 | 8/2012 |
| WO | WO-2012101065 | A2 | 8/2012 |
| WO | WO-2013001310 | A1 | 1/2013 |
| WO | WO-2013026874 | A1 | 2/2013 |
| WO | WO-2013059634 | A1 | 4/2013 |
| WO | WO-2013116786 | A1 | 8/2013 |
| WO | WO-2013122609 | A1 | 8/2013 |
| WO | WO-2013188406 | A1 | 12/2013 |
| WO | WO-2014063068 | A1 | 4/2014 |
| WO | WO-2014134169 | A1 | 9/2014 |
| WO | WO-2014139328 | A1 | 9/2014 |
| WO | WO-2014151444 | A1 | 9/2014 |
| WO | WO-2014159999 | A1 | 10/2014 |
| WO | WO-2014160017 | A1 | 10/2014 |
| WO | WO-2014160028 | A1 | 10/2014 |
| WO | WO-2014194201 | A2 | 12/2014 |
| WO | WO-2014194245 | A2 | 12/2014 |
| WO | WO-2014204859 | A2 | 12/2014 |
| WO | WO-2015049325 | A1 | 4/2015 |
| WO | WO-2015058140 | A1 | 4/2015 |
| WO | WO-2015119712 | A1 | 8/2015 |
| WO | WO-2015154022 | A1 | 10/2015 |
| WO | WO-2015154038 | A1 | 10/2015 |
| WO | WO-2015154039 | A2 | 10/2015 |
| WO | WO-2016009076 | A1 | 1/2016 |
| WO | WO-2016058544 | A1 | 4/2016 |
| WO | WO-2016061144 | A1 | 4/2016 |
| WO | WO-2016100782 | A1 | 6/2016 |
| WO | WO-2016105528 | A2 | 6/2016 |
| WO | WO-2017001354 | A1 | 1/2017 |
| WO | WO-2017011590 | A1 | 1/2017 |
| WO | WO-2017091836 | A1 | 6/2017 |
| WO | WO-2017160797 | A1 | 9/2017 |
| WO | WO-2017185023 | A1 | 10/2017 |
| WO | WO-2017185034 | A1 | 10/2017 |
| WO | WO-2017202719 | A1 | 11/2017 |
| WO | WO-2018013867 | A1 | 1/2018 |
| WO | WO-2018027082 | A1 | 2/2018 |
| WO | WO-2018136202 | A2 | 7/2018 |
| WO | WO-2018156858 | A1 | 8/2018 |
| WO | WO-2018187357 | A1 | 10/2018 |
| WO | WO-2018192273 | A1 | 10/2018 |
| WO | WO-2018231859 | A1 | 12/2018 |
| WO | WO-2019031990 | A1 | 2/2019 |
| WO | WO-2019058348 | A1 | 3/2019 |
| WO | WO-2019068613 | A1 | 4/2019 |
| WO | WO-2019099298 | A1 | 5/2019 |
| WO | WO-2019143719 | A1 | 7/2019 |
| WO | WO-2019143730 | A1 | 7/2019 |
| WO | WO-2019209825 | A1 | 10/2019 |
| WO | WO-2019242471 | A1 | 12/2019 |
| WO | WO-2020027704 | A1 | 2/2020 |
| WO | WO-2020071550 | A1 | 4/2020 |
| WO | WO-2020092314 | A1 | 5/2020 |
| WO | WO-2020093006 | A1 | 5/2020 |
| WO | WO-2020093011 | A1 | 5/2020 |
| WO | WO-2020117988 | A1 | 6/2020 |
| WO | WO-2020186196 | A1 | 9/2020 |
| WO | WO-2020202232 | A1 | 10/2020 |
| WO | WO-2020219650 | A1 | 10/2020 |
| WO | WO-2020228513 | A1 | 11/2020 |
| WO | WO-2020244612 | A1 | 12/2020 |
| WO | WO-2020259556 | A1 | 12/2020 |
| WO | WO-2020264499 | A1 | 12/2020 |

(56) References Cited

FOREIGN PATENT DOCUMENTS

| | | | | |
|---|---|---|---|---|
| WO | WO-2021077010 A1 | | 4/2021 | |
| WO | WO-2021087096 A1 | | 5/2021 | |
| WO | WO-2021087138 A1 | | 5/2021 | |
| WO | WO-2021108581 A1 | | 6/2021 | |
| WO | WO-2021172359 A1 | | 9/2021 | |
| WO | WO-2021182914 A1 | | 9/2021 | |
| WO | WO-2021217036 A1 | | 10/2021 | |
| WO | WO-2021227904 A1 | | 11/2021 | |
| WO | WO-2021242602 A1 | | 12/2021 | |
| WO | WO-2021260578 A1 | | 12/2021 | |
| WO | WO-2022017533 A1 | | 1/2022 | |
| WO | WO-2022028556 A1 | | 2/2022 | |
| WO | WO-2022061155 A1 | | 3/2022 | |
| WO | WO-2022064009 A1 | | 3/2022 | |
| WO | WO-2022081928 A1 | | 4/2022 | |
| WO | WO-2022082056 A1 | | 4/2022 | |
| WO | WO-2022084930 A2 | | 4/2022 | |
| WO | WO-2022098843 A1 | | 5/2022 | |
| WO | WO-2022098989 A1 | * | 5/2022 | ......... C07K 14/4702 |
| WO | WO-2022136174 A1 | | 6/2022 | |
| WO | WO-2024112611 A1 | | 5/2024 | |
| WO | WO-2024211684 A1 | | 10/2024 | |

OTHER PUBLICATIONS

Cortiguera, M.G., García-Gaipo, L., Wagner, S.D. et al. Suppression of BCL6 function by HDAC inhibitor mediated acetylation and chromatin modification enhances BET inhibitor effects in B-cell lymphoma cells. Sci Rep 9, 16495 (2019). https://doi.org/10.1038/s41598-019-52714-4 (Year: 2019).*

Troup et al., Explor Target Antitumor Ther. 2020;1:273-312 (Year: 2020).*

Nance JP, Bélanger S, Johnston RJ, Hu JK, Takemori T, Crotty S. Bcl6 middle domain repressor function is required for T follicular helper cell differentiation and utilizes the corepressor MTA3. Proc Natl Acad Sci U S A. Oct. 27, 2015;112(43):13324-9. (Year: 2015).*

Cortiguera, M.G., García-Gaipo, L., Wagner, S.D. et al. Suppression of BCL6 function by HDAC inhibitor mediated acetylation and chromatin modification enhances BET inhibitor effects in B-cell lymphoma cells. Sci Rep 9, 16495 (2019)) (Year: 2019).*

Abrahams et al. SFARI Gene 2.0: a community-driven knowledgebase for the autism spectrum disorders (ASDs). Mol Autism 4(1):36 (2013).

Agarwal et al. Factors limiting the utility of bronchoalveolar lavage in the diagnosis of COVID-19. Eur Respir 56(5):2003116 (Nov. 2020).

Ali et al. The development of a selective cyclin-dependent kinase inhibitor that shows antitumor activity. Cancer Res. 69(15):6208-6215 (2009).

Allen et al. Thirst-associated preoptic neurons encode an aversive motivational drive. Science 357(6356):1149-55 (2017).

Alsfouk. Small molecule inhibitors of cyclin-dependent kinase 9 for cancer therapy. J Enzyme Inhib Med Chem. 36(1):693-706 (2021).

Anderson et al. Rates of 5 common antidepressant side effects among new adult and adolescent cases of depression: a retrospective US claims study. Clin Ther 34(1):113-123 (2012).

Bader. Inhibition of serotonin synthesis: A novel therapeutic paradigm. Pharmacol Ther 205:107423 (Oct. 2020).

Bailey et al. Comprehensive Characterization of Cancer Driver Genes and Mutations. Cell 174(4):1034-1035 (2018).

Bal et al. Super-enhancer hypermutation alters oncogene expression in B cell lymphoma. Nature 607:808-815 (2022).

Beguelin et al., EZH2 and BCL6 Cooperate to Assemble CBX8-BCOR Complex to Repress Bivalent Promoters, Mediate Germinal Center Formation and Lymphomagenesis. Cancer Cell 30:197-213 (2016).

Bellenie et al. Achieving In Vivo Target Depletion through the Discovery and Optimization of Benzimidazolone BCL6 Degraders. J Med Chem 63(8):4047-4068 (Apr. 2020).

Belshaw et al. Controlling protein association and subcellular localization with a synthetic ligand that induces heterodimerization of proteins. PNAS USA 93(10):4604-7 (1996).

Benzekhroufa et al. Targeting central serotonergic neurons with lentiviral vectors based on a transcriptional amplification strategy. Gene Ther 16(5):681-8 (2009).

Bera et al. Fluorogenic Detection of Monoamine Neurotransmitters in Live Cells. ACS Chem Neurosci 9(3):469-74 (2018).

Bouillet et al., Proapoptotic Bcl-2 relative Bim required for certain apoptotic responses, leukocyte homeostasis, and to preclude autoimmunity. Science 286:1735-1738 (1999).

Boyden et al. Millisecond-timescale, genetically targeted optical control of neural activity. Nature Neurosci 8(9):1263-8 (2005).

Braun et al. Rapid and reversible epigenome editing by endogenous chromatin regulators. Nat Commun 8(1):560 (2017).

Brunet et al. Akt promotes cell survival by phosphorylating and inhibiting a Forkhead transcription factor. Cell 96(6):857-68 (1999).

Buchanan et al. Time-dependent effects of PCPA on social aggression in chicks. Pharmacol Biochem Behav 49(3):483-8 (1994).

Bundgard, H. Design of Prodrugs. 1985; pp. 7-9, 21-24 (Elsevier, Amsterdam).

Bushweller. Targeting transcription factors in cancer—from undruggable to reality. Nat Rev Cancer 19(11):611-24 (2019).

Cai et al. Citalopram attenuates social behavior deficits in the BTBR T(+)ltpr3(tf)/J mouse model of autism. Brain Res Bull 150:75-85 (2019).

Campagne et al. Nuclear magnetic resonance analysis of protein-DNA interactions. J R Soc Interface 8(61):1065-78 (2011).

Cao et al. Zbtb1 Safeguards Genome Integrity and Prevents p53-Mediated Apoptosis in Proliferating Lymphoid Progenitors. J Immunol 197(4):1199-1211 (2016).

Castellanos et al. Eukaryotic transcription factors can track and control their target genes using DNA antennas. Nat Comm 11(1):540 (Jan. 2020).

Chapuy et al. Molecular subtypes of diffuse large B cell lymphoma are associated with distinct pathogenic mechanisms and outcomes. Nat Med 24:679-690 (2018).

Chaudhury et al. Rapid regulation of depression-related behaviours by control of midbrain dopamine neurons. Nature 493(7433):532-6 (2013).

Chen et al. DNA binding by GATA transcription factor suggests mechanisms of DNA looping and long-range gene regulation. Cell Reports 2(5):1197-206 (2012).

Chen et al. ZBTB Transcription Factors: Key Regulators of the Development, Differentiation and Effector Function of T Cells. 12:713294 (2021).

Chen et al. Cyclin-dependent kinase inhibitor fadraciclib (CYC065) depletes anti-apoptotic protein and synergizes with venetoclax in primary chronic lymphocytic leukemia cells. Leukemia 36:1596-1608 (2022).

Chiarella et al. Dose-dependent activation of gene expression is achieved using CRISPR and small molecules that recruit endogenous chromatin machinery. Nat Biotechnol 38(1):50-5 (Jan. 2020).

Chiarella et al. Epigenetic Control of a Local Chromatin Landscape. Int J Mol Sci 21(3):943 (Jan. 2020).

Cidado et al. AZD4573 Is a Highly Selective CDK9 Inhibitor That Suppresses MCL-1 and Induces Apoptosis in Hematologic Cancer Cells. Clin Cancer Res 26:922-934 (Feb. 2020).

Clark et al. Glucocorticoid modulation of tryptophan hydroxylase-2 protein in raphe nuclei and 5-hydroxytryptophan concentrations in frontal cortex of C57/B16 mice. Mol Psychiatry 13(5):498-506 (2008).

Collaborators GBDCoD. Global, regional, and national age-sex-specific mortality for 282 causes of death in 195 countries and territories, 1980-2017: a systematic analysis for the Global Burden of Disease Study 2017. Lancet 392(10159):1736-88 (2018).

Cooper et al. Structures of the Ets Protein DNA-binding Domains of Transcription Factors Etv1, Etv4, Etv5, and Fev: Determinants of DNA Binding and Redox Regulation by Disulfide Bond Formation. J Biol Chem 290(22):13692-709 (2015).

Czodrowdki et al. Structure-Based Optimization of Potent, Selective, and Orally Bioavailable CDK8 Inhibitors Discovered by High-Throughput Screening. J Med Chem 59(20):9337-9349 (2016).

(56) References Cited

OTHER PUBLICATIONS

Dale et al. A selective chemical probe for exploring the role of CDK8 and CDK19 in human disease. Nat Chem Biol 11:973-980 (2015).
Dey et al. Voruciclib, a clinical stage oral CDK9 inhibitor, represses MCL-1 and sensitizes high-risk Diffuse Large B-cell Lymphoma to BCL2 inhibition. Sci Rep 7:18007 (2017).
Doan et al. Autism Sequencing C, Freitag CM, Daly MJ, Walsh CA, Buxbaum JD, Yu TW. Recessive gene disruptions in autism spectrum disorder. Nature Genet 51(7):1092-8 (2019).
Dodonova et al. Nucleosome-bound SOX2 and SOX11 structures elucidate pioneer factor function. Nature 580(7805):669-72 (Apr. 2020).
Dolen et al. Social reward requires coordinated activity of nucleus accumbens oxytocin and serotonin. Nature 501(7466):179-84 (2013).
Dyer et al. A new human B-cell non-Hodgkin's lymphoma cell line (Karpas 422) exhibiting both t(14;18) and t(4;11) chromosomal translocations. Blood 75:709-714 (1990).
Eaton et al. Autocrine BDNF secretion enhances the survival and serotonergic differentiation of raphe neuronal precursor cells grafted into the adult rat CNS. Exp Neurol 140(2):105-14 (1996).
Erwin et al. Synthetic transcription elongation factors license transcription across repressive chromatin. Science 358(6370):1617-22 (2017).
Faber et al. Apoptosis in targeted therapy responses: the role of BIM. Adv Pharmacol 65:519-542 (2012).
Farrelly et al. Histone serotonylation is a permissive modification that enhances TFIID binding to H3K4me3. Nature 567(7749):535-9 (2019).
Filippakopoulos et al. Selective inhibition of BET bromodomains. Nature 468(7327):1067-73 (2010).
Fitzsimmons et al. Highly cooperative recruitment of Ets-1 and release of autoinhibition by Pax5. J Mol Biol 392(2):452-64 (2009).
Fornes et al. JASPAR 2020: update of the open-access database of transcription factor binding profiles. Nucleic Acids Res 48(D1):D87-D92 (Jan. 2020).
Fox et al. Engrailed is required in maturing serotonin neurons to regulate the cytoarchitecture and survival of the dorsal raphe nucleus. J Neurosci 32(23):7832-42 (2012).
Gamberi et al. Molecular diagnosis in Ewing family tumors: the Rizzoli experience—222 consecutive cases in four years. J Mol Diagn 13(3):313-24 (2011).
Gao et al. Integrative analysis of complex cancer genomics and clinical profiles using the cBioPortal. Science signaling 6(269):11 (2013).
Garvie et al. Structural studies of Ets-1/Pax5 complex formation on DNA. Mol Cell 8(6):1267-76 (2001).
Garvie et al. Structural analysis of the autoinhibition of Ets-1 and its role in protein partnerships. J Biol Chem 277(47):45529-36 (2002).
George et al. Comprehensive genomic profiles of small cell lung cancer. Nature 524:47-53 (2015).
Ghetu et al. Structure of a BCOR corepressor peptide in complex with the BCL6 BTB domain dimer. Mol Cell 29(3):384-391 (2008).
Gomez et al. Chemogenetics revealed: DREADD occupancy and activation via converted clozapine. Science 357(6350):503-7 (2017).
Gorgulla et al. An open-source drug discovery platform enables ultra-large virtual screens. Nature 580(7805):663-8 (Mar. 2020).
Gourisankar et al. Rewiring cancer drivers to activate apoptosis. bioRxiv: https://www.biorxiv.org/content/biorxiv/early/2022/12/07/2022.12.04.517548.full.pdf (Dec. 7, 2022).
Gourisankar et al. Rewiring cancer drivers to activate apoptosis. Nature doi: 10.1038/s41586-023-06348-2 (Online ahead of print—2023).
Gourisankar et al. Rewiring cancer drivers to activate apoptosis. Nature Supplementary Material (23 pgs) (2023).
Guo et al. Design and Synthesis of Dual EZH2/BRD4 Inhibitors to Target Solid Tumors. J Med Chem 65(9):6573-6592 (2022).
Hains et al. Engraftment of serotonergic precursors enhances locomotor function and attenuates chronic central pain behavior following spinal hemisection injury in the rat. Exp Neurol 171(2):361-78 (2001).
Halgren. Identifying and characterizing binding sites and assessing druggability. J Chem Inf Model 49(2):377-89 (2009).
Hatcher et al. Development of Highly Potent and Selective Steroidal Inhibitors and Degraders of CDK8. Acs Med. Chem. Lett. 9:540-545 (2018).
Hathaway et al. Dynamics and memory of heterochromatin in living cells. Cell 149(7):1447-60 (2012).
Haugas et al. Gata2 and Gata3 regulate the differentiation of serotonergic and glutamatergic neuron subtypes of the dorsal raphe. Development 143(23):4495-4508 (2016).
Heiderscheit et al. Reprogramming cell fate with artificial transcription factors. FEBS Lett 592(6):888-900 (2018).
Hendricks et al. The ETS domain factor Pet-1 is an early and precise marker of central serotonin neurons and interacts with a conserved element in serotonergic genes. J Neurosci. 19(23):10348-56 (1999).
Hiroi et al. Estrogen receptor-beta regulates human tryptophan hydroxylase-2 through an estrogen response element in the 5' untranslated region. J Neurochem 127(4):487-95 (2013).
Ho et al. Dimeric ligands define a role for transcriptional activation domains in reinitiation. Nature 382(6594):822-6 (1996).
Horn et al. First-Line Atezolizumab plus Chemotherapy in Extensive-Stage Small-Cell Lung Cancer. N Eng J Med 379:2220-2229 (2018).
Hsing et al. ETS transcription factors as emerging drug targets in cancer. Med Res Rev 40(1):413-30 (Jan. 2020).
Huang et al. Molecular and anatomical organization of the dorsal raphe nucleus. eLife 8:e46464 (2019).
Huynh et al. BCoR, a novel corepressor involved in BCL-6 repression. Genes Dev 14(14):1810-1823 (2000).
Ikegaki et al. Expression of bcl-2 in small cell lung carcinoma cells. Cancer Res. 54:6-8 (1994).
Ishimura et al. Quantitative analysis of the distribution of serotonin-immunoreactive cell bodies in the mouse brain. Neurosci Lett 91(3):265-70 (1988).
Jequier et al. Tryptophan hydroxylase inhibition: the mechanism by which p-chlorophenylalanine depletes rat brain serotonin. Mol Pharmacol 3(3):274-8 (1967).
Jolma et al. DNA-dependent formation of transcription factor pairs alters their binding specificity. Nature 527(7578):384-8 (2015).
Joshi et al. P276-00, a novel cyclin-dependent inhibitor induces G1-G2 arrest, shows antitumor activity on cisplatin-resistant cells and significant in vivo efficacy in tumor models. Mol Cancer Ther. 6(3):926-34 (2007).
Junco et al. Structure of the polycomb group protein PCGF1 in complex with BCOR reveals basis for binding selectivity of PCGF homologs. Structure 21:665-671 (2013).
Kadia et al. Phase II Study of Venetoclax Added to Cladribine + Low Dose AraC (LDAC) Alternating with 5-Azacytidine Demonstrates High Rates of Minimal Residual Disease (MRD) Negative Complete Remissions (CR) and Excellent Tolerability in Older Patients with Newly Diagnosed Acute Myeloid Leukemia (AML). Blood 136(Supplement 1):17-19 (Nov. 2020).
Kadoch et al. Dynamics of BAF-Polycomb complex opposition on heterochromatin in normal and oncogenic states. Nature Genet. 49(2):213-22 (2017).
Kalan et al. Activation of the p53 Transcriptional Program Sensitizes Cancer Cells to Cdk7 Inhibitors. Cell Reports 21(2):467-481 (2017).
Karlsson et al. A single-cell type transcriptomics map of human tissues. Science Advances 7(31):eabh2169 (2021).
Kerres et al. Chemically Induced Degradation of the Oncogenic Transcription Factor BCL6. Cell Rep 20:2860-2875 (2017).
Khalil et al. Discovery and development of Seliciclib. How systems biology approaches can lead to better drug performance. J Biotechnol 202:40-49 (2015).
Kim et al. Transcriptional repressor ZBTB1 promotes chromatin remodeling and translesion DNA synthesis. Mol Cell 54(1):107-118 (2014).

(56) References Cited

OTHER PUBLICATIONS

Kim et al. Abstract 5133: TP-1287, an oral prodrug of the cyclin-dependent kinase-9 inhibitor alvocidib. Cancer Res 77(13_ Supplement):5133 (2017).
Koh et al. Rapid chromatin repression by Aire provides precise control of immune tolerance. Nature Immunol 19(2):162-72 (2018).
Lacerda et al. Local serotonin mediates cyclic strain-induced phenotype transformation, matrix degradation, and glycosaminoglycan synthesis in cultured sheep mitral valves. Am J Physiol Heart Circ Physiol 302(10):H1983-90 (2012).
Lachmann et al. Massive mining of publicly available RNA-seq data from human and mouse. Nat Commun 9(1):1366 (2018).
Lambert et al. The Human Transcription Factors. Cell 172:650-665 (Feb. 2018).
Lau et al. Targeted Transgene Activation in the Brain Tissue by Systemic Delivery of Engineered AAV1 Expressing CRISPRa. Mol Ther Nucleic Acids 16:637-49 (2019).
Li et al. The Sequence Alignment/Map format and SAMtools. Bioinformatics 25:2078-2079 (2009).
Little et al. Amplification and expression of the c-myc oncogene in human lung cancer cell lines. Nature 306:194-196 (1983).
Liu et al. Eradication of large colon tumor xenografts by targeted delivery of maytansinoids. PNAS USA 93:8618-8623 (1996).
Liu et al. Pet-1 is required across different stages of life to regulate serotonergic function. Nature Neurosci 13(10):1190-8 (2010).
Love et al. Moderated estimation of fold change and dispersion for RNA-seq data with DESeq2. Genome Biol 15(12):550 (2014).
Lozano et al. Deep brain stimulation: current challenges and future directions. Nat Rev Neurol 15(3):148-60 (2019).
Lucking. Identification of Atuveciclib (BAY 1143572), the First Highly Selective, Clinical PTEFb/CDK9 Inhibitor for the Treatment of Cancer. ChemMedChem. 12(21):1776-1793 (2017).
Matthes et al. Peripheral Serotonin Synthesis as a New Drug Target. Trends Pharmacol Sci 39(6):560-72 (2018).
Maze et al. Critical Role of Histone Turnover in Neuronal Transcription and Plasticity. Neuron 87(1):77-94 (2015).
Mccoull et al., Development of a Novel B-Cell Lymphoma 6 (BCL6) PROTAC to Provide Insight into Small Molecule Targeting of BCL6. ACS Chem Biol 13:3131-3141 (2018).
Meltzer et al. Lorcaserin and pimavanserin: emerging selectivity of serotonin receptor subtype-targeted drugs. J Clin Invest 123(12):4986-91 (2013).
Miller et al. TOP2 synergizes with BAF chromatin remodeling for both resolution and formation of facultative heterochromatin. Nat Struct Mol Biol 24(4):344-52 (2017).
Mondoloni et al. Cell-Specific Neuropharmacology. Trends Pharmacol Sci 40(9):696-710 (2019).
Nagai et al. Deschloroclozapine, a potent and selective chemogenetic actuator enables rapid neuronal and behavioral modulations in mice and monkeys. Nature Neurosci 23(9):1157-1167 (Sep. 2020).
Nagy et al. Nuclear receptor repression mediated by a complex containing SMRT, mSin3A, and histone deacetylase. Cell 89:373-380 (1997).
Nakamura et al. CDK8/19 inhibition induces premature G1/S transition and ATR-dependent cell death in prostate cancer cells. Oncotarget 9(17):13474-13487 (2018).
Nawa et al. Functional characterization of the neuron-restrictive silencer element in the human tryptophan hydroxylase 2 gene expression. J Neurochem 142(6):827-40 (2017).
Nicholson et al., The International Association for the Study of Lung Cancer Lung Cancer Staging Project: Proposals for the Revision of the Clinical and Pathologic Staging of Small Cell Lung Cancer in the Forthcoming Eighth Edition of the TNM Classification for Lung Cancer. J Thorac Oncol 11:300-311 (2016).
Oberoi et al. Structural basis for the assembly of the SMRT/NCoR core transcriptional repression machinery. Nat Struct Mol Biol 18:177-184 (2011).
Okaty et al. Multi-Scale Molecular Deconstruction of the Serotonin Neuron System. Neuron 88(4):774-91 (2015).
Okaty et al. A single-cell transcriptomic and anatomic atlas of mouse dorsal raphe Pet1 neurons. eLife 9:e55523 (Jun. 2020).
Olson et al. Pharmacological perturbation of CDK9 using selective CDK9 inhibition or degradation. Nature Chem Biol 14:163-173 (2018).
Otarola. Role of Estrogen in Serotonergic Neuronal Development and Function [ePoster]. 2020 AAAS Student E-poster Competition 2020 [updated Feb. 13, 2020]. Available from: https://aaas.confex.com/aaas/2020/meetingapp.cgi/Paper/27179.
Pasqualucci et al. Genetics of diffuse large B-cell lymphoma. Blood 131:2307-2319 (2018).
Paz-Ares et al. Durvalumab plus platinum-etoposide versus platinum-etoposide in first-line treatment of extensive-stage small-cell lung cancer (CASPIAN): a randomised, controlled, open-label, phase 3 trial. Lancet 394:1929-1939 (2019).
Petrassi et al. Identification of a Novel Allosteric Inhibitory Site on Tryptophan Hydroxylase 1 Enabling Unprecedented Selectivity Over all Related Hydroxylases. Front Pharmacol 8:240 (2017).
Phan et al. The BCL6 proto-oncogene suppresses p53 expression in germinal-centre B cells. Nature 432:635-639 (2004).
Polo et al. Specific peptide interference reveals BCL6 transcriptional and oncogenic mechanisms in B-cell lymphoma cells. Nat Med 10(12):1329-1335 (2004).
Quinlan et al. BEDTools: a flexible suite of utilities for comparing genomic features Bioinformatics 26:841-842 (2010).
Ramírez et al. deepTools2: a next generation web server for deep-sequencing data analysis. Nucleic Acids Res 44:W160-W165 (2016).
Reddy et al. Genetic and Functional Drivers of Diffuse Large B Cell Lymphoma. Cell 171:481-494 e415 (2017).
Ren et al. Single-cell transcriptomes and whole-brain projections of serotonin neurons in the mouse dorsal and median raphe nuclei. eLife 8:e49424 (2019).
Rogan et al. Remote control of neuronal signaling. Pharmacol Reviews 63(2):291-315 (2011).
Rohilla et al. Virtual Screening, pharmacophore development and structure based similarity search to identify inhibitors against IdeR, a transcription factor of *Mycobacterium tuberculosis*. Scientific Reports 7(1):4653 (2017).
Rost et al. Optogenetic Tools for Subcellular Applications in Neuroscience. Neuron 96(3):572-603 (2017).
Rudin et al., Small-cell lung cancer. Nat Rev Dis Primers 7:3 (2021).
Rzymski et al. SEL120-34A is a novel CDK8 inhibitor active in AML cells with high levels of serine phosphorylation of STAT1 and STAT5 transactivation domains. Oncotarget 8(20):33779-33795 (2017).
Saba et al. Miz-1 is required to coordinate the expression of TCRbeta and p53 effector genes at the pre-TCR beta-selection checkpoint. J Immunol 187(6):2982-2992 (2011).
Santo et al. AT7519, A novel small molecule multi-cyclin-dependent kinase inhibitor, induces apoptosis in multiple myeloma via GSK-3beta activation and RNA polymerase II inhibition. Oncogene 29:2325-2336 (2010).
Saqub et al. Dinaciclib, a cyclin-dependent kinase inhibitor, suppresses cholangiocarcinoma growth by targeting CDK2/5/9. Sci Rep 10:18489 (Oct. 2020).
Scheuch et al. Characterization of a functional promoter polymorphism of the human tryptophan hydroxylase 2 gene in serotonergic raphe neurons. Biol Psychiatry 62(11):1288-94 (2007).
Schmitz et al. Genetics and Pathogenesis of Diffuse Large B-Cell Lymphoma. N Engl J Med 378:1396-1407 (2018).
Scholz et al. The oral multitarget tumour growth inhibitor, ZK 304709, inhibits growth of pancreatic neuroendocrine tumours in an orthotopic mouse model. Gut 58:261-270 (2009).
Schreiber. The Rise of Molecular Glues. Cell 184(1):3-9 (2021).
Senova et al. Experimental assessment of the safety and potential efficacy of high irradiance photostimulation of brain tissues. Scientific Reports 7:43997 (2017).
Shen et al. Challenges for Therapeutic Applications of Opsin-Based Optogenetic Tools in Humans. Frontiers Neural Circuits 14:41 (Jul. 2020).
Shillito. The effect of parachlorophenylalanine on social interaction of male rats. Br J Pharmacol 38(2):305-15 (1970).

(56) References Cited

OTHER PUBLICATIONS

Slabicki et al. Small-molecule-induced polymerization triggers degradation of BCL6. Nature 588(7836):164-168 (Dec. 2020).
Spencer et al. Controlling signal transduction with synthetic ligands. Science 262(5136):1019-24 (1993).
Stanton et al. Chemically induced proximity in biology and medicine. Science 359(6380):eaao5902 (2018).
Stead et al. Structure of the wild-type human BCL6 POZ domain. Acta Crystallogr Sect F Struct Biol Cryst Commun 64:1101-1104 (2008).
Strasser et al. Apoptosis signaling. Annu Rev Biochem 69:217-245 (2000).
Sun et al. Phase III trial of concurrent thoracic radiotherapy with either first- or third-cycle chemotherapy for limited-disease small-cell lung cancer. Ann Oncol 24:2088-2092 (2013).
Sung et al. Global Cancer Statistics 2020: GLOBOCAN Estimates of Incidence and Mortality Worldwide for 36 Cancers in 185 Countries. CA Cancer J Clin 71:209-249 (2021).
Trigo et al. Lurbinectedin as second-line treatment for patients with small-cell lung cancer: a single-arm, open-label, phase 2 basket trial. Lancet Oncol 21(5):645-654 (May 2020).
Tu et al. Design, Synthesis, and Evaluation of VHL-Based EZH2 Degraders to Enhance Therapeutic Activity against Lymphoma. J Med Chem 64(14):10167-10184 (2021).
Varghese et al. Small-cell lung cancers in patients who never smoked cigarettes. J Thorac Oncol 9:892-896 (2014).
Vierstra et al. Global reference mapping of human transcription factor footprints. Nature 583(7818):729-36 (Jul. 2020).
Walsh et al. 5-HT release in nucleus accumbens rescues social deficits in mouse autism model. Nature 560(7720):589-94 (2018).
Walther et al. Synthesis of serotonin by a second tryptophan hydroxylase isoform. Science 299(5603):76 (2003).
Wang et al. CDK7-dependent transcriptional addiction in triple-negative breast cancer. Cell 163:174-186 (2015).
Wang et al. Discovery of novel CDK8 inhibitors using multiple crystal structures in docking-based virtual screening. Eur J Med Chem. 129:275-286 (2017).
Wenderski et al. Loss of the neural-specific BAF subunit ACTL6B relieves repression of early response genes and causes recessive autism. PNAS USA 117(18):10055-66 (May 2020).
Whiteford et al. The global burden of mental, neurological and substance use disorders: an analysis from the Global Burden of Disease Study 2010. PloS One 10(2):e0116820 (2015).
Wu et al. Sono-optogenetics facilitated by a circulation-delivered rechargeable light source for minimally invasive optogenetics. PNAS USA 116(52):26332-26342 (2019).
Wu et al. Phase I Study of Zotiraciclib in Combination with Temozolomide for Patients with Recurrent High-grade Astrocytomas. Clin Cancer Res 27(12):3298-3306 (2021).
Young et al. The role of serotonin in human mood and social interaction. Insight from altered tryptophan levels. Pharmacol Biochem Behav 71(4):857-65 (2002).
Yu et al. PUMA induces the rapid apoptosis of colorectal cancer cells. Mol Cell 7:673-682 (2001).
Yu et al. PUMA mediates the apoptotic response to p53 in colorectal cancer cells. PNAS USA 100:1931-1936 (2003).
Yu et al. Allele-specific p53 mutant reactivation. Cancer Cell 21:614-625 (2012).
Yuan et al. YAP1/TAZ-TEAD transcriptional networks maintain skin homeostasis by regulating cell proliferation and limiting KLF4 activity. Nature Commun 11(1):1472 (Mar. 2020).
Zak et al. Structural basis for small molecule targeting of the programmed death ligand 1 (PD-L1). Oncotarget 7(21):30323-35 (2016).
Zeidner et al. A prospective biomarker analysis of alvocidib followed by cytarabine and mitoxantrone in MCL-1-dependent relapsed/refractory acute myeloid leukemia. Blood Cancer Journal 11(10):175 (2021).
Zhang et al. A Selective and Orally Bioavailable Quinoline-6-Carbonitrile-Based Inhibitor of CDK8/19 Mediator Kinase with Tumor-Enriched Pharmacokinetics. J Med Chem 65(4):3420-3433 (2022).
Zhao et al. Lmx1b is required for maintenance of central serotonergic neurons and mice lacking central serotonergic system exhibit normal locomotor activity. J Neurosci. 26(49):12781-8 (2006).
International Search Report for PCT Application No. PCT/US2021/058231 mailed Mar. 24, 2022, 18 pages.
International Search Report for PCT Application No. PCT/US2023/020719 mailed Aug. 10, 2023, 25 pages.
Boyd et al., Design and Applications of Bifunctional Small Molecules in Biology, Biochimica et Biophysica Acta (BBA)—Proteins and Proteomics, 1869(1):140534 (Jan. 2021).
Butler et al., Targeted Gene Repression Using Novel Bifunctional Molecules to Harness Endogenous Histone Deacetylation Activity, ACS Synth Biol, 7(1):38-45 (Jan. 19, 2018).
Gryder et al., Selectively targeting prostate cancer with antiandrogen equipped histone deacetylase inhibitors, ACS Chem Biol, 8(11):2550-60 (Nov. 15, 2013).
Lafrate et al., Steroidal bivalent ligands for the estrogen receptor: design, synthesis, characterization and binding affinities, Bioorg Med Chem, 17(10):3528-35 (May 15, 2009).
Shan et al., Nonsteroidal Bivalent Estrogen Ligands: An Application of the Bivalent Concept to the Estrogen Receptor, ACS Chem Biol, 8(4):707-15 (Apr. 19, 2013).
Kolker, Antibodies and the written description requirement of 35 U.S.C.112(a), Sep. 17, 2020, 36 slides.
Corson et al., Design and Applications of Bifunctional Small Molecules: Why Two Heads Are Better Than One, ACS Chem Biol, 3(11):677-692 (2008).
Gerry et al., Unifying principles of bifunctional, proximity-inducing small molecules, Nat Chem Biol, 16(4):369-378 (Apr. 16, 2020).
Lin et al., Androgen and its receptor promote Bax-mediated apoptosis, Mol Cell Biol, 26(5):1908-1916 (2006).
Schacter et al., Estrogen regulation of anti-apoptotic Bcl-2 family member Mcl-1 expression in breast cancer cells, PLoS One, 9(6):1-12, e100364 (2014).

* cited by examiner

JWZ-7-7

DMSO  0.24  0.49  0.98  2.00  3.91  7.82  15.63  31.25  62.50  125  250  nM

MYC
P21
FOXO3
BCL6
GAPDH

A

B

A)

SNS-032

B)

11

7

14

25a

FX1

BI-3812

C)

BAK-04-023

BAK-04-022

BAK-04-021

BAK-04-028

BAK-04-029

BAK-04-030

BAK-04-016

BAK-04-015

BAK-04-014

CDK9 TCIP CDK9 Inhibitors

| Name | Reference | Structure |
|---|---|---|
| THAL-SNS-032 | Nature Chem Biol, 2018, 14, 163-173 |  |
| NVP-2 | WO/2011/01266 |  |
| KI-ARv-03 | *ACS Med. Chem. Lett.* 2018, 9, 6, 540–545 |  |
| KB-0742 | *ACS Med. Chem. Lett.* 2018, 9, 6, 540–545 |  |
| BAY-1143572 | *ChemMedChem 2017, 12, 1776 – 1793* |  |
| AZD-4573 | *Clin Cancer Res 2020, 26, 922–934.* |  |
| Alvocidib | *Blood Cancer Journal (2021) 11:175* |  |

| | | |
|---|---|---|
| TP-1287 | Cancer Res *(2017) 77 (13_Supplement): 5133* |  |
| Riviciclib | Mol Cancer Ther. 2007 Mar;6(3):926-34. |  |
| Voruciclib | Scientific Reports, 2017, 7, 18007 |  |
| ZK-304709 | *Gut* 2009;58:261-270 |  |
| BAY-1251152 | J Enzyme Inhib Med Chem. 2021; 36(1): 693–706. |  |
| Zotiraciclib (TG-02) | *Clin Cancer Res* (2021) 27 (12): 3298–3306. |  |
| Seliciclib | Journal of Biotechnology 202 (2015) 40–49 |  |

| | | |
|---|---|---|
| Fadraciclib | Leukemia volume 36, pages1596–1608 (2022) |  |
| Dinaciclib | Scientific Reports volume 10, Article number: 18489 (2020) |  |
| AT7519 | Oncogene volume 29, pages2325–2336 (2010) |  |
| BTX-A51 | *Clarivate Analytics Integrity. https://integrity.clarivate.com*<br><br>Blood (2020) 136 (Supplement 1) : 18. |  |

CDK8 Inhibitors

| Name | Reference | Structure | Comments |
|---|---|---|---|
| BI-1347 | WO2017202719A1 |  | |

| | | | |
|---|---|---|---|
| Cortistatin A | ACS Med. Chem. Lett. 2018, 9, 540-545 |  | |
| JH-VIII-49 | ACS Med. Chem. Lett. 2018, 9, 540-545 |  | |
| CCT251545 | *Nat Chem Biol 11, 973–980 (2015).* |  | |
| MSC253818 | *J. Med. Chem. 2016, 59, 20, 9337–9349* |  | |
| Senexin C | *J. Med. Chem. 2022, 65, 4, 3420–3433* |  | Other derivatives include Senexin A,B |
| Sel 120-34A | *Oncotarget, 2017, Vol. 8, (No. 20), pp: 33779-33795* |  | Phase 1 |

| | | | |
|---|---|---|---|
| W-34 | *Eur J Med Chem. 2017 Mar 31;129:275-286.* |  | |
| T-814 | *Oncotarget. 2018 Mar 2; 9(17): 13474–13487.* |  | |

CDK7 Inhibitors

| Name | Reference | Structure | Comments |
|---|---|---|---|
| BS-181 | *Cancer Res* (2009) 69 (15): 6208–6215. |  | |
| CT7001 | *US20160362410A1* |  | |
| THZ2 | *Wang et al., 2015, Cell 163, 174–186* |  | Other derivatives include THZ1 |
| YKL-1-116 | *Kalan et al., 2017, Cell Reports 21, 467–481* |  | Other Derivatives include YLK-5-124 |

(BI-3802)

(14)

(6)

(CCT369347)

(CCT372064)

(CCT37566)

(CCTT369260)

(26c)

(TMX-2164)

(BCl-1)

(GSK-137)

(79-6)

A.

| Name | Reference | Structure | Comments |
|---|---|---|---|
| BI-3812 | *Cell Reports* 2017, *20*, 2860–2875 |  | |
| BI-3802 | *Cell Reports* 2017, *20*, 2860–2875 |  | monovalent degrader |
| Cmpd 15 | *ACS Chem. Biol.* 2018, *13*, 3131 - 3141 |  | bivalent degrader |
| Cmpd 6 | *ACS Chem. Biol.* 2018, *13*, 3131 - 3141 |  | |
| CCT369347 | *J. Med. Chem.* 2021, *64*, 17079 - 17097 |  | |
| CCT372064 | *J. Med. Chem.* 2022, *ASAP* |  | |

| | | | |
|---|---|---|---|
| CCT373566 | *J. Med. Chem.* 2022, *ASAP* |  | monovalent degrader |
| CCTT369260 | *J. Med. Chem.* 2020, *63*, 4047 - 4068 |  | monovalent degrader |
| Cmpd 26c | *J. Med. Chem.* 2020, *63*, 4047 - 4068 |  | |
| TMX-2164 | *ACS Med. Chem. Lett.* 2020, *11*, 1269–1273 |  | covalent, Tyr58 |
| BCl-i | *Biochemistry* 2018, *57*, 1369–1379 |  | covalent, Cys53 |
| Cmpd 11 | *J. Med. Chem.* 2017, *60*, 4386–4402 |  | |
| Cmpd 7 | *J. Med. Chem.* 2017, *60*, 4358–4368 |  | |

| | | | |
|---|---|---|---|
| GSK137 | *J. Biol. Chem.* 2021, *297*, 100928 |  | |
| Cmpd 79-6 | *J. Med. Chem.* 2017, *60*, 4358–4368 |  | |

B. Androgen receptor agonists

*Steroidal*

*Non-steroidal*

C. Androgen receptor antagonists

D. Linkers

BAK-04-083 (C2)

RCS-02-063 (C3)

RCS-02-093 (C4)

BAK-04-003 (C5)

RCS-02-085 (C6)

BAK-04-006 (C8)

RCS-02-060 (peg1)

RCS-02-058 (peg2)

RCS-02-061 (peg3)

RCS-02-062 (peg4)

RCS-02-075 (AR-BCL6 neg. control 1)

RCS-02-155 (AR-BCL6 neg. control 2)

BAK-04-039

BAK-04-083

BAK-04-084

RCS-02-160

RCS-02-176

A.

B.

TCIP1 Relocalizes 10% of
Enhancer BRD4

Enhancers,
super enhancers
90% of BRD4

TCIP1 Produces a
50% Increase at BCL6 Targets

BCL6 targets- 10% of BRD4
p53
Bim
NOXA
FOXO3

COMPOSITIONS, SYSTEMS, AND METHODS FOR MODULATING A TARGET GENE

CROSS-REFERENCE TO RELATED APPLICATIONS

This application is a continuation of PCT Application No. PCT/US2023/020719 filed on May 2, 2023, which application claims the benefit of U.S. Provisional Application No. 63/337,330, filed on May 2, 2022; U.S. Provisional Application No. 63/388,386, filed on Jul. 12, 2022; U.S. Provisional Application No. 63/406,128, filed on Sep. 13, 2022; U.S. Provisional Application No. 63/406,602, filed on Sep. 14, 2022; and U.S. Provisional Application No. 63/406,570, filed on Sep. 14, 2022, each of which is incorporated herein by reference in its entirety.

GOVERNMENT RIGHTS

This invention was made with Government support under contracts CA163915, CA268848, CA276167, HD103339, and MH126720 awarded by the National Institutes of Health. The Government has certain rights in the invention.

BACKGROUND

Methods of controlled regulation of gene expression have been increasingly important in a wide range of areas, including, but not limited to, gene therapy, synthetic biology, plant management, environmental clean-up, bacterial and microbial management and synthetic genetic circuits. Control of gene expression holds vast potential at revolutionizing therapeutics, animal models, and biotechnological processes and is useful to integrate multiple input signals for cell-based therapy and animal model development. Despite rapid advances in recent years, precise control of gene expression remains a challenge due to unpredictability stemming from unintended interactions between biological components, such as transcription factors, etc. A fundamental goal in cellular engineering is to predictably and efficiently express genes at a desired level and under precise control. Such genetically engineered cells hold great promise for advancing therapeutics, diagnostics, animal models, and biotechnological processes.

To date, a variety of different gene modulation technologies for modulating gene expression in a cell have been developed. Such gene modulation technologies include RNA interference, DNA editing and expression, and chemical compounds that suppress, enhance, or modify gene expression. These can be in the form of RNA, DNA, or protein, and can be introduced into cells in culture through direct application to media, lipofection, electroporation, or viral transduction.

However, because of the wide applicability of gene modulation to both research and therapeutic applications, there is a continued interest in the development of new ways to modulate transcription of a target gene in a cell, specifically to modulate expression of genes without genetic modification.

SUMMARY

Methods and compositions of regulating expression of a target gene in a cell are provided. Aspects of the methods include contacting the cell with a compound having a first moiety covalently linked to a second moiety, wherein: (i) the first moiety exhibits specific binding to a first endogenous protein that binds to the target gene (or a region near the target gene, such as a promoter or a regulatory region) (ii) the second moiety exhibits specific binding to a second endogenous protein distinct from the first endogenous protein; and (iii) upon contacting the cell, the first endogenous protein and the second endogenous protein are spatially complexed to each other via the compound to yield a gain-of-function in the cell. In some embodiments, the gain-of-function is characterized by modulating expression of the target gene in a manner dependent on the presence of the second endogenous protein bound to the compound. Embodiments of the methods provide one or more beneficial features, including but not limited to: achieving the gain-of-function by utilizing less than about 50% of an amount of the first and/or second endogenous proteins present in the cell; mediation of the gain-of-function with an EC50 of less than about 1 micromolar; modulation of expression of the target gene in less than or equal to about 16 hours.

Accordingly, provided herein in one aspect is a compound of formula I:

BR-L-BC (I)

wherein:

BR is a ligand that specifically binds to bromodomain-containing protein 4 (BRD4);

BC is a ligand that specifically binds to B-cell lymphoma 6 (BCL-6) (or a homologue thereof); and L is a linker, or a pharmaceutically acceptable salt thereof.

In another aspect, provided herein is a method of treating a subject for a malignancy, the method comprising: administering to the subject an effective amount of a transcriptional chemical inducer of proximity (TCIP) which links BCL-6 and BRD4 to treat the subject for the malignancy.

In another aspect, provided herein is a pharmaceutical composition comprising: transcriptional chemical inducer of proximity (TCIP) for treating malignancy, the TCIP comprising a first ligand that specifically binds to BCL-6 and a second ligand that specifically binds to BRD4; and delivery vehicle.

In yet another aspect, provided herein is a method of treating a subject for Diffuse Large B-Cell Lymphoma (DLBCL), the method comprising: administering to the subject an effective amount of a chemical inducer of proximity (CIP) which links BCL-6 and an estrogen receptor treat the subject for DLBCL.

In yet another aspect, provided herein is a method of treating a subject for a malignancy, the method comprising: administering to the subject an effective amount of a transcriptional chemical inducer of proximity (TCIP) which links BCL-6 (or a homologue thereof) and cyclic dependent kinase to treat the subject for the malignancy.

In yet another aspect, provided herein is a transcriptional chemical inducer of proximity (TCIP) for treating malignancy, the TCIP comprising a first ligand that specifically binds to BCL-6 (or a homologue thereof) and a second ligand that specifically binds to a CDK.

In yet another aspect, provided herein is a pharmaceutical composition comprising: transcriptional chemical inducer of proximity (TCIP) for treating malignancy, the TCIP comprising a first ligand that specifically binds to BCL-6 (or a homologue thereof) and a second ligand that specifically binds to a CDK; and delivery vehicle.

In yet another aspect, provided herein is a method of treating a subject for a malignancy, the method comprising: administering to the subject an effective amount of a transcriptional chemical inducer of proximity (TCIP) which links BCL-6 (or a homologue thereof) and an androgen receptor (AR) to treat the subject for the malignancy. In yet another aspect, provided is a transcriptional chemical inducer of proximity (TCIP) for treating malignancy, the TCIP comprising a first ligand that specifically binds to BCL-6 (or a homologue thereof) joined by a linker to a second ligand that specifically binds to an AR.

In yet another aspect, provided herein is a pharmaceutical composition comprising: transcriptional chemical inducer of proximity (TCIP) for treating malignancy, the TCIP comprising a first ligand that specifically binds to BCL-6 (or a homologue thereof) joined by a linker to a second ligand that specifically binds to an AR; and delivery vehicle.

In yet another aspect, provided herein is a method of regulating expression of a target gene in a cell comprising a first endogenous protein and a second endogenous protein, the method comprising: contacting the cell with a compound having a first moiety covalently linked to a second moiety, wherein: (a) the first moiety exhibits specific binding to the first endogenous protein that binds to the target gene or a region near the target gene (e.g., promoter, regulatory region); (b) the second moiety exhibits specific binding to the second endogenous protein distinct from the first endogenous protein; and (c) upon contacting the cell, the first endogenous protein and the second endogenous protein are spatially complexed to each other via the compound to yield a gain-of-function in the cell, wherein the gain-of-function is characterized by modulating expression of the target gene in a manner dependent on presence of the second endogenous protein bound to the compound, and wherein the gain-of-function is achieved by utilizing less than about 50% of an amount of the second endogenous protein present in the cell.

In yet another aspect, provided herein is a method of regulating expression of a target gene in a cell comprising a first endogenous protein and a second endogenous protein, the method comprising: contacting the cell with a compound having a first moiety covalently linked to a second moiety, wherein: (a) the first moiety exhibits specific binding to the first endogenous protein that binds the target gene; (b) the second moiety exhibits specific binding to the second endogenous protein distinct from the first endogenous protein; and (c) upon contacting the cell, the first endogenous protein and the second endogenous protein are spatially complexed to each other via the compound to yield a gain-of-function in the cell, wherein the gain-of-function is characterized by modulating expression of the target gene in a manner dependent on presence of the second endogenous protein bound to the compound, and wherein the compound mediates the gain-of-function with an $EC_{50}$ of less than about 1 micromolar.

In yet another aspect, provided herein is a method of regulating expression of a plurality of target genes in a cell comprising a first endogenous protein and a second endogenous protein, the method comprising: contacting the cell with a compound having a first moiety covalently linked to a second moiety, wherein: (a) the first moiety exhibits specific binding to the first endogenous protein that reduces expression of a target gene in absence of the compound; (b) the second moiety exhibits specific binding to the second endogenous protein that enhances expression of an additional target gene in absence of the compound; and (c) upon contacting the cell, the first endogenous protein and the second endogenous protein are spatially paired to one another via the compound to yield a gain-of-function in the cell, and wherein the gain-of-function is characterized in that (i) expression of the target gene is enhanced as compared to that in absence of the compound, and (ii) expression of the additional target gene is reduced as compared to that in absence of the compound.

In yet another aspect, provided herein is a method of regulating expression of a target gene in a cell comprising a first endogenous protein and a second endogenous protein, the method comprising: contacting the cell with an effective amount of a compound having a first moiety covalently linked to a second moiety, wherein: (a) the first moiety exhibits specific binding to the first endogenous protein that binds the target gene; (b) the second moiety exhibits specific binding to the second endogenous protein distinct from the first endogenous protein; and (c) upon contacting the cell, the first endogenous protein and the second endogenous protein are bound to the compound to form a complex to yield a gain-of-function in the cell, wherein the gain-of-function is characterized by modulating expression of the target gene in a manner dependent on presence of the second endogenous protein bound to the compound, and wherein the expression of the target gene is modulated in less than or equal to about 16 hours after the contacting.

In yet another aspect, provided herein is a compound of formula (I):

A-B (I), wherein:

(a) A is a first moiety exhibiting specific binding to a first endogenous protein in a cell that binds a target gene;

(b) B is a second moiety exhibiting specific binding to a second endogenous protein in the cell that is distinct from the first endogenous protein; and (c) the compound spatially complexes the first endogenous protein and the second endogenous protein to each other to yield a gain-of-function in the cell, wherein the gain-of-function is characterized by modulating expression of the target gene in a manner dependent on presence of the second endogenous protein bound to the compound, and wherein:

(i) the gain-of-function is achieved by utilizing less than about 50% of an amount of the second endogenous protein present in the cell;

(ii) the compound mediates the gain-of-function with an $EC_{50}$ of less than about 1 micromolar; and/or (iii) the first endogenous protein reduces the expression of the target gene in absence of the compound and the second endogenous protein enhances expression of an additional target gene in absence of the compound, wherein the gain-of-function is characterized in that (iii(a)) expression of the target gene is enhanced as compared to that in absence of the compound, and (iii(b)) expression of the additional target gene is reduced as compared to that in absence of the compound.

In Yet Another Aspect, Provided Herein is a Compound of Formula (I):

A-B (I), wherein:

(a) A is a first moiety exhibiting specific binding to a first endogenous protein in a cell that binds a target gene;

(b) B is a second moiety exhibiting specific binding to a second endogenous protein in the cell that is distinct from the first endogenous protein; and (c) the compound binds to the first endogenous protein and the second endogenous protein to form a complex, wherein the complex is capable of modulating the expression of the target gene in a manner dependent on presence of the second endogenous protein in the complex, and wherein the complex modulates expression of the target gene in less than or equal to about 16 hours.

BRIEF DESCRIPTION OF THE DRAWINGS

As illustrated in FIG. 12, a small molecule that binds the transcriptional activator, CDK9, is used to recruit CDK9 to the promoter of a gene that activates the expression of cell death genes. BCL6 as well as some of its homologues are normally repressors of cell death, but the TCIPs described herein in accordance with embodiments of the disclosure prevent this repressive effect and set the stage for activation by the CDK9 molecule.

BCL-6 is a transcription factor and oncogene that prevents death of a variety of cancer cells including prostate cancer cells by binding epigenetic repressors, BCOR, NCOR and SMRT (PMID 18280243, 15531890, 10898795). Chemical linkage of BCL-6 inhibitors, such as BI-3812 (PMID33208943) to ligands for AR that then bind and induce proximity to the cell death (proapoptotic) promoters, such as those for TP53, PUMA, BIM and others, convert the inhibitor of cell death to a powerful activator of cell death. Normally androgen will bind to the AR and induce proliferation. As illustrated in FIG. 19, a TCIP linking the AR to BCL6 which binds and coordinately activates killer genes results in robust and rapid death of prostate cancer cells. The illustrated approach provides therapy for prostatic cancer driven by the AR, which includes over 80% of human prostatic cancer.

DETAILED DESCRIPTION

Figure 1:
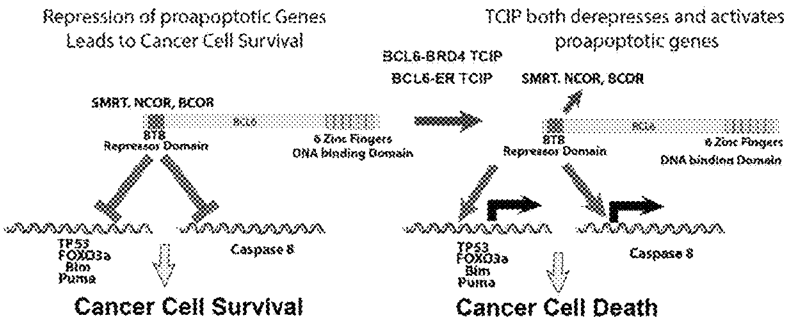
FIG. 1 illustrates a non-limiting example of the design of a compound of the disclosure (e.g., a CIP or a TCIP) to hijack BCL-6 to kill BRD4-positive DLBCL cells, SLCL cells or ER-positive DLBCL cells, in accordance with embodiments provided herein. BCL-6 is a transcription factor and oncogene that prevents death of a variety of cancer cells including SLCL cancer cells and DLBCL cancer cells by binding epigenetic repressors, BCOR, NCOR and SMRT (PMID 18280243, 15531890, 10898795). Chemical linkage of inhibitors of BCL6 (and/or homologues thereof), such as BI3812(PMID33208943) to ligands for BRD4 or estrogen compounds that then bind and induce proximity to the cell death (proapoptotic) promoters, such as those for TP53, PUMA, BIM and others, convert the inhibitor of cell death to a powerful activator of cell death, and illustrates the gain-of-function provided by the compounds of the disclosure (e.g., a TCIP).

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($—CH_2—$), ethylene ($—CH_2CH_2—$), the propylene isomers (e.g., $—CH_2CH_2CH_2—$ and $—CH(CH_3)CH_2—$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical $—C(O)R^{30}$, where $R^{31}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, propionyl, succinyl, and malonyl, and the like.

The term "aminoacyl" refers to the group $—C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical $—OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical $—C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnaphthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O-S—, —$NR^{37}R^{38}$—, .═N—N═, —N═N—, —N═N—$NR^{39}R^{40}$, —$PR^{41}$—, —$P(O)_2$—, —$POR^{42}$—, —O—$P(O)_2$—, —S—O—, —S—(O)—, —$SO_2$—, —$SnR^{43}R^{44}$— and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —O—, ═O, —$OR^{60}$, —$SR^{60}$, —S—, ═S, —$NR^{60}R^{61}$═$NR^{60}$, —$CF_3$, —CN, —OCN, —SCN, —NO, —$NO_2$, ═$N_2$, —$N_3$, —$S(O)_2O$—, —$S(O)_2OH$, —$S(O)_2R^{60}$, —$OS(O)_2O$—, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —N $R^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring.

In certain embodiments, substituents include -M, —$R^{60}$, =O, —$OR^{60}$, —$SR^{60}$, —S—, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —C(O)O—, —$NR^{62}C(O)NR^{60}R^{61}$. In certain embodiments, substituents include -M, -$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —C(O) $NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

Provided herein are compositions, systems, and methods for regulating expression of a target gene in a target cell. The compositions, systems, and methods can be used to regulate expression of a target gene in a target cell by bringing different endogenous proteins expressed by the target cell into spatial proximity such the target gene is regulatable by a protein that, in the absence of the compound, would not ordinarily be regulatable by said protein. The compositions, systems, and methods generally involve a compound that specifically binds to at least a first endogenous protein and a second, different endogenous protein, each expressed by the target cell. The first endogenous protein is generally a protein that can bind to a target gene, or to a region near a target gene, such as a promoter or regulatory region, and serves as an anchor for the complex. The second endogenous protein is a protein that, in the absence of the compound, does not substantially regulate expression of the target gene, but when recruited by the compound to the target gene or the region near the target gene, is capable of regulating expression of the target gene. Advantageously, the compositions, systems, and methods provided herein do not require any genetic modification to the target cell. Instead, the compositions, systems, and methods provided herein rely on the presence of proteins endogenously expressed in the target cell. In addition, the compound is generally a small molecule that can be administered to a subject (e.g., by oral administration, by intravenous administration, etc.).

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

The terms "about" or "approximately" generally mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The section headings used herein are for organizational purposes only and are not to be construed as limiting the subject matter described.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Systems, Compositions, and Methods Thereof for Regulating Expression of A Target Gene In one aspect, provided herein is a method of regulating expression of a target gene in a cell comprising a first endogenous protein and a second endogenous protein, the method comprising contacting the cell with a compound having a first moiety (e.g., covalently) linked to a second moiety, wherein (a) the first moiety exhibits specific binding to the first endogenous protein, wherein the first endogenous protein binds to the target gene, or a region near the target gene (e.g., a promoter, a regulatory region, etc.); (b) the second moiety exhibits specific binding to the second endogenous protein distinct from the first endogenous protein; and (c) upon contacting the cell, the first endogenous protein and the second endogenous protein are spatially complexed to each other via the compound to yield a gain-of-function in the cell, wherein the gain-of-function is characterized by modulating expression of the target gene in a manner dependent on the presence of the second endogenous protein bound to the compound. The method further provides that the gain-of-function is achieved by utilizing less than about 50% of an amount of the second endogenous protein present in the cell.

In another aspect, provided herein is a method of regulating expression of a target gene in a cell comprising a first endogenous protein and a second endogenous protein, the method comprising contacting the cell with a compound having a first moiety covalently linked to a second moiety, wherein (a) the first moiety exhibits specific binding to the first endogenous protein, wherein the first endogenous protein binds to the target gene, or to a region near the target gene (e.g., a promoter, a regulatory region, etc.); (b) the second moiety exhibits specific binding to the second endogenous protein distinct from the first endogenous protein; and (c) upon contacting the cell, the first endogenous protein and the second endogenous protein are spatially complexed to each other via the compound to yield a gain-of-function in the cell, wherein the gain-of-function is characterized by modulating expression of the target gene in a manner dependent on the presence of the second endogenous protein bound to the compound. The method further provides that the compound mediates the gain-of-function with an EC50 of less than about 1 micromolar.

In another aspect, provided herein is a method of regulating expression of a plurality of target genes in a cell comprising a first endogenous protein and a second endogenous protein, the method comprising contacting the cell with a compound having a first moiety covalently linked to a second moiety, wherein: (a) the first moiety exhibits specific binding to the first endogenous protein, wherein the first endogenous protein reduces expression of a target gene in the absence of the compound; (b) the second moiety exhibits specific binding to the second endogenous protein, wherein the second endogenous protein enhances expression of an additional target gene in the absence of the compound; and (c) upon contacting the cell, the first endogenous protein and the second endogenous protein are spatially paired to one another via the compound to yield a gain-of-function in the cell. The method further provides that the gain-of-function is characterized in that (i) expression of the target gene is enhanced as compared to that in the absence of the compound; and (ii) expression of the additional target gene is reduced as compared to that in the absence of the compound.

In another aspect, provided herein is a method of regulating expression of a target gene in a cell comprising a first endogenous protein and a second endogenous protein, the method comprising contacting the cell with an effective amount of a compound having a first moiety covalently linked to a second moiety, wherein (a) the first moiety exhibits specific binding to the first endogenous protein, wherein the first endogenous protein binds to the target gene, or to a region near the target gene (e.g., a promoter, a regulatory region); (b) the second moiety exhibits specific binding to the second endogenous protein distinct from the first endogenous protein; and (c) upon contacting the cell, the first endogenous protein and the second endogenous protein are bound to the compound to form a complex to yield a gain-of-function in the cell, wherein the gain-of-function is characterized by modulating expression of the target gene in a manner dependent on the presence of the second endogenous protein bound to the compound. The method further provides that the expression of the target gene is modulated in less than or equal to about 16 hours after the contacting.

Further provided herein are compositions and systems suitable for performing any of the aforementioned methods, as described further herein.

As summarized above, the present disclosure provides methods of regulating expression of a target gene in a cell, and systems and compositions to achieve the same. The methods may be viewed as inducible methods of regulating expression of a target gene. As the methods are inducible, the regulation of expression of the target gene is not constitutive, but instead occurs in response to an applied stimulus, e.g., the provision of a compound as described in greater detail below, in the cell. As the methods are methods of inducibly regulating expression of a target gene, they are methods of changing the expression or expression profile of a target gene in some manner, e.g., enhancing expression of a target gene or reducing expression of a target gene. The magnitude of change in expression (relative to a suitable control, e.g., an identical system but for the absence of the compound), may vary, where in some instances the magnitude of the change, e.g., enhancement or reduction, is 2-fold or greater, such as 5-fold or greater, e.g., 10-fold or greater. The target gene can be any gene, as described herein or known in the art. The target gene can be a wild-type gene or a mutated gene.

As summarized above, the present disclosure provides methods of regulating the expression of a target gene (including without limitation a BCL6 target gene). The term gene refers to a genomic region that encodes a functional RNA, including non-coding RNAs, microRNAs, enhancer RNAs or RNAs that may be translated into a protein product. The term gene is used in its conventional sense to refer to a region or domain of a chromosome that includes not only a coding sequence, e.g., in the form of exons separated by introns, but also regulatory sequences, e.g., enhancers/silencers, promoters, terminators, non-coding RNAs, micro RNAs etc.

The specific target gene that is the focus of a given method may vary. The target gene can be any gene of interest whose expression is to be modulated by the compositions, systems, and methods provided herein. In some instances, the target gene is a gene whose expression is to be enhanced. Non-limiting examples of genes whose expression is to be enhanced by the compositions, systems, and methods provided herein, include pro-apoptotic genes (e.g., PUMA (BBC3), BIM (BCL2L11), BID, BAX, BAK, BOK, BAD, HRK, BIK, BMF, and NOXA(PMAIP1). In some instances, the target gene is a gene whose expression is to be inhibited or reduced. Non-limiting examples of genes whose expression is to be inhibited or reduced by the compositions, systems, and methods provided herein include anti-apoptotic genes, such as BCL6, and genes that promote cell survival and proliferation, such as MYC. In some instances, the target gene is a therapeutic gene whose expression (e.g., increased or enhanced) can yield a beneficial effect in the cell or on a subject, such as, but not limited to, a rate-limiting enzyme (e.g., TPH2), a haploinsufficient gene (e.g., ARID1B), etc. In some instances, the target gene is a gene whose expression whose expression has a harmful effect on a cell or a subject, and/or causes disease or a disorder in a subject (e.g., a mutated gene), and whose expression is to be inhibited or reduced by the compositions, systems, and methods provided herein. In some instances, the target gene is an over-expressed gene whose expression is to be inhibited or reduced by the compositions, systems, and methods provided herein, such as, but not limited to, an oncogene (e.g., MYC), a trisomy gene (e.g., a chromosome 21 gene), an amplified gene, etc.

The above categories of genes are merely exemplary of the types of genes that may be target genes of the subject methods. Any gene whose expression is to be regulated (e.g., enhanced, reduced) by the compositions, systems, and methods provided herein can be a target gene. Additional examples of target genes include, but are not limited to: developmental genes (e.g., adhesion molecules, cyclin kinase inhibitors, cytokines/lymphokines and their receptors, determinants of tumor immunogenicity, growth/differentiation factors and their receptors, immune-checkpoint receptors and ligands, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextranases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5), the RNA component of telomerase, vascular endothelial growth factor (VEGF), VEGF receptor, tumor necrosis factors nuclear factor kappa B, transcription factors, cell adhesion molecules, Insulin-like growth factor, transforming growth factor beta family members, cell surface receptors, RNA binding proteins (e.g. small nucleolar RNAs, RNA transport factors), translation factors, telomerase reverse transcriptase); and the like.

As described above, in some instances, the target gene is a therapeutic gene (e.g., a gene that, when expressed, has a beneficial effect on a cell or a subject). Examples of therapeutic target genes suitable for regulation using the compositions, systems, and methods provided herein include, but are not limited to, those provided in Table 1 below.

TABLE 1

| Examples of therapeutic target genes | | | | |
|---|---|---|---|---|
| GAMT | FHDC1 | ANKHD1- | AOC2 | PHKB |
| B3GALNT2 | PNOC | EIF4EBP3 | TLE3 | SLC9A3R1 |
| HEXIM1 | ATG2A | TMOD3 | AOC3 | ERICD |
| CFAP70 | RPL23AP97 | FOS | PLXNC1 | MED29 |
| HPCAL1 | C19ORF25 | DHRS2 | USP6 | ADRA2A |
| C12ORF76 | ZNF497 | ASPRV1 | FBXWB | H4C15 |
| TMEM81 | CFD | GNMT | CD160 | H4C14 |
| GRIN3A | SNORD3B-2 | TUBB4B | ADAMTSL4- | DGKQ |
| CAPN14 | SNORD3B-1 | TUBB4A | AS1 | FSCN1 |
| MT-TA | HHLA3 | ADAT3 | FAM106A | STAG3L5P- |
| CCS | ITSN1 | MAP1A | ADAMTSL4- | PVRIG2P- |
| MTHFD2 | UXS1 | SPSB3 | AS2 | PILRB |
| ARMC5 | H2AC17 | CLIP1 | EMC1-AS1 | GLYR1 |
| HSPA1A | TEX29 | SLC7A5P1 | GOLM1 | LINC02447 |
| TNFSF9 | TMEM187 | NMNAT1 | VRK3 | ANKRD33B |
| TARS1 | ASB16-AS1 | FOSB | SLC9B1 | LINC01232 |
| LINC00641 | H2AC19 | NDUFA4L2 | PNRC1 | LINC02202 |
| ASF1B | CHTF1B | RPL23AP53 | SDCBP2 | CNP |
| TCL6 | RNF213 | LINC00868 | KIAA1614 | INSIG1 |
| PLCD3 | FCRLB | ZNF213 | SKI | H2BC19P |
| HSPA1B | RPSAP58 | LGR4 | PDCD4 | KRCC1 |
| EMC3-AS1 | H2AC11 | ZNF333 | SQSTM1 | CORO1C |
| CYFIP1 | PDGFD | BSCL2 | SLC25A34 | RNF213- |
| CNTF | NAPRT | FH | OSBP2 | AS1 |
| SERPINE3 | HMOX1 | CDKN1B | NATD1 | C1ORF50 |
| RETSAT | NKX3-1 | CDKN1A | CCNT1 | SNN |
| XYLT1 | IER2 | TCF25 | GPS2 | SESN2 |
| CRABP2 | LINC00894 | PRSS27 | LSMEM1 | PMEPA1 |
| NPIPB13 | IER5 | MAP2K4P1 | DLST | SESN3 |
| IER5L | JUNB | GUCA1B | FOXO3 | ZNF528 |
| SLC5A3 | IER3 | FSTL1 | PAPSS2 | ANKRD11 |
| TOB2 | GSDME | TMEM54 | SH3BP5-AS1 | LINC01588 |
| TOB1 | DUSP5 | EFCAB8 | KIAA0513 | SRGAP2 |
| NXF1 | FUCA1 | TUBA1A | BCL2L11 | RAB4A |
| CRACR2B | GPR18 | GLI4 | ZFP36 | FIRRE |
| MSANTD2 | WDR37 | SUMO2P17 | RBBP6 | TRIM66 |
| CYP2D6 | COLCA2 | LFNG | TUBB3 | ZK5CAN2 |
| FAM120C | JUN | TMSB4X | HAS1 | PDCD4-AS1 |

TABLE 1-continued

| Examples of therapeutic target genes | | | | |
|---|---|---|---|---|
| MSANTD1 | DUSP4 | C16ORF74 | FLNA | ZKSCAN1 |
| FAM120B | RARA-AS1 | ING4 | HAS3 | C1ORF162 |
| PIP4K2A | COLCA1 | H3C14 | ZNF789 | KCNJ14 |
| HOXA4 | PTCH2 | H3C15 | TSPOAP1 | ELAC1 |
| MVB12A | WDR31 | ADAMTSL4 | CLBA1 | ASMTL |
| HES1 | NIPA2 | LIMD1-AS1 | ZNF425 | OGA |
| PKNOX2 | CSNK1G2- | MIR22HG | C11ORF68 | NSUN5P1 |
| ST3GAL3 | AS1 | RPL13P5 | NDOR1 | BMX |
| LINC01963 | TMEM175 | ZSWIM6 | LINC00476 | BCL6 |
| RPL32P29 | SIRT3 | NUDT14 | LINC02413 | SP6 |
| JUND | FAM222A | STUM | SLC16A4 | BCL2 |
| LINC00672 | ADI1 | TMEM44-AS1 | NIFK-AS1 | ZNF878 |
| MIR663AHG | LINC00847 | MYLIP | LDLR | SLC26A4 |
| ABCA7 | PXMP2 | PTPN1 | C21ORF58 | NFE2L3 |
| CEL | BHLHE41 | RBM15 | CCDC17 | MIPEP |
| WDR53 | RAPGEF1 | HSPA6 | SLC15A2 | SLC25A4 |
| H1-2 | PCYOX1L | LIMK1 | FBXO39 | NUFIP2 |
| KLF15 | ZNF236-DT | RHBDD2 | LINC00273 | FAM149B1 |
| EIF1 | IL18BP | SETD1B | RBPMS | RPL21P40 |
| CCSAP | ZNF233 | H28C17 | RABL2A | ORC6 |
| EHD1 | ZNF596 | TICRR | CYB561A3 | LBH |
| ABTB2 | BTG2 | GVQW3 | TNFRSF10D | MDK |
| SLC6A8 | BTG1 | TGFBR1 | LRP4-AS1 | DNAJB1 |
| C12ORF49 | LRRC39 | COQ6 | CNR1 | HSPB1 |
| PARD6G-AS1 | LITAF | ARHGAP27P2 | TOGARAM2 | MF5D3 |
| GPRASP2 | SHB | GCNA | REELD1 | MKNK2 |
| DLGAP4 | WDR25 | TCTE1 | POLH. | CCDC180 |
| BRD2 | MED19 | IQCN | MAP6D1 | SCN3B |
| NANOS1 | PINK1-AS | ACTA2 | PAOX | CFAP43 |
| ANKRD30BL | CASP10 | MYH3 | UCN | RBM14 |
| SLC2A11 | TRIM4 | LPIN1 | IDI1 | PDLIM7 |
| CDKN2B | | EEF1D | C2ORF42 | TMED7- |
| ZNF580 | | H2BC11 | DIPK1B | TICAM2 |
| STAT2 | | H2BC12 | | |
| DGAT1 | | | | |
| DSE | PLEKHH1 | COG2 | PPCS | ATP1B2 |
| MROH6 | CNNM4 | VASN | GPAA1 | CLEC17A |
| RDH10 | ZNF720 | SCARNA9 | PSMC3IP | LINC00926 |
| PSMG3-AS1 | KLRA1P | ADCK1 | MAP1LC3B | CDK2AP2 |
| DNAJB4 | LINC02035 | ASTL | NEU1 | SCG5 |
| ZNF627 | RPS4XP16 | WNK4 | GSE1 | MPHOSPH8 |
| ACP4 | SLC12A6 | ADCK5 | CTSK | FAM92A |
| PHACTR1 | LRRN4 | PLPP4 | CPB2-AS1 | ALDH16A1 |
| AMH | RSAD2 | FBXL6 | LINC01004 | CAPS |
| TRIM45 | MEIG1 | SUGP1 | ASIC3 | CD86 |
| ERVMER34- | MTUS2 | JPT1 | WBP1LP2 | VWCE |
| 1 | ALOX12-AS1 | FAM89B | H3-3B | UBE3B |
| SMIM14 | MAPK8IP2 | ARL6IP1 | STK31 | HDLBP |
| FAM209A | SNORC | NUMA1 | SDCBP2-AS1 | NDRG1 |
| RALGAPA2 | P5MD6-AS2 | PITPNB | ZFR | TMEM242 |
| LRRC8A | NIN | CREBRF | PYY2 | ASB16 |
| VPS33B | IL23A | JMJD1C | IGIP | REM2 |
| ALMS1P1 | APLF | ZBED5-AS1 | RFTN2 | TMEM128 |
| HTR3B | SUB1 | RASSF2 | BOLA3-AS1 | CSKMT |
| CIRBP | PARS2 | CHTF8 | HCK | LINC00910 |
| BPGM | UBAP1L | RASSF3 | GAN | CMTR2 |
| KLF5 | ULK1 | ZNHIT2 | RTN4IP1 | MORC3 |
| KLF2 | ALDH8A1 | TSPAN7 | FOXD2-AS1 | OR2B6 |
| SLC25A18 | BCORL1 | FTH1 | PNPLA7 | CA14 |
| PPM1D | TECPR2 | FAM53C | PNPLA2 | BORCS6 |
| PFKL | CALM1 | ARLGIP4 | RANP4 | REPS2 |
| MYO1A | MINCR | SOX9 | H2AX | OPN3 |
| DNAJA4 | LINC01176 | APOE | AHCY | GBAP1 |
| DOP1B | SLC23A3 | RNA5-8SN2 | TNFRSF13B | PCDHB19P |
| QTRT1 | HNRNPCP7 | PPP1R10 | CTNNB1 | TCAF1 |
| TXNIP | NUDT4P2 | RNA5-8SN1 | MIR663B | LRRIQ3 |
| DTL | RBM26-AS1 | RNA5-8SN3 | PTMS | SGMS1-AS1 |
| NPIPB2 | MS6ST1 | ARGLU1 | CRIP1 | PSPN |
| KCTD13 | MRNIP | RALGPS2 | MIR663A | ARHGEF18 |
| CD226 | CASP16P | PPM1K-DT | NUDT4 | H2AC6 |
| LCT | CCDC102B | CTSB | NPW | ESR2 |
| NECTIN4 | PARD6G | TMEM150A | ENC1 | ACSF2 |
| NPIPB7 | AKAP3 | IZUMO4 | CXCR4 | NR4A3 |
| CCDC62 | TONSL | LINC01145 | SERTAD1 | TBCK |
| HDAC5 | NNAT | FFAR1 | CHRNA10 | ADGRF1 |
| EIF4A3 | NHLH1 | LINC00293 | SPTAN1 | MXD1 |
| ALAS1 | INTS6-AS1 | ZNNT1 | CORIN | AMACR |

TABLE 1-continued

| Examples of therapeutic target genes | | | | |
|---|---|---|---|---|
| SMIM29 | SHOC2 | CLDN11 | GDF11 | C16ORF46 |
| DNHD1 | LINC02137 | LAT2 | CCDC157 | RSRP1 |
| ZBTB43 | TSSK5P | TG | CPSF6 | ACBD4 |
| LENG8 | H4C9 | P4HA1 | TGFB1 | LY86-AS1 |
| PPM1K | H4C8 | ALDH6A1 | PUS3 | GCM1 |
| STIM2-AS1 | LINC01089 | KCNS1 | H2BC8 | MXD4 |
| PIK3C2B | MIR3648-1 | PTPRB | HNRNPA1P59 | MIDN |
| HHEX | EGR3 | ID3 | G6PD | CCDC121 |
| POLR2A | MIR3648-2 | CCNG2 | H2BC6 | SYS1 |
| EFR3A | SURF1 | RTCA-AS1 | H2BC7 | KLHL15 |
| KCTD21 | ARRDC1 | RAPSN | UNC5CL | ARHGAP17 |
| HAUS8 | PAQR6 | PABPC1 | H2BC4 | LTBP2 |
| WDR6 | ST6GAL1 | TAX1BP3 | H2BC5 | DAPP1 |
| ZNF846 | HSD17B1P1 | ALDOC | DNAJB13 | NR4A1 |
| MIF-AS1 | GADD45B | ARHGEF9 | ARID3A | NME1- |
| TRIM28 | ARRDC3 | RANBP10 | ARID3B | NME2 |
| SPDL1 | CRY2 | ZCCHC14 | PDPK1 | RGS2 |
| TNFAIP8 | MASP2 | CSRNP2 | DCXR | UBB |
| SMG1P2 | TRIB3 | FASTKD1 | DSTNP2 | FAM174B |
| PMEL | CCDC168 | FAM43A | KCTD5 | NMRK1 |
| SMG1P3 | HMGCL | FMNL1 | FMNL2 | CDH23 |
| OSER1-DT | CD27-AS1 | ALDH1A3 | TRAPPC6A | USP32P2 |
| ZNF192P1 | ALDH2 | INAFM1 | GALE | ABCC5 |
| SMG1P6 | H2BC21 | PITHD1 | PPDPF | |
| TRPS1 | | ABHD17A | | |
| SMG1P7 | | | | |
| ALOX12 | | | | |
| CHD2 | | | | |

In some instances, the target gene is a non-coding gene. Non-coding genes of interest include, but are not limited to, those provided in Table 2.

TABLE 2

| Non-limiting examples of non-coding genes. | | | |
|---|---|---|---|
| MIR663AHG | LINC00847 | LINC00641 | Snhg16 |
| MIR663A | LINC01089 | LINC02035 | Snhg3 |
| MIR663B | LINC01963 | LINC02447 | Snhg4 |
| MIR3648-1 | LINC02413 | LINC00672 | Snhg5 |
| MIR3648-2 | LINC01588 | LINC01232 | Snhg6 |
| MIR22HG | LINC01176 | LINC01004 | Snhg8 |
| LINC00273 | LINC00894 | SNORD3B-2 | |
| LINC02202 | LINC01145 | SNORD3B-1 | |
| LINC00868 | LINC00926 | Mir22hg | |
| LINC00476 | LINC00910 | Snhg1 | |
| LINC02137 | LINC00293 | Snhg12 | |

Genes that may be targeted by one or more compounds as provided herein (e.g., a chemical inducer of proximity (CIP), a transcriptional chemical inducer of proximity (TCIP), etc.)) are also provided in PCT application serial no. PCT/US2021/058231, published as WO 2022/098989; the disclosure of which is herein incorporated by reference in its entirety.

In some cases, a target gene that can be regulated by the systems, compositions, and methods provided herein can be a chromosomal gene or an epichromosomal gene. In some cases, the target gene can be an endogenous gene. Alternatively, or additionally, the target gene can be a heterologous gene, such as, for example, a gene present on a plasmid or a vector that is introduced (e.g., transfected via a transfection agent, transduced virally, etc.) to the cell. Prior to being regulated by the systems, compositions, and methods provided herein, such heterologous gene may or may not have been integrated into the genome of the cell.

As described herein, the compositions, systems, and methods provided herein involve the use of compounds that have at least a first moiety and a second moiety, where the first moiety specifically binds to a first endogenous protein expressed in a target cell, and the second moiety specifically binds to a second endogenous protein expressed in the target cell. A moiety of the compound may be referred to as a ligand throughout the present disclosure, and the terms “moiety” and “ligand” (or “moieties” and “ligands”) may be used interchangeably herein. The first endogenous protein and the second endogenous proteins are each originated from and are expressed in the cell. In particular, the first endogenous protein and the second endogenous protein are both present or expressed in the cell at the time in which a compound (e.g., including CIP or TCIP) disclosed herein is administered. The compositions, systems, and methods provided herein, generally do not require concurrent exogenous introduction (such as transfecting, transducing, and the like) of the first and/or the second endogenous protein into the cell to which a subject compound is administered in order to achieve the gain of function. The compositions, systems, and methods provide specificity such that the gain of function is only achieved in a specific target cell where both the first endogenous protein and the second endogenous protein are expressed. In some embodiments, the compounds of the disclosure comprise at least a first moiety and a second moiety that bind to at least a first endogenous protein and a second endogenous protein, thereby forming a ternary complex between the compound, the first endogenous protein, and the second endogenous protein. The first endogenous protein and the second endogenous protein are associated in spatial proximity to one another.

The ternary complex (e.g., between the compound, the first endogenous protein, and the second endogenous protein) is a non-naturally occurring complex that would otherwise not exist in the cell in the absence of the compound and both the first and second endogenous proteins. Accordingly, such a compound may be referred to herein as a “chemical inducer of proximity” or a “CIP”. In some cases, such as when the compound binds to an endogenous anchor transcription factor and an endogenous transcription modulating factor, the compound may be referred to herein as a "transcriptional chemical inducer of proximity", a "transcription chemical inducer of proximity", or a "TCIP". The first and second moieties of the compound can be derived from naturally occurring and/or synthetic substances. Applicable and readily observable or measurable criteria for selecting the moieties can include, but are not limited to: (A) the moiety is physiologically acceptable (e.g., lacks undue toxicity towards the cell or animal for which it is to be used); (B) the moiety has a reasonable therapeutic dosage range (e.g., as ascertained by yielding a desired expression profile of a target gene, or a desired cellular activity in the cell); (C) the moiety can cross the cellular and other membranes, as necessary; and/or (D) the moiety binds to one or more target domains of the first and/or second endogenous protein, such as an endogenous anchor transcription factor and/or an endogenous transcription modulating factor as provided herein). For example, a desirable criterion is that the compound is chemically stable and capable to form the complex. In some instances, a moiety (e.g., the first and/or second moiety) of the compound can be non-peptide and non-nucleic acid. Alternatively or additionally, at least a portion of the first and/or second moiety of the compound can be a peptide and/or a nucleic acid.

A composition comprising at least the compound (e.g., a pharmaceutical composition) can be administered to a subject, e.g., to treat a condition or a disease of the subject. A mode of the administration can be, for example, intraarticular, oral, parenteral, intravenous, intramuscular, rectal, cutaneous, subcutaneous, topical, transdermal, sublingual, nasal, vaginal, intravesicular, intraurethral, intrathecal, epidural, aural, and/or ocular administration. For example, the composition can be taken orally (e.g., compounds that are stable in the gastrointestinal system and can be absorbed into the vascular system).

The compounds can be small molecules. The compounds can be non-toxic. By small molecule is meant a molecule having a molecular weight of 5000 g/mole (Dalton) or less, such as 2500 g/mole (Dalton) or less, including 1000 g/mole (Dalton) or less, e.g., 500 g/mole (Dalton) or less. In some instances, the CIP employed in embodiments of the disclosure has a molecular weight ranging from 250 to 1500 g/mole, such as 300 to 1200 g/mole.

The compound can comprise a plurality of moieties (such as a first and second moiety) to bind to a plurality of endogenous proteins, respectively. Within a single compound, the first and second moieties can be coupled or linked to one another via a linker (e.g., a linker having at least one atom). The linker can be present to provide a distance (e.g., a desired distance) between the two moieties. Alternatively, the two moieties can be directly coupled to one another in absence of a linker (e.g., the two moieties can be coupled to one another via a direct chemical bond between two atoms of the two moieties). For example, the compound can comprise two moieties with a chemical bond directly between the two moieties, such that the two moieties of the compound form two sides (or two surfaces) of the compound that each bind to its respective protein.

The compound can comprise a plurality of moieties, each moiety binding to a different endogenous protein. For example, the compound can comprise at least or up to about 2 moieties, at least or up to about 3 moieties, at least or up to about 4 moieties, at least or up to about 5 moieties, at least or up to about 6 moieties, at least or up to about 7 moieties, at least or up to about 8 moieties, at least or up to about 9 moieties, or at least or up to about 10 moieties. The compound can bind to and form a complex with at least or up to 2 endogenous proteins, at least or up to 3 endogenous proteins, at least or up to 4 endogenous proteins, at least or up to 5 endogenous proteins, at least or up to 6 endogenous proteins, at least or up to 7 endogenous proteins, at least or up to 8 endogenous proteins, at least or up to 9 endogenous proteins, or at least or up to 10 endogenous proteins. In some cases, at least one of the endogenous proteins can be a wild-type protein or a mutated protein comprising one or more amino acid mutations (e.g., one or more point mutations, one or more amino acid insertions, one or more amino acid deletions, one or more amino acid translocations, and the like) to cause the mutated protein to exhibit a function or activity that is different from the wild-type protein. For example, the mutated protein can be a disease-causing protein, such as a mutated protein whose activity promotes survival, proliferation, and/or spread of a diseased cell (e.g., a cancer cell). In some cases, the protein can be expressed from a wild-type gene or from a mutated gene or a mutated protein arising from a fusion transcript (e.g., due to chromosomal rearrangement, transcriptional errors in splicing, inversions, interchromosomal or intrachromosomal translocation, chromothripsis, etc.).

In some cases, the first endogenous protein is a protein that binds to a target gene, or to a region near a target gene, such as a promoter or a regulatory region. The first endogenous protein may bind to the target gene, or a region near the target gene, in the absence of the compound. In some cases, the binding of the first endogenous protein to the target gene (or region near the target gene) may be direct binding. In other cases, the binding of the first endogenous protein to the target gene (or region near the target gene) may be indirect binding, such as by binding to one or more co-factors, which co-factor(s) binds directly to the target gene. The first endogenous protein may bind to a moiety of the compound and form a ternary complex with the compound and the second endogenous protein. In such scenarios, the first endogenous protein (in the ternary complex) may bind to the target gene, or a region near the target gene, and bring the second endogenous protein into close proximity to the target gene, or the region near the target gene. In some embodiment, the first endogenous protein may act as an "anchor protein" because the first endogenous protein anchors the ternary complex to the target gene, and, specifically when the first endogenous protein is a transcription factor, it may act as an "anchor transcription factor". In some cases, the first endogenous protein may regulate expression of the target gene in the absence of the compound. For example, the first endogenous protein may enhance expression of the target gene or may reduce or inhibit expression of the target gene, in the absence of the compound. In other examples, the first endogenous protein may not have any effect on expression of the target gene (e.g., the first endogenous protein may bind to the target gene (or region near the target gene) but not have any effect on expression of the target gene. The first endogenous protein can be any protein that can bind (e.g., directly or indirectly) to the target gene, or a region near the target gene, regardless of whether or not the first endogenous protein has any effect on expression of the target gene. In some instances, the first endogenous protein can be a transcriptional modulator, such as a transcription factor, a transcriptional activator, a transcriptional repressor, and/or an epigenetic modulator and/or a signaling intermediate such as but not limited to a kinase or phosphatase.

The first endogenous protein can bind (e.g., directly or indirectly) to a coding sequence (or a portion of the coding sequence) of the target gene. Alternatively or additionally, the first endogenous protein can bind (e.g., directly or indirectly) to a non-coding sequence of the target gene, such as a regulatory region of the coding sequence, such as an enhancer sequence, a promoter sequence, a CCAAT box, a TATA box, and the like. Alternatively or additionally, the first endogenous protein can bind (e.g., directly or indirectly) to a sequence near the coding sequence of the target gene. For example, the first endogenous protein can bind to a sequence at least or up to about 1 nucleobase, at least or up to about 2 nucleobases, at least or up to about 5 nucleobases, at least or up to about 10 nucleobases, at least or up to about 15 nucleobases, at least or up to about 20 nucleobases, at least or up to about 30 nucleobases, at least or up to about 40 nucleobases, at least or up to about 50 nucleobases, at least or up to about 100 nucleobases, at least or up to about 200 nucleobases, at least or up to about 300 nucleobases, at least or up to about 400 nucleobases, at least or up to about 500 nucleobases, at least or up to about 1,000 nucleobases, at least or up to about 2,000 nucleobases, at least or up to about 3,000 nucleobases, at least or up to about 4,000 nucleobases, at least or up to about 5,000 nucleobases, at least or up to about 6,000 nucleobases, at least or up to about 7,000 nucleobases, at least or up to about 8,000 nucleobases, at least or up to about 9,000 nucleobases, at least or up to about 10,000 nucleobases, at least or up to about 11,000 nucleobases, at least or up to about 12,000 nucleobases, at least or up to about 13,000 nucleobases, at least or up to about 14,000 nucleobases, at least or up to about 15,000 nucleobases, or at least or up to about 20,000 nucleobases from the coding sequence of the target gene.

In some cases, the second endogenous protein is a protein that, in the absence of the compound or formation of a ternary complex with the compound, substantially lacks any effect on expression of the target gene, but in the presence of the compound (e.g., when it forms a ternary complex with the compound and the first endogenous protein) is recruited to the target gene and is capable of regulating expression of the target gene. In some cases, the second endogenous protein is a transcriptional modulator, such as a transcription factor, a transcriptional activator, a transcriptional repressor, and/or an epigenetic modulator and/or a signaling intermediate such as but not limited to a kinase or phosphatase, as described herein. In some cases, the second endogenous protein can be a co-factor of the transcriptional modulator, such as a component of a mediator complex that assists the transcriptional modulator. An epigenetic modulator can be a protein or a domain that results in the epigenetic modification of DNA, for example chromosomal DNA. Epigenetic modifications can include, but are not limited to, DNA methylation and demethylation; histone modifications including methylation and demethylation (e.g., mono-, di-, tri-methylation), histone acetylation and deacetylation, as well as histone ubiquitylation, phosphorylation, and sumoylation.

In some cases, the compound can comprise a first moiety (e.g., covalently) linked to a second moiety, wherein: (i) the first moiety exhibits specific binding to a first endogenous protein that binds the target gene or a region near the target gene (e.g., a promoter, a regulatory region, etc.); and (ii) the second moiety exhibits specific binding to a second endogenous protein distinct from the first endogenous protein.

In some cases, the second endogenous protein, in the absence of the compound or absence of formation of the ternary complex, can regulate expression or activity levels of an additional target gene that is different from the target gene of the first endogenous protein. Administering the compound (e.g., CIP or TCIP) to a cell can recruit the second endogenous protein to form a ternary complex comprising the compound, the first endogenous protein, and the second endogenous protein, which ternary complex can bind to the target gene of the first endogenous protein and modulate expression and/or activity levels of the target gene, as abovementioned. The administration of the compound may also modulate expression of the additional target gene. For example, recruitment of the second endogenous protein away from the additional target gene (of the second endogenous protein) and to the ternary complex may reduce the presence (e.g., amount, concentration, probability) of the second endogenous protein at or adjacent to the additional target gene, thereby disrupting the modulating effect of the second endogenous protein on the expression or activity levels of the additional target gene. In this example, the second endogenous protein may be recruited away from the additional target gene to the target gene, and may modulate expression of the target gene. Yet in another example, the complex may also form at or adjacent to the additional target gene to recruit the first endogenous protein to the additional target gene, and the first endogenous protein can modulate the expression or activity levels of the additional target gene (e.g., partially or entirely reverse the effect of the second endogenous protein on the additional target gene prior to formation of the complex). For instance, the second endogenous protein may, in the absence of the compound, reduce (e.g., inhibit) expression or activity levels of the additional target gene, and in the presence of the compound (and formation of the complex), the expression or activity levels of the additional target gene may increase (e.g., because the second endogenous protein has been recruited away from the additional target gene); simultaneously, expression of the target gene may now be regulatable by the second endogenous protein that is part of the complex. Alternatively, treatment with the compound (e.g., CIP) and the resulting formation of the complex may not, or need not, effect modulation of the expression or activity levels of the additional target gene of the second endogenous protein.

In some cases, the second endogenous protein may not be configured to regulate expression or activity level of any target gene in absence of the compound.

Further provided herein are compounds suitable for use in performing the methods provided herein.

In various aspects, a compound is provided of formula (I) or (II):

A-linker-B (I); or

A-B (II)

wherein:

(a) A is a first moiety exhibiting specific binding to a first endogenous protein in a cell, wherein the first endogenous protein binds to a target gene or a region near a target gene (e.g., a promoter, a regulatory region);

(b) B is a second moiety exhibiting specific binding to a second endogenous protein in the cell that is distinct from the first endogenous protein; and (c) the compound spatially complexes the first endogenous protein and the second endogenous protein to each other to yield a gain-of-function in the cell, wherein the gain-of-function is characterized by modulating expression of the target gene in a manner dependent on the presence of the second endogenous protein bound to the compound. In some cases, the gain-of-function is achieved by utilizing less than about 50% of an amount of the second endogenous protein present in the cell. In some cases, the compound mediates the gain-of-function with an EC50 of less than about 1 micromolar. In some cases, the first endogenous protein reduces the expression of the target gene in the absence of the compound and the second endogenous protein enhances expression of an additional target gene in the absence of the compound, wherein the gain-of-function is characterized in that (iii(a)) expression of the target gene is enhanced as compared to that in the absence of the compound, and (iii(b)) expression of the additional target gene is reduced as compared to that in the absence of the compound. In some cases, expression of the target gene is regulated in less than or equal to about 16 hours.

In some cases, the linker is any linker as described herein. In some cases, the linker is absent such that moiety A and moiety B are directly linked to each other (e.g., a compound of Formula (II).

The terms "specific binding," "specifically bind," and the like, refer to the ability of the first and second ligands or moieties to preferentially bind directly to their corresponding first and second endogenous proteins relative to other molecules or moieties in the cell. In certain embodiments, the affinity between a given ligand or moiety and its corresponding endogenous protein when they are specifically bound to each other in a binding complex is characterized by a KD (dissociation constant) of $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, or $10^{-15}$ M or less (it is noted that these values can apply to other specific binding pair interactions mentioned elsewhere in this description, in certain embodiments). First moieties, second moieties, and linkers that may be employed in embodiments of the disclosure are described in greater detail below. When provided in a cell, e.g., by contacting the cell with a compound (e.g., a CIP), the first endogenous protein and the second endogenous protein are spatially paired (e.g., spatially complexed) to one another via the compound to yield a gain-of-function in the cell, e.g., as described in greater detail below.

The compound as provided herein (e.g., a chemical inducer of proximity or "CIP") can bind to a plurality of different proteins (e.g., a plurality of different endogenous proteins) to spatially complex the plurality of different proteins (or form a complex with the plurality of different proteins), thereby yielding a gain-of-function in the cell that would otherwise not exist in the absence of the compound. The term "gain-of-function" as used herein refers to a function that is achieved in the presence of the compound, which may result in the formation of a ternary complex formed between a first endogenous protein, a second endogenous protein, and a compound (e.g., a CIP) of the disclosure, said gain of function would not otherwise have been achieved in the absence of the compound. The gain-of-function is not achieved when either of the first or the second endogenous protein is not expressed in the cell, where the ternary complex cannot be formed. A non-limiting example of a gain-of-function, as used herein, is the use of the compounds provided herein to recruit the second endogenous protein to a target gene such that the second endogenous protein is capable of modulating expression of the target gene in the presence of the compound, a function the second endogenous protein would not have in the absence of the compound. In some embodiments, the second endogenous protein has substantially no effect on the expression or activity levels of the target gene. In some other embodiments, the second endogenous protein modulates the target genes in a manner opposite to that effectuated by the compound disclosed herein. In some other embodiments, the second endogenous protein may be an endogenous cancer driver that is recruited to a target pro-apoptotic gene by a ternary complex formed between the endogenous cancer driver, a first endogenous protein that binds to the target pro-apoptotic gene, and the compound, such that expression of the pro-apoptotic gene is enhanced. The number of different proteins bound by the compound to form the ternary complex can be at least or up to about 2 different proteins, at least or up to about 3 different proteins, at least or up to about 4 different proteins, at least or up to about 5 different proteins, at least or up to about 6 different proteins, at least or up to about different 7 proteins, at least or up to about 8 different proteins, at least or up to about 9 different proteins, at least or up to about 10 different proteins, at least or up to about 15 different proteins, or at least or up to about 20 different proteins. The plurality of different proteins can be different proteins exhibiting different activities (e.g., innate or natural activities) in the cell, such as, but not limited to, binding to and regulating different genes in the cell.

Conventional drug development involves the identification of a target and then the construction of ways to inhibit, degrade, remove the RNA or gene encoding the target. This conventional means of drug development then requires that the target be largely removed. In contrast the gain of function approach described herein uses only a fraction of the target to provide a new therapeutic function to the cell. Advantageously, the gain-of-function described herein does not require recruitment of all of the second endogenous protein present in the cell. In some instances, only a small fraction of the second endogenous protein present in the cell need be recruited to the target gene to achieve the gain-of-function. Not wishing to be bound by any particular theory, the usage of a small amount of second endogenous protein renders the subject composition more efficacious with larger therapeutic window as compared to other conventional therapeutics that require large bioavailability or exposure to be effective. In some instances, the gain-of-function may be achieved (e.g., regulation of the target gene by the second endogenous protein in the presence of the compound, which otherwise would not be regulatable by the second endogenous protein in the absence of the compound) by recruiting to the target gene, or by utilizing, less than or equal to about 50%, less than or equal to about 45%, less than or equal to about 40%, less than or equal to about 35%, less than or equal to about 30%, less than or equal to about 25%, less than or equal to about 20%, less than or equal to about 15%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of an amount of the second endogenous protein present in the cell.

In some cases, the gain-of-function may be achieved (e.g., regulation of the target gene by the second endogenous protein in the presence of the compound, which otherwise would not be regulatable by the second endogenous protein in the absence of the compound) by recruiting to the target gene, or by utilizing less than or equal to about 50% of the amount of the second endogenous protein present in the cell. In some cases, the gain-of-function may be achieved by recruiting to the target gene, or by utilizing less than or equal to about 10% of the amount of the second endogenous protein present in the cell. In some instances, the gain-of-function may be achieved by recruiting to the target gene, or by utilizing, about 1% to about 30%, about 1% to about 20%, about 1% to about 15%, or about 1% to about 10%, of the amount of the second endogenous protein present in the cell. In some cases, the gain-of-function may be achieved by recruiting to the target gene, or by utilizing, about 2% to about 20% of the amount of the second endogenous protein present in the cell. In some cases, the gain-of-function may be achieved by recruiting to the target gene, or by utilizing, about 2% to about 10% of the amount of the second endogenous protein present in the cell.

In some instances, the gain-of-function may be achieved by utilizing at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, substantially about 100%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 2% to about 50%, about 2% to about 45%, about 2% to about 40%, about 2% to about 35%, about 2% to about 30%, about 2% to about 25%, about 2% to about 20%, about 2% to about 15%, or about 2% to about 10% of the first endogenous protein and/or the second endogenous protein present in the cell.

The amount of the first endogenous protein and/or second endogenous protein required to yield the gain-of-function as provided herein can be ascertained by various methods, such as, for example, chromatin immunoprecipitation (ChIP) sequencing that can identify (i) the amount of the first endogenous protein that is spatially associated with (e.g., bound to) a target gene of the second protein and/or (ii) the amount of the second protein that is spatially associated with (e.g., bound to) a target gene of the first protein. Such information can be utilized along with a total of the first endogenous protein and/or the second endogenous protein to determine a proportion (e.g., percentage) of the first endogenous protein and/or the second endogenous protein required to yield the gain-of-function.

The compound as provided herein (e.g., a chemical inducer of proximity or "CIP") can bind to a plurality of different proteins (e.g., a plurality of different endogenous proteins) to spatially complex the plurality of different proteins (or form a complex with the plurality of different proteins), to yield a gain-of-function in the cell. The gain-of-function can be characterized by eliciting or promoting a characteristic in the cell (which otherwise would not be achieved in the absence of the compound). Non-limiting examples of such characteristics in the cell can include death of the cell (e.g., inducing death of the cell within at most about 5 days, at most about 4 days, at most about 3 days, at most about 2 days, at most about 1 day, at most about 18 hours, at most about 12 hours, at most about 8 hours, etc., after contacting the cell with the compound, as compared to that in absence of the compound), survival of the cell (e.g., enhancing survival of the cell by at least about 12 hours, at least about 18 hours, at least about 1 day, at least about 2 days, at least about 7 days, at least about 2 weeks, at least about 4 weeks, etc., after contacting the cell with the compound, as compared to that in absence of the compound), proliferation of the cell (e.g., enhancing proliferation of the cell by at least about 1%, at least about 5%, at least about 10%, at least about 20%, at least about 50%, at least about 100%, at least about 200%, at least about 400%, etc., as compared to that in absence of the compound), enhanced expression or activity level of a target gene (e.g., by at least about 1%, at least about 5%, at least about 10%, at least about 20%, at least about 50%, at least about 100%, at least about 200%, at least about 400%, etc., as compared to that in absence of the compound), reduced expression or activity level of a target gene (e.g., by at least about 1%, at least about 5%, at least about 10%, at least about 20%, at least about 30%, at least about 40%, at least about 50%, at least about 60%, at least about 70%, at least about 80%, at least about 90%, or substantially about 100%, as compared to that in absence of the compound).

In some cases, the compound can mediate the gain-of-function with an EC50 (e.g., for eliciting the characteristic in the cell) of less than or equal to about 10 micromolar, less than or equal to about 5 micromolar, less than or equal to about 2 micromolar, less than or equal to about 1 micromolar, less than or equal to about 900 nanomolar, less than or equal to about 800 nanomolar, less than or equal to about 700 nanomolar, less than or equal to about 600 nanomolar, less than or equal to about 500 nanomolar, less than or equal to about 400 nanomolar, less than or equal to about 300 nanomolar, less than or equal to about 200 nanomolar, less than or equal to about 100 nanomolar, less than or equal to about 90 nanomolar, less than or equal to about 80 nanomolar, less than or equal to about 70 nanomolar, less than or equal to about 60 nanomolar, less than or equal to about 50 nanomolar, less than or equal to about 40 nanomolar, less than or equal to about 30 nanomolar, less than or equal to about 20 nanomolar, less than or equal to about 10 nanomolar, less than or equal to about 9 nanomolar, less than or equal to about 8 nanomolar, less than or equal to about 7 nanomolar, less than or equal to about 6 nanomolar, less than or equal to about 5 nanomolar, less than or equal to about 4 nanomolar, less than or equal to about 3 nanomolar, less than or equal to about 2 nanomolar, less than or equal to about 1 nanomolar, less than or equal to about 0.9 nanomolar, less than or equal to about 0.8 nanomolar, less than or equal to about 0.7 nanomolar, less than or equal to about 0.6 nanomolar, less than or equal to about 0.5 nanomolar, less than or equal to about 0.4 nanomolar, less than or equal to about 0.3 nanomolar, less than or equal to about 0.2 nanomolar, or less than or equal to about 0.1 nanomolar. In an example, the compound can mediate the gain-of-function with an EC50 of less than or equal to about 1 micromolar. In another example, the compound can mediate the gain-of-function with an EC50 of less than or equal to about 500 nanomolar. In another example, the compound can mediate the gain-of-function with an EC50 of less than or equal to about 200 nanomolar. In another example, the compound can mediate the gain-of-function with an EC50 of less than or equal to about 100 nanomolar. In another example, the compound can mediate the gain-of-function with an EC50 of less than or equal to about 50 nanomolar. In another example, the compound can mediate the gain-of-function with an EC50 of less than or equal to about 20 nanomolar. The term "EC50", as used herein in the context of an in vitro or in vivo assay, generally refers to the concentration of a test moiety (e.g., a compound as described herein, such as a small molecule) that induces a response (e.g., a desired response or a target response) that is about 50% of the maximal response (i.e., halfway between the maximal response and a baseline in absence of the test moiety).

In some cases, the gain-of-function may be characterized by inhibiting the characteristic of the cell as provided herein. Accordingly, the compound can mediate the gain-of-function with an IC50 (e.g., for inhibiting the characteristic of the cell) of less than or equal to about 10 micromolar, less than or equal to about 5 micromolar, less than or equal to about 2 micromolar, less than or equal to about 1 micromolar, less than or equal to about 900 nanomolar, less than or equal to about 800 nanomolar, less than or equal to about 700 nanomolar, less than or equal to about 600 nanomolar, less than or equal to about 500 nanomolar, less than or equal to about 400 nanomolar, less than or equal to about 300 nanomolar, less than or equal to about 200 nanomolar, less than or equal to about 100 nanomolar, less than or equal to about 90 nanomolar, less than or equal to about 80 nanomolar, less than or equal to about 70 nanomolar, less than or equal to about 60 nanomolar, less than or equal to about 50 nanomolar, less than or equal to about 40 nanomolar, less than or equal to about 30 nanomolar, less than or equal to about 20 nanomolar, less than or equal to about 10 nanomolar, less than or equal to about 9 nanomolar, less than or equal to about 8 nanomolar, less than or equal to about 7 nanomolar, less than or equal to about 6 nanomolar, less than or equal to about 5 nanomolar, less than or equal to about 4 nanomolar, less than or equal to about 3 nanomolar, less than or equal to about 2 nanomolar, less than or equal to about 1 nanomolar, less than or equal to about 0.9 nanomolar, less than or equal to about 0.8 nanomolar, less than or equal to about 0.7 nanomolar, less than or equal to about 0.6 nanomolar, less than or equal to about 0.5 nanomolar, less than or equal to about 0.4 nanomolar, less than or equal to about 0.3 nanomolar, less than or equal to about 0.2 nanomolar, or less than or equal to about 0.1 nanomolar. The term "IC50", as used herein in the context of an in vitro or in vivo assay, generally refers to the concentration of a test moiety (e.g., a compound as described herein, such as a small molecule) that reduces a response (e.g., a desired response or a target response) to about 50% of the maximal response in absence of the test moiety.

The compound as provided herein (e.g., a chemical inducer of proximity or "CIP") can bind to a plurality of different proteins (e.g., a plurality of different endogenous proteins) to spatially complex the plurality of different proteins (or form a complex with the plurality of different proteins), to yield a gain-of-function in the cell. The gain-of-function can be characterized by modulated (e.g., enhanced or reduced) expression or activity level of a target gene by the second endogenous protein which, in the absence of the compound, does not substantially affect expression or activity levels of the target gene). In some cases, the gain-of-function can be characterized in that the expression or activity level of the target gene is enhanced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 150%, at least or up to about 200%, at least or up to about 300%, at least or up to about 400%, at least or up to about 500%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 110-fold, at least or up to about 120-fold, at least or up to about 130-fold, at least or up to about 140-fold, at least or up to about 150-fold, at least or up to about 200-fold, or at least or up to about 500-fold, as compared to that in the absence of the compound. In some cases, the gain-of-function can be characterized in that the expression or activity level of the target gene is reduced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, or at least or up to about 100-fold, as compared to that in absence of the compound.

In some cases, the compound can comprise a plurality of different moieties exhibiting specific binding to a plurality of different endogenous proteins. The plurality of different endogenous proteins can comprise (i) a first endogenous protein that effects reduced (or enhanced) expression of a first target gene and (ii) a second endogenous protein that effects enhanced (or reduced) expression of a second target gene. In such scenarios, the gain-of-function achieved by the compound can be characterized by changing (e.g., reversing or inducing an opposite effect on) the expression profiles of the first target gene and/or the second target gene.

In some cases, the gain-of-function can be characterized in that (1) the expression of the first target gene is enhanced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 150%, at least or up to about 200%, at least or up to about 300%, at least or up to about 400%, at least or up to about 500%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 110-fold, at least or up to about 120-fold, at least or up to about 130-fold, at least or up to about 140-fold, at least or up to about 150-fold, at least or up to about 200-fold, or at least or up to about 500-fold, and/or (2) the expression of the second target gene is reduced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 95%, substantially about 100%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, or at least or up to about 100-fold.

Vice versa, the gain-of-function can be characterized in that (1) the expression of the first target gene is reduced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 150%, at least or up to about 200%, at least or up to about 300%, at least or up to about 400%, at least or up to about 500%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 110-fold, at least or up to about 120-fold, at least or up to about 130-fold, at least or up to about 140-fold, at least or up to about 150-fold, at least or up to about 200-fold, or at least or up to about 500-fold, and/or (2) the expression of the second target gene is enhanced by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 95%, substantially about 100%, at least or up to about 0.1-fold, at least or up to about 0.5-fold, at least or up to about 1-fold, at least or up to about 2-fold, at least or up to about 3-fold, at least or up to about 4-fold, at least or up to about 5-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, or at least or up to about 100-fold.

In some cases, the gain-of-function achieved by the compositions, systems, and methods provided herein can be characterized by modulated (e.g., enhanced or reduced) expression or activity levels of a target gene (e.g., by the second endogenous protein in the presence of the compound, where the second endogenous protein has substantially no effect on expression or activity levels of the target gene in the absence of the compound). In some other cases, the second endogenous protein modulates the target genes in a manner opposite to that effectuated by the compound disclosed herein. In some cases, the expression or activity levels of a target gene may be modulated (e.g., enhanced or reduced) in less than or equal to about 16 hours, in less than or equal to about 15 hours, in less than or equal to about 14 hours, in less than or equal to about 13 hours, in less than or equal to about 12 hours, in less than or equal to about 11 hours, in less than or equal to about 10 hours, in less than or equal to about 9 hours, in less than or equal to about 8 hours, in less than or equal to about 7 hours, in less than or equal to about 6 hours, in less than or equal to about 5 hours, in less than or equal to about 4 hours, in less than or equal to about 3 hours, in less than or equal to about 2 hours, or in less than or equal to about 1 hour, after contacting the cell with the compound, as compared to that in the absence of the compound. In an example, the expression or activity levels of a target gene may be modulated (e.g., enhanced or reduced) in less than or equal to about 16 hours after contacting the cell with the compound, as compared to that in the absence of the compound. In another example, the expression or activity levels of a target gene may be modulated (e.g., enhanced or reduced) in less than or equal to about 8 hours after contacting the cell with the compound, as compared to that in the absence of the compound.

Any modulation of expression level of a target gene as provided herein can be induced or observed (e.g., via experimentation) in less than or equal to about 48 hours, less than or equal to about 42 hours, less than or equal to about 36 hours, less than or equal to about 30 hours, less than or equal to about 24 hours, less than or equal to about 18 hours, less than or equal to about 12 hours, less than or equal to about 10 hours, less than or equal to about 9 hours, less than or equal to about 8 hours, less than or equal to about 7 hours, less than or equal to about 6 hours, less than or equal to about 5 hours, less than or equal to about 4 hours, less than or equal to about 3 hours, less than or equal to about 2 hours, less than or equal to about 1 hour, less than or equal to about 45 minutes, less than or equal to about 30 minutes, less than or equal to about 20 minutes, less than or equal to about 15 minutes, or less than or equal to about 10 minutes.

The first endogenous protein, the second endogenous protein, or both, may effect or exhibit an activity in the cell, in the absence of the compound and/or in the presence of the compound. Non-limiting examples of such activity can include one or more members from transcriptional activation activity, transcriptional repression activity, methyltransferase activity, demethylase activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and/or demyristoylation activity. The first endogenous protein, the second endogenous protein, or both, may exhibit such activity in the absence of the compound (e.g., a chemical inducer of proximity or "CIP"). Alternatively or additionally, the first endogenous protein, the second endogenous protein, or both, can effect or exhibit such activity in the presence of the compound. When bound to the compound, the first endogenous protein, the second endogenous protein, or both, can exhibit at least or up to about 1%, at least or up to about 2%, at least or up to about 5%, at least or up to about 10%, at least or up to about 15%, at least or up to about 20%, at least or up to about 25%, at least or up to about 30%, at least or up to about 40%, at least or up to about 50%, at least or up to about 60%, at least or up to about 70%, at least or up to about 80%, at least or up to about 90%, at least or up to about 95%, or substantially about 100% of the activity of the first endogenous protein, the second endogenous protein, or both, in the absence of the compound.

The first endogenous protein, the second endogenous protein, or both (e.g., that form the ternary complex with the compound) may be any protein of interest having any desired activity. Non-limiting examples of the first endogenous protein and/or the second endogenous protein may include a secretory protein, a non-secretory protein, a chaperone protein, a transposase, an integrase, a recombinase, a resolvase, an invertase, a protease, a helicase, a methyltransferase, a demethylase, an acetylase, a deacetylase, a phosphatase, a kinase, a nuclease, a transcription repressor, a transcription activator, a transcription co-activator, a transcription-protein recruiting protein, a cellular uptake activity associated protein, a nucleic acid binding protein, a nucleic acid structuring protein, a signal peptide or protein, a nuclear protein, a cytoplastic or cytosolic protein, a membrane protein (e.g., transmembrane protein or intracellular membrane protein), a non-membrane protein, any fragment thereof, any variants thereof, and any combinations thereof. In some cases, the first endogenous protein, the second endogenous protein, or both, can be a transcription factor, such as a transcription repressor, a transcription activator, and/or a transcription co-activator. In some cases, the first endogenous protein, the second endogenous protein, or both, can be an epigenetic modulator exhibiting enzymatic activity that results in the epigenetic modification of a target gene (e.g., DNA, such as chromosomal DNA). Epigenetic modifications can include, but are not limited to, DNA methylation and demethylation, histone modifications including methylation and demethylation (e.g., mono-, di- and tri-methylation), histone acetylation and deacetylation, histone ubiquitylation, histone phosphorylation, and histone sumoylation. In some cases, a protein as used herein may refer to the protein in its entirety or a portion (e.g., a fragmented portion) of the protein, or a functional domain of the protein. In some cases, the protein (e.g., the first and/or second endogenous protein) is a non-viral protein (e.g., a mammalian protein). Alternatively, the protein (e.g., the first and/or second endogenous protein) can be a viral protein (e.g., derived from a viral genome).

In some cases, the protein (e.g., first endogenous protein and/or second endogenous protein) that is bound by the compound is not a protease and/or does not affect degradation of an additional protein. For example, a first endogenous protein and a second endogenous protein can be bound by a compound to form a ternary complex, and (i) the first endogenous protein in the ternary complex does not directly or indirectly induce degradation of the second endogenous protein and/or (ii) the second endogenous protein in the ternary complex does not directly or indirectly induce degradation of the first endogenous protein. Alternatively, the first endogenous protein that is bound in the ternary complex may be a protease and/or may effect degradation of the second endogenous protein in the same complex.

In some cases, the protein (e.g., first and/or second endogenous protein) that is bound to the compound as provided herein may be a functional protein, e.g., exhibiting its innate or natural function (e.g., binding, associating with, and/or regulating expression of a target gene) prior to complexing with the compound. Thus, at least a portion of such activity may be reduced (e.g., by at least or up to about 1%, at least or up to about 2%, at least or up to about 5%, at least or up to about 10%, at least or up to about 15%, at least or up to about 20%, at least or up to about 25%, at least or up to about 30%, at least or up to about 40%, at least or up to about 50%, at least or up to about 60%, at least or up to about 70%, at least or up to about 80%, at least or up to about 90%, at least or up to about 95%, or substantially about 100%) upon complexing with the compound.

In some cases, the first endogenous protein as provided herein can be, e.g., an anchor transcription factor, and the second endogenous protein as provided herein can be, e.g., a transcription modulating factor. In such scenarios, the compound may be referred to as a "TCIP".

In certain non-limiting embodiments, the first endogenous protein includes a BTB domain. The terms "BTB domain," "BR-C, ttk and bab domain," "POZ domain," and "Pox virus and Zinc finger domain," are used interchangeably herein, and generally refer to a domain (e.g., a structural domain) of a protein that mediates multimerization of proteins (e.g., homomeric dimerization, heteromeric dimerization, etc.). Specific examples of such proteins are provided in greater detail below (e.g., see example proteins comprising a BTB domain in Table 3).

In certain non-limiting embodiments, the second endogenous protein may vary. Examples of second endogenous proteins include, but are not limited to: BET proteins, e.g., BRD2, BRD3, BRD4, BRD5, BRD7, BRD9, and BRDT; intracellular receptors, hormone receptors, e.g., estrogen receptors, androgen receptors, kinases, phosphatases; etc.

First and Second Moieties (A and B)

The nature of the first and second moieties (also referred to herein as first and second ligands), as well as the linker components (when used), of the CIP compounds may vary. In any given CIP compound, the first and second ligands are chosen based on the nature of the corresponding first endogenous protein and second endogenous protein, to which the moieties bind. Certain non-limiting examples of corresponding anchor (e.g., first endogenous protein) and transcription modulating factors (e.g., second endogenous protein, and their corresponding ligands are provided below. Specificity of activity with respect to a particular cell type may be provided through selection of the first and second ligands of the CIP, which can be configured to recruit the first endogenous protein and the second endogenous protein in a manner that provides for desired cell or conditional specificity. For example, CIPs can be engineered to induce proximity of a first endogenous protein and a second endogenous protein that are primarily present in a target cell of interest, such that the CIP exhibits highly selective activity for that cell. The selectivity of a given CIP may be described by the following formula:

(selectively of expression of the first endogenous protein)×(selectively of expression of the second endogenous protein)×(genomic specificity of the first endogenous protein)=selectivity of induced activity Examples of first and second moieties (e.g., A and B in the compound formula provided herein, also referred to herein as first and second ligands) that may be employed in various CIPs are reviewed in greater detail below. Suitable first and second moieties, as well as methods of identifying the same, that may be employed in CIPs of embodiments of the disclosure are also provided in PCT application serial no. PCT/US2021/058231, published as WO 2022/098989; the disclosure of which is herein incorporated by reference.

Linkers

As described above, the present disclosure provides compounds (e.g., CIPs) having two ligands, e.g., a BCL-6 (B-cell lymphoma 6) ligand and a second ligand (e.g., BRD4 (bromodomain-containing 4) ligand, an ER ligand, an AR ligand, a CDK ligand, etc., that are covalently bonded through a linker. When employed, any convenient linker may be employed to link the first and second ligands to each other. Linkers of interest are linkers that provide for a stable association of the first and second ligands in a manner such that the first and second ligands are capable of specifically binding to their respective endogenous factors in the cell. As the linker provides for stably associating the first and second ligands with each other, the first and second ligands do not dissociate from each other under cellular conditions, e.g., conditions at the surface of a cell, conditions inside of a cell, etc. Linkers may be provided for stable association of the first and second ligands using any convenient binding, such as covalent or non-covalent binding, where in some instances the linker component is covalently bound to both the first and second ligands. Linking protocols of interest include, but are not limited to, addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the linkers employ reactive linking chemistry such as where reactive linker pairs (e.g., as provided by moieties on the ligands and linkers) include, but are not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide. In certain embodiments, a linker employs a cycloaddition reaction, such as a [1+2]-cycloaddition, a [2+2]-cycloaddition, a [3+2]-cycloaddition, a [2+4]-cycloaddition, a [4+6]-cycloaddition, or cheletropic reactions, including linkers that undergo a 1,3-dipolar cycloaddition (e.g., azide-alkyne Huisgen cycloaddition), a Diels-Alder reaction, an inverse electron demand Diels Alder cycloaddition, an ene reaction or a [2+2] photochemical cycloaddition reaction. In some embodiments, the linker may include an alkyl chain, an alkoxy chain, an alkenyl chain or an alkynyl chain, where the number of carbon atoms in the chain may vary, ranging in some instances from 2 to 25, such as 5 to 20, where one or more carbon atoms are replaced with NH or CH3—N as reactive functionalities for covalent bonding.

In some instances, the linker is selected from a group having the following, where n refers to the total number of carbon or carbon-substituent atoms which may be present, sub-counted by k, m, and/or p:

In some instances, the linker is selected from a group comprising the following, where n refers to the total number of carbon or carbon-substituent atoms which may be present, sub-counted by k, m, and/or p:

a) A Cn alkyl chain, L, including the case where one or more carbon atoms are replaced with NH or $CH_3$—N b) A Cn alkoxy chain, L, including the case where one or more carbon atoms are replaced with NH or $CH_3$—N c) A Cn alkenyl or alkenyloxy chain, L, including the case where one or more carbon atoms are replaced with NH or $CH_3$—N d) A Cn alkynyl or alkynyloxy chain, L, including the case where one or more carbon atoms are replaced with NH or $CH_3$—N e) $L^1$-Ar-$L^2$ or $L^1$-Het-$L^2$, where L1 and $L^2$ can be a bond, alkenyl, alkynyl, alkynyloxy, alkenyloxy, alkoxy, or alkyl chain, e.g., of 1-10 atoms, that are either carbon or optionally substituted nitrogens, such as $CH_2N(H)CH_2$, $CH_2OCH_2$, $C_5H_{10}OCH_2$, and others; Ar is a 6 membered optionally substituted aryl; and Het is a 4 to 6 membered heterocycloalkyl or a 9 to 10 membered spirocyclic bicyclic heterocycloalkyl or a 3 to 6 membered optionally substituted heteroaryl.

In some embodiments, the linker includes a C(1-16) alkyl chain. In some instances, the linker includes a C(1-16) alkyl chain, wherein one or more of the methylene groups is replaced by NH or $CH_3$—N. In some instances, the linker includes a C(1-16) alkoxy chain. In some instances, the linker includes a C(1-16) alkoxy chain, wherein one or more of the methylene groups is replaced by NH or $CH_3$—N. In certain instances, the linker includes a $L^1$-Cyclo-$L^2$, $L^1$-HeteroCyclo-$L^2$, $L^1$-Ar-$L^2$ or $L^1$-Het-$L^2$, where $L^1$ and $L^2$ can be a bond, alkenyl, alkynyl, alkynyloxy, alkenyloxy, alkoxy, or alkyl chain, where:

cyclo is a C(3-8) cycloalkyl or substituted C(3-8) cycloalkyl;

heterocyclo is a C(3-8) heterocycloalkyl or substituted C(3-8) heterocycloalkyl;

Ar is an aryl group or substituted aryl group; and

Het is a heteroaryl group or substituted heteroaryl group.

In certain embodiments, the linker is selected from:

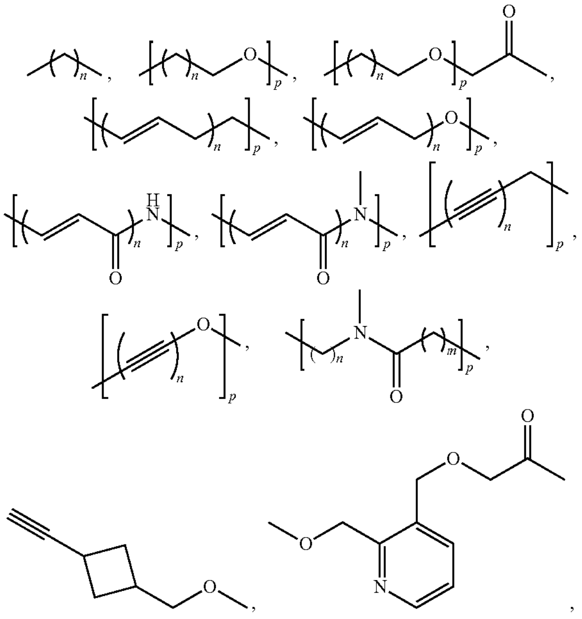

-continued

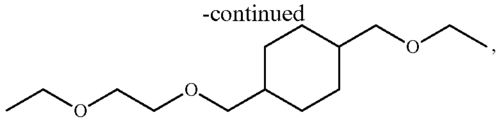

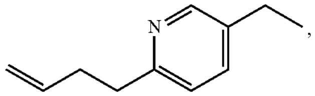

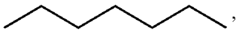

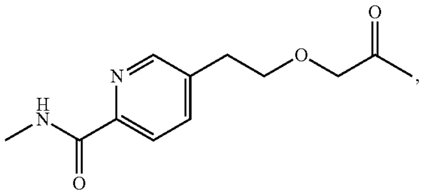

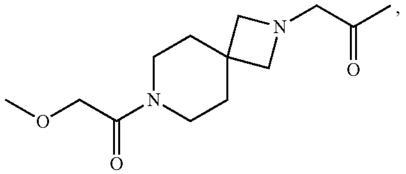

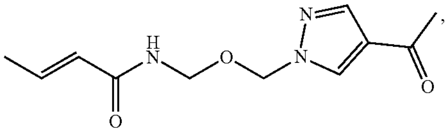

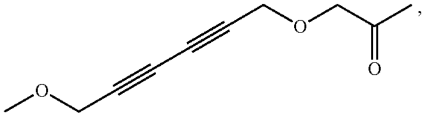

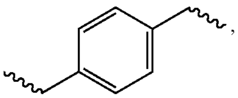

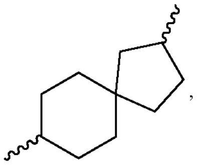

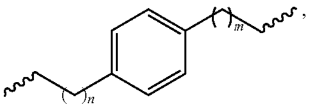

-continued

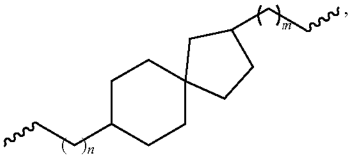

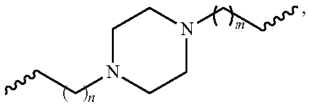

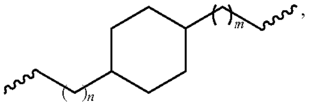

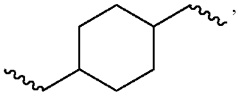

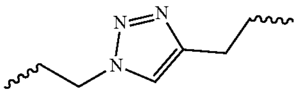

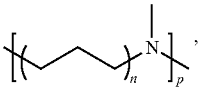

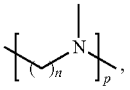

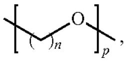

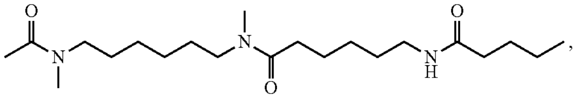

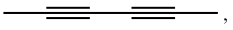

where m, n and p are independently selected from 0 or an integer of from 1-12.

Suitable linkers that may be employed in embodiments of the present disclosure are further described in International Patent Publication Nos. WO2020219650 and WO2017185023, as well as U.S. Pat. No. 10,532,103 and United States Patent Application Publication No. 20190111143; the disclosures of which are herein incorporated by reference.

In some embodiments, linkers of interest include those such as described in International Patent Publication No. WO2020/264499, the disclosure of which is herein incorporated by reference. For example, the linker may be selected from:

(1)

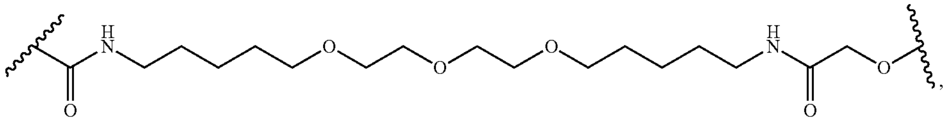

(2)

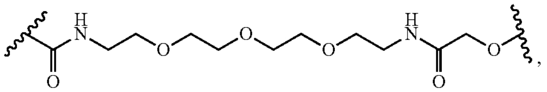

(3)

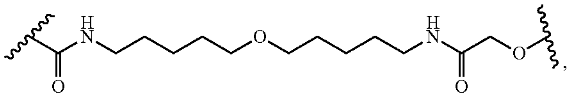

(4)

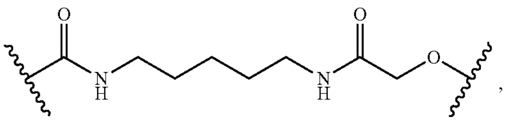

-continued
(5)
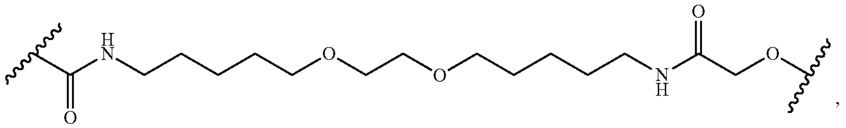
(6)
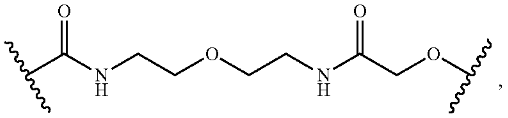
(7)
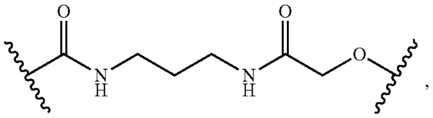
(8)
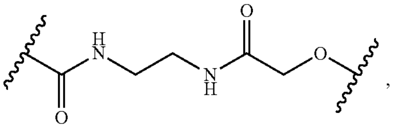
(9)
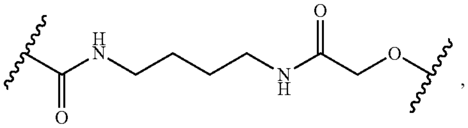
(10)
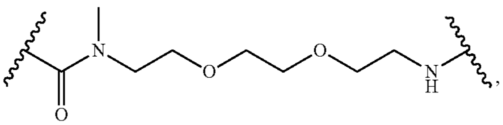
(11)
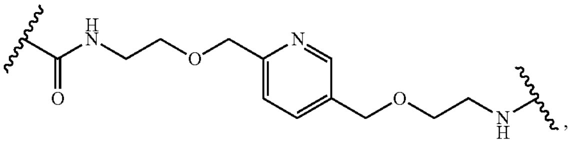
(12)
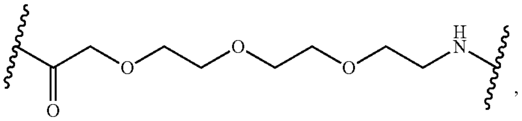
(13)
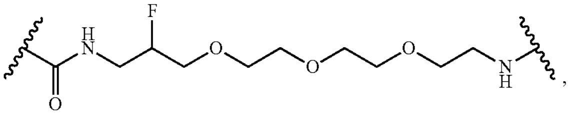
(14)
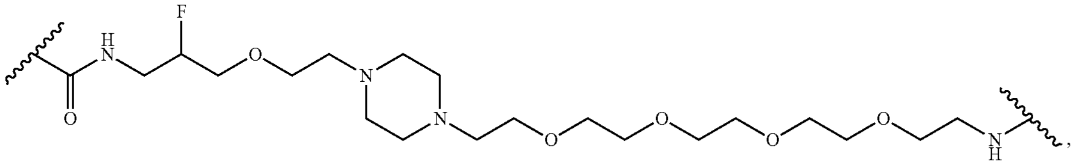
(15)
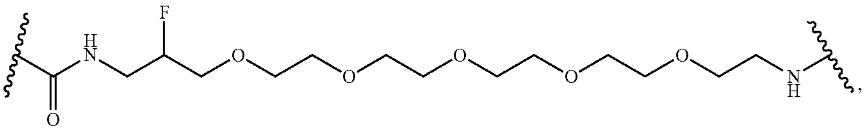
(16)
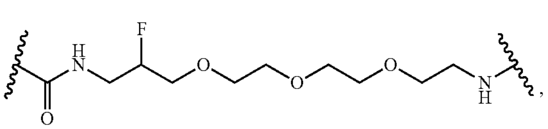
(17)
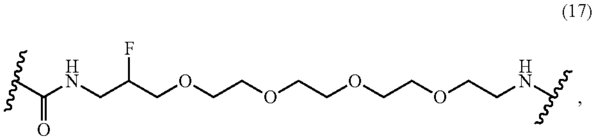
(18)
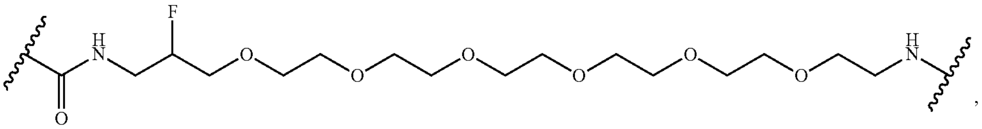
(19)
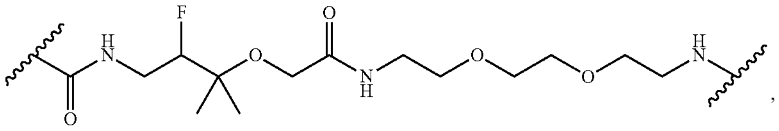

-continued
(20)
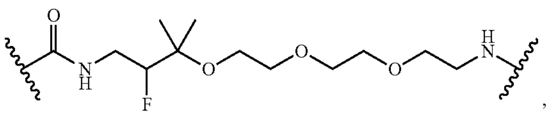
(21)
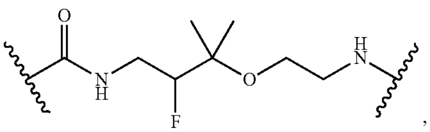
(22)
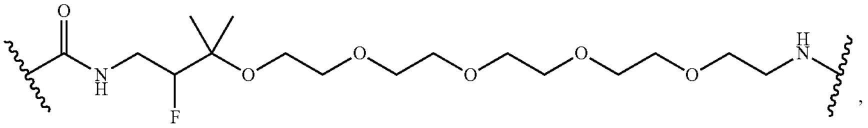
(23)
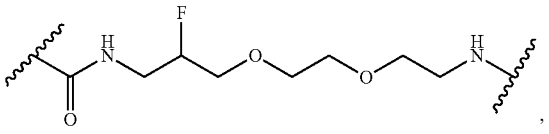
(24)
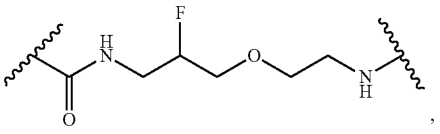
(25)
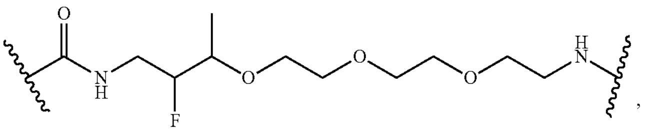
(26)
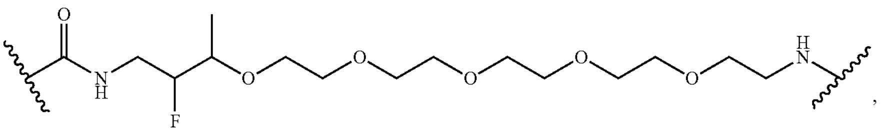
(27)
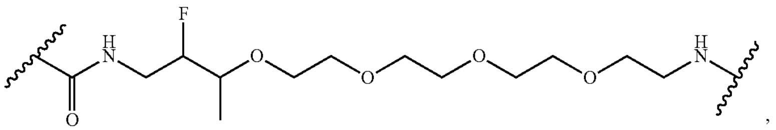
(28)
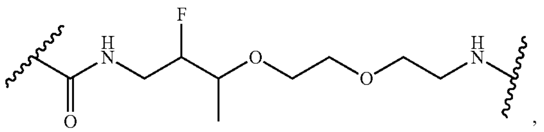
(29)
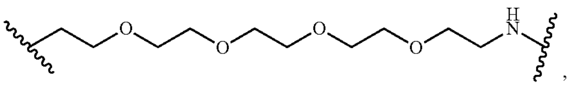
(30)
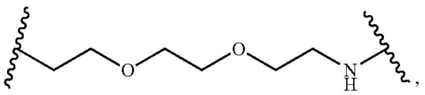
(31)
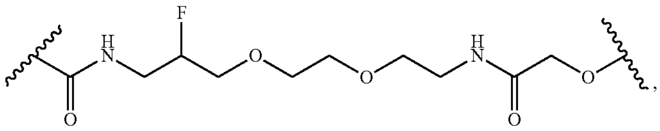
(32)
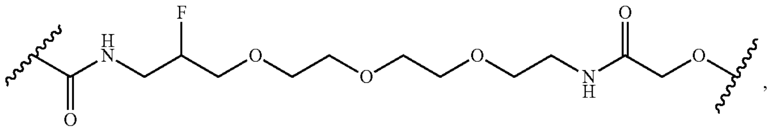
(33)
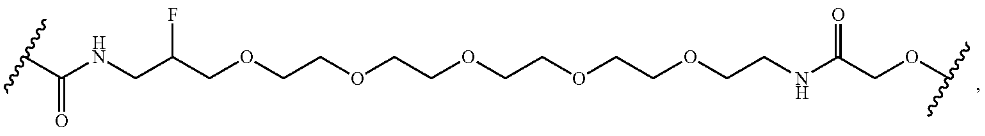

-continued
(34)
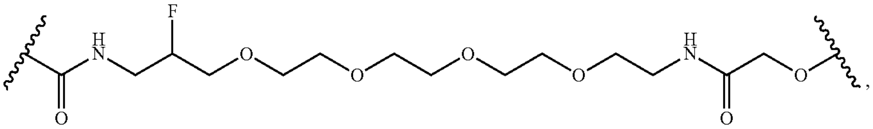,
(35)
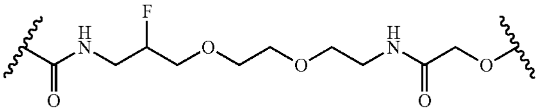,
(36)
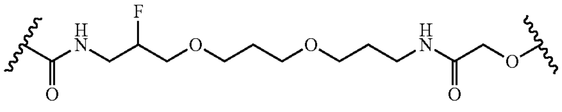,
(37)
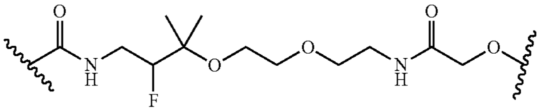,
(38)
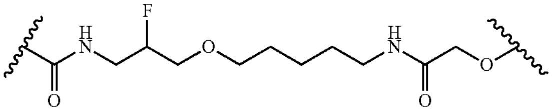,
(39)
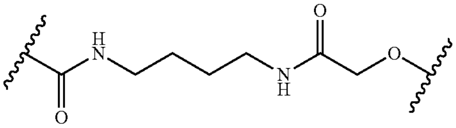,
(40)
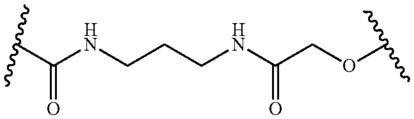,
(41)
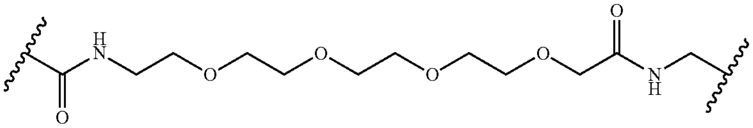
(42)
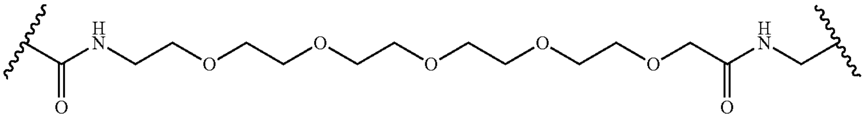,
(43)
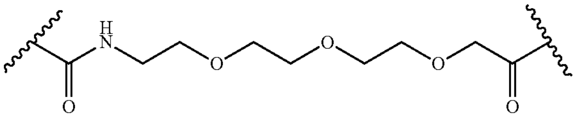,
(44)
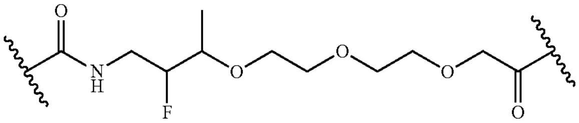,
(45)
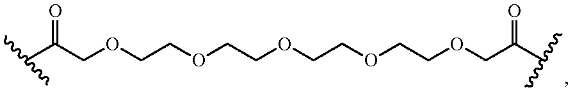,
(46)
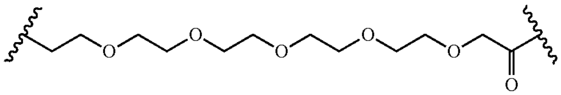,
(47)
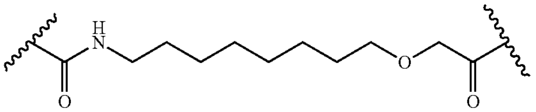,
(49)
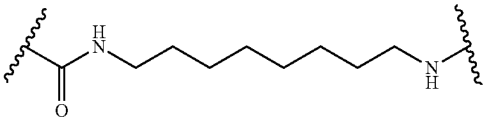,
(50)
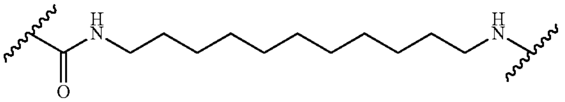,
(51)
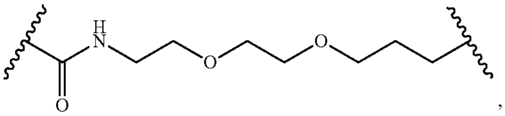,
(52)
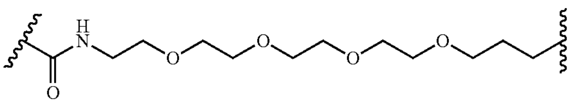,
(53)
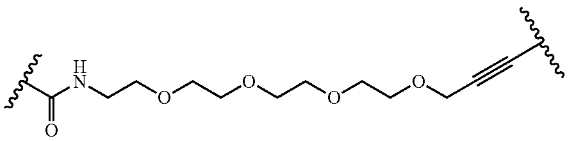, -continued
(54)
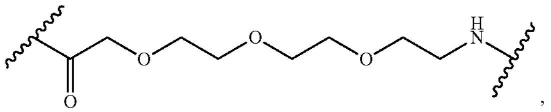
(55)
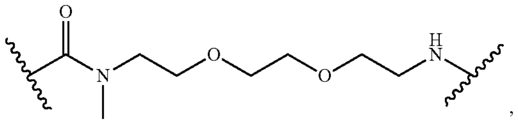
(56)
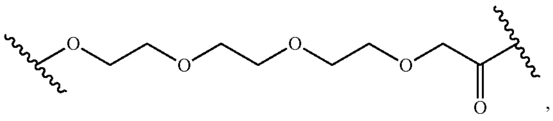
(57)
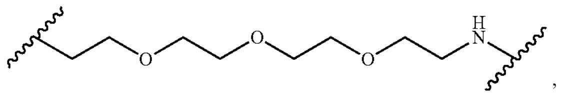
(58)
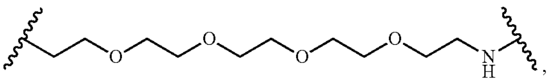
(59)
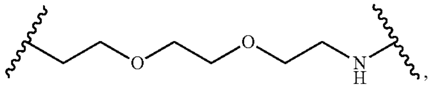
(60)
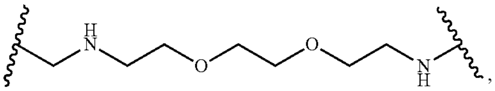
(61)
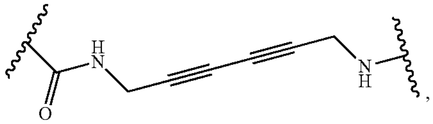
(62)
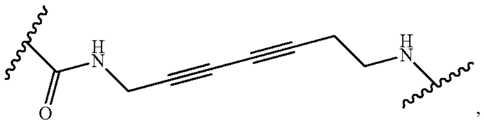
(63)
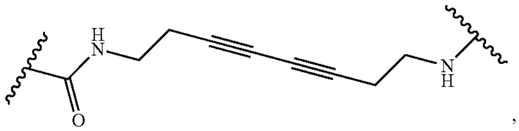
(64)
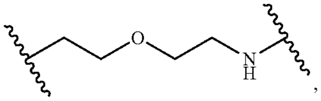
(65)
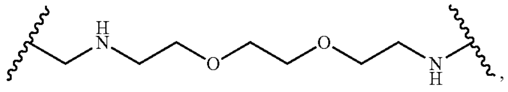
(66)
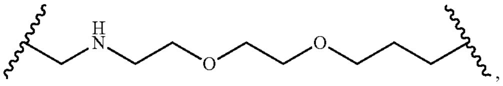
(67)
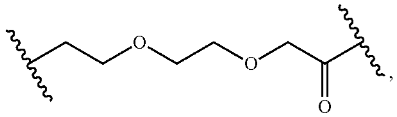
(68)
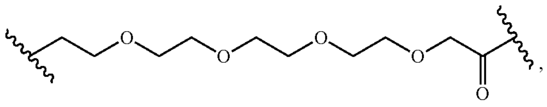
(69)
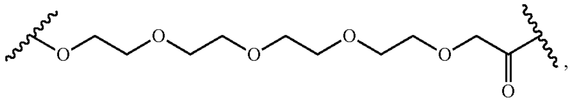
(70)
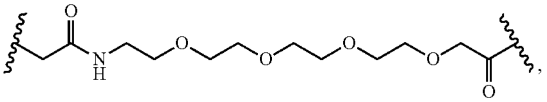
(71)
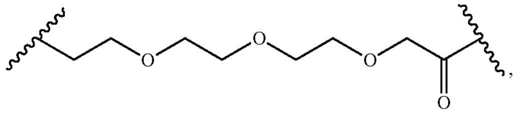
(72)
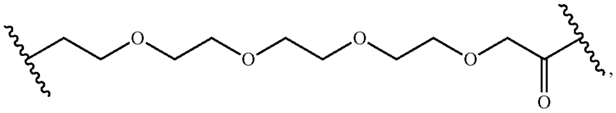
(73)
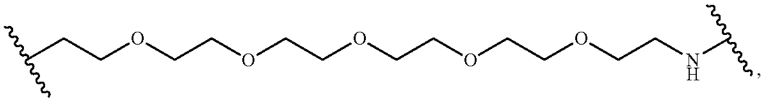
(74)
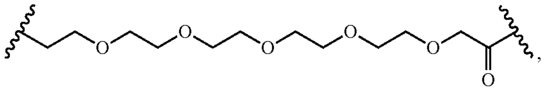
(75)
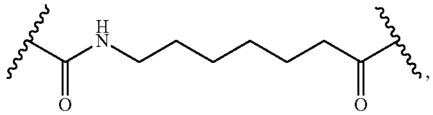

-continued
(76)
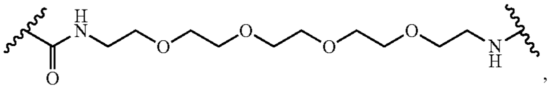
,
(77)
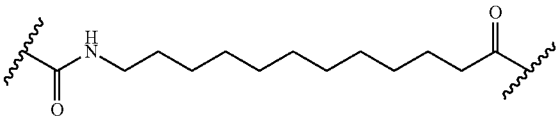
,
(78)
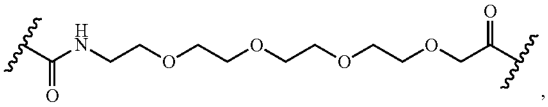
,
(79)
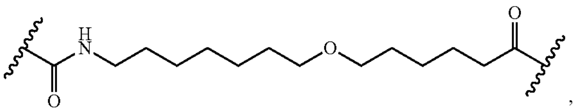
,
(80)
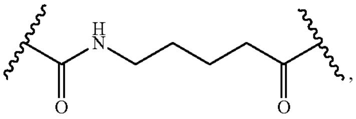
,
(81)
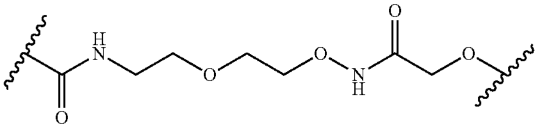
,
(82)
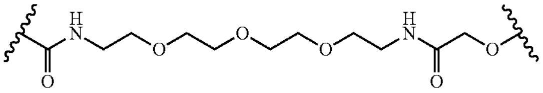
,
(83)
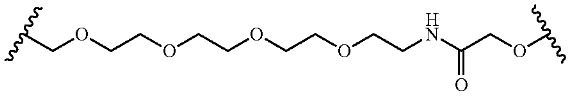
,
(84)
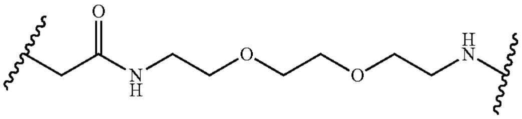
,
(85)
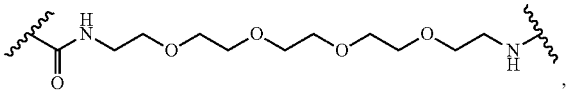
,
(86)
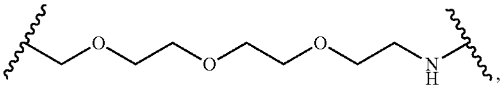
,
(87)
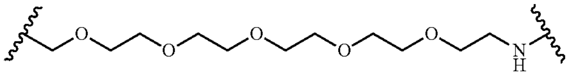
,
(88)
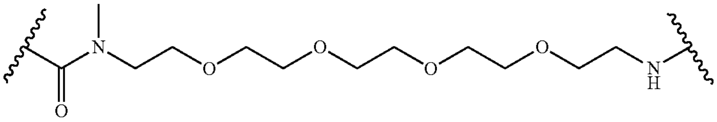
,
(89)
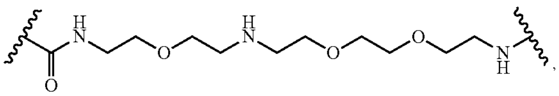
,
(90)
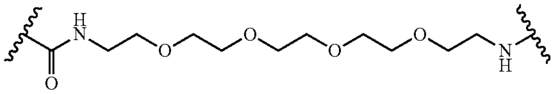
,
(91)
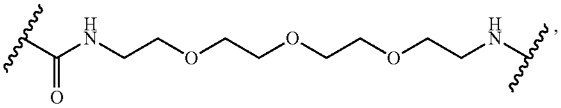
,
(92)
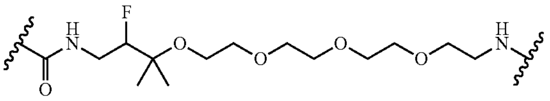
,
(93)
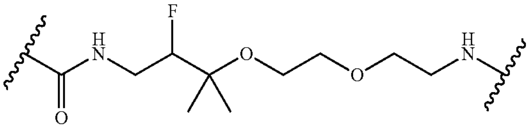
,
(94)
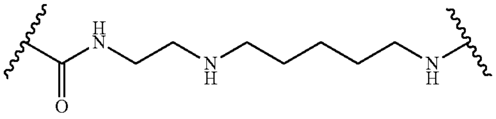
,

(95)
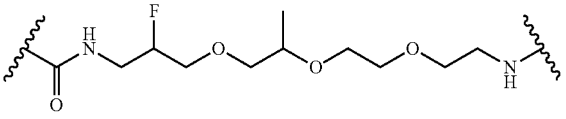,
(96)
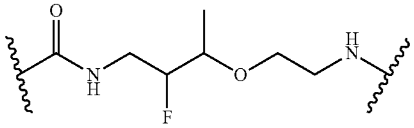,
(97)
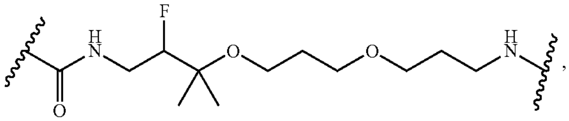,
(98)
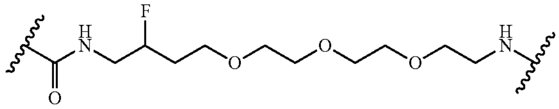,
(99)
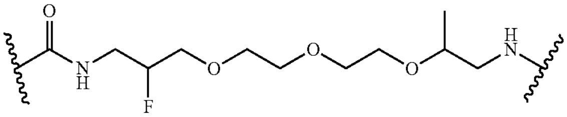,
(100)
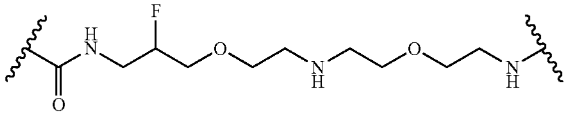,
(101)
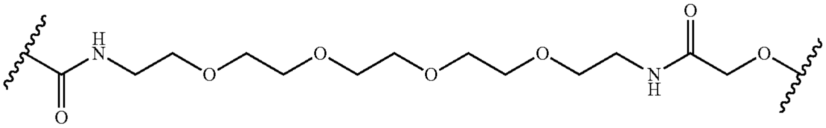,
(102)
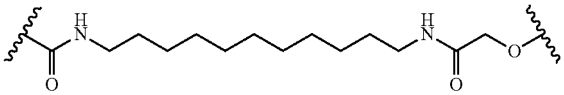,
(103)
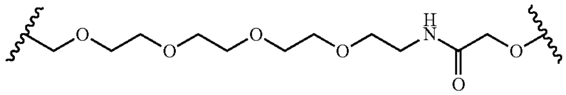,
(104)
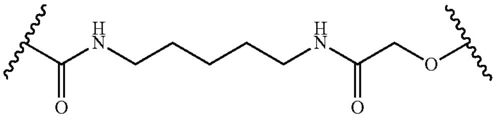,
(105)
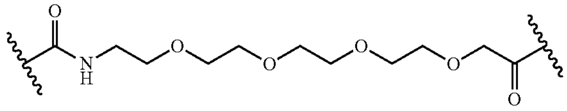,
(106)
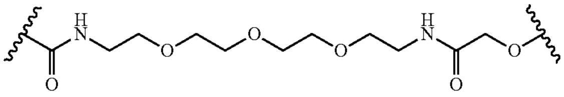,
(107)
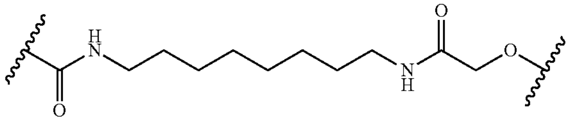,
(108)
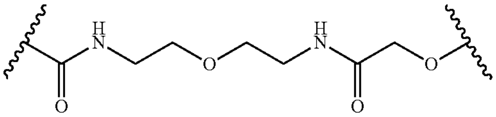,
(109)
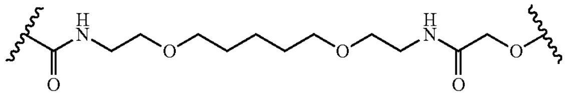,
(110)
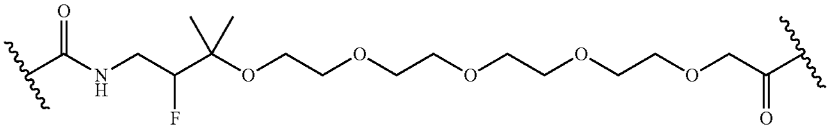,
(111)
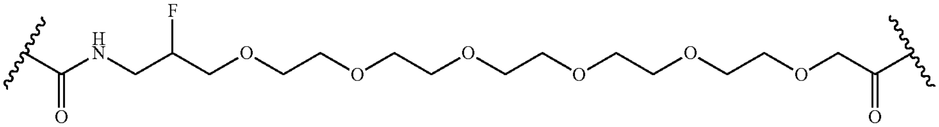,
(112)
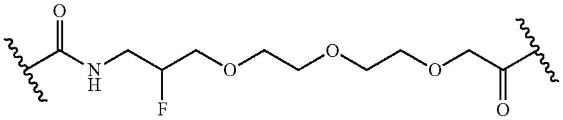, -continued
(113)
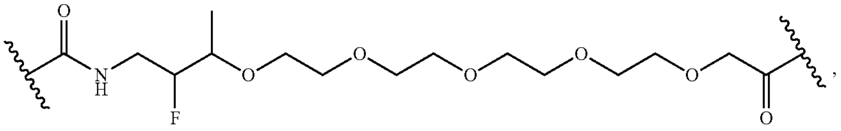
(114)
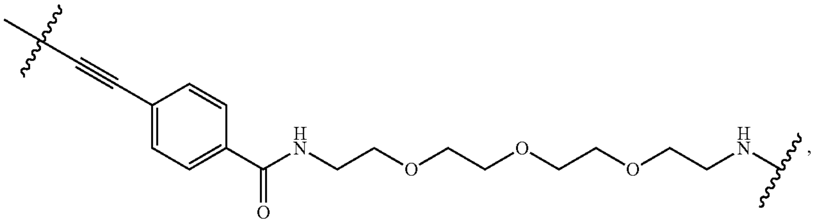
(115)
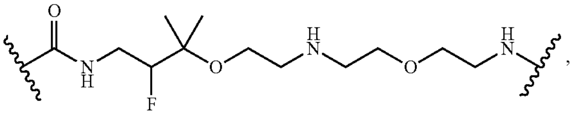
(116)
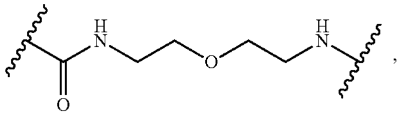
(117)
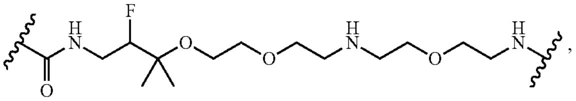
(118)
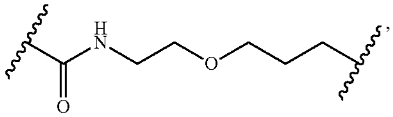
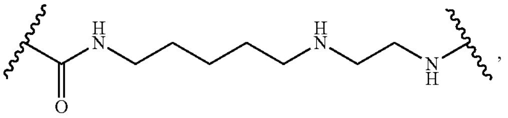
(119)
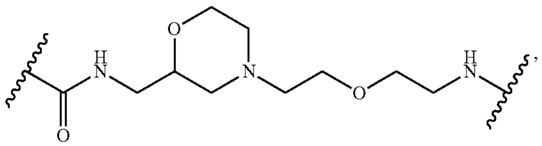
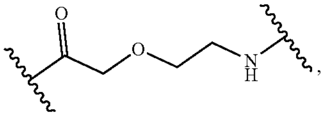
(120)
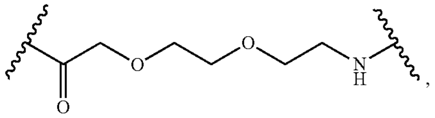
(121)
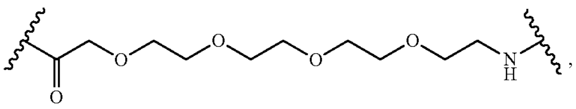
(122)
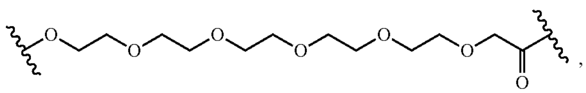
(123)
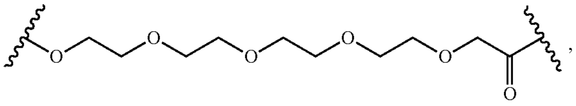
(124)
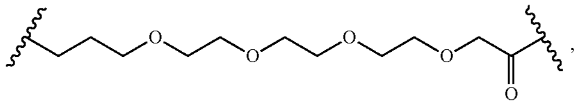
(125)
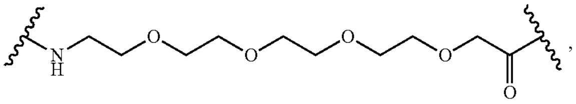
(126)
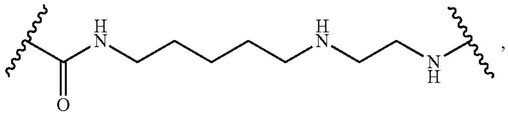
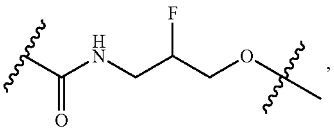
(127)
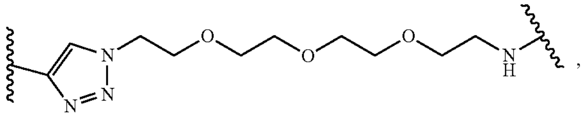

-continued
(128)
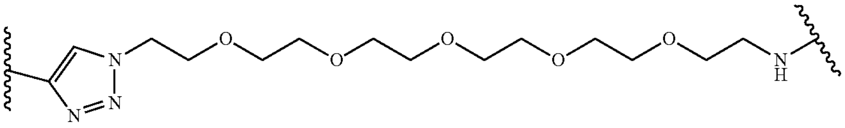,
(129)
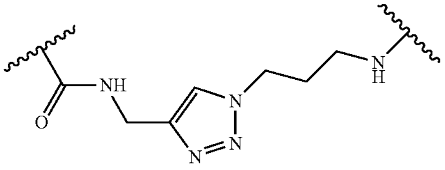,
(130)
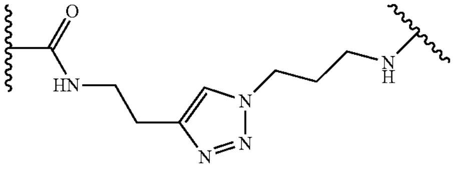,
(131)
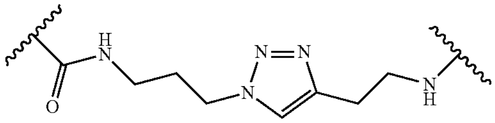,
(132)
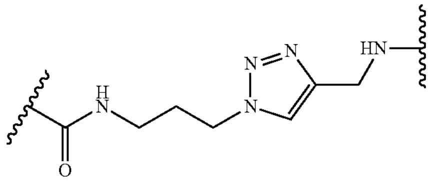,
(133)
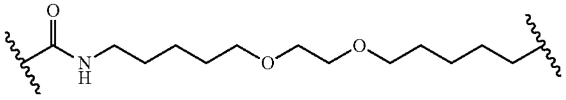,
(134)
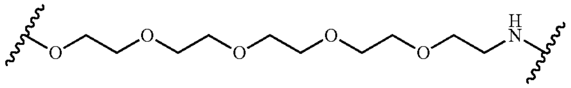,
(135)
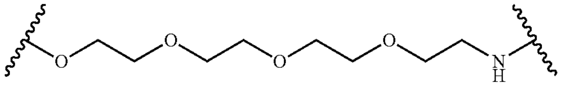,
(136)
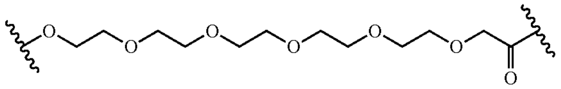,
(137)
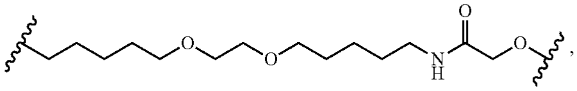,
(138)
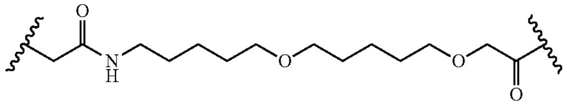,
(139)
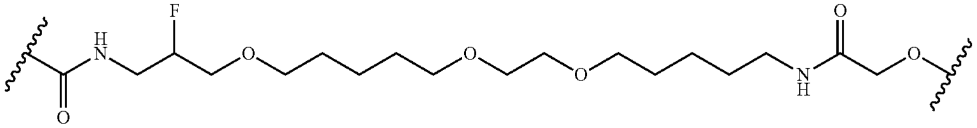,
(140)
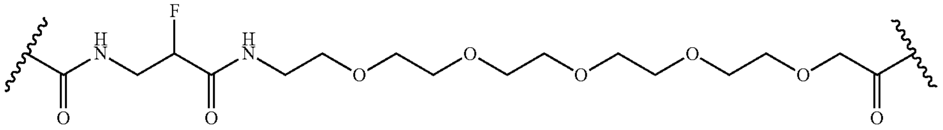,
(141)
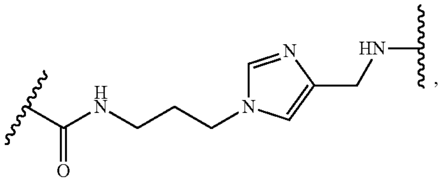,
(142)
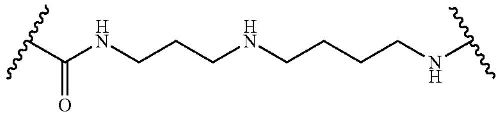,
(143)
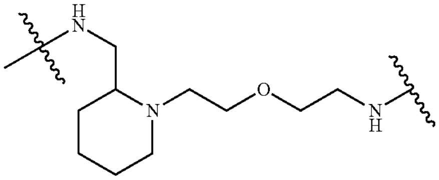,
(144)
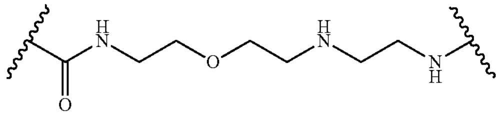, -continued
(145)
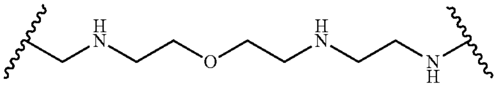,
(146)
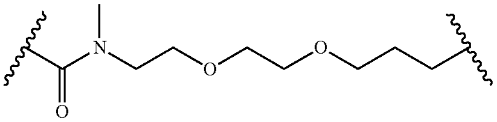,
(147)
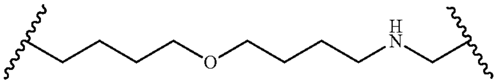,
(148)
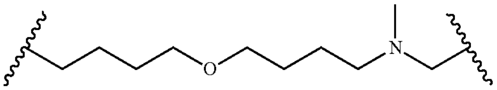,
(149)
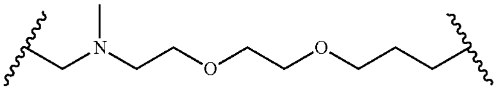,
(150)
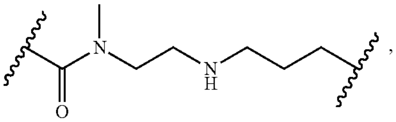,
(151)
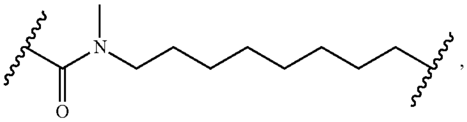,
(152)
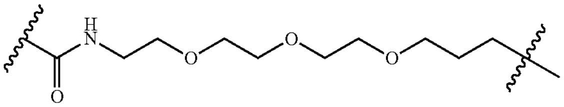,
(153)
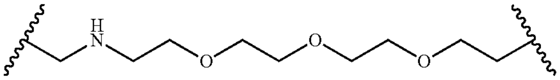,
(154)
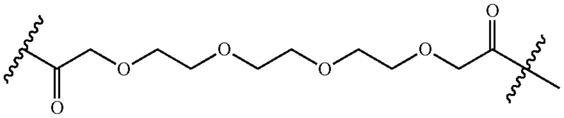,
(155)
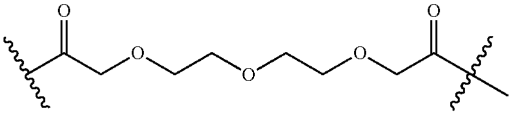,
(156)
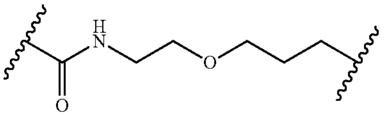,
(157)
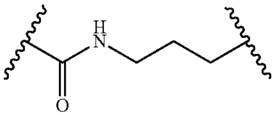,
(158)
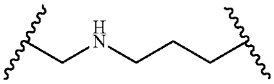,
(159)
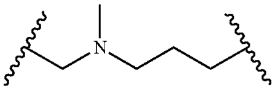,
(160)
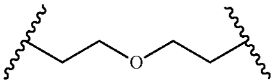,
(161)
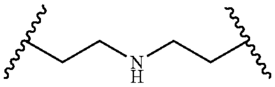,
(162)
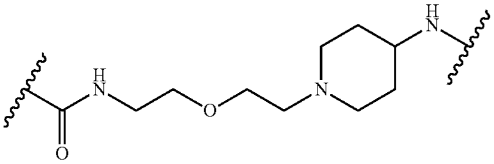,
(163)
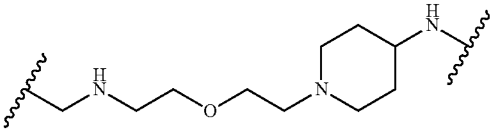,
(164)
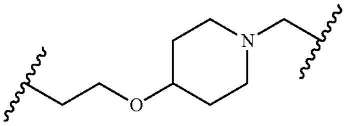,
(165)
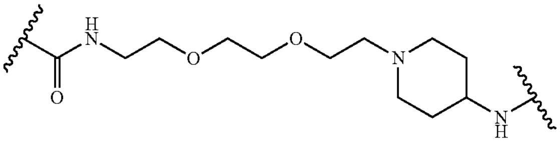,
(166)
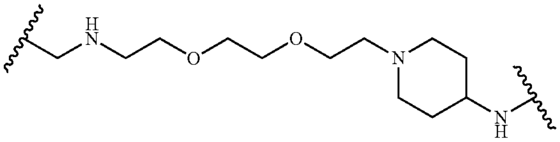, -continued
(167)
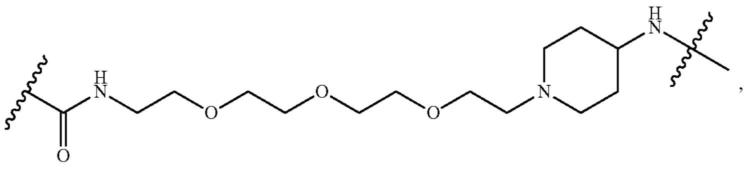
(168)
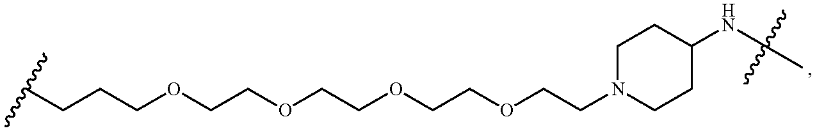
(169)
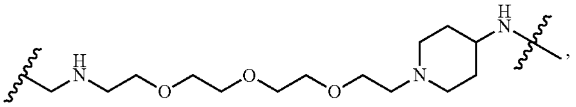
(170)
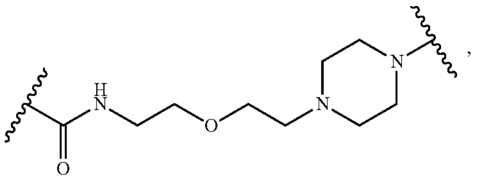
(171)
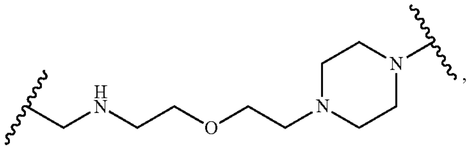
(172)
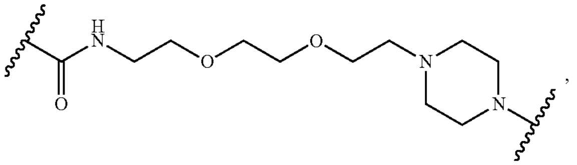
(173)
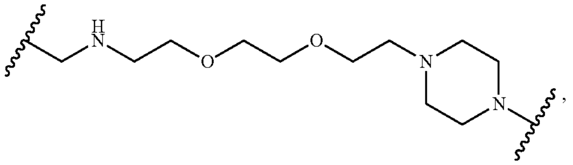
(174)
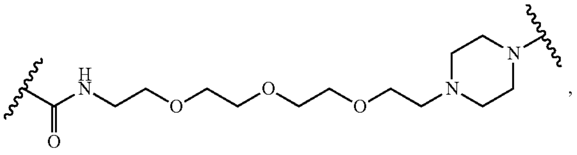
(175)
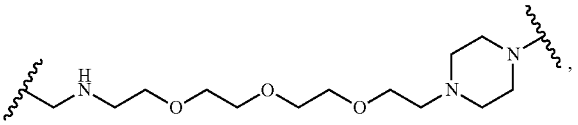
(176)
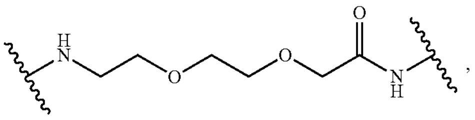
(177)
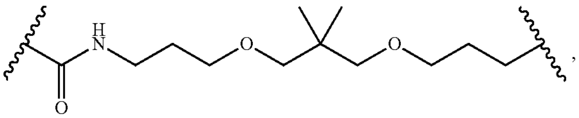
(178)
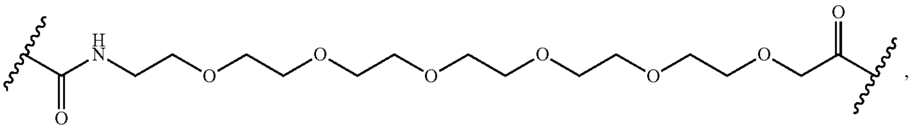
(179)
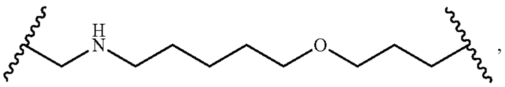
(180)
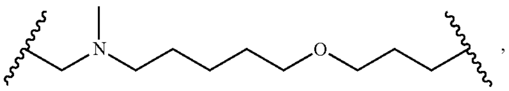
(181)
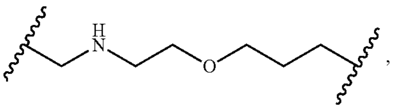
(182)
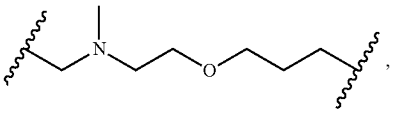

-continued
(183)
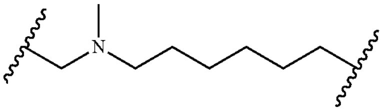,
(184)
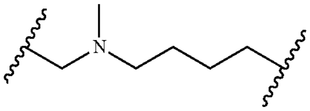,
(185)
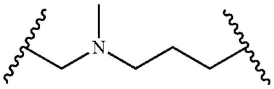,
(186)
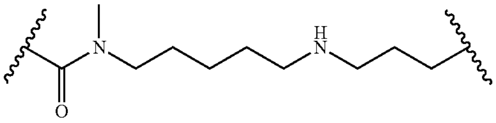,
(187)
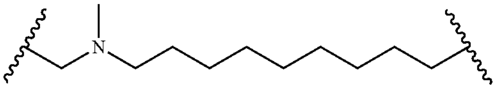,
(188)
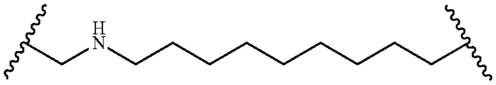,
(189)
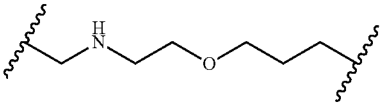,
(190)
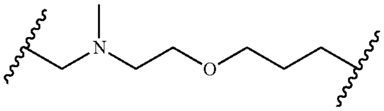,
(191)
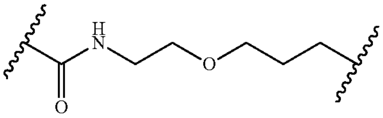,
(192)
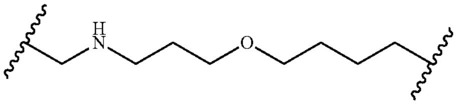,
(193)
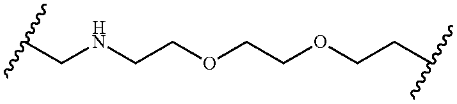,
(194)
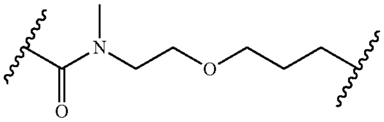,
(195)
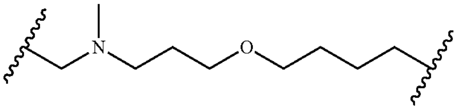,
(196)
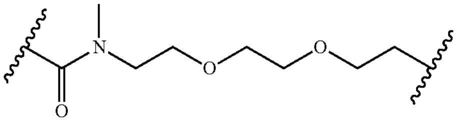,
(197)
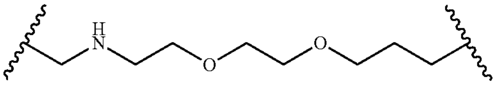,
(198)
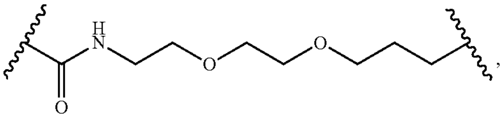,
(199)
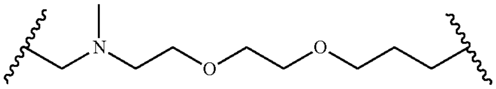,
(200)
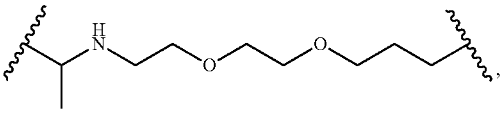,
(201)
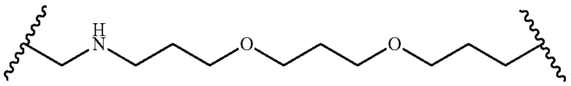,
(202)
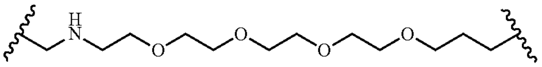,
(203)
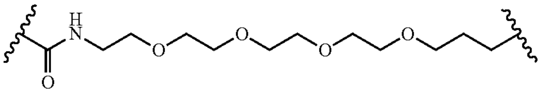, -continued
(204)
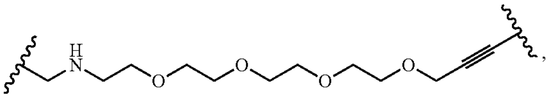
(205)
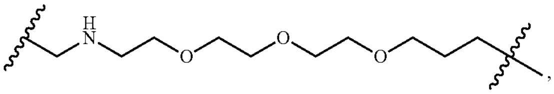
(206)
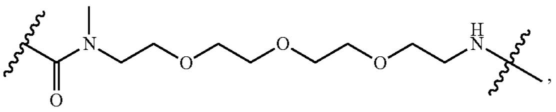
(207)
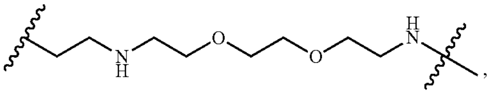
(208)
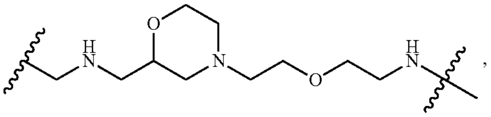
(209)
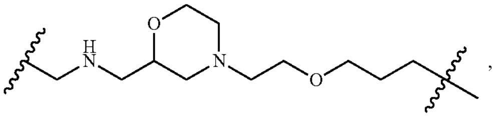
(210)
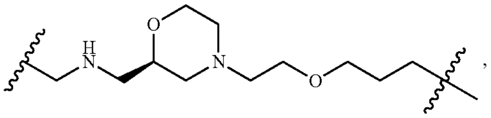
(211)
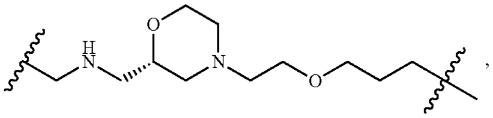
(212)
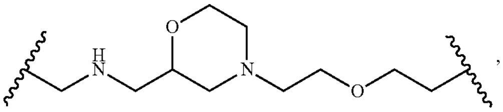
(213)
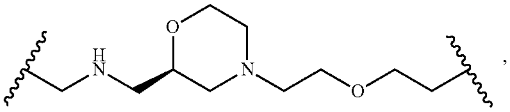
(214)
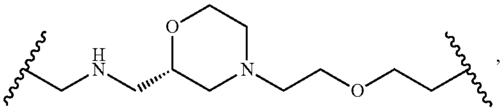
(215)
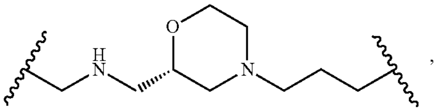
(216)
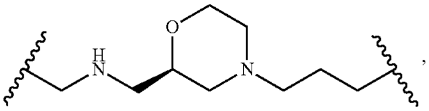
(217)
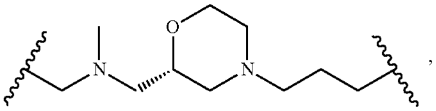
(218)
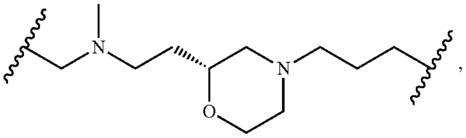
(219)
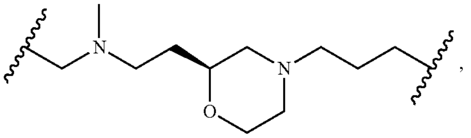
(220)
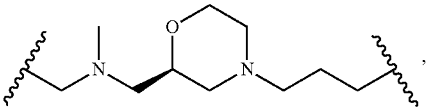
(221)
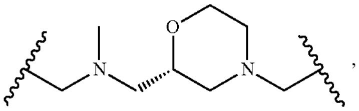
(222)
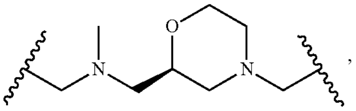
(223)
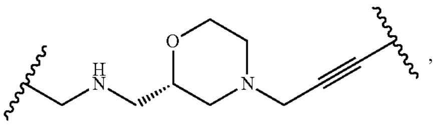
(224)
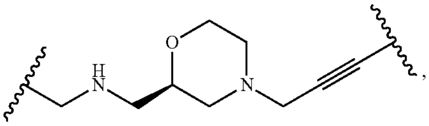
(225)
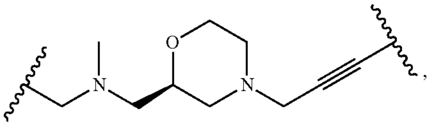

-continued
(226)
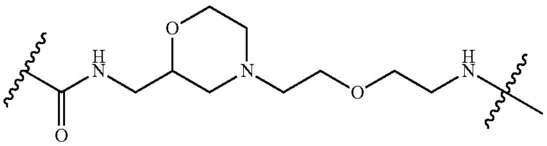,
(227)
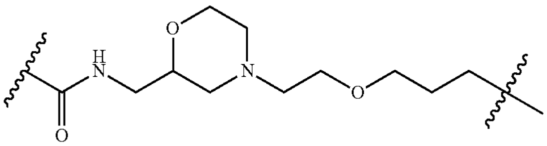,
(228)
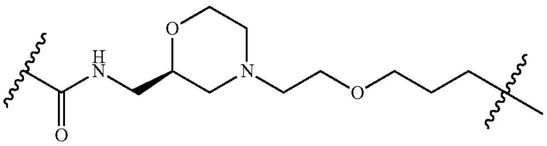,
(229)
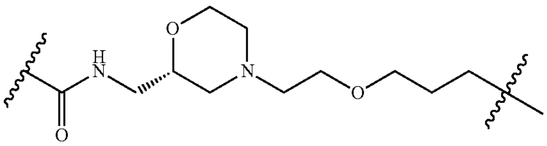,
(230)
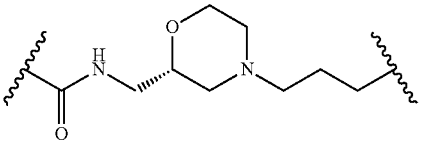,
(231)
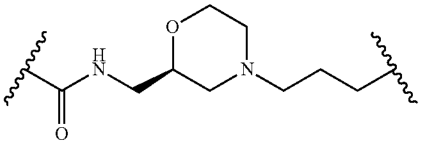,
(232)
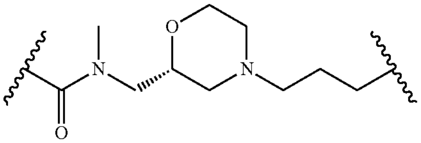,
(233)
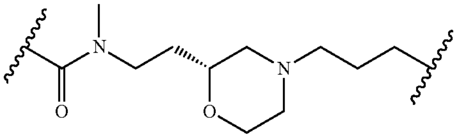,
(234)
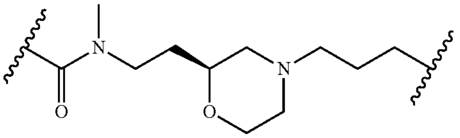,
(235)
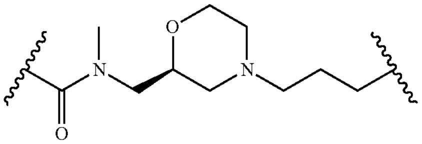,
(236)
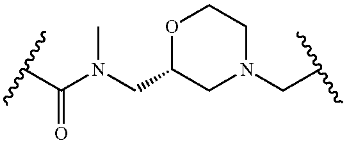,
(237)
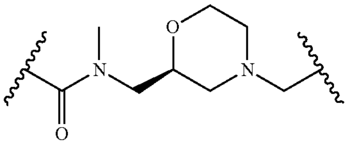,
(238)
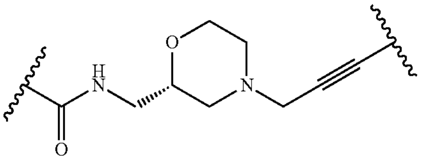,
(239)
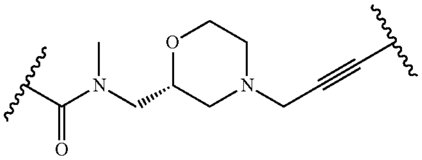,
(240)
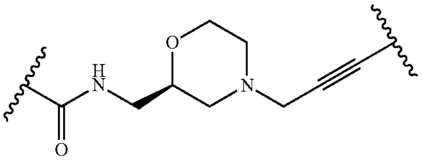,
(241)
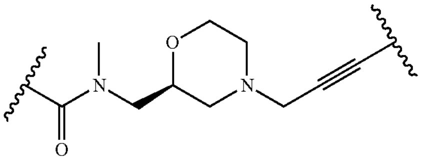,
(242)
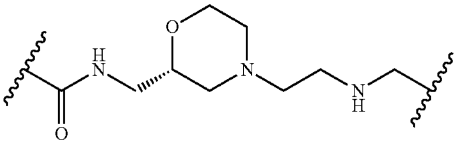,
(243)
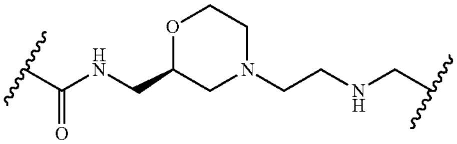,
(244)
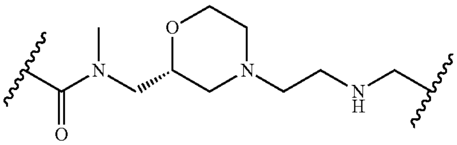,
(245)
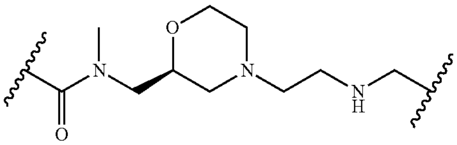, -continued
(246)
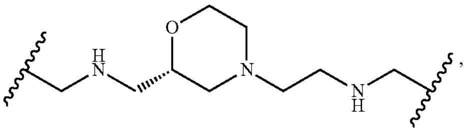
(247)
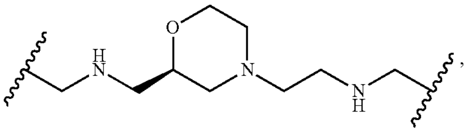
(248)
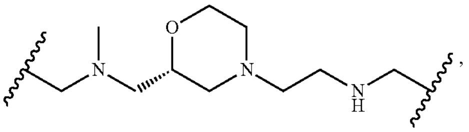
(249)
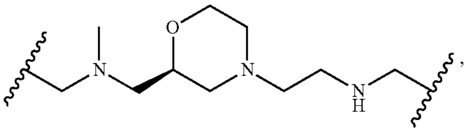
(250)
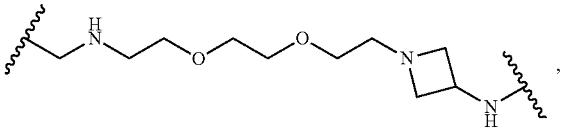
(251)
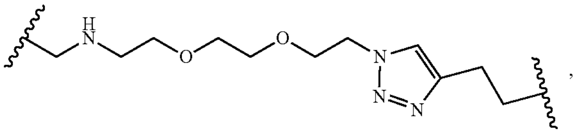
(253)
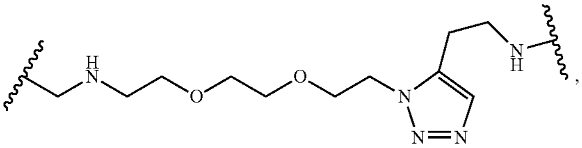
(254)
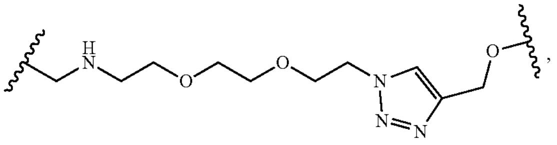
(255)
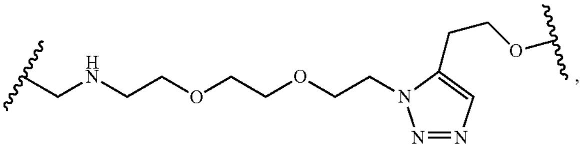
(256)
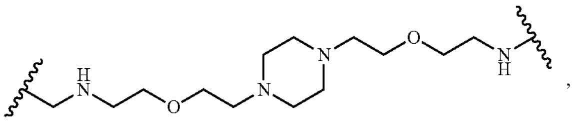
(257)
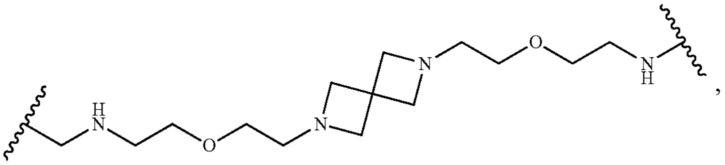
(258)
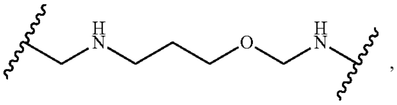
(259)
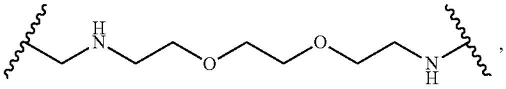
(260)
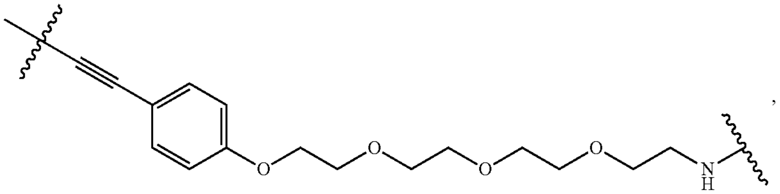
(261)
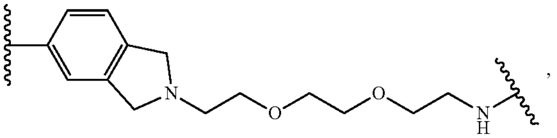
(262)
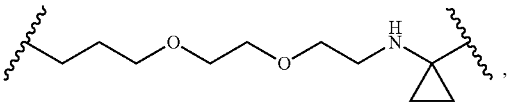

-continued
(263)
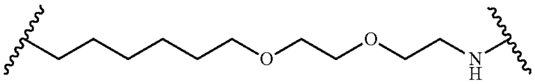
,
(264)
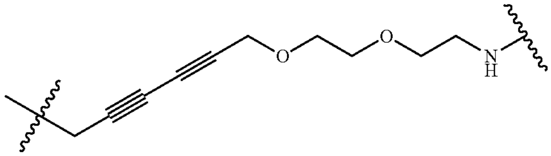
,
(265)
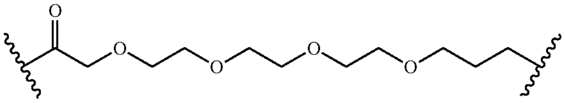
,
(266)
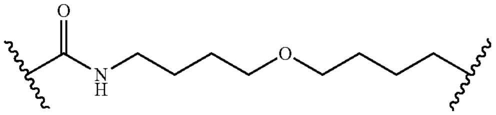
,
(267)
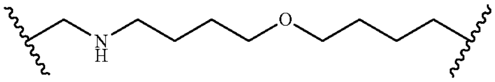
,
(268)
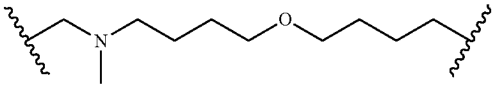
,
(269)
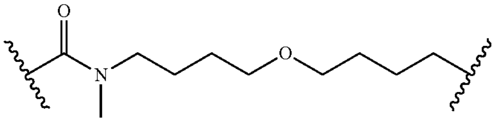
,
(270)
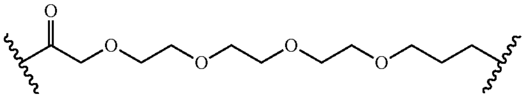
,
(271)
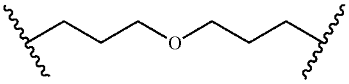
,
(272)
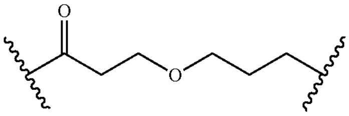
,
(273)
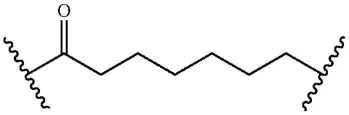
,
(274)
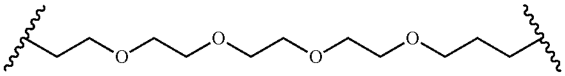
,
(275)
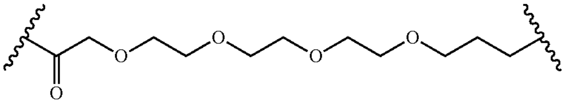
,
(276)
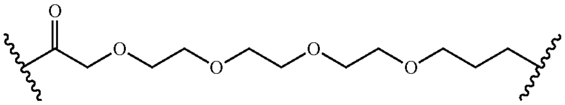
,
(277)
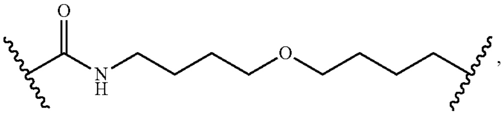
,
(278)
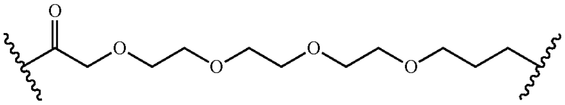
,
(279)
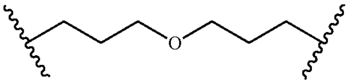
,
(280)
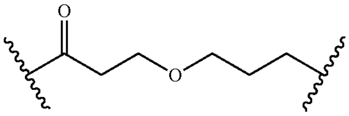
,
(281)
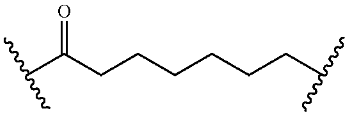
,
(282)
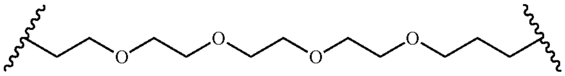
,
(283)
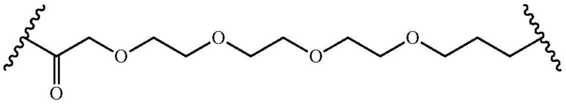
,
(284)
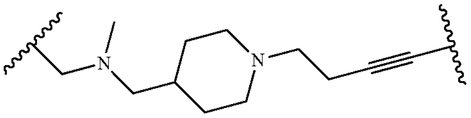
, -continued
(285)
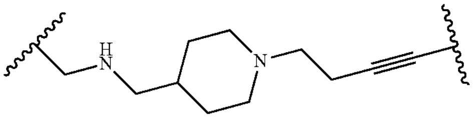,
(286)
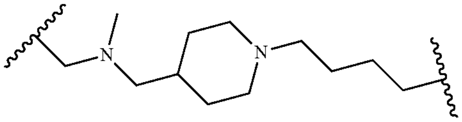,
(287)
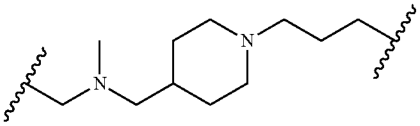,
(288)
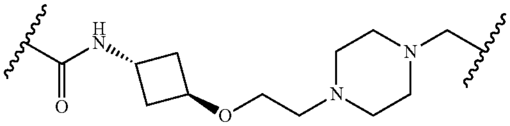,
(289)
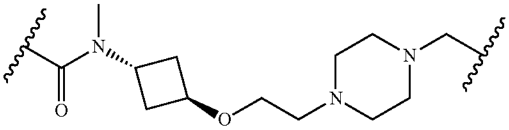,
(290)
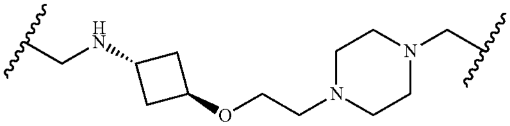,
(291)
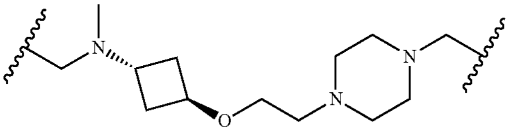,
(292)
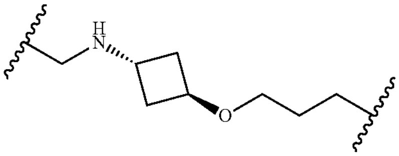,
(293)
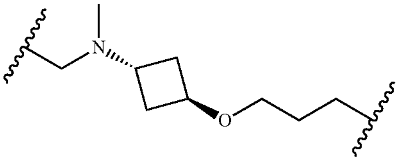,
(294)
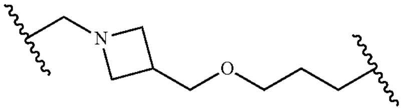,
(293)
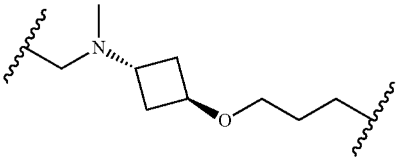,
(294)
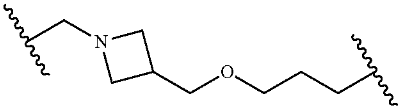,
(295)
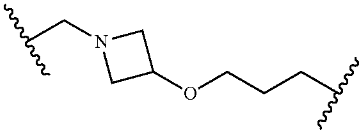,
(296)
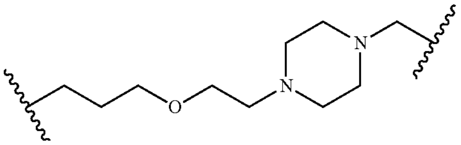,
(297)
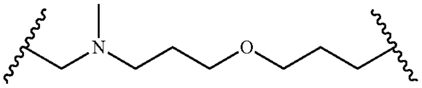,
(298)
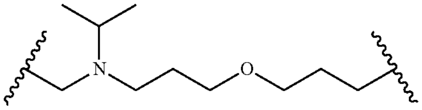,
(299)
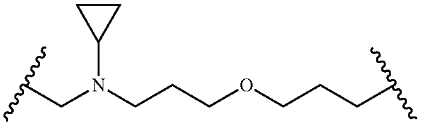,
(300)
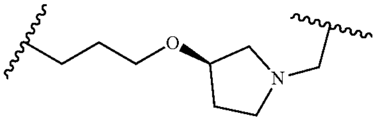,
(301)
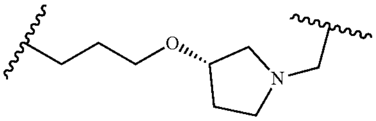,
(302)
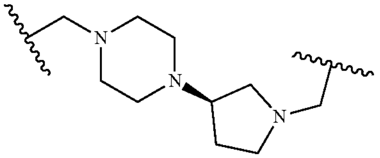, -continued
(303)
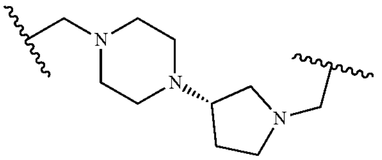
,
(304)
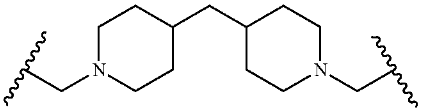
,
(305)
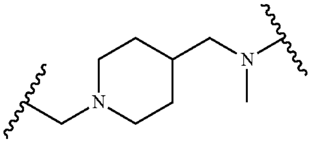
,
(306)
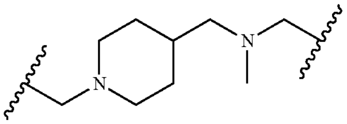
,
(307)
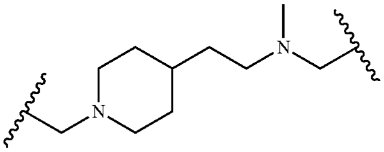
,
(308)
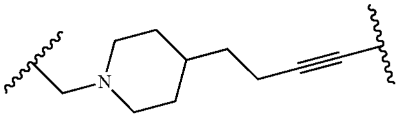
,
(309)
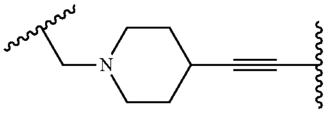
,
(310)
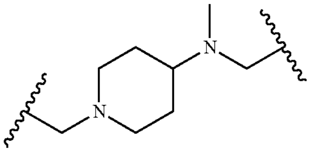
,
(311)
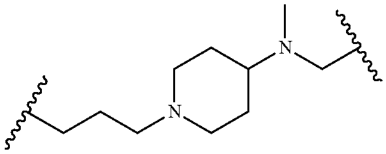
,
(312)
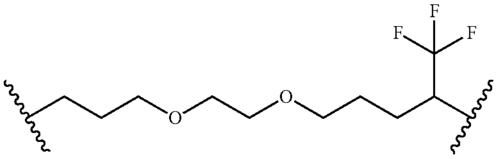
,
(313)
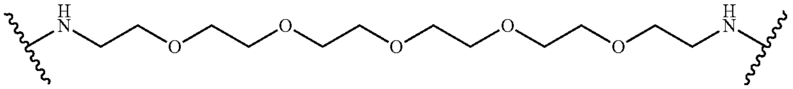
,
(314)
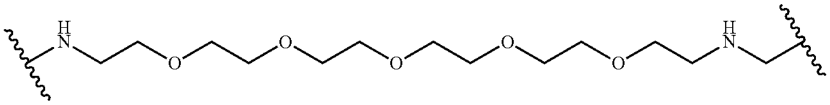
,
(315)
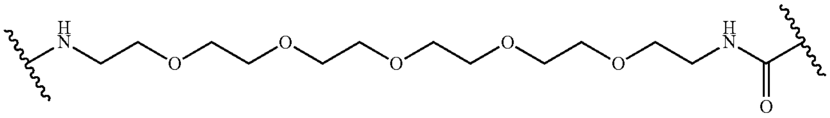
,
(316)
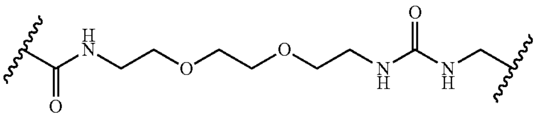
,
(317)
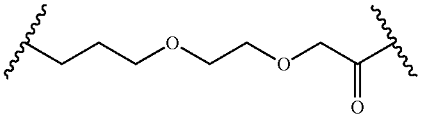
,
(318)
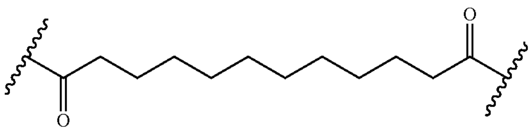
,
(319)
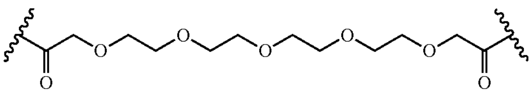
, -continued
(320)
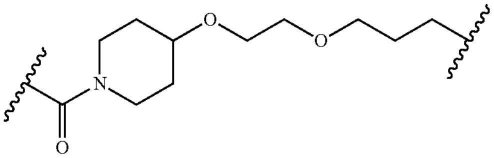
,
(321)
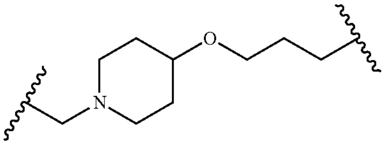
,
(322)
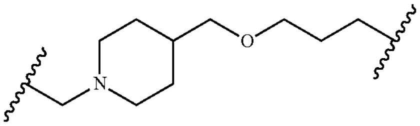
,
(323)
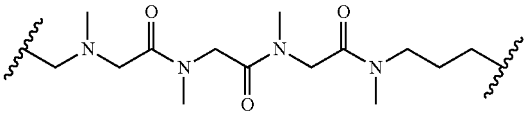
,
(324)
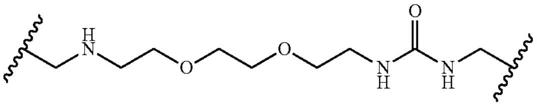
,
(325)
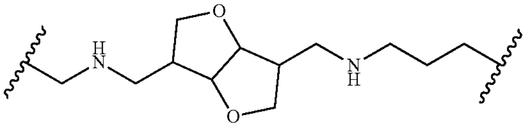
,
(326)
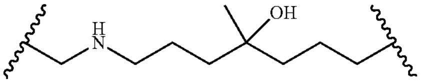
,
(327)
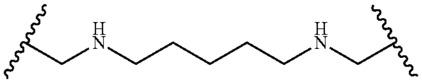
,
(328)
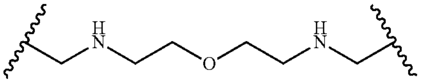
,
(329)
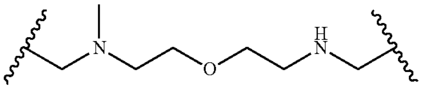
,
(330)
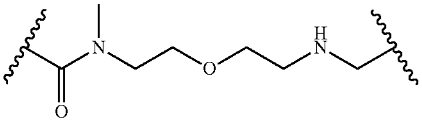
,
(331)
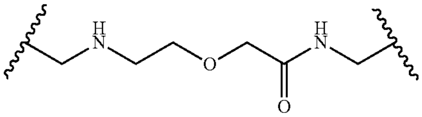
,
(332)
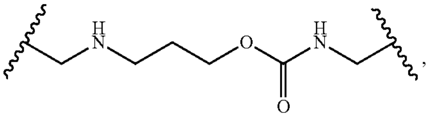
,
(333)
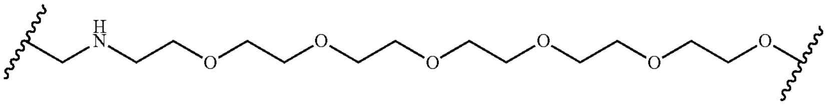
,
(334)
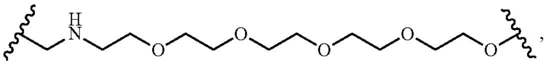
,
(335)
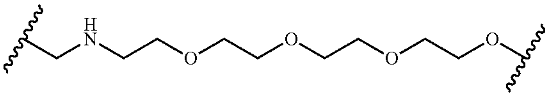
,
(336)
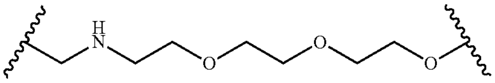
,
(337)
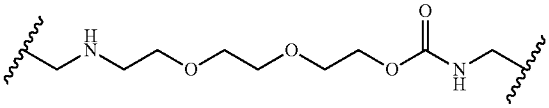
,
(338)
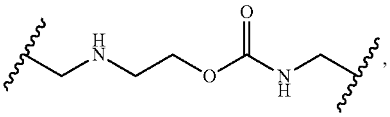
,
(339)
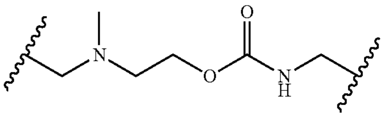
, -continued
(340)
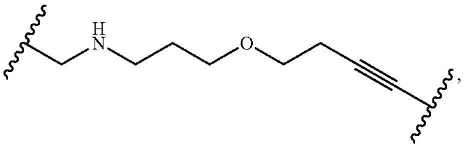,
(341)
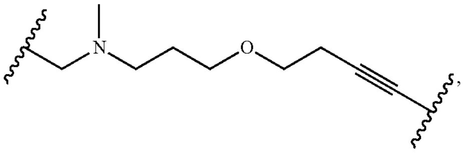,
(342)
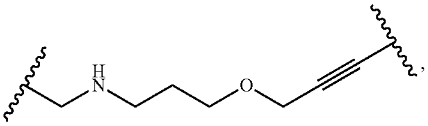,
(343)
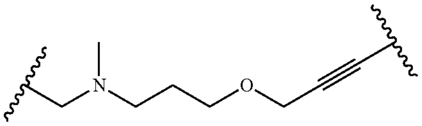,
(344)
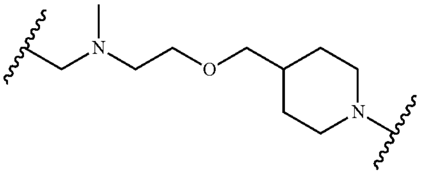,
(345)
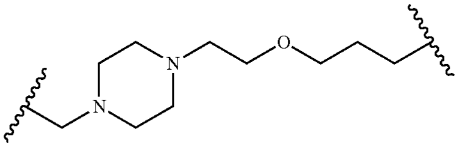,
(346)
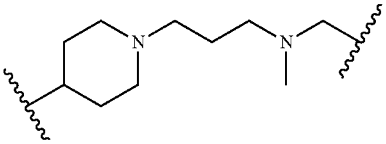,
(347)
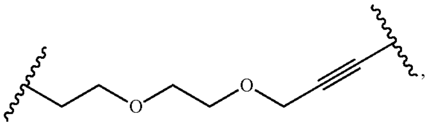,
(348)
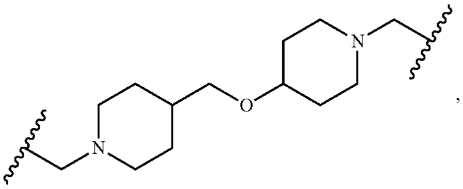,
(349)
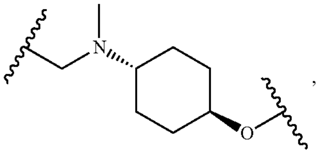,
(350)
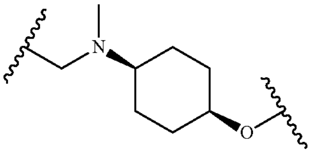,
(351)
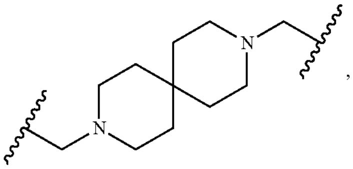,
(352)
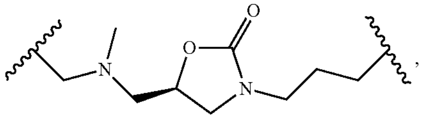,
(353)
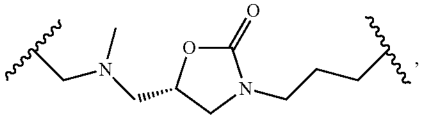,
(354)
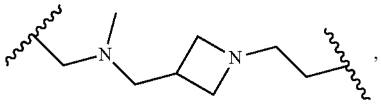,
(355)
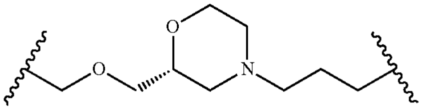,
(356)
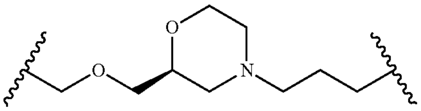,
(357)
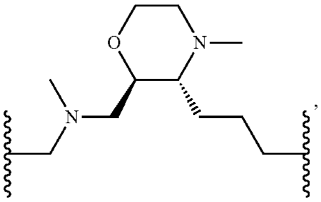, -continued
(358)
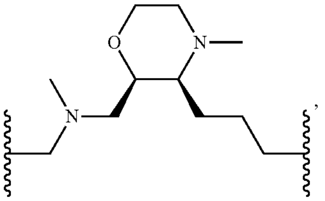
(359)
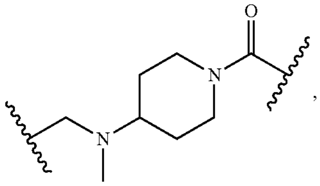
(360)
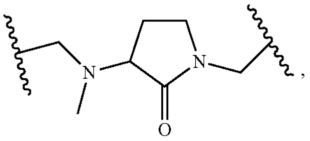
(361)
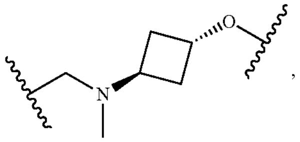
(362)
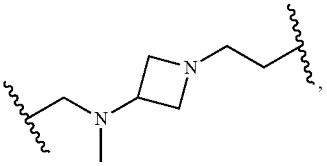
(363)
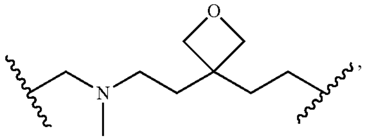
(364)
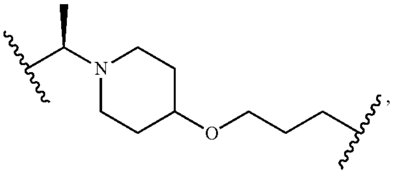
(365)
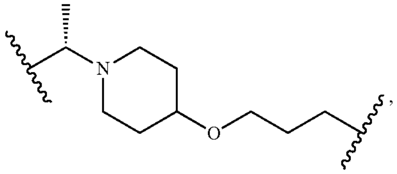
(366)
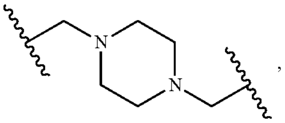
(367)
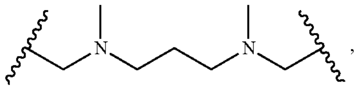
(368)
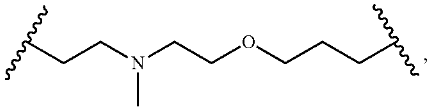
(369)
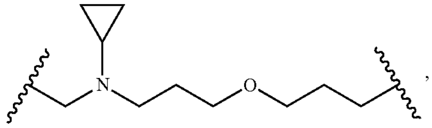
(370)
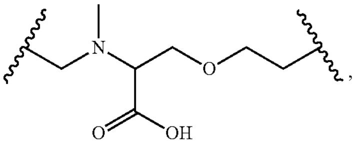
(371)
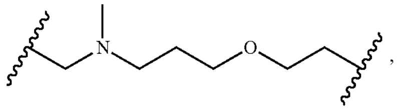
(372)
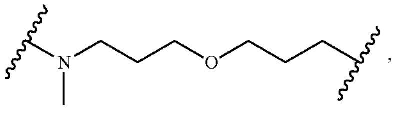
(373)
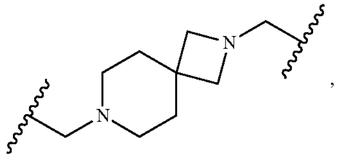
(374)
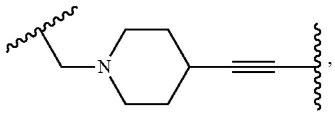
(375)
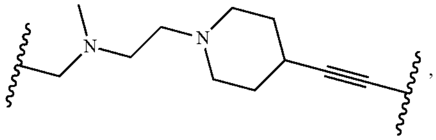
(376)
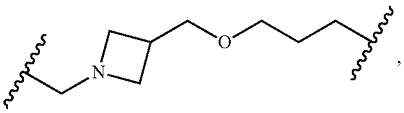
(377)
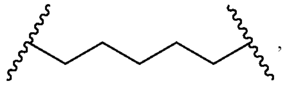

-continued
(378)
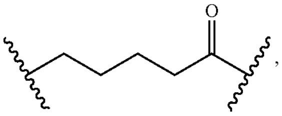
(379)
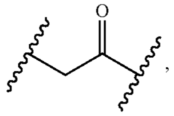
(380)
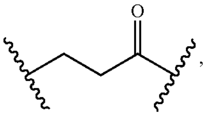
(381)
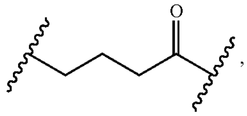
(382)
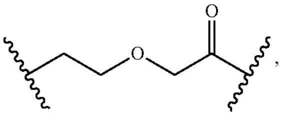
(383)
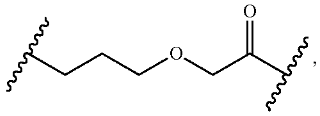
(384)
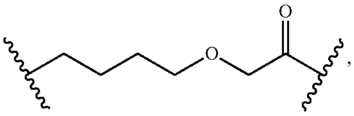
(385)
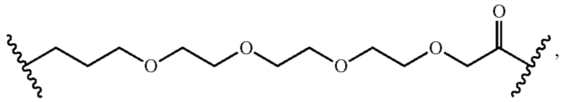
(386)
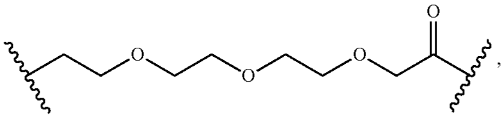
(387)
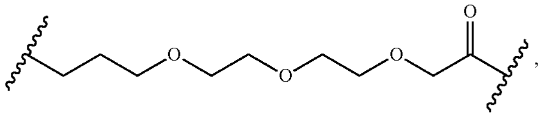
(388)
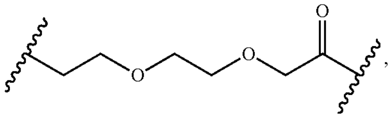
(389)
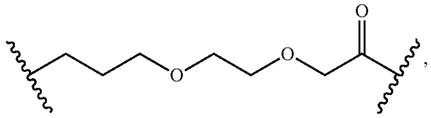
(390)
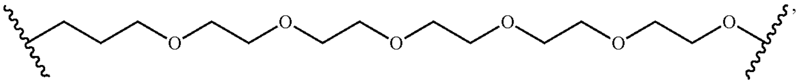
(391)
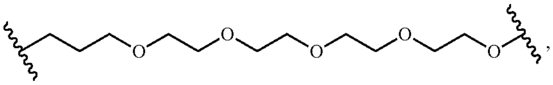
(392)
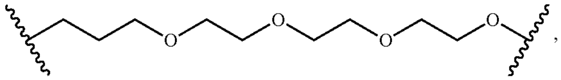
(393)
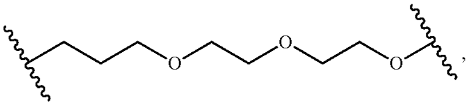
(394)
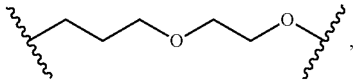
(395)
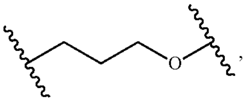
(396)
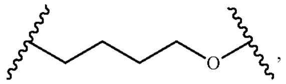
(397)
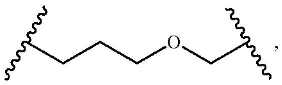
(398)
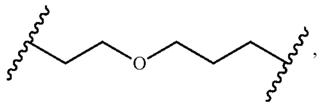
(399)
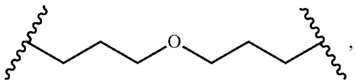
(400)
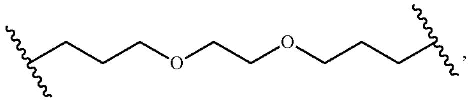

-continued
(401)
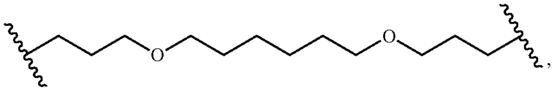,
(402)
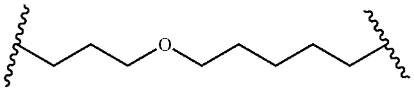,
(403)
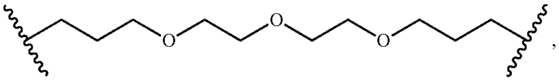,
(404)
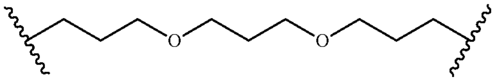,
(405)
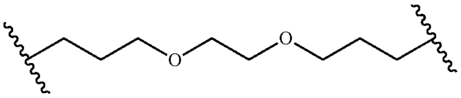,
(406)
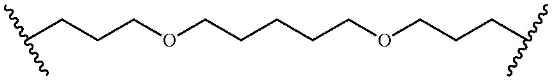,
(407)
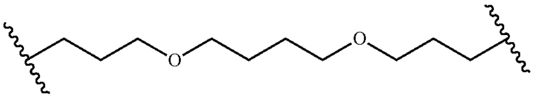,
(408)
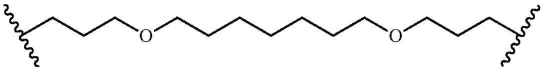,
(409)
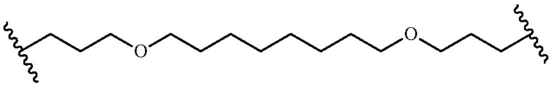,
(410)
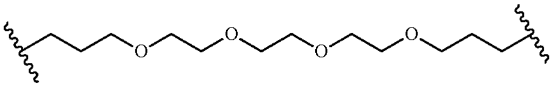,
(411)
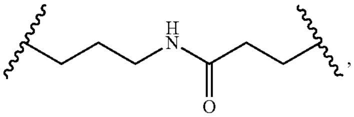,
(412)
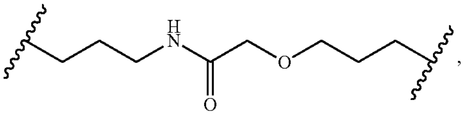,
(413)
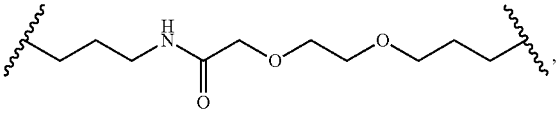,
(414)
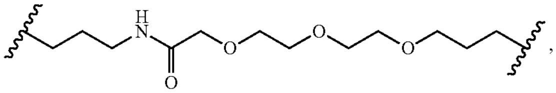,
(415)
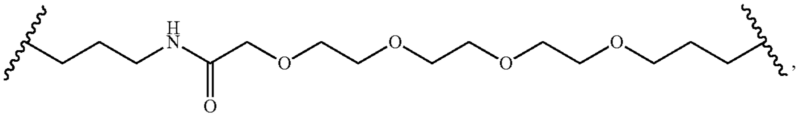,
(416)
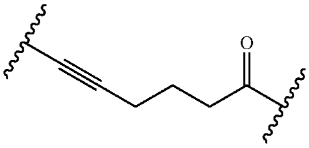,
(417)
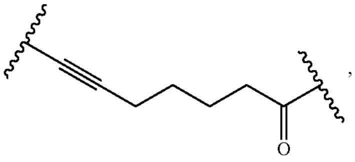,
(418)
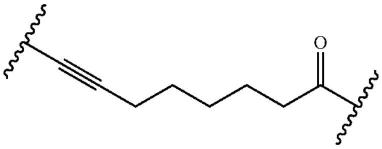,
(419)
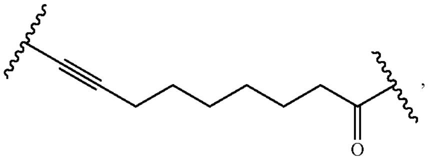,
(420)
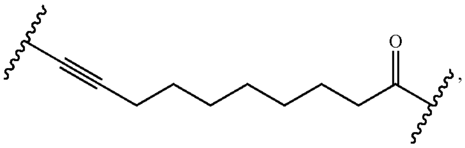,
(421)
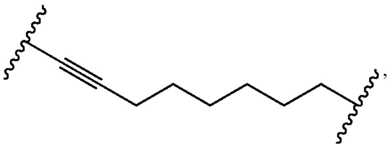, -continued
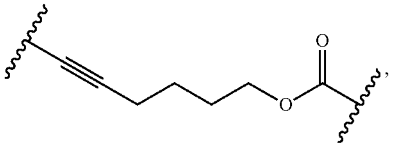
(422)
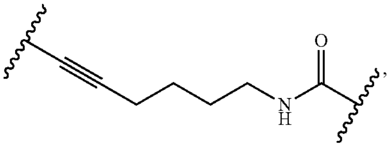
(423)
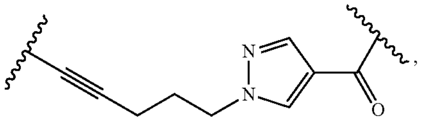
(424)
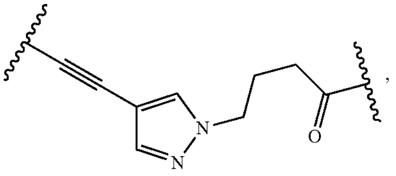
(425)
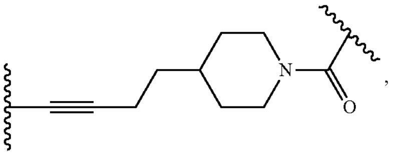
(426)
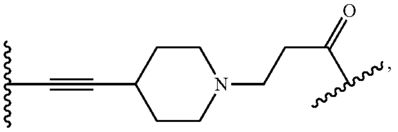
(427)
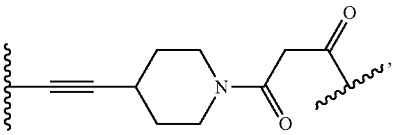
(428)
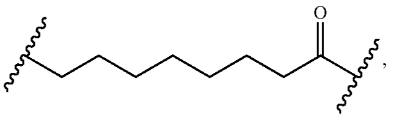
(429)
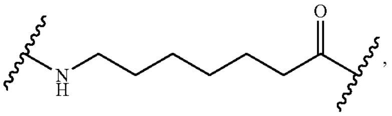
(430)
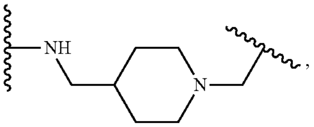
(431)
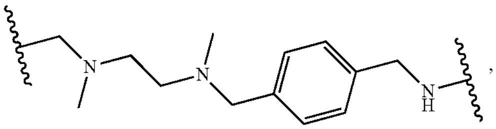
(432)
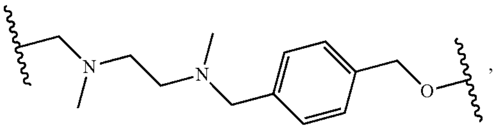
(433)
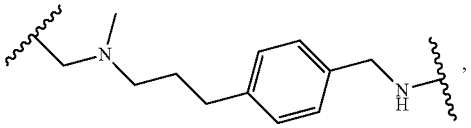
(434)
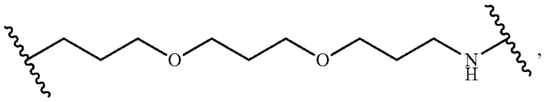
(435)
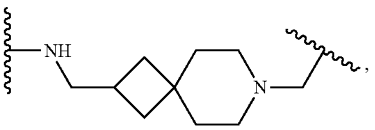
(436)
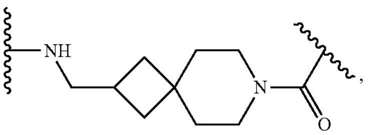
(437)
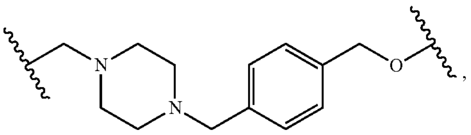
(438)
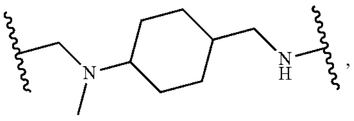
(439)
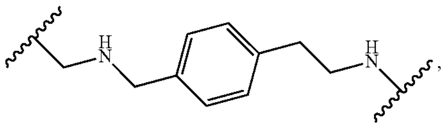
(440)
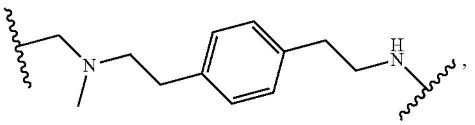
(441)

-continued
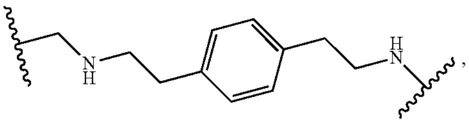
(442)
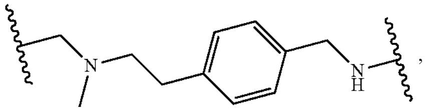
(443)
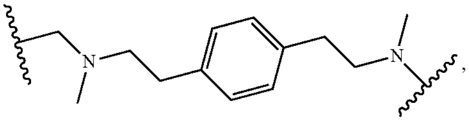
(444)
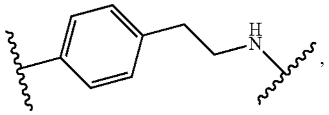
(445)
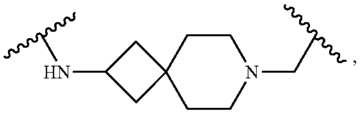
(446)
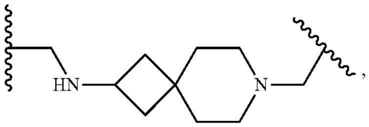
(447)
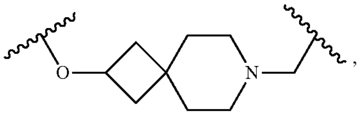
(448)
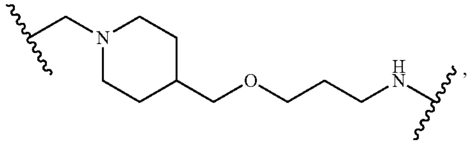
(449)
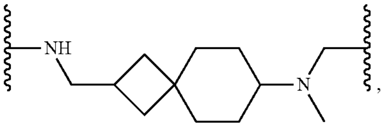
(450)
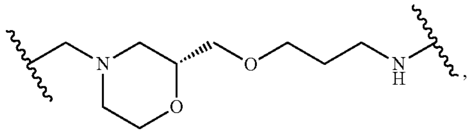
(451)
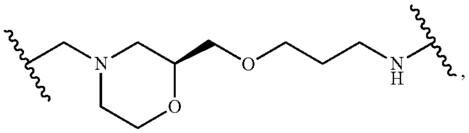
(452)
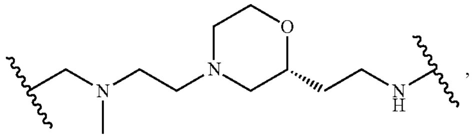
(453)
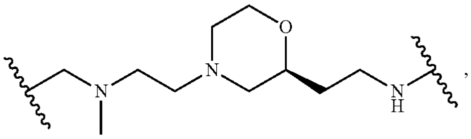
(454)
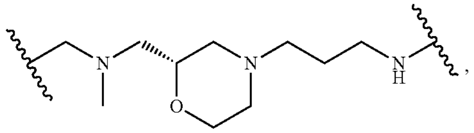
(455)
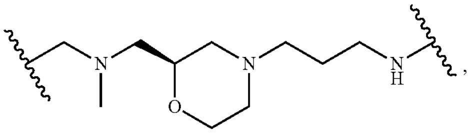
(456)
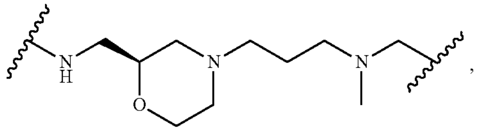
(457)
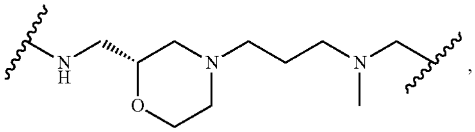
(458)
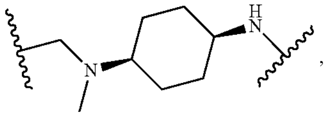
(459)
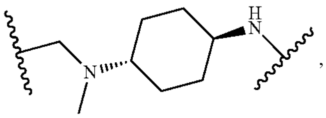
(460)
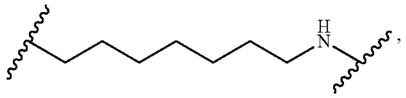
(461)

-continued
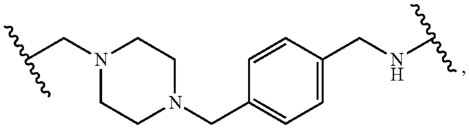
(462)
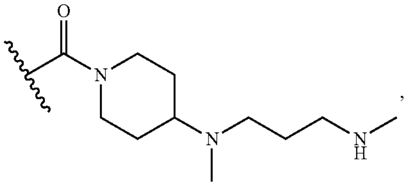
(463)
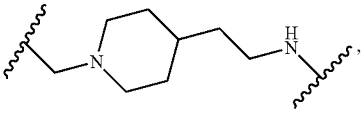
(464)
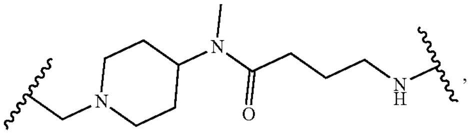
(465)
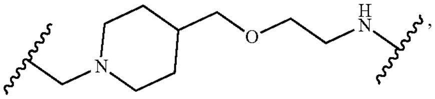
(466)
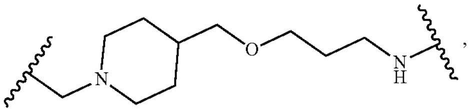
(467)
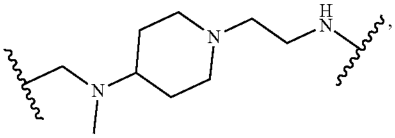
(468)
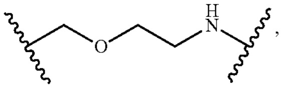
(469)
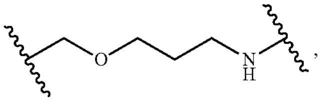
(470)
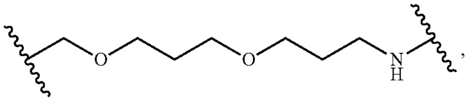
(471)
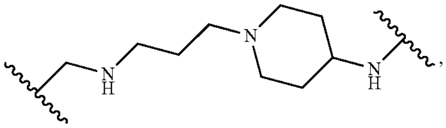
(472)
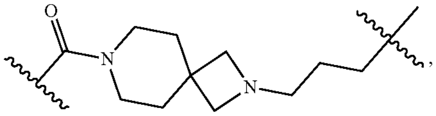
(473)
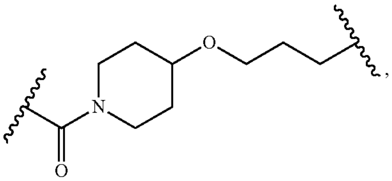
(474)
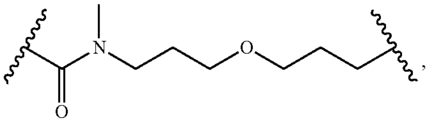
(475)
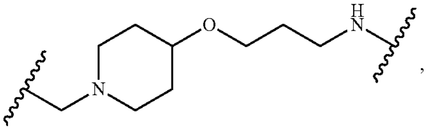
(475)
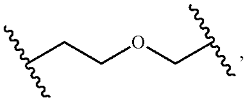
(476)
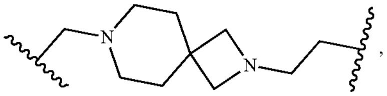
(477)
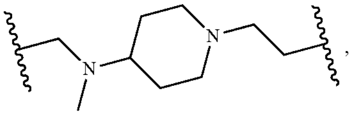
(478)
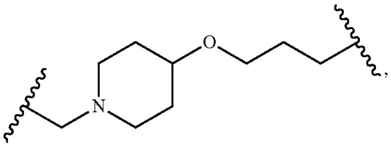
(479)
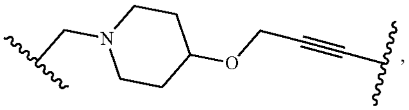
(480)

-continued
(481)
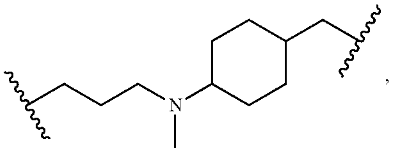
(482)
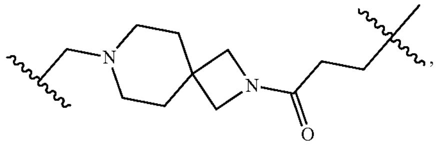
(483)
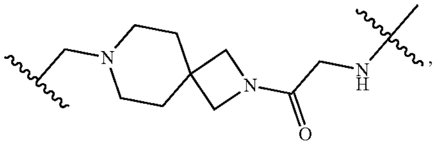
(484)
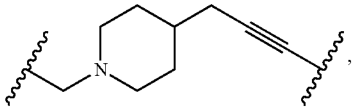
(485)
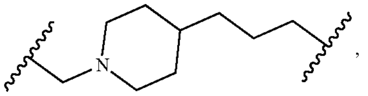
(486)
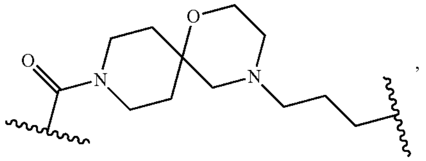
(487)
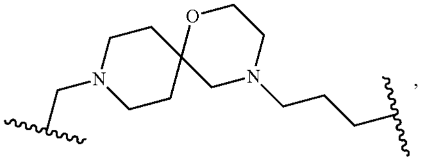
(488)
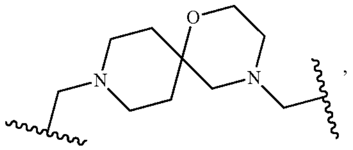
(489)
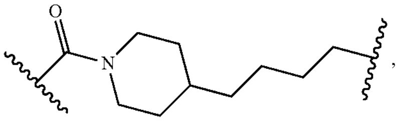
(490)
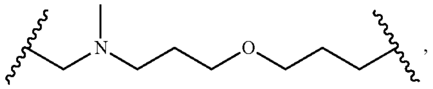
(491)
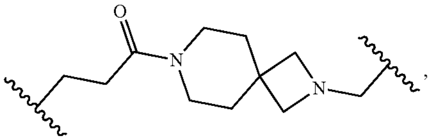
(492)
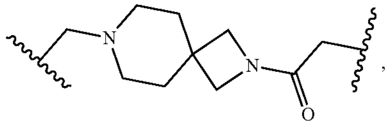
(493)
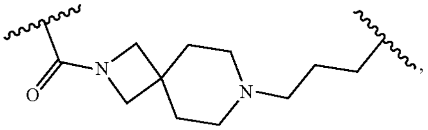
(494)
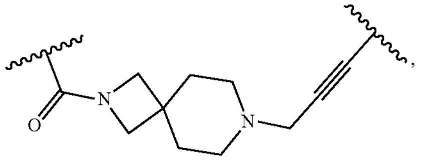
(495)
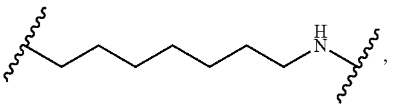
(496)
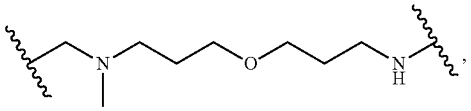
(497)
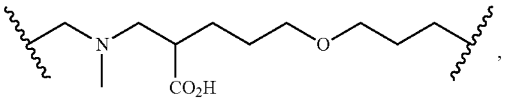
(498)
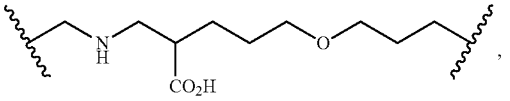
-continued
(499)
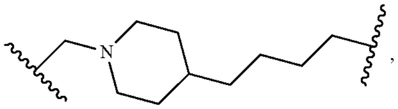
(500)
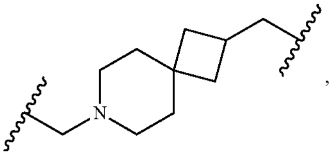

-continued
(501)
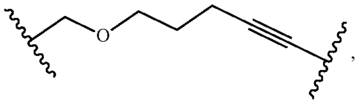,
(502)
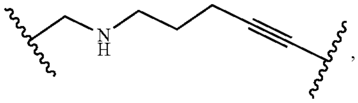,
(503)
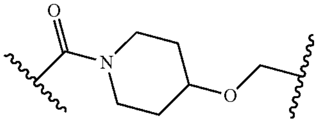,
(504)
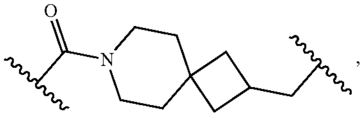,
(505)
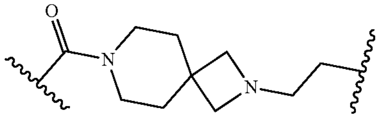,
(506)
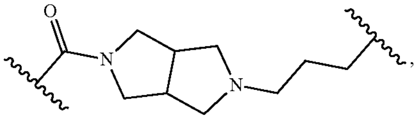,
(507)
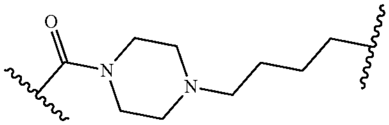,
(508)
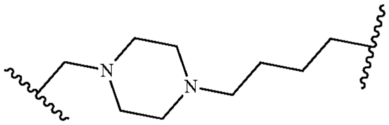,
(509)
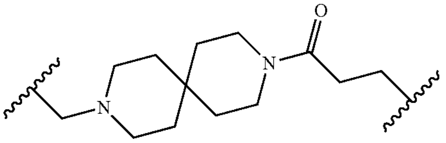,
(510)
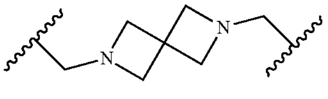,
(511)
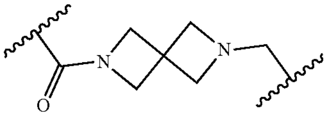,
(512)
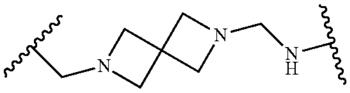,
-continued
(513)
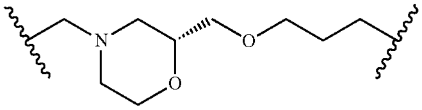,
(514)
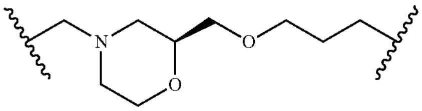,
(515)
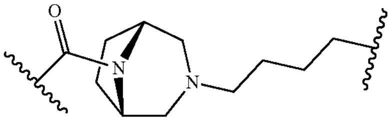,
(516)
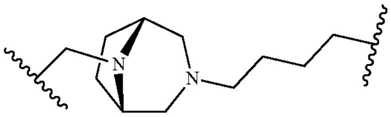,
(517)
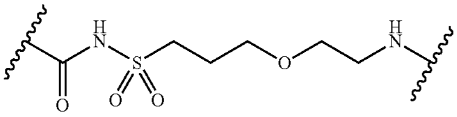,
(518)
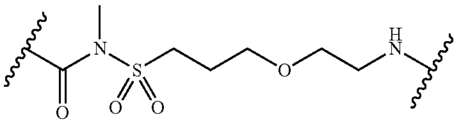,
(519)
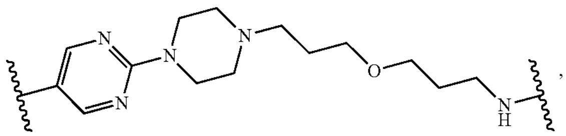,
(520)
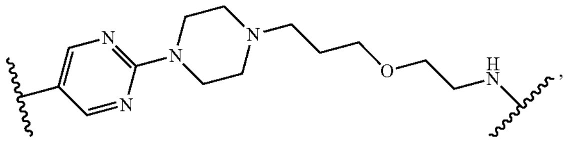,
(521)
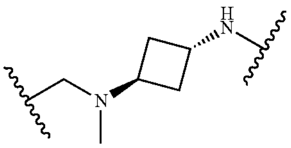,
(522)
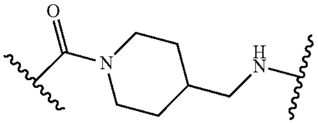,
(523)
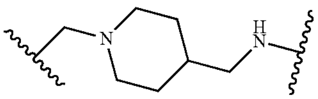, -continued
(524)
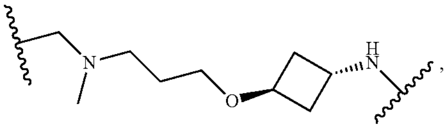
(525)
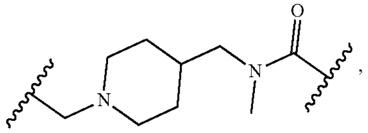
(526)
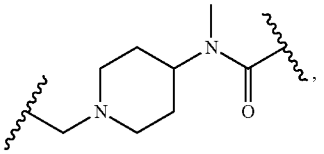
(527)
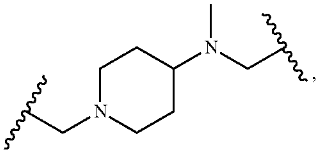
(528)
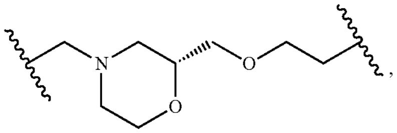
(529)
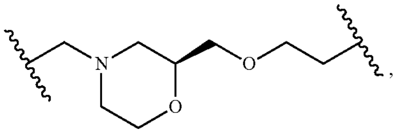
(530)
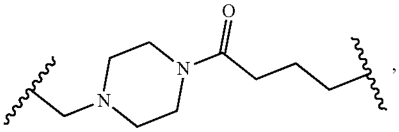
(531)
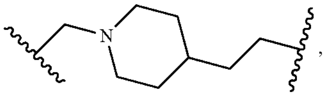
(532)
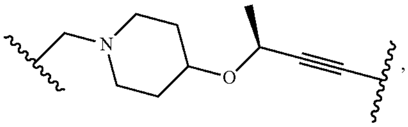
(533)
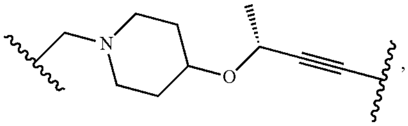
(534)
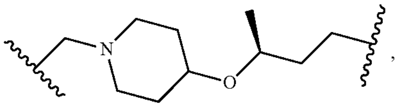
-continued
(535)
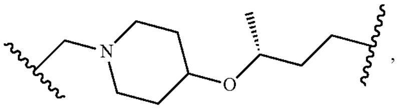
(536)
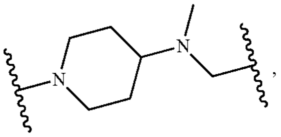
(537)
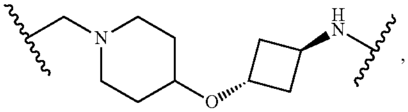
(538)
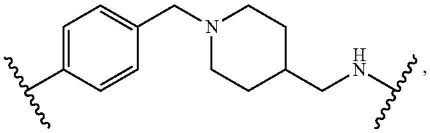
(539)
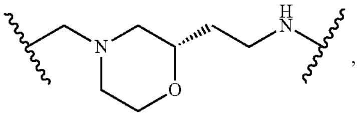
(540)
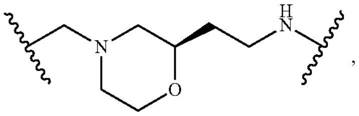
(541)
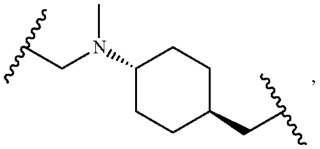
(542)
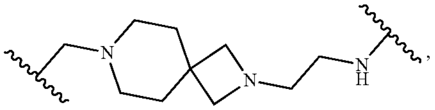
(543)
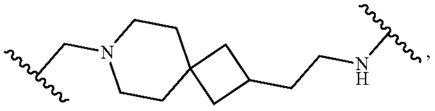
(544)
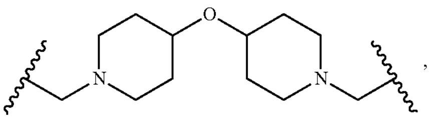
(545)
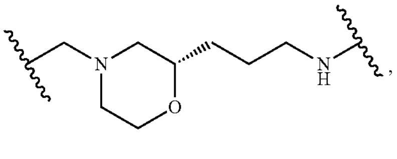

-continued
(546)
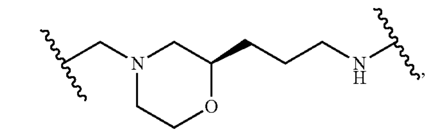
(547)
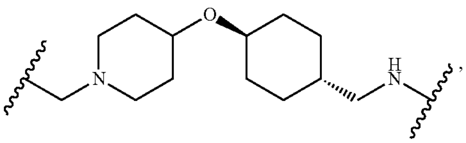
(548)
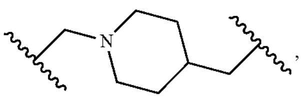
(549)
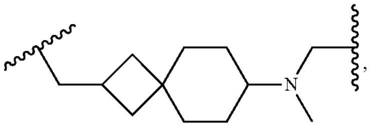
(550)
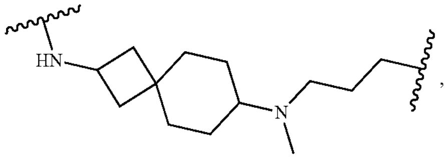
(551)
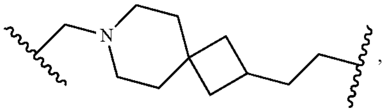
(552)
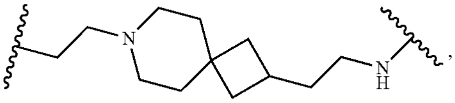
(553)
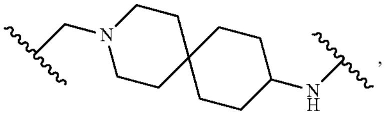
(554)
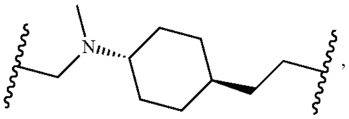
(555)
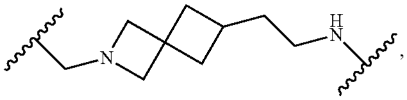
(556)
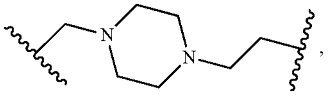
(557)
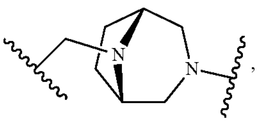
-continued
(558)
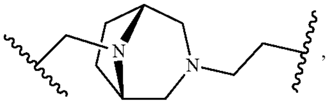
(559)
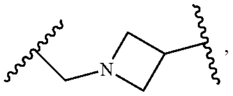
(560)
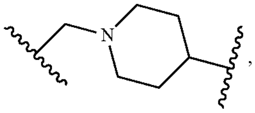
(561)
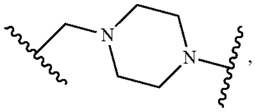
(562)
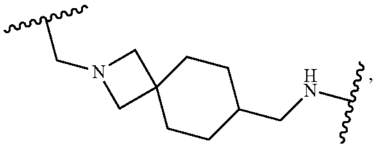
(563)
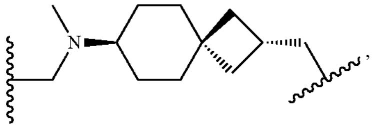
(564)
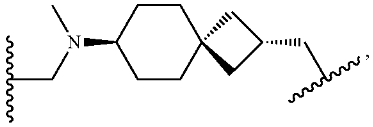
(565)
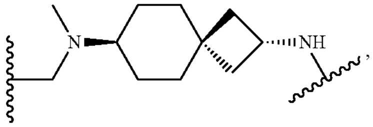
(566)
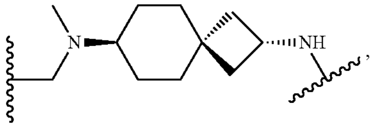
(567)
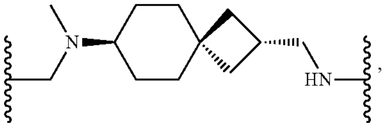
(568)
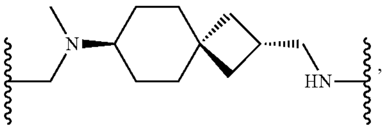
(569)
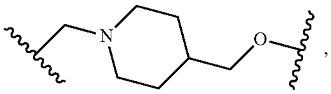

-continued
(570)
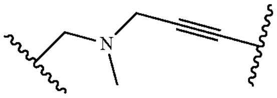,
(571)
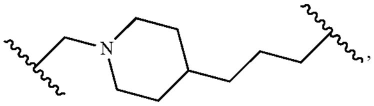,
(572)
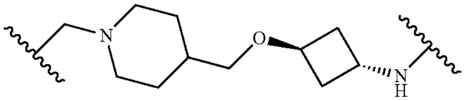,
(573)
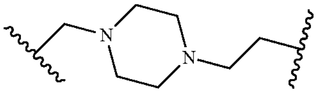,
(574)
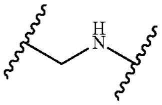,
(575)
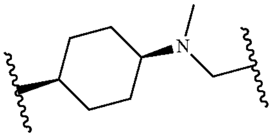,
(576)
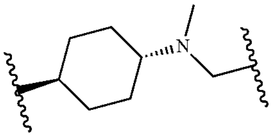,
(577)
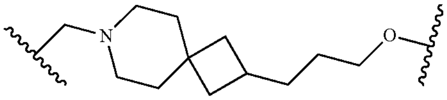,
(578)
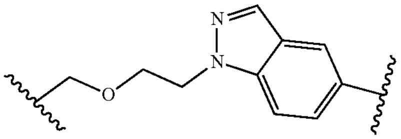,
(579)
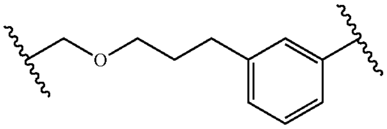,
(580)
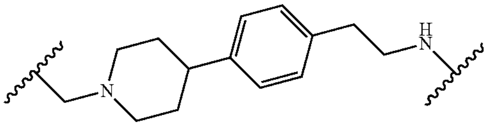,
(581)
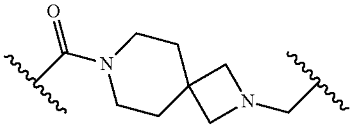,
-continued
(582)
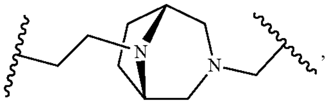,
(583)
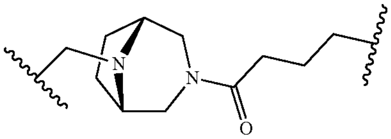,
(584)
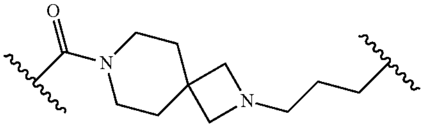,
(585)
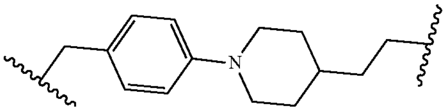,
(586)
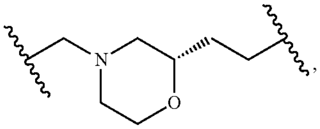,
(587)
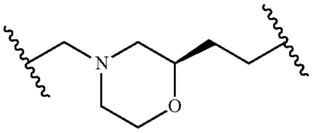,
(588)
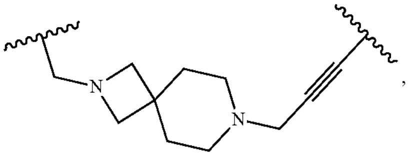,
(589)
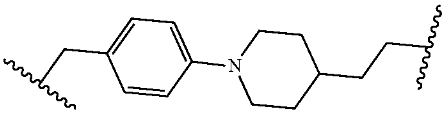,
(590)
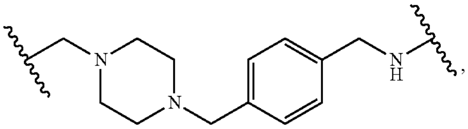,
(591)
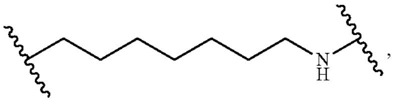,
(592)
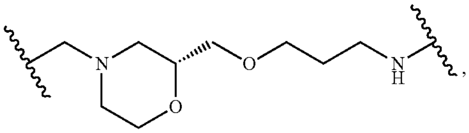, -continued
(593)
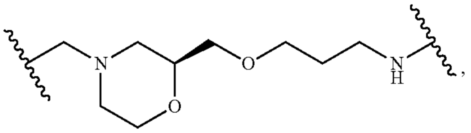
(594)
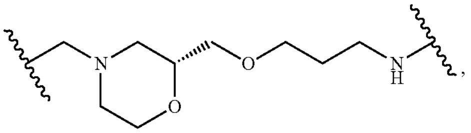
(595)
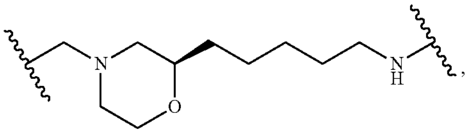
(596)
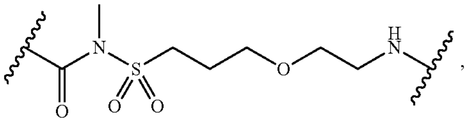
(597)
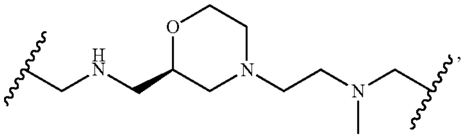
(598)
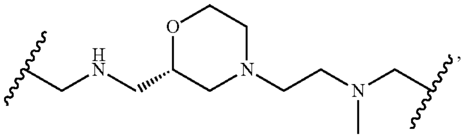
(599)
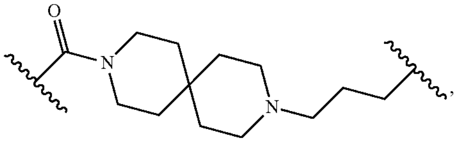
(600)
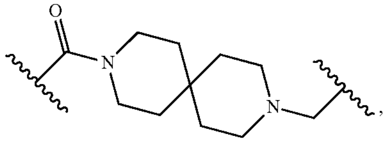
(601)
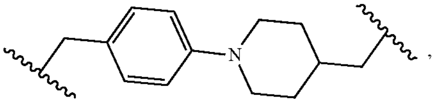
(602)
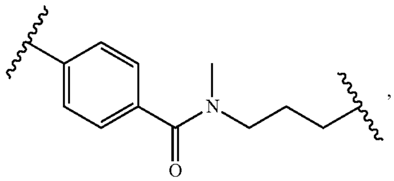
(603)
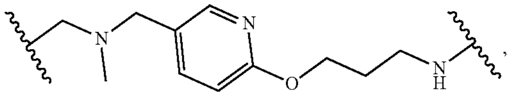
-continued
(604)
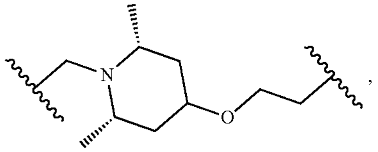
(605)
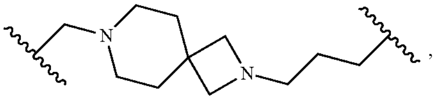
(606)
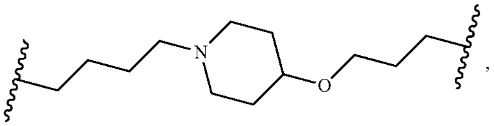
and
(607)
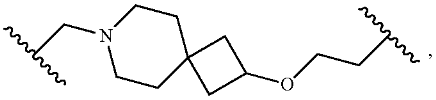
(608)
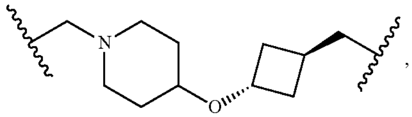
(609)
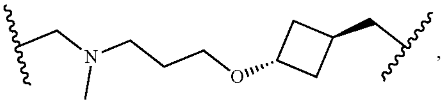
(610)
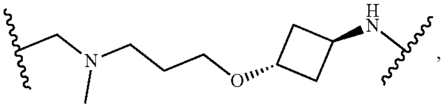
(611)
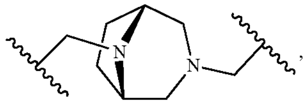
(612)
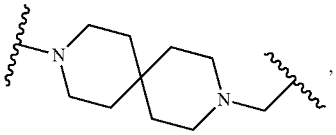
(613)
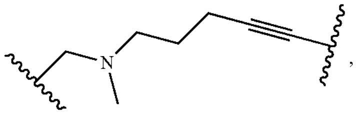
(614)
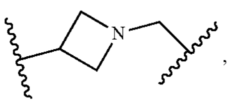
(615)
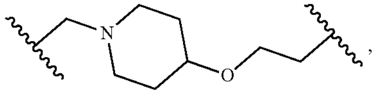

-continued (616)

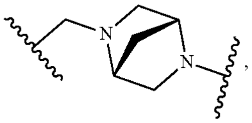

(617)

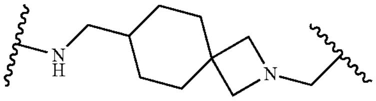

(618)

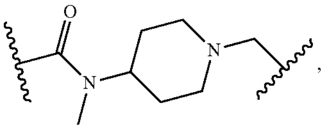

(619)

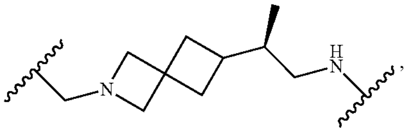

(620)

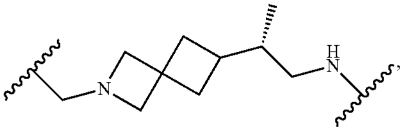

(621)

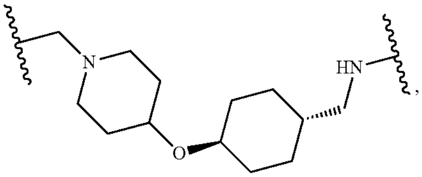

(622)

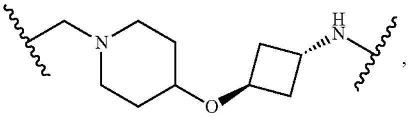

(623)

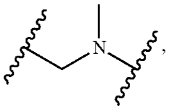

(624)

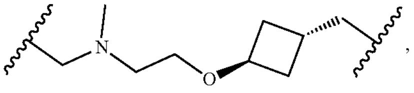

(625)

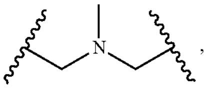

(626)

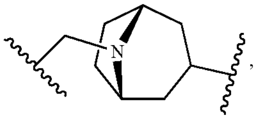

(627)

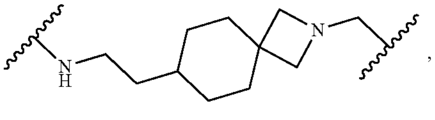

-continued (628)

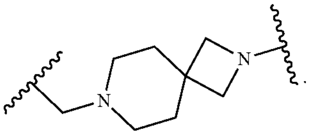

In some embodiments, the linker suitable for use in the compounds of the present disclosure (e.g., CIP, TCIP) are provided in U.S. Publication Number 2019/0076540A1, which is herein incorporated by reference for its disclosure of said linkers.

In some embodiments, the linker suitable for use in the compounds of the present disclosure (e.g., CIP, TCIP) can include one or more members selected from the following:

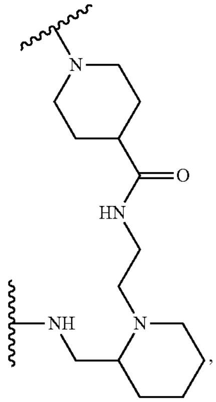

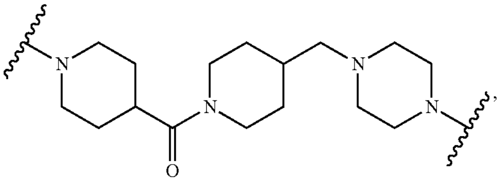

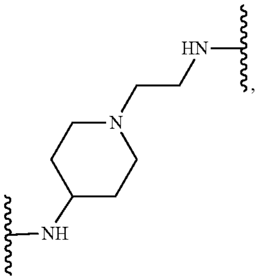

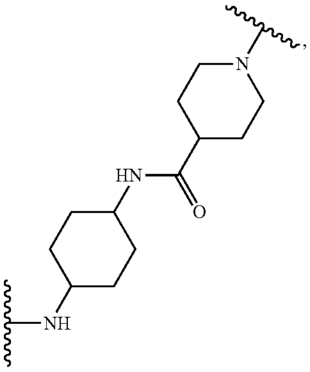

-continued
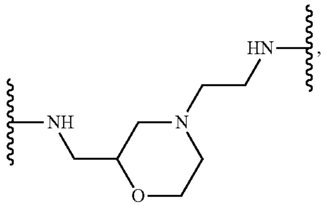
,
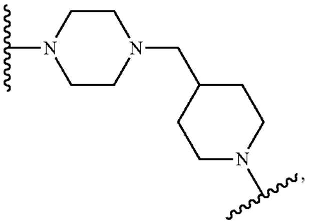
,
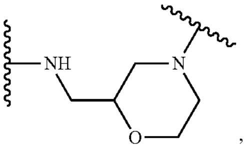
,
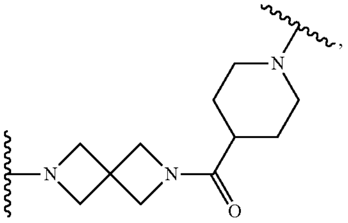
,
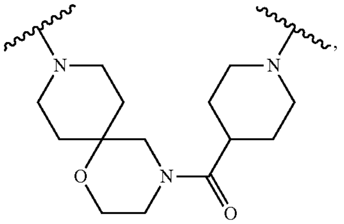
,
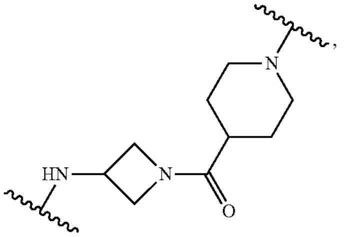
,
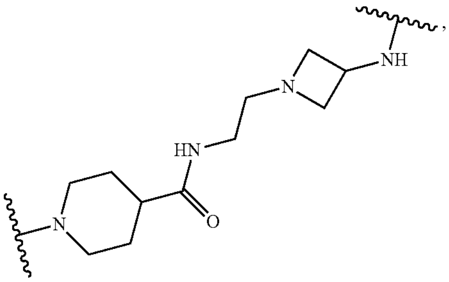
,
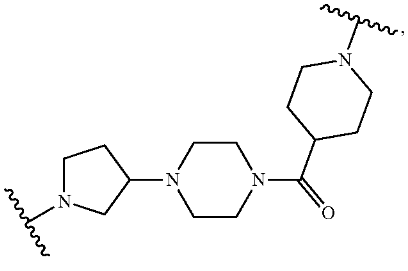
,
-continued
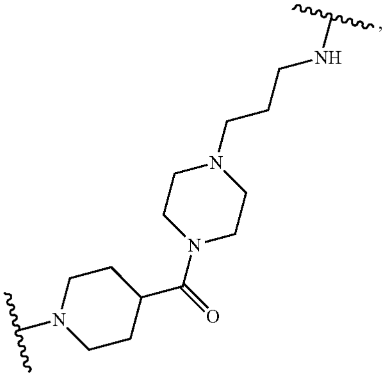
,
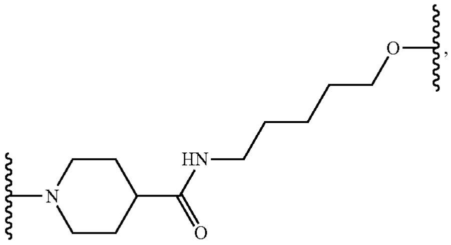
,
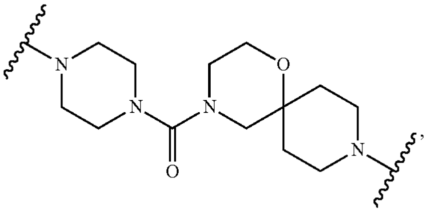
,
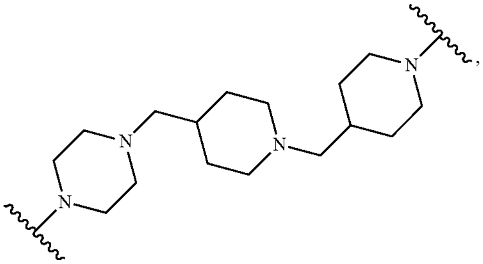
,
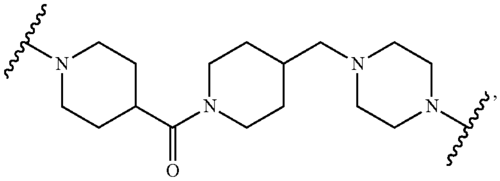
,
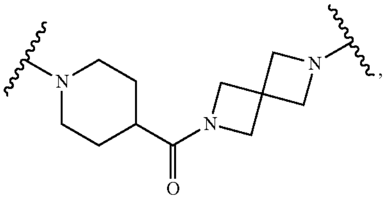
,
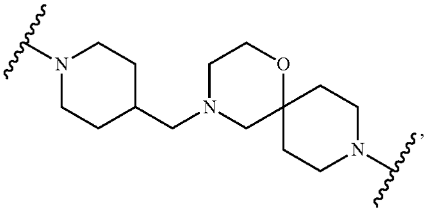
, -continued
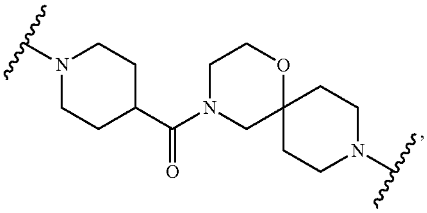
,
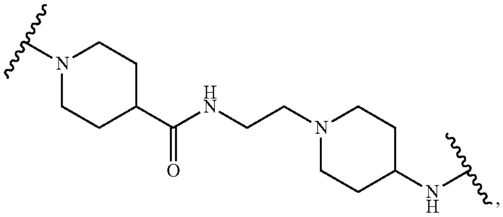
,
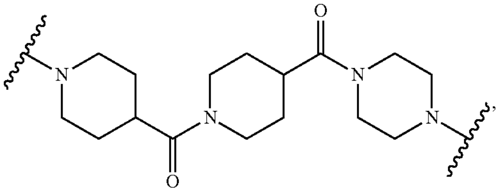
,
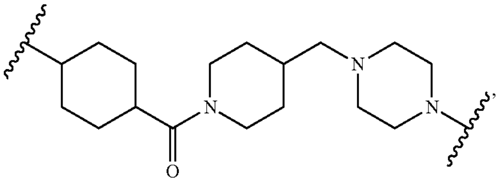
,
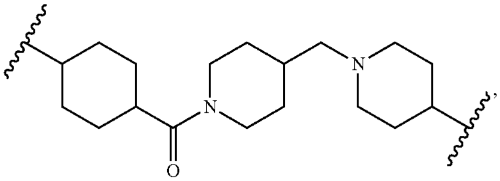
,
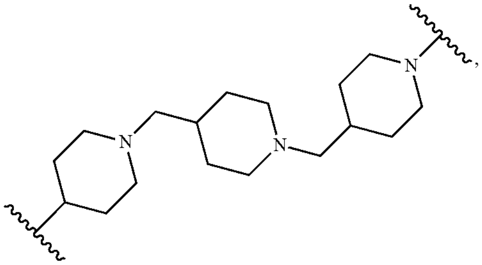
,
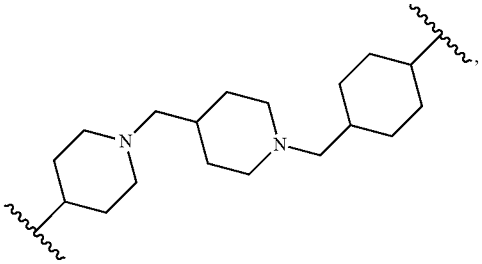
,
-continued
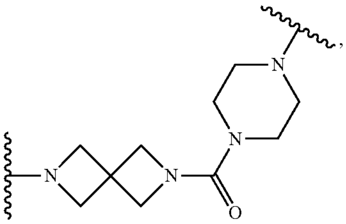
,
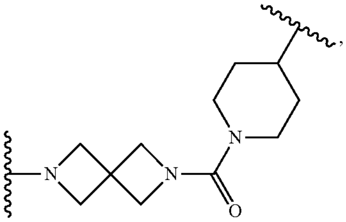
,
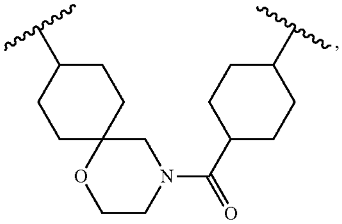
,
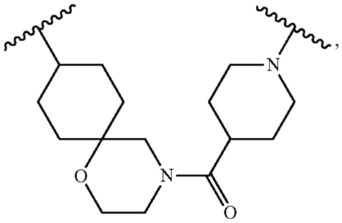
,
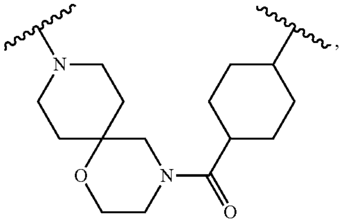
,
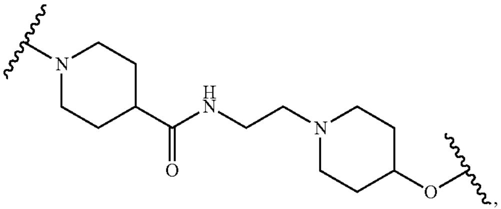
,
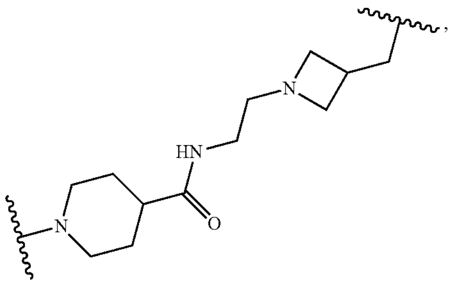
, -continued
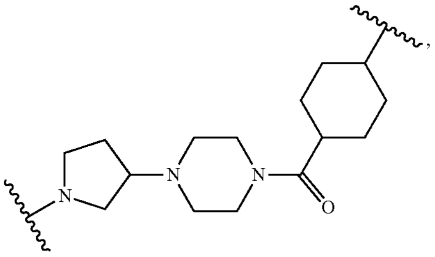
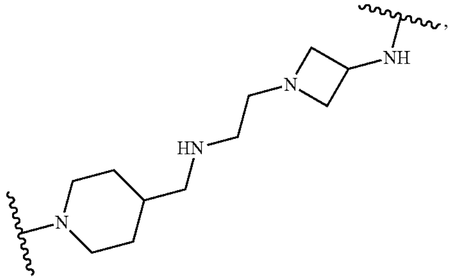
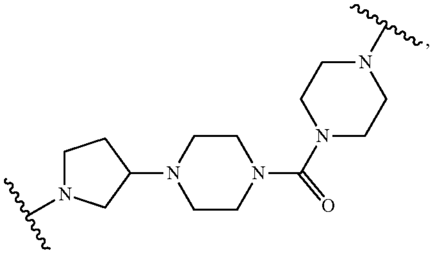
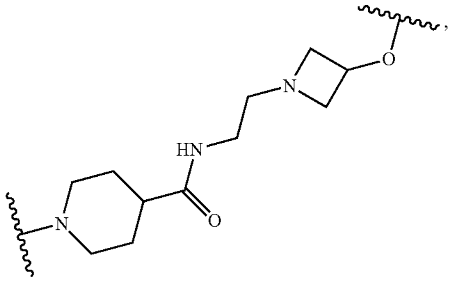
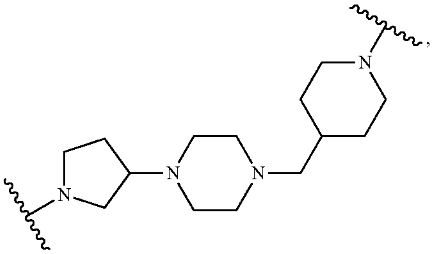
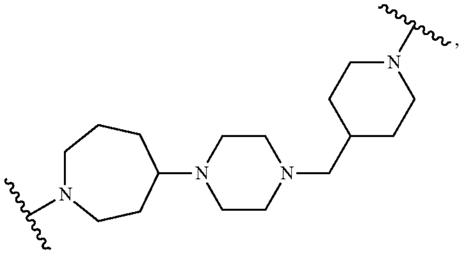
-continued
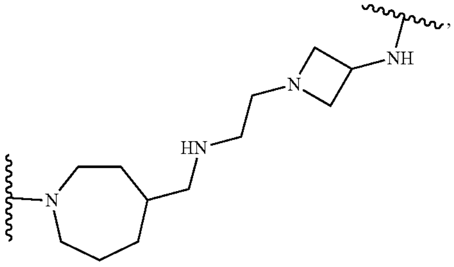
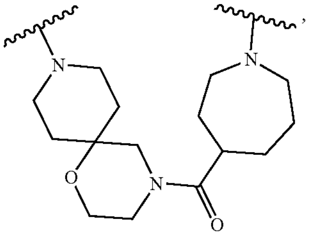
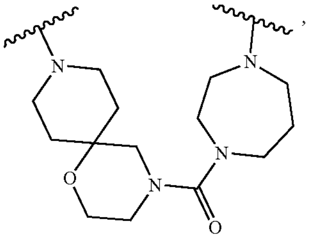
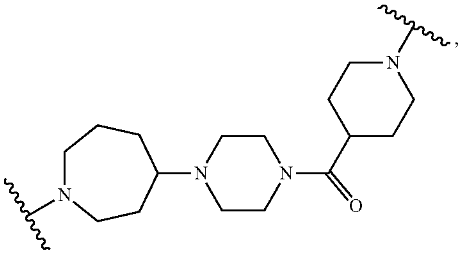
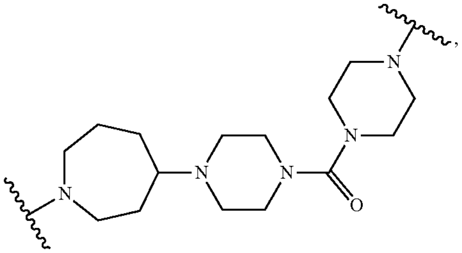
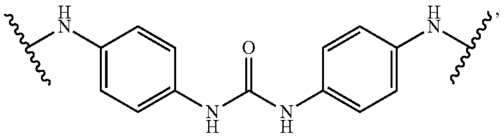
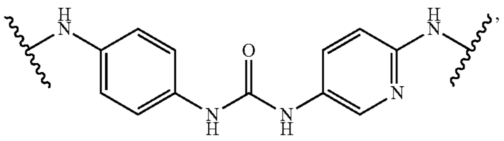
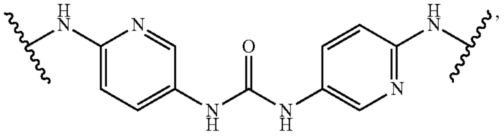

-continued
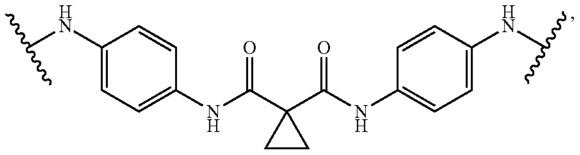,
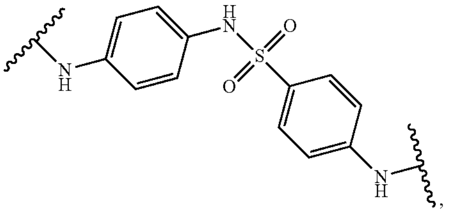,
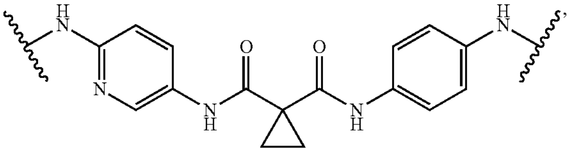,
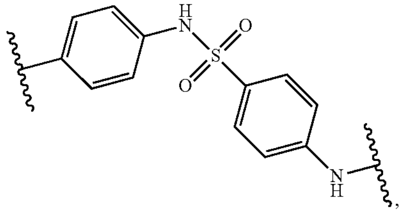,
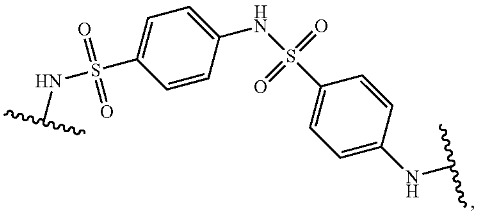,
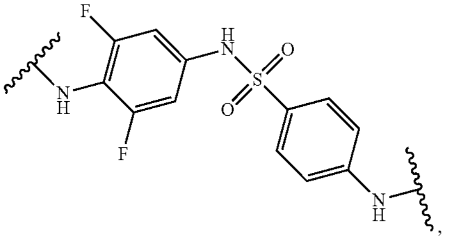,
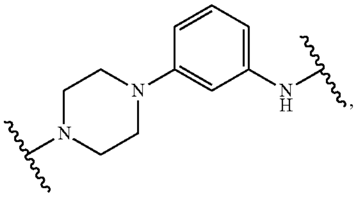,
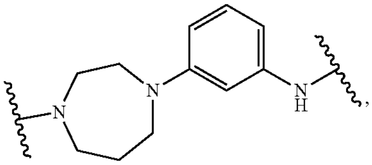,
-continued
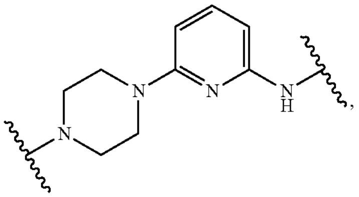,
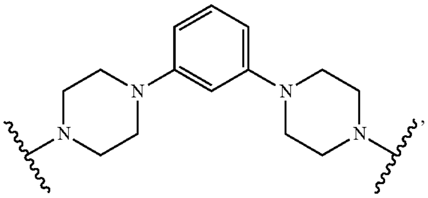,
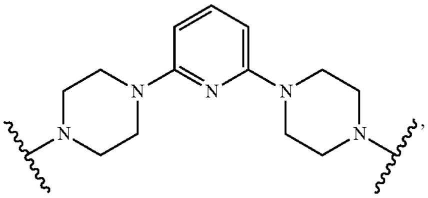,
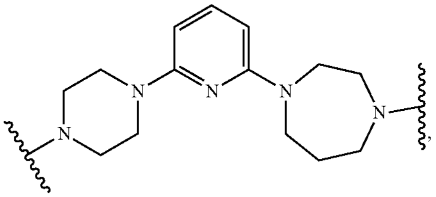,
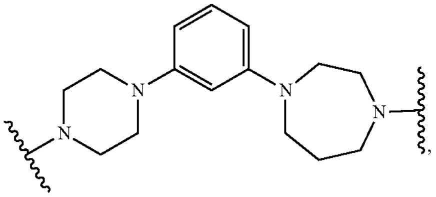,
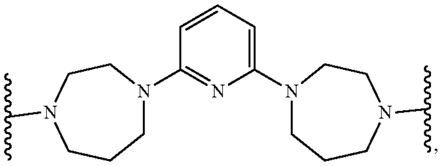,
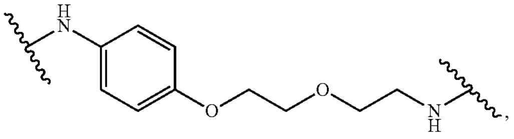,
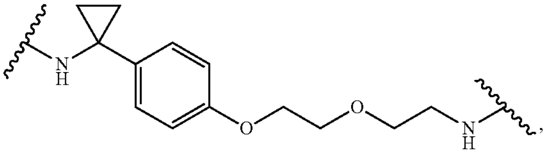,
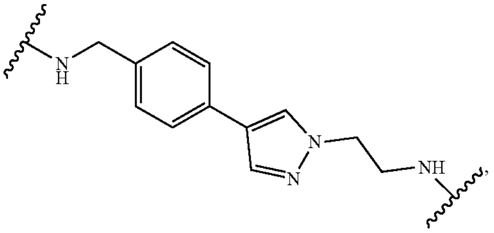, -continued
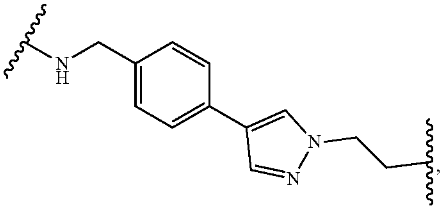
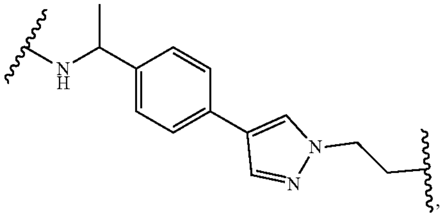
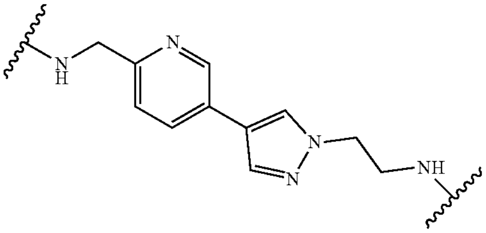
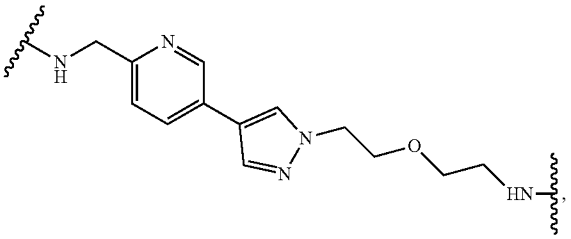
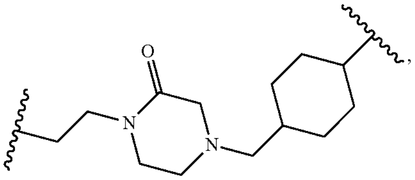
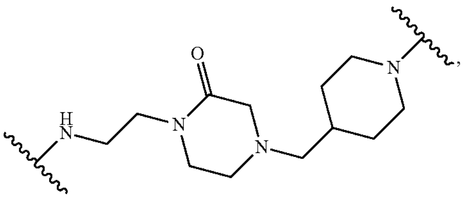
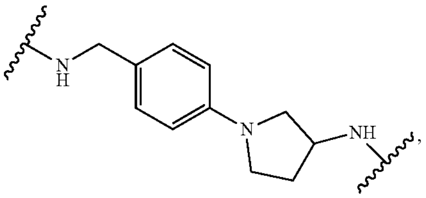
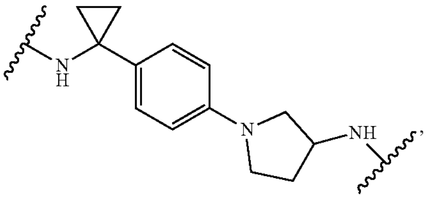
-continued
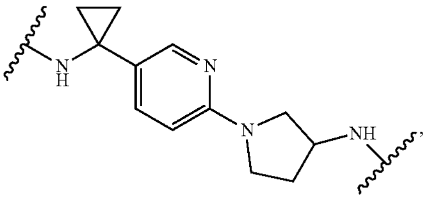
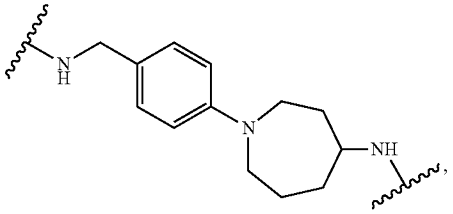
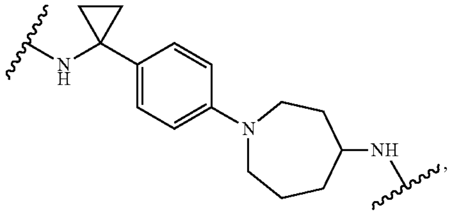
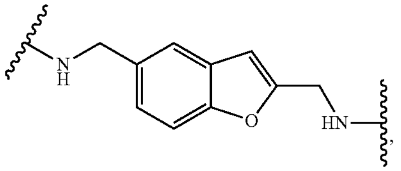
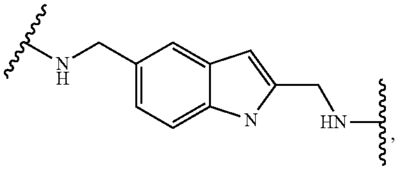
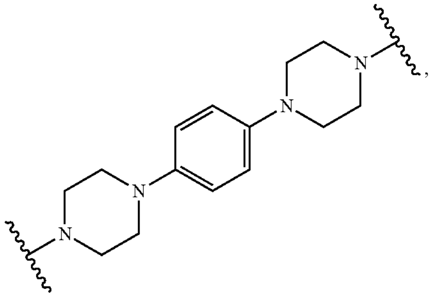
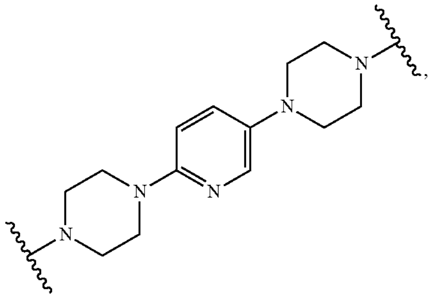

-continued

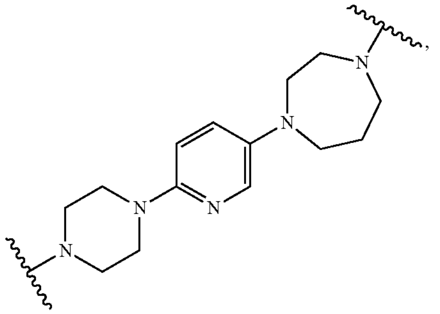

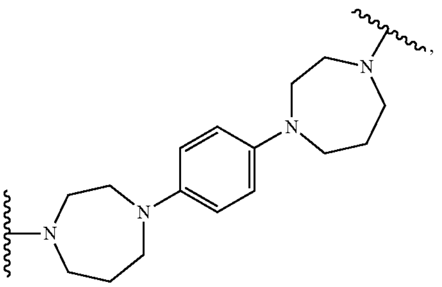

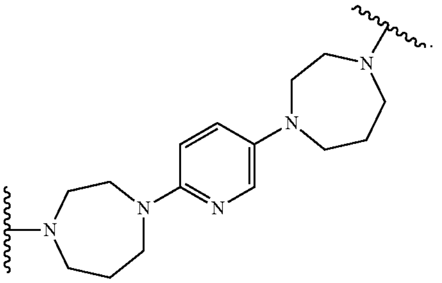

In some embodiments, the Linker is selected from the group consisting of: Formula LI, Formula LII, Formula LIII, Formula LIV, Formula LV, Formula LVI, and Formula LVII:

(L1)

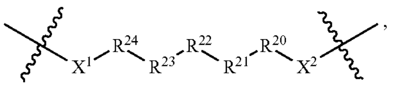

(LII)

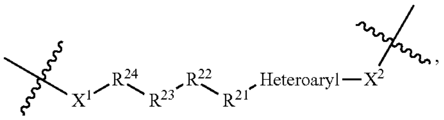

(LIII)

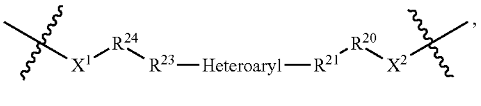

(LIV)

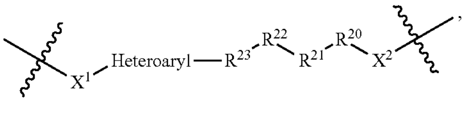

(LV)

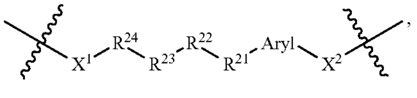

-continued (LVI)

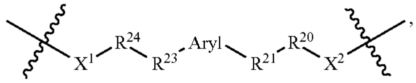

and (LVII)

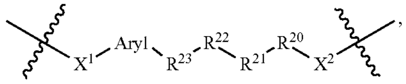

wherein:

$X^1$ and $X^2$ are independently selected from bond, NH, $NR^{25}$, $CH_2$, $CHR^{25}$, $C(R^{25})_2$, O, and S;

$R^{20}$, $R^{21}$, $R^{22}$, $R^{23}$, and $R^{24}$ are independently selected from bond, alkyl, —C(O)—C(O)O—, —OC(O)—, —C(O)alkyl, —C(O)Oalkyl, —C(S)—, —$SO_2$—, —S(O)—, —C(S)—, —C(O)NH—, —NHC(O)—, —N(alkyl)C(O)—, —C(O)N(alkyl)-, —O—, —S—, —NH—, —N(alkyl)—, —CH(—O—$R^{26}$)—, —CH(—$NHR^{25}$)—, —CH(—$NH_2$)—, —CH(—$NR^{25}{}_2$)—, —C(—O—$R^{26}$)alkyl-, —C(—$NHR^{25}$)alkyl-, —C(—$NH_2$)alkyl-, —C(—$NR^{25}{}_2$)alkyl-, —C($R^4R^4$)—, -alkyl($R^{27}$)-alkyl($R^{28}$)—, —C($R^{27}R^{28}$)—, —P(O)($OR^{26}$)O—, —P(O)($OR^{26}$)—, —NHC(O)NH—, —N($R^{25}$)C(O)N($R^{25}$)—, —N(H)C(O)N($R^{25}$)—, polyethylene glycol, poly(lactic-co-glycolic acid), alkene, haloalkyl, alkoxy, and alkyne;

or $R^{20}$, $R^{21}$, $R^{22}$, $R^{23}$, and $R^{24}$ can in addition to those above be independently selected from heteroarylalkyl, aryl, arylalkyl, heterocycle, aliphatic, heteroaliphatic, heteroaryl, polypropylene glycol, lactic acid, glycolic acid, carbocycle, or —O—$(CH_2)_{1-12}$—O—, —NH—$(CH_2)_{1-12}$—NH—, —NH—$(CH_2)_{1-12}$—O—, or —O—$(CH_2)_{1-12}$—NH—, —S—$(CH_2)_{1-12}$—O—, —O—$(CH_2)_{1-12}$—S—, —S—$(CH_2)_{1-12}$—S—, —S—$(CH_2)_{1-12}$—NH—, —NH—$(CH_2)_{1-12}$—S—, (and wherein the 1-12 can be independently 1, 2, 3, 4, 5, 6, 7, 8, 9, 10, 11 or 12, and wherein one or more of the $CH_2$ or NH can be modified by substitution of a H for a methyl, ethyl, cyclopropyl, F (if on carbon), etc, as described herein), and optionally, a heteroatom, heteroalkyl, aryl, heteroaryl or cycloaliphatic group is interspersed in the chain).

Certain nonlimiting examples include —O—$CH(CH_3)$—$CH(CH_3)CH$—O—, —O—$CH_2$—$CH(CH_3)CH$—O—, —O—$CH(CH_3)$—$CH_2CH$—O—, etc. each of which $R^{20}$, $R^{21}$, $R^{22}$, $R^{23}$, and $R^{24}$ is optionally substituted with one or more substituents selected from $R^{101}$ or alternatively as described herein;

$R^{25}$ is selected at each instance from: alkyl, —C(O)H, —C(O)OH, —C(O)alkyl, —C(O)Oalkyl, alkenyl, or alkynyl or alternatively can be aliphatic, heteroaliphatic, aryl, heteroaryl or heterocyclic;

$R^{26}$ is hydrogen, alkyl, silane, arylalkyl, heteroarylalkyl, alkene, and alkyne; or in addition to these can also be selected from aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C═$CH_2$, a $C_3$-$C_6$ spirocarbocycle, or a 4-, 5-, or 6-membered spiroheterocycle comprising 1 or 2 heteroatoms selected from N and O, or form a 1 or 2 carbon bridged ring; $R^{10'}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, -COOalkyl, COOH, $NO_2$, F, Cl, Br, I, $CF_3$, $NH_2$, NHalkyl, $N(alkyl)_2$, $NR^{25}R^{25}$, $NHR^{25}$, aliphatic, heteroaliphatic, and $COR^4$; and $R^4$ is selected from hydrogen, alkyl, aliphatic, heteroaliphatic, aryl, heteroaryl, carbocyclic, hydroxyl, alkoxy, amine, —NHalkyl, or —$Nalkyl_2$;

In an additional embodiment, the Linker may be selected from the group consisting of: Formula LVIII, LIX, and LX:

(LVIII)

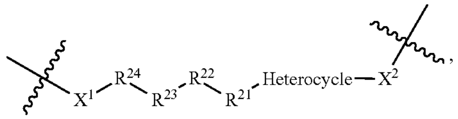

(LIX)

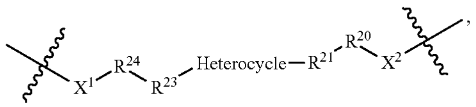

and (LX)

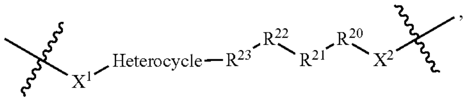

wherein each variable is as it is defined in Formula LI. In alternative embodiments of LVIII, LIX and LX, a carbocyclic ring is used in place of the heterocycle.

The following are non-limiting examples of Linkers that can be used in this disclosure. As certain non-limiting examples, Formula LI, Formula LII, Formula LIII, Formula LIV, Formula LV, Formula LVI, or Formula LVII include:

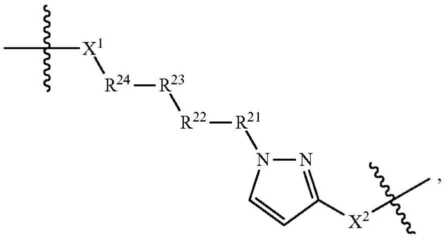

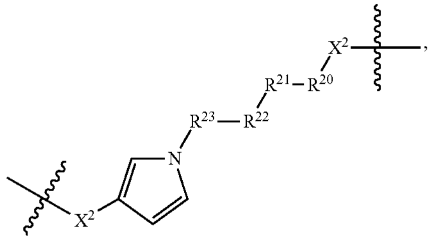

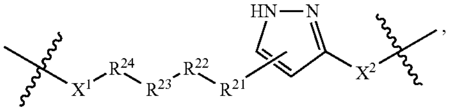

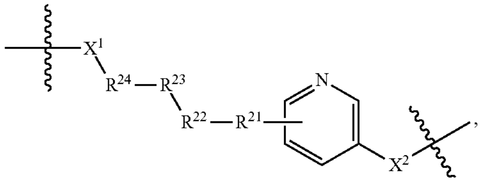

-continued

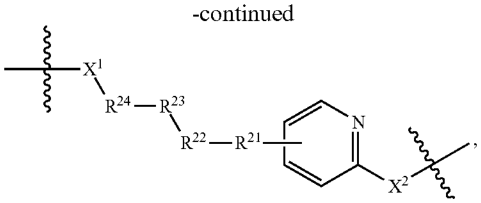

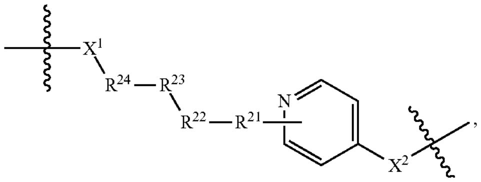

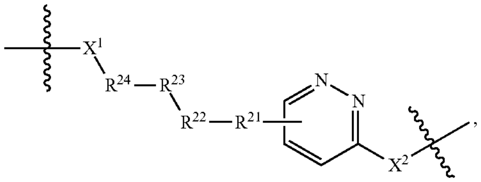

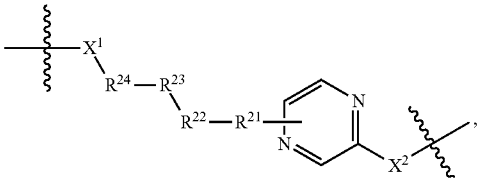

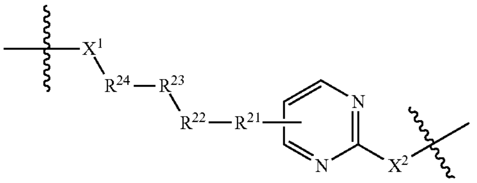

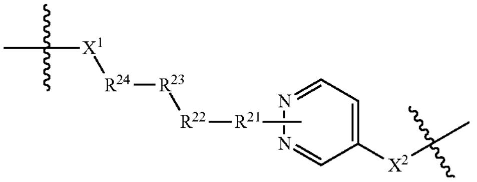

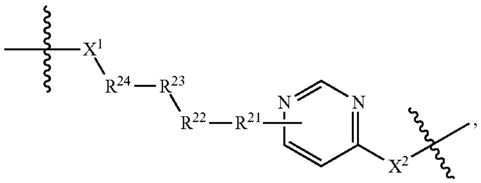

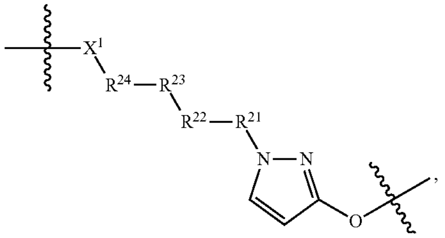

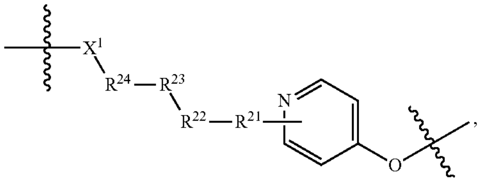

-continued
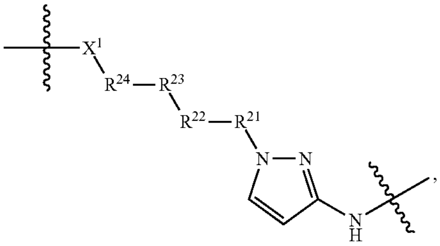
,
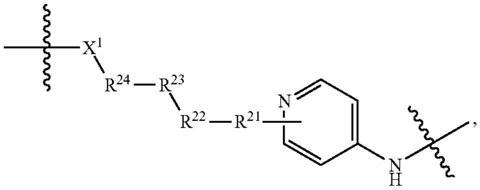
,
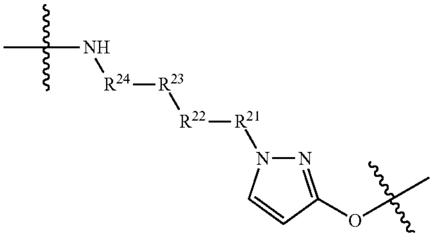
,
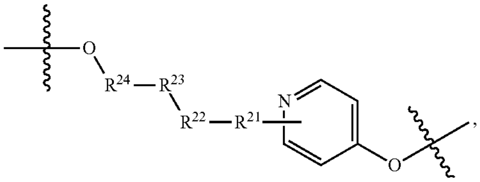
,
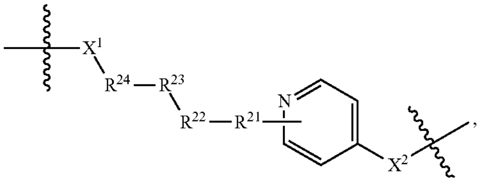
,
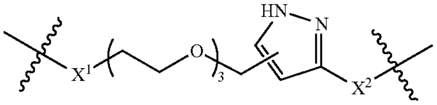
,
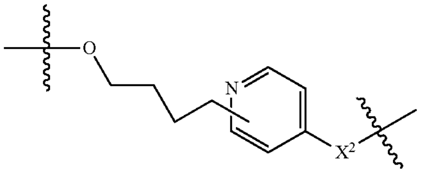
,
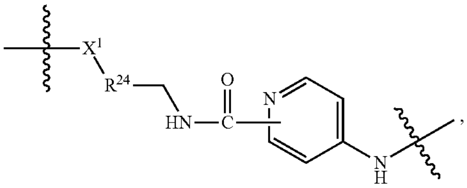
,
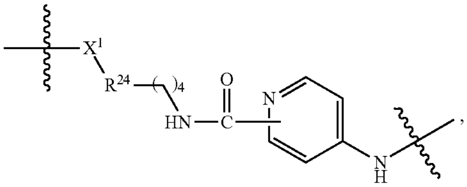
,
-continued
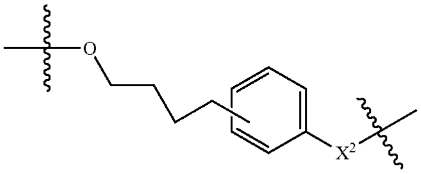
,
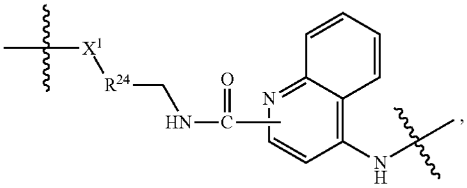
,
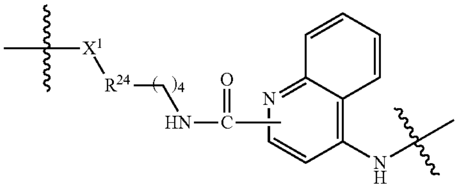
, and
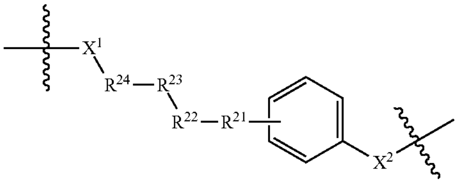
.
In Some Embodiments, the Linker May be Selected from:
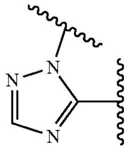
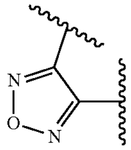
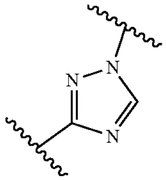
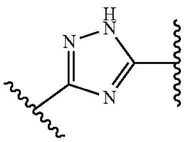
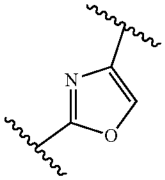
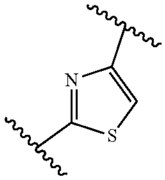
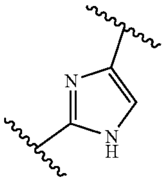
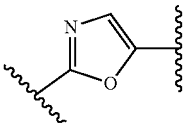
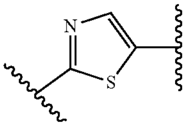

In Some Embodiments, the Linker May be Selected from:

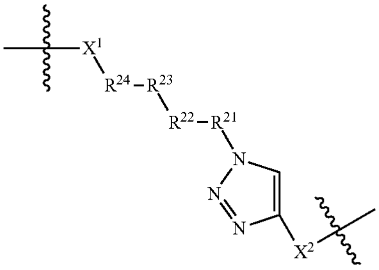

,

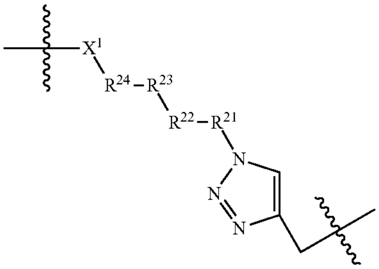

,

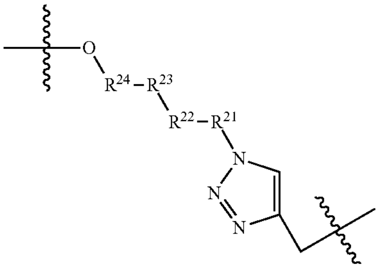

,

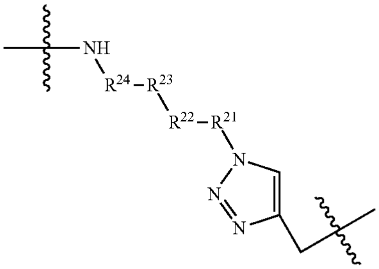

,

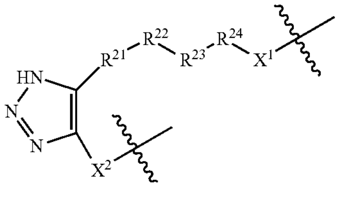

,

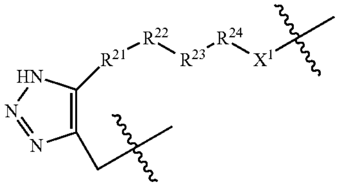

,

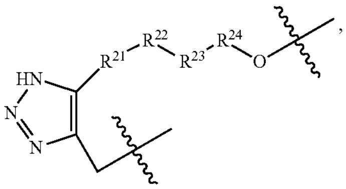

, and

-continued

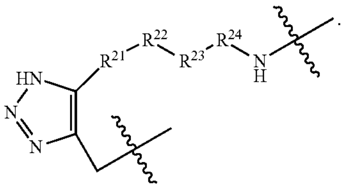

.

In some embodiments, $X^1$ may be attached to the first moiety and/or the second moiety (of a compound of the disclosure). In other embodiments, $X^2$ may be attached to the first moiety and/or the second moiety (of a compound of the disclosure).

Non-Limiting Examples of Moieties of $R^{20}$, $R^{21}$, $R^{22}$, $R^{23}$, and $R^{24}$ Include:

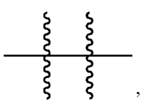

,

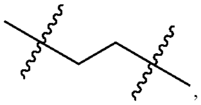

,

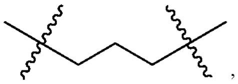

,

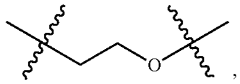

,

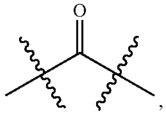

,

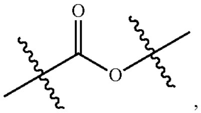

,

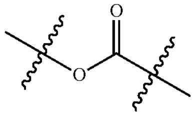

,

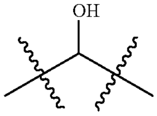

,

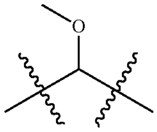

,

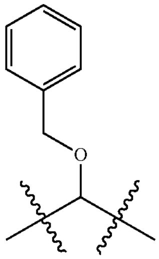

,

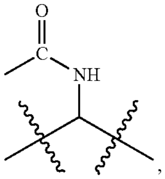

,

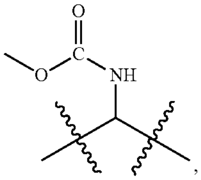

,

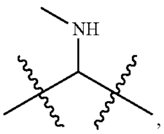

,

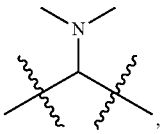

,

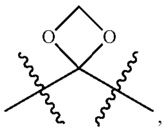

,

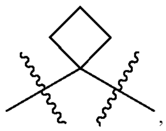

,

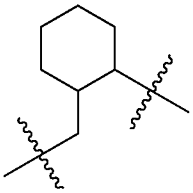

,

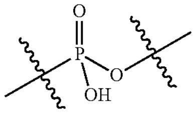

, and

-continued
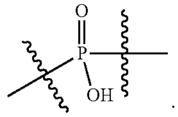.
Additional non-limiting examples of moieties of $R^{20}$, $R^{21}$, $R^{22}$, $R^{23}$, and $R^{24}$ include:
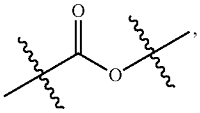, 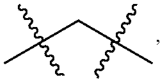,
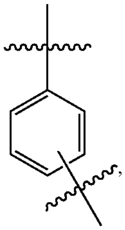, 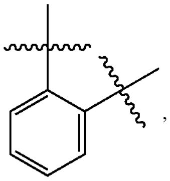, 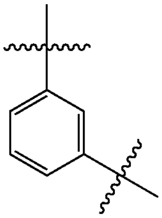,
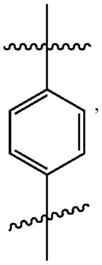, 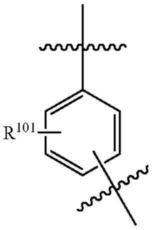, 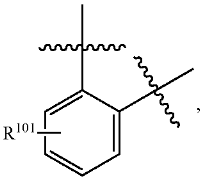,
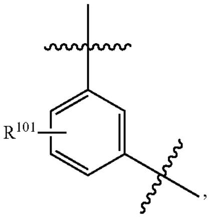, 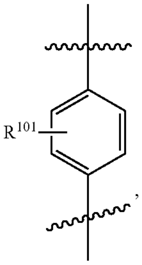,
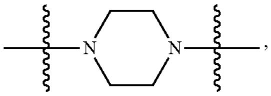, 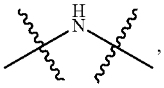,
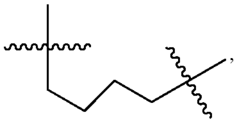, 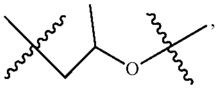,
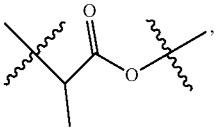, 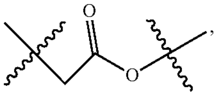,
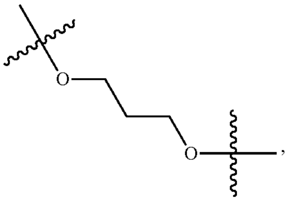,
-continued
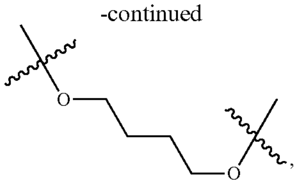,
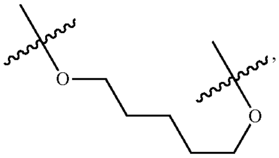, 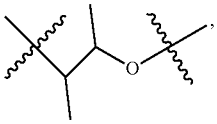,
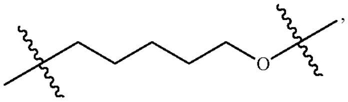,
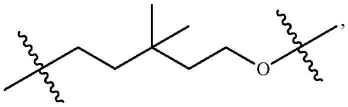,
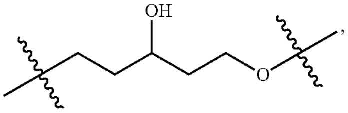,
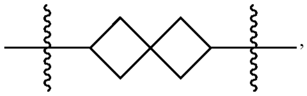,
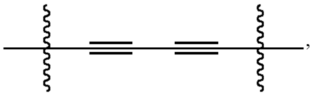,
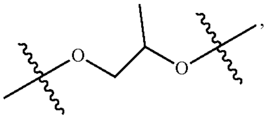,
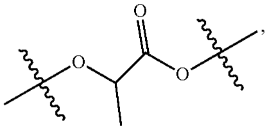, 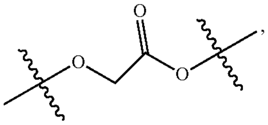,
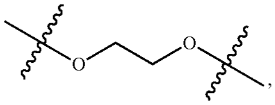, and
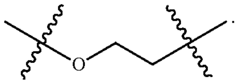.
Additional non-limiting examples of moieties of $R^{20}$, $R^{21}$, $R^{22}$, $R^{23}$, and $R^{24}$ include:
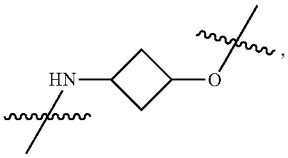,
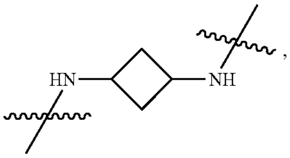, -continued

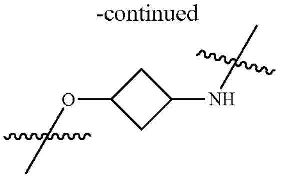

,

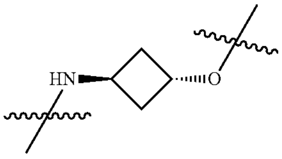

,

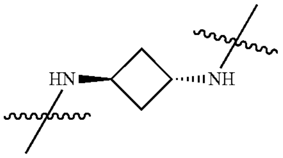

,

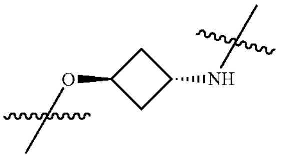

,

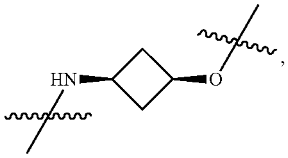

,

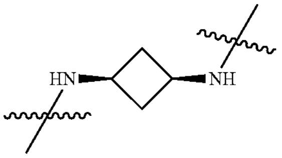

,

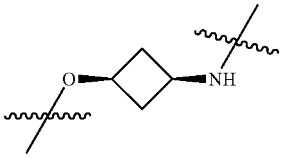

,

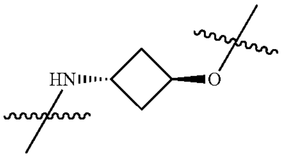

,

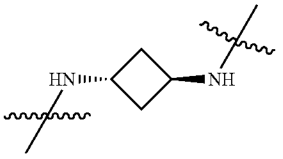

,

In some embodiments, the Linker group may be an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In some embodiments, the Linker may be flanked, substituted, or interspersed with an aryl, phenyl, benzyl, alkyl, alkylene, or heterocycle group. In some embodiments, the Linker may be asymmetric or symmetrical. In some embodiments, the Linker may be a substituted or unsubstituted polyethylene glycol group ranging in size from about 1 to about 12 ethylene glycol units, from 1 to about 10 ethylene glycol units, about 2 about 6 ethylene glycol units, about 2 to about 5 ethylene glycol units, or about 2 to about 4 ethylene glycol units. In any of the embodiments of the compounds described herein, the Linker group may be any suitable moiety as described herein.

In Some Embodiments, the Linker May be Selected from:

$—NR^{61}(CH_2)_{n1}$—(lower alkyl)-, $—NR^{61}(CH_2)_{n1}$—(lower alkoxyl)-, $—NR^{61}(CH_2)_{n1}$—(lower alkoxyl)-$OCH_2$—, $—NR^{61}(CH_2)_{n1}$—(lower alkoxyl)-(lower alkyl)-$OCH_2$—, $—NR^{61}(CH_2)_{n1}$—(cycloalkyl)-(lower alkyl)-$OCH_2$—, $—NR^{61}(CH_2)_{n1}$—(heterocycloalkyl)-, $—NR^{61}(CH_2CH_2O)_{n1}$-(lower alkyl)-O—$CH_2$—, $—NR^{61}(CH_2CH_2O)_{n1}$-(heterocycloalkyl)-O—$CH_2$—, $—NR^{61}(CH_2CH_2O)_{n1}$-Aryl-O—$CH_2$—, $—NR^{61}(CH_2CH_2O)_{n1}$-(heteroaryl)-O—$CH_2$—, $—NR^{61}(CH_2CH_2O)_{n1}$-(cycloalkyl)—O—(heteroaryl)-O—$CH_2$—, $—NR^{61}(CH_2CH_2O)_{n1}$-(cycloalkyl)—O—Aryl-O—$CH_2$—, $—NR^{61}(CH_2CH_2O)_{n1}$-(lower alkyl)—NH—Aryl—O—$CH_2$—, $—NR^{61}(CH_2CH_2O)_{n1}$-(lower alkyl)—O—Aryl-$CH_2$, $—NR^{61}(CH_2CH_2O)$n-cycloalkyl—O—Aryl-, $—NR^{61}(CH_2CH_2O)$n-cycloalkyl—O—heteroaryl-, $—NR^{61}(CH_2CH_2)_{n1}$-(cycloalkyl)—O—(heterocycle)-$CH_2$, $—NR^{61}(CH_2CH_2)_{n1}$-(heterocycle)-(heterocycle)-$CH_2$, and $—NR^{61}$-(heterocycle)-$CH_2$;

wherein n1 is 0, 1, 2, 3, 4, 5, 6, 7, 8, 9, or 10; and $R^{61}$ is H, methyl, or ethyl.

In Some Embodiments, the Linker May be Selected from:

$—N(R^{61})—(CH_2)_{m1}-O(CH_2)_{n2}-O(CH_2)_{o1}-O(CH_2)_{p1}-O(CH_2)_{q1}-O(CH_2)_{r1}-OCH_2—$, $—O—(CH_2)_{m1}-O(CH_2)_{n2}-O(CH_2)_{o1}-O(CH_2)_{p1}-O(CH_2)_{q1}-O(CH_2)_{r1}-OCH_2$-, $—O—(CH_2)_{m1}-O(CH_2)_{n2}-O(CH_2)_{o1}-O(CH_2)_{p1}-O(CH_2)_{q1}-O(CH_2)_{r1}—O—$;

$—N(R^{61})—(CH_2)_{m1}-O(CH_2)_{n2}-O(CH_2)_{o1}-O(CH_2)_{p1}-O(CH_2)_{q1}-O(CH_2)_{r1}—O—$;

$—(CH_2)_{m1}-O(CH_2)_{n2}-O(CH_2)_{o1}-O(CH_2)$pr-$O(CH_2)_{q1}-O(CH_2)_{r1}—O—$;

$—(CH_2)_{m1}-O(CH_2)_{n2}-O(CH_2)_{o1}-O(CH_2)_{p1}-O(CH_2)_{q1}-O(CH_2)_{r1}-OCH_2—$;

$—O(CH_2)_{m1}-O(CH_2)_{n2}—O(CH_2)_{p1}—O(CH_2)_{q1}—OCH_2—$;

$—O(CH_2)_{m1}—O(CH_2)_{n2}—O(CH_2)_{p1}—O(CH_2)_{q1}—OCH_2—$; wherein m1, n2, o1, p1, q1, and r1 are independently 1, 2, 3, 4, or 5; and $R^{61}$ is H, methyl, or ethyl.

In Some Embodiments, the Linker May be Selected from:

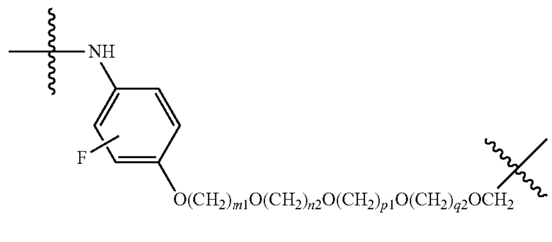

,

-continued
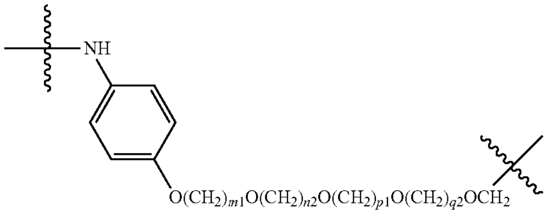
,
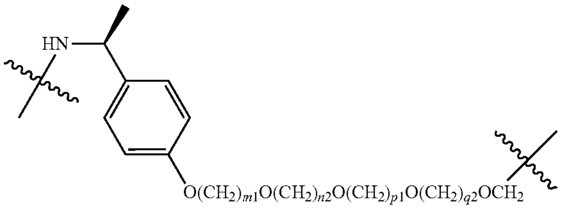
,
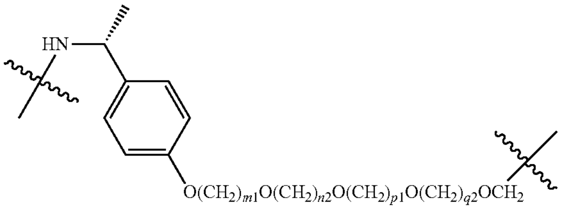
,
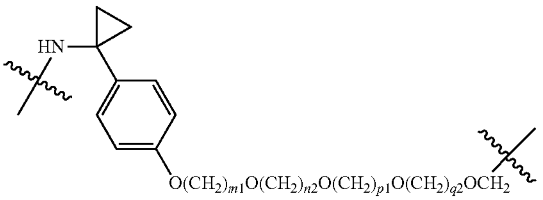
,
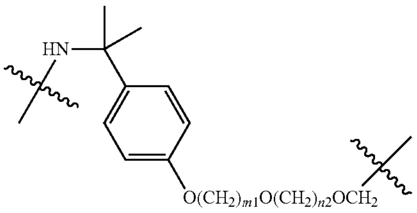
,
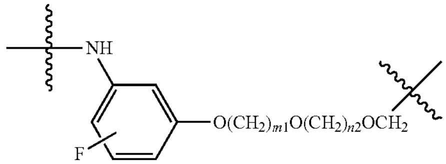
,
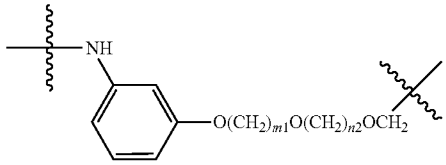
,
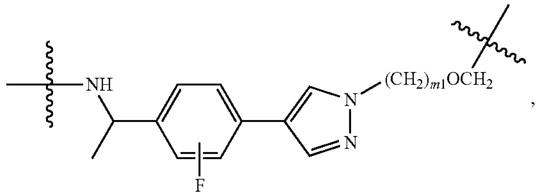
,
wherein m1, n2, 01, p1, q2, and r1 are independently 1, 2, 3, 4, or 5.
In Some Embodiments, the Linker May be Selected from:
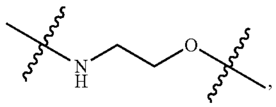
,
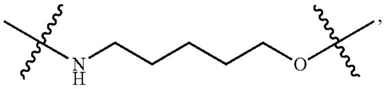
,
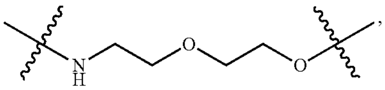
,
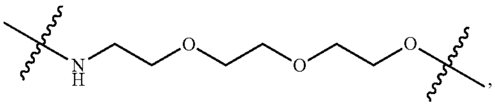
,
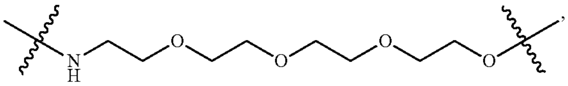
,
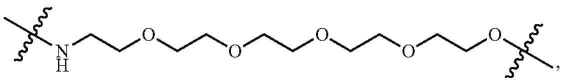
,
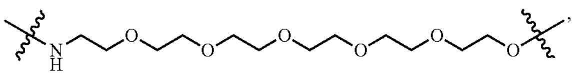
,
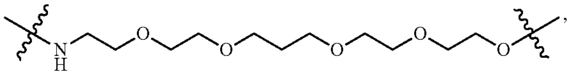
,
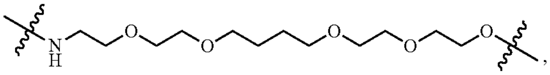
,
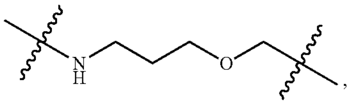
,
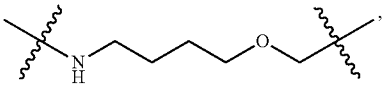
,
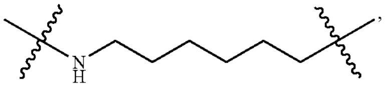
,
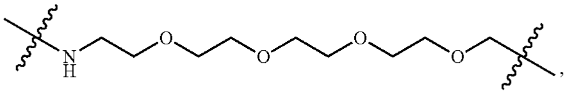
,
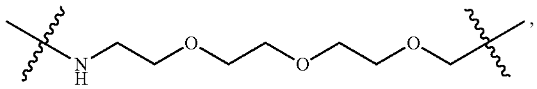
,
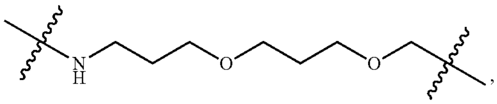
,
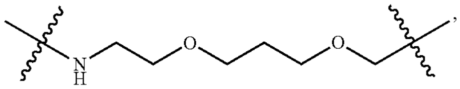
,
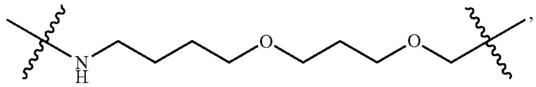
,
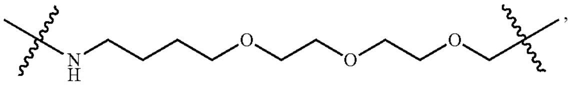
,

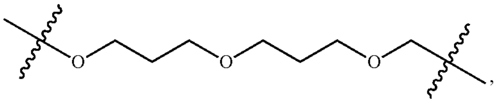
,
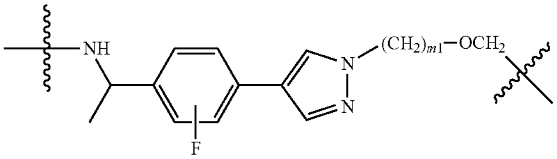
,
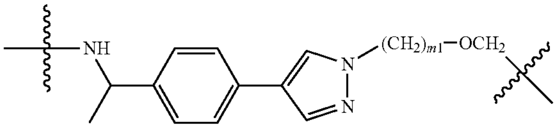
,
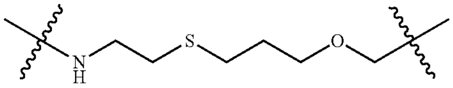
,
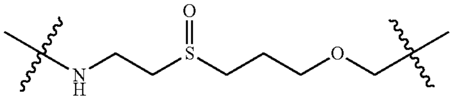
,
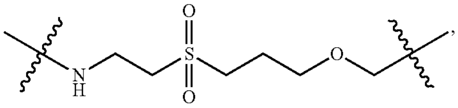
,
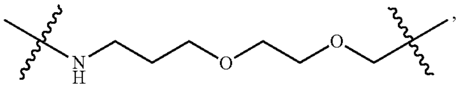
,
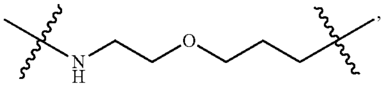
,
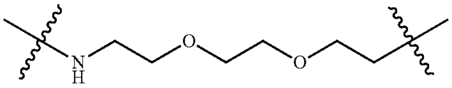
,
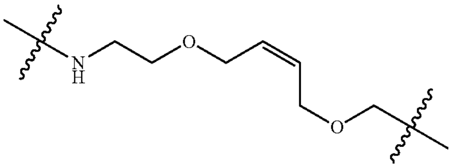
,
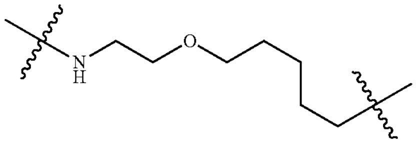
,
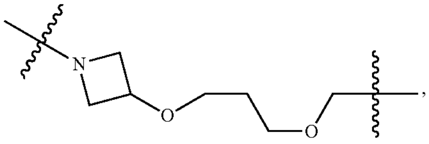
,
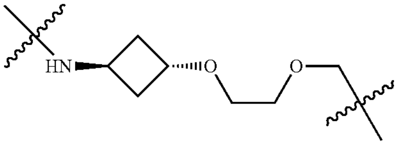
,
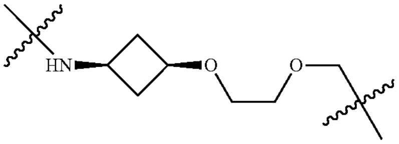
,
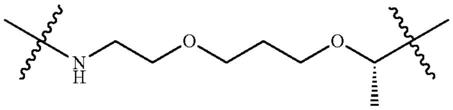
,
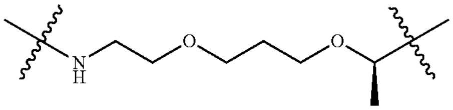
,
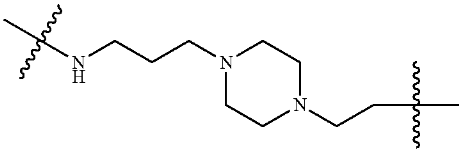
,
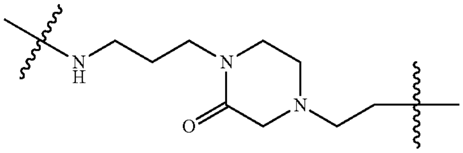
,
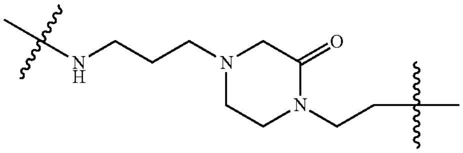
,
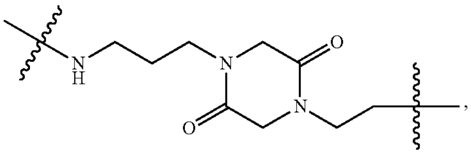
,
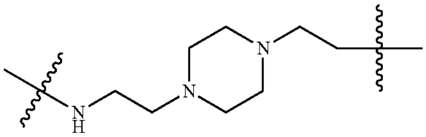
,
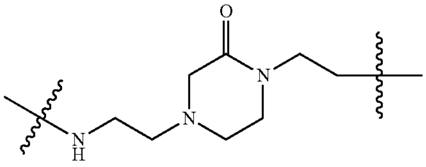
,
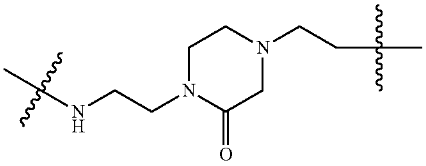
,
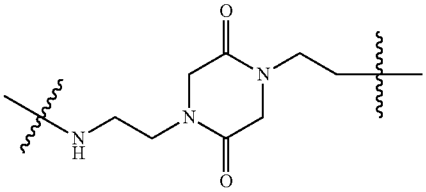
,
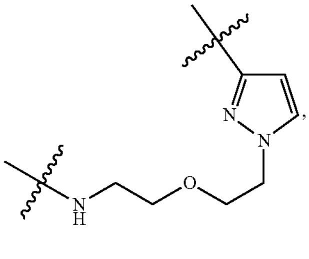
, -continued
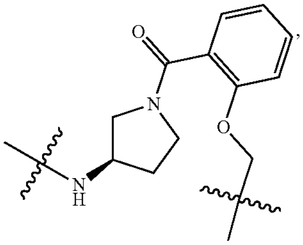
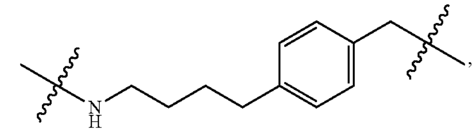
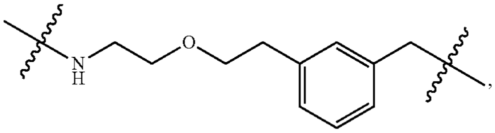
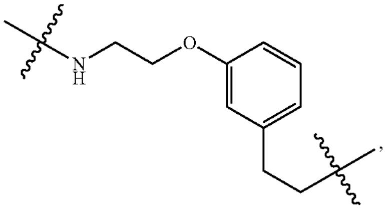
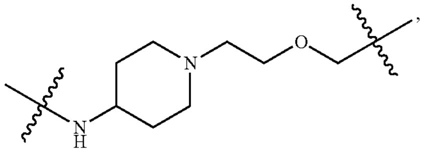
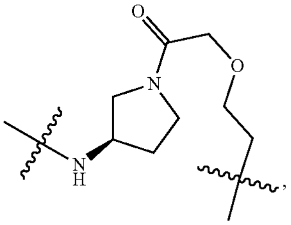
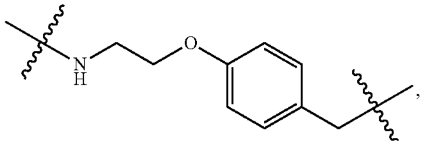
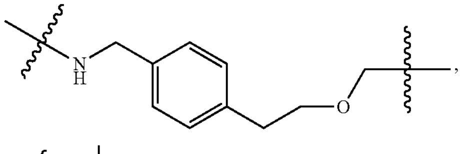
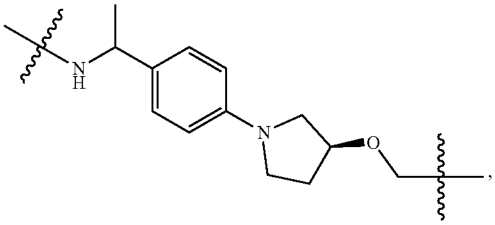
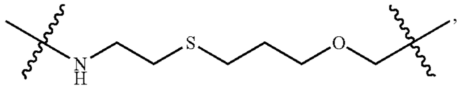
-continued
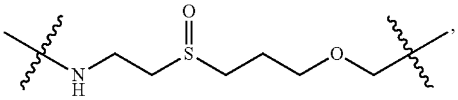
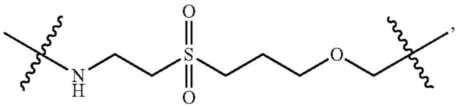
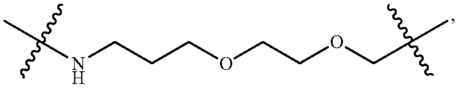
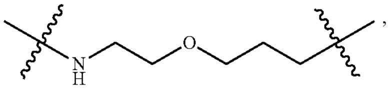
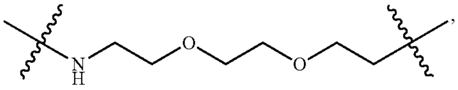
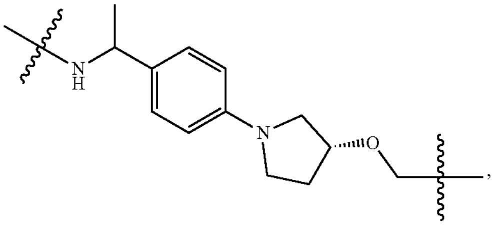
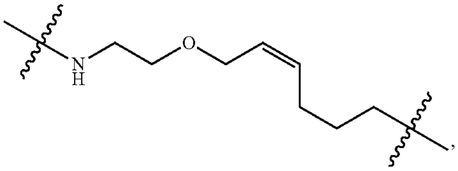
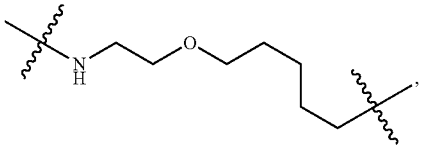
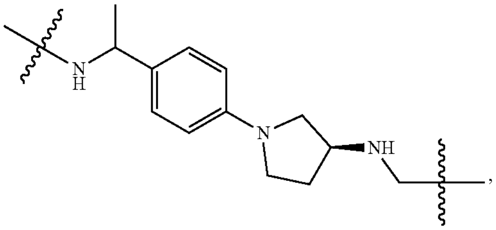
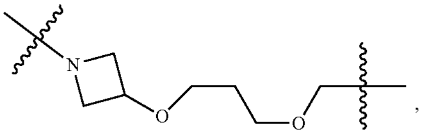
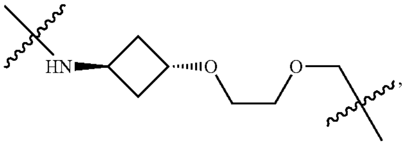
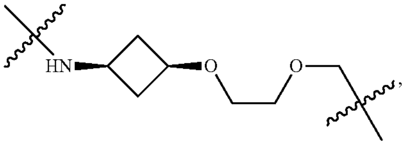

-continued
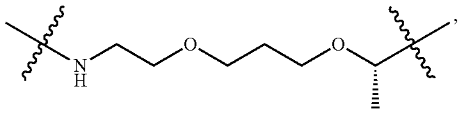,
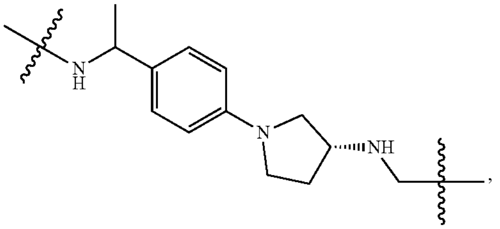,
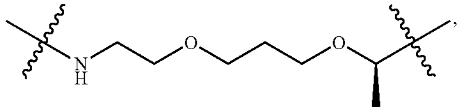,
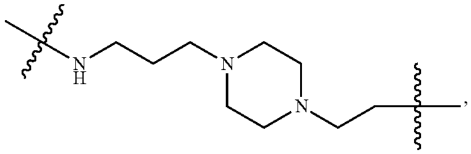,
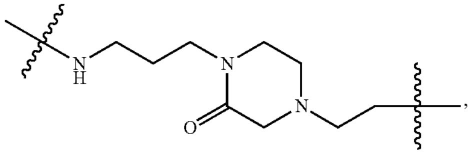,
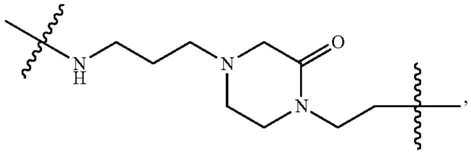,
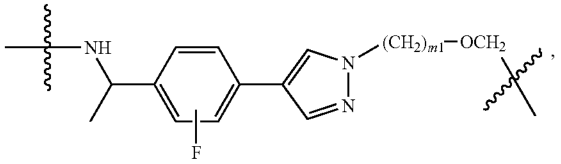,
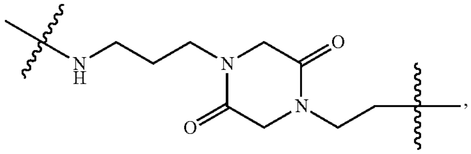,
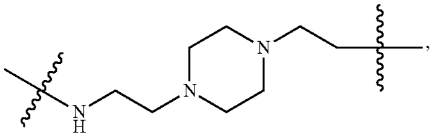,
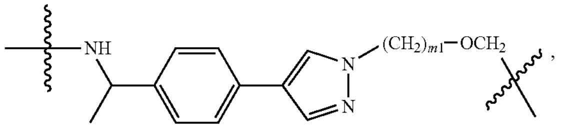,
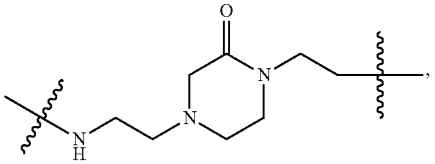,
-continued
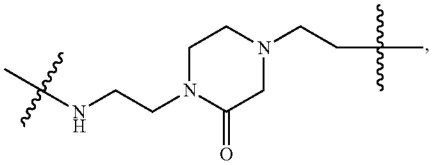,
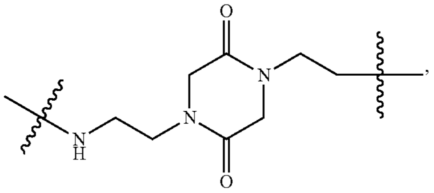,
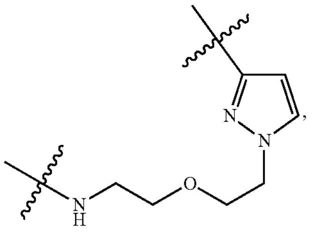,
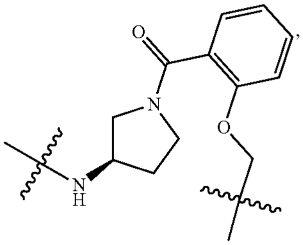,
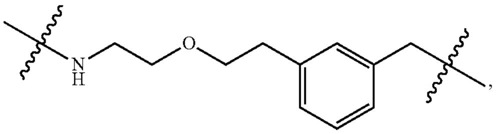,
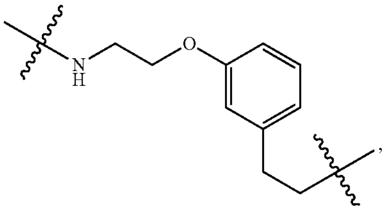,
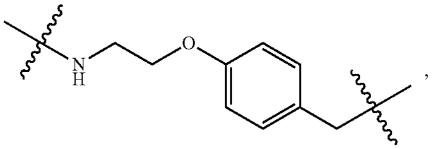,
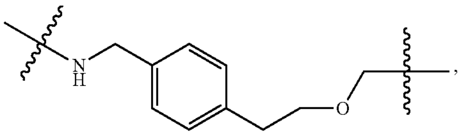,
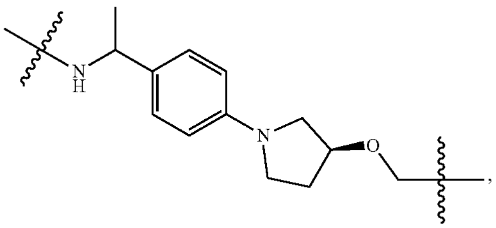, -continued
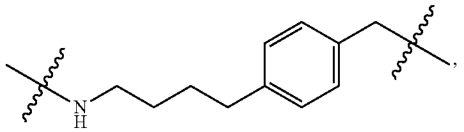,
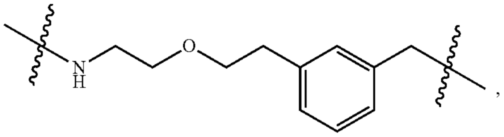,
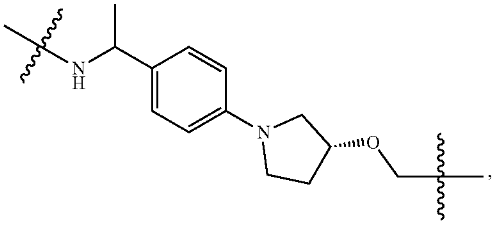,
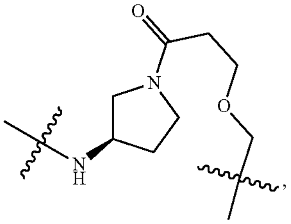,
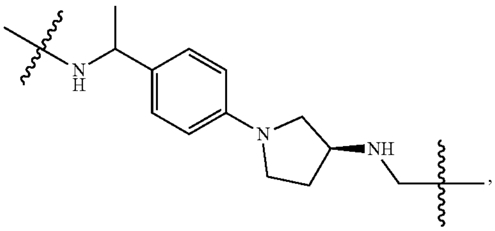,
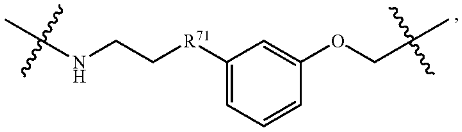,
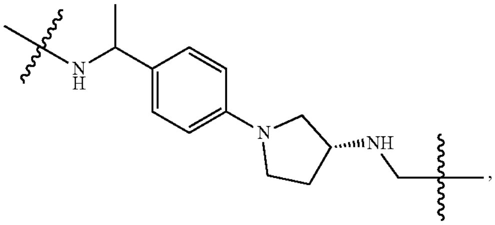,
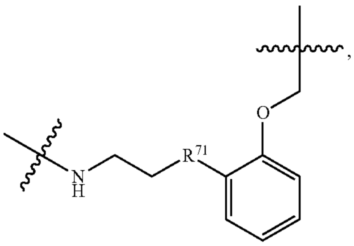,
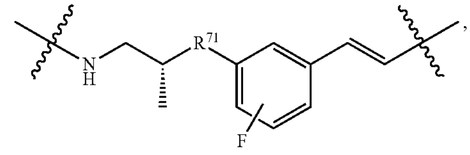,
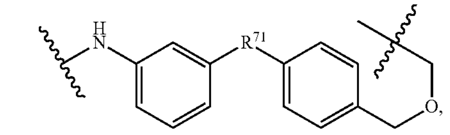,
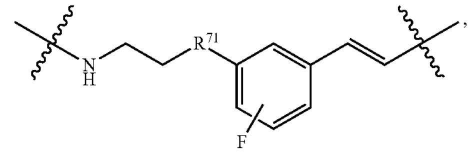,
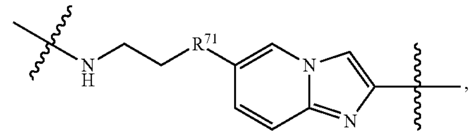,
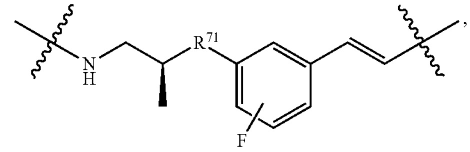,
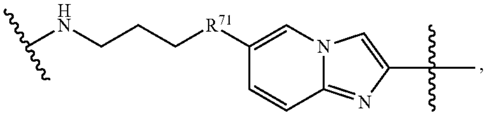,
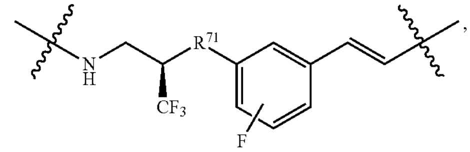,
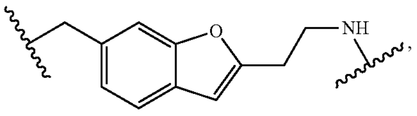,
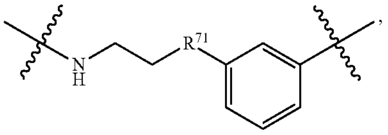,
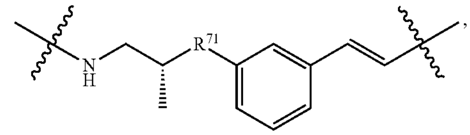,
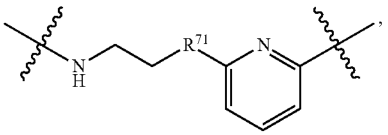,
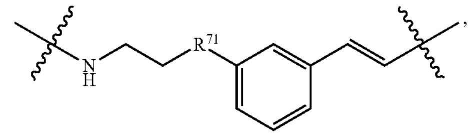, -continued
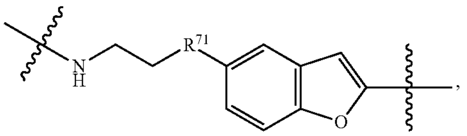
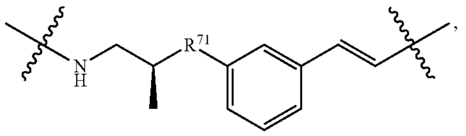
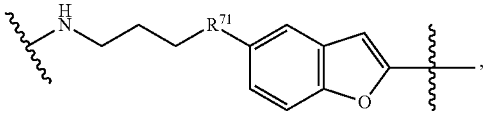
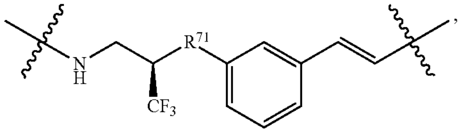
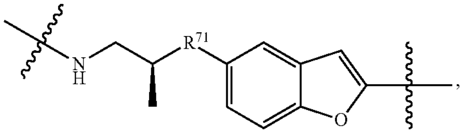
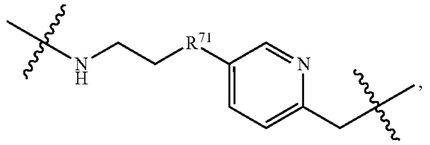
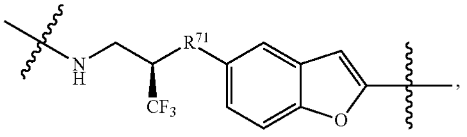
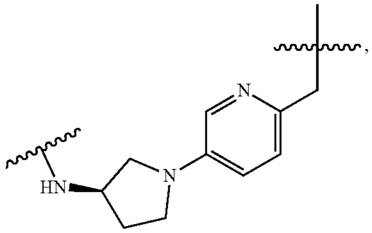
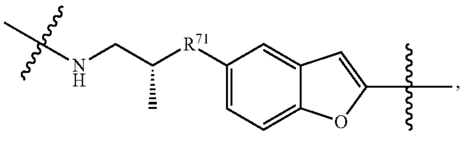
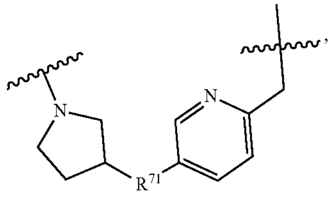
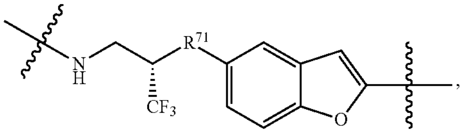
-continued
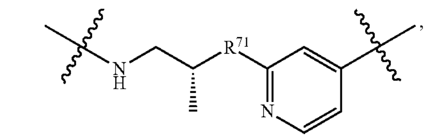
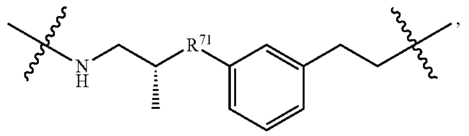
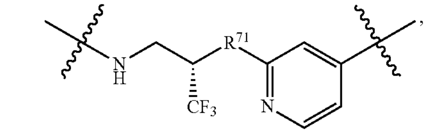
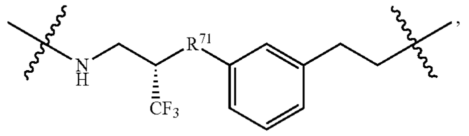
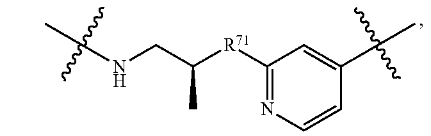
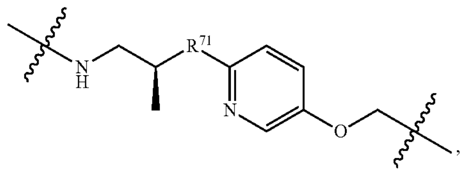
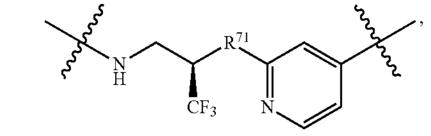
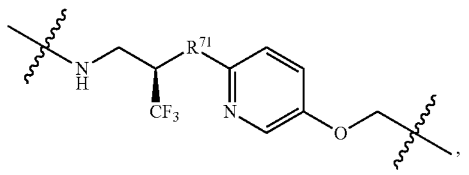
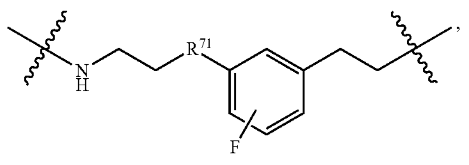
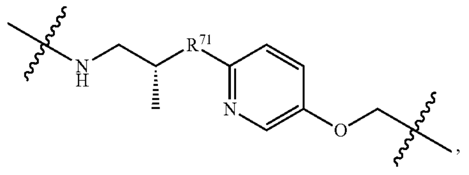
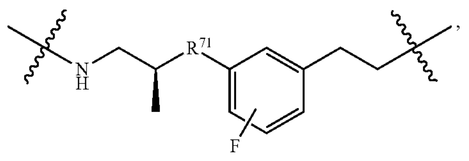

-continued
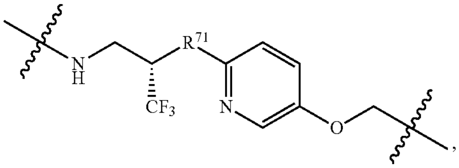,
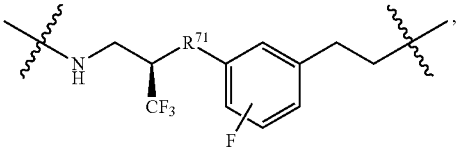,
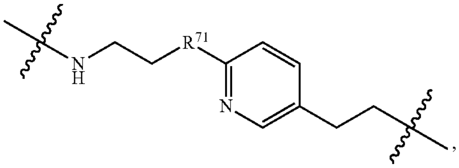,
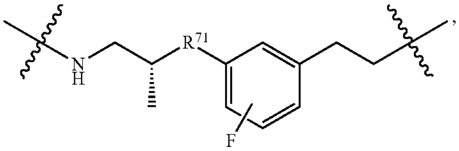,
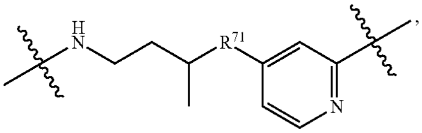,
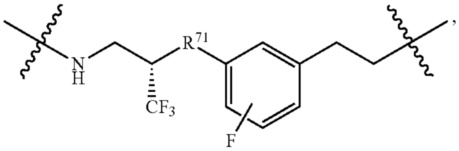,
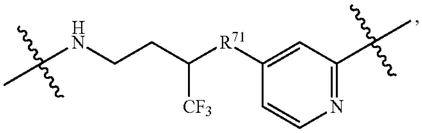,
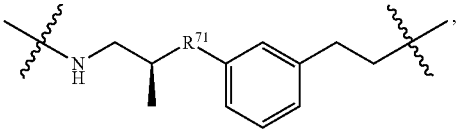,
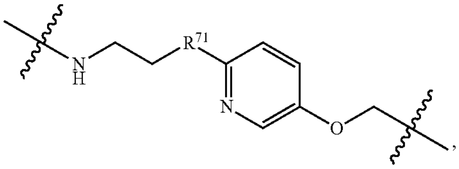,
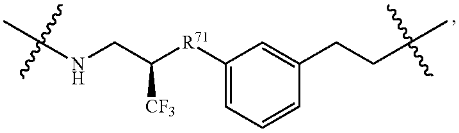,
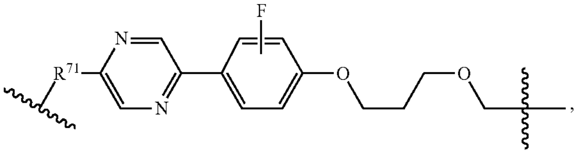,
-continued
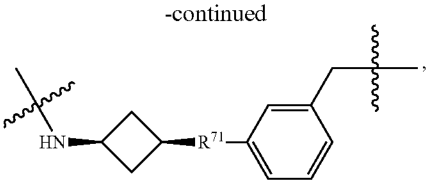,
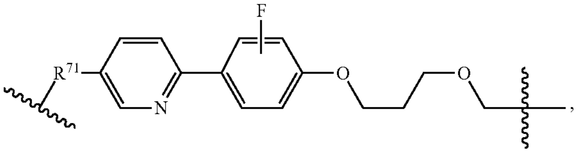,
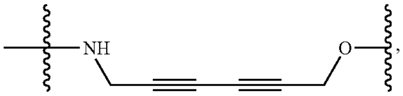,
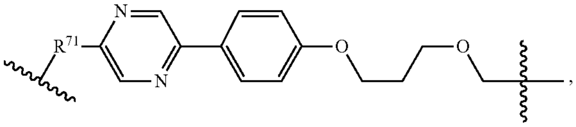,
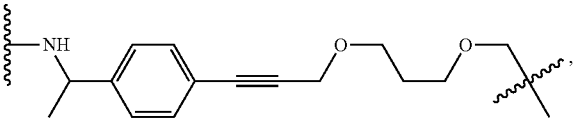,
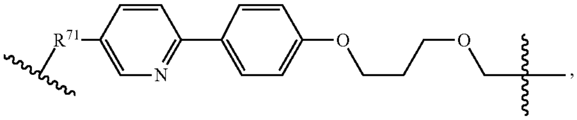,
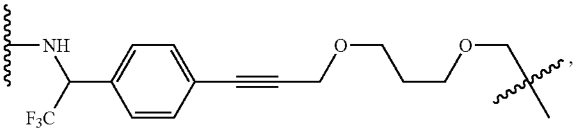,
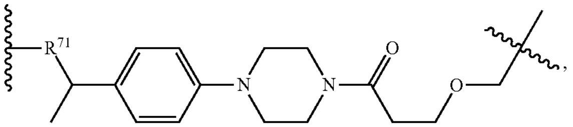,
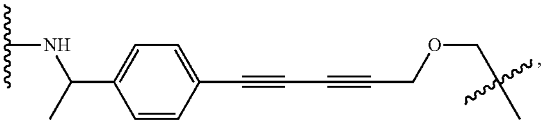,
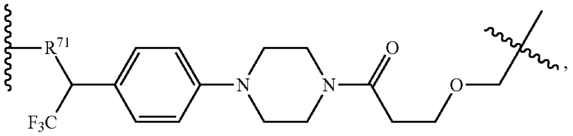,
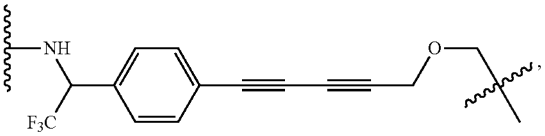,
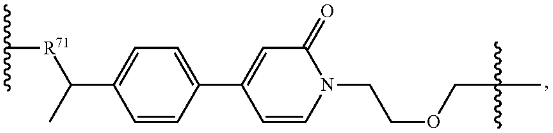,
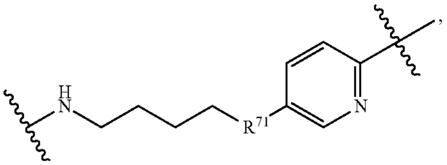, -continued
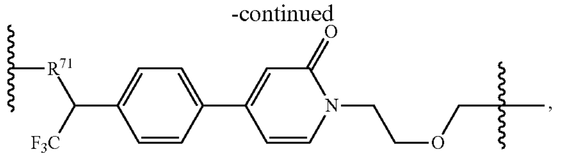
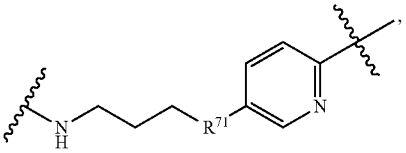
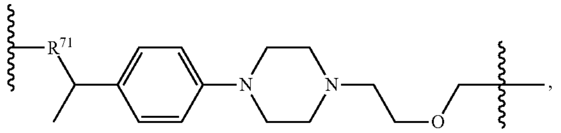
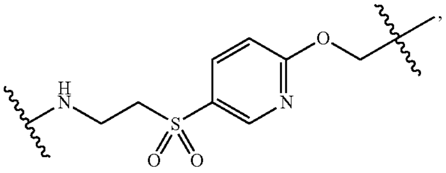
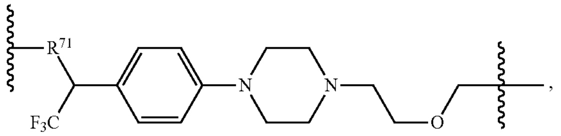
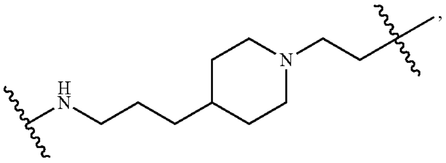
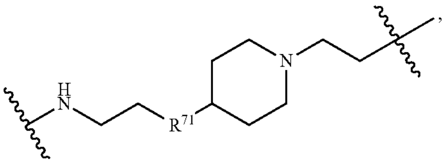
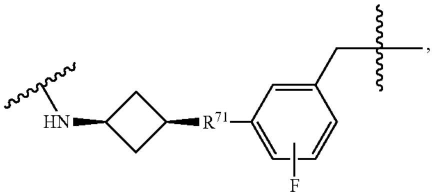
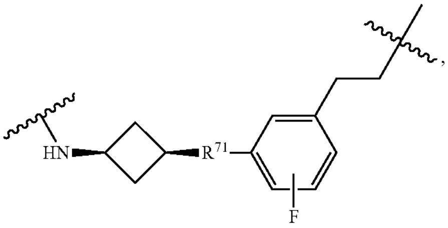
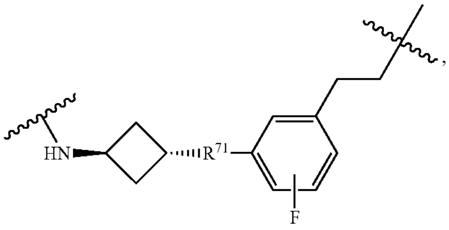
-continued
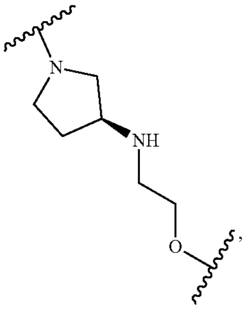
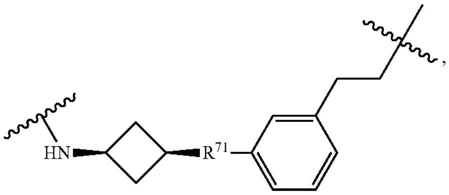
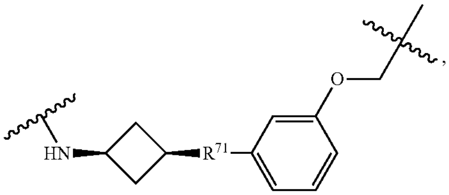
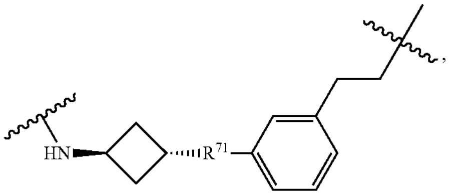
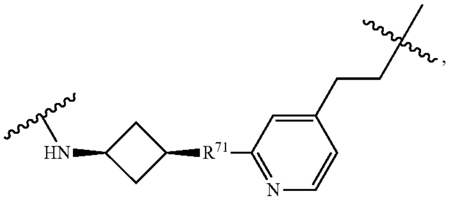
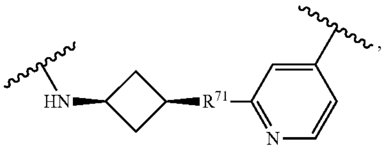
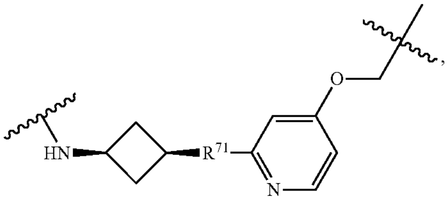
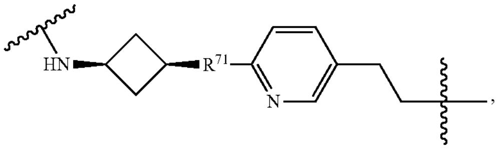

-continued
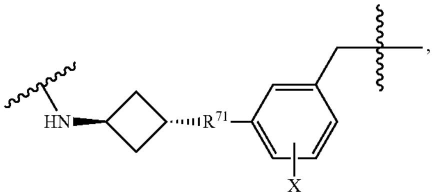
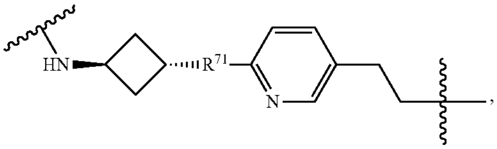
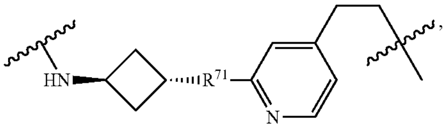
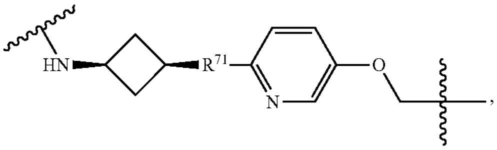
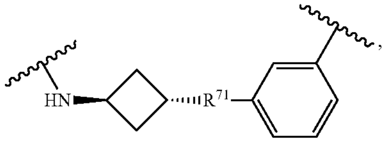
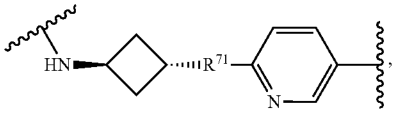
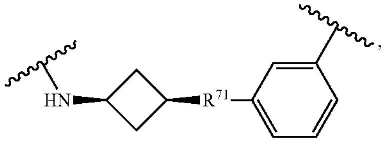
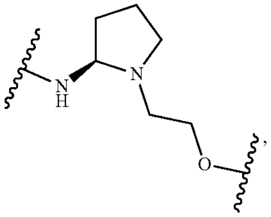
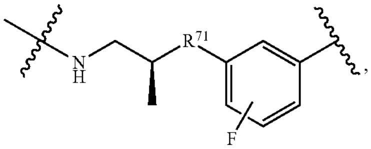
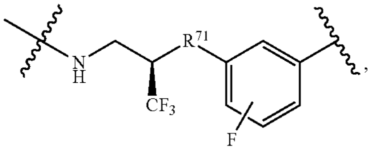
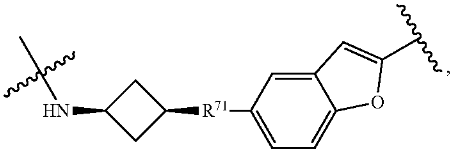
-continued
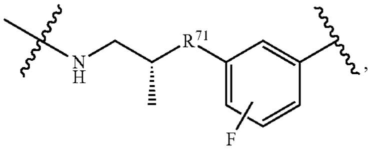
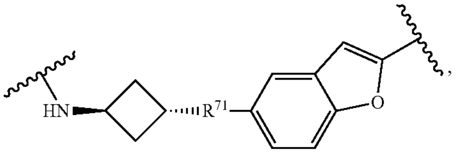
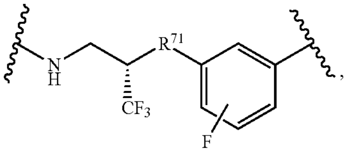
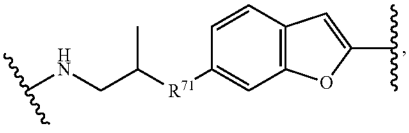
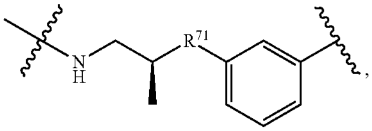
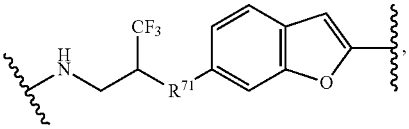
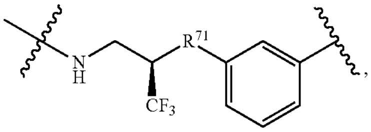
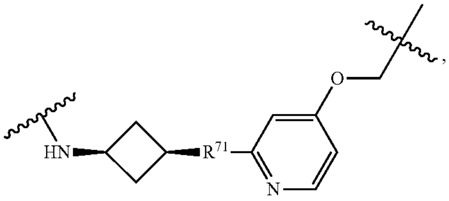
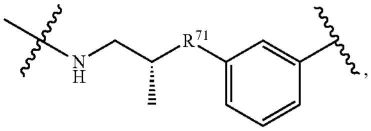
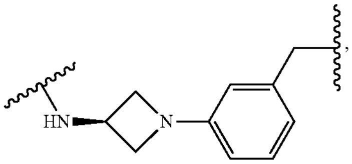
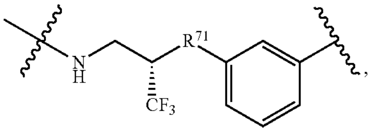

-continued
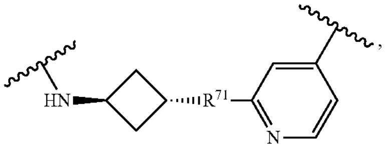
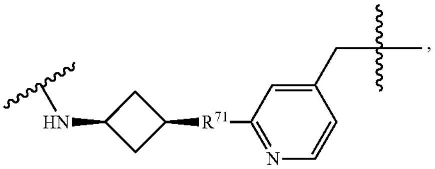
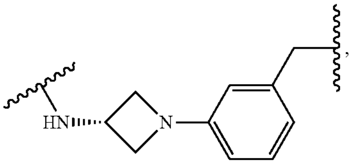
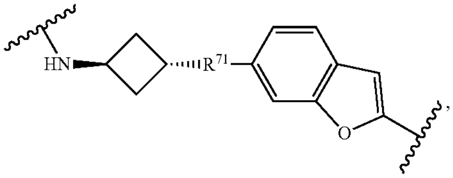
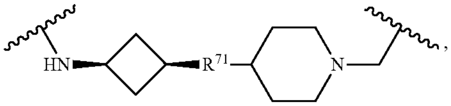
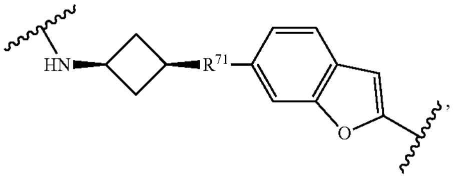
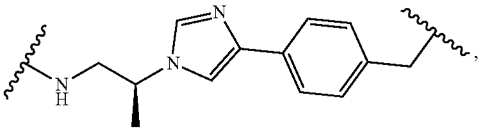
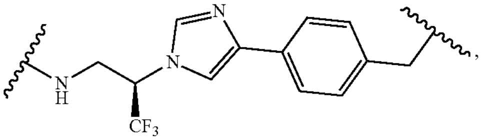
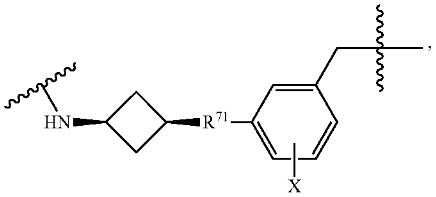
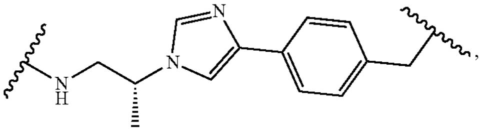
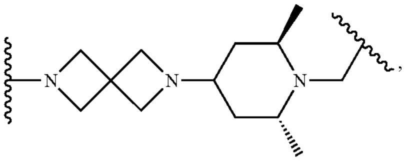
-continued
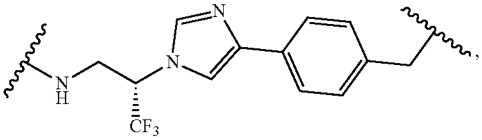
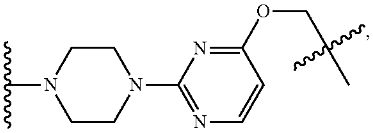
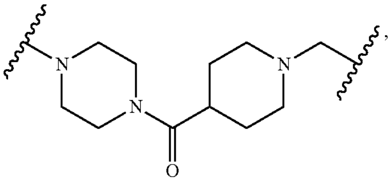
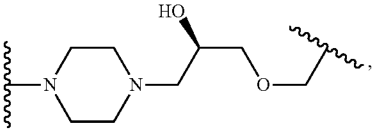
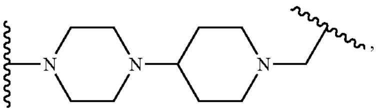
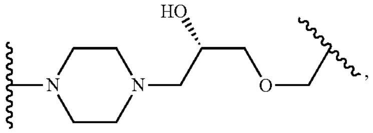
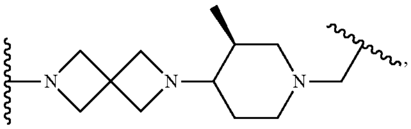
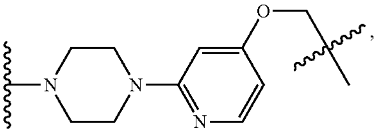
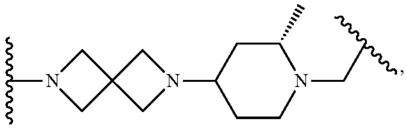
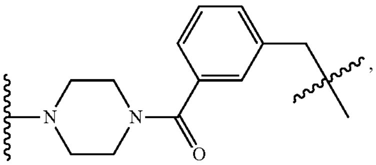
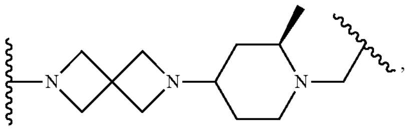
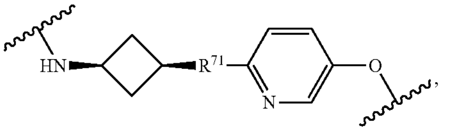

-continued
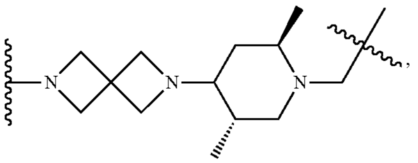
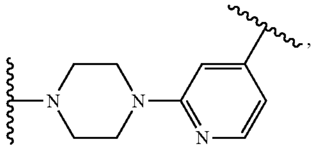
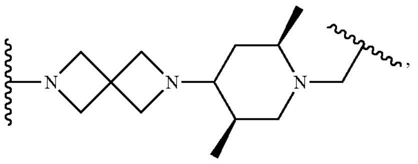
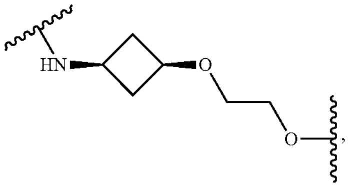
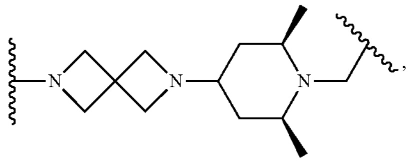
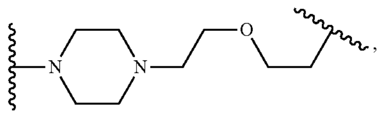
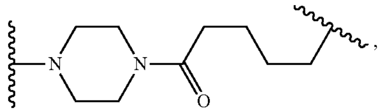
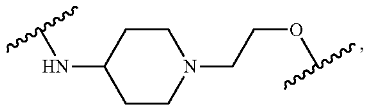
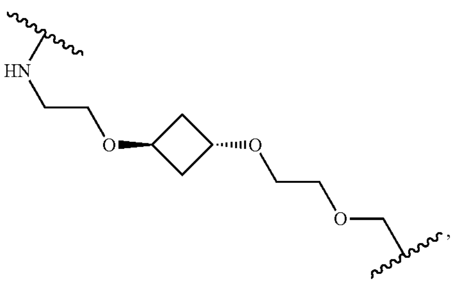
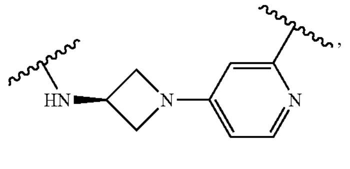
-continued
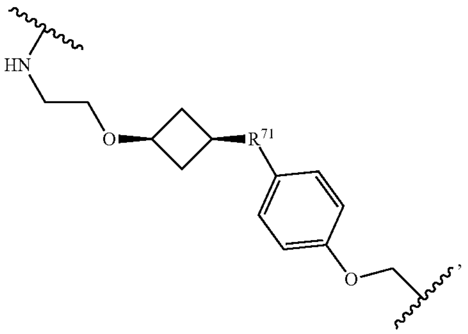
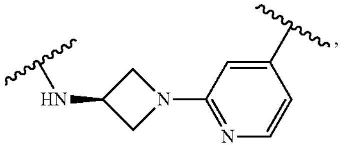
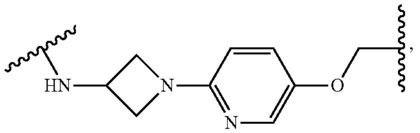
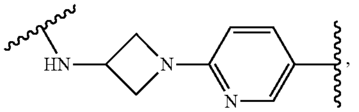
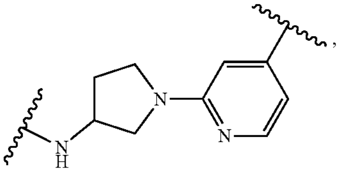
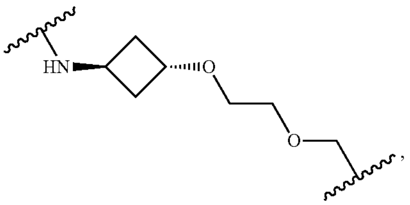
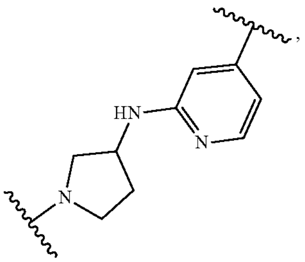
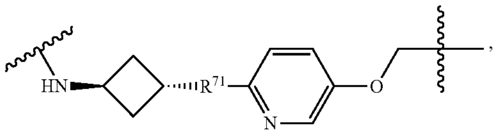
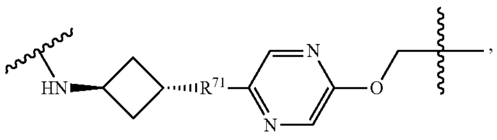

-continued
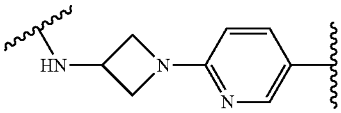,
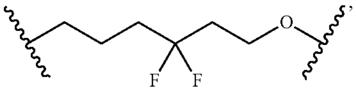,
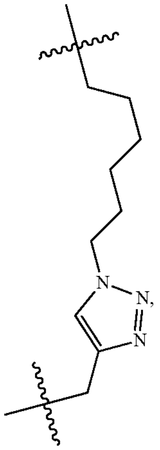,
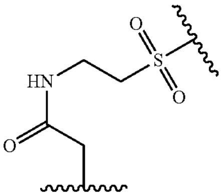,
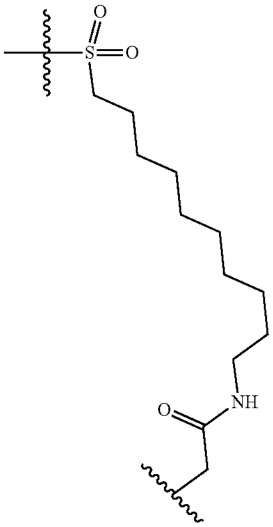,
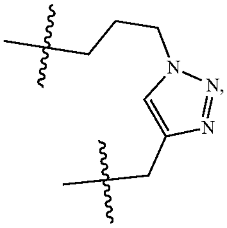,
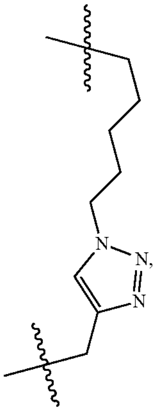,
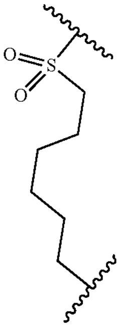,
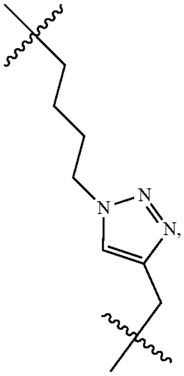,
-continued
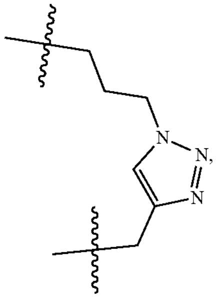,
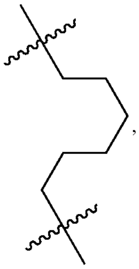,
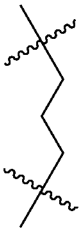,
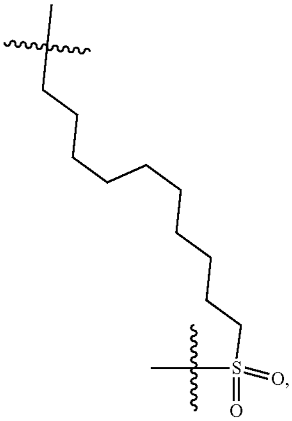,
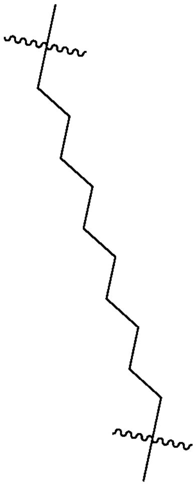,
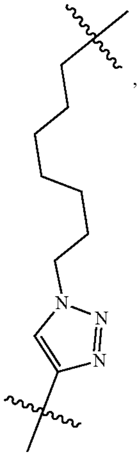,
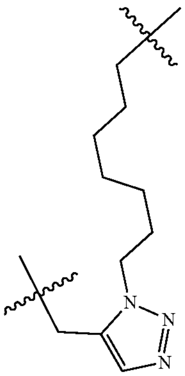,
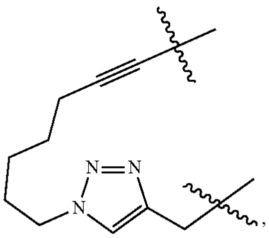,
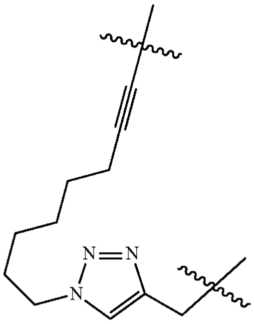, -continued
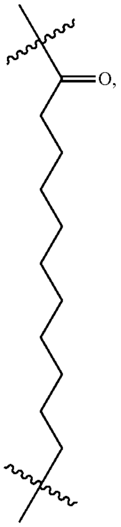
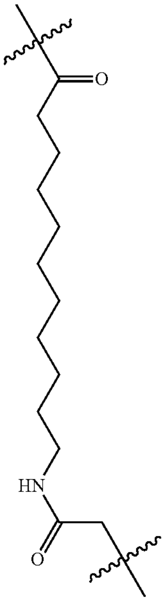
,
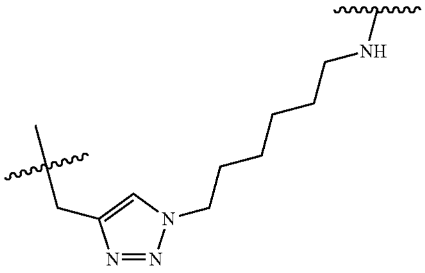
,
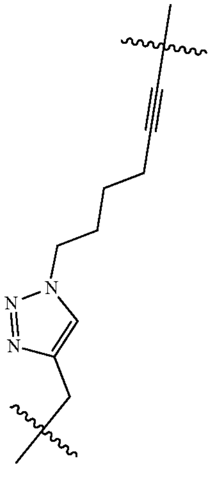
,
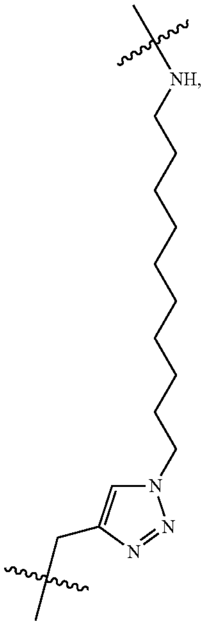
-continued
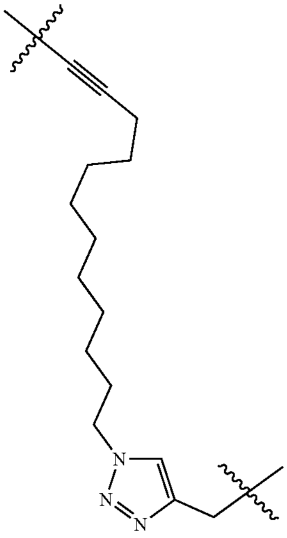
,
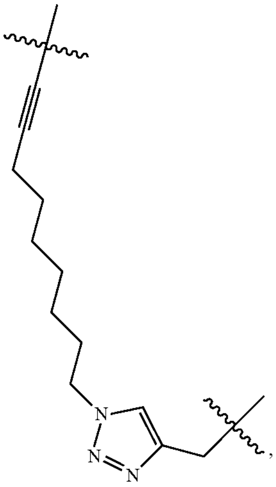
,
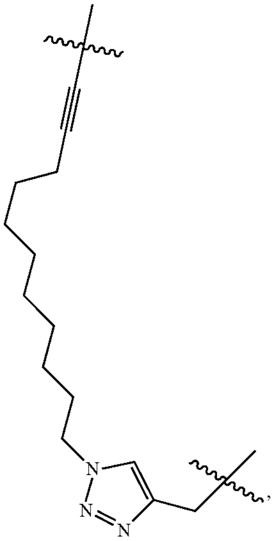
,
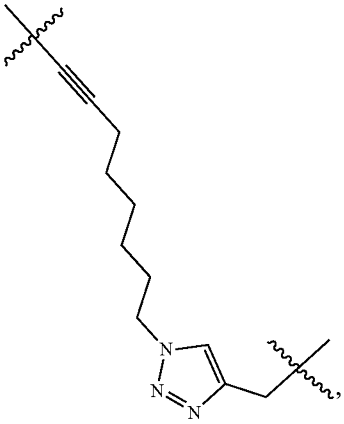
, -continued
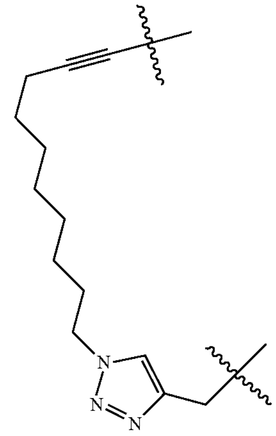
,
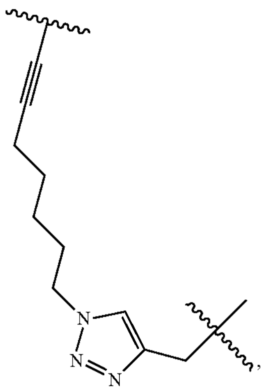
,
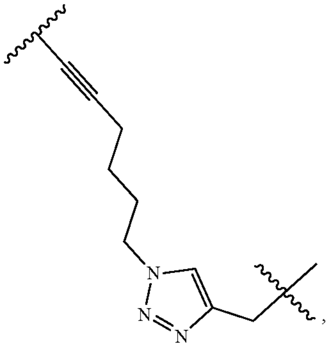
,
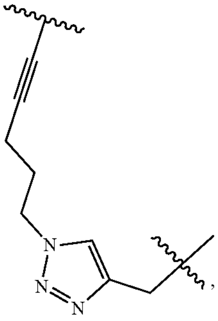
,
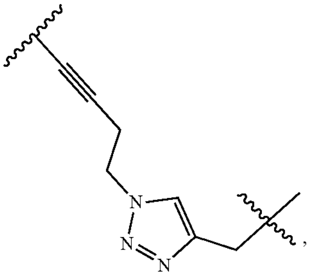
,
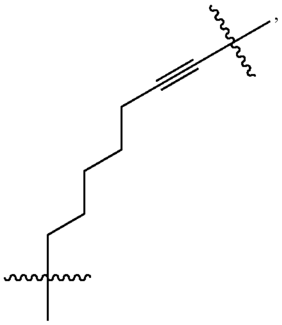
,
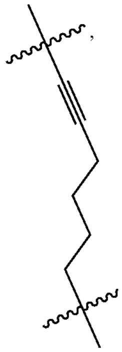
,
-continued
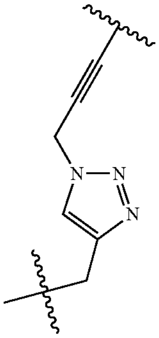
,
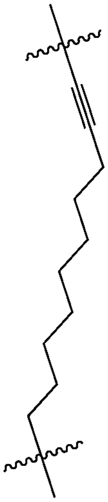
,
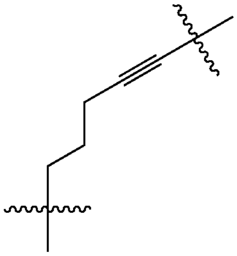
,
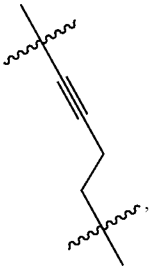
,
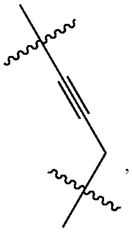
,
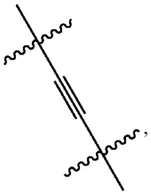
,
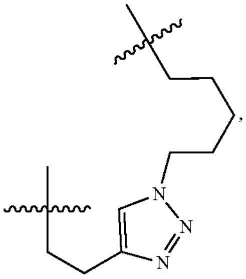
,
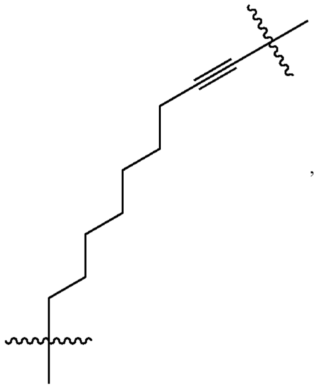
,
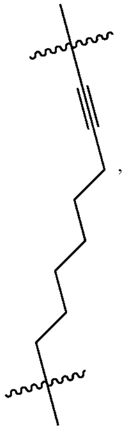
,
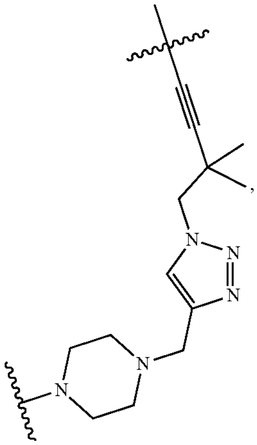
, -continued
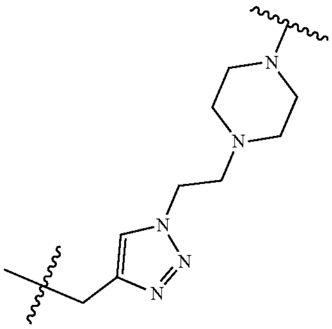
,
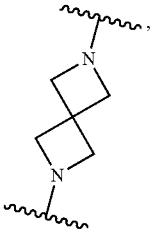
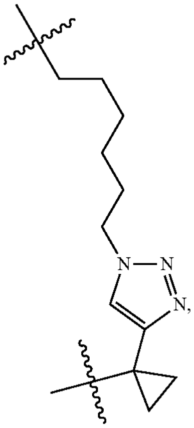
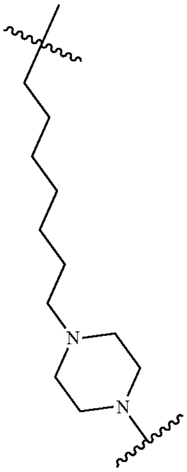
,
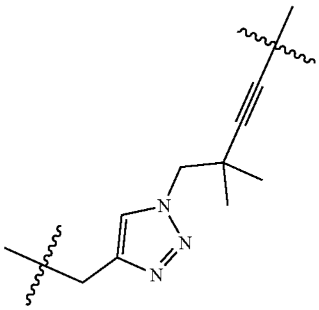
,
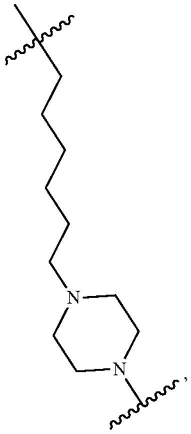
-continued
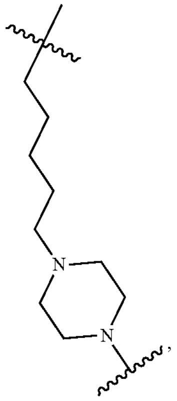
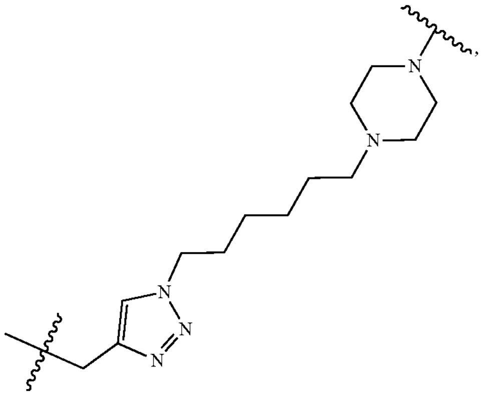
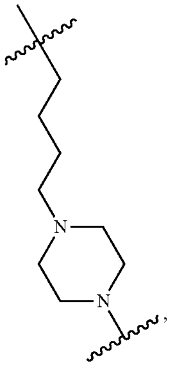
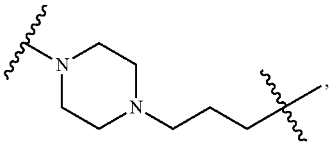

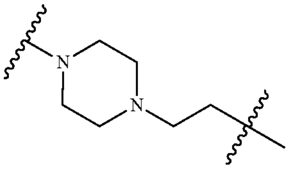, 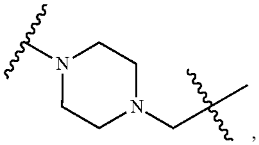, 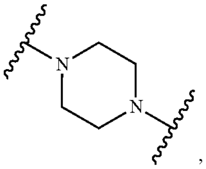, 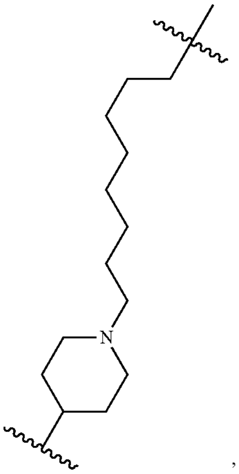,
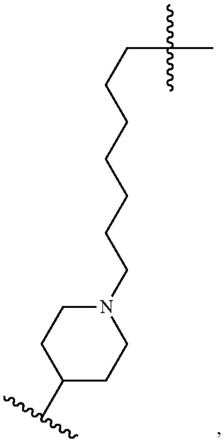, 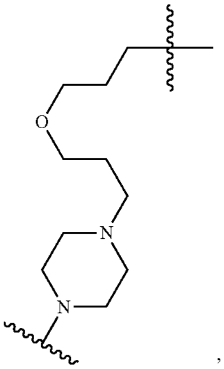, 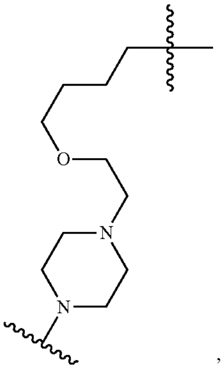, 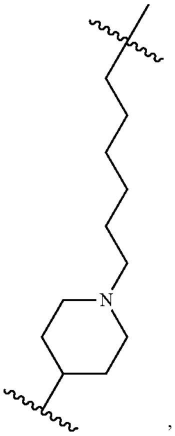, 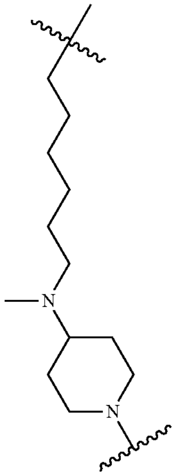, 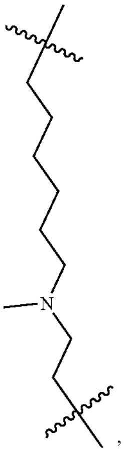,
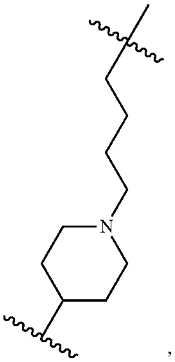, 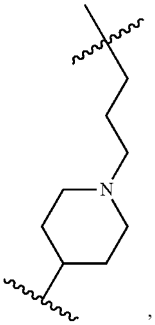, 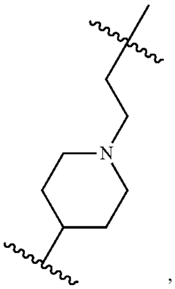, 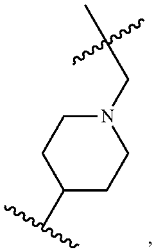, 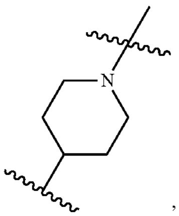, 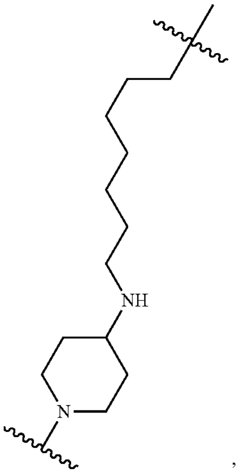, -continued
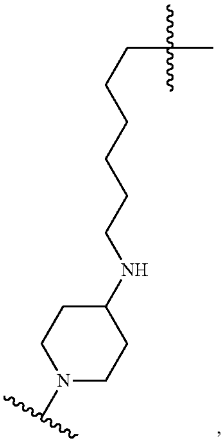 , 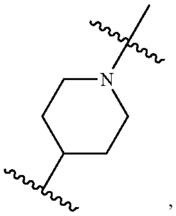 , 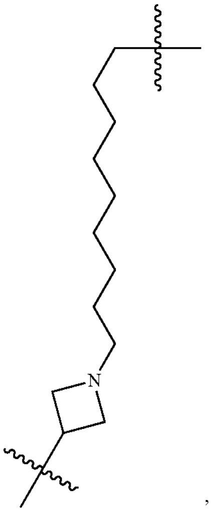 , 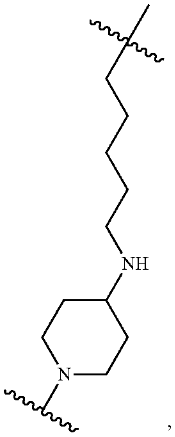 , 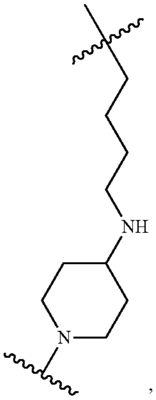 , 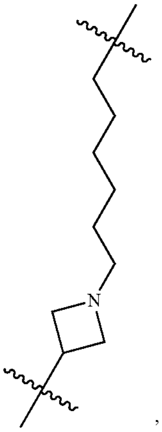 ,
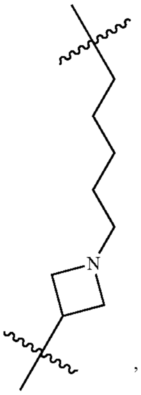 , 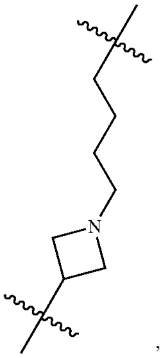 , 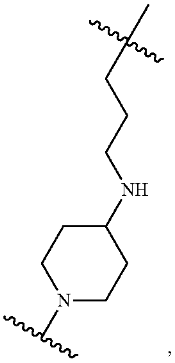 , 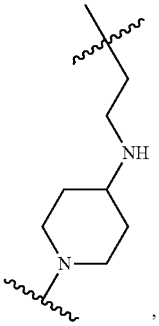 , 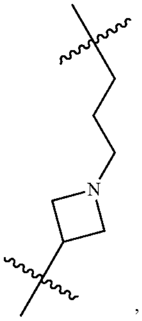 , 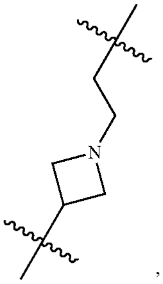 , 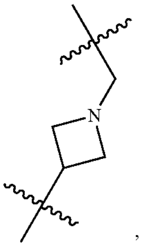 ,
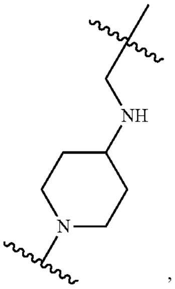 , 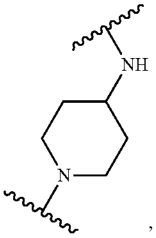 , 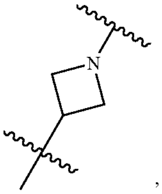 , 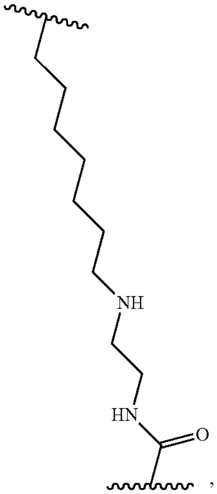 , 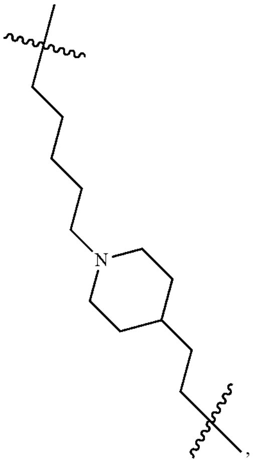 , -continued
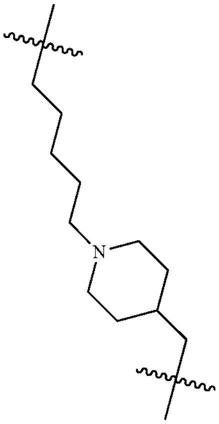,
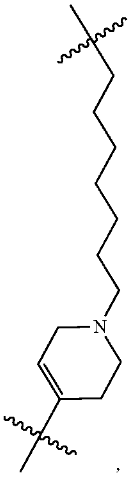,
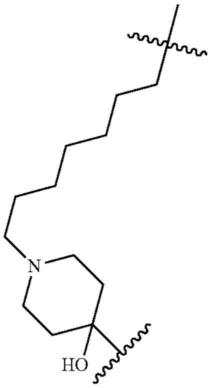,
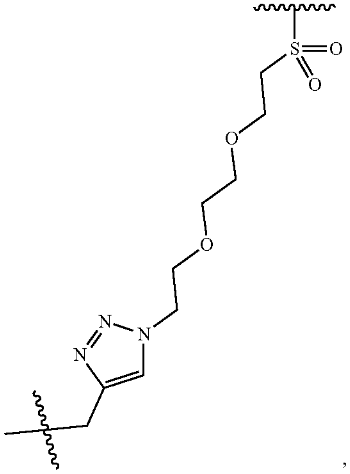,
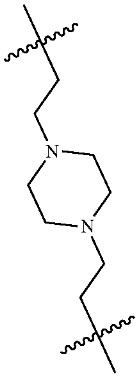,
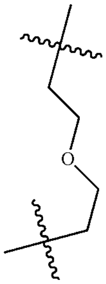,
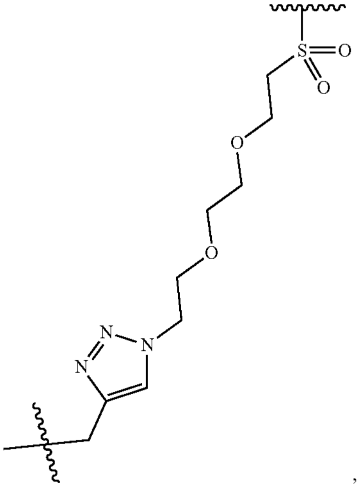,
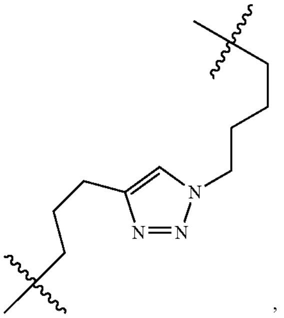,
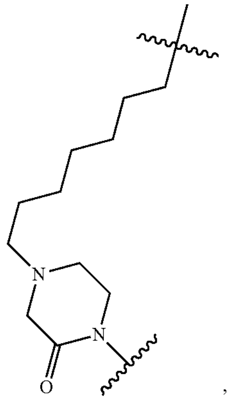,
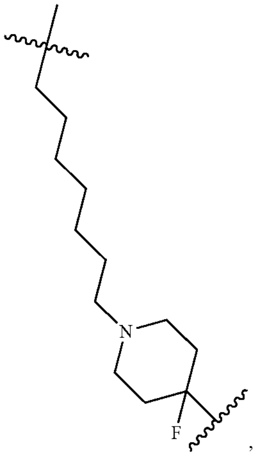,
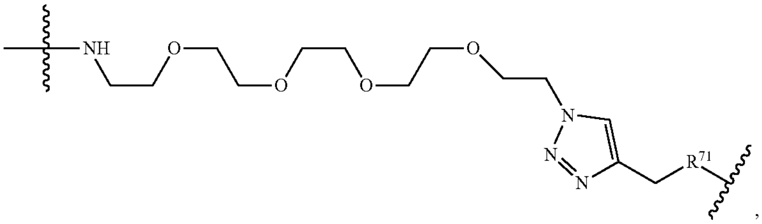,
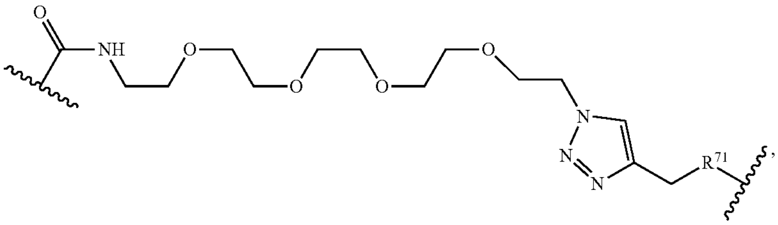, -continued
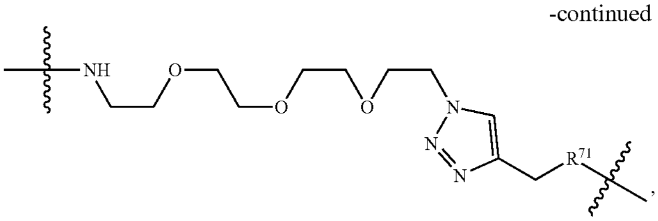,
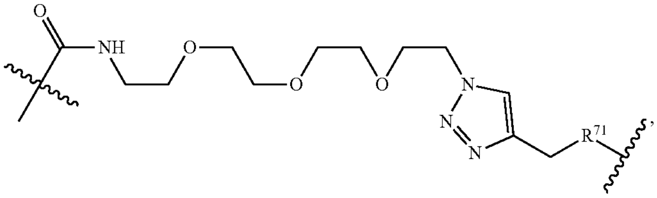,
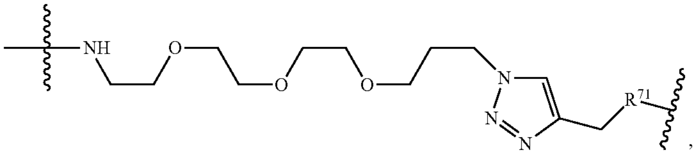,
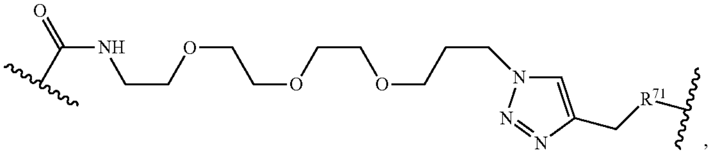, 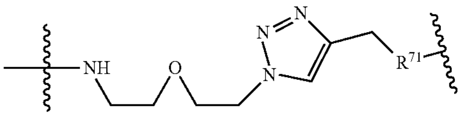,
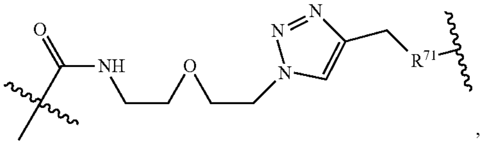, 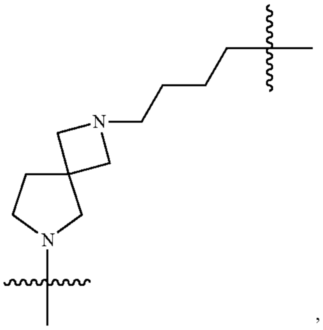, 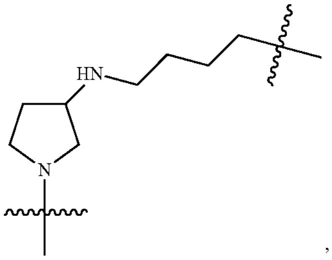,
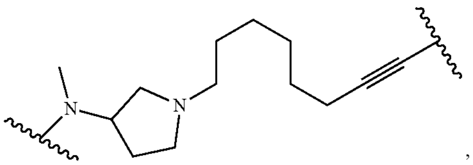, 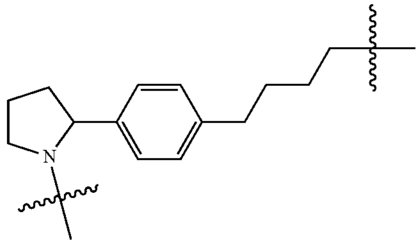,
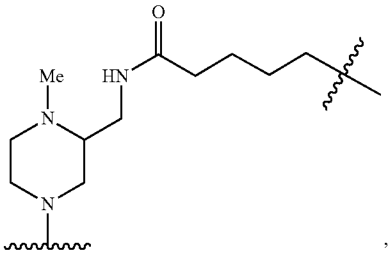, 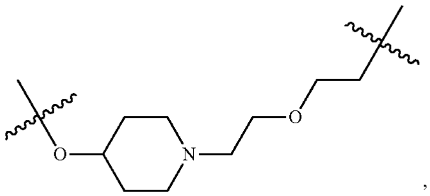,
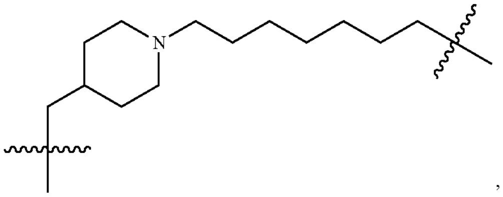, 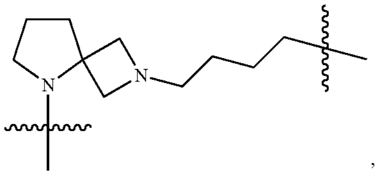, -continued
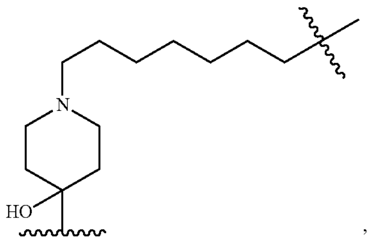 , 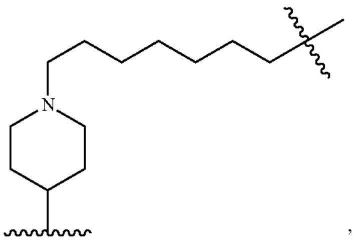 ,
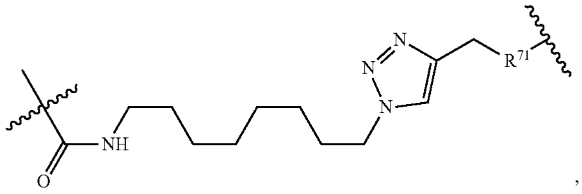 , 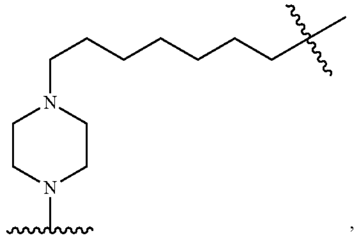 ,
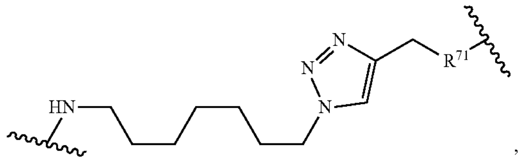 , 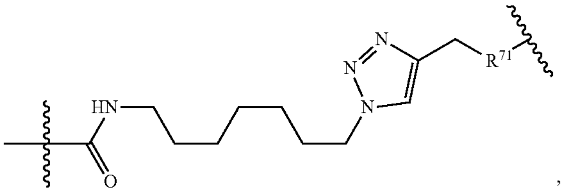 ,
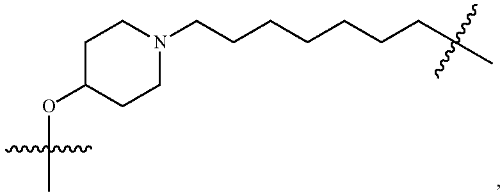 , 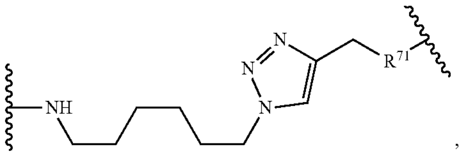 ,
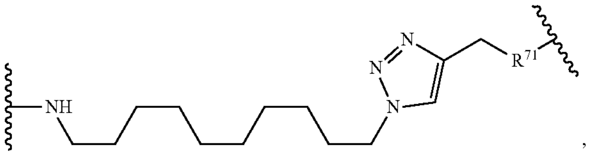 , 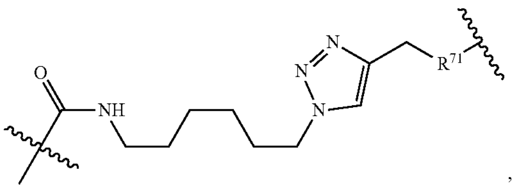 ,
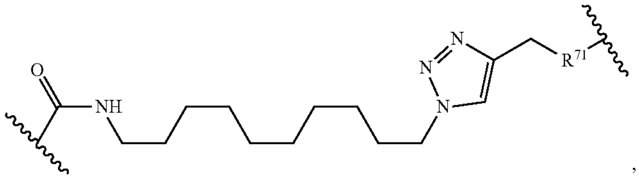 , 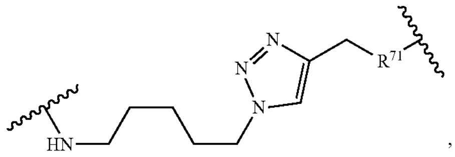 ,
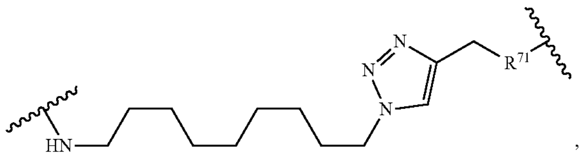 , 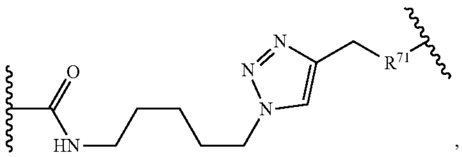 ,
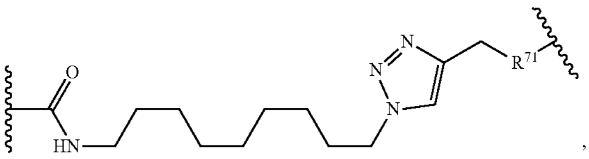 , 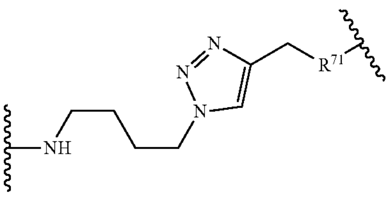 , -continued
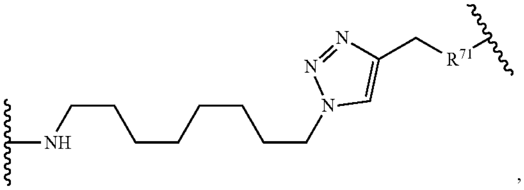
,
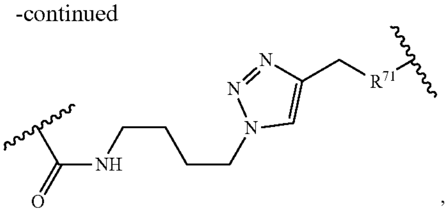
,
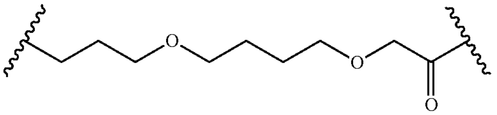
,
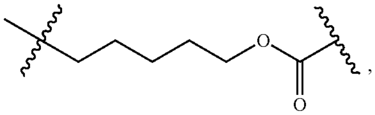
,
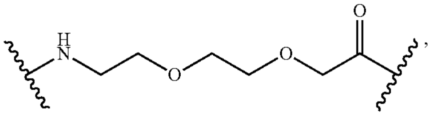
,
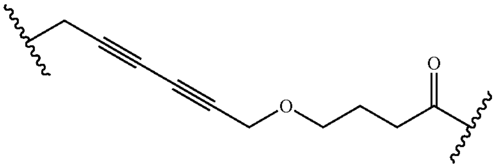
,
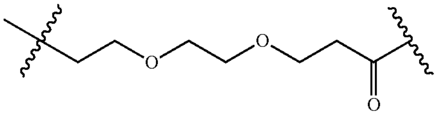
,
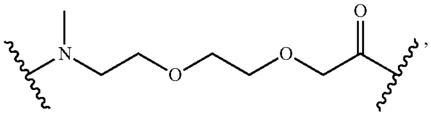
,
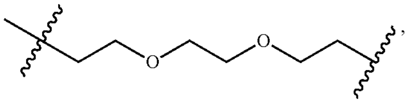
,
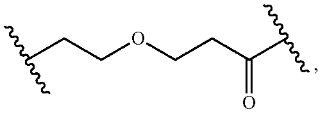
,
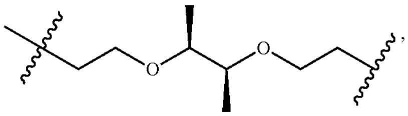
,
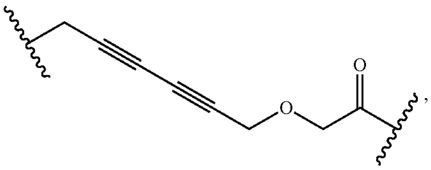
,
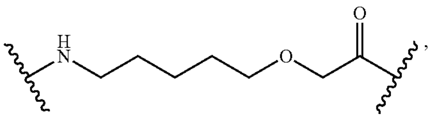
,
-continued
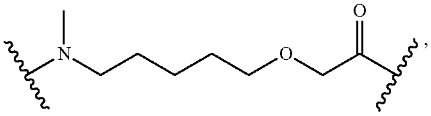
,
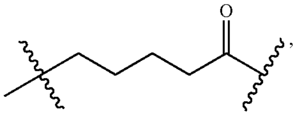
,
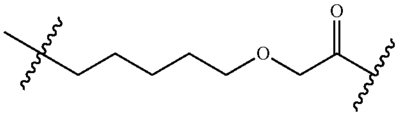
,
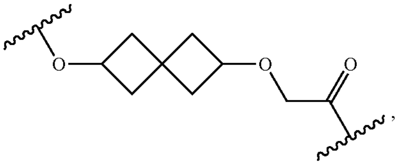
,
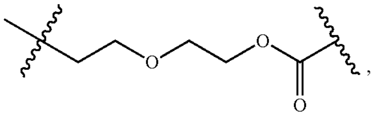
,
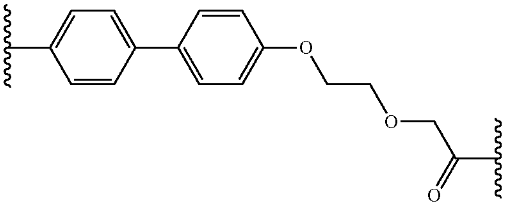
,
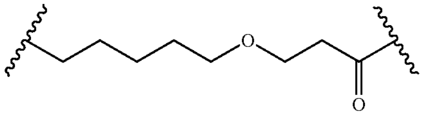
,
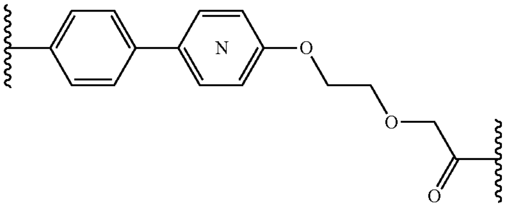
,
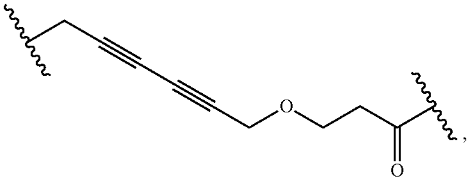
, -continued
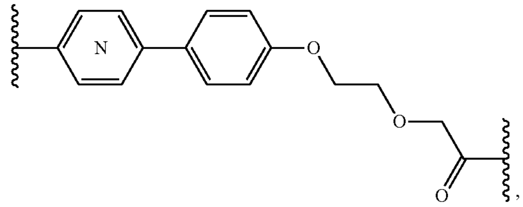,
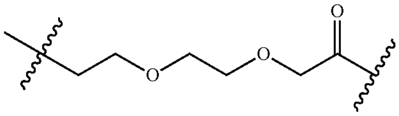,
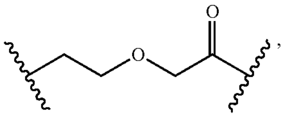,
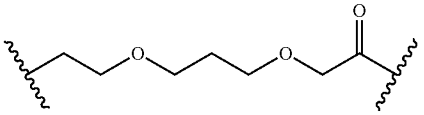,
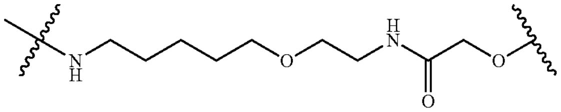,
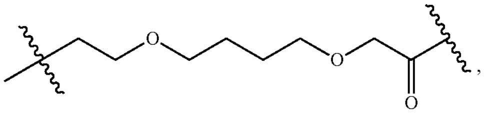,
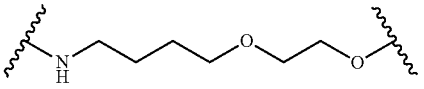,
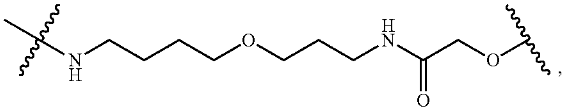,
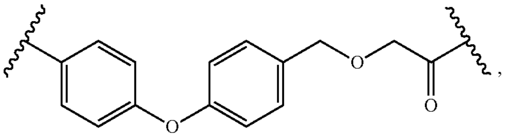,
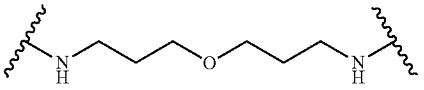,
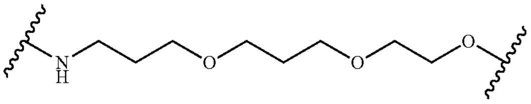,
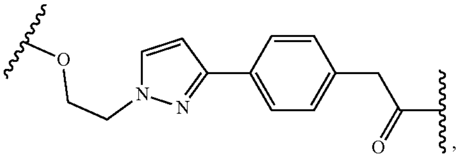,
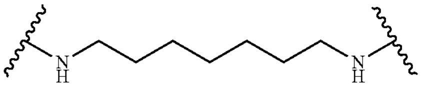,
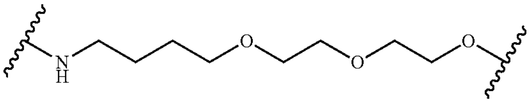,
-continued
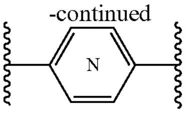,
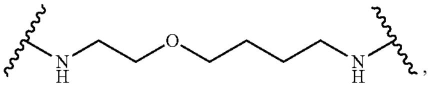,
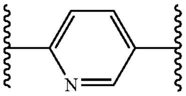,
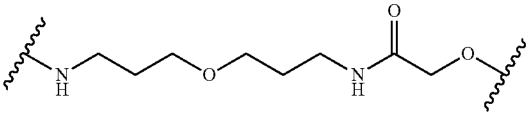,
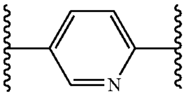,
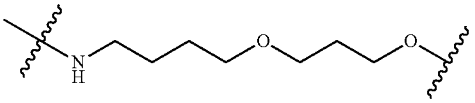,
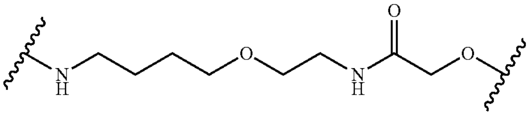,
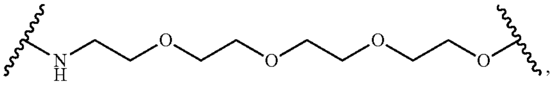,
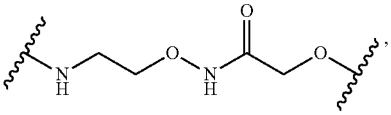,
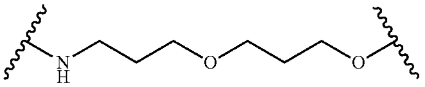,
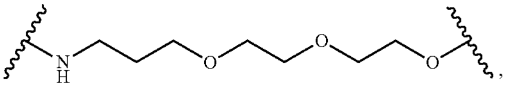,
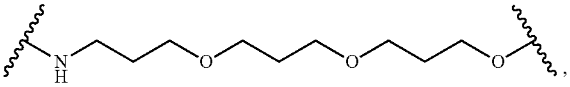,
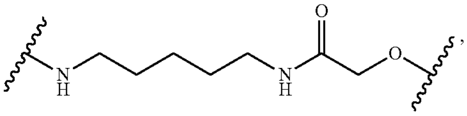,
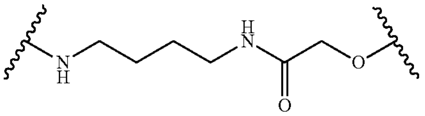,
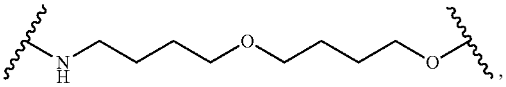,
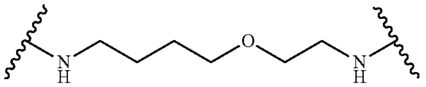,
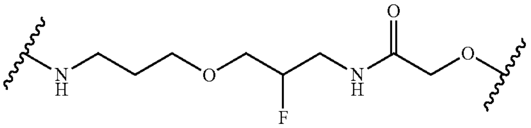, -continued

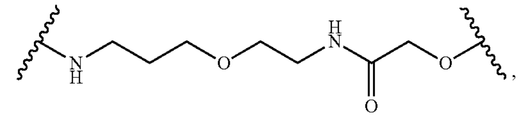,
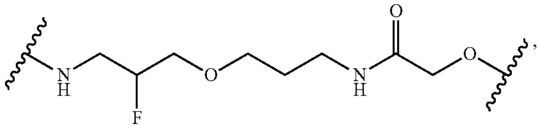,
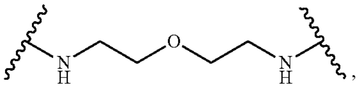,
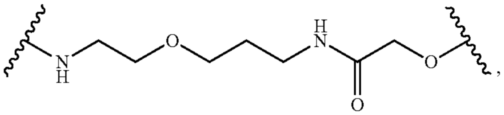,
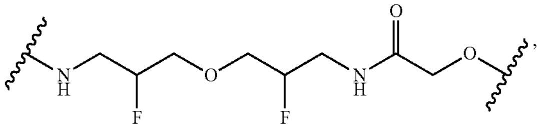,
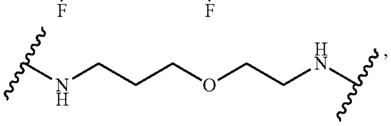,
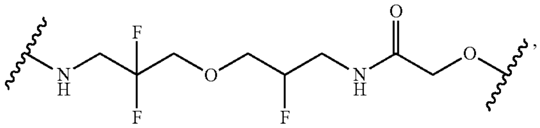,
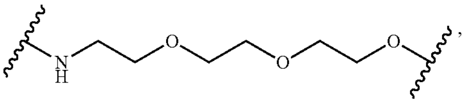,
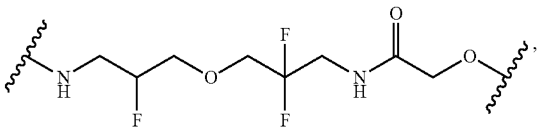,
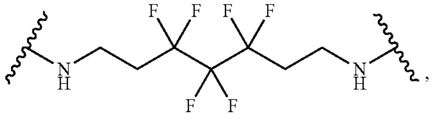,
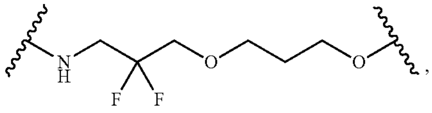,
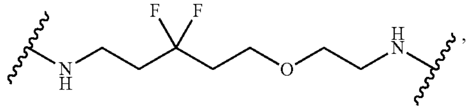,
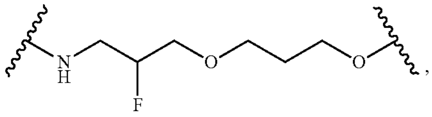,
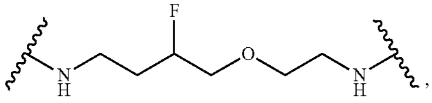,
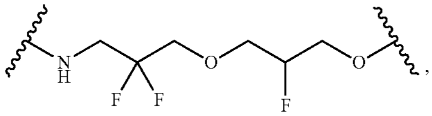, -continued

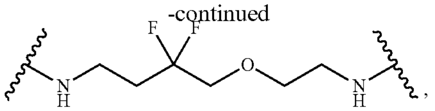,
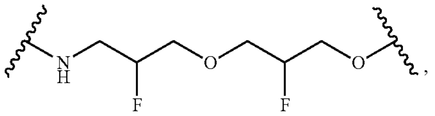,
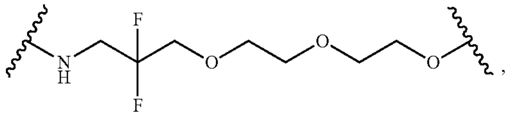,
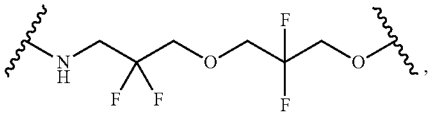,
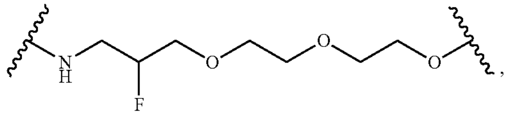,
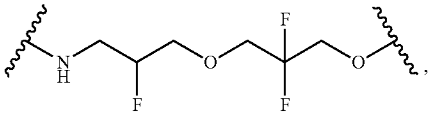,
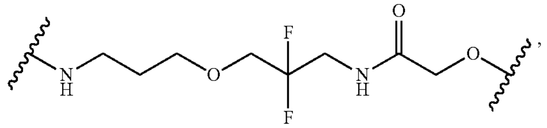,
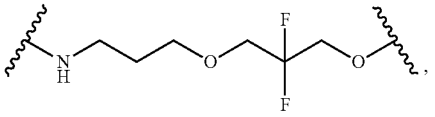,
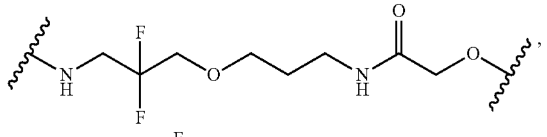,
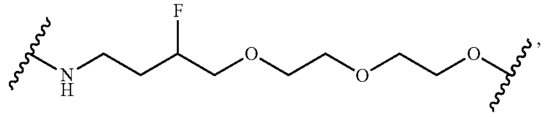, wherein $R^{71}$ is —O—, —NH, —NMe, —Nalkyl, N(aliphatic), —N(heteroaliphatic).

In some embodiments, the Linker can be a nonlinear chain, and can be, or include, aliphatic or aromatic or heteroaromatic cyclic moieties.

In some embodiments, the Linker may include contiguous, partially contiguous, or non-contiguous ethylene glycol unit groups ranging in size from about 1 to about 12 ethylene glycol units, about 1 to about 10 ethylene glycol units, about 2 to about 6 ethylene glycol units, about 2 to about 5 ethylene glycol units, about 2 to about 4 ethylene glycol units, for example, 1, 2, 3, 4, 6, 6, 7, 8, 9, 10, 11 or 12 ethylene glycol units.

In some embodiments, the Linker may have 1, 2, 3, 4, 5, 6, 7, 8, 9, 10, 11, 12, 13, 14, or fluorine substituents. In another embodiment, the Linker may be perfluorinated. In yet another embodiment, the Linker may be a partially or fully fluorinated poly ether. Nonlimiting examples of fluorinated Linkers include:

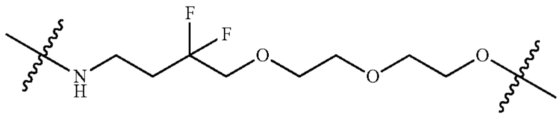
,
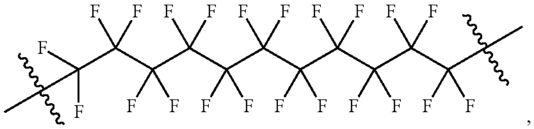
,
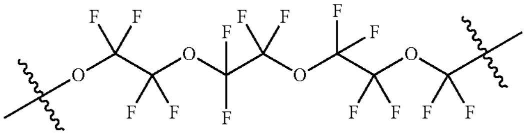
,
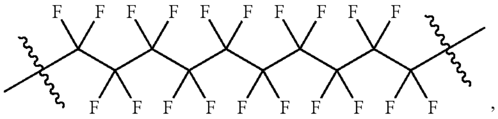
,
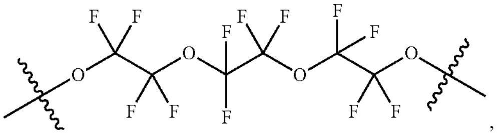
,
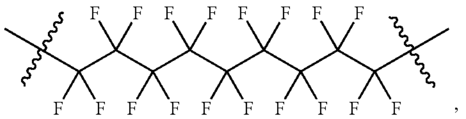
,
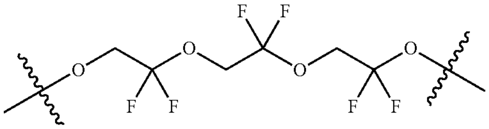
,
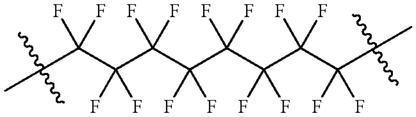
,
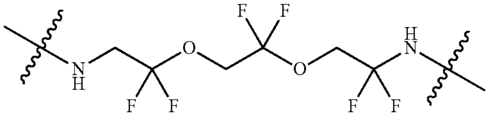
,
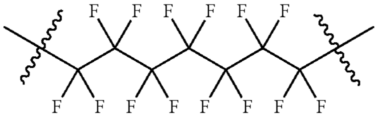
,
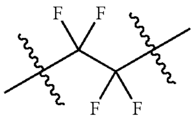
,
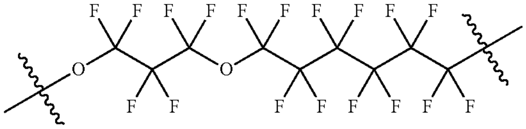
,
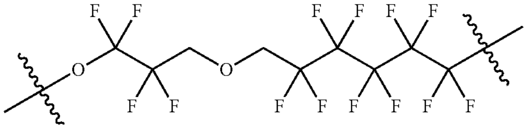
, -continued

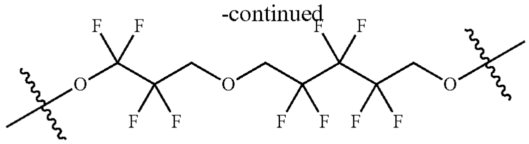
,

Providing the Compound of the Disclosure (e.g., TCIP) in the Cell

The present disclosure provides providing a compound of the disclosure (e.g., a TCIP or a CIP) into a cell, e.g., as described above, in a manner sufficient to induce proximity of the first endogenous protein and the second endogenous protein, e.g., as described above. Any convenient protocol for providing the CIP compound in the cell may be employed. The particular protocol that is employed may vary, e.g., depending on whether the target cell is in vitro or in vivo. In certain instances, the CIP compound is provided in the cell by contacting the cell with the CIP compound. For in vitro protocols, contact of the CIP compound with the target cell may be achieved using any convenient protocol. For example, target cells may be maintained in a suitable culture medium, and the CIP compound introduced into the culture medium as described specifically in the figures.

For in vivo protocols, any convenient administration protocol may be employed. Depending upon the binding affinity of the CIP compound, the response desired, the manner of administration, the half-life, the number of cells present, various protocols may be employed. Thus, the CIP can be incorporated into a variety of formulations, e.g., pharmaceutically acceptable vehicles (also referred to herein as pharmaceutical delivery vehicles or carriers), for therapeutic administration. More particularly, the CIP of the present disclosure can be formulated into pharmaceutical compositions to be used for intravenous administration over a period of days or weeks. This can be done by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents (e.g., compounds of the disclosure) can be achieved in various ways, including oral, buccal, rectal, parenteral, intraperitoneal, intradermal, transdermal, intratracheal, intravenous, intravesical, subcutaneous, intramuscular, etc., administration. In pharmaceutical dosage forms, the CIPs may be administered alone or in appropriate association, as well as in combination, with other pharmaceutically active compounds. The following examples are illustrative and not limiting. In some cases, the compounds of the disclosure can be formulated and/or administered in such a way that they can cross the blood-brain barrier.

For oral preparations, the agents (e.g., compounds of the disclosure) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents (e.g., compounds of the disclosure) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents (e.g., compounds of the disclosure) can be utilized in aerosol formulation to be administered via inhalation. The compounds of the present disclosure can be formulated into pressurized acceptable propellants such as dichlorodifluoromethane, propane, nitrogen and the like.

Furthermore, the agents (e.g., compounds of the disclosure) can be made into suppositories by mixing with a variety of bases such as emulsifying bases or water-soluble bases. The compounds of the present disclosure can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

In those embodiments where an effective amount of an active agent (e.g., a compound of the disclosure) is administered to a living subject, the amount or dosage is effective when administered for a suitable period of time, such as one week or longer, including two weeks or longer, such as 3 weeks or longer, 4 weeks or longer, 8 weeks or longer, etc., so as to evidence a desired therapeutic effect. For example, an effective dose is the dose that, when administered for a suitable period of time, such as at least about one week, and may be about two weeks, or more, up to a period of about 3 weeks, 4 weeks, 8 weeks, or longer, will results in a desired therapeutic effect. In some instances, an effective amount or dose of active agent (e.g., a compound of the disclosure) will not only slow or halt the progression of the disease condition but will also induce the reversal of the condition, i.e., will cause an improvement one or more symptoms of the condition. For example, in some instances, an effective amount is the amount that when administered for a suitable period of time, usually at least about one week, and may be about two weeks, or more, up to a period of about 3 weeks, 4 weeks, 8 weeks, or longer will improve one or more symptoms of a subject suffering from a disease condition, where the magnitude of improvement (e.g., as measured using a suitable protocol with relevant control) may vary, for example 1.5-fold, 2-fold, 3-fold, 4-fold, 5-fold, in some instances 6-fold, 7-fold, 8-fold, 9-fold, or 10-fold or more.

In certain embodiments, the methods include removing the CIP from the cell at some point after provision of the CIP. Removal of the CIP from the cell may be accomplished using any convenient protocol, e.g., by removing the CIP from the medium in which the cell is present, by ceasing administration of the CIP to the animal comprising the cell, by contacting the cell with an inhibitor of the CIP induced proximity, by contacting the cells with a molecule that displaces the CIP and binds to only one of the first endogenous protein or the second endogenous protein, etc. One specific type of inhibitor of the action of the CIP would be a one-sided molecule consisting of the ligand for either the first endogenous protein or the second endogenous protein without the linker or other moiety.

As summarized above, the disclosure further provides methods of inducibly modulating transcription of a target gene. In a non-limiting example, the target gene is a proapoptotic gene. As described above, proapoptotic genes are genes the expression products of which promote or cause apoptosis, i.e., programmed cell death that occurs in multicellular organisms, which may be characterized by a variety of cell changes, such as blebbing, cell shrinkage, nuclear fragmentation, chromatin condensation, chromosomal DNA fragmentation, and global mRNA decay, and death. Specific proapoptotic genes of interest for transcription that may be enhanced in embodiments of the disclosure include, but are not limited to: PUMA (BBC3), BIM (BCL2L11), BID, BAX, BAK, BOK, BAD, HRK, BIK, BMF, and NOXA, and the like. In such instances, the magnitude of enhancement may vary, where examples include from substantially no to some expression, and in some instances the magnitude may be 2-fold or greater, such a 5-fold or greater, including 10-fold or greater. In another non-limiting example, the target gene is a survival factor (e.g., BCL-2, BCLX, and other factors that promote cell proliferation) and expression of the survival factor may be reduced using the compositions, systems, and methods provided herein.

In some instances, the cell is a malignant cell, e.g., a cell of a subject suffering from a malignant condition (such as cancer), i.e., a cell obtained from such a subject or a cell that is part of such a subject. For example, the cell may be cell having elevated levels of BCL6 (or another BTB domain containing protein) and normal or above normal levels of the other factor, e.g., ER, BRD4, target CDK (e.g., CDK9, CDK8, and/or CDK7), AR, etc.) such as a malignant/cancer cell such as but not limited to lung cancer cells (e.g. SCLC), or lymphoma cells, (e.g., DCBCL) cell, prostatic cancer cells, leukemia cells, breast cancer cells etc.

As summarized above, the present disclosure further provides methods of inducibly modulating transcription of a target gene. Such methods include providing a chemical inducer of proximity (CIP) in a cell (e.g., a eukaryotic cell) containing a first endogenous protein and a second endogenous protein, e.g., as described above, under conditions sufficient to modulate transcription of the target gene. The CIP and cell may be as described above. The transcription modulation may vary. In some instances, the modulating includes enhancing transcription of the gene, e.g., where the gene is beneficial with respect to the disease condition, e.g., by enhancing a desired activity in the cell, such as increasing expression of a proapoptotic gene where death of the cell is desired, increasing expression of a therapeutically beneficial gene where increased amounts of the product of such gene are beneficial with respect to a given disease condition, etc. In such instances, the magnitude of enhancement may vary, where examples include from substantially none to some expression, and in some instances the magnitude may be 2-fold or greater, such as 5-fold or greater, including 10-fold or greater. In some instances, the modulating includes reducing transcription of the target gene, e.g., where the gene is harmful, e.g., c-myc or a triplet expansion gene, e.g., such as Huntington, etc. In such instances, the magnitude of reduction may vary, where examples include from some expression to substantially none, if any, expression, and in some instances the magnitude of reduction may be 2-fold or greater, such a 5-fold or greater, including 10-fold or greater.

In some instances, the cell is a cell of a subject suffering from, diagnosed with, having, or suspected of having a disease condition, i.e., a cell obtained from such a subject or a cell that is part of such a subject. Disease conditions from which the subject may be suffering, may be diagnosed with, may have, or may be suspected of having may vary, where examples of such disease conditions include, but are not limited to: neoplastic disease conditions, e.g., cancers; neurological conditions, neurodevelopmental disorders, immune disorders, gastrointestinal diseases, cardiovascular diseases and the like.

The compositions, systems, and methods of the disclosure find use in the treatment of a variety of different conditions in which the modulation of target gene transcription in a host is desired. By treatment is meant that at least an amelioration of one or more of the symptoms associated with the condition afflicting the host is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the host no longer suffers from the condition, or at least the symptoms that characterize the condition.

Where the methods are methods of treating a subject for a condition, the methods may further include assessing that the subject has the given condition, e.g., so as to confirm that a given CIP is suitable for use in treating the subject for the condition. Any convenient diagnostic protocol appropriate for a given condition may be employed, where the choice of such protocol will necessarily depend on the specific condition to be treated.

Non-limiting examples of conditions or diseases of a subject (e.g., a patient) that can be treated or ameliorated by the compositions, systems, and methods of the disclosure can include multiple sclerosis, various malignancies, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, and Turner syndrome.

Additional non-limiting examples of such conditions or diseases can include those caused by a microbial agent or other exogenous agent such as a virus, bacteria, fungus, protozoa, or other microbe.

In some cases the condition or disease of the subject can be cancer. Non-limiting examples of cancer can include Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic and Intrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Colon Cancer, Colorectal Cancer, Craniopharyngioma, Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Head and Neck Cancer, Heart Cancer, Hepatocellular (Liver) Cancer, Histiocytosis (e.g., Langerhans Cell, etc.), Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic Leukemia (ALL), Acute Myeloid Leukemia (AML), Aleukemic Leukemia, Acute Nonlymphocytic Leukemia, Acute Monocytic Leukemia, Acute Granulocytic Leukemia, Acute Promyelocytic Leukemia, Chronic Lymphocytic Leukemia (CLL), Chronic Myelocytic Leukemia (CML), Chronic Granulocytic Leukemia, Adult T-cell Leukemia, Basophylic Leukemia, Eosinophilic Leukemia, Histiocytic Leukemia, Mast cell Leukemia, Megakaryocytic Leukemia, Blast Cell Leukemia, Leukemia Cutis, Hairy-Cell Leukemia, Stem cell Leukemia, Leukopenic Leukemia, Lymphatic Leukemia, Lymphoblastic Leukemia, Lymphocytic Leukemia, Lymphogenous Leukemia, Lymphoid Leukemia, Lymphosarcoma cell Leukemia, Monocytic Leukemia, Myeloblastic Leukemia, Myelocytic Leukemia, Plasma cell Leukemia, Multiple Myeloma, Plasmacytic Leukemia, Promyelocytic Leukemia), Lip and Oral Cavity Cancer, Liver Cancer (Primary), Lobular Carcinoma In Situ (LCIS), Lung Cancer (e.g., Non-Small Cell, Small Cell, etc.), Lymphoma (Non-Hodgkin Lymphoma or Hodgkin's Lymphoma: e.g. Small Lymphocytic Lymphoma, Mantle Cell Lymphoma, Follicular Lymphoma, Marginal Zone Lymphoma, Extranodal (MALT) Lymphoma, Nodal (monocytoid B-cell) Lymphoma, T-cell Lymphoma, Splenic Lymphoma, Diffuse Large Cell B-cell Lymphoma, Burkitt's Lymphoma, Lymphoblastic Lymphoma, Immunoblastic Large Cell Lymphoma, or Precursor B-Lymphoblastic Lymphoma, Cutaneous T-cell Lymphoma, Peripheral T-cell Lymphoma, Anaplastic Large Cell Lymphoma, Mycosis Fungoides, Primary Central Nervous System (CNS) Lymphoma and Precursor T-Lymphoblastic Lymphoma), Macroglobulinemia (e.g., Waldenström, etc), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, , Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sezary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like. Cancers that may be treated further include, epithelial cancers, such as carcinomas, such as acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchioloalveolar carcinoma, bronchogenic carcinoma, cholangiocellular carcinoma, chorionic carcinoma, clear cell carcinoma, colloid carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in si'tu, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma simplex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like.

A variety of subjects are treatable according to the subject methods. In some instances, the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans.

Chemical Inducers of Proximity and Treatment of Malignancy

In various aspects, the compositions, systems, and methods provided herein are particularly useful for the treatment of malignancies (e.g., cancer). In some aspects of the disclosure, the compositions, systems, and methods are used for treating malignancies (e.g., cancer).

Malignancy is a term for diseases in which abnormal cells divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that begins in blood-forming tissue, such as the bone marrow, and causes too many abnormal blood cells to be made. Lymphoma and multiple myeloma are malignancies that begin in the cells of the immune system. Central nervous system cancers are malignancies that begin in the tissues of the brain and spinal cord.

Lung cancer is the leading cause of cancer mortality worldwide with 2.2 million new cases and 1.8 million deaths in 2020 alone (Sung et al., CA Cancer J. Clin. (2021) 71: 209-249). While pharmacologic and surgical advancements have improved survival in most of the subtypes of lung cancer, small cell lung cancer (SCLC) remains the most lethal with a median survival after diagnosis of less than 2 years if identified early and ~1 year for patients with metastatic disease (Rudin et al., Nat. Rev. Dis. Primers (2021) 7:3. Therefore, novel therapeutics for SCLC patients is urgently needed.

SCLC is a high-grade neuroendocrine carcinoma that represents 15% of all lung cancer cases, which approximates to 250,000 new cases and 200,000 global deaths annually. About 98% of patients with SCLC have some history of smoking with additional links to environmental toxin exposures (Varghese et al., J. Thorac. Oncol. (2014) 9:892-896). Up to 70% of patients present at TNM stage IV at the time of diagnosis with 8% survival by 24 months (Nicholson et al., J. Thorac. Oncol. (2016) 11:300-311). At the time of initial diagnosis, the mass is often located centrally with lymph node and/or metastatic involvement, leading to limited surgical options (Rudin, supra). Genomic characterizations of SCLC have identified simultaneous inactivation of tumor suppressors TP53 and RB in a significant proportion of SCLC cases (George et al., Nature (2015) 524:47-53). Furthermore, other cellular machinery involved in cell cycle arrest and apoptosis are occasionally dysregulated in SCLC, such as MYC amplification and BCL-2 amplification (Little et al., Nature (1983) 306:194-196; Ikegaki et al., Cancer Res. (1994) 54: 6-8). However, to date there has not been a pathway or a molecular target that has been robustly leveraged for therapeutic development.

The non-Hodgkin lymphomas (NHLs) are a diverse group of blood cancers that include any kind of lymphoma except Hodgkin's lymphomas. Types of NHL vary significantly in their severity, from indolent to very aggressive. Less aggressive non-Hodgkin lymphomas are compatible with a long survival while more aggressive non-Hodgkin lymphomas can be rapidly fatal without treatment. They can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma. Prognosis and treatment depend on the stage and type of disease.

Diffuse Large Cell B Cell Lymphoma (DLBCL) DLBCL is the most common lymphoma and originates from germinal center B-cells. Frontline treatment with R-CHOP, an aggressive and highly toxic regimen, is successful in -60% of patients but leaves some patients with permanent neurologic or cardiovascular impairment. DLBCL that is resistant to R-CHOP is difficult to treat and an area of significant need. BCL6, MYC, BCL2 and STAT3 are well-established drivers of DLBCL that are targeted by genetic translocations and amplifications that activate them or increase their expression (Pasqualucci and Dalla-Favera, "Genetics of diffuse large B-cell lymphoma," Blood (2018) 131: 2307-2319; Schmitz, et al., "Genetics and Pathogenesis of Diffuse Large B-Cell Lymphoma," N Engl J Med (2018) 378: 1396-1407; and Reddy et al., "Genetic and Functional Drivers of Diffuse Large B Cell Lymphoma," Cell (2017) 171: 481-494 e415). These driver events occur in combination with each other, in the case of double-hit/triple-hit lymphoma, and with numerous other genetic alterations that define no less than 5 genetic subtypes of DLBCL (Schmitz et al., supra; Chapuy et al., "Molecular subtypes of diffuse large B cell lymphoma are associated with distinct pathogenic mechanisms and outcomes," Nat Med (2018) 24: 679-690). Clearly new treatments are needed that are less toxic and engage the problem of multiple drivers for DLBCL.

Prostate cancer is the second most frequently diagnosed cancer and the sixth leading cause of cancer death in males, accounting for 14% (903,500) of the total new cancer cases and 6% (258,400) of the total cancer deaths in males worldwide. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

The incidence of cancer continues to climb as the general population ages, as new cancers develop, and as susceptible populations grow. A tremendous demand therefore exists for new methods and compositions that can be used to treat patients with cancer.

CIPs for Treatment of Malignancy

The present disclosure provides methods of treating a subject for a malignancy, e.g., lung cancer, upper aerodigestive cancer, hematologic malignancies such as lymphoma, leukemia, sarcoma, GI cancer (such as bile duct, pancreatic, liver, colorectal, esophageal, gastric cancer), breast cancer, prostate cancer, CNS malignancies (such as glioblastoma, astrocytoma), renal cancer, urinary tract cancer, thyroid cancer, melanoma, ovarian cancer, soft tissue malignancies, uterine cancer, cervical cancer etc. As reviewed above, embodiments of the methods employ a CIP, such as a Transcriptional Chemical Inducer of Proximity (TCIP)). A TCIP is a compound that induces proximity of a first endogenous anchor transcription factor, e.g., BCL-6 (and/or a functional homologue thereof), that binds to a promoter of the target gene, e.g., a proapoptotic gene, and a second endogenous transcription modulating factor, e.g., a cancer cell driver, e.g., a SCLC or DLBCL driver, such as BRD4 or a CDK (e.g., CDK9, CDK8, CDK7), a prostatic cancer driver, e.g., an androgen receptor (AR), an estrogen receptor, etc., under intracellular conditions. As some CIPs of the disclosure induce proximity of at least one endogenous transcription factor or epigenetic regulator with another endogenous transcription modulating factor (e.g., BRD4, a CDK, estrogen receptor, AR, etc.), such CIPs of the disclosure may be referred to as Transcription-Chemical Inducers of Proximity (TCIP). TCIPs of the disclosure may be viewed as transcriptional and epigenetic Chemical Inducers of Proximity. By "induces proximity", when used in reference to the compounds of the disclosure (CIPs or TCIPs) is meant that the first and second endogenous proteins are spatially associated with each other through a binding event mediated by the compound, which is configured to simultaneously bind to both endogenous proteins, such that the compound may be viewed as a bifunctional compound or a molecular glue. Spatial association is characterized by the presence of a ternary complex that includes the CIP, the first endogenous protein, and the second endogenous protein (e.g., BRD4, a CDK, estrogen receptor, AR, etc.). In the ternary complex, each member or component of the ternary complex is bound to at least one other member of the ternary complex. In this ternary complex, binding amongst the various components may vary. For example, the CIP may simultaneously bind to domains of the first and second endogenous factors or proteins, thereby producing the ternary complex and desired spatial association, e.g., which ultimately results in the desired transcriptional modulating of the target gene. This ternary complex is made up of three distinct, non-covalently bound components, e.g., the first endogenous protein, the second endogenous protein, and the CIP. In the example of a TCIP, the ternary complex is made up of three distinct, non-covalently bound components (e.g., the endogenous anchor transcription factor, the endogenous transcription modulating factor, and the TCIP). Further details regarding CIPs and TCIPs may be found in pending PCT Application Serial No. PCT/US2021/058231 published as WO 2022/098989, the disclosure of which is herein incorporated by reference.

TCIP compounds employed in embodiments of the disclosure may include a first ligand that specifically binds to the anchor transcription factor, e.g., BCL-6 (and/or a functional homologue thereof), and a second ligand, which may be a second covalently linked second ligand, that specifically binds to the transcription modulating factor, e.g., BRD4, a CDK, estrogen receptor, AR, etc. The first and second ligands may be stably associated with the other e.g., via a linkage, which linkage may be a bond or a linking group, e.g., that provides for a covalent linkage between the first and second ligand, either directly or via a linking group, as desired. In other words, in embodiments the TCIP compounds include a linker component, which may be a bond or a linking moiety, which links covalently a first ligand that specifically binds to the anchor transcription factor and a second ligand that specifically binds to the transcription modulating factor. The terms "specific binding," "specifically bind," and the like, when used in reference to a TCIP, refer to the ability of the first and second ligands to preferentially bind directly to their corresponding anchor and transcription modulator factors relative to other molecules or moieties in the cell.

In some instances, the first and second ligands of the TCIPs are small molecules, which in some instances each have a molecular weight ranging from 50 Daltons to 1000 Daltons, such as to 400 to 800 Daltons. The chemical structures of the first and second ligands may vary widely, where the first and second ligands may be chosen to provide for the desired specific binding to the target anchor transcription or transcription modulatory factors. The first and second ligands may be selected so as to have little, if any, impact on the activity of the endogenous factor, e.g., anchor transcription factor or transcription modulating factor, to which they are configured to bind.

As summarized above, the present disclosure provides compounds that are chemical inducers of proximity. Below are specific examples of compounds that may be used in the compositions, systems, and methods provided herein. In specific embodiments, compounds of interest include a BCL-6 (B-cell lymphoma 6) inhibitor and a BRD4 (bromodomain-containing 4) ligand. In some embodiments, the BCL-6 inhibitor and the BRD4 ligand are covalently bonded through a linker. In some embodiments, chemical inducers of proximity include a compound of formula I:

(BR or EL or CL or AL)-L-BC (I)

where:

EL is a ligand that specifically binds to an estrogen receptor;

BR is a ligand that specifically binds to bromodomain-containing protein 4 (BRD4);

CL is a ligand that specifically binds to a CDK, e.g., CDK9, CDK8 and/or CDK7;

AL is a ligand that specifically binds to an androgen receptor;

BC is a ligand that specifically binds to B-cell lymphoma 6 (BCL-6) or a BCL6 BTB-domain family member; and L is a linker (optional), or a pharmaceutically acceptable salt thereof.

In some embodiments, "salts" of the compounds of the present disclosure may include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a compound of Formula I (BR-L-BC) or a salt thereof, and one or more molecules of a solvent. Such solvates may be crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the compounds described herein exist in their isotopically labeled forms. For example, the compounds disclosed herein include isotopically labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as 2H, 3H, 13C, 14C, 15N, 17O, 18O, 31P, 32P, 35S, 18F, and 36Cl, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically labeled compounds, for example those into which radioactive isotopes such as 3H and 14C are incorporated, are useful in drug and/or substrate tissue distribution assays. Tritiated, i.e., 3H and carbon 14, i.e., 14C, isotopes are particularly preferred for their ease of preparation and detectability. Further, substitution with heavy isotopes such as deuterium, i.e., 2H, produces certain therapeutic advantages resulting from greater metabolic stability, for example increased in vivo half life or reduced dosage requirements. In some embodiments, the isotopically labeled compounds, pharmaceutically acceptable salt, ester, solvate, hydrate, or derivative thereof is prepared by any suitable method.

Compounds disclosed herein encompass prodrugs thereof. "Prodrug" as used herein is meant to indicate a compound that may be converted under physiological conditions or by solvolysis to a biologically active compound described herein. The term "prodrug" refers to a precursor of a biologically active compound that is pharmaceutically acceptable. A prodrug may be inactive when administered to a subject, but is converted in vivo to an active compound, for example, by hydrolysis. The prodrug compound may offer advantages of solubility, tissue compatibility and/or delayed release in a mammalian organism (see, e.g., Bundgard, H., Design of Prodrugs (1985), pp. 7 9, 21 24 (Elsevier, Amsterdam). A discussion of prodrugs is provided in Higuchi, T., et al., "Pro drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. Prodrugs of an active compound, as described herein, may be prepared by modifying functional groups present in the active compound in such a way that the modifications are cleaved, either in routine manipulation or in vivo, to the parent active compound.

BR: Bromodomain-Containing 4 (BRD4) Ligands

Methods of treating a subject for a malignancy, e.g., Lung Cancer (e.g., Small Cell Lung Cancer (SCLC)) or Lymphoma (e.g., Diffuse Large Cell B Cell Lymphoma (DLBCL), are provided. In some cases, the methods can include administering a transcriptional chemical inducer of proximity (TCIP) which links a BTB-domain containing protein, e.g., BCL-6 or a related family member, and BRD4 to treat the subject for the malignancy, e.g., SCLC or DLBCL. Also provided are compositions that find use in practicing methods of the disclosure.

TCIPs employed in these embodiments of the disclosure include a ligand for a transcription modulator, such as oncogenic transcription factor, e.g., BRD4. This embodiment is of particular significance in treatment of cancer, where the CIP causes the cancer cell to kill itself with its own driver. Oncogenic transcription factors are transcription factors whose activity contributes to a neoplastic, e.g., cancerous, disease condition. The oncogenic transcription factor may vary, where examples of oncogenic transcription factors that may be employed in treating SCLC include, but are not limited to: BRD4, c-myc, oncogenic fusions, and the like. Any convenient ligands for these oncogenic transcription factors may be employed, where suitable ligands include small molecule ligands that are capable of specifically binding to the target oncogenic transcription factor without any relevant negative impact on the target oncogenic transcription factor's ability to enhance transcription of the target proapoptotic gene when complexed with the anchor transcription factor by a TCIP, i.e., the transcription-activating activity of the oncogenic transcription factor. The molecular weight of these ligands may vary, and in some instances ranges from 150 Daltons to 500 Daltons such as 250 Daltons to 400 Daltons.

Suitable ligands for BRD4 include, but are not limited to, those described in U.S. Pat. Nos. 11,279,703; 11,267,820; 11,117,865; 11,020,404; 10,975,059; 10,738,016; 10,689,395; 10,526,291; 10,328,074; 10,300,073; 10,106,507; 10,071,129; 9,840,526; 9,814,728; 9,610,332; 9,387,231; 9,266,891; 9,255,089; 9,249,161; 9,108,953, as well as those described in United States Patent Application Publication Nos. 20220185820; 20220177459; 20220119370; 20220047596; 20210355088; 20210221821; 20210147419; 20200407328; 20200405809; 20200385408; 20200339595; 20200338065; 20200255450; 20200095252; 20200046726; 20190367530; 20190381013; 20190359573; 20190292168; 20190262355; 20190055203; 20180290984; 20180282316; 20180237453; 20180050043; 20170304315; 20170226065; 20160129001; 20160075695; 20160060260; 20160031868; 20150148344; 20150148333; 20150133436; 20150087636; 20140371157; 20140336190; 20140296246; 20140296243; 20140243322; 20140243286; 20140005169; 20140044770; 20120208800; 20120157428; the disclosures of which are herein incorporated by reference.

Suitable ligands for BRD4 include, but are not limited to: JQ1, AZD5153, ABBV-075, BMS-986158, CPI-0610, GSK525762; OTX-015, PLX51107, INCB054329, INCB057643, I-BET151, RVX-208 and the like. The structures are provided below:

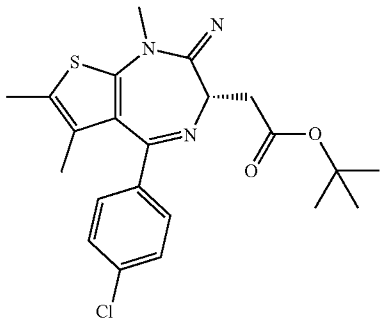

JQ1

-continued

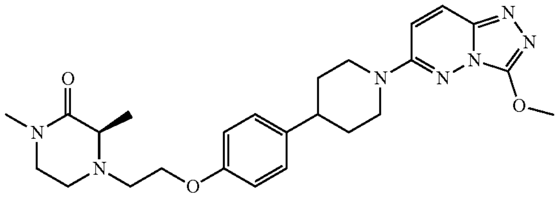

AZD5153

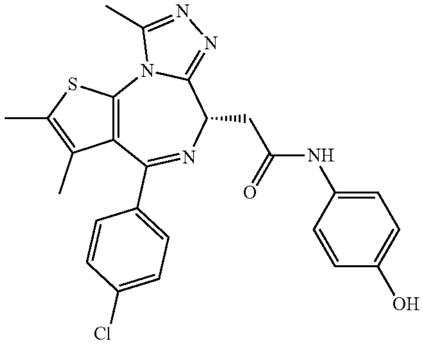

OTX-015

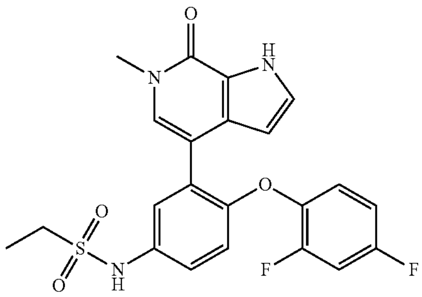

ABBV-075

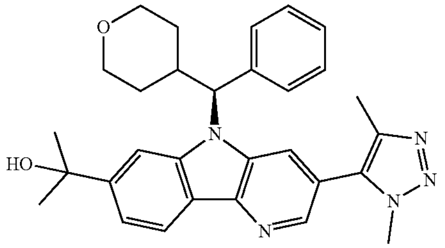

BMS-986158

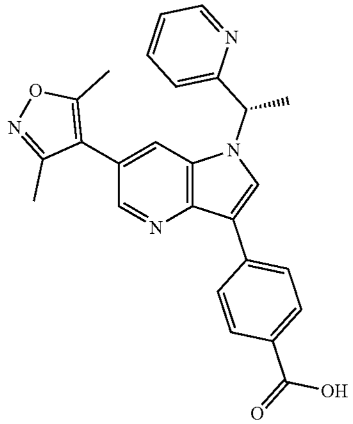

PLX51107

-continued

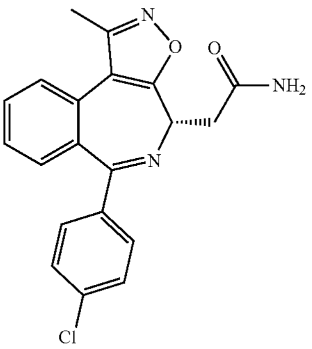

CPI-0610

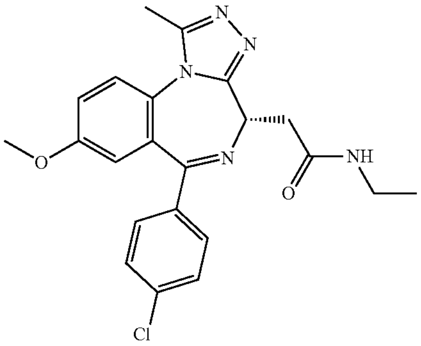

CSK525762

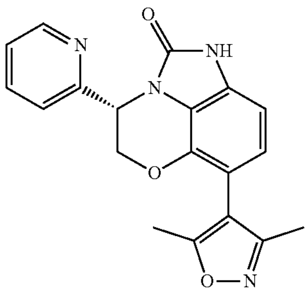

INC054329

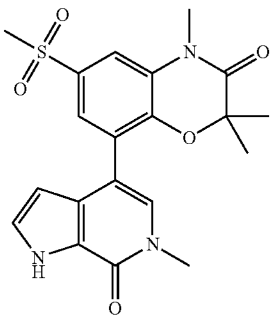

INC057643

-continued

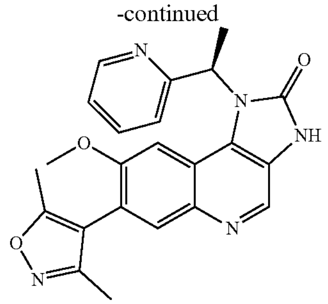

I-BET151

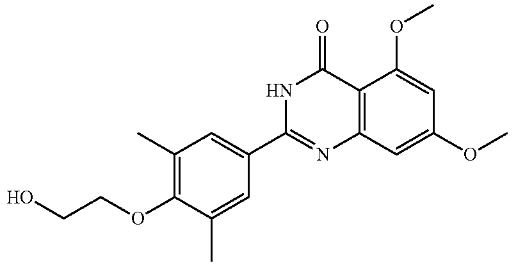

RVX-208

In some embodiments, the bromodomain-containing 4 ligand (BR) is of formula IA:

(IA)

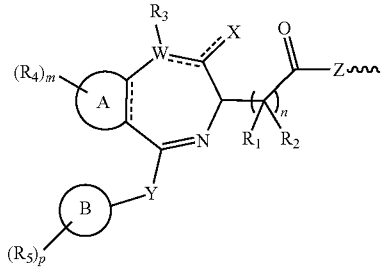

where:

n is an integer from 0 to 12;

m is an integer from 0 to 5;

p is an integer from 0 to 5;

A is a 5-8 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

B is a 3-12 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

W is C, N, O or S;

X is oxygen or sulfur, or: $R^3$ and X are taken together with their intervening atoms to form an optionally substituted 5-6 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

Y is a covalent bond, alkyl, substituted alkyl, alkenyl, substituted alkenyl, alkynyl, substituted alkynyl, or a substituted bivalent C(1-6) hydrocarbon chain wherein one or more methylene units is optionally replaced by —NR'—, —N(R')C(O)—, —C(O)N(R, —N(R')

$SO_2$—, —$SO_2N(R)$—, —O—, —C(O)—, —OC(O)—, —C(O)O—, —S—, —SO— or —$SO_2$—;

Z is —$CH_2$, —NH, —O— or —S—

==== represents a single or double bond;

∿∿∿ represents a bond to the linker;

each of $R_1$, $R_2$, $R_3$, $R_4$ and $R_5$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine and substituted sulfoximine.

In some embodiments, A is a 5-membered fused heteroaryl ring having 2 heteroatoms independently selected from nitrogen, oxygen, or sulfur. In some instances, A is a 5-membered fused heteroaryl ring having 2 heteroatoms independently selected from nitrogen or oxygen. In some instances, A is a 5-membered fused heteroaryl ring having 2 heteroatoms selected from nitrogen and oxygen. In some instances, A is a 5-membered fused heteroaryl ring having 2 heteroatoms independently selected from nitrogen or sulfur. In some instances, A is a 5-membered fused heteroaryl ring having 2 heteroatoms selected from nitrogen and sulfur. In certain instances, A is selected from thiazolo, isothiazolo, oxazolo, isoxazolo, pyrazolo, and imidazolo rings. In certain instances, A is isothiazolo.

In some embodiments, A is benzo, or a 5-6 membered fused heteroaryl ring having 1-3 heteroatoms independently selected from nitrogen, oxygen, or sulfur. In some instances, A is a 5-membered fused heteroaryl ring having 2-3 heteroatoms independently selected from nitrogen, oxygen, or sulfur, or a 6-membered fused heteroaryl ring having 2-3 nitrogen atoms. In some instances, A is benzo. In some embodiments, A is a 5-6 membered fused heteroaryl ring having 1-3 heteroatoms independently selected from nitrogen, oxygen, or sulfur. In some instances, A is a 6-membered fused heteroaryl ring having 1-3 nitrogen atoms. In certain instance, A is selected from pyrido, pyrimidino, pyrazino, pyridazino, and triazino, rings. In certain instances, A is a 5-membered fused heteroaryl ring having 1 heteroatom selected from nitrogen, oxygen, or sulfur. In certain instances, A is thieno. In certain instances, A is furano. In certain instances, A is pyrrolo.

In some embodiments, B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is phenyl. In some instances, B is a 3-7 membered saturated or partially unsaturated carbocyclic ring. In certain instances, B is cyclopropyl, cyclobutyl, cyclopentyl, cyclohexyl, or cycloheptyl. In certain instances, B is cyclopentenyl, cyclohexenyl, or cycloheptenyl.

In some embodiments, B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrodinyl, pyrrohdonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, B is a 5-6 membered monocyclic heteroaryl ring having 1-3 heteroatoms independently selected from nitrogen, oxygen, and sulfur. In some instances, B is 6-membered heteroaryl ring having 1-3 nitrogen atoms. In some instances, B is a 6-membered heteroaryl ring having 1 nitrogen atom. In some instances, B is a 6-membered heteroaryl ring having 2 nitrogen atoms. In some instances, B is a 6-membered heteroaryl ring having 3 nitrogen atoms.

In some embodiments, B is a 5-membered heteroaryl ring having 1-3 heteroatoms independently selected from nitrogen, oxygen, or sulfur. In some instances, B is a 5-membered heteroaryl ring having 1 heteroatom independently selected from nitrogen, oxygen, or sulfur. In some instances, B is a 5-membered heteroaryl ring having 2 heteroatoms independently selected from nitrogen, oxygen, or sulfur. In some instances, B is a 5-membered heteroaryl ring having 2 heteroatoms independently selected from nitrogen and oxygen. In some instances, B is a 5-membered heteroaryl ring having 2 heteroatoms independently selected from nitrogen and sulfur. In some instances, B is a 5-membered heteroaryl ring having 1-3 nitrogen atoms. In certain instances, B is selected from thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is a 5,5-fused-, 5,6-fused, or 6,6-fused saturated, partially unsaturated, or aromatic bicyclic ring. In some instances, B is a 5,5-fused, 5,6-fused, or 6,6-fused aromatic bicyclic ring. In some instances, B is a naphthalenyl, indanyl or indenyl group.

In some embodiments, B is a 7-10 membered bicyclic saturated or partially unsaturated heterocyclic ring having 1-4 heteroatoms independently selected from nitrogen, oxygen, and sulfur. In some instances, B is a 7-8 membered bicyclic saturated heterocyclic ring having 1-3 heteroatoms independently selected from nitrogen, oxygen, and sulfur. In some instances, B is a 7-8 membered bicyclic partially unsaturated heterocyclic ring having 1-3 heteroatoms independently selected from nitrogen, oxygen, and sulfur. In some instances, B is a 9-10 membered bicyclic saturated heterocyclic ring having 1-3 heteroatoms independently selected from nitrogen, oxygen, and sulfur. In some instances, B is a 9-10 membered bicyclic partially unsaturated heterocyclic ring having 1-3 heteroatoms independently selected from nitrogen, oxygen, and sulfur. In some instances, B is tetrahydroquinolinyl, tetrahydroisoquinolinyl, decahydroquinolinyl, or quinuclidinyl. In some instances, B is selected from indolinyl, 3H-indolyl, chromanyl, phenanthridinyl, 2-azabicyclo[2.2.1]heptanyl, octahydroindolyl, or tetrahydroquinolinyl.

In some embodiments, B is a 8-10 membered bicyclic heteroaryl ring having 1-4 heteroatoms independently selected from nitrogen, oxygen, and sulfur. In some instances, B is a 5,5-fused, 5,6-fused, or 6,6-fused saturated, partially unsaturated, or aromatic bicyclic ring having 1-4 heteroatoms, independently selected from nitrogen, oxygen, or sulfur. In some instances, B is a 5,5-fused, 5,6-fused, or 6,6-fused heteroaryl ring having 1-4 heteroatoms, independently selected from nitrogen, oxygen, or sulfur. In certain instances, B is a 5,5-fused, 5,6-fused, or 6,6-fused heteroaryl ring having 1-4 nitrogen atoms. In certain instances, B is a 5,6-fused heteroaryl ring having 1-4 nitrogen atoms. In certain instances, B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphthenyl, or benzofuranyl. In certain instances, B is selected from an indolizinyl, purinyl, naphthyridinyl, or pteridinyl.

In some embodiments, $R^3$ and X are taken together with their intervening atoms to form a heteroaryl ring having 1-4 heteroatoms independently selected from nitrogen, oxygen, or sulfur. In certain instances, $R^3$ and X are taken together with their intervening atoms to form an optionally substituted triazolyl ring. In some instances, $R_3$ is an optionally substituted C(1-6) aliphatic. In some embodiments, $R_3$ is substituted. In some embodiments, $R_3$ is unsubstituted. In certain embodiments, $R_3$ is C(1-6) alkyl. In certain embodiments, $R_3$ is C(1-4) alkyl. In certain embodiments, $R_3$ is methyl, ethyl, propyl, or isopropyl.

In some embodiments, X is oxygen or sulfur, or $R_3$ and X are taken together with their intervening atoms to form an optionally substituted 5-membered heteroaryl ring having 1-4 heteroatoms independently selected from nitrogen, oxygen, or sulfur. In some embodiments, X is oxygen. In some embodiments, X is sulfur. In some embodiments, $R_3$ and X are taken together with their intervening atoms to form an optionally substituted 5-membered heteroaryl ring having 1-4 heteroatoms independently selected from nitrogen, oxygen, or sulfur. In some embodiments, $R_3$ and X are taken together with their intervening atoms to form a substituted 5-membered heteroaryl ring having 1-4 heteroatoms independently selected from nitrogen, oxygen, or sulfur. In some embodiments, $R_3$ and X are taken together with their intervening atoms to form an unsubstituted 5-membered heteroaryl ring having 1-4 heteroatoms independently selected from nitrogen, oxygen, or sulfur. In certain embodiments, $R_3$ and X are taken together with their intervening atoms to form an optionally substituted 5-membered heteroaryl ring having 1-2 heteroatoms independently selected from nitrogen, oxygen, or sulfur. In certain embodiments, $R_3$ and X are taken together with their intervening atoms to form an optionally substituted pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl ring.

In some embodiments, $R^4$ is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, or —OC(O)N(R')$_2$, where R and R are as defined and described herein. In some embodiments, $R^4$ is -R. In certain embodiments, $R^4$ is hydrogen. In certain other embodiments, $R^4$ is halogen. In some embodiments, $R^4$ is —OR, —SR, or —N(R')$_2$— In certain instances, $R^4$ is -OR. In certain instances, $R^4$ is —CN or —NO$_2$. In certain instances, $R^4$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In certain instances, $R^4$ is —S(O)R, —SO$_2$R, or —SO$_2$N(R')$_2$. In certain instances, $R^4$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain instances, $R^4$ is —C=NN(R')$_2$, -C=NOR, —C(=N(R'))N(R')$_2$. In certain instances, $R^4$ is —OC(O)R or —OC(O)N(R')$_2$.

In some embodiment m is an integer from 0 to 5. In some instances, m is 1. In some instances, m is 2. In some instances, m is 3. In some instances, m is 4. In certain instances, m is 5.

In some embodiments, $R^5$ is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, or —OC(O)N(R')$_2$, where R and R' are as defined and described herein. In some embodiments, $R^5$ is -R. In certain embodiments, $R^5$ is hydrogen. In certain other embodiments, $R^5$ is halogen. In some embodiments, $R^4$ is —OR, —SR, or —N(R')$_2$— In certain embodiments, $R^5$ is -OR. In other embodiments, $R^5$ is —CN or —NO$_2$. In some embodiments, $R^5$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^5$ is —S(O)R, —SO$_2$R, or —SO$_2$N(R')$_2$. In certain embodiments, $R^5$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^5$ is —C=NN(R')$_2$, —C=NOR, —C(=N(R'))N(R')$_2$. In yet other embodiments, $R^5$ is —OC(O)R or —OC(O)N(R')$_2$.

In some embodiment p is an integer from 0 to 5. In some instances, p is 1. In some instances, p is 2. In some instances, p is 3. In some instances, p is 4. In some instances, p is 5.

In some embodiments, Y is a covalent bond. In some instances, Y is an optionally substituted bivalent C(1-6) hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In some instances, Y is an optionally substituted bivalent C(1-3) hydrocarbon chain wherein one methylene unit is optionally replaced by —NR'—, —N(R')C(O)—, —C(O)N(R, —N(R')SO$_2$—, —SO$_2$N(R')—, —O—, —C(O)—, —OC(O)—, —C(O)O—, —S—, —SO— or —SO$_2$—. In certain embodiments, Y is a Cr-3 hydrocarbon chain wherein one methylene unit is optionally replaced by —NH—, —O—, —S—, —S(O)—, or —SO$_2$—.

In some embodiments, each $R_1$ is independently selected from hydrogen, halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, —OC(O)N(R')$_2$, or —(CH$_2$)$_q$R$^x$ wherein q is 0-3 and $R^x$ is halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R or —OC(O)N(R')$_2$. In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each $R_1$ is independently selected from C(1-6) aliphatic, —OR, —N(R')$_2$, —C(O)R, —OC(O)R, —N(R')C(O)R, —C(O)NR', or —$CO_2$R.

In some embodiments, each $R_2$ is independently selected from hydrogen, halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, —OC(O)N(R')$_2$, or —$(CH_2)_qR^x$ wherein q is 0-3 and $R^x$ is halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R or —OC(O)N(R')$_2$. In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —$CO_2$R.

In some embodiments, n is an integer from 0 to 12. In some instances, n is 1. In some instances, n is 2. In some instances, n is 3. In some instances, n is 4. In some instances, n is 5. In some instances, n is 6.

In some embodiments, Z is —$CH_2$. In some instances, Z is —NH. In some instances, Z is —O—. In some instances, Z is —S—.

In some embodiments, the bromodomain-containing 4 ligand (BR) is of formula IA1:

(IA1)

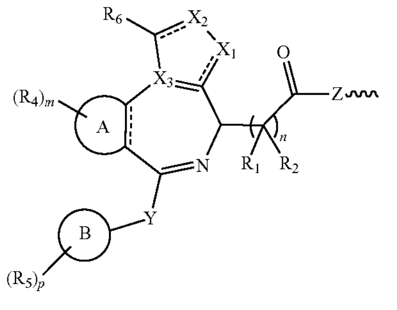

where:

$X_1$ is from C, N, O or S;

$X_2$ is from C, N, O or S;

$X_3$ is C or N;

---- represents a single or double bond; and $R_6$ is hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, X1 is N or O; X2 is N; and X3 is C or N. In some instances, $X_1$ is N; $X_2$ is N; and $X_3$ is N. In some instances, $X_1$ is O; $X_2$ is N; and $X_3$ is C.

In some instances, $R_e$ is hydrogen or a C(1-6) alkyl. In some instances, $R_6$ is selected from methyl, ethyl, n-propyl, isopropyl, n-butyl, iso-butyl or tert-butyl. In certain instances, $R_6$ is methyl.

In some embodiments, n is an integer from 0 to 4. In some instances, n is 1. In some instances, n is 2. In some instances, n is 3. In some instances, n is 4. In some instances, n is 5. In some instances, n is 6.

In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each $R_1$ is independently selected from C(1-6) aliphatic, —OR, —N(R')$_2$, —C(O)R, —OC(O)R, —N(R')C(O)R, —C(O)NR', or —$CO_2$R. In some instances, each $R_1$ is hydrogen or a C(1-6) alkyl. In some instances, each $R_1$ is selected from methyl, ethyl, n-propyl, isopropyl, n-butyl, iso-butyl or tert-butyl. In certain instances, each $R_1$ is methyl.

In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —$CO_2$R. In some instances, each $R_2$ is hydrogen or a C(1-6) alkyl. In some instances, each $R_2$ is selected from methyl, ethyl, n-propyl, isopropyl, n-butyl, iso-butyl or tert-butyl. In certain instances, each $R_2$ is methyl.

In certain embodiments, n is an integer from 1-4; and each of $R_1$ and $R_2$ are independently selected from hydrogen and a C(1-6) alkyl. In certain instances, n is an integer from 1-4 and each of $R_1$ and $R_2$ are independently selected from methyl, ethyl, n-propyl, isopropyl, n-butyl, iso-butyl or tert-butyl. In certain instances, n is an integer from 1-4 and each of $R_1$ and $R_2$ are methyl. In certain instances, n is 1 and each of $R_1$ and $R_2$ are hydrogen. In certain instances, n is 1 and each of $R_1$ and $R_2$ are methyl.

In some embodiments, A is a 5-membered fused heteroaryl ring having 2 heteroatoms independently selected from nitrogen, oxygen, or sulfur. In some instances, A is a 5-membered fused heteroaryl ring having 2 heteroatoms independently selected from nitrogen or oxygen. In some instances, A is a 5-membered fused heteroaryl ring having 2 heteroatoms selected from nitrogen and oxygen. In some instances, A is a 5-membered fused heteroaryl ring having 2 heteroatoms independently selected from nitrogen or sulfur. In some instances, A is a 5-membered fused heteroaryl ring having 2 heteroatoms selected from nitrogen and sulfur. In certain instances, A is selected from thiazolo, isothiazolo, oxazolo, isoxazolo, pyrazolo, and imidazolo rings. In certain instances, A is isothiazolo.

In some embodiments, A is benzo, or a 5-6 membered fused heteroaryl ring having 1-3 heteroatoms independently selected from nitrogen, oxygen, or sulfur. In some instances, A is a 5-membered fused heteroaryl ring having 2-3 heteroatoms independently selected from nitrogen, oxygen, or sulfur, or a 6-membered fused heteroaryl ring having 2-3 nitrogen atoms. In some instances, A is benzo. In some embodiments, A is a 5-6 membered fused heteroaryl ring having 1-3 heteroatoms independently selected from nitrogen, oxygen, or sulfur. In some instances, A is a 6-membered fused heteroaryl ring having 1-3 nitrogen atoms. In certain instance, A is selected from pyrido, pyrimidino, pyrazino, pyridazino, and triazino, rings. In certain instances, A is a 5-membered fused heteroaryl ring having 1 heteroatom selected from nitrogen, oxygen, or sulfur. In certain instances, A is thieno. In certain instances, A is furano. In certain instances, A is pyrrolo.

In some embodiments, B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is phenyl. In some instances, B is a 3-7 membered saturated or partially unsaturated carbocyclic ring. In certain instances, B is cyclopropyl, cyclobutyl, cyclopentyl, cyclohexyl, or cycloheptyl. In certain instances, B is cyclopentenyl, cyclohexenyl, or cycloheptenyl.

In some embodiments, B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrohdinyl, pyrrohdonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, B is a 5-6 membered monocyclic heteroaryl ring having 1-3 heteroatoms independently selected from nitrogen, oxygen, and sulfur. In some instances, B is 6-membered heteroaryl ring having 1-3 nitrogen atoms. In some instances, B is a 6-membered heteroaryl ring having 1 nitrogen atom. In some instances, B is a 6-membered heteroaryl ring having 2 nitrogen atoms. In some instances, B is a 6-membered heteroaryl ring having 3 nitrogen atoms.

In some embodiments, B is a 5-membered heteroaryl ring having 1-3 heteroatoms independently selected from nitrogen, oxygen, or sulfur. In some instances, B is a 5-membered heteroaryl ring having 1 heteroatom independently selected from nitrogen, oxygen, or sulfur. In some instances, B is a 5-membered heteroaryl ring having 2 heteroatoms independently selected from nitrogen, oxygen, or sulfur. In some instances, B is a 5-membered heteroaryl ring having 2 heteroatoms independently selected from nitrogen and oxygen. In some instances, B is a 5-membered heteroaryl ring having 2 heteroatoms independently selected from nitrogen and sulfur. In some instances, B is a 5-membered heteroaryl ring having 1-3 nitrogen atoms. In certain instances, B is selected from thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is a 5,5-fused-, 5,6-fused, or 6,6-fused saturated, partially unsaturated, or aromatic bicyclic ring. In some instances, B is a 5,5-fused, 5,6-fused, or 6,6-fused aromatic bicyclic ring. In some instances, B is a naphthalenyl, indanyl or indenyl group.

In some embodiments, B is a 7-10 membered bicyclic saturated or partially unsaturated heterocyclic ring having 1-4 heteroatoms independently selected from nitrogen, oxygen, and sulfur. In some instances, B is a 7-8 membered bicyclic saturated heterocyclic ring having 1-3 heteroatoms independently selected from nitrogen, oxygen, and sulfur. In some instances, B is a 7-8 membered bicyclic partially unsaturated heterocyclic ring having 1-3 heteroatoms independently selected from nitrogen, oxygen, and sulfur. In some instances, B is a 9-10 membered bicyclic saturated heterocyclic ring having 1-3 heteroatoms independently selected from nitrogen, oxygen, and sulfur. In some instances, B is a 9-10 membered bicyclic partially unsaturated heterocyclic ring having 1-3 heteroatoms independently selected from nitrogen, oxygen, and sulfur. In some instances, B is tetrahydroquinolinyl, tetrahydroisoquinolinyl, decahydroquinolinyl, or quinuclidinyl. In some instances, B is selected from indolinyl, 3H-indolyl, chromanyl, phenanthridinyl, 2-azabicyclo[2.2.1]heptanyl, octahydroindolyl, or tetrahydroquinolinyl.

In some embodiments, B is a 8-10 membered bicyclic heteroaryl ring having 1-4 heteroatoms independently selected from nitrogen, oxygen, and sulfur. In some instances, B is a 5,5-fused, 5,6-fused, or 6,6-fused saturated, partially unsaturated, or aromatic bicyclic ring having 1-4 heteroatoms, independently selected from nitrogen, oxygen, or sulfur. In some instances, B is a 5,5-fused, 5,6-fused, or 6,6-fused heteroaryl ring having 1-4 heteroatoms, independently selected from nitrogen, oxygen, or sulfur. In certain instances, B is a 5,5-fused, 5,6-fused, or 6,6-fused heteroaryl ring having 1-4 nitrogen atoms. In certain instances, B is a 5,6-fused heteroaryl ring having 1-4 nitrogen atoms. In certain instances, B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphthenyl, or benzofuranyl. In certain instances, B is selected from an indolizinyl, purinyl, naphthyridinyl, or pteridinyl.

In some embodiments, $R^4$ is —R, halogen, —OR, —SR, —$N(R')_2$, —CN, —$NO_2$, —C(O)R, —C(S)R, —$CO_2R$, —$C(O)N(R')_2$, —C(O)SR, —C(O)C(O)R, —$C(O)CH_2C(O)$R, —$C(S)N(R')_2$, —C(S)OR, —S(O)R, —$SO_2R$, —$SO_2N(R')_2$, —N(R')C(O)R, —N(R')C(O)$N(R')_2$, —N(R')C(S)$N(R')_2$, —N(R')$SO_2R$, —N(R')$SO_2N(R')_2$, —N(R')$N(R')_2$, —N(R')C(=N(R'))$N(R')_2$, —C=$NN(R')_2$, -C=NOR, —C(=N(R'))$N(R')_2$, —OC(O)R, or —OC(O)$N(R')_2$, where R and R' are as defined and described herein. In some embodiments, $R^4$ is -R. In certain embodiments, $R^4$ is hydrogen. In certain other embodiments, $R^4$ is halogen. In some embodiments, $R^4$ is —OR, —SR, or —$N(R')_2$— In certain instances, $R^4$ is -OR. In certain instances, $R^4$ is —CN or —$NO_2$. In certain instances, $R^4$ is —C(O)R, —$CO_2R$, —$C(O)N(R')_2$, —C(O)SR, —C(O)C(O)R, —$C(O)CH_2C(O)$R, —$C(S)N(R')_2$, or —C(S)OR. In certain instances, $R^4$ is —S(O)R, —$SO_2R$, or —$SO_2N(R')_2$. In certain instances, $R^4$ is —N(R')C(O)R, —N(R')C(O)$N(R')_2$, —N(R')$SO_2R$, —N(R')SO$_2$N(R')$_2$, —N(R')N(R')$_2$, or —N(R')C(=N(R'))N(R')$_2$. In certain instances, $R^4$ is —C=NN(R')$_2$, -C=NOR, —C(=N(R'))N(R')$_2$. In certain instances, $R^4$ is —OC(O)R or —OC(O)N(R')$_2$.

In some embodiment m is an integer from 0 to 5. In some instances, m is 1. In some instances, m is 2. In some instances, m is 3. In some instances, m is 4. In certain instances, m is 5.

In some embodiments, $R^5$ is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, or —OC(O)N(R')$_2$, where R and R are as defined and described herein. In some embodiments, $R^5$ is -R. In certain embodiments, $R^5$ is hydrogen. In certain other embodiments, $R^5$ is halogen. In some embodiments, $R^4$ is —OR, —SR, or —N(R')$_2$— In certain embodiments, $R^5$ is -OR. In other embodiments, $R^5$ is —CN or —NO$_2$. In some embodiments, $R^5$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^5$ is —S(O)R, —SO$_2$R, or —SO$_2$N(R')$_2$. In certain embodiments, $R^5$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^5$ is —C=NN(R')$_2$, —C=NOR, —C(=N(R'))N(R')$_2$. In yet other embodiments, $R^5$ is —OC(O)R or —OC(O)N(R')$_2$.

In some embodiment p is an integer from 0 to 5. In some instances, p is 1. In some instances, p is 2. In some instances, p is 3. In some instances, p is 4. In some instances, p is 5.

In some embodiments, Y is a covalent bond. In some instances, Y is an optionally substituted bivalent C(1-6) hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In some instances, Y is an optionally substituted bivalent C(1-3) hydrocarbon chain wherein one methylene unit is optionally replaced by —NR'—, —N(R')C(O)—, —C(O)N(R, —N(R')SO$_2$—, —SO$_2$N(R')—, —O—, —C(O)—, —OC(O)—, —C(O)O—, —S—, —SO— or —SO$_2$—. In certain embodiments, Y is a $C_{1-3}$ hydrocarbon chain wherein one methylene unit is optionally replaced by —NH—, —O—, —S—, —S(O)—, or —SO$_2$—.

In some embodiments, each $R_1$ is independently selected from hydrogen, halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, —OC(O)N(R')$_2$, or —(CH$_2$)$_q$R$^x$ wherein q is 0-3 and $R^x$ is halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R or —OC(O)N(R')$_2$. In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each $R_1$ is independently selected from C(1-6) aliphatic, —OR, —N(R')$_2$, —C(O)R, —OC(O)R, —N(R')C(O)R, —C(O)NR', or —CO$_2$R.

In some embodiments, each $R_2$ is independently selected from hydrogen, halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R, —OC(O)N(R')$_2$, or —(CH$_2$)$_q$R$^x$ wherein q is 0-3 and $R^x$ is halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, -C=NOR, —C(=N(R'))N(R')$_2$, —OC(O)R or —OC(O)N(R')$_2$. In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —CO$_2$R.

In some embodiments, n is an integer from 0 to 12. In some instances, n is 1. In some instances, n is 2. In some instances, n is 3. In some instances, n is 4. In some instances, n is 5. In some instances, n is 6.

In some embodiments, Z is —CH$_2$. In some instances, Z is —NH. In some instances, Z is —O—. In some instances, Z is —S—.

In some embodiments, the bromodomain-containing 4 ligand (BR) is of formula IA2:

(IA2)

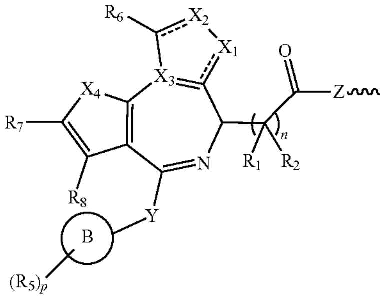

where:

$X_1$ is from C, N, O or S;

$X_2$ is from C, N, O or S;

$X_3$ is C or N;

$X_4$ is from $CH_2$, NH, O or S;

---- represents a single or double bond; and each of $R_6$, $R_7$ and $R_e$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some embodiments, $X_4$ is S. In certain instances, ---- represents a double bond.

In some embodiments, $X_1$ is N or O; $X_2$ is N; and $X_3$ is C or N. In some embodiments, $X_1$ is N; $X_2$ is N; and $X_3$ is N.

In some instances, $R_6$ is hydrogen or a C(1-6) alkyl. In some instances, $R_6$ is selected from methyl, ethyl, n-propyl, isopropyl, n-butyl, iso-butyl or tert-butyl. In certain instances, $R_6$ is methyl. In some instances, $R_7$ is hydrogen or a C(1-6) alkyl. In some instances, $R_7$ is selected from methyl, ethyl, n-propyl, isopropyl, n-butyl, iso-butyl or tert-butyl. In certain instances, $R_7$ is methyl. In some instances, $R_8$ is hydrogen or a C(1-6) alkyl. In some instances, $R_6$ is selected from methyl, ethyl, n-propyl, isopropyl, n-butyl, iso-butyl or tert-butyl. In certain instances, $R_6$ is methyl. In certain instances, each of $R_6$, $R_7$ and $R_a$ is methyl.

In some embodiments, B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is phenyl. In some instances, B is a 3-7 membered saturated or partially unsaturated carbocyclic ring. In certain instances, B is cyclopropyl, cyclobutyl, cyclopentyl, cyclohexyl, or cycloheptyl. In certain instances, B is cyclopentenyl, cyclohexenyl, or cycloheptenyl.

In some embodiments, B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrohdinyl, pyrrohdonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, B is a 5-6 membered monocyclic heteroaryl ring having 1-3 heteroatoms independently selected from nitrogen, oxygen, and sulfur. In some instances, B is 6-membered heteroaryl ring having 1-3 nitrogen atoms. In some instances, B is a 6-membered heteroaryl ring having 1 nitrogen atom. In some instances, B is a 6-membered heteroaryl ring having 2 nitrogen atoms. In some instances, B is a 6-membered heteroaryl ring having 3 nitrogen atoms.

In some embodiments, B is a 5-membered heteroaryl ring having 1-3 heteroatoms independently selected from nitrogen, oxygen, or sulfur. In some instances, B is a 5-membered heteroaryl ring having 1 heteroatom independently selected from nitrogen, oxygen, or sulfur. In some instances, B is a 5-membered heteroaryl ring having 2 heteroatoms independently selected from nitrogen, oxygen, or sulfur. In some instances, B is a 5-membered heteroaryl ring having 2 heteroatoms independently selected from nitrogen and oxygen. In some instances, B is a 5-membered heteroaryl ring having 2 heteroatoms independently selected from nitrogen and sulfur. In some instances, B is a 5-membered heteroaryl ring having 1-3 nitrogen atoms. In certain instances, B is selected from thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is a 5,5-fused-, 5,6-fused, or 6,6-fused saturated, partially unsaturated, or aromatic bicyclic ring. In some instances, B is a 5,5-fused, 5,6-fused, or 6,6-fused aromatic bicyclic ring. In some instances, B is a naphthalenyl, indanyl or indenyl group.

In some embodiments, B is a 7-10 membered bicyclic saturated or partially unsaturated heterocyclic ring having 1-4 heteroatoms independently selected from nitrogen, oxygen, and sulfur. In some instances, B is a 7-8 membered bicyclic saturated heterocyclic ring having 1-3 heteroatoms independently selected from nitrogen, oxygen, and sulfur. In some instances, B is a 7-8 membered bicyclic partially unsaturated heterocyclic ring having 1-3 heteroatoms independently selected from nitrogen, oxygen, and sulfur. In some instances, B is a 9-10 membered bicyclic saturated heterocyclic ring having 1-3 heteroatoms independently selected from nitrogen, oxygen, and sulfur. In some instances, B is a 9-10 membered bicyclic partially unsaturated heterocyclic ring having 1-3 heteroatoms independently selected from nitrogen, oxygen, and sulfur. In some instances, B is tetrahydroquinolinyl, tetrahydroisoquinolinyl, decahydroquinolinyl, or quinuclidinyl. In some instances, B is selected from indolinyl, 3H-indolyl, chromanyl, phenanthridinyl, 2-azabicyclo[2.2.1]heptanyl, octahydroindolyl, or tetrahydroquinolinyl.

In some embodiments, B is a 8-10 membered bicyclic heteroaryl ring having 1-4 heteroatoms independently selected from nitrogen, oxygen, and sulfur. In some instances, B is a 5,5-fused, 5,6-fused, or 6,6-fused saturated, partially unsaturated, or aromatic bicyclic ring having 1-4 heteroatoms, independently selected from nitrogen, oxygen, or sulfur. In some instances, B is a 5,5-fused, 5,6-fused, or 6,6-fused heteroaryl ring having 1-4 heteroatoms, independently selected from nitrogen, oxygen, or sulfur. In certain instances, B is a 5,5-fused, 5,6-fused, or 6,6-fused heteroaryl ring having 1-4 nitrogen atoms. In certain instances, B is a 5,6-fused heteroaryl ring having 1-4 nitrogen atoms. In certain instances, B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphthenyl, or benzofuranyl. In certain instances, B is selected from an indolizinyl, purinyl, naphthyridinyl, or pteridinyl.

In some embodiments, $R^5$ is —R, halogen, —OR, —SR, —$N(R')_2$, —CN, —$NO_2$, —C(O)R, —C(S)R, —$CO_2R$, —$C(O)N(R')_2$, —C(O)SR, —C(O)C(O)R, —$C(O)CH_2C(O)R$, —$C(S)N(R')_2$, —C(S)OR, —S(O)R, —$SO_2R$, —$SO_2N(R')_2$, —N(R')C(O)R, —$N(R')C(O)N(R')_2$, —$N(R')C(S)N(R')_2$, —$N(R')SO_2R$, —$N(R')SO_2N(R')_2$, —$N(R')N(R')_2$, —$N(R')C(=N(R'))N(R')_2$, —$C{=}NN(R')_2$, -C=NOR, —$C(=N(R'))N(R')_2$, —OC(O)R, or —$OC(O)N(R')_2$, where R and R' are as defined and described herein. In some embodiments, $R^5$ is -R. In certain embodiments, $R^5$ is hydrogen. In certain other embodiments, $R^5$ is halogen. In some embodiments, $R^4$ is —OR, —SR, or —N(R')$_2$— In certain embodiments, $R^5$ is -OR. In other embodiments, $R^5$ is —CN or —$NO_2$. In some embodiments, $R^5$ is —C(O)R, —$CO_2$R, —C(O)N(R')$_2$, —C(O)SR, —C(O)C(O)R, —C(O)$CH_2$C(O)R, —C(S)N(R')$_2$, or —C(S)OR. In other embodiments, $R^5$ is —S(O)R, —$SO_2$R, or —$SO_2$N(R')$_2$. In certain embodiments, $R^5$ is —N(R')C(O)R, —N(R')C(O)N(R')$_2$, —N(R')$SO_2$R, —N(R')$SO_2$N(R')$_2$, —N(R')N(R')$_2$, or —N(R')C(═N(R'))N(R')$_2$. In certain other embodiments, $R^5$ is —C═NN(R')$_2$, —C═NOR, —C(═N(R'))N(R')$_2$. In yet other embodiments, $R^5$ is —OC(O)R or —OC(O)N(R')$_2$.

In some embodiment p is an integer from 0 to 5. In some instances, p is 1. In some instances, p is 2. In some instances, p is 3. In some instances, p is 4. In some instances, p is 5.

In some embodiments, Y is a covalent bond. In some instances, Y is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, Y is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, Y is a $C_{1-3}$ hydrocarbon chain wherein one methylene unit is optionally replaced by —NH—, —O—, —S—, —S(O)—, or —$SO_2$—.

In some embodiments, each $R_1$ is independently selected from hydrogen, halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, —OC(O)N(R')$_2$, or —$(CH_2)_q R^x$ wherein q is 0-3 and $R^x$ is halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R or —OC(O)N(R')$_2$. In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each R, is independently selected from C(1-6) aliphatic, —OR, —N(R')$_2$, —C(O)R, —OC(O)R, —N(R')C(O)R, —C(O)NR', or —$CO_2$R.

In some embodiments, each $R_2$ is independently selected from hydrogen, halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, —OC(O)N(R')$_2$, or —$(CH_2)_q R^x$ wherein q is 0-3 and $R^x$ is halogen, optionally substituted C(1-6) aliphatic, —OR, —SR, —CN, —N(R')$_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R or —OC(O)N(R')$_2$. In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —$CO_2$R.

In some embodiments, n is an integer from 0 to 12. In some instances, n is 1. In some instances, n is 2. In some instances, n is 3. In some instances, n is 4. In some instances, n is 5. In some instances, n is 6.

In some embodiments, Z is —$CH_2$. In some instances, Z is —NH. In some instances, Z is —O—. In some instances, Z is —S—.

In some embodiments, the bromodomain-containing 4 ligand (BR) is of formula IA3:

(IA3)

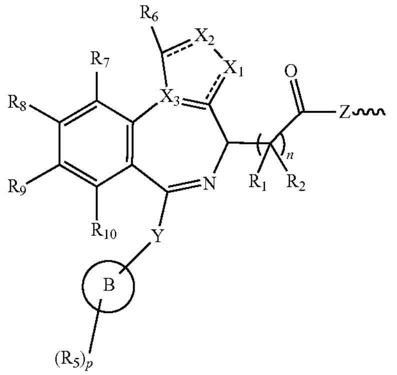

wherein:

$X_1$ is from C, N, O or S;

$X_2$ is from C, N, O or S;

$X_3$ is C or N;

---- represents a single or double bond; and each of $R_6$, $R_7$, $R_8$, $R_9$ and $R_{10}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, $X_1$ is N or O; $X_2$ is N; and $X_3$ is C or N. In some instances, X, is N; $X_2$ is N; and $X_3$ is N. In some instances, $X_1$ is O; $X_2$ is N; and $X_3$ is C.

In some instances, $R_6$ is hydrogen or a C(1-6) alkyl. In some instances, $R_e$ is selected from methyl, ethyl, n-propyl, isopropyl, n-butyl, iso-butyl or tert-butyl. In certain instances, $R_6$ is methyl. In some instances, $R_7$ is hydrogen or a C(1-6) alkyl. In some instances, $R_7$ is selected from methyl, ethyl, n-propyl, isopropyl, n-butyl, iso-butyl or tert-butyl. In certain instances, $R_7$ is hydrogen. In some instances, $R_8$ is hydrogen or a C(1-6) alkyl. In some instances, $R_8$ is selected from methyl, ethyl, n-propyl, isopropyl, n-butyl, iso-butyl or tert-butyl. In certain instances, $R_8$ is hydrogen. In some instances, $R_9$ is hydrogen or a C(1-6) alkyl. In some instances, $R_e$ is selected from methyl, ethyl, n-propyl, isopropyl, n-butyl, iso-butyl or tert-butyl. In certain instances, $R_9$ is hydrogen. In some instances, $R_{10}$ is selected from methyl, ethyl, n-propyl, isopropyl, n-butyl, iso-butyl or tert-butyl. In certain instances, $R_{10}$ is hydrogen. In certain instances, $R_6$ is methyl and each of $R_7$, $R_8R_9$ and $R_{10}$ is hydrogen.

In some instances, $$CR_6 \overset{---}{=\!=} X_2$$

represents a double bond; and $$CX_3 \overset{---}{=\!=} X_1$$

represents a single bond.

In some embodiments, B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is phenyl. In some instances, B is a 3-7 membered saturated or partially unsaturated carbocyclic ring. In certain instances, B is cyclopropyl, cyclobutyl, cyclopentyl, cyclohexyl, or cycloheptyl. In certain instances, B is cyclopentenyl, cyclohexenyl, or cycloheptenyl.

In some embodiments, B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrohdinyl, pyrrohdonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, B is a 5-6 membered monocyclic heteroaryl ring having 1-3 heteroatoms independently selected from nitrogen, oxygen, and sulfur. In some instances, B is 6-membered heteroaryl ring having 1-3 nitrogen atoms. In some instances, B is a 6-membered heteroaryl ring having 1 nitrogen atom. In some instances, B is a 6-membered heteroaryl ring having 2 nitrogen atoms. In some instances, B is a 6-membered heteroaryl ring having 3 nitrogen atoms.

In some embodiments, B is a 5-membered heteroaryl ring having 1-3 heteroatoms independently selected from nitrogen, oxygen, or sulfur. In some instances, B is a 5-membered heteroaryl ring having 1 heteroatom independently selected from nitrogen, oxygen, or sulfur. In some instances, B is a 5-membered heteroaryl ring having 2 heteroatoms independently selected from nitrogen, oxygen, or sulfur. In some instances, B is a 5-membered heteroaryl ring having 2 heteroatoms independently selected from nitrogen and oxygen. In some instances, B is a 5-membered heteroaryl ring having 2 heteroatoms independently selected from nitrogen and sulfur. In some instances, B is a 5-membered heteroaryl ring having 1-3 nitrogen atoms. In certain instances, B is selected from thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In some instances, B is a 5,5-fused-, 5,6-fused, or 6,6-fused saturated, partially unsaturated, or aromatic bicyclic ring. In some instances, B is a 5,5-fused, 5,6-fused, or 6,6-fused aromatic bicyclic ring. In some instances, B is a naphthalenyl, indanyl or indenyl group.

In some embodiments, B is a 7-10 membered bicyclic saturated or partially unsaturated heterocyclic ring having 1-4 heteroatoms independently selected from nitrogen, oxygen, and sulfur. In some instances, B is a 7-8 membered bicyclic saturated heterocyclic ring having 1-3 heteroatoms independently selected from nitrogen, oxygen, and sulfur. In some instances, B is a 7-8 membered bicyclic partially unsaturated heterocyclic ring having 1-3 heteroatoms independently selected from nitrogen, oxygen, and sulfur. In some instances, B is a 9-10 membered bicyclic saturated heterocyclic ring having 1-3 heteroatoms independently selected from nitrogen, oxygen, and sulfur. In some instances, B is a 9-10 membered bicyclic partially unsaturated heterocyclic ring having 1-3 heteroatoms independently selected from nitrogen, oxygen, and sulfur. In some instances, B is tetrahydroquinolinyl, tetrahydroisoquinolinyl, decahydroquinolinyl, or quinuclidinyl. In some instances, B is selected from indolinyl, 3H-indolyl, chromanyl, phenanthridinyl, 2-azabicyclo[2.2.1]heptanyl, octahydroindolyl, or tetrahydroquinolinyl.

In some embodiments, B is a 8-10 membered bicyclic heteroaryl ring having 1-4 heteroatoms independently selected from nitrogen, oxygen, and sulfur. In some instances, B is a 5,5-fused, 5,6-fused, or 6,6-fused saturated, partially unsaturated, or aromatic bicyclic ring having 1-4 heteroatoms, independently selected from nitrogen, oxygen, or sulfur. In some instances, B is a 5,5-fused, 5,6-fused, or 6,6-fused heteroaryl ring having 1-4 heteroatoms, independently selected from nitrogen, oxygen, or sulfur. In certain instances, B is a 5,5-fused, 5,6-fused, or 6,6-fused heteroaryl ring having 1-4 nitrogen atoms. In certain instances, B is a 5,6-fused heteroaryl ring having 1-4 nitrogen atoms. In certain instances, B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphthenyl, or benzofuranyl. In certain instances, B is selected from an indolizinyl, purinyl, naphthyridinyl, or pteridinyl.

In some embodiments, $R^5$ is —R, halogen, —OR, —SR, —N(R')$_2$, —CN, —$NO_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, or —OC(O)N(R')$_2$, where R and R' are as defined and described herein. In some embodiments, $R^5$ is -R. In certain embodiments, $R^5$ is hydrogen. In certain other embodiments, $R^5$ is halogen. In some embodiments, $R^4$ is —OR, —SR, or —N(R')$_2$— In certain embodiments, $R^5$ is -OR. In other embodiments, $R^5$ is —CN or —NO$_2$. In some embodiments, $R^5$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^5$ is —S(O)R, —SO$_2$R, or —SO$_2$N(R')$_2$. In certain embodiments, $R^5$ is —N(R')C(O)R, —N(R')C(O)N(R')$_2$, —N(R')SO$_2$R, —N(R')SO$_2$N(R')$_2$, —N(R')N(R')$_2$, or —N(R')C(═N(R'))N(R')$_2$. In certain other embodiments, $R^5$ is —C═NN(R')$_2$, —C═NOR, —C(═N(R'))N(R')$_2$. In yet other embodiments, $R^5$ is —OC(O)R or —OC(O)N(R')$_2$.

In some embodiment p is an integer from 0 to 5. In some instances, p is 1. In some instances, p is 2. In some instances, p is 3. In some instances, p is 4. In some instances, p is 5.

In some embodiments, Y is a covalent bond. In some instances, Y is an optionally substituted bivalent C(1-6) hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In some instances, Y is an optionally substituted bivalent C(1-3) hydrocarbon chain wherein one methylene unit is optionally replaced by —NR'—, —N(R')C(O)—, —C(O)N(R, —N(R')SO$_2$—, —SO$_2$N(R')—, —O—, —C(O)—, —OC(O)—, —C(O)O—, —S—, —SO— or —SO$_2$—. In certain embodiments, Y is a $C_{1-3}$ hydrocarbon chain wherein one methylene unit is optionally replaced by —NH—, —O—, —S—, —S(O)—, or —SO$_2$—.

In some embodiments, each $R_1$ is independently selected from hydrogen, halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, —OC(O)N(R')$_2$, or —(CH$_2$)$_q$$R^x$ wherein q is 0-3 and $R^x$ is halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R or —OC(O)N(R')$_2$. In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each $R_1$ is independently selected from C(1-6) aliphatic, —OR, —N(R')$_2$, —C(O)R, —OC(O)R, —N(R')C(O)R, —C(O)NR', or —CO$_2$R.

In some embodiments, each $R_2$ is independently selected from hydrogen, halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, -SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, —OC(O)N(R')$_2$, or —(CH$_2$)$_q$$R^x$ wherein q is 0-3 and $R^x$ is halogen, optionally substituted C(1-6) aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R or —OC(O)N(R')$_2$. In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —CO$_2$R.

In some embodiments, n is an integer from 0 to 12. In some instances, n is 1. In some instances, n is 2. In some instances, n is 3. In some instances, n is 4. In some instances, n is 5. In some instances, n is 6.

In some embodiments, Z is —CH$_2$. In some instances, Z is —NH. In some instances, Z is —O—. In some instances, Z is —S—.

In some embodiments, the bromodomain-containing 4 ligand (BR) is of formula IA4:

(IA4)

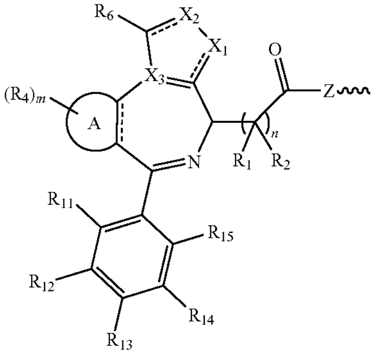

where:

n is an integer from 0 to 12;

m is an integer from 0 to 5;

$X_1$ is from C, N, O or S;

$X_2$ is from C, N, O or S;

$X_3$ is C or N;

represents a single or double bond;

represents a bond to the linker; and each of $R_1$, $R_2$, $R_4$, $R_6$, $R_{11}$, $R_{12}$, $R_{13}$, $R_{14}$ and $R_{15}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, $X_1$ is N or O; $X_2$ is N; and $X_3$ is C or N. In some instances, $X_1$ is N; $X_2$ is N; and $X_3$ is N. In some instances, $X_1$ is O; $X_2$ is N; and $X_3$ is C.

In some instances, $R_6$ is hydrogen or a C(1-6) alkyl. In some instances, $R_6$ is selected from methyl, ethyl, n-propyl, isopropyl, n-butyl, iso-butyl or tert-butyl. In certain instances, $R_6$ is methyl.

In some instances, $R_{11}$ is selected from hydrogen, halogen or a C(1-6) alkyl. In some instances, $R_{11}$ is selected from methyl, ethyl, n-propyl, isopropyl, n-butyl, iso-butyl or tert-butyl. In certain instances, $R_{11}$ is hydrogen. In some instances, $R_{12}$ is selected from hydrogen, halogen or a C(1-6) alkyl. In some instances, $R_{12}$ is selected from methyl, ethyl, n-propyl, isopropyl, n-butyl, iso-butyl or tert-butyl. In certain instances, $R_{12}$ is hydrogen. In some instances, $R_{13}$ is selected from hydrogen, halogen or a C(1-6) alkyl. In some instances, $R_{13}$ is selected from methyl, ethyl, n-propyl, isopropyl, n-butyl, iso-butyl or tert-butyl. In certain instances, $R_{13}$ is hydrogen. In certain instances, $R_{13}$ is halogen. In certain instances, $R_{13}$ is selected from fluorine, chlorine, bromine and iodine. In certain instances, $R_{13}$ is chlorine. In some instances, $R_{14}$ is selected from hydrogen, halogen or a C(1-6) alkyl. In some instances, $R_{14}$ is selected from methyl, ethyl, n-propyl, isopropyl, n-butyl, iso-butyl or tert-butyl. In certain instances, $R_{14}$ is hydrogen. In some instances, $R_{15}$ is selected from hydrogen, halogen or a C(1-6) alkyl. In some instances, $R_{15}$ is selected from methyl, ethyl, n-propyl, isopropyl, n-butyl, iso-butyl or tert-butyl. In certain instances, $R_{15}$ is hydrogen. In certain embodiments, each one of $R_1$, $R^1{}_2$, $R_{14}$ and $R_{15}$ is hydrogen and $R_{13}$ is selected from fluorine, chlorine, bromine and iodine. In certain embodiments, each one of $R_{11}$, $R_{12}$, $R_{14}$ and $R_{15}$ is hydrogen and $R_{13}$ is chlorine.

In some embodiments, A is a 5-membered fused heteroaryl ring having 2 heteroatoms independently selected from nitrogen, oxygen, or sulfur. In some instances, A is a 5-membered fused heteroaryl ring having 2 heteroatoms independently selected from nitrogen or oxygen. In some instances, A is a 5-membered fused heteroaryl ring having 2 heteroatoms selected from nitrogen and oxygen. In some instances, A is a 5-membered fused heteroaryl ring having 2 heteroatoms independently selected from nitrogen or sulfur. In some instances, A is a 5-membered fused heteroaryl ring having 2 heteroatoms selected from nitrogen and sulfur. In certain instances, A is selected from thiazolo, isothiazolo, oxazolo, isoxazolo, pyrazolo, and imidazolo rings. In certain instances, A is isothiazolo.

In some embodiments, A is benzo, or a 5-6 membered fused heteroaryl ring having 1-3 heteroatoms independently selected from nitrogen, oxygen, or sulfur. In some instances, A is a 5-membered fused heteroaryl ring having 2-3 heteroatoms independently selected from nitrogen, oxygen, or sulfur, or a 6-membered fused heteroaryl ring having 2-3 nitrogen atoms. In some instances, A is benzo. In some embodiments, A is a 5-6 membered fused heteroaryl ring having 1-3 heteroatoms independently selected from nitrogen, oxygen, or sulfur. In some instances, A is a 6-membered fused heteroaryl ring having 1-3 nitrogen atoms. In certain instance, A is selected from pyrido, pyrimidino, pyrazino, pyridazino, and triazino, rings. In certain instances, A is a 5-membered fused heteroaryl ring having 1 heteroatom selected from nitrogen, oxygen, or sulfur. In certain instances, A is thieno. In certain instances, A is furano. In certain instances, A is pyrrolo.

In some embodiments, $R^4$ is —R, halogen, —OR, —SR, —N(R')$_2$, —CN, —$NO_2$, —C(O)R, —C(S)R, —$CO_2$R, —C(O)N(R')$_2$, —C(O)SR, —C(O)C(O)R, —C(O)$CH_2$C(O)R, —C(S)N(R')$_2$, —C(S)OR, —S(O)R, —$SO_2$R, —$SO_2$N(R')$_2$, —N(R')C(O)R, —N(R')C(O)N(R')$_2$, —N(R')C(S)N(R')$_2$, —N(R')$SO_2$R, —N(R')$SO_2$N(R')$_2$, —N(R')N(R')$_2$, —N(R')C(═N(R'))N(R')$_2$, —C═NN(R')$_2$, -C═NOR, —C(═N(R'))N(R')$_2$, —OC(O)R, or —OC(O)N(R')$_2$, where R and R' are as defined and described herein. In some embodiments, $R^4$ is -R. In certain embodiments, $R^4$ is hydrogen. In certain other embodiments, $R^4$ is halogen. In some embodiments, $R^4$ is —OR, —SR, or —N(R')$_2$— In certain instances, $R^4$ is -OR. In certain instances, $R^4$ is —CN or —$NO_2$. In certain instances, $R^4$ is —C(O)R, —$CO_2$R, —C(O)N(R')$_2$, —C(O)SR, —C(O)C(O)R, —C(O)$CH_2$C(O)R, —C(S)N(R')$_2$, or —C(S)OR. In certain instances, $R^4$ is —S(O)R, —$SO_2$R, or —$SO_2$N(R')$_2$. In certain instances, $R^4$ is —N(R')C(O)R, —N(R')C(O)N(R')$_2$, —N(R')$SO_2$R, —N(R')$SO_2$N(R')$_2$, —N(R')N(R')$_2$, or —N(R')C(═N(R'))N(R')$_2$. In certain instances, $R^4$ is —C═NN(R')$_2$, -C═NOR, —C(═N(R'))N(R')$_2$. In certain instances, $R^4$ is —OC(O)R or —OC(O)N(R')$_2$.

In some embodiment m is an integer from 0 to 5. In some instances, m is 1. In some instances, m is 2. In some instances, m is 3. In some instances, m is 4. In certain instances, m is 5.

In some embodiments, each $R_1$ is independently selected from hydrogen and a C(1-6) alkyl. In some instances, each $R_1$ is independently selected from methyl, ethyl, n-propyl, isopropyl, n-butyl, iso-butyl or tert-butyl. In certain instances, each $R_1$ is independently selected from C(1-6) aliphatic, —OR, —N(R')$_2$, —C(O)R, —OC(O)R, —N(R')C(O)R, —C(O)NR', or —$CO_2$R. In some instances, each $R_1$ is hydrogen or a C(1-6) alkyl. In some instances, each $R_1$ is selected from methyl, ethyl, n-propyl, isopropyl, n-butyl, iso-butyl or tert-butyl. In certain instances, each $R_1$ is methyl.

In some embodiments, each $R_2$ is independently selected from hydrogen and a C(1-6) alkyl. In some instances, each $R_2$ is independently selected from methyl, ethyl, n-propyl, isopropyl, n-butyl, iso-butyl or tert-butyl. In certain instances, each $R_2$ is independently selected from C(1-6) aliphatic, —OR, —N(R')$_2$, —C(O)R, —OC(O)R, —N(R')C(O)R, —C(O)NR', or —$CO_2$R. In some instances, each $R_2$ is hydrogen or a C(1-6) alkyl. In some instances, each $R_2$ is selected from methyl, ethyl, n-propyl, isopropyl, n-butyl, iso-butyl or tert-butyl. In certain instances, each $R_2$ is methyl.

In certain embodiments, n is an integer from 1-4; and each of $R_1$ and $R_2$ are independently selected from hydrogen and a C(1-6) alkyl. In certain instances, n is an integer from 1-4 and each of $R_1$ and $R_2$ are independently selected from methyl, ethyl, n-propyl, isopropyl, n-butyl, iso-butyl or tert-butyl. In certain instances, n is an integer from 1-4 and each of $R_1$ and $R_2$ are methyl. In certain instances, n is 1 and each of $R_1$ and $R_2$ are hydrogen. In certain instances, n is 1 and each of $R_1$ and $R_2$ are methyl.

In some embodiments, Z is —$CH_2$. In some instances, Z is —NH. In some instances, Z is —O—. In some instances, Z is —S—.

In certain embodiments, the bromodomain-containing 4 ligand (BR) is a compound as described in International Patent Publication No. WO2012/075456, the disclosure of which is incorporated by reference.

In certain embodiments, the bromodomain-containing 4 ligand (BR) is selected from:

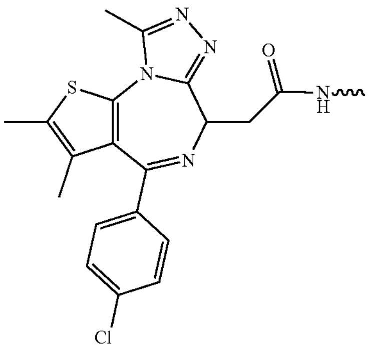

or

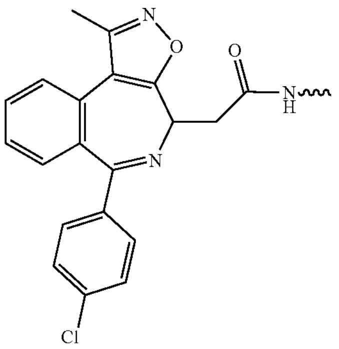

where ∿∿ represents a bond to the linker.

In certain embodiments, the bromodomain-containing 4 ligand (BR) is of formula IA5:

(IA5)

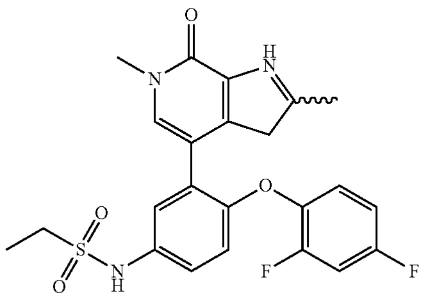

where ∿∿ represents a bond to the linker.

In certain embodiments, the bromodomain-containing 4 ligand (BR) is selected from:

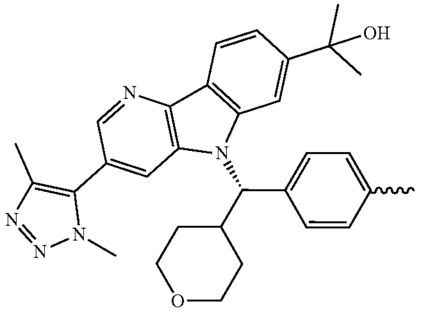

or

-continued

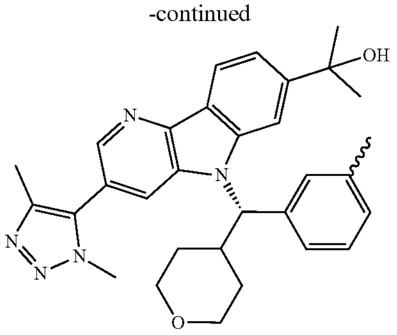

where ∿∿ represents a bond to the linker.

In certain embodiments, the bromodomain-containing 4 ligand (BR) is selected from:

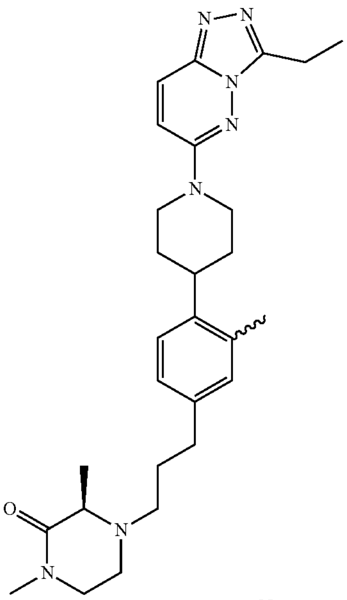

or

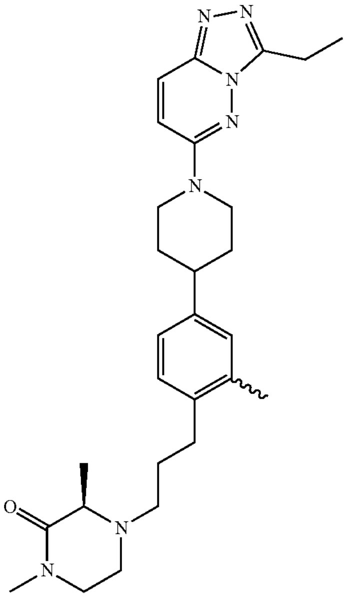

where ∿∿ represents a bond to the linker.

In certain embodiments, the bromodomain-containing 4 ligand (BR) is selected from:
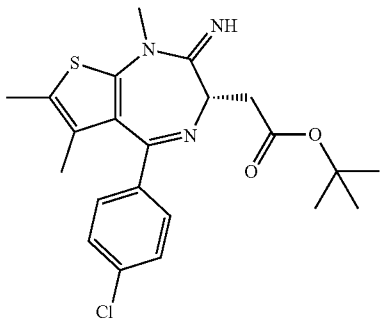
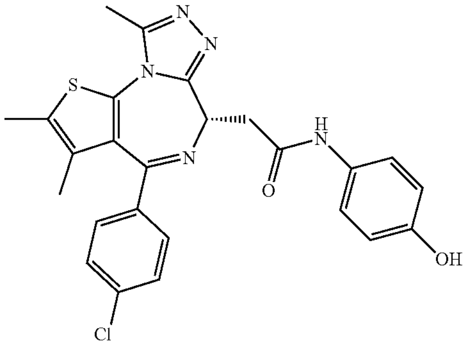
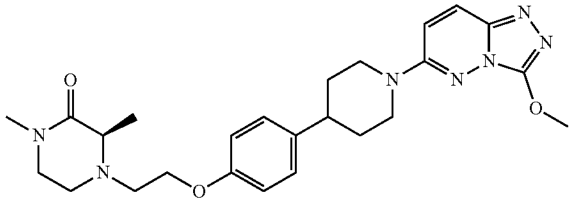
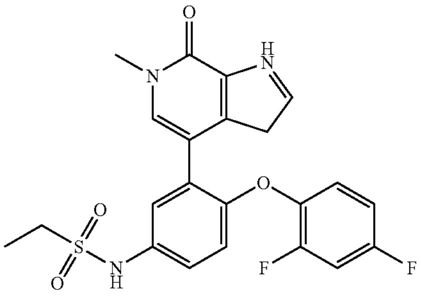
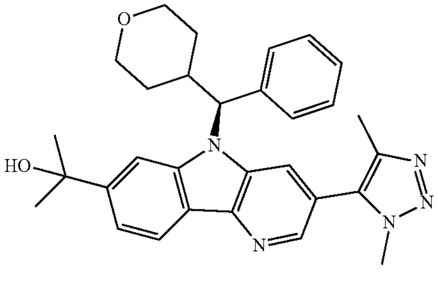
-continued
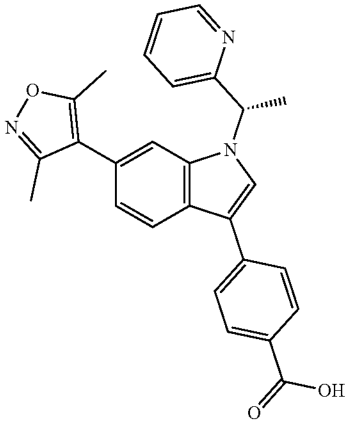
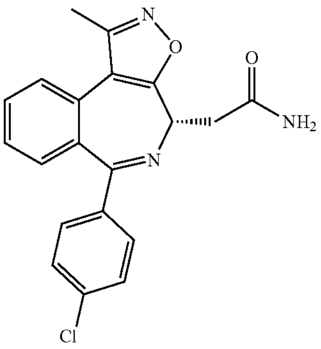
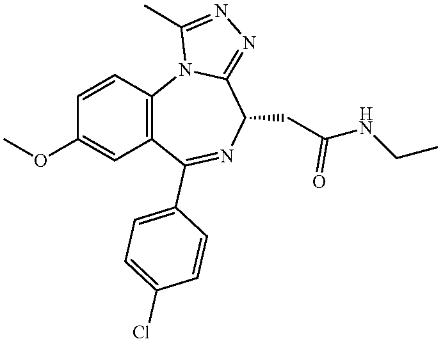
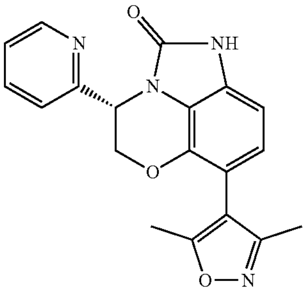
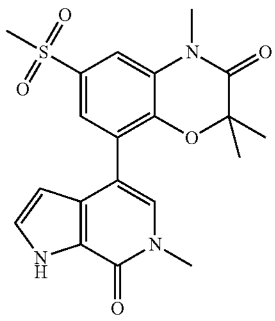

-continued

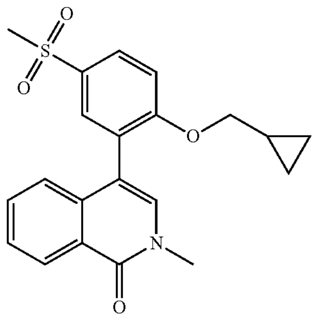

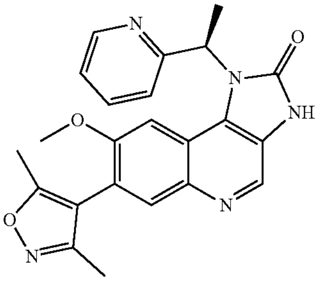

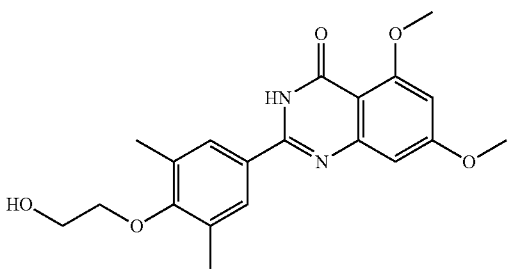

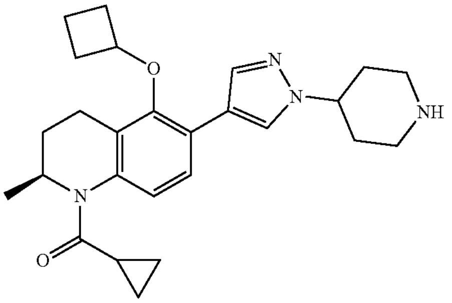

-continued

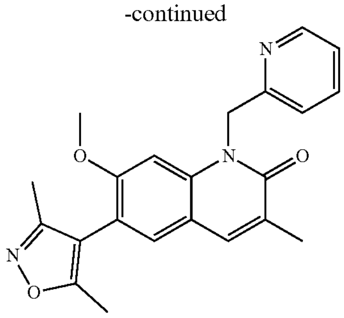

In some instances, the ligand is JQ1.

EL: Estrogen Receptor Ligands

Methods of treating a subject for Diffuse Large B-Cell Lymphoma (DLBCL) are provided. In some cases, the methods can include administering a chemical inducer of proximity (CIP) to treat the subject for DLBCL. Also provided are compositions that find use in practicing methods of the disclosure.

CIPs employed in embodiments of the disclosure include a ligand for an oncogenic transcription factor, e.g., an estrogen receptor. This embodiment is of particular significance in treatment of cancer, where the CIP causes the cancer cell to kill itself with its own driver. Oncogenic transcription factors are transcription factors whose activity contributes to a neoplastic, e.g., cancerous, disease condition. The oncogenic transcription factor may vary, e.g., depending on the particular nature of the disease condition being treated, where examples of oncogenic transcription factors include, but are not limited to: hormonal receptors (e.g., estrogen, androgen and progesterone receptors and the like), oncogene drivers (e.g., MYC, MLL fusion proteins, ETS fusion proteins, SS18-SSX fusion proteins and the like), translocated fusion oncogenes and proteins that regulate cell cycle entry (e.g., E2F family members and the like), etc. In some instances, the oncogenic transcription factor is a hormonal receptor. Hormonal receptors that may be employed as the oncogenic transcription factor in embodiments of the disclosure include, but are not limited to: estrogen receptor (ER), and the like. Any convenient ligands for these hormonal receptors may be employed, where suitable ligands include small molecule ligands that are capable of specifically binding to the target hormonal receptor without any relevant negative impact on the hormonal receptor's ability to enhance transcription of the target proapoptotic gene when complexed with the anchor transcription factor by a CIP, i.e., the transcription-activating activity of the oncogenic transcription factor. The molecular weight of these ligands may vary, and in some instances ranges from 150 Daltons to 500 Daltons such as 250 Daltons to 400 Daltons. Suitable ligands for an estrogen receptor include, but are not limited to:

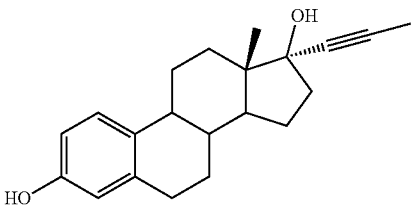

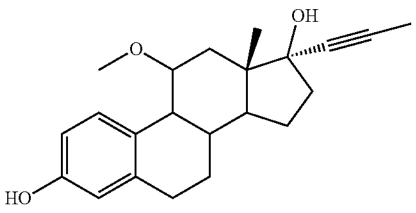

-continued
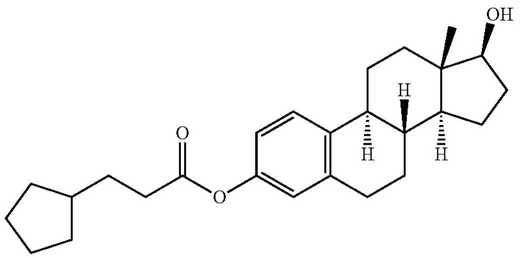
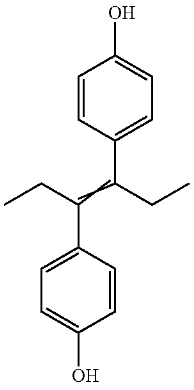
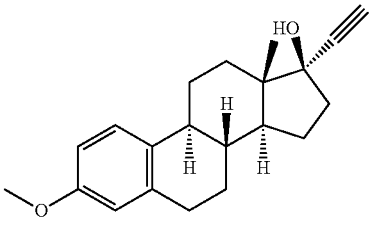
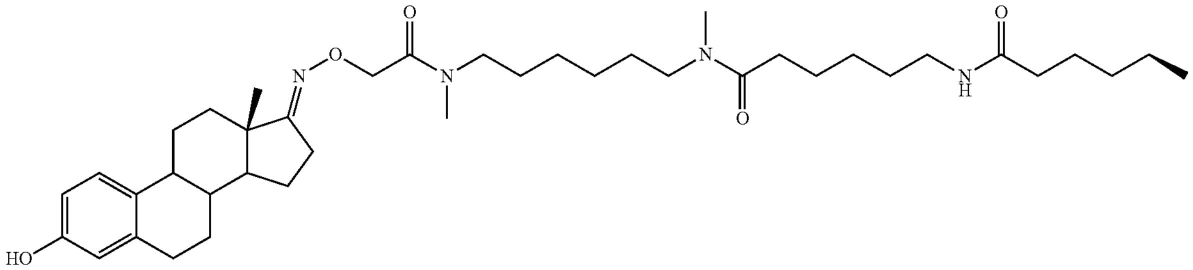
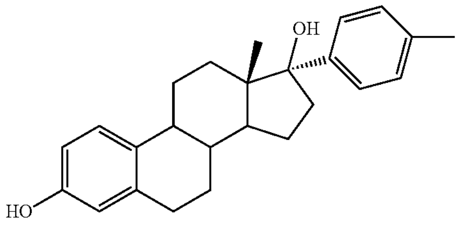
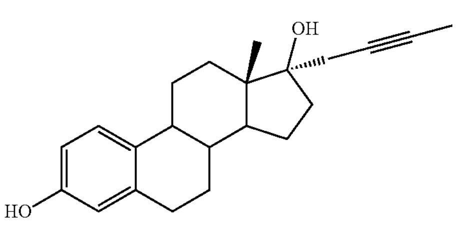
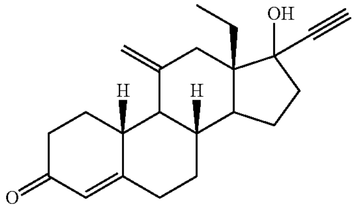
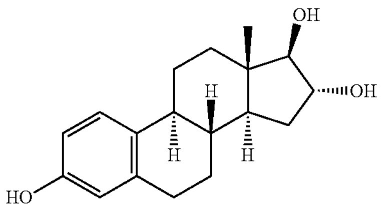
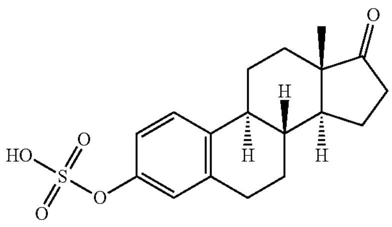
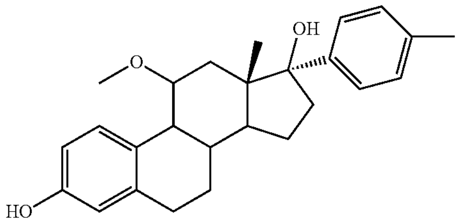
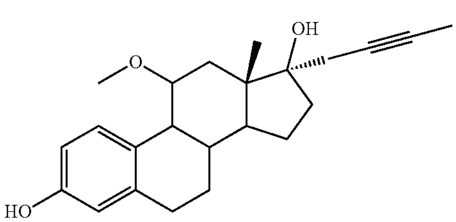
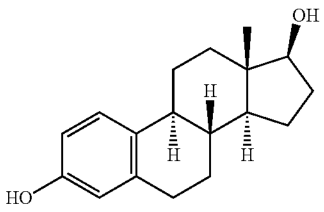
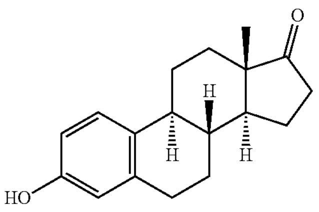
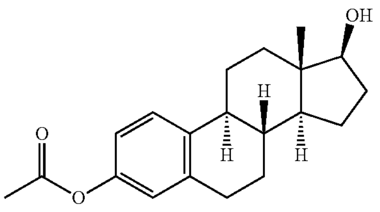

-continued

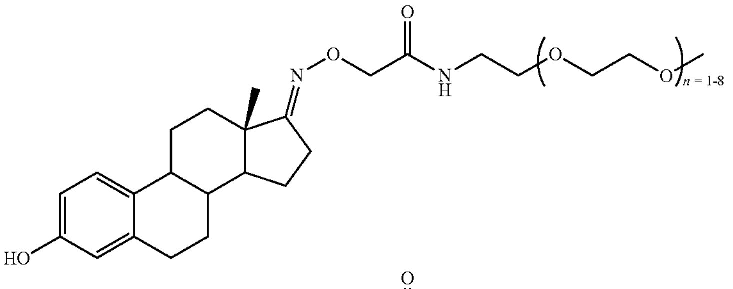

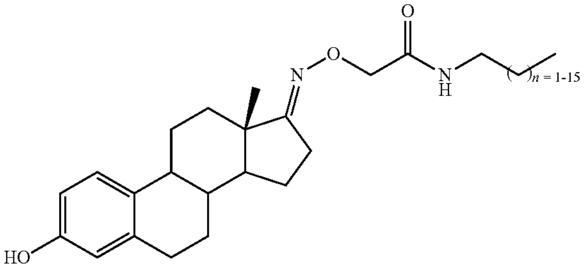

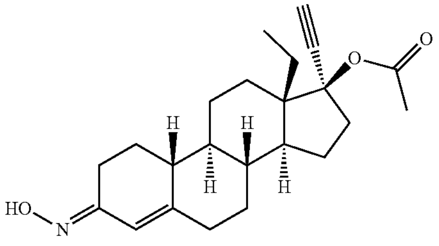

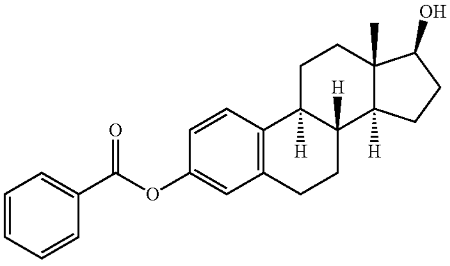

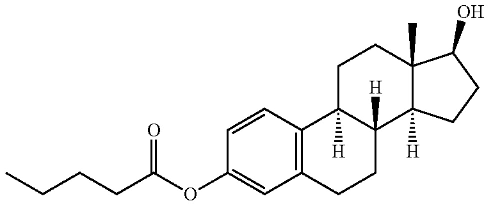

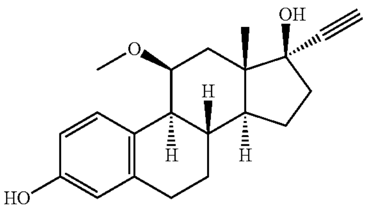

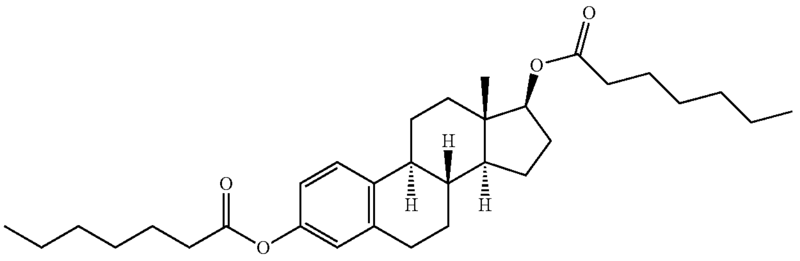

In some instances, the ligand is estrone.

CDK Ligands

Methods of treating a subject for a malignancy, e.g., lymphoma (e.g., DLBCL), Lung cancer (e.g., SCLC), breast cancer, etc., are provided. In some cases, the methods can include administering a transcriptional chemical inducer of proximity (TCIP) which links a BTB-domain containing protein, e.g., BCL-6 or a related family member, and a cyclin dependent kinase (CDK) to treat the subject for the malignancy. Also provided are compositions that find use in practicing methods of the disclosure.

TCIPs employed in embodiments of the disclosure may include a ligand for a transcription modulator, such as a CDK, e.g., CDK9, CDK8, CDK12, or CDK7. This embodiment is of particular significance in treatment of cancer, where the CIP causes the cancer cell to kill itself with its own CDK driver. Any convenient CDK ligands may be employed, where suitable ligands include small molecule ligands that are capable of specifically binding to the target CDK without any relevant negative impact on CDK's ability to enhance transcription of the target proapoptotic gene when complexed with the anchor transcription factor by a TCIP, i.e., the transcription-activating activity of the CDK. The molecular weight of these ligands may vary, and in some instances ranges from 150 Daltons to 500 Daltons such as 250 Daltons to 400 Daltons.

In some instances, the CDK is a CDK9. Suitable ligands for CDK9 include, but are not limited to, those described in published PCT application Publication Nos.: WO/2022/098843; WO/2022/028556; WO/2021/260578; WO/2021/227904; WO/2021/172359; WO/2020/259556; WO/2020/244612; WO/2020/228513; WO/2020/202232; WO/2020/117988; WO/2020/092314; WO/2019/242471; WO/2019/209825; WO/2019/058348 WO/2018/192273; WO/2017/185023; WO/2017/001354; WO/2016/061144; WO/2015/119712; WO/2014/160028; WO/2014/159999; WO/2014/160017; WO/2014/151444; WO/2014/139328; WO/2013/059634; WO/2013/026874; WO/2012/101062; WO/2012/101065; WO/2007/117653; and WO/2005/027902; WO/2004/002226; the disclosures of which are herein incorporated by reference.

Specific CDK9 Ligands of Interest Include, but are not Limited to:

| Name | Reference | Structure |
| --- | --- | --- |
| SNS-032 | Nature Chem Biol, 2018, 14, 163-173 | 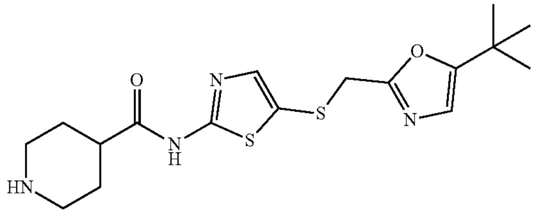 [SMILES: CC(C)(C)c1cnc(CSc2cnc(NC(=O)C3CCNCC3)s2)o1] |
| NVP-2 | WO/2011/01266 | 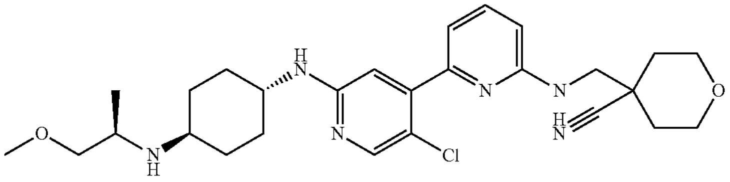 |
| KI-ARv-03 | *ACS Med. Chem. Lett.* 2018, 9, 6, 540-545 | 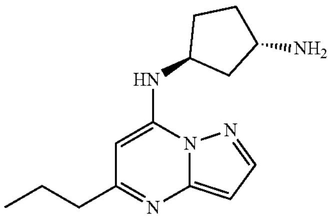 [SMILES: CCCc1cc(N[C@H]2CC[C@H](N)C2)n2nccc2n1] |
| KB-0742 | *ACS Med. Chem. Lett.* 2018, 9, 6, 540-545 | 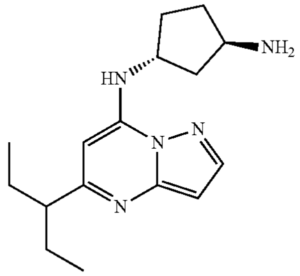 [SMILES: CCC(CC)c1cc(N[C@@H]2CC[C@@H](N)C2)n2nccc2n1] |
| BAY-1143572 | *ChemMedChem* 2017, 12, 1776-1793 | 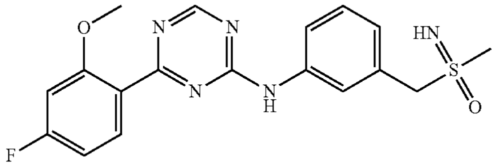 [SMILES: COc1cc(F)ccc1-c1ncnc(Nc2cccc(CS(C)(=N)=O)c2)n1] |
| AZD-4573 | *Clin Cancer Res* 2020, 26, 922-934. | 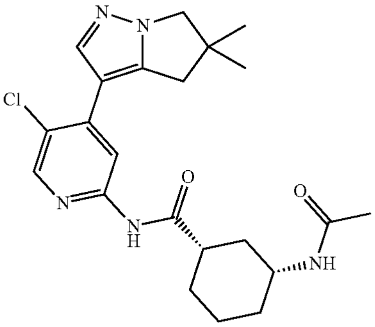 [SMILES: CC(=O)N[C@@H]1CCC[C@H](C(=O)Nc2cc(-c3cnn4c3CC(C)(C)C4)c(Cl)cn2)C1] |

-continued
| Name | Reference | Structure |
| --- | --- | --- |
| Alvocidib | *Blood Cancer Journal* (2021) 11:175 | 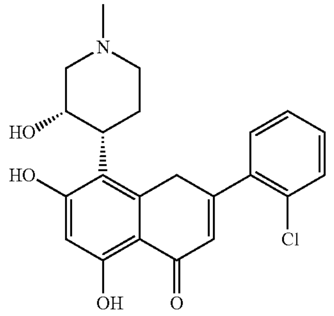 [SMILES: CN1CC[C@H](c2c(O)cc(O)c3c2CC(c2ccccc2Cl)=CC3=O)[C@H](O)C1] |
| TP-1287 | Cancer Res (2017) 77 (13_Supplement): 5133 | 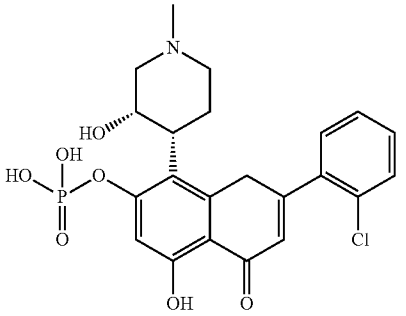 [SMILES: CN1CC[C@H](c2c(OP(=O)(O)O)cc(O)c3c2CC(c2ccccc2Cl)=CC3=O)[C@H](O)C1] |
| Riviciclib | *Mol Cancer Ther.* 2007 Mar; 6(3): 926-34. | 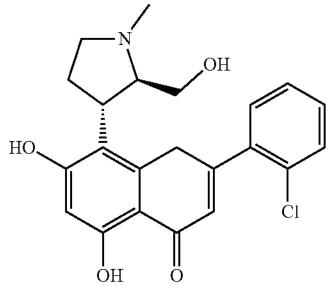 [SMILES: CN1CC[C@@H](c2c(O)cc(O)c3c2CC(c2ccccc2Cl)=CC3=O)[C@@H]1CO] |
| Voruciclib | Scientific Reports, 2017, 7, 18007 | 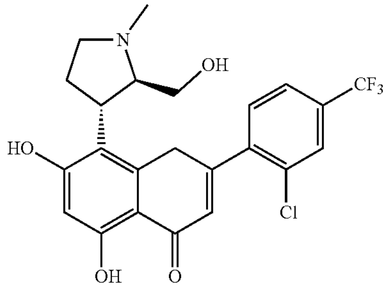 [SMILES: CN1CC[C@@H](c2c(O)cc(O)c3c2CC(c2ccc(C(F)(F)F)cc2Cl)=CC3=O)[C@@H]1CO] |
| ZK-304709 | Gut 2009; 58: 261-270 | 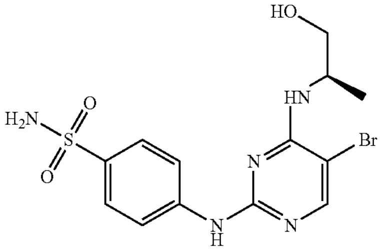 [SMILES: C[C@H](CO)Nc1nc(Nc2ccc(S(N)(=O)=O)cc2)ncc1Br] |

-continued
| Name | Reference | Structure |
|---|---|---|
| BAY-1251152 | *J Enzyme Inhib Med Chem.* 2021; 36(1): 693-706. | 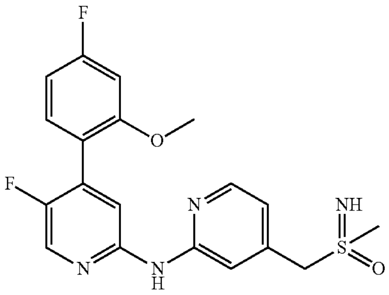 [SMILES: COc1cc(F)ccc1-c1cc(Nc2cc(CS(C)(=N)=O)ccn2)ncc1F] |
| Zotiraciclib (TG-02) | *Clin Cancer Res* (2021) 27 (12): 3298-3306. | 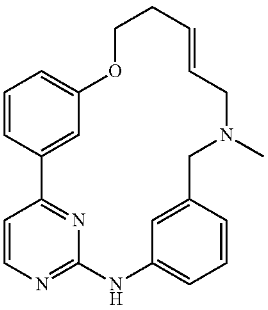 [SMILES: CN1C/C=C/CCOc2cccc(c2)-c2ccnc(n2)Nc2cccc(c2)C1] |
| Seliciclib | Journal of Biotechnology 202 (2015) 40-49 | 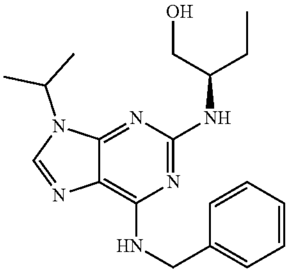 [SMILES: CC[C@H](CO)Nc1nc(NCc2ccccc2)c2ncn(C(C)C)c2n1] |
| Fadraciclib | *Leukemia* volume 36, pages 1596-1608 (2022) | 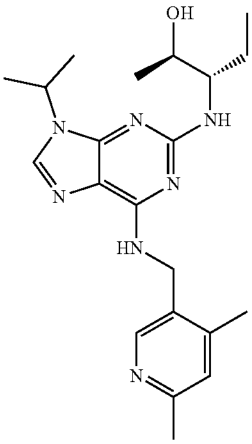 [SMILES: CC[C@H](Nc1nc(NCc2cnc(C)cc2C)c2ncn(C(C)C)c2n1)[C@@H](C)O] |

-continued

| Name | Reference | Structure |
|---|---|---|
| Dinaciclib | *Scientific Reports* volume 10, Article number: 18489 (2020) | 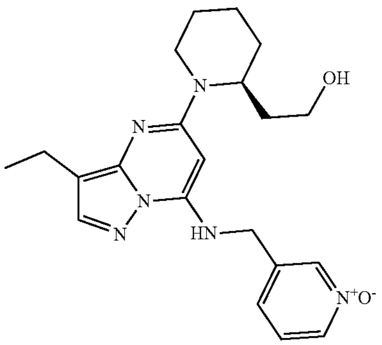 |
| AT7519 | *Oncogene* volume 29, pages 2325-2336 (2010) | 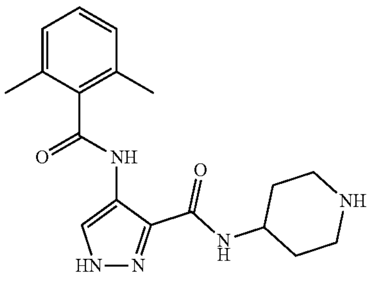 [SMILES: Cc1cccc(C)c1C(=O)Nc1c[nH]nc1C(=O)NC1CCNCC1] |
| BTX-A51 | *Clarivate Analytics Integrity.* https://integrity.clarivate.com Blood (2020) 136 (Supplement 1): 18. | 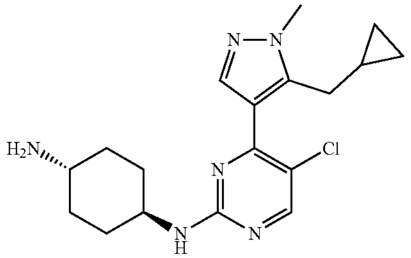 [SMILES: Cn1ncc(-c2nc(N[C@H]3CC[C@H](N)CC3)ncc2Cl)c1CC1CC1] |
| LY2857785 | | 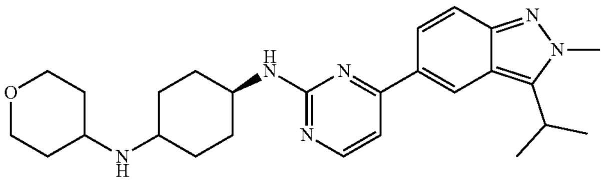 |

In some instances, the CDK is a CDK8. Suitable ligands for CDK8 include, but are not limited to, those described in published PCT application Publication Nos.: WO/2021/108581; WO/2020/071550; WO/2020/027704; WO/2019/068613; WO/2019/031990 WO/2018/156858; WO/2018/136202; WO/2018/027082; WO/2017/202719; WO/2017/185034; WO/2017/091836; WO/2016/100782; WO/2016/009076; WO/2015/049325; WO/2014/194245; WO/2014/194201; WO/2014/134169; WO/2013/122609; WO/2013/116786; and WO/2013/001310; the disclosures of which are herein incorporated by reference.

Specific CDK8 Ligands of Interest Include, but are not limited to:

| Name | Reference | Structure |
|---|---|---|
| BI-1347 | WO2017202719A1 | 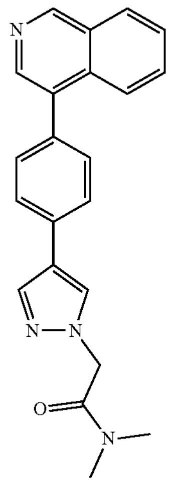 [SMILES: CN(C)C(=O)Cn1cc(-c2ccc(-c3cncc4ccccc34)cc2)cn1] |
| Cortistatin A | ACS Med. Chem. Lett. 2018, 9, 540-545 | 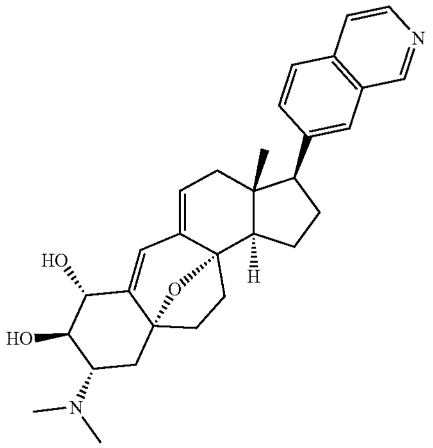 [SMILES: CN(C)[C@H]1C[C@@]23CC[C@@]4(O2)C(=CC[C@]2(C)[C@@H](c5ccc6ccncc6c5)CC[C@H]24)C=C3[C@@H](O)[C@@H]1O] |
| JH-VIII-49 | ACS Med. Chem. Lett. 2018, 9, 540-545 | 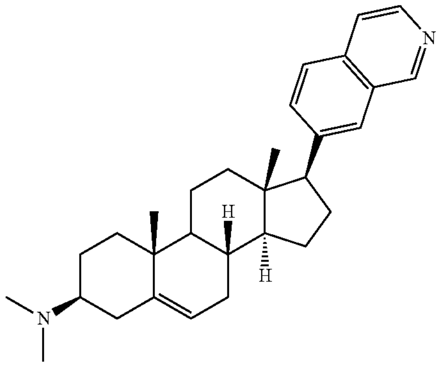 |
| CCT251545 | *Nat Chem Biol* 11, 973-980 (2015). | 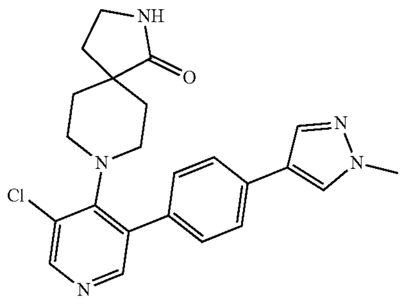 [SMILES: Cn1cc(-c2ccc(-c3cncc(Cl)c3N3CCC4(CCNC4=O)CC3)cc2)cn1] |

-continued
| Name | Reference | Structure |
| --- | --- | --- |
| MSC253818 | *J. Med. Chem.* 2016, 59, 20, 9337-9349 | 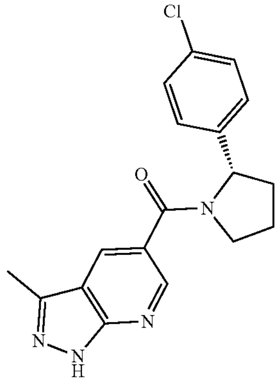 [SMILES: Cc1n[nH]c2ncc(C(=O)N3CCC[C@H]3c3ccc(Cl)cc3)cc12] |
| Senexin C | *J. Med. Chem.* 2022, 65, 4, 3420-3433 | 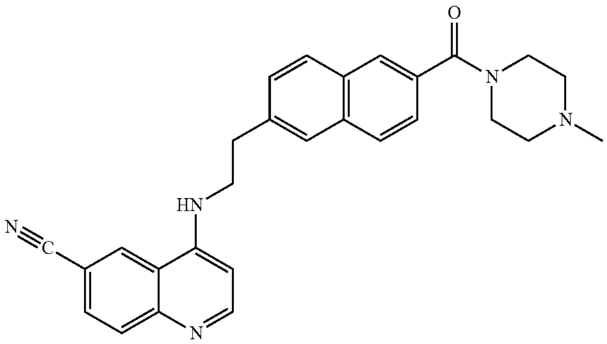 [SMILES: CN1CCN(C(=O)c2ccc3cc(CCNc4ccnc5ccc(C#N)cc45)ccc3c2)CC1] |
| Sel 120-34A | *Oncotarget,* 2017, Vol. 8, (No. 20), pp: 33779-33795 | 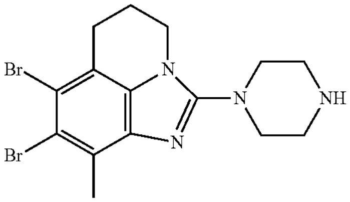 |
| W-34 | *Eur J Med Chem.* 2017 Mar. 31; 129:275-286. | 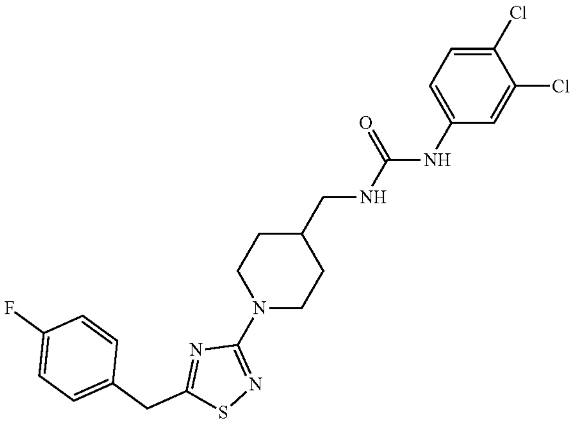 [SMILES: O=C(NCC1CCN(c2nsc(Cc3ccc(F)cc3)n2)CC1)Nc1ccc(Cl)c(Cl)c1] |

-continued

| Name | Reference | Structure |
| --- | --- | --- |
| T-814 | *Oncotarget.* 2018 Mar. 2; 9(17): 13474-13487. | 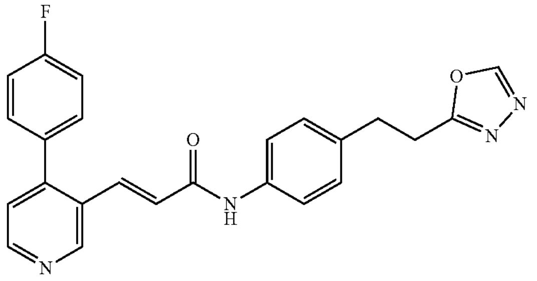 [SMILES: O=C(/C=C/c1cnccc1-c1ccc(F)cc1)Nc1ccc(CCc2nnco2)cc1] |

In some instances, the CDK is a CDK7. Suitable ligands for CDK7 include, but are not limited to, those described in published PCT application Publication Nos.: WO/2022/136174; WO/2022/084930; WO/2022/082056; WO/2022/064009; WO/2022/061155; WO/2022/017533; WO/2021/242602; WO/2021/182914; WO/2021/087138; WO/2020/186196; WO/2020/093006; WO/2020/0930111; WO/2019/143730; WO/2019/143719; WO/2019/099298; WO/2018/231859; WO/2018/187357; WO/2018/013867; WO/2017/160797; WO/2016/105528; WO/2016/058544; WO/2015/154022; WO/2015/154038; WO/2015/154039; WO/2015/058140; and WO/2014/063068; the disclosures of which are herein incorporated by reference.

Specific CDK7 Ligands of Interest Include, but are not limited to:

| Name | Reference | Structure |
| --- | --- | --- |
| BS-181 | *Cancer Res* (2009) 69 (15): 6208-6215. | 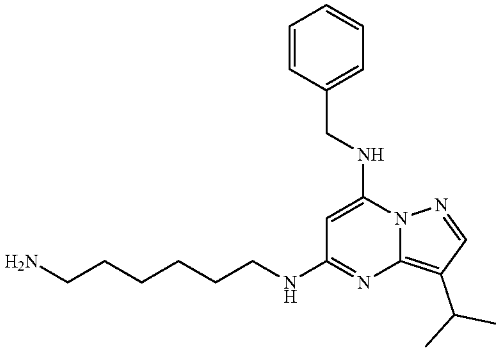 [SMILES: CC(C)c1cnn2c(NCc3ccccc3)cc(NCCCCCCN)nc12] |
| CT7001 | US20160362410A1 | 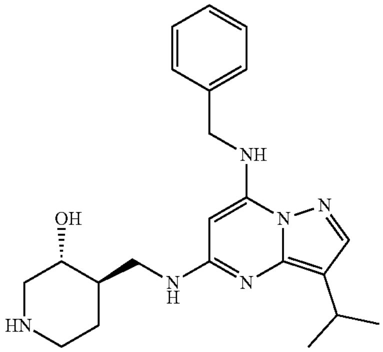 [SMILES: CC(C)c1cnn2c(NCc3ccccc3)cc(NC[C@H]3CCNC[C@@H]3O)nc12] |
| THZ2 Other derivatives include THZ1 | Wang et al., 2015, *Cell* 163, 174-186 | 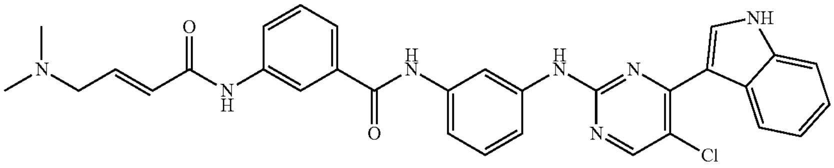 [SMILES: CN(C)C/C=C/C(=O)Nc1cccc(C(=O)Nc2cccc(Nc3ncc(Cl)c(-c4c[nH]c5ccccc45)n3)c2)c1] |

-continued
| Name | Reference | Structure |
|---|---|---|
| THZ2 reversible compound | | 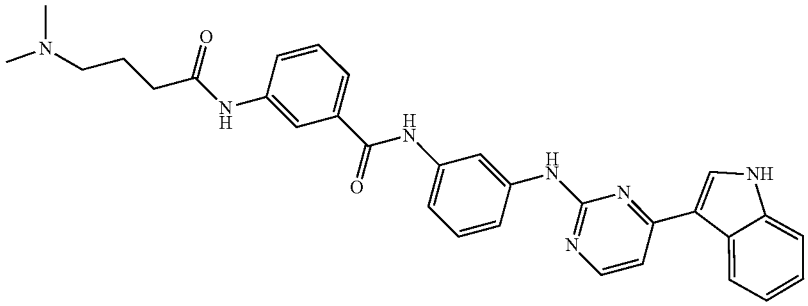 [SMILES: CN(C)CCCC(=O)Nc1cccc(C(=O)Nc2cccc(Nc3nccc(-c4c[nH]c5ccccc45)n3)c2)c1] |
| YKL-1-116 Other Derivatives include YLK-5-124 | Kalan et al., 2017, *Cell Reports* 21, 467-481 | 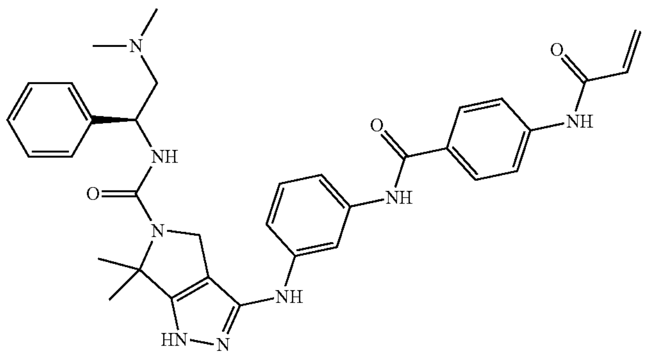 [SMILES: C=CC(=O)Nc1ccc(C(=O)Nc2cccc(Nc3n[nH]c4c3CN(C(=O)N[C@H](CN(C)C)c3ccccc3)C4(C)C)c2)cc1] |
| YKL-5-124 | | 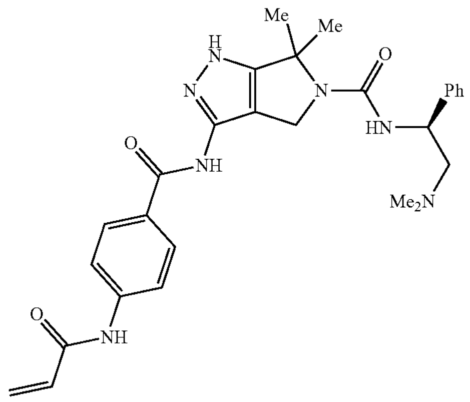 [SMILES: C=CC(=O)Nc1ccc(C(=O)Nc2n[nH]c3c2CN(C(=O)N[C@H](CN(C)C)c2ccccc2)C3(C)C)cc1] |
| YKL-5-124 Reversible compound | | 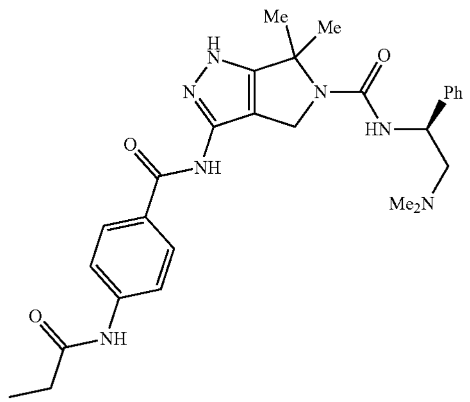 [SMILES: CCC(=O)Nc1ccc(C(=O)Nc2n[nH]c3c2CN(C(=O)N[C@H](CN(C)C)c2ccccc2)C3(C)C)cc1] |

-continued

| Name | Reference | Structure |
|---|---|---|
| SY-1365 and the reversible compound thereof (structure not shown) | | 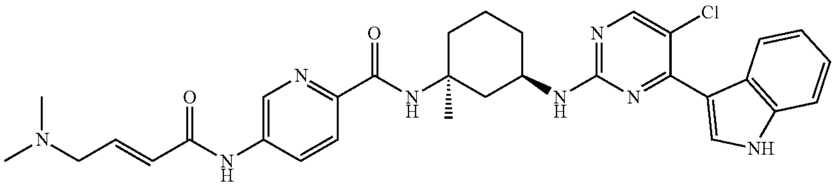 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)nc1] |
| SY5609 | | 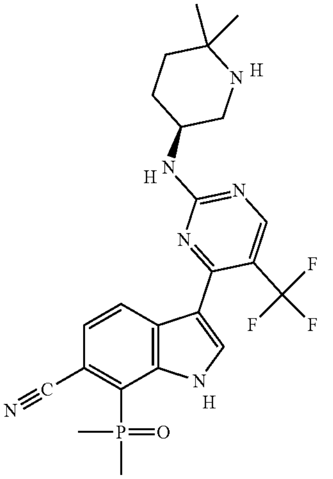 |
| LY3405105 and the reversible compound thereof (structure no shown) | | 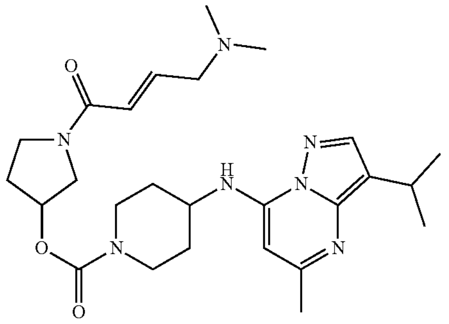 [SMILES: Cc1cc(NC2CCN(C(=O)OC3CCN(C(=O)/C=C/CN(C)C)C3)CC2)n2ncc(C(C)C)c2n1] |
| LDC4279 | | 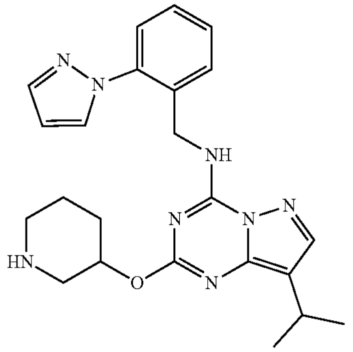 [SMILES: CC(C)c1cnn2c(NCc3ccccc3-n3cccn3)nc(OC3CCCNC3)nc12] |

AR Ligands Methods of treating a subject for a malignancy, e.g., prostate cancer, are provided. In some cases, the methods can include administering a transcriptional chemical inducer of proximity (TCIP) which links a BTB-domain containing protein, e.g., BCL-6 or a related family member, and an androgen receptor (AR) to treat the subject for the malignancy. Also provided are compositions that find use in practicing methods of the disclosure and procedures for selection of the sensitive patient population.

TCIPs employed in embodiments of the disclosure may include a ligand for a transcription modulator, such as oncogenic transcription factor, e.g., AR. This embodiment is of particular significance in treatment of cancer, where the CIP causes the cancer cell to kill itself with its own driver. Oncogenic transcription factors are transcription factors whose activity contributes to a neoplastic, e.g., cancerous, disease condition. The oncogenic transcription factor may vary, where examples of oncogenic transcription factors that may be employed include AR. Any convenient ligands for these oncogenic transcription factors may be employed, where suitable ligands include small molecule ligands that are capable of specifically binding to the target oncogenic transcription factor without any relevant negative impact on the target oncogenic transcription factor's ability to enhance transcription of the target proapoptotic gene when complexed with the anchor transcription factor by a TCIP, i.e., the transcription-activating activity of the oncogenic transcription factor. The molecular weight of these ligands may vary, and in some instances ranges from 150 Daltons to 500 Daltons such as 250 Daltons to 400 Daltons.

Suitable ligands for AR include, but are not limited to, those described in U.S. Pat. Nos. 11,358,938; 11,332,465; 11,242,324; 11,185,549; 10,934,271; 10,815,221; 10,766,875; 10,662,148; 10,556,882; 10,526,310; 10,434,075; 10,308,630; 10,150,739; 10,053,418; 9,994,545; 9,969,683; 9,889,110; 9,884,038; 9,744,149; 9,963,433; 9,622,992; 9,611,225; 9,604,916; 9,481,663; 9,359,285; 9,340,524; 9,085,539; 9,809,583; 8,865,918; 8,802,689; 8,580,811; 8,519,158; 8,445,507; 8,420,694; 8,193,357; 8,183,388; 7,816,372; 7,727,980; 7,365,202; 7,288,553; 7,214,690; 7,026,484; 6,960,474; 6,534,516; 6,462,038; 6,017,924; and 5,677,336; the disclosures of which are herein incorporated by reference.

Suitable ligands for AR include, but are not limited to: AR agonists, such as steroidal AR agonists, including but not limited to:

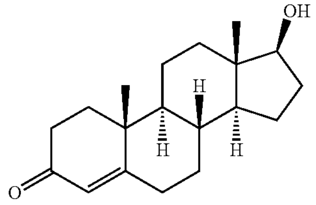

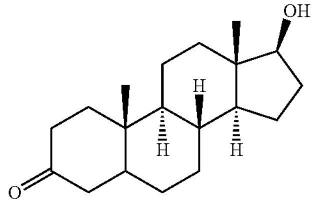

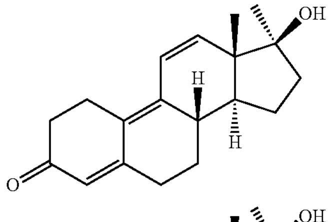

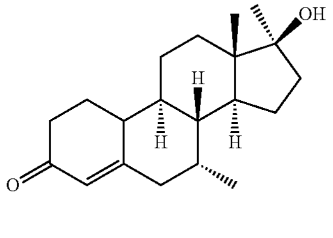

-continued

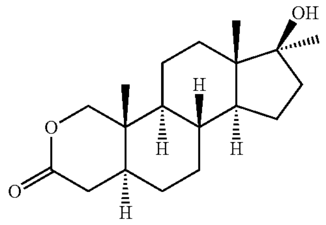

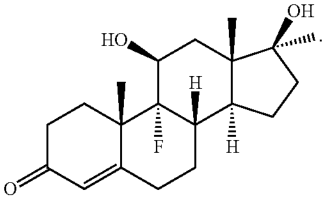

Also of Interest are Non-Steroidal AR Agonists, Such as but not Limited to:

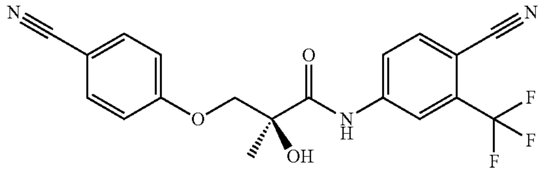

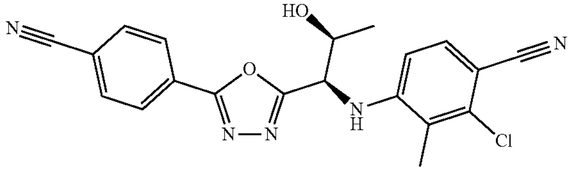

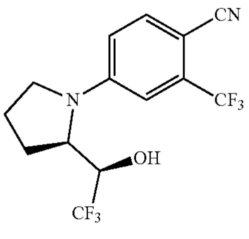

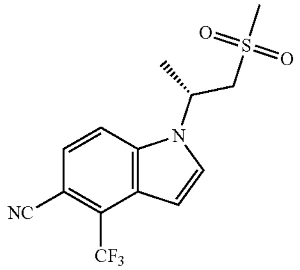

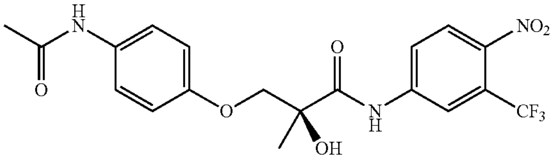

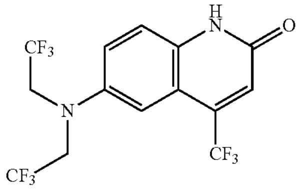

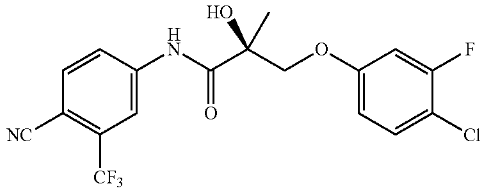

-continued

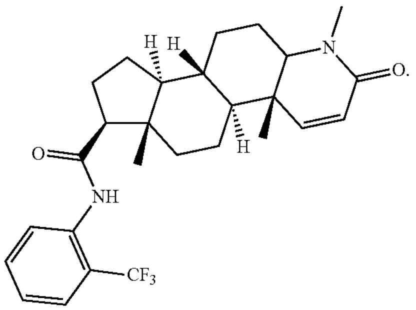

In some instances, the AR ligand is an AR antagonist, such as a non-steroidal AR antagonist, where examples of non-steroidal AR antagonists include, but are not limited to:

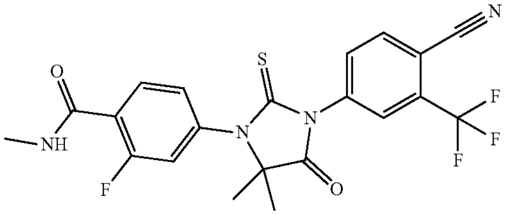

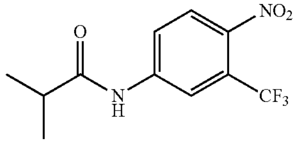

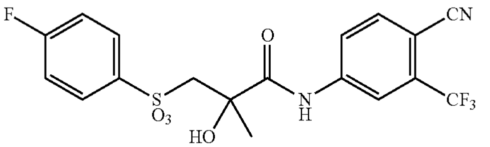

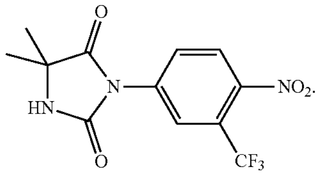

In some instances, the AR antagonist is a steroidal AR antagonist, where examples of steroidal AR antagonists include, but are not limited to:

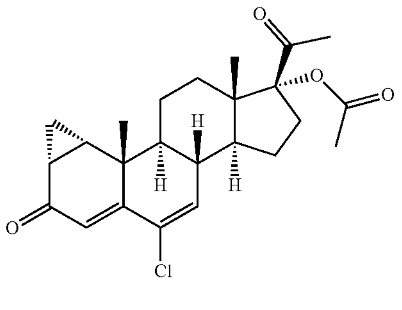

-continued

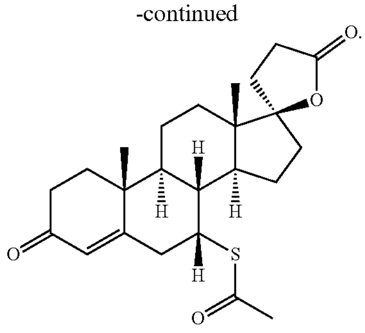

Anchor Transcription Factor Ligands

Any one of the methods of the present disclosure can comprise providing in the cell, e.g., via a protocol such as described below, a transcriptional chemical inducer of proximity (TCIP) which links a first endogenous anchor transcription factor that binds to a promoter of the proapoptotic gene, e.g., BCL-6, (and/or a functional homologue thereof, Table 3), and a second endogenous transcription modulating factor, e.g., an ER, a CDK, BRD4, an AR, etc., wherein CIP mediated linkage of these factors enhances transcription of the proapoptotic gene in the cell. In some instances, TCIPs employed in these embodiments are generally as described above and include a first ligand that specifically binds to the anchor transcription factor, e.g., BCL-6, and a second ligand that specifically binds to a transcription modulating factor, e.g., an ER, BRD4, a CDK9, an AR, where these first and second ligands are joined by a bond or suitable linker, e.g., as described below.

A variety of different anchor transcription factors may be employed in methods of these embodiments. Anchor transcription factors of interest include, but are not limited to: BCL-6, TFAP2A, TFAP2C, SP3, TFDP1, ELK3, SREBF1, SREBF2, THRA, SMAD2, TFDP1, TCF3, USF1, USF2, VEZF1, PBX1, HIF1A, RARA, FOXO3A, MAZ, E2F1, E2F2, PAX9, STAT1, SPDEF, CREB3L1, BATF, XBP1, SIX4, AR, LEF1, MYB, RUNX1, and PPARG. In some instances, the anchor transcription factor is BCL-6.

Of interest in certain embodiments are BTB-domain containing proteins, e.g., BCL-6 and related family members. The small molecules that bind BTB domains, such as BI3812 and others mentioned above, could produce their effects by binding to BCL6 and/or anyone or several of the 131 BTB domain-containing proteins encoded in the human genome that are listed in Table 3, below. In general, these BTB domain proteins also have DNA binding domains. Because they are often expressed in a tissue-specific way, they allow the activation of different biologic programs in different cell types by the TCIP. In the case of a specific cancer, selective expression of the BTB-domain containing protein could produce cell death, e.g., by removing repression due to a variety of epigenetic mechanisms, including removal of polycomb repressive complexes, removal of histone deacetylation complexes or other means. In addition, the recruitment to the genetic locus occupied by the BTB-domain containing protein could produce death of the cancer cell by steric interference or other mechanisms. In addition, the BTB-domain containing protein recruited to make a ternary complex could empower it with a new activity of therapeutic usefulness. For example, the cell type specific BTB domain protein could prevent the binding of BRD4 to chromatin in specific types of cancer cells such as SCLC, thereby providing tissue-specific inhibition of the actions of BRD4.

BTB domain containing proteins, BCL6 homologues, shown in Table 3, include family members which are known to repress cell death genes including p53, Puma, Bim and others (doi:10.4049/jimmunol.1600013; doi: 10.4049/jimmunol.1101451; doi: 10.3389/fimmu.2021.713294; dx.doi.org/10.1016/j.molcel.2014.02.017). Repression of cell death genes is due to the binding of epigenetic repressors such as BCOR, SMRT, NCOR and others. The BTB domain of this family is critical for this repression and point mutations in the BTB domain near the corepressor binding sites release repression and result in abnormal cell death (doi:10.4049/jimmunol.1 600013). Because the BTB family have functional similarities to BCL6, ligands for their BTB domains are useful for building TCIPs similar to the ones described in this application for BCL6.

TABLE 3

| BTB domain containing proteins useful for designing and synthesizing CIPs and TCIPs |
|---|
| ABTB1 |
| ABTB2 |
| ABTB3 |
| ANFY1 |
| ARMC5 |
| ATP7B |
| AURKB |
| BACD1 |
| BACD2 |
| BACD3 |
| BACH1 |
| BACH2 |
| BCL6 |
| BCL6B |
| BRMS1 |
| BTBD1 |
| BTBD2 |
| BTBD3 |
| BTBD6 |
| BTBD7 |
| BTBD8 |
| BTBD9 |
| BTBDA |
| BTBDG |
| BTBDH |
| BTBDI |
| BTBDJ |
| CALI |
| CTND1 |
| DAXX |
| ENC1 |
| FXL17 |
| GAN |
| GMCL1 |
| GMCL2 |
| GZF1 |
| H2AY |
| HIC1 |
| HIC2 |
| IBTK |
| IPP |
| KAISO |
| KBTB2 |
| KBTB3 |
| KBTB4 |
| KBTB6 |
| KBTB7 |
| KBTB8 |
| KBTBB |
| KBTBC |
| KBTBD |
| KCA10 |
| KCD11 |
| KCD14 |
| KCD15 |
| KCD16 |
| KCD17 |

TABLE 3-continued

| BTB domain containing proteins useful for designing and synthesizing CIPs and TCIPs |
|---|
| KCD18 |
| KCD19 |
| KCD20 |
| KCD21 |
| KCNA1 |
| KCNA2 |
| KCNA3 |
| KCNA4 |
| KCNA5 |
| KCNA6 |
| KCNA7 |
| KCNB1 |
| KCNB2 |
| KCNC1 |
| KCNC2 |
| KCNC3 |
| KCNC4 |
| KCND1 |
| KCND2 |
| KCND3 |
| KCNF1 |
| KCNG1 |
| KCNG2 |
| KCNG3 |
| KCNG4 |
| KCNRG |
| KCNS1 |
| KCNS2 |
| KCNS3 |
| KCNV1 |
| KCNV2 |
| KCTD1 |
| KCTD2 |
| KCTD3 |
| KCTD4 |
| KCTD5 |
| KCTD6 |
| KCTD7 |
| KCTD8 |
| KCTD9 |
| KEAP1 |
| KLH10 |
| KLH11 |
| KLH12 |
| KLH13 |
| KLH14 |
| KLH15 |
| KLH17 |
| KLH18 |
| KLH20 |
| KLH21 |
| KLH22 |
| KLH23 |
| KLH24 |
| KLH25 |
| KLH26 |
| KLH28 |
| KLH29 |
| KLH30 |
| KLH31 |
| KLH32 |
| KLH34 |
| KLH35 |
| KLH36 |
| KLH38 |
| KLH40 |
| KLH41 |
| KLH42 |
| KLHL1 |
| KLHL2 |
| KLHL3 |
| KLHL4 |
| KLHL5 |
| KLHL6 |
| KLHL7 |
| KLHL8 |
| KLHL9 |

TABLE 3-continued

| BTB domain containing proteins useful for designing and synthesizing CIPs and TCIPs |
|---|
| LASP1 |
| LG3BP |
| LZTR1 |
| MYNN |
| NACC1 |
| NACC2 |
| NCOR2 |
| NF2L2 |
| NPTXR |
| NS1BP |
| PATZ1 |
| PLAG1 |
| RBX1 |
| RCBT1 |
| RCBT2 |
| RHBT1 |
| RHBT2 |
| RHBT3 |
| RHOA |
| RNF4 |
| SANBR |
| SHKB1 |
| SLX4 |
| SPOP |
| SPOPL |
| TIF1B |
| TZAP |
| UBA1 |
| Z355P |
| ZBT10 |
| ZBT11 |
| ZBT12 |
| ZBT14 |
| ZBT16 |
| ZBT17 |
| ZBT18 |
| ZBT20 |
| ZBT21 |
| ZBT22 |
| ZBT24 |
| ZBT25 |
| ZBT26 |
| ZBT32 |
| ZBT34 |
| ZBT37 |
| ZBT38 |
| ZBT39 |
| ZBT40 |
| ZBT41 |
| ZBT42 |
| ZBT43 |
| ZBT44 |
| ZBT45 |
| ZBT46 |
| ZBT47 |
| ZBT49 |
| ZBT7A |
| ZBT7B |
| ZBT7C |
| ZBT8A |
| ZBT8B |
| ZBTB1 |
| ZBTB2 |
| ZBTB3 |
| ZBTB4 |
| ZBTB5 |
| ZBTB6 |
| ZBTB9 |
| ZF69B |
| ZIM3 |
| ZN124 |
| ZN131 |
| ZN132 |
| ZN133 |
| ZN155 |
| ZN254 |
| ZN347 |

TABLE 3-continued

| BTB domain containing proteins useful for designing and synthesizing CIPs and TCIPs |
|---|
| ZN484 |
| ZN529 |
| ZN564 |
| ZN577 |
| ZN582 |
| ZN611 |
| ZN675 |
| ZN676 |
| ZN724 |
| ZN805 |
| ZN846 |
| ZN880 |
| ZNF66 |
| ZNF99 |
| ZSC10 |

In TCIPs of these embodiments, any convenient ligand for these anchor transcription factors may be employed, where suitable ligands include small molecule ligands that are capable of specifically binding to the target anchor transcription factor without any relevant negative impact on the anchor transcription factor's ability to bind to target DNA binding site. The molecular weight of these ligands may vary, and in some instances ranges from 50 Daltons to 1200 Daltons such as 200 to 500 Daltons. Suitable ligands for the anchor transcription factor may be chosen using any convenient protocol, such as in silico screening protocols, and the like, such as described below.

Where the anchor transcription factor is BCL-6, suitable ligands include, but are not limited to, those described in U.S. Pat. Nos. 11,242,351; 11,192,880; 11,161,839; 11,001,570; 9,943,506; 8,791,075; 8,703,503; 8,338,464; and 7,919,578, as well as those described in United States Patent Application Publication Nos. 20210330672; 20210206756; 20210163497; 20210147382; 20210053978; 20200331921; 20200325119; 20200308147; 20200071297; 20160166549; 20120014979; 20100130564; 20090018083; the disclosures of which are herein incorporated by reference.

In Some Embodiments, the B-Cell Lymphoma 6 Ligand (BC) is of Formula IB:

(IB)

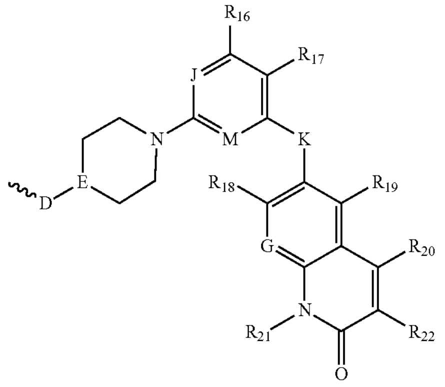

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, —C(1-4) alkyl, —O—C(1-14) alkyl, —O—C(1-4) haloalkyl, —C(1-4) haloalkyl and halogen;

J is —CH or nitrogen;

M is —CH or nitrogen;

K is —$CH_2$, O, S or —NH;

∿∿∿ represents a bond to the linker; and each of $R_{16}$, $R_{17}$, $R_{18}$, $R_{19}$, $R_{20}$, $R_{21}R_{22}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, D is an amide. In some embodiments, D is an optionally substituted C(1-6) aliphatic. In some embodiments, D is substituted. In some embodiments, D is unsubstituted. In certain embodiments, D is C(1-6) alkyl. In certain embodiments, D is C(1-4) alkyl. In certain embodiments, D is methyl, ethyl, propyl, or isopropyl. In some instances, D is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, D is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, D is a C(1-3) hydrocarbon chain wherein one methylene unit is optionally replaced by —NH—, —O—, —S—, —S(O)—, or —$SO_2$—.

In certain instances, E is nitrogen. In certain instances, E is —CH.

In some instances, $R_{16}$ is selected from hydrogen, halogen or a C(1-6) alkyl. In some instances, $R_{16}$ is selected from methyl, ethyl, n-propyl, isopropyl, n-butyl, iso-butyl or tert-butyl. In certain instances, $R_{16}$ is hydrogen. In certain instances, $R_{16}$ is halogen. In some instances, $R_{16}$ is selected from fluorine, chlorine, bromine and iodine. In some instances, $R_{16}$ is chlorine.

In some instances, $R_{17}$ is selected from hydrogen, halogen or a C(1-6) alkyl. In some instances, $R_{17}$ is selected from methyl, ethyl, n-propyl, isopropyl, n-butyl, iso-butyl or tert-butyl. In certain instances, $R_{17}$ is hydrogen. In certain instances, $R_{17}$ is halogen. In some instances, $R_{17}$ is selected from fluorine, chlorine, bromine and iodine. In some instances, $R_{17}$ is chlorine. In certain instances, $R_{16}$ is hydrogen and $R_{17}$ is chlorine.

In some embodiments, $R_{18}$ is selected from hydrogen, —C(1-4) alkyl, -—O—C(1-4) alkyl and halogen. In some instances, $R_{18}$ is selected from methyl, ethyl, n-propyl, isopropyl, n-butyl, iso-butyl or tert-butyl. In some instances, $R_{18}$ is selected from methoxy, ethoxy, n-propoxy, isopropoxy, n-butoxy, iso-butoxy or tert-butoxy. In some instances, $R_{18}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{18}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R^{18}$ is a C(1-3) hydrocarbon chain wherein one methylene unit is optionally replaced by —NH—, —O—, —S—, —S(O)—, or —$SO_2$—. In some instances, $R_{18}$ is selected from fluorine, chlorine, bromine and iodine.

In some instances, $R_{19}$ is selected from hydrogen, halogen or a C(1-6) alkyl. In some instances, $R_{19}$ is selected from methyl, ethyl, n-propyl, isopropyl, n-butyl, iso-butyl or tert-butyl. In certain instances, $R^1{}_9$ is hydrogen. In certain instances, $R_{19}$ is halogen. In some instances, Rig is selected from fluorine, chlorine, bromine and iodine. In some instances, $R_1$ is chlorine. In certain instances, $R^1{}_6$ is hydrogen, $R_{17}$ is chlorine and $R_{19}$ is hydrogen.

In some embodiments, G is $CR_{23}$ and $R_{23}$ is selected from hydrogen, C(1-4) alkyl, —O—C(1-4) alkyl, —O—C(1-4) haloalkyl, and halogen. In some instances, $R_{23}$ is hydrogen, —C(1-4) alkyl, —O—C(1-4) alkyl and halogen. In some instances, $R_{23}$ is selected from methyl, ethyl, n-propyl, isopropyl, n-butyl, iso-butyl or tert-butyl. In some instances, $R_{23}$ is selected from methoxy, ethoxy, n-propoxy, isopropoxy, n-butoxy, iso-butoxy or tert-butoxy. In some instances, $R_{23}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{23}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{23}$ is a C(1-3) hydrocarbon chain wherein one methylene unit is optionally replaced by —NH—, —O—, —S—, —S(O)—, or —$SO_2$—. In some instances, $R_{23}$ is selected from fluorine, chlorine, bromine and iodine.

In some instances, J is —CH. In some instances, J is nitrogen. In some instances, M is —CH. In some instances, M is nitrogen. In some instances, K is —$CH_2$. In some instances, K is oxygen. In some instances, K is sulfur. In some instances, K is —NH.

In some embodiments, $R_{21}$ is selected from hydrogen, —C(1-6) alkyl optionally substituted with one group selected from —OH, —$NH_2$, —O—$C_{1-4}$ alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl. In some instances, $R_{21}$ is selected from —C(1-4) alkyl, optionally substituted with one group selected from —OH, —C(3-6) cycloalkyl and —N($C_{1-4}$ alkyl)$_2$. In some embodiments, $R_{21}$ is selected from —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$. In some instances, $R_{21}$ is hydrogen or a C(1-6) alkyl. In some instances, $R_{21}$ is selected from methyl, ethyl, n-propyl, isopropyl, n-butyl, iso-butyl or tert-butyl. In certain instances, $R_{21}$ is methyl.

In some embodiments, $R_{20}$ is selected from hydrogen, —C(1-4) alkyl, —O—C(1-4) alkyl and halogen. In certain instances, $R_{20}$ is hydrogen. In some instances, $R_{20}$ is selected from methyl, ethyl, n-propyl, isopropyl, n-butyl, iso-butyl or tert-butyl. In some instances, $R_{20}$ is selected from methoxy, ethoxy, n-propoxy, isopropoxy, n-butoxy, iso-butoxy or tert-butoxy. In some instances, $R_{20}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{20}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{20}$ is a C(1-3) hydrocarbon chain wherein one methylene unit is optionally replaced by —NH—, —O—, —S—, —S(O)—, or —$SO_2$—. In some instances, $R_{20}$ is selected from fluorine, chlorine, bromine and iodine.

In some embodiments, $R_{22}$ is —$L_1$—C($R_{24}R^{2}_{5}$)—$R_{26}$ or —CH═CH—$R_{26}$ wherein $L_1$ is —O— or —S—; $R_{24}$ is hydrogen or C(1-4) alkyl; $R_{25}$ is hydrogen or C(1-4) alkyl; or $R_{24}$ and $R_{25}$ taken together form a —C(3-5) cycloalkyl; $R_{26}$ is —COOH, —$CONH_2$, —C(O)$R_{27}$, —C(O)O$R_{27}$, —C(O)N$R_{27}R_{28}$, —S(O)—$C_{1-6}$ alkyl, —S$(O)_2$—C(1-6) alkyl, —P(O)—$(C_{1-6}$ alkyl$)_2$, —C(NH)$NH_2$, $R_{27}$ is a 3-6 membered heterocyclyl or —C(1-4) alkyl optionally substituted by one or more, identical or different groups selected from —OH, —$CF_3$, —N($C_{1-4}$ alkyl$)_2$, —C(3-6) cycloalkyl, 3-6 membered heterocyclyl, —C(2-4) alkenyl, —$C_{2-4}$alkynyl; and $R_{28}$ is hydrogen or C(1-4) alkyl. In certain instances, $R_{22}$ is selected from:

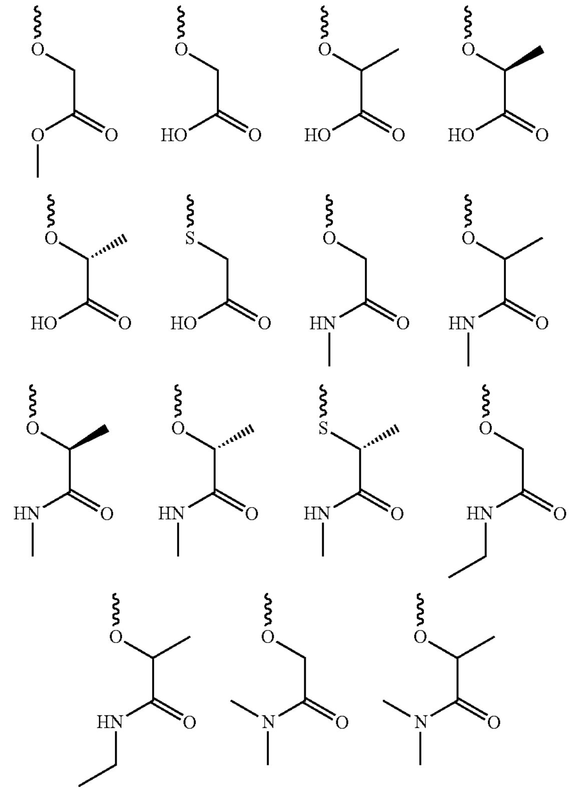

-continued

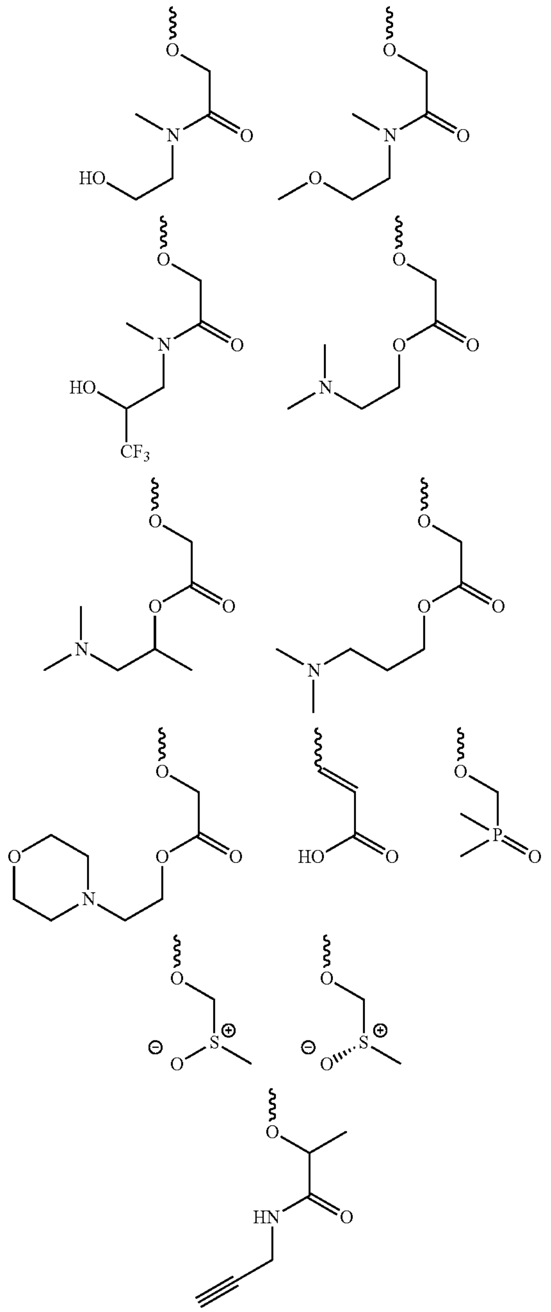

In some embodiments, $R_{22}$ is:

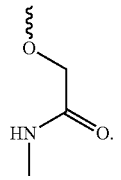

In certain embodiments, the B-cell lymphoma 6 ligand (BC) is of formula IB1:

(IB1)

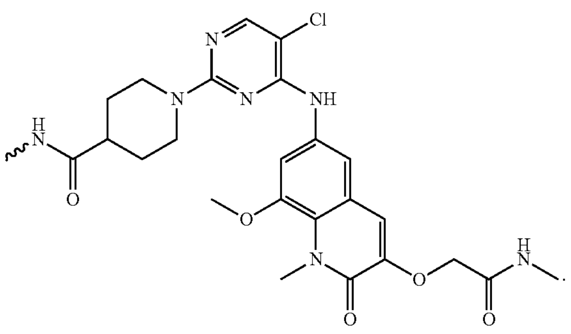

In certain embodiments, the B-cell lymphoma 6 ligand (BC) is of formula IB2:

(IB2)

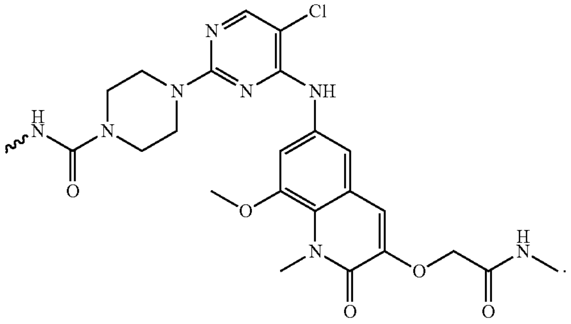

In certain embodiments, the B-cell lymphoma 6 ligand (BC) is of formula IB3:

(IB3)

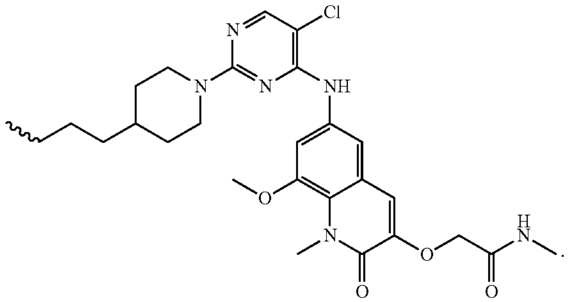

In certain embodiments, the B-cell lymphoma 6 ligand (BC) is of formula IB4:

(IB4)

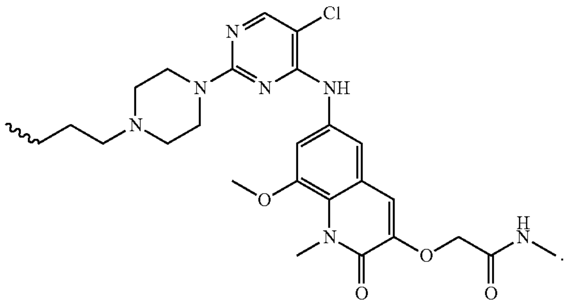

In certain embodiments, the B-cell lymphoma 6 ligand (BC) is of formula IB5:

(IB5)

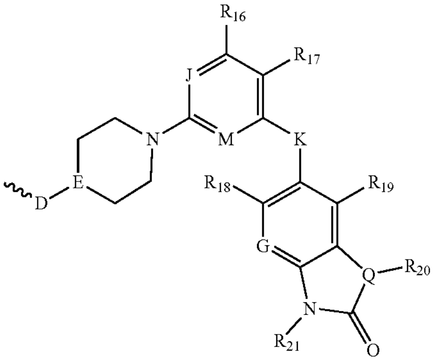

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, —C(1-4) alkyl, —O—C(1-14) alkyl, —O—C(1-4) haloalkyl, —C(1-4) haloalkyl and halogen;

J is —CH or nitrogen;

M is —CH or nitrogen;

Q is —CH or nitrogen;

K is —$CH_2$, O, S or NH;

represents a bond to the linker; and each of $R_{16}$, $R_{17}$, $R_{18}$, $R_{19}$, $R_{20}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, D is an amide. In some embodiments, D is an optionally substituted C(1-6) aliphatic. In some embodiments, D is substituted. In some embodiments, D is unsubstituted. In certain embodiments, D is C(1-6) alkyl. In certain embodiments, D is C(1-4) alkyl. In certain embodiments, D is methyl, ethyl, propyl, or isopropyl. In some instances, D is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, D is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, D is a C(1-3) hydrocarbon chain wherein one methylene unit is optionally replaced by —NH—, —O—, —S—, —S(O)—, or —$SO_2$—.

In certain instances, E is nitrogen. In certain instances, E is —CH.

In some instances, $R_{16}$ is selected from hydrogen, halogen or a C(1-6) alkyl. In some instances, $R_{18}$ is selected from methyl, ethyl, n-propyl, isopropyl, n-butyl, iso-butyl or tert-butyl. In certain instances, $R_{18}$ is hydrogen. In certain instances, $R_{18}$ is halogen. In some instances, $R_{16}$ is selected from fluorine, chlorine, bromine and iodine. In some instances, $R_{16}$ is chlorine.

In some instances, $R_{17}$ is selected from hydrogen, halogen or a C(1-6) alkyl. In some instances, $R_{17}$ is selected from methyl, ethyl, n-propyl, isopropyl, n-butyl, iso-butyl or tert-butyl. In certain instances, $R_{17}$ is hydrogen. In certain instances, $R_{17}$ is halogen. In some instances, $R_{17}$ is selected from fluorine, chlorine, bromine and iodine. In some instances, $R_{16}$ is chlorine. In certain instances, $R_{18}$ is hydrogen and $R_{17}$ is chlorine.

In some embodiments, $R_{18}$ is selected from hydrogen, —C(1-4) alkyl, —O—C(1-4) alkyl and halogen. In some instances, $R_{18}$ is selected from methyl, ethyl, n-propyl, isopropyl, n-butyl, iso-butyl or tert-butyl. In some instances, $R_{18}$ is selected from methoxy, ethoxy, n-propoxy, isopropoxy, n-butoxy, iso-butoxy or tert-butoxy. In some instances, $R^1{}_8$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{18}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{18}$ is a C(1-3) hydrocarbon chain wherein one methylene unit is optionally replaced by —NH—, —O—, —S—, —S(O)—, or —$SO_2$—. In some instances, $R_{18}$ is selected from fluorine, chlorine, bromine and iodine.

In some instances, $R_{19}$ is selected from hydrogen, halogen or a C(1-6) alkyl. In some instances, $R_{19}$ is selected from methyl, ethyl, n-propyl, isopropyl, n-butyl, iso-butyl or tert-butyl. In certain instances, $R_{19}$ is hydrogen. In certain instances, $R_{19}$ is halogen. In some instances, $R_{19}$ is selected from fluorine, chlorine, bromine and iodine. In some instances, $R_{19}$ is chlorine. In certain instances, $R_{18}$ is hydrogen, $R_{17}$ is chlorine and $R_{19}$ is hydrogen.

In some embodiments, G is $CR_{23}$ and $R_{23}$ is selected from hydrogen, C(1-4) alkyl, —O—C(1-4) alkyl, —O—C(1-4) haloalkyl, and halogen. In some instances, $R_{23}$ is hydrogen, —C(1-4) alkyl, —O—C(1-4) alkyl and halogen. In some instances, $R_{23}$ is selected from methyl, ethyl, n-propyl, isopropyl, n-butyl, iso-butyl or tert-butyl. In some instances, $R_{23}$ is selected from methoxy, ethoxy, n-propoxy, isopropoxy, n-butoxy, iso-butoxy or tert-butoxy. In some instances, $R_{23}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{23}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{23}$ is a C(1-3) hydrocarbon chain wherein one methylene unit is optionally replaced by —NH—, —O—, —S—, —S(O)—, or —$SO_2$—. In some instances, $R_{23}$ is selected from fluorine, chlorine, bromine and iodine.

In some instances, J is —CH. In some instances, J is nitrogen. In some instances, M is —CH. In some instances, M is nitrogen. In some instances, K is —$CH_2$. In some instances, K is oxygen. In some instances, K is sulfur. In some instances, K is —NH.

In some embodiments, $R_{20}$ is selected from hydrogen, —C(1-4) alkyl, —O—C(1-4) alkyl and halogen. In certain instances, $R_{20}$ is hydrogen. In some instances, $R_{20}$ is selected from methyl, ethyl, n-propyl, isopropyl, n-butyl, iso-butyl or tert-butyl. In some embodiments, $R_{20}$ is methyl. In some instances, $R_{20}$ is selected from methoxy, ethoxy, n-propoxy, isopropoxy, n-butoxy, iso-butoxy or tert-butoxy. In some instances, $R_{20}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{20}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{20}$ is a C(1-3) hydrocarbon chain wherein one methylene unit is optionally replaced by —NH—, —O—, —S—, —S(O)—, or —$SO_2$—. In some instances, $R_{20}$ is selected from fluorine, chlorine, bromine and iodine.

In some embodiments, $R_{21}$ is selected from hydrogen, —C(1-6) alkyl optionally substituted with one group selected from —OH, —$NH_2$, —O—$C_{1-4}$ alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl. In some instances, $R_{21}$ is selected from —C(1-4) alkyl, optionally substituted with one group selected from —OH, —C(3-6) cycloalkyl and —N($C_4$ alkyl)$_2$. In some instances, $R_{21}$ is selected from —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$. In certain embodiments, $R_{21}$ is OH.

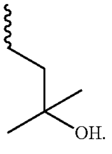

In some instances, $R_{21}$ is selected from —C(1-4) alkyl, optionally substituted with one group selected from —OH, —C(3-6) cycloalkyl and —$N(C_{1-4}$ alkyl$)_2$. In some embodiments, $R_{21}$ is selected from —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$— cyclopropyl and —$(CH_2)_2N(CH_3)_2$. In some instances, $R_{21}$ is hydrogen or a C(1-6) alkyl. In some instances, $R_{21}$ is selected from methyl, ethyl, n-propyl, isopropyl, n-butyl, iso-butyl or tert-butyl. In certain instances, $R_{21}$ is methyl.

In certain embodiments, the B-cell lymphoma 6 ligand (BC) is of formula IB6:

(IB6)

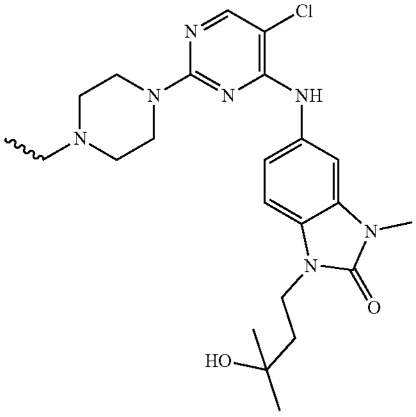

where ~~~ represents a bond to the linker.

In some embodiments, the B-cell lymphoma 6 ligand (BC) is of formula IB7:

(IB7)

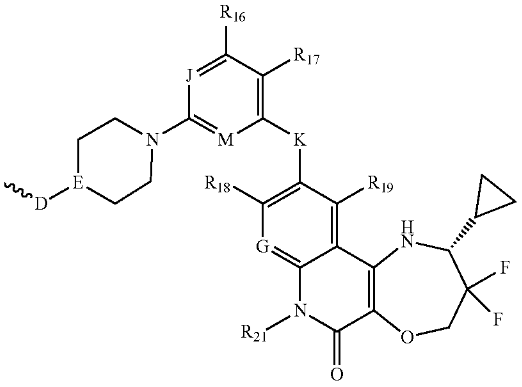

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, —C(1-4) alkyl, —O—C(1-14) alkyl, —O—C(1-4) haloalkyl, —C(1-4) haloalkyl and halogen;

J is —CH or nitrogen;

M is —CH or nitrogen;

K is —$CH_2$, O, S or NH;

~~~ represents a bond to the linker; and each of $R_{16}$, $R_{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, D is an amide. In some embodiments, D is an optionally substituted C(1-6) aliphatic. In some embodiments, D is substituted. In some embodiments, D is unsubstituted. In certain embodiments, D is C(1-6) alkyl. In certain embodiments, D is C(1-4) alkyl. In certain embodiments, D is methyl, ethyl, propyl, or isopropyl. In some instances, D is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, D is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, D is a C(1-3) hydrocarbon chain wherein one methylene unit is optionally replaced by —NH—, —O—, —S—, —S(O)—, or —$SO_2$—.

In certain instances, E is nitrogen. In certain instances, E is —CH.

In some instances, $R_{16}$ is selected from hydrogen, halogen or a C(1-6) alkyl. In some instances, $R_{16}$ is selected from methyl, ethyl, n-propyl, isopropyl, n-butyl, iso-butyl or tert-butyl. In certain instances, $R_{16}$ is hydrogen. In certain instances, $R_{16}$ is halogen. In some instances, $R_{16}$ is selected from fluorine, chlorine, bromine and iodine. In some instances, $R_{16}$ is chlorine.

In some instances, $R_{17}$ is selected from hydrogen, halogen or a C(1-6) alkyl. In some instances, $R_{17}$ is selected from methyl, ethyl, n-propyl, isopropyl, n-butyl, iso-butyl or tert-butyl. In certain instances, $R_{17}$ is hydrogen. In certain instances, $R_{17}$ is halogen. In some instances, $R_{17}$ is selected from fluorine, chlorine, bromine and iodine. In some instances, $R_{17}$ is chlorine. In certain instances, $R_{16}$ is hydrogen and $R_{17}$ is chlorine.

In some embodiments, $R_{18}$ is selected from hydrogen, —C(1-4) alkyl, —O—C(1-4) alkyl and halogen. In some instances, $R_{18}$ is selected from methyl, ethyl, n-propyl, isopropyl, n-butyl, iso-butyl or tert-butyl. In some instances, $R_{18}$ is selected from methoxy, ethoxy, n-propoxy, isopropoxy, n-butoxy, iso-butoxy or tert-butoxy. In some instances, $R_{18}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{18}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{18}$ is a C(1-3) hydrocarbon chain wherein one methylene unit is optionally replaced by
~~~

—NH—, —O—, —S—, —S(O)—, or —$SO_2$—. In some instances, $R_{18}$ is selected from fluorine, chlorine, bromine and iodine.

In some instances, $R_{19}$ is selected from hydrogen, halogen or a C(1-6) alkyl. In some instances, $R_{19}$ is selected from methyl, ethyl, n-propyl, isopropyl, n-butyl, iso-butyl or tert-butyl. In certain instances, $R_{19}$ is hydrogen. In certain instances, $R_{19}$ is halogen. In some instances, $R_{19}$ is selected from fluorine, chlorine, bromine and iodine. In some instances, $R_{19}$ is chlorine. In certain instances, $R_{16}$ is hydrogen, $R_{17}$ is chlorine and $R_{19}$ is hydrogen.

In some embodiments, G is $CR_{23}$ and $R_{23}$ is selected from hydrogen, C(1-4) alkyl, —O—C(1-4) alkyl, —O—C(1-4) haloalkyl, and halogen. In some instances, $R_{23}$ is hydrogen, —C(1-4) alkyl, —O—C(1-4) alkyl and halogen. In some instances, $R_{23}$ is selected from methyl, ethyl, n-propyl, isopropyl, n-butyl, iso-butyl or tert-butyl. In some instances, $R_{23}$ is selected from methoxy, ethoxy, n-propoxy, iso-propoxy, n-butoxy, iso-butoxy or tert-butoxy. In some instances, $R_{23}$ is an optionally substituted bivalent C(1-6) hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—. In some instances, $R_{23}$ is an optionally substituted bivalent C(1-3) hydrocarbon chain wherein one methylene unit is optionally replaced by —NR'—, —N(R')C(O)—, —C(O)N(R, —N(R')$SO_2$—, —$SO_2$N(R')—, —O—, —C(O)—, —OC(O)—, —C(O)O—, —S—, —SO— or —$SO_2$—. In certain embodiments, $R_{23}$ is a C(1-3) hydrocarbon chain wherein one methylene unit is optionally replaced by —NH—, —O—, —S—, —S(O)—, or —$SO_2$—. In some instances, $R_{23}$ is selected from fluorine, chlorine, bromine and iodine.

In some instances, J is —CH. In some instances, J is nitrogen. In some instances, M is —CH. In some instances, M is nitrogen. In some instances, K is —$CH_2$. In some instances, K is oxygen. In some instances, K is sulfur. In some instances, K is —NH.

In some embodiments, $R_{21}$ is selected from hydrogen, —C(1-6) alkyl optionally substituted with one group selected from —OH, —$NH_2$, —O—$C_{1-4}$ alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl. In some instances, $R_{21}$ is selected from —C(1-4) alkyl, optionally substituted with one group selected from —OH, —C(3-6) cycloalkyl and —N($C_{1-4}$ alkyl)$_2$. In some embodiments, $R_{21}$ is selected from —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$. In some instances, $R_{21}$ is hydrogen or a C(1-6) alkyl. In some instances, $R_{21}$ is selected from methyl, ethyl, n-propyl, isopropyl, n-butyl, iso-butyl or tert-butyl. In certain instances, $R_{21}$ is methyl.

In certain embodiments, the B-cell lymphoma 6 ligand (BC) is of formula IB8:

(IB8)

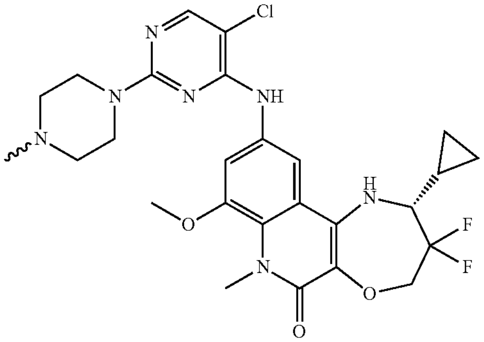

wherein 〰 represents a bond to the linker.

In some embodiments the B-cell lymphoma 6 ligand (BC) is of formula IB9:

(IB9)

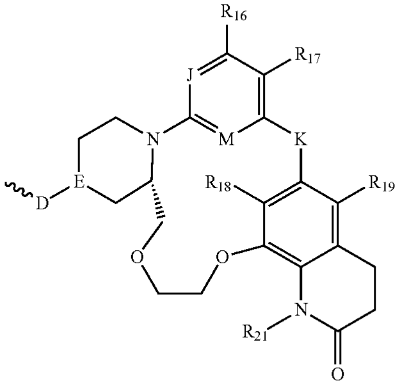

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

J is —CH or nitrogen;

M is —CH or nitrogen;

K is —$CH_2$, O, S or NH;

〰 represents a bond to the linker; and each of $R_{16}$, $R_{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

In some instances, D is an amide. In some embodiments, D is an optionally substituted C(1-6) aliphatic. In some embodiments, D is substituted. In some embodiments, D is unsubstituted. In certain embodiments, D is C(1-6) alkyl. In certain embodiments, D is C(1-4) alkyl. In certain embodiments, D is methyl, ethyl, propyl, or isopropyl. In some instances, D is an optionally substituted bivalent C(1-6) hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In some instances, D is an optionally substituted bivalent C(1-3) hydrocarbon chain wherein one methylene unit is optionally replaced by —NR'—, —N(R')C(O)—, —C(O)N(R, —N(R')SO$_2$—, —SO$_2$N(R')—, —O—, —C(O)—, —OC(O)—, —C(O)O—, —S—, —SO— or —SO$_2$—. In certain embodiments, D is a C(1-3) hydrocarbon chain wherein one methylene unit is optionally replaced by —NH—, —O—, —S—, —S(O)—, or —SO$_2$—.

In certain instances, E is nitrogen. In certain instances, E is —CH.

In some instances, $R_{16}$ is selected from hydrogen, halogen or a C(1-6) alkyl. In some instances, $R_{16}$ is selected from methyl, ethyl, n-propyl, isopropyl, n-butyl, iso-butyl or tert-butyl. In certain instances, $R_{16}$ is hydrogen. In certain instances, $R_{16}$ is halogen. In some instances, $R_{16}$ is selected from fluorine, chlorine, bromine and iodine. In some instances, $R_{16}$ is chlorine.

In some instances, $R_{17}$ is selected from hydrogen, halogen or a C(1-6) alkyl. In some instances, $R_{17}$ is selected from methyl, ethyl, n-propyl, isopropyl, n-butyl, iso-butyl or tert-butyl. In certain instances, $R_{17}$ is hydrogen. In certain instances, $R_{17}$ is halogen. In some instances, $R_{17}$ is selected from fluorine, chlorine, bromine and iodine. In some instances, $R_{17}$ is chlorine. In certain instances, $R_{16}$ is hydrogen and $R_{17}$ is chlorine.

In some embodiments, $R_{18}$ is selected from hydrogen, —C(1-4) alkyl, —O—C(1-4) alkyl and halogen. In some instances, $R_{18}$ is selected from methyl, ethyl, n-propyl, isopropyl, n-butyl, iso-butyl or tert-butyl. In some instances, $R_{18}$ is selected from methoxy, ethoxy, n-propoxy, isopropoxy, n-butoxy, iso-butoxy or tert-butoxy. In some instances, $R_{18}$ is an optionally substituted bivalent C(1-6) hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In some instances, $R_{18}$ is an optionally substituted bivalent C(1-3) hydrocarbon chain wherein one methylene unit is optionally replaced by —NR'—, —N(R')C(O)—, —C(O)N(R, —N(R')SO$_2$—, —SO$_2$N(R')—, —O—, —C(O)—, —OC(O)—, —C(O)O—, —S—, —SO— or —SO$_2$—. In certain embodiments, $R_{18}$ is a C(1-3) hydrocarbon chain wherein one methylene unit is optionally replaced by —NH—, —O—, —S—, —S(O)—, or —SO$_2$—. In some instances, $R_{18}$ is selected from fluorine, chlorine, bromine and iodine.

In some instances, $R_{19}$ is selected from hydrogen, halogen or a C(1-6) alkyl. In some instances, $R_{19}$ is selected from methyl, ethyl, n-propyl, isopropyl, n-butyl, iso-butyl or tert-butyl. In certain instances, $R_{19}$ is hydrogen. In certain instances, $R_{19}$ is halogen. In some instances, $R_{19}$ is selected from fluorine, chlorine, bromine and iodine. In some instances, $R_{19}$ is chlorine. In certain instances, $R_{16}$ is hydrogen, $R_{17}$ is chlorine and $R_{19}$ is hydrogen.

In some instances, J is —CH. In some instances, J is nitrogen. In some instances, M is —CH. In some instances, M is nitrogen. In some instances, K is —CH$_2$. In some instances, K is oxygen. In some instances, K is sulfur. In some instances, K is —NH.

In some embodiments, $R_{21}$ is selected from hydrogen, —C(1-6) alkyl optionally substituted with one group selected from —OH, —NH$_2$, —O—C$_4$ alkyl, —NH—C(1-4) alkyl, —N(C$_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl. In some instances, $R_{21}$ is selected from —C(1-4) alkyl, optionally substituted with one group selected from —OH, —C(3-6) cycloalkyl and —N(C$_{1-4}$ alkyl)$_2$. In some embodiments, $R_{21}$ is selected from —CH$_3$, —CH$_2$CH$_3$, —CH$_2$CH$_2$CH$_3$, —CH(CH$_3$)$_2$, —(CH$_2$)$_3$OH, —(CH$_2$)$_2$(CH$_3$)$_2$, —CH$_2$-cyclopropyl and —(CH$_2$)$_2$N(CH$_3$)$_2$. In some instances, $R_{21}$ is hydrogen or a C(1-6) alkyl. In some instances, $R_{21}$ is selected from methyl, ethyl, n-propyl, isopropyl, n-butyl, iso-butyl or tert-butyl. In certain instances, $R_{21}$ is methyl.

Where the anchor transcription factor is BCL-6, suitable ligands may include, but are not limited to:

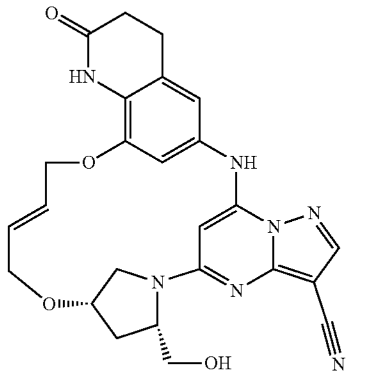

11

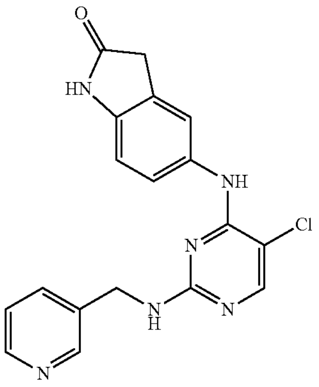

7

-continued
14
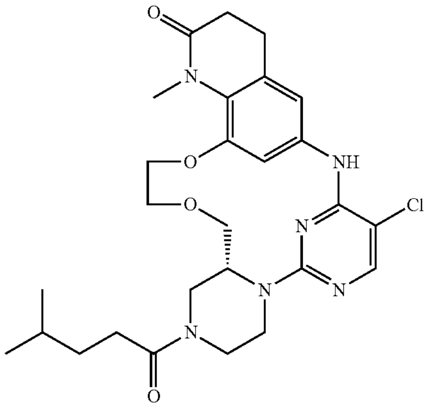
25a
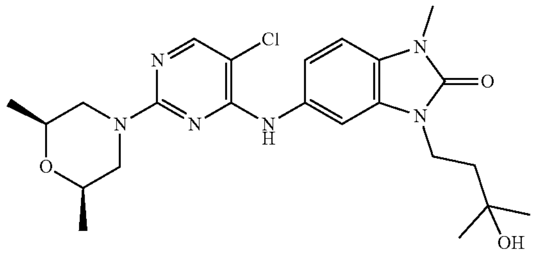
FX1
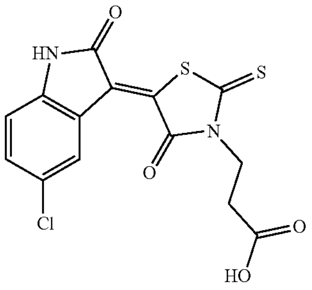
BI-3812
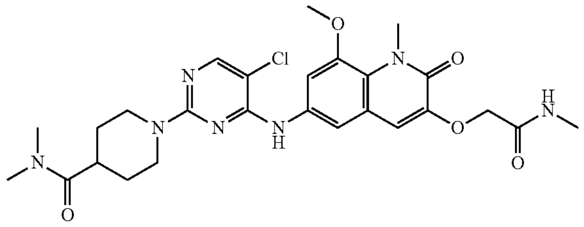
(BI-3802)
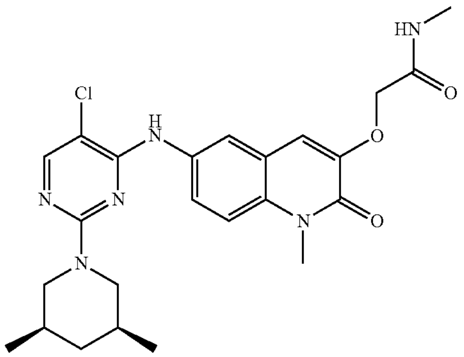
(14)
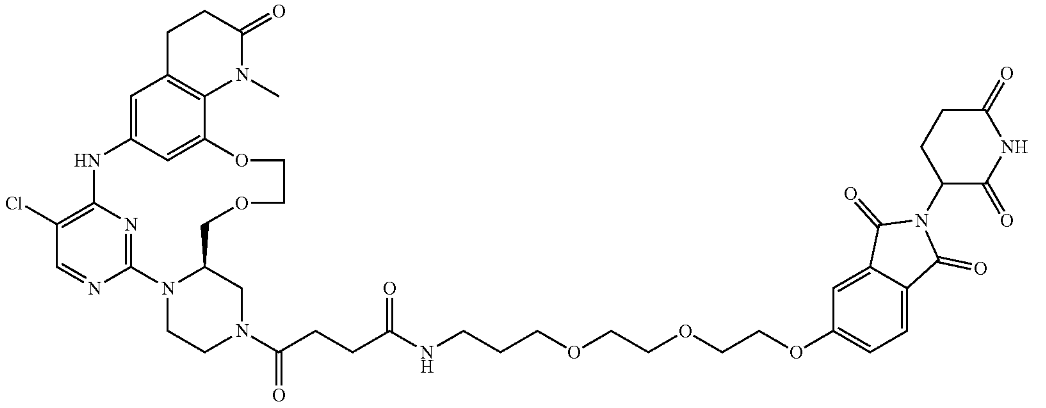

-continued
(6)
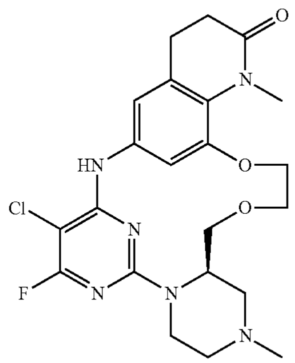
(CCT369347)
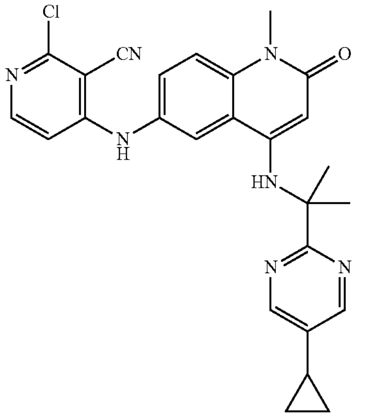
(CCT372064)
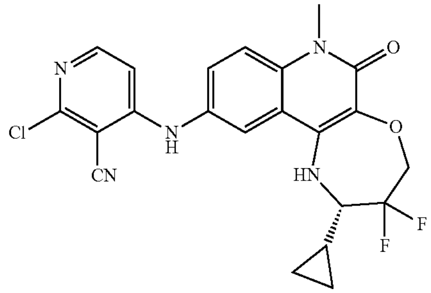
(CT37566)
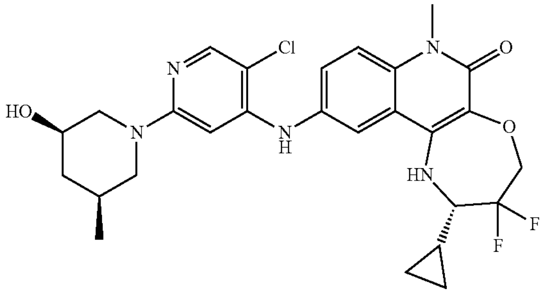
(CCTT369260)
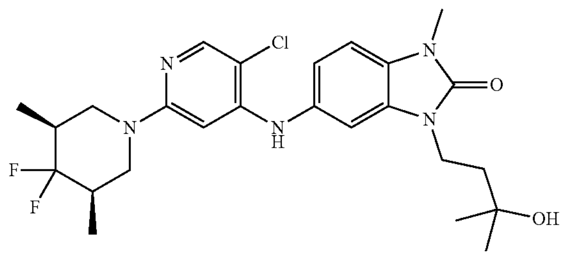
(26c)
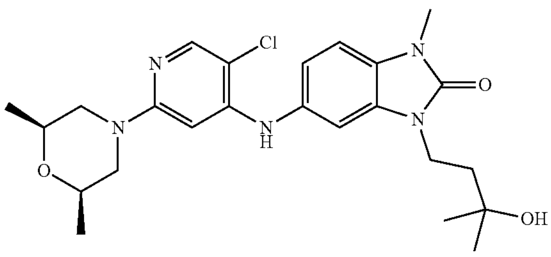
(TMX-2164)
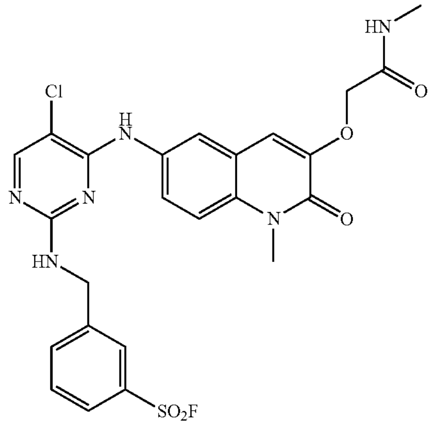
(BCI-1)
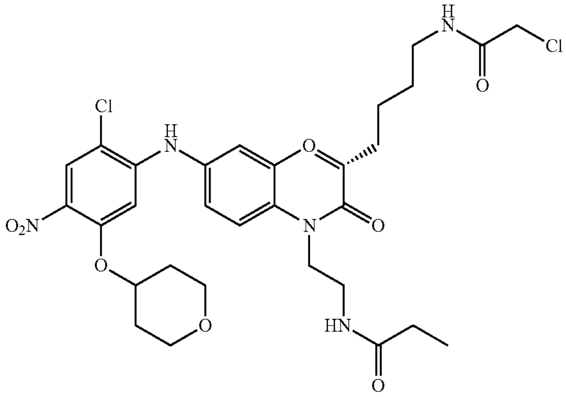

-continued

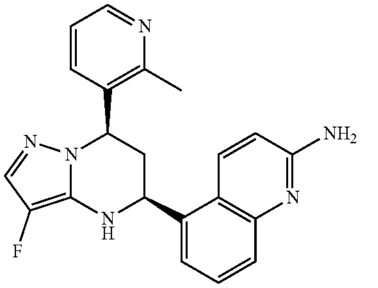

(GSK-137)

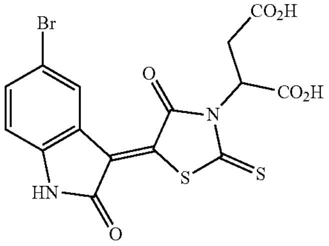

(79-6)

In certain embodiments, the B-cell lymphoma 6 ligand (BC) is of formula IB10:

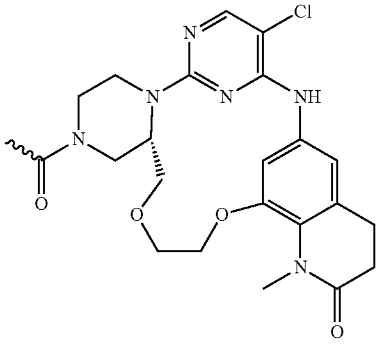

(IB10)

where ∿∿∿ represents a bond to the linker.

In certain embodiments, the B-cell lymphoma 6 ligand (BC) is a compound such as those described in United States Patent Publication No. 2020/0071297, the disclosure of which is herein incorporated by reference.

In certain embodiments, the BCL6 ligand is able to bind to other BTB domain containing proteins, such as those shown in Table 3. These ligands can be produced based on the crystal structure of the BCL6 BTB domain occupied by any of the compounds listed above and the primary sequence of the specific BTB domain containing protein. In other embodiments that BCL6 BTB ligands described above bind to a different BTB domain containing proteins and produce their therapeutic effects by this means.

Linkers

As described above, the present disclosure provides chemical inducers of proximity having two ligands, e.g., a BCL-6 (B-cell lymphoma 6) ligand and a second ligand (e.g., BRD4 (bromodomain-containing 4) ligand, an ER ligand, an AR ligand, a CDK ligand, etc., that are covalently bonded through a linker. When employed, any convenient linker may be employed to link the first and second ligands to each other. Linkers of interest are linkers that provide for a stable association of the first and second ligands in a manner such that the first and second ligands are capable of specifically binding to their respective endogenous factors in the cell. As the linker provides for stably associating the first and second ligands with each other, the first and second ligands do not dissociate from each other under cellular conditions, e.g., conditions at the surface of a cell, conditions inside of a cell, etc. Linkers may be provided for stable association of the first and second ligands using any convenient binding, such as covalent or non-covalent binding, where in some instances the linker component is covalently bound to both the first and second ligands. Suitable linkers include, but are not limited to, those linkers described above.

Additional Details

TCIPs employed in embodiments of the disclosure are those that enhance transcription of a pro-apoptotic gene in a cell, e.g., as illustrated in FIG. 1. By enhancing transcription of a pro-apoptotic gene is meant increasing transcription of the pro-apoptotic gene. The magnitude of increase in transcription may vary. In those instances where transcription of the pro-apoptotic gene is not detectable by a suitable assay, embodiments of the methods result in an enhancement of transcription so that transcription is detectable, e.g., by detecting the expression product of the proapoptotic gene or activity thereof, e.g., apoptosis or an indicator thereof. In those instances where there is a base level of transcription that is detectable, the magnitude of increase may vary and, in some instances, may be 1.5-fold or more, 2-fold or more, such as 5-fold or more, including 10-fold or more.

The methods may result in enhancing transcription of a variety of different proapoptotic genes. Proapoptotic genes are genes the expression products of which promote or cause apoptosis, i.e., programmed cell death that occurs in multicellular organisms, which may be characterized by a variety of cell changes, such as blebbing, cell shrinkage, nuclear fragmentation, chromatin condensation, chromosomal DNA fragmentation, and global mRNA decay, and death. Specific proapoptotic genes of interest for transcription that may be enhanced in embodiments of the disclosure include, but are not limited to: PUMA (BBC3), BIM (BCL2L11), BID, BAX, BAK, BOK, BAD, HRK, BIK, BMF, and NOXA, and the like. Their relative ability to kill breast cancer cells when simply overexpressed are shown in Table 4. These measurements are useful in picking transcription factors and ligands for targeting the TOIP to a specific effective pro-apoptotic gene, such as BMF, BIM and HRK.

TABLE 4

| Instructive Examples of the Method of Selection of Pro-apoptotic Genes for Hijacking Cancer Drivers to Intrinsic Cell Death Pathways | | | | |
|---|---|---|---|---|
| Gene | Class/Function | % viable MCF7 cells after* overexpression (24 h & 48 h) | | % increase in apoptotic MCF7 cells (24 h)** |
| BIM (BCL2L11) | BH3 activator | 66% | 42% | 23% |
| BID | BH3 activator | 100% | 89% | 6% |
| PUMA (BBC3) | BH3 activator/sensitizer | 98% | 90% | 8% |
| BAD | BH3 sensitizer | 100% | 98% | 17% |
| NOXA (PMAIP1) | BH3 sensitizer | 91% | 69% | 37% |
| HRK | BH3 sensitizer | 88% | 57% | 39% |
| BMF | BH3 sensitizer | 83% | 55% | 51% |
| BIK | BH3 sensitizer | 91% | 79% | 18% |
| BAX | Direct pore former | 100% | 87% | 19% |
| BAK | Direct pore former | 99% | 80% | 38% |
| BOK | Alternative pore former | 97% | 90% | 32% |

*Values shown on the right are the actual experimental values found after inducing expression in MCF7 ER-positive breast cancer. (see experimental section)

Pro-apoptotic genes are of particular interest because they are expressed at levels that balance the antiapoptotic genes, allowing the cell to survive by virtue of this balanced steady state. Another example is the master transcriptional activator of cell death FOXO3, which activates other proapoptotic genes (Akt promotes cell survival by phosphorylating and inhibiting a Forkhead transcription factor. Brunet A, Bonni A, Zigmond M J, Lin M Z, Juo P, Hu L S, Anderson M J, Arden K C, Blenis J, Greenberg M E. Cell. 1999 Mar. 19; 96(6):857-68. doi: 10.1016/s0092-8674(00)80595-4. PMID: 10102273)

BRD4-BCL6 TCIPs

As reviewed above, in some embodiments, chemical inducers of proximity include a compound of formula I:

BR-L-BC (I)

where:

BR is a ligand that specifically binds to bromodomain-containing protein 4 (BRD4);

BC is a ligand that specifically binds to B-cell lymphoma 6 (BCL-6) or a BCL6 BTB-domain family member; and L is a linker (optional), or a pharmaceutically acceptable salt thereof.

FIG. 1 provides an illustration of how to build a TCIP by rational design using existing components. As shown in FIG. 1, the design of a TCIP configured to hijack BCL6 to kill BRD4-positive DCBCL or SLCL cells is shown. BCL6 is a transcription factor and oncogene that prevents death of a variety of cancer cells, including lymphoma and SCLC cells, by binding the repressors BCOR, NCO and SMRT (PMID: 30335946) on the promoters of cell death genes. Several inhibitors of BCL6's repressive function have been produced that prevent the binding of BCOR, NCOR and SMRT to a site formed by the dimeric surface of BCL6 (PMID: 18280243) However, these inhibitors have not been sufficiently active to be used therapeutically (PMID:30335946).

Chemical linkage of BCL-6 inhibitors, such as BI3812 (PM1D32275432), to BRD4 ligand compounds, e.g., JQ1, that then bind and induce proximity to the cell death (pro-apoptotic) promoters, such as those for TP53, PUMA and BIM, convert the inhibitor of cell death to an activator of cell death in cells expressing BRD4, such as DCBLC or SCLC cells.

In certain embodiments, chemical inducers of proximity of interest having a BCL-6 (B-cell lymphoma 6) ligand and a BRD4 (bromodomain-containing 4) ligand include a compound selected from:

Compound I-1

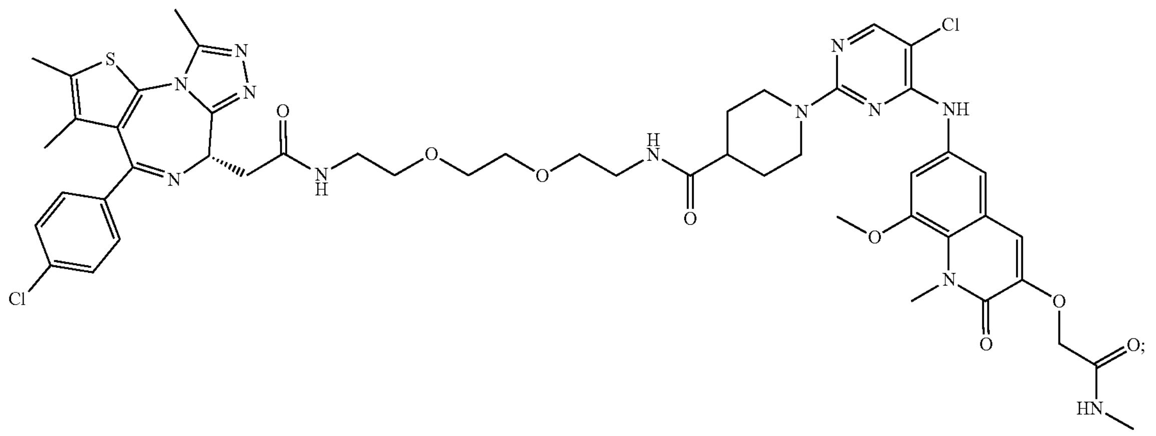

;

-continued
Compound I-2
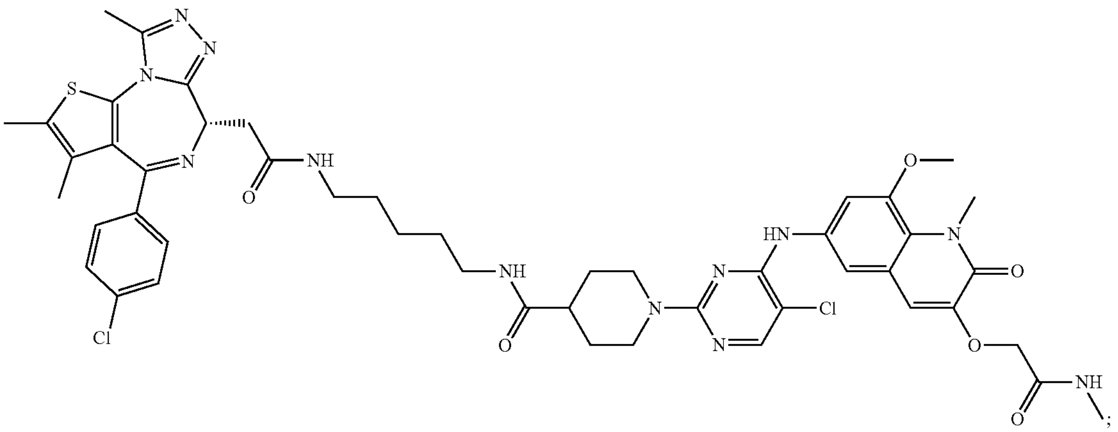
Compound I-3
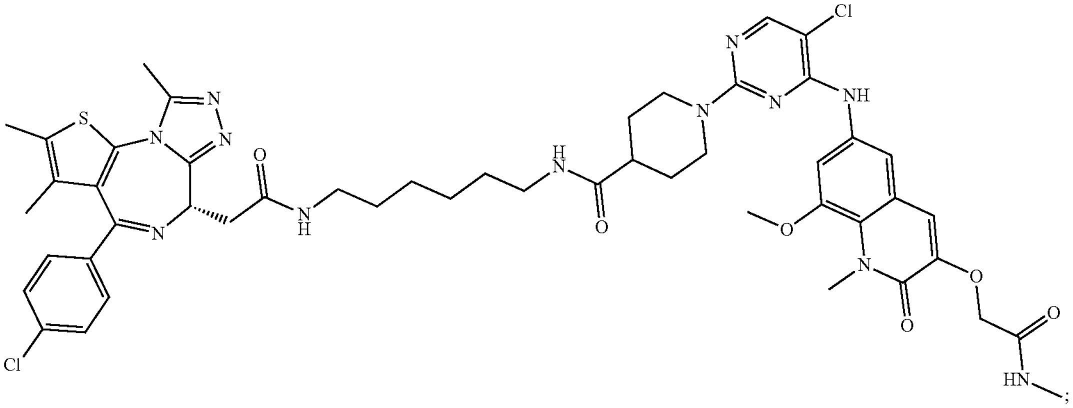
Compound I-4
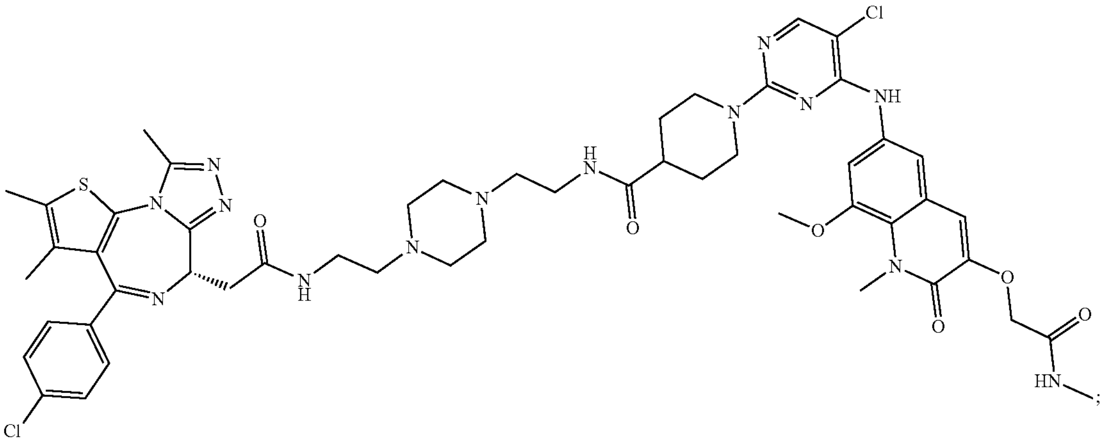

-continued
Compound I-5
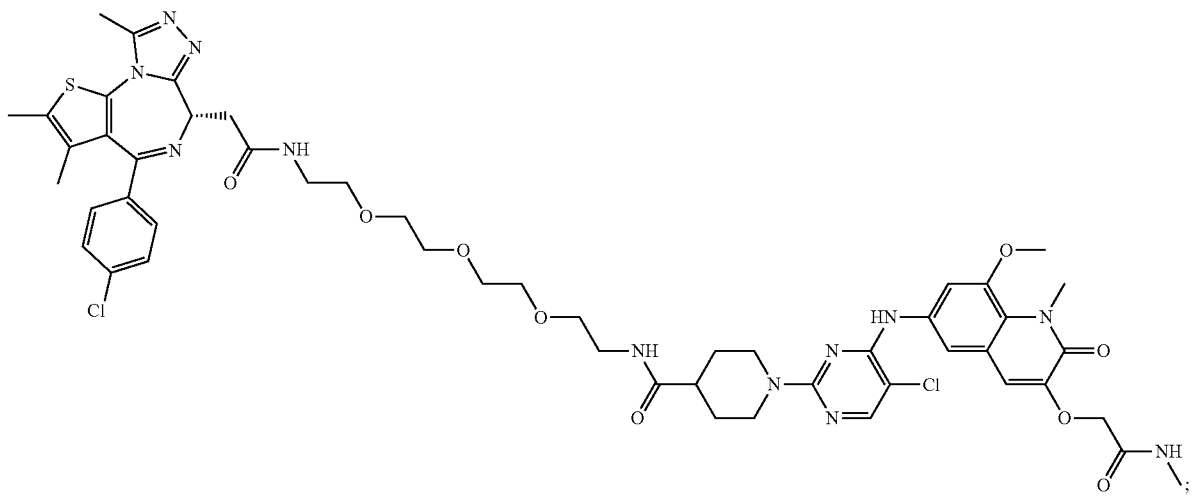
Compound I-6
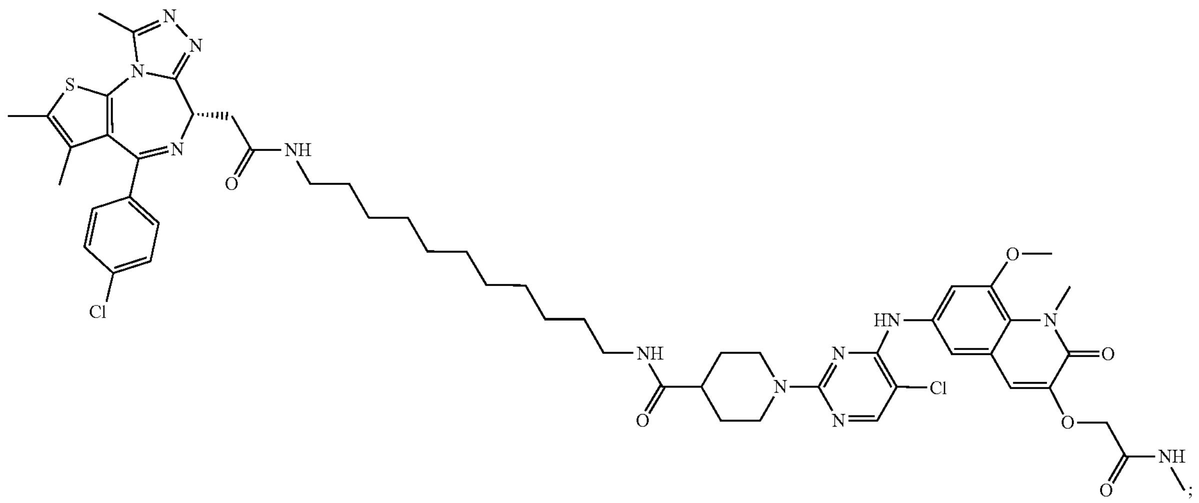
Compound I-7
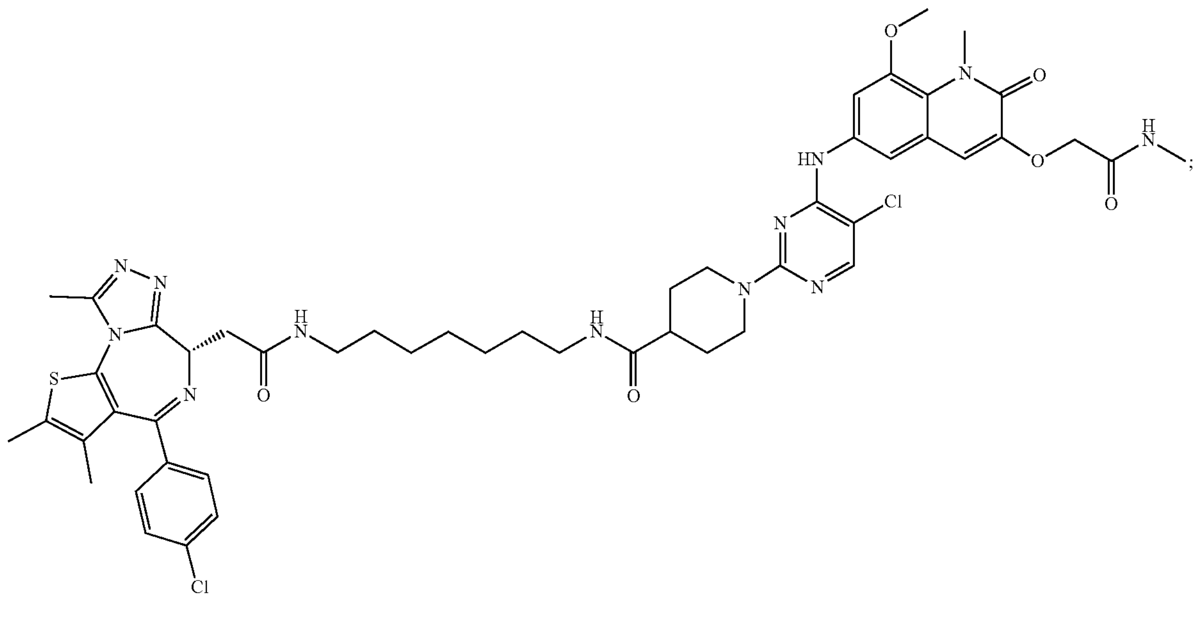

-continued
Compound I-8
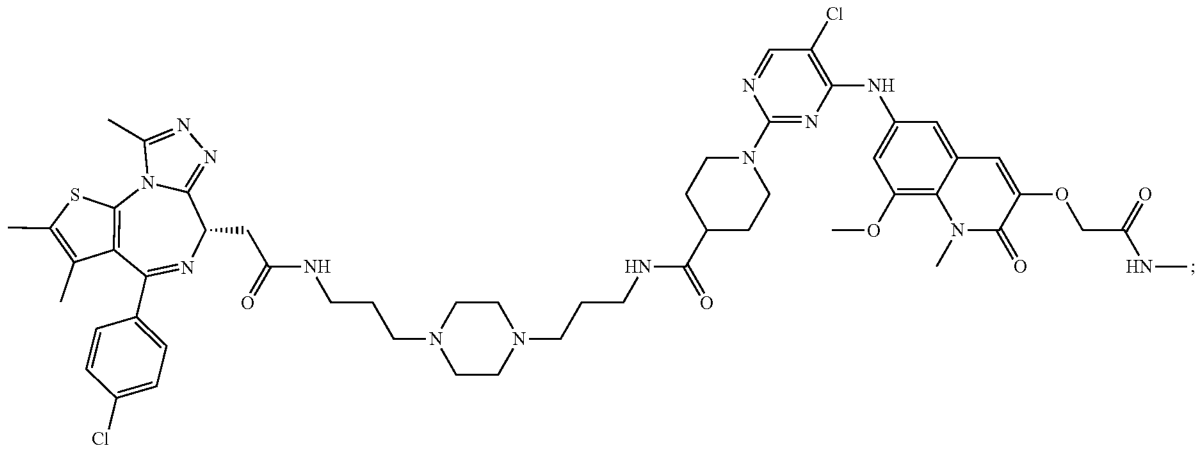
Compound I-9
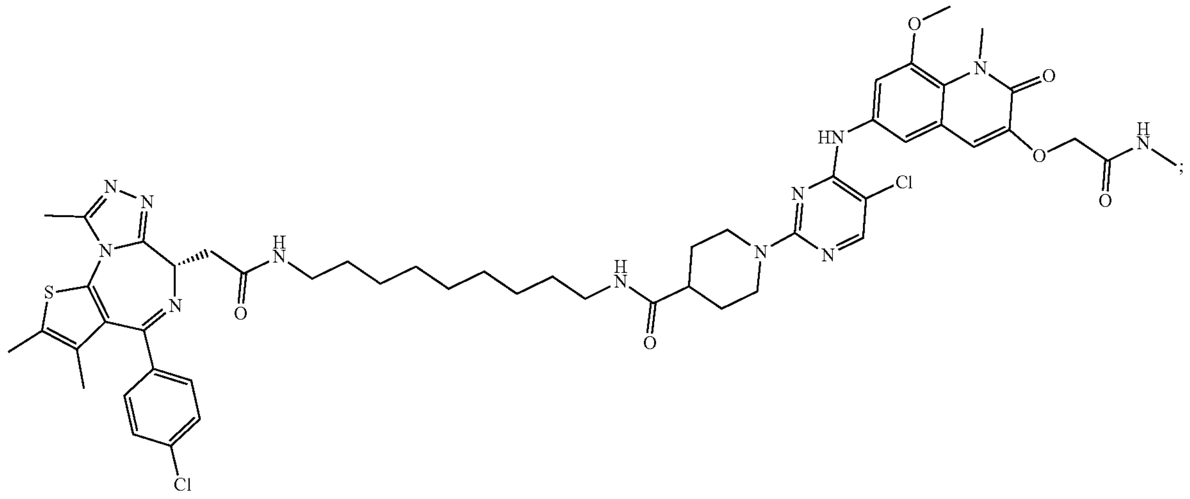
Compound I-10
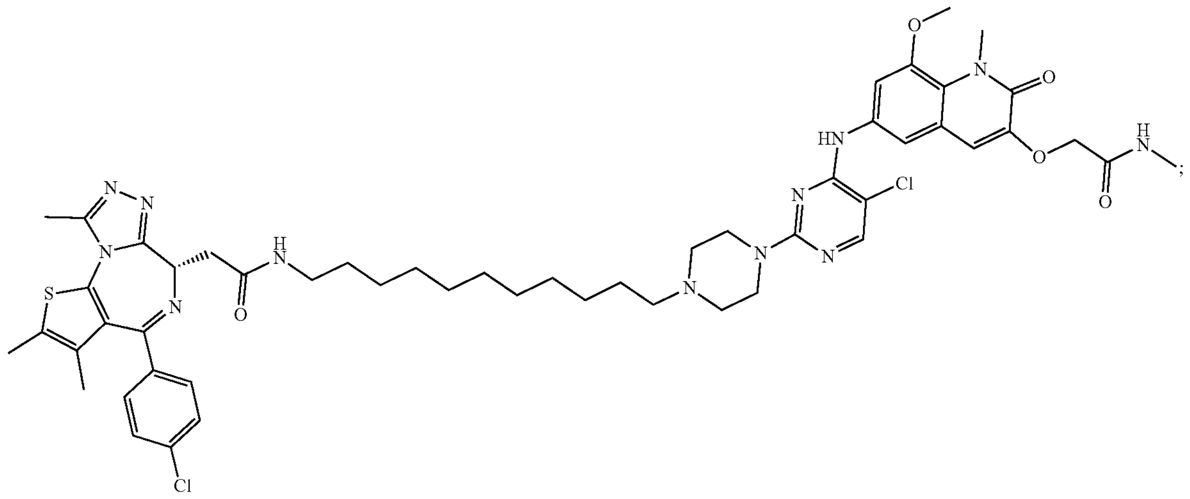

-continued
Compound I-11
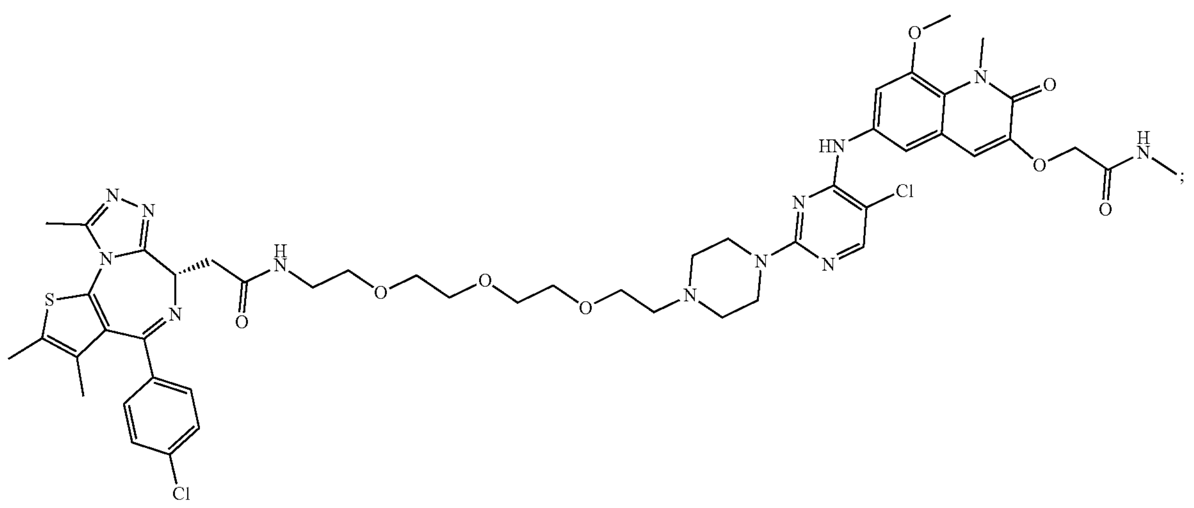
Compound I-12
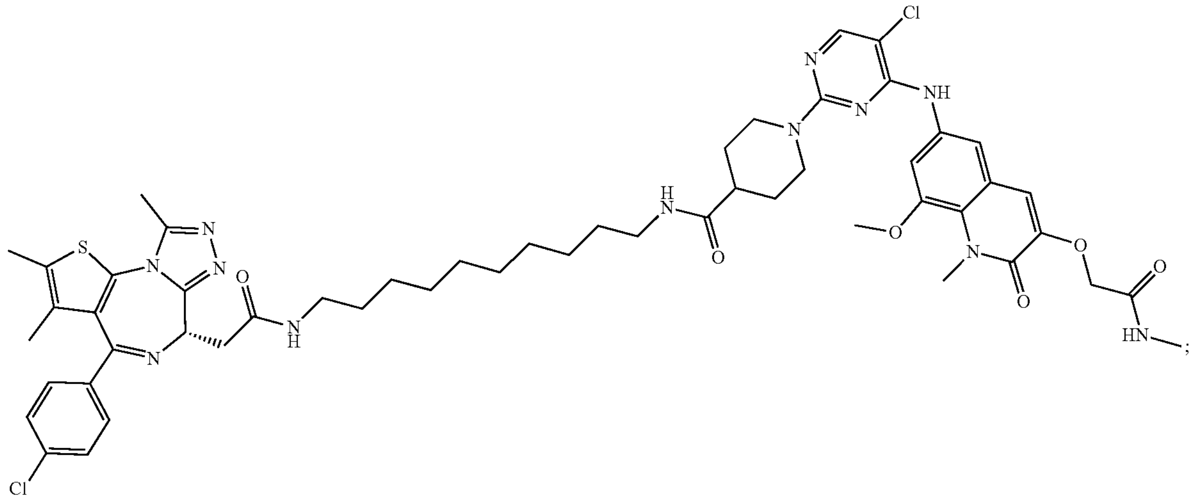
Compound I-13
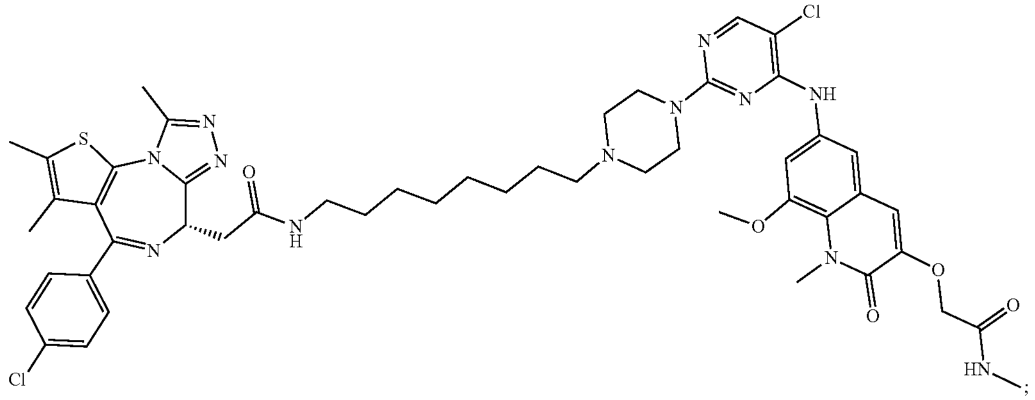

-continued
Compound I-14
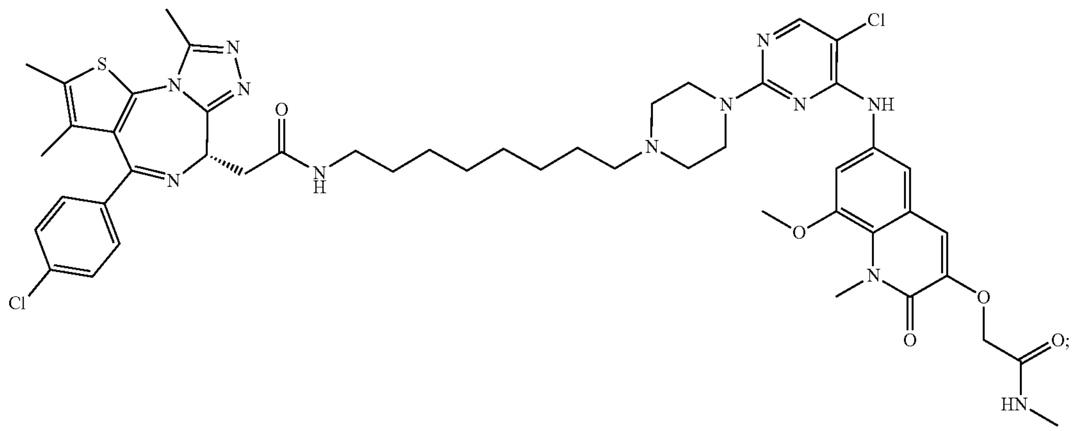
Compound I-15
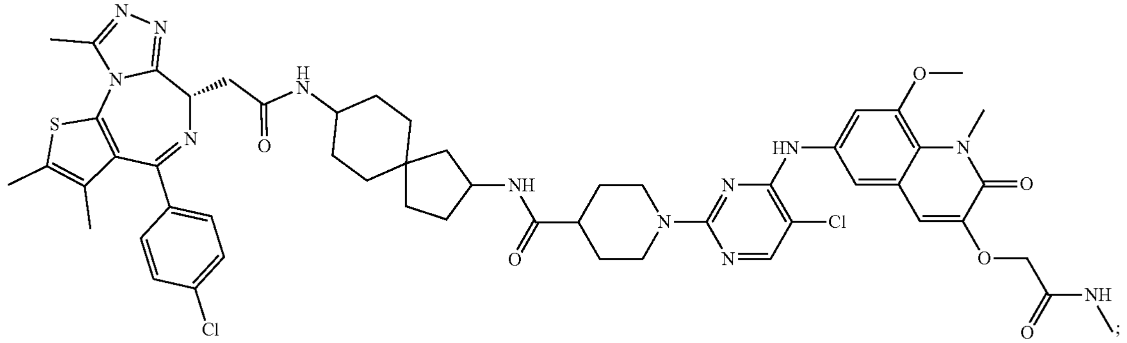
Compound I-16
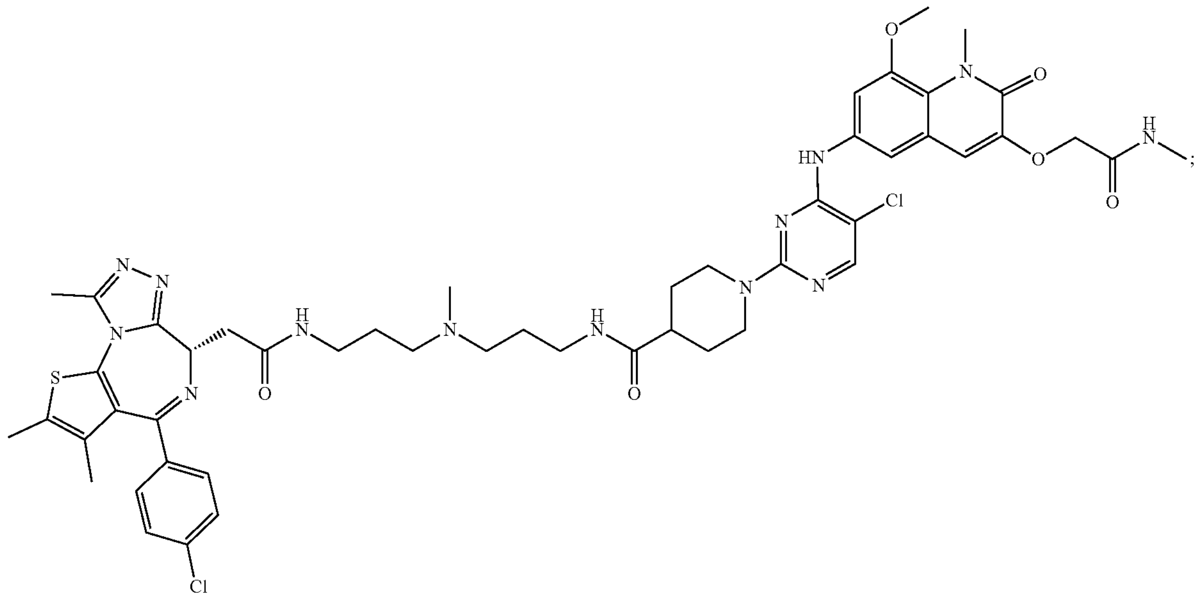

-continued
Compound I-17
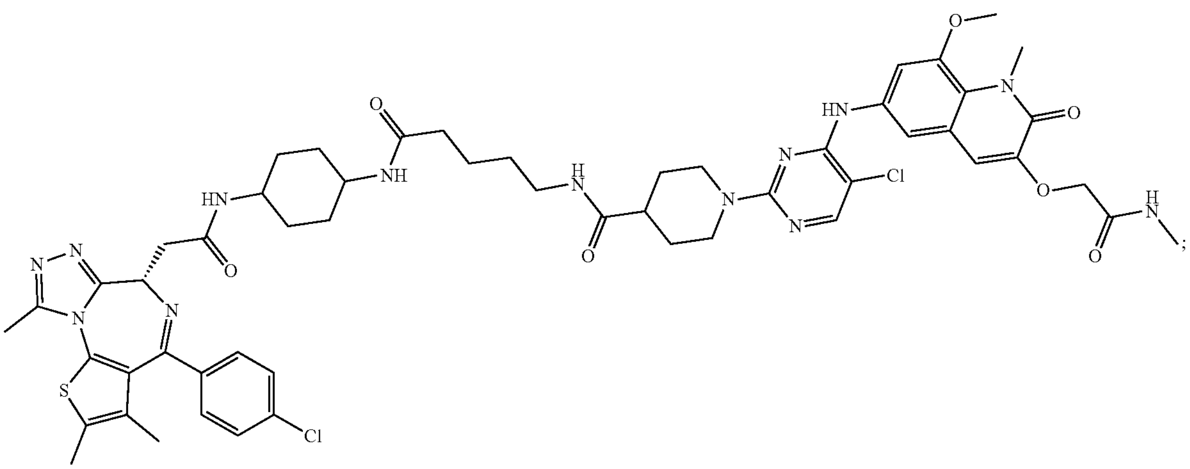
Compound I-18
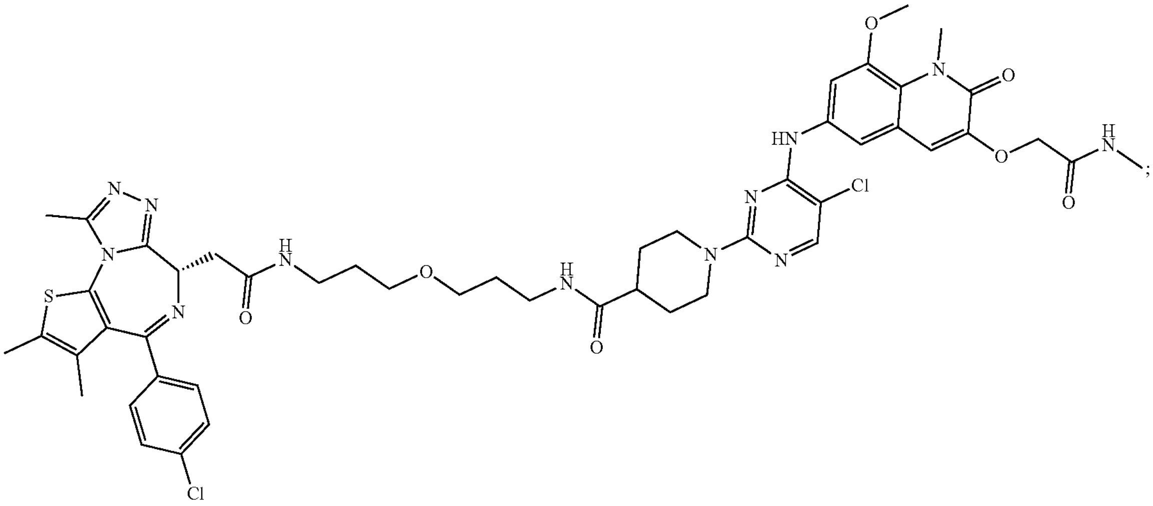
and
Compound I-19
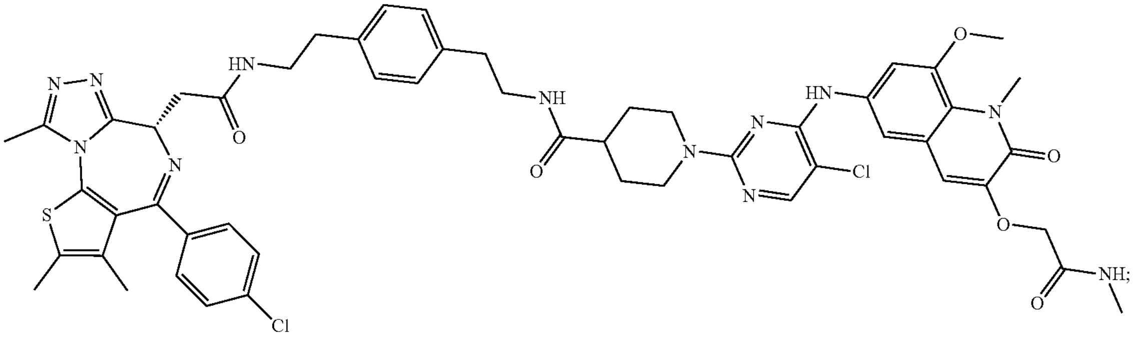

Figure 2:
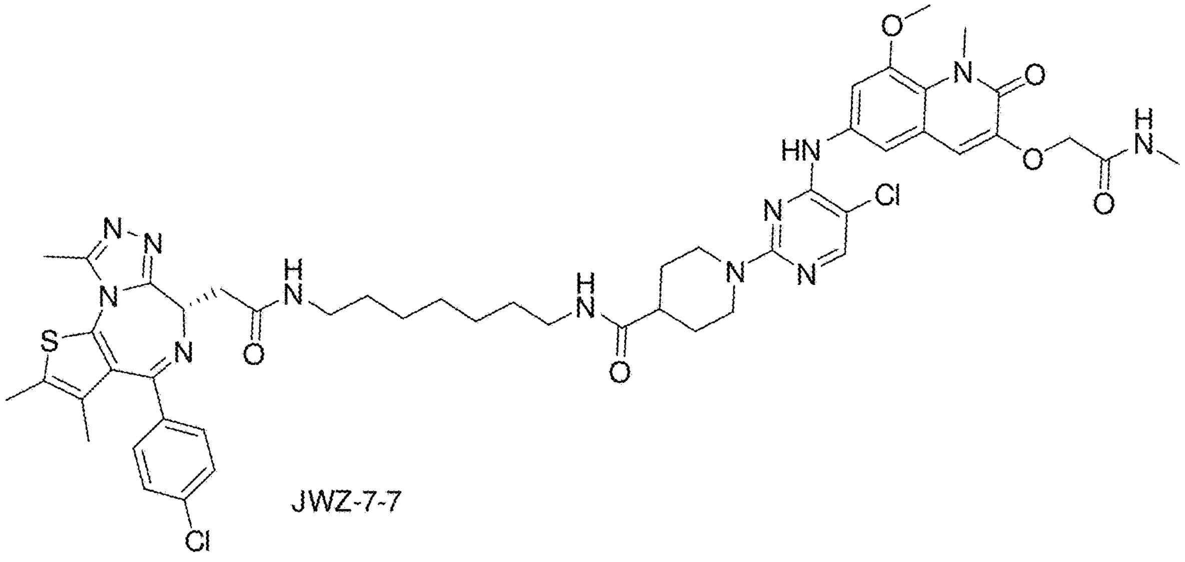
FIG. 2 provides the structure of the TCIP JWZ-7-7.

Compound I-20
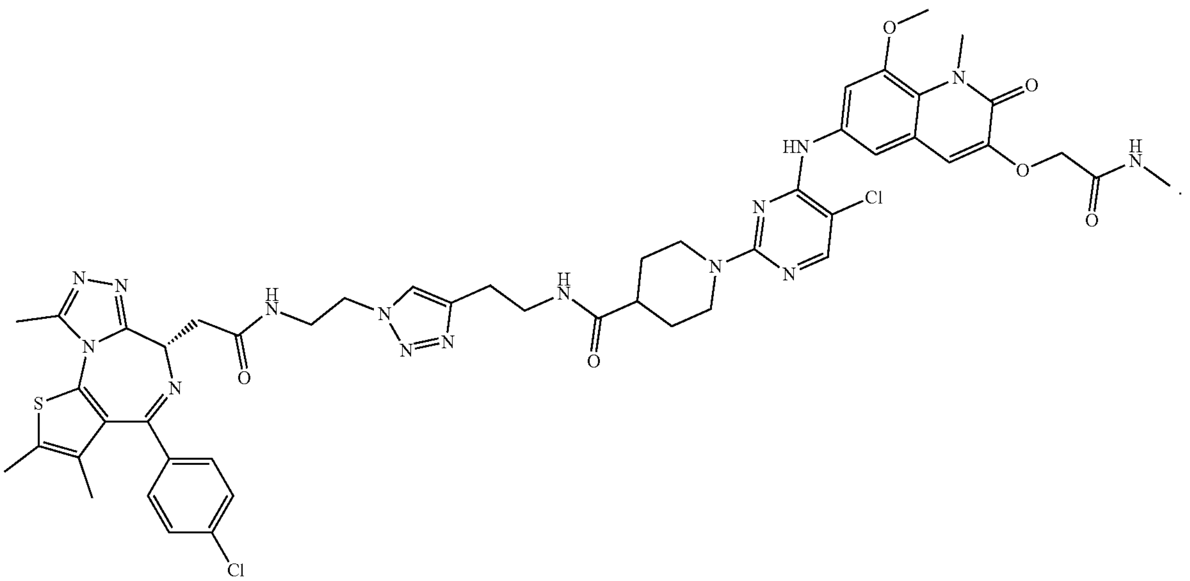
In some instances, the TCIP is JWZ-7-7 having the structure provided in FIG. 2.
In some examples, compounds (e.g., CIP, TCIP) having a BCL-6 (B-cell lymphoma 6) ligand and a BRD4 (bromodomain-containing 4) ligand can include one or more members selected from the following:
JWZ-224
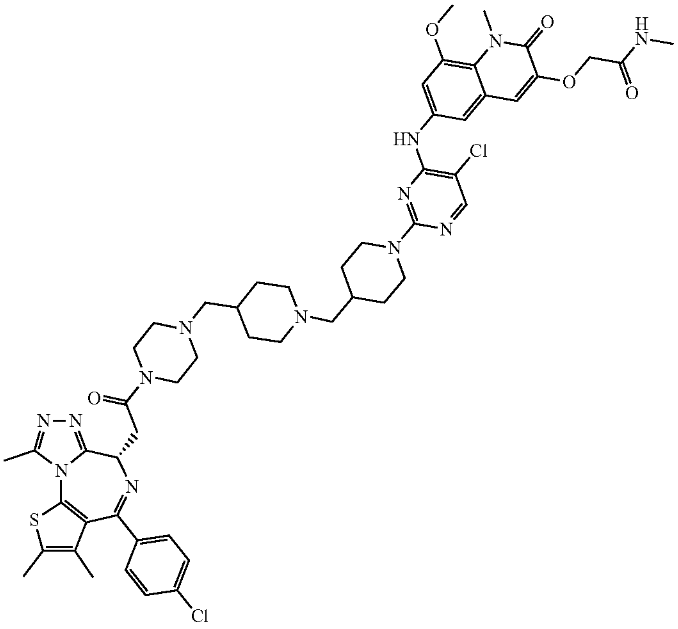

-continued
JWZ-228
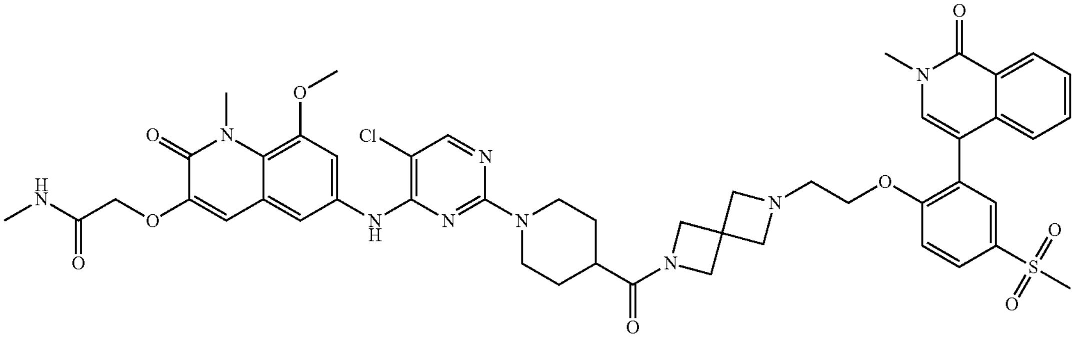
JWZ-231
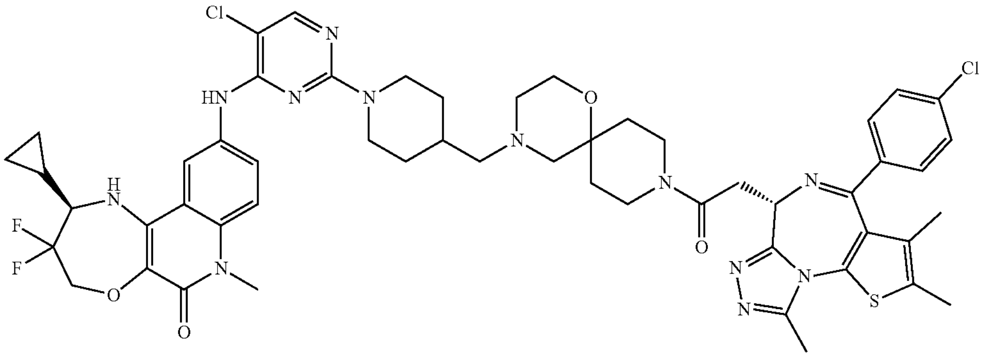
JWZ-219
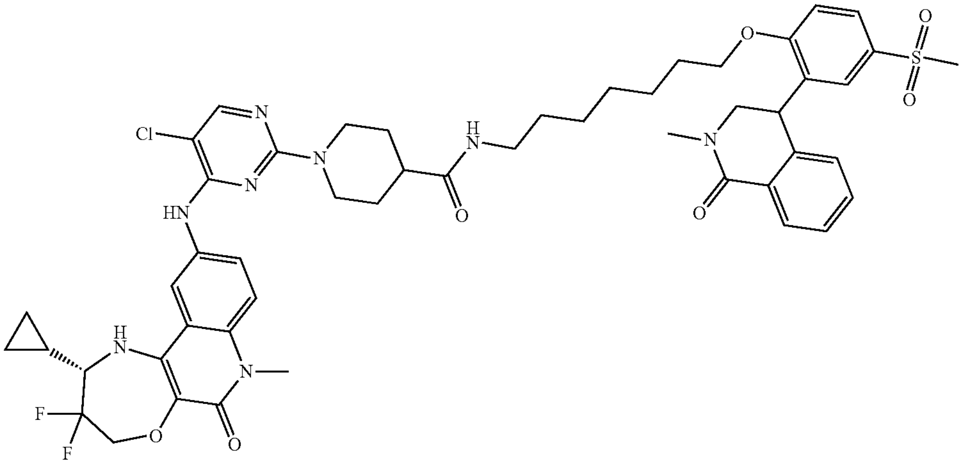

-continued
JWZ-220
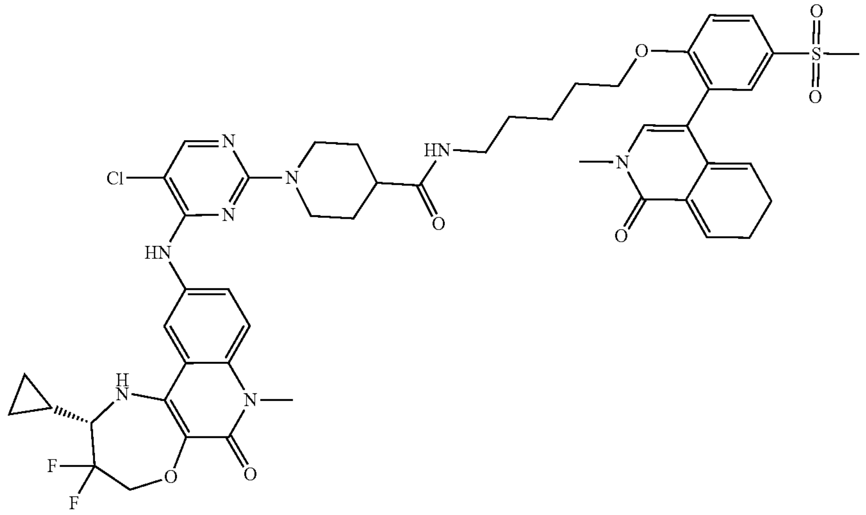
JWZ-221
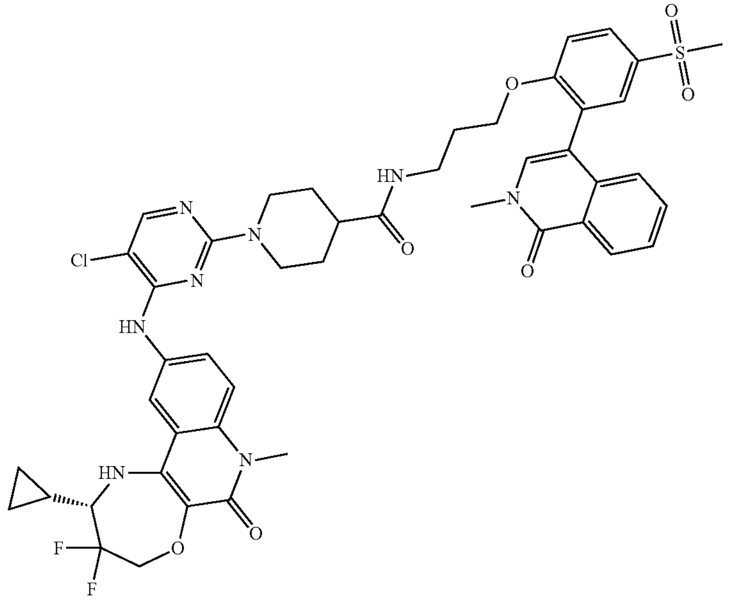
JWZ-226
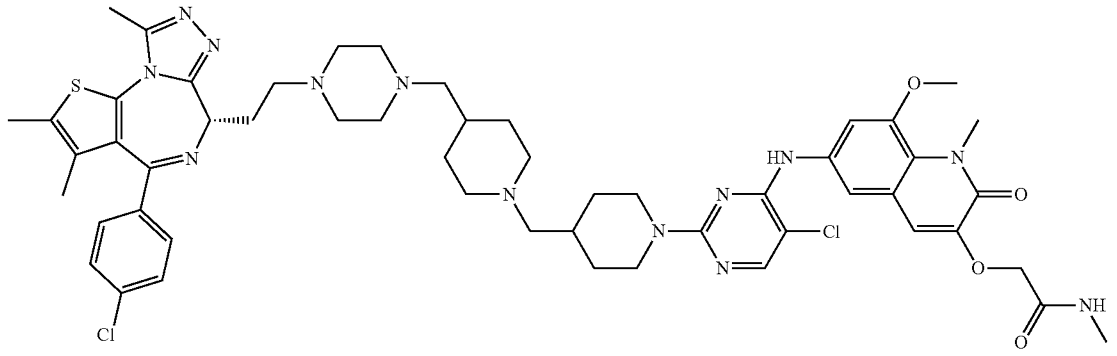

-continued
JWZ-227
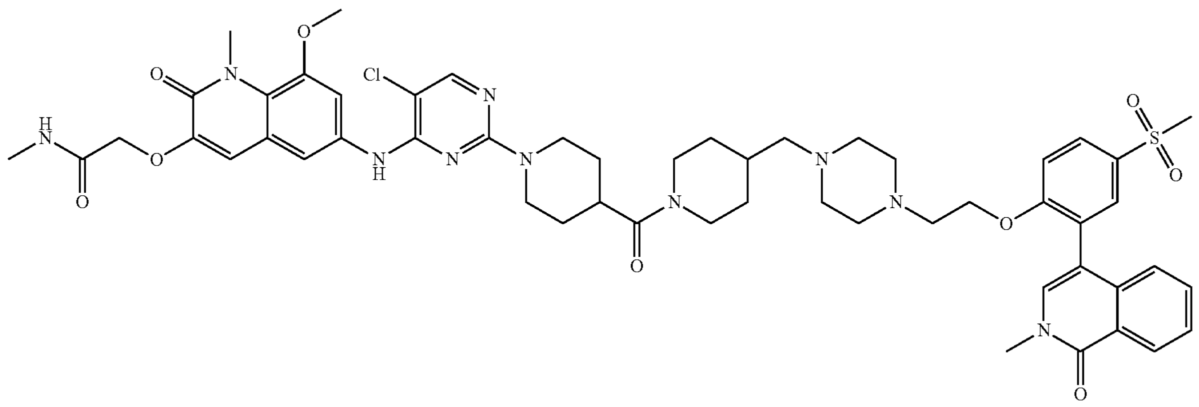
JWZ-229
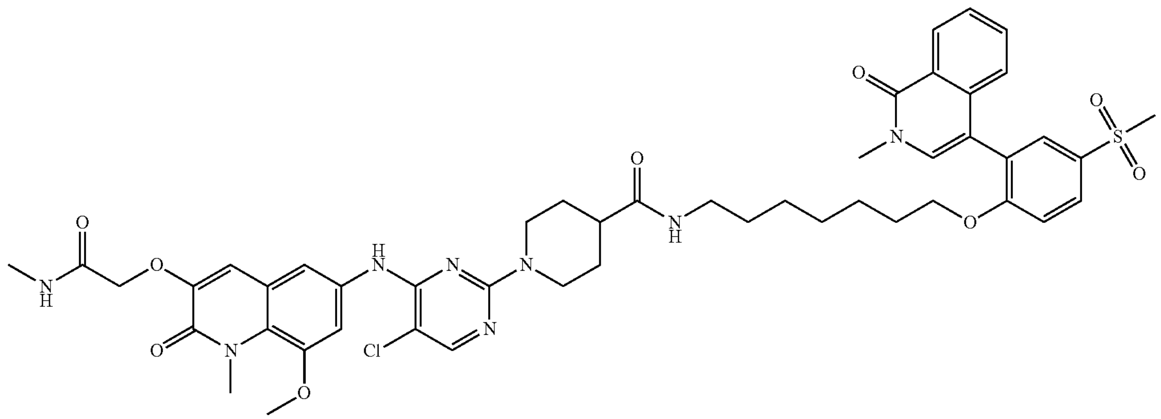
JWZ-230
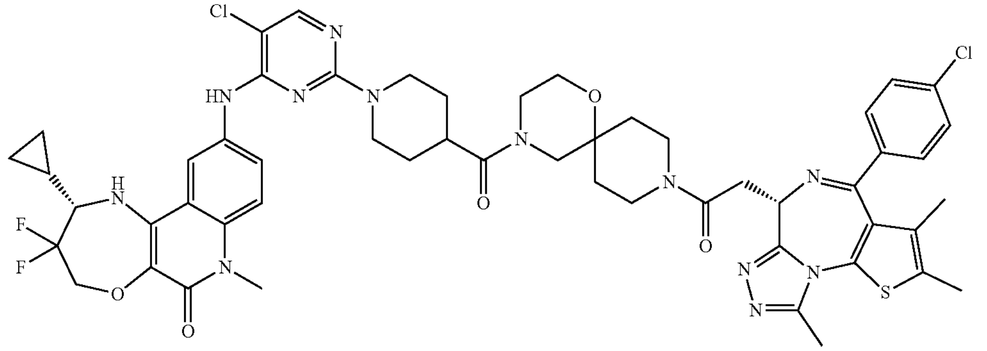
JWZ-232
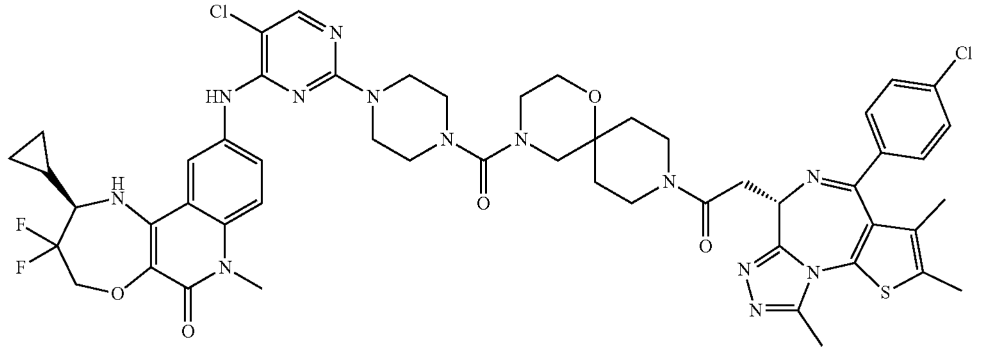

-continued
JWZ-233
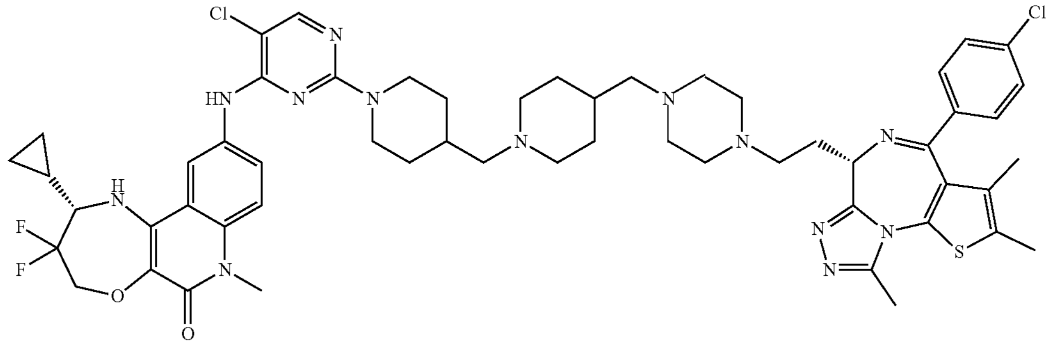
JWZ-235
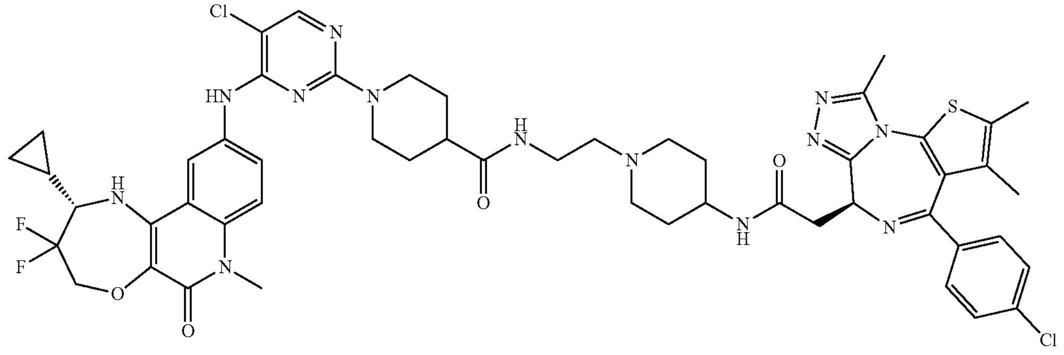
JWZ-234
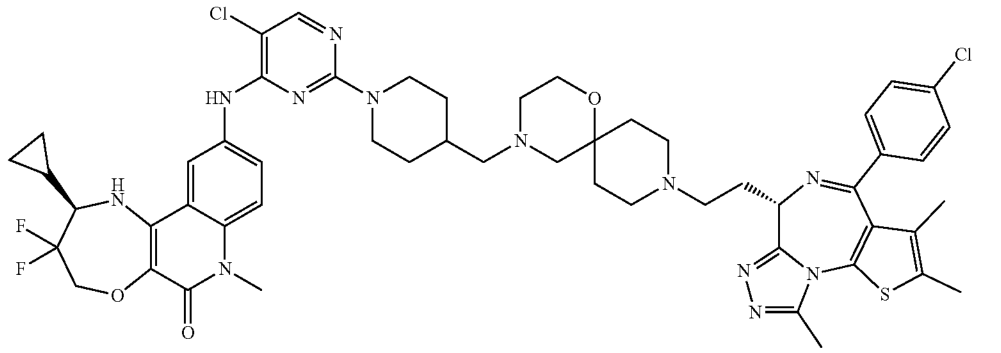
JWZ-201
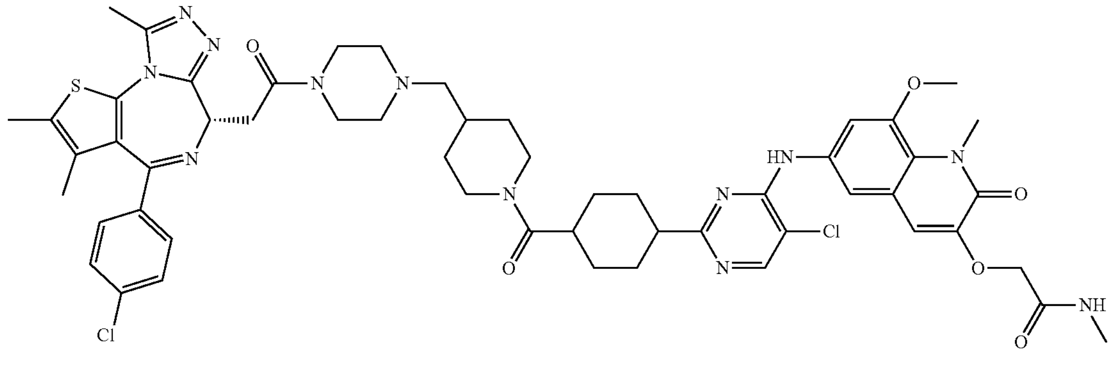

-continued
JWZ-202
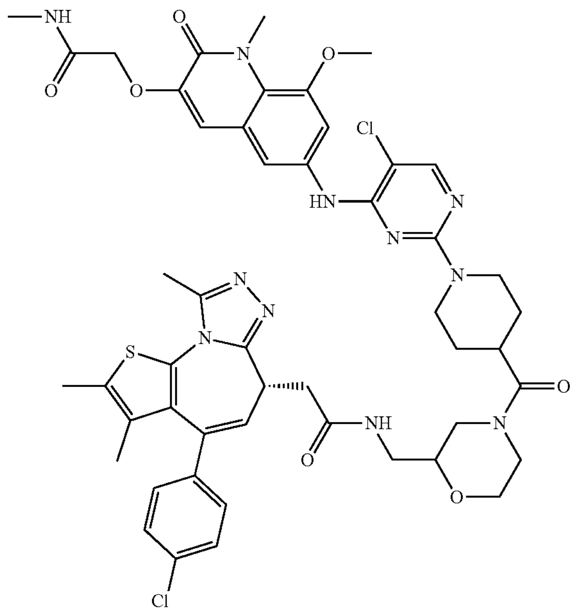
JWZ-203
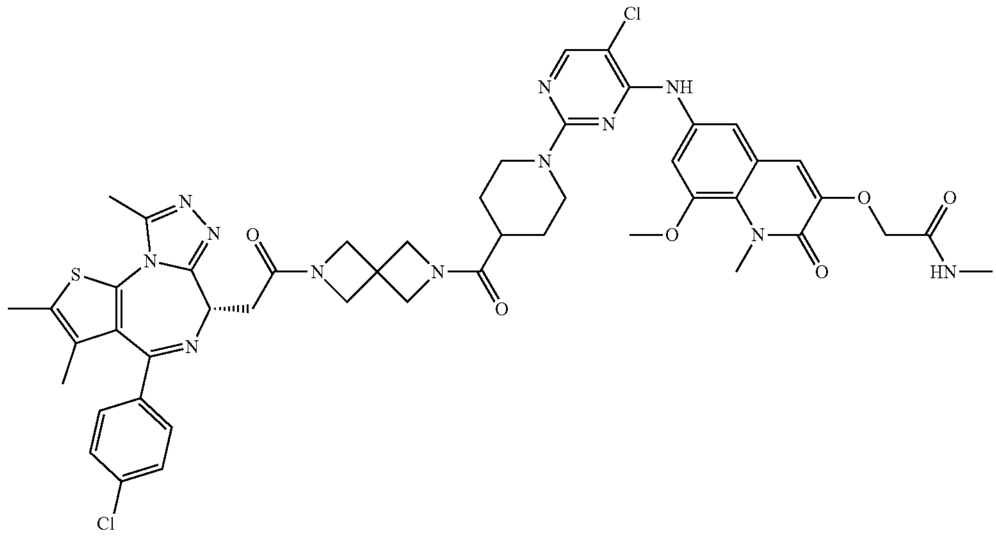
JWZ-205
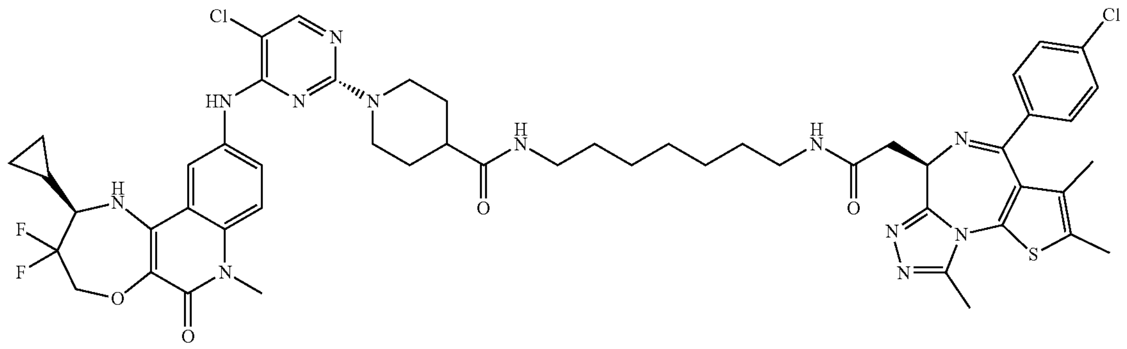

-continued
JWZ-207
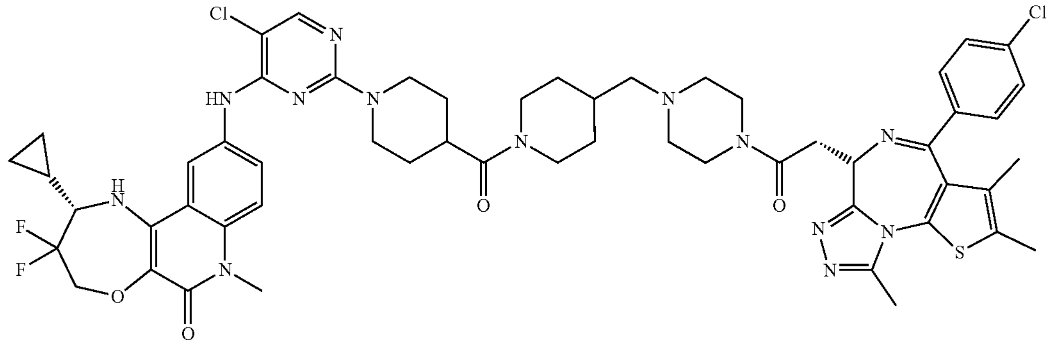
JWZ-204
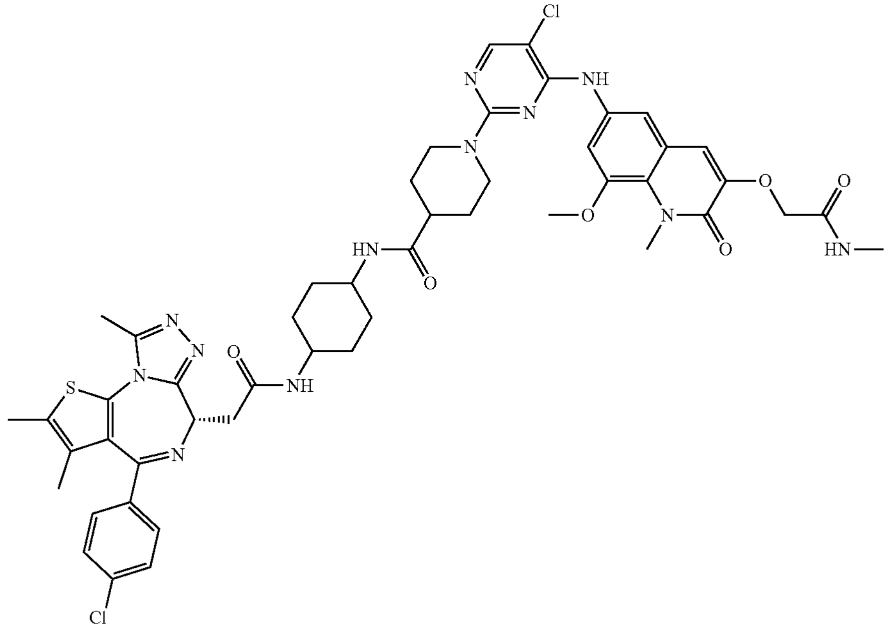
JWZ-209
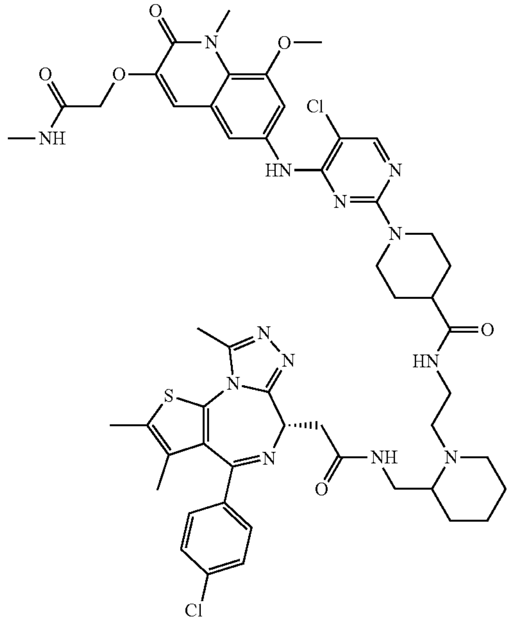

-continued
JWZ-210
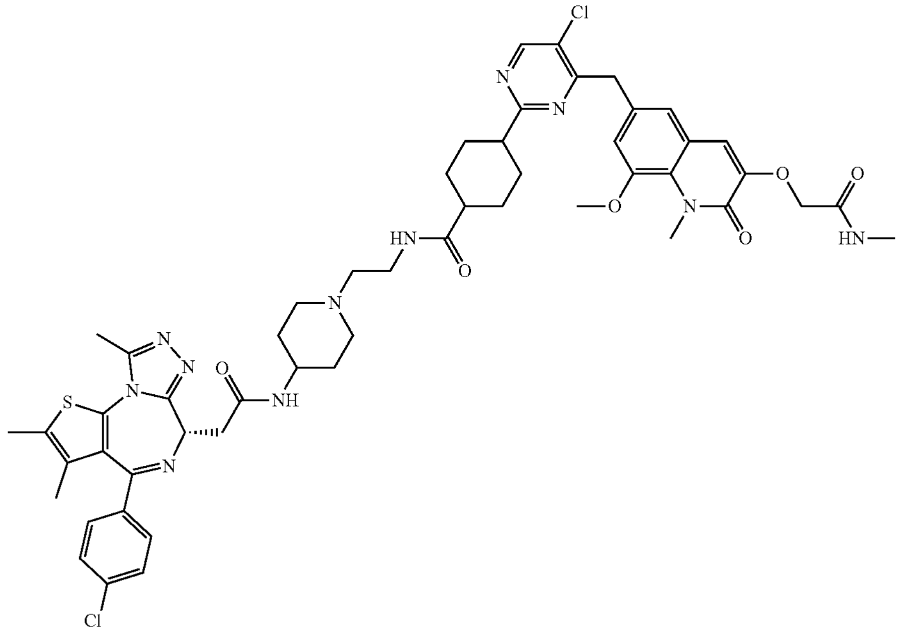
JWZ-211
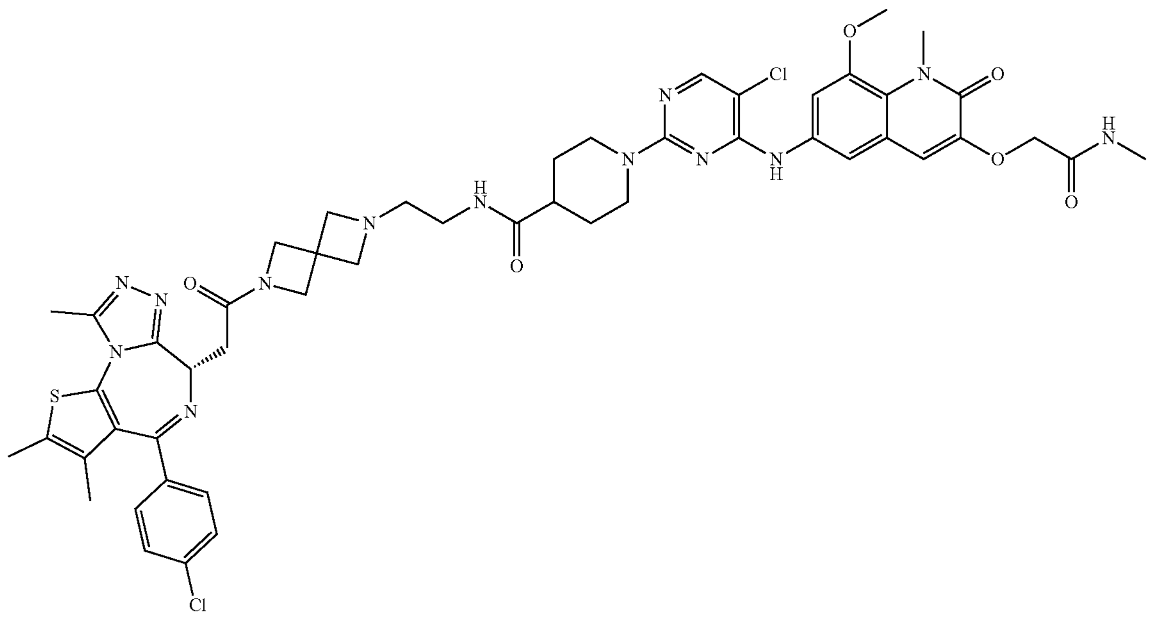

-continued
JWZ-213
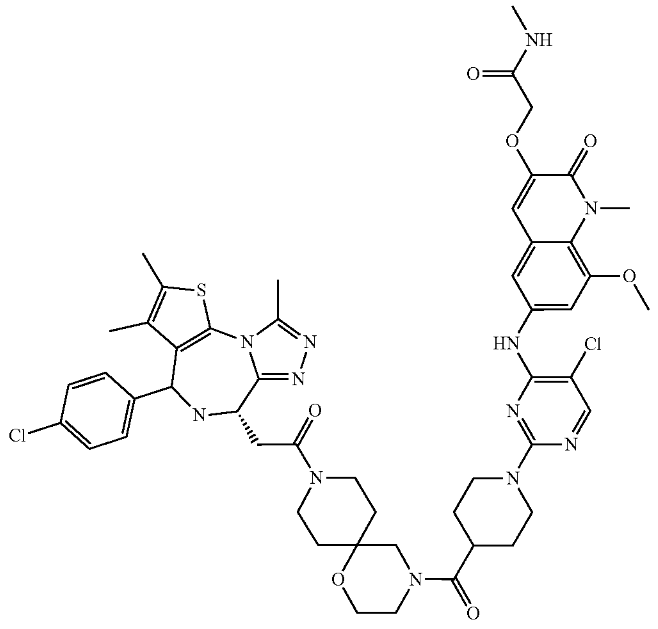
JWZ-214
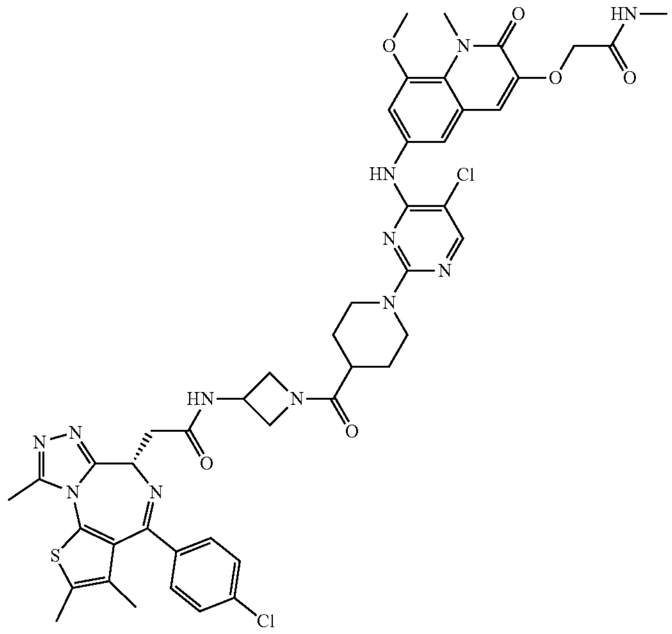

-continued
JWZ-215
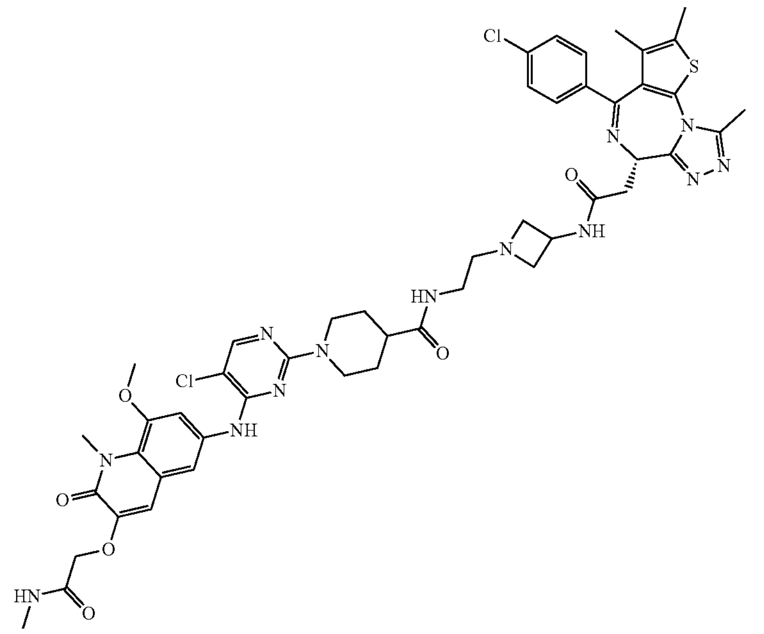
JWZ-212
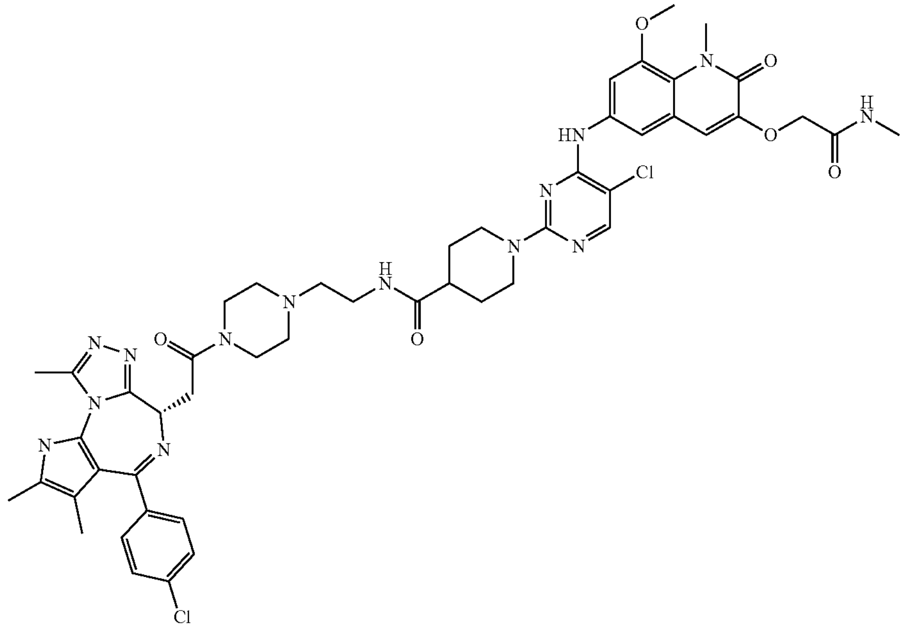

-continued
JWZ-208
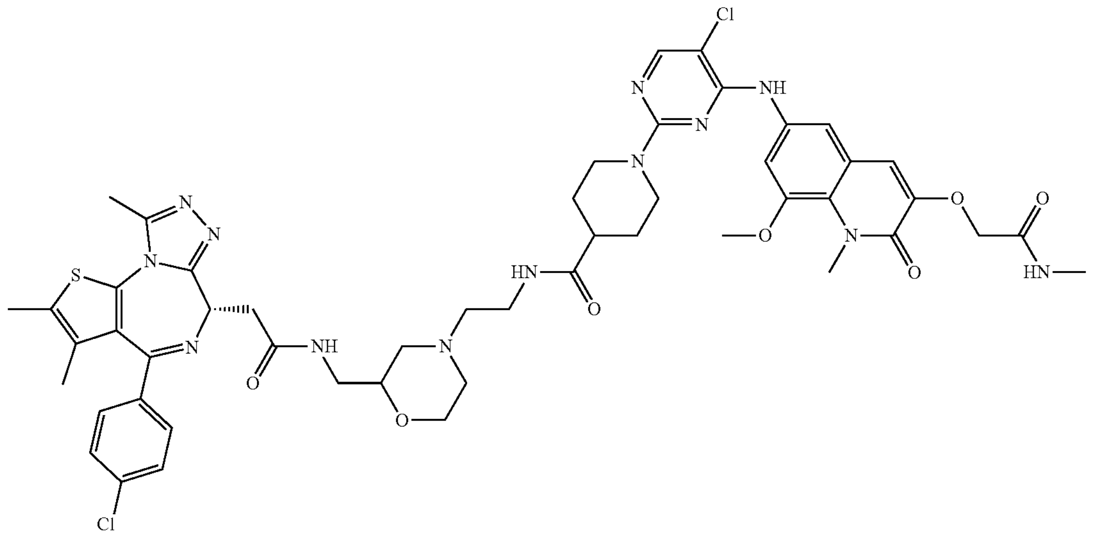
JWZ-216
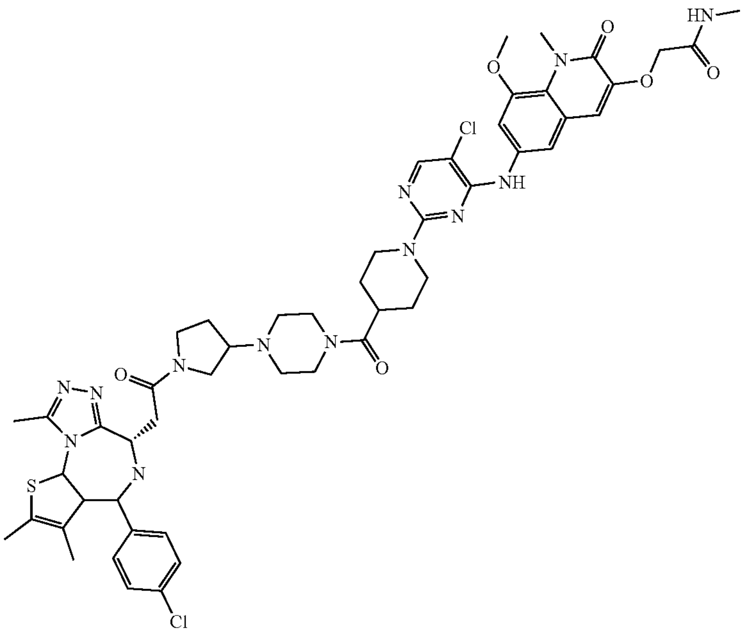

-continued

JWZ-217

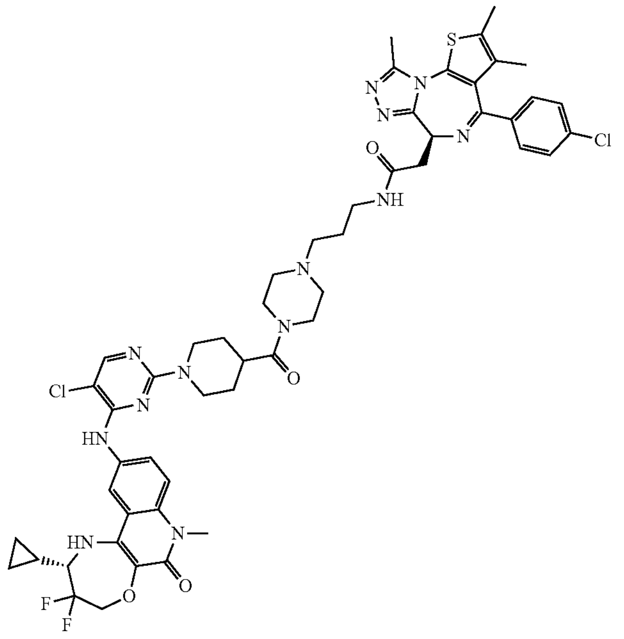

Methods of enhancing transcription of pro-apoptotic genes, e.g., as described herein, find use in, for example, treatment of malignancies. The target malignancy treated by embodiments of the disclosure may be any malignancy having cells that are susceptible to activity of a TCIP, such as described herein. In some instances, the malignancy is characterized by the presence of malignant cells having elevated levels of BCL6 and normal or above normal levels of BRD4. In some instances, the malignancy is SCLC, a lymphoma, such as non-Hodgkin's lymphoma, e.g., DLBCL, including refractory DLBCL, such as CHOP-resistant DLBCL; and the like. In some instances, the methods are methods of treating SCLC. In some instances the methods are methods of treating a lymphoma, such as non-Hodgkin's lymphoma, e.g., DLBCL, including refractory DLBCL, such as CHOP-resistant DLBCL.

Embodiments of the methods may include assessing whether a subject suffering from a neoplastic disease has a particular type of malignancy (i.e., cancer) For examples, embodiments of methods may include assessing whether the subject has a susceptible lung cancer, such as SCLC, including BRD4 positive SCLC, which SCLC may be refractory SCLC. For example, the methods may include assessing whether the SCLC is BRD4 positive, and then employing an appropriate TCIP to treat the particular cancer. For example, if the SCLC is BRD4 positive, a CIP having a ligand that binds to BRD4 may be employed. Embodiments of the methods may include assessing whether a subject suffering from a neoplastic disease has a particular type of DLBCL, including BRD4 positive DLBCL, which DLBCL may be refractory DLBCL, such as CHOP-resistant DLBCL. For example, the methods may include assessing whether the DLBCL is BRD4 positive or BCL6 positive, and then employing an appropriate TCIP to treat the particular cancer. For example, if the DLBCL is BRD4 positive or BCL6 positive, a CIP having a ligand that binds to BRD4 or BCL6 may be employed.

Where the target malignancy is SCLC, in some instances the target patient population includes patients with SCLC either contained or metastatic at the time of presentation or discovery. Among patients with SCLC, those to be treated for SCLC can be chosen by measuring the level of expression of BCL6 (and/or other BTB domain containing protein) and BRD4 (and/or other BET family proteins) in their tumors. These levels can be measured by RNA-seq, Western blotting or immunohistochemistry using antibodies against these proteins, mass spectrometry, intracellular FACS, etc. Patents whose tumors have high level expression of BRD4 and BCL6 or its homologues will be the target population that would be expected to respond favorably. About 40% of patients treated with R-CHOP therapy fail to go into remission. These patients would be candidates for treatment with a TCIP, e.g., JWZ-7-7, particularly those whose tumor has high levels of BCL6 or one of its homologues and those whose tumor expresses BRD4 or one of its homologues. These levels can be measured by RNA-seq, Western blotting or immunohistochemistry using antibodies against these proteins. About 70% of patients with small cell lung cancer have distant metastasis at the time of diagnosis. The median survival of this group untreated is about 3 months. With treatment the median survival is 6 to 8 months. Those patients that have metastasis at the time of treatment and whose tumor expressed high levels of BRD4 and BCL6 would be likely to benefit from treatment with JWZ-7-7. A similar approach may be employed to identify appropriate patient populations suffering from other malignancies, e.g., lymphomas, such as DCBLC, such as described above.

ER-BCL6 TCIPs

FIG. 1 provides an illustration of how to build a CIP by rational design using existing components. As shown in FIG. 1, the design of a CIP configured to hijack BCL6 to kill ER-positive DLBCL cells is shown. BCL6 is a transcription factor and oncogene that prevents death of a variety of cancer cells, including breast cancer cells, by binding epigenetic the repressors BCOR, NCOR and SMRT (PMID: 30335946) on the promoters of cell death genes. Several inhibitors of BCL6's repressive function have been produced that prevent the binding of BCOR, NCOR and SMRT to a site formed by the dimeric surface of BCL6 (PMID: 18280243) However, these inhibitors have not been sufficiently active to be used therapeutically (PMID:30335946).

Figure 9:
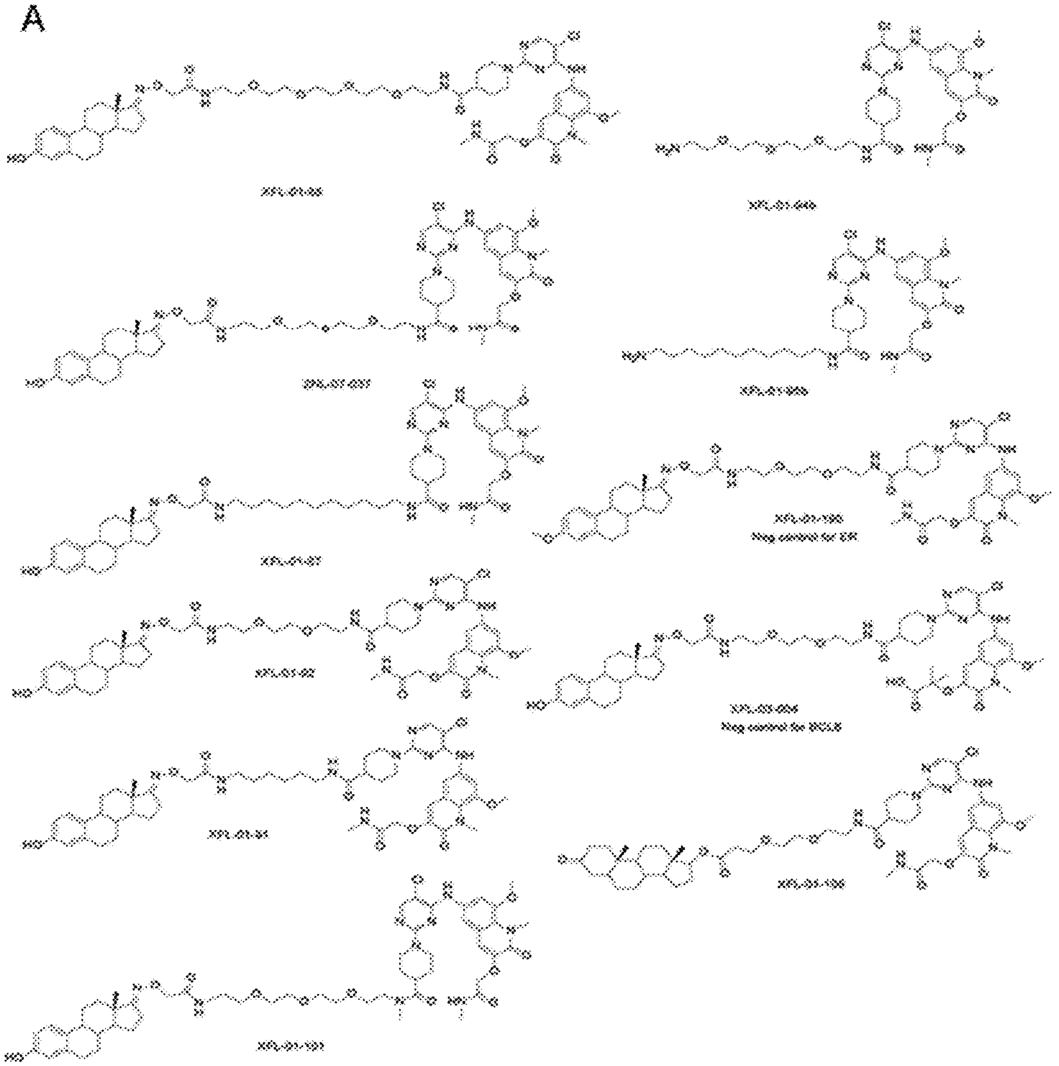
FIG. 9 depicts non-limiting examples of structures and activities of ER-BCL6 TCIPs. Panel A: Non-limiting examples of structures of compounds of the disclosure (e.g., TCIPs) based on estrone and BI3812. Also shown are structures of molecules synthesized to test the effect of the linkers on estrone and on BI3812 as well as negative controls not binding ER (XFL-01-190 and 106)) or BCL6 (XFL-03-004). Panel B: Viability of Karpas DLBCL 48 hours after adding estrone, BI3812, BI3802 (BCL6 degrader) and XFL-01-92. Note that XFL-01-92 is far more active at specifically killing these cells which over express ER as well as BCL6 than either parent compound. The androgen (XFL-01-108) or linker compounds as well as the two negative control compounds were all inactive.
Figure 9:
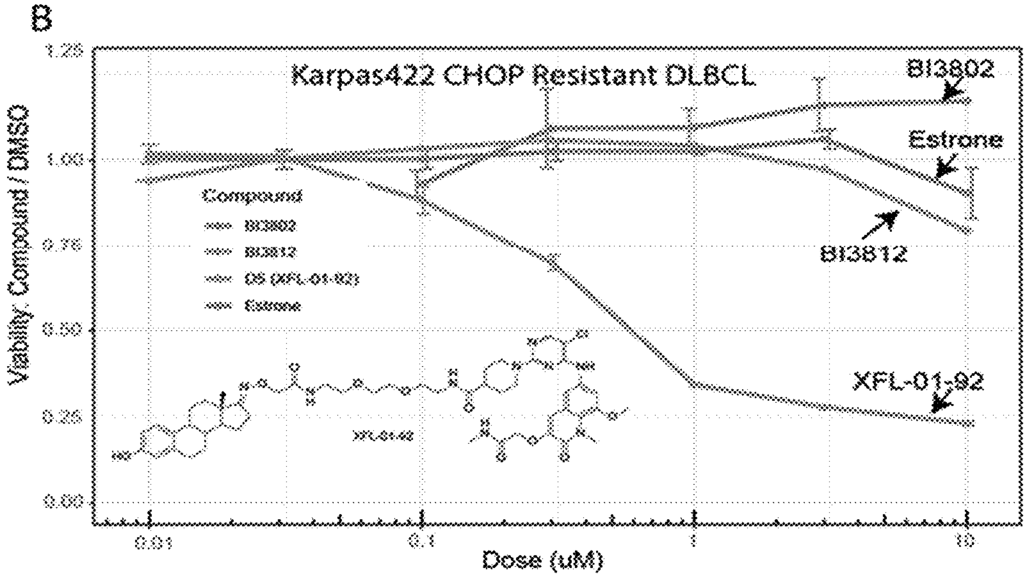

Chemical linkage of BCL-6 inhibitors, such as BI3812 (PMID32275432), to estrogen compounds, e.g., estrone, that then bind and induce proximity to the cell death (pro-apoptotic) promoters, such as those for TP53, PUMA and BIM, convert the inhibitor of cell death to an activator of cell death in cells having high concentrations of estrogen receptors, such as but not limited to breast cancer cells and estrogen sensitive lymphoma cells. Examples of the CIPs synthesized by the above protocol and designed to hijack BCL-6's repressive activity and convert it to an activator of cell death are shown in FIG. 9, Panel A. Details of the synthesis of the compounds are provided in Example I, below. Each structure includes an estrogen receptor binding moiety connected by a chemical linker to a BCL6 inhibitor based on the previously described molecule BI3812 (PMID32275432). These types of molecules may find use in treating DLBCL, including refractory DLBCL, such as CHOP resistant DLBCL.

Any one of the methods of these embodiments can comprise providing in the cell, e.g., via a protocol such as described below, a chemical inducer of proximity (CIP) which links a first endogenous anchor transcription factor that binds to a promoter of the proapoptotic genes, e.g., BCL-6, and a second endogenous oncogenic transcription factor, e.g., an estrogen receptor, wherein CIP mediated linkage of anchor and oncogenic transcription factors enhances transcription of the proapoptotic gene in the cell. In some instances, CIPs employed in these embodiments are generally as described above and include a first ligand that specifically binds to the anchor transcription factor, e.g., BCL-6, and a second ligand that specifically binds to the oncogenic transcription factor, e.g., an estrogen receptor, where these first and second ligands are joined by a bond suitable linker, e.g., as described above.

Methods of enhancing transcription of pro-apoptotic genes, e.g., as described herein, find use in, for example, treatment of lymphomas, such as non-Hodgkins lymphomas, e.g., DLBCL. In some instances, the DLBCL is refractory DLBCL, such as CHOP-resistant DLBCL.

Embodiments of the methods may include assessing whether a subject suffering from a neoplastic disease has a particular type of cancer, such as DLBCL, including ER positive DLBCL, which DLBCL may be refractory DLBCL, such as CHOP-resistant DLBCL. For example, the methods may include assessing whether the DLBCL is ER positive, and then employing an appropriate CIP to treat the particular cancer. For example, if the DLBCL is ER positive, a CIP having a ligand that binds to ERα may be employed.

CDK9-BCL6 TCIPs

As reviewed above, in some embodiments, chemical inducers of proximity include a compound of formula I:

CL-L-BC(1)

where:

CL is a ligand that specifically binds to a CDK, e.g., CDK9, CDK8 and/or CDK7;

BC is a ligand that specifically binds to B-cell lymphoma 6 (BCL-6) or a BCL6 BTB-domain family member; and L is a linker (optional), or a pharmaceutically acceptable salt thereof.

Figure 12:
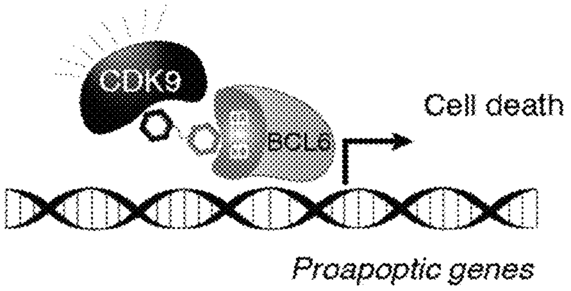
FIG. 12 illustrates a non-limiting example of the design of a compound of the disclosure (e.g., a TCIP) to hijack BCL-6 to kill CDK-positive cancer cells. BCL-6 is a transcription factor and oncogene that prevents death of a variety of cancer cells including prostate cancer cells by binding epigenetic repressors, BCOR, NCOR and SMRT (PMID 18280243, 15531890, 10898795). Chemical linkage of BCL-6 inhibitors, such as BI-3812(PMID33208943) to ligands for CDK9 that then bind and induce proximity to the cell death (proapoptotic) promoters, such as those for TP53, PUMA, BIM and others, convert the inhibitor of cell death to a powerful activator of cell death.
Figure 13:
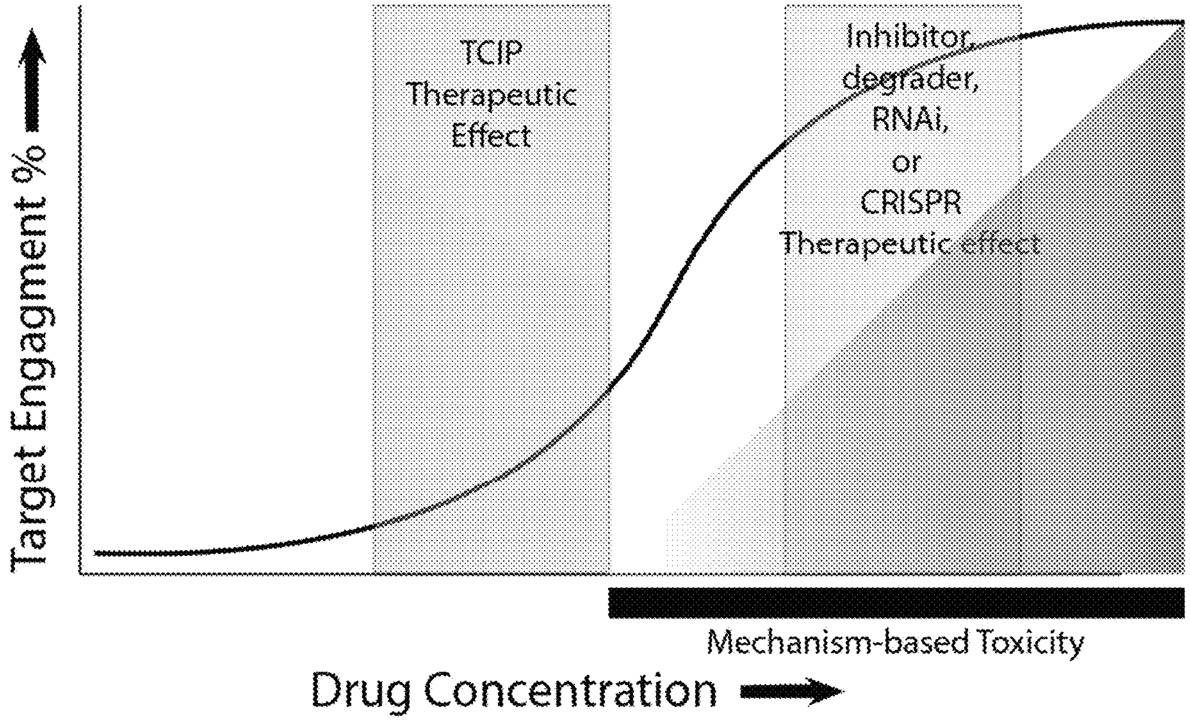
FIG. 13 illustrates the advantage of the TCIP approach in accordance with embodiments of the disclosure. Conventional therapeutics, such as inhibitors, degraders, RNAi and CRISPR, must inhibit nearly all of the activity of the target protein inevitably giving rise to mechanism-based toxicity that is due to loss of function of the normal functions of the target protein. In contrast, TCIPs need to borrow only a small fraction of the target for activation of the cell death mechanisms, which is the gain-of-function induced by the TCIP. This approach avoids mechanism-based toxicity inherent to conventional therapeutics.

FIG. 12 provides an illustration of how to build a TCIP by rational design using existing components. As shown in FIG. 12, the design of a TCIP configured to hijack BCL6 to kill CDK9-positive cancer cells is shown. BCL6 is a transcription factor and oncogene that prevents death of a variety of cancer cells, including lymphoma and SCLC cells, by binding the repressors BCOR, NCO and SMRT (PMID: 30335946) on the promoters of cell death genes. Several inhibitors of BCL6's repressive function have been produced that prevent the binding of BCOR, NCOR and SMRT to a site formed by the dimeric surface of BCL6 (PMID: 18280243) However, these inhibitors have not been sufficiently active to be used therapeutically (PMID:30335946).

Chemical linkage of BCL-6 inhibitors, such as BI3812 (PMID32275432), to CDK ligand compounds, e.g., CDK9 inhibitors, that then bind and induce proximity to the cell death (pro-apoptotic) promoters, such as those for TP53, PUMA and BIM, convert the inhibitor of cell death to an activator of cell death in cells having high concentrations of CDK9, such as DCBLC or SCLC cells.

Specific TCIPs Finding Use in Embodiments of the Disclosure Include, but are not Limited to:

BAK-04-023

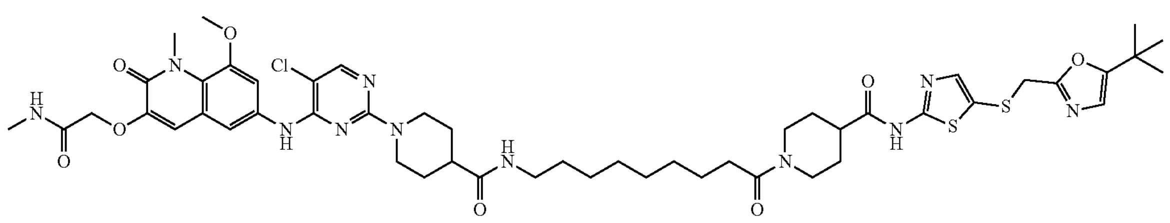

-continued
BAK-04-022
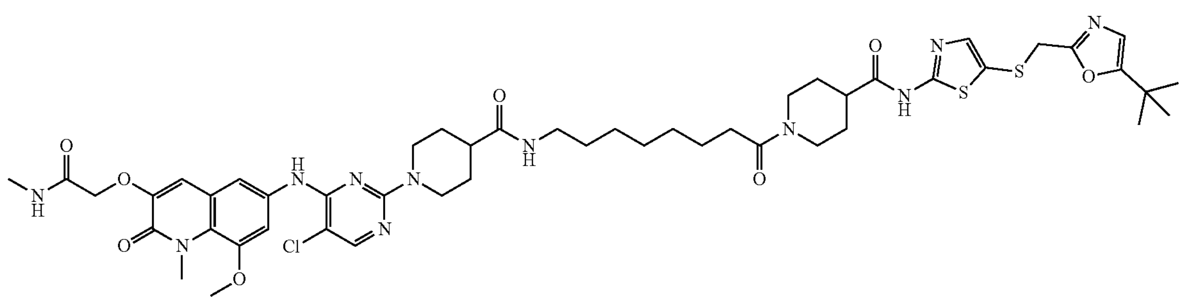
BAK-04-021
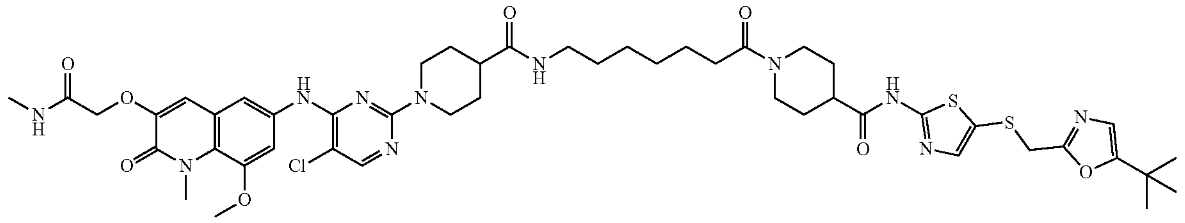
BAK-04-028
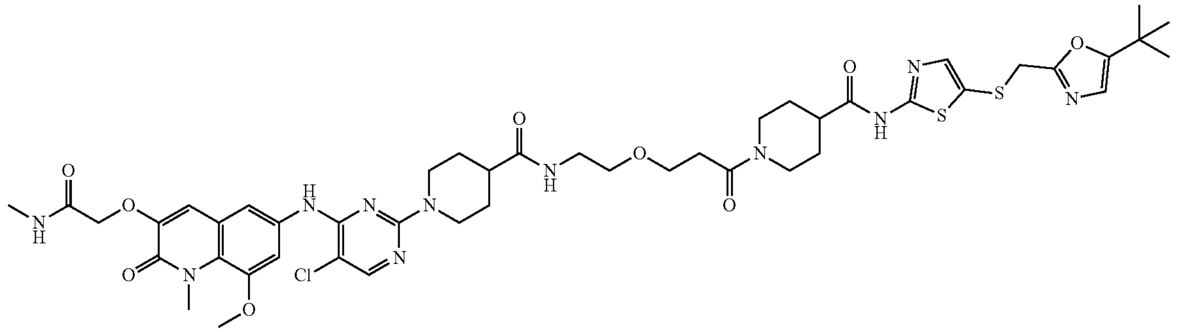
BAK-04-029
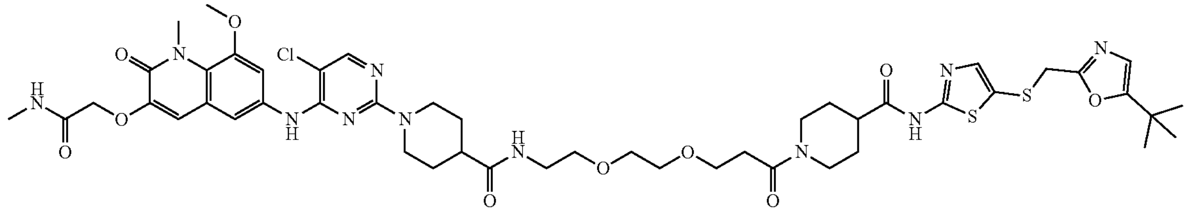
BAK-04-030
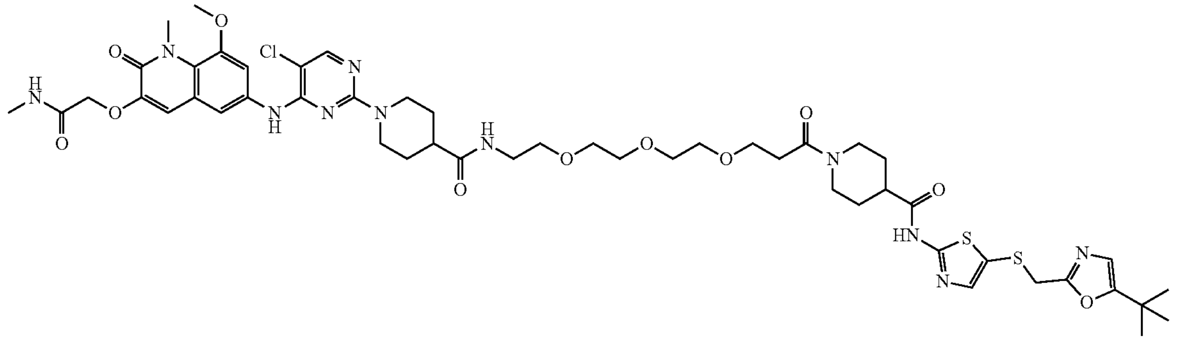

-continued
BAK-04-016
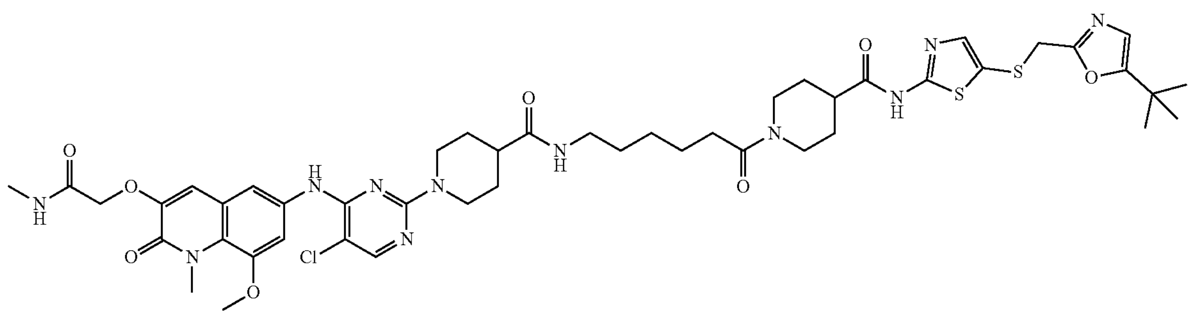
BAK-04-015
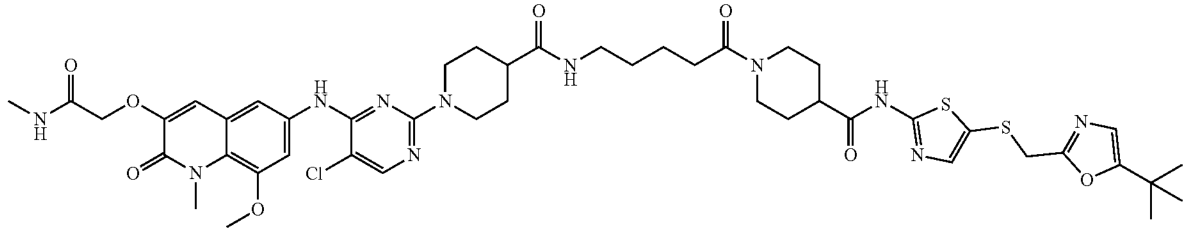
BAK-04-014
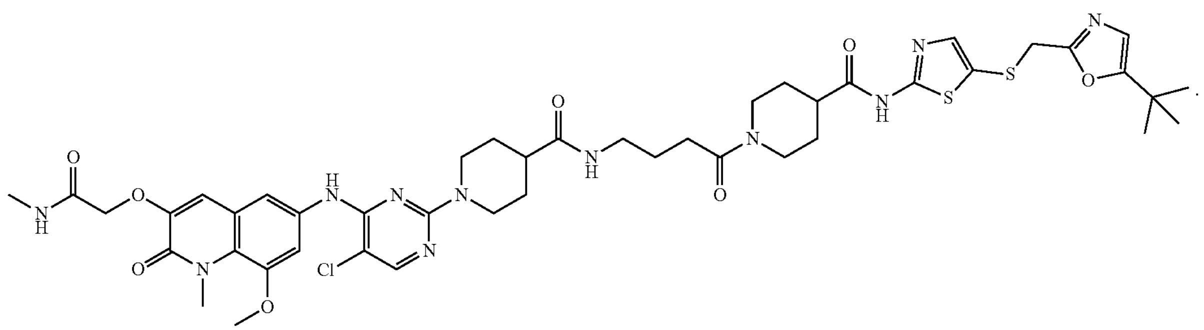
Additional CDK7 TCIPs Include:
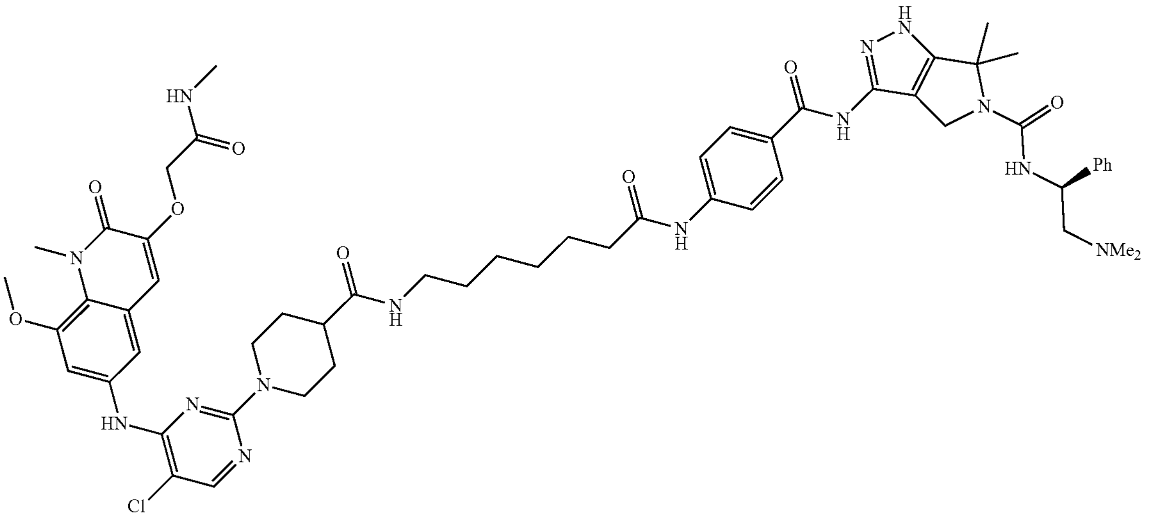

-continued
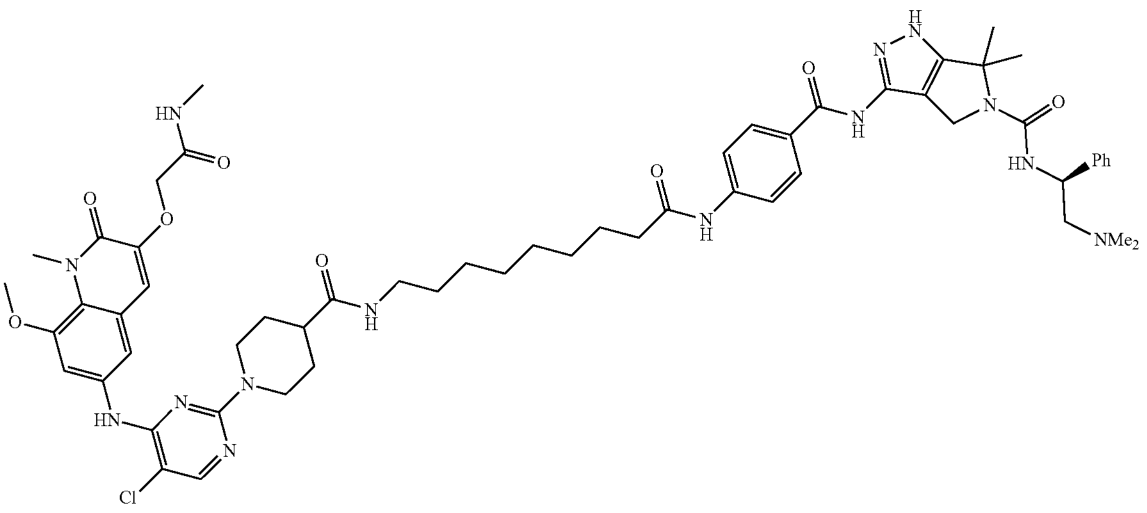
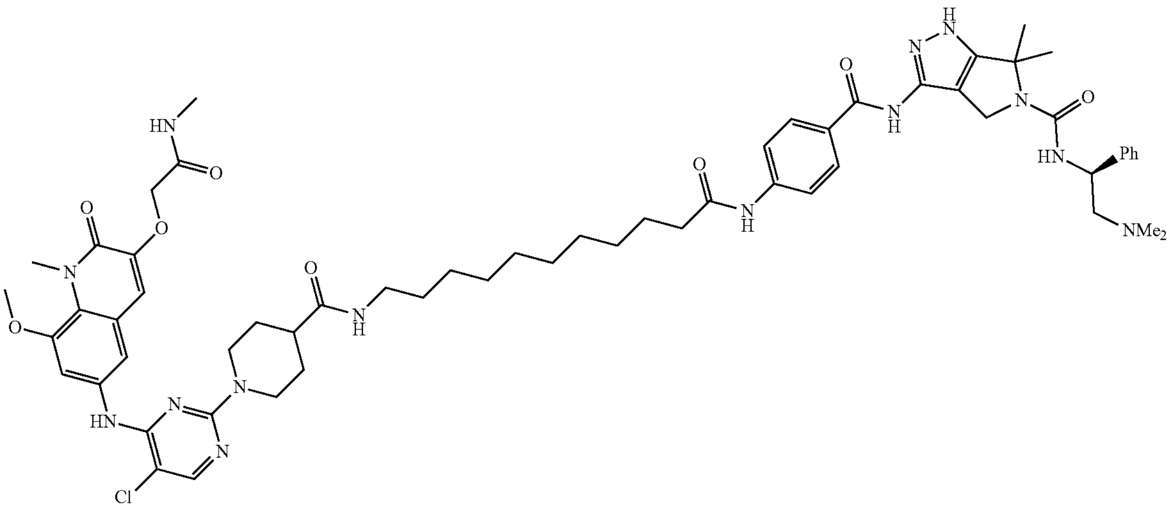
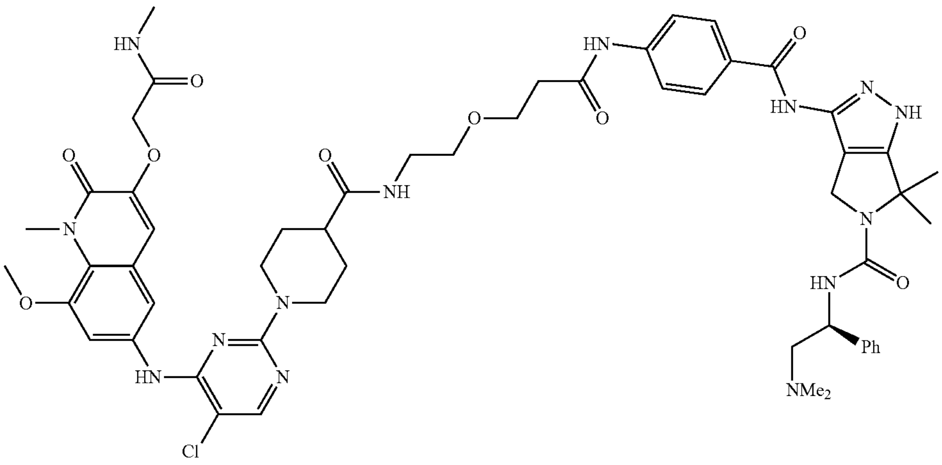

-continued
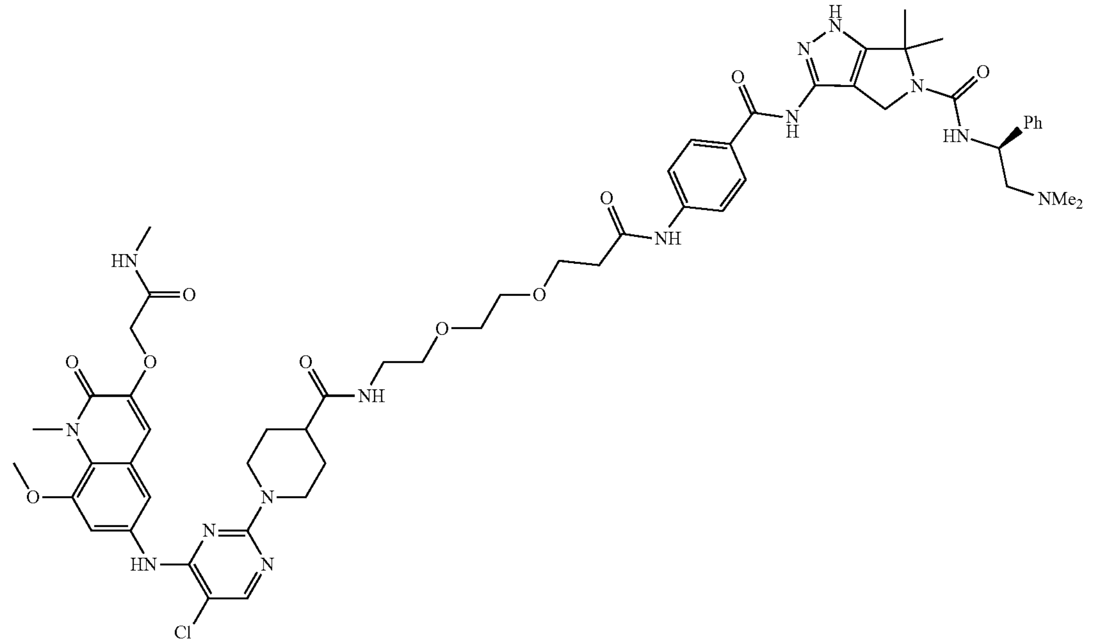
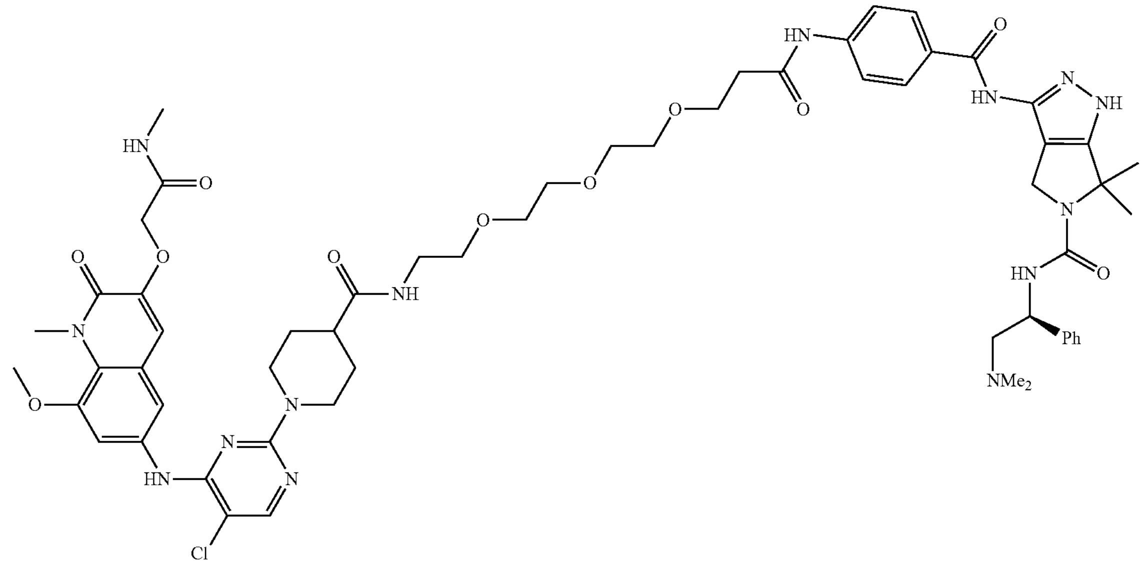
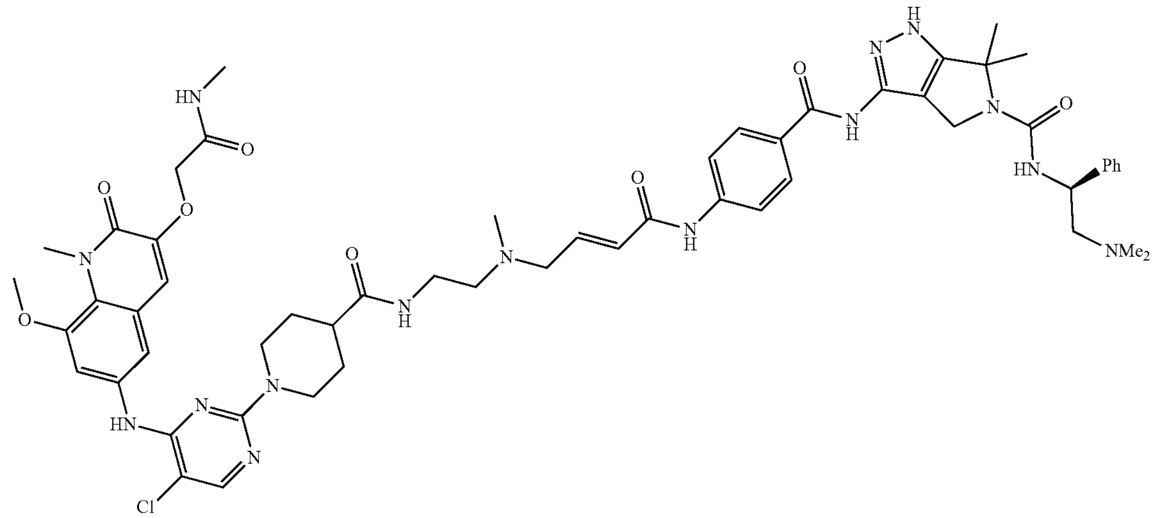

-continued

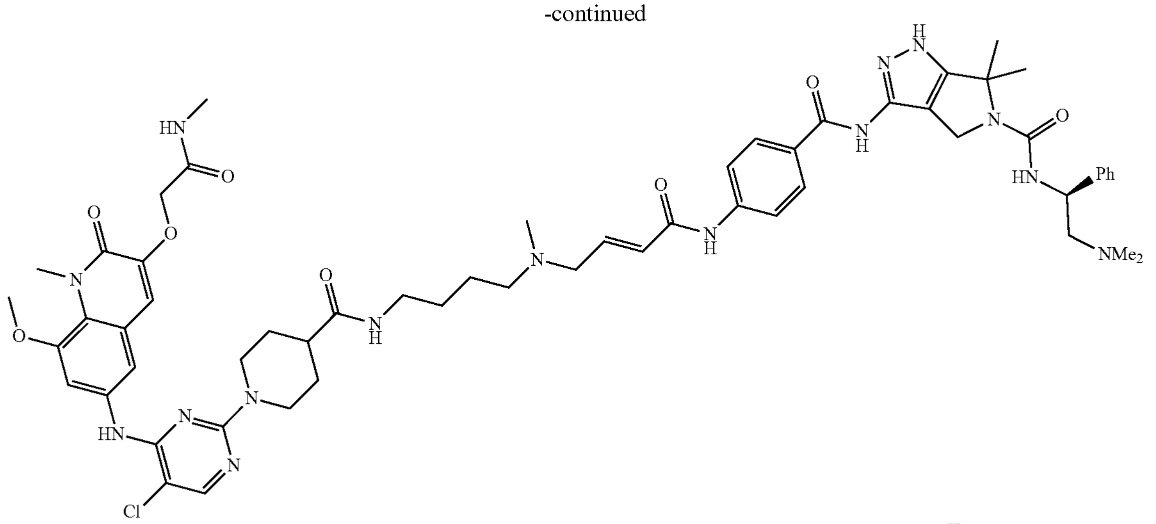

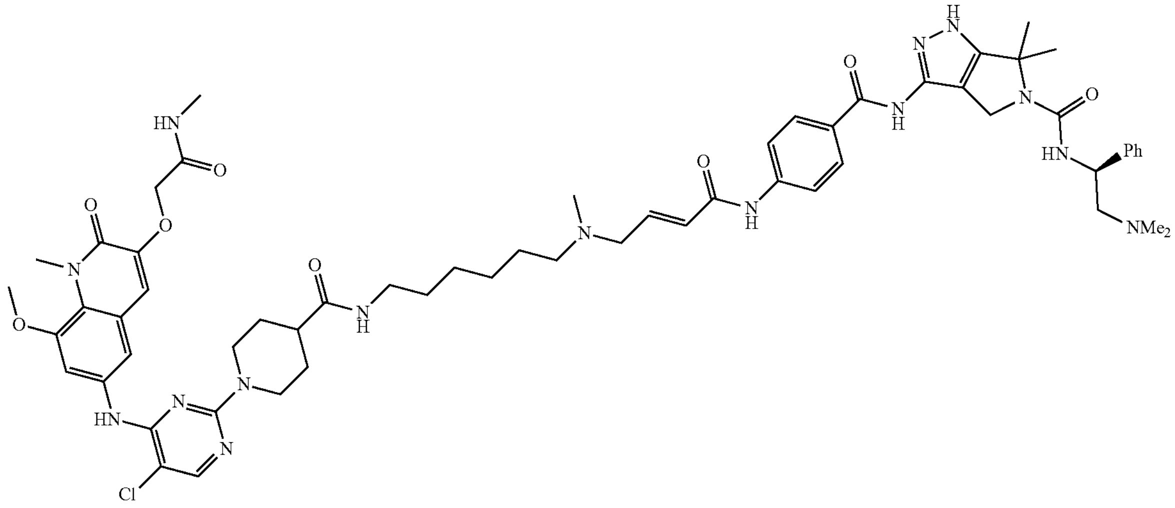

Methods of Use

Any of the compositions disclosed herein (including CIPs and TCIPs) may be applicable for the treatment of a disease or a condition in a subject. Further provided herein are methods of using the compositions provided herein (including CIPs and TCIPs) in a method of treating a disease or condition in a subject. In some cases, the disease or condition is a malignant disease or condition. In some cases, the compositions, systems, and methods provided herein may be used for the treatment of neoplastic disease conditions, e.g., cancer. Specific cancers of interest that may be treated according to embodiments of the disclosure include, but are not limited to: Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic and Intrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Colon Cancer, Colorectal Cancer, Craniopharyngioma, Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Head and Neck Cancer, Heart Cancer, Hepatocellular (Liver) Cancer, Histiocytosis (e.g., Langerhans Cell, etc.), Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic Leukemia (ALL), Acute Myeloid Leukemia (AML), Aleukemic Leukemia, Acute Nonlymphocytic Leukemia, Acute Monocytic Leukemia, Acute Granulocytic Leukemia, Acute Promyelocytic Leukemia, Chronic Lymphocytic Leukemia (CLL), Chronic Myelocytic Leukemia (CML), Chronic Granulocytic Leukemia, Adult T-cell Leukemia, Basophylic Leukemia, Eosinophilic Leukemia, Histiocytic Leukemia, Mast cell Leukemia, Megakaryocytic Leukemia, Blast Cell Leukemia, Leukemia Cutis, Hairy-Cell Leukemia, Stem cell Leukemia, Leukopenic Leukemia, Lymphatic Leukemia, Lymphoblastic Leukemia, Lymphocytic Leukemia, Lymphogenous Leukemia, Lymphoid Leukemia, Lymphosarcoma cell Leukemia, Monocytic Leukemia, Myeloblastic Leukemia, Myelocytic Leukemia, Plasma cell Leukemia, Multiple Myeloma, Plasmacytic Leukemia, Promyelocytic Leukemia), Lip and Oral Cavity Cancer, Liver Cancer (Primary), Lobular Carcinoma In Situ (LCIS), Lung Cancer (e.g., Non-Small Cell, Small Cell, etc.), Lymphoma (Non-Hodgkin Lymphoma or Hodgkin's Lymphoma: e.g. Small Lymphocytic Lymphoma, Mantle Cell Lymphoma, Follicular Lymphoma, Marginal Zone Lymphoma, Extranodal (MALT) Lymphoma, Nodal (monocytoid B-cell) Lymphoma, T-cell Lymphoma, Splenic Lymphoma, Diffuse Large Cell B-cell Lymphoma, Burkitt's Lymphoma, Lymphoblastic Lymphoma, Immunoblastic Large Cell Lymphoma, or Precursor B-Lymphoblastic Lymphoma, Cutaneous T-cell Lymphoma, Peripheral T-cell Lymphoma, Anaplastic Large Cell Lymphoma, Mycosis Fungoides, Primary Central Nervous System (CNS) Lymphoma and Precursor T-Lymphoblastic Lymphoma.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, , Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like. Cancers that may be treated further include, epithelial cancers, such as carcinomas, such as acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchioloalveolar carcinoma, bronchogenic carcinoma, cholangiocellular carcinoma, chorionic carcinoma, clear cell carcinoma, colloid carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in si'tu, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma simplex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like.

Methods of enhancing transcription of pro-apoptotic genes, e.g., as described herein, find use in, for example, treatment of malignancies. The target malignancy treated by embodiments of the disclosure may be any malignancy having cells that are susceptible to activity of a TCIP, such as described herein. In some instances, the malignancy is characterized by the presence of malignant cells having elevated levels of BCL6 and normal or above normal levels of a CDK, e.g., CDK9, CDK8, or CDK7. In some instances, the malignancy is SCLC, a lymphoma, such as non-Hodgkin's lymphoma, e.g., DLBCL, including refractory DLBCL, such as CHOP-resistant DLBCL, breast cancer; and the like. In some instances, the methods are methods of treating SCLC. In some instances, the methods are methods of treating a lymphoma, such as non-Hodgkin's lymphoma, e.g., DLBCL, including refractory DLBCL, such as CHOP-resistant DLBCL. In some instances the methods are methods of treating breast cancer.

Embodiments of the methods may include assessing whether a subject suffering from a neoplastic disease has a particular type of malignancy (i.e., cancer) For examples, embodiments of methods may include assessing whether the subject has a susceptible malignancy, such as SCLC, including CDK positive SCLC, which SCLC may be refractory SCLC. For example, the methods may include assessing whether the SCLC is CDK positive, e.g., CDK9, CDK8, and/or CDK7 positive, and then employing an appropriate TCIP to treat the particular cancer. For example, if the SCLC is CDK9 positive, a CIP having a ligand that binds to CDK9 may be employed. Embodiments of the methods may include assessing whether a subject suffering from a neoplastic disease has a particular type of DLBCL, including CDK positive DLBCL, which DLBCL may be refractory DLBCL, such as CHOP-resistant DLBCL. For example, the methods may include assessing whether the DLBCL is CDK9 positive, and then employing an appropriate TCIP to treat the particular cancer. For example, if the DLBCL is CDK9 positive, a CIP having a ligand that binds to CDK9 may be employed.

Where the target malignancy is SCLC, in some instances the target patient population includes patients with SCLC either contained or metastatic at the time of presentation or discovery. Among patients with SCLC, those to be treated for SCLC can be chosen by measuring the level of expression of BCL6 and target CDK, e.g., CDK9, CDK8 and/or CDK7, in their tumors. This can be done by RNA-seq, Western blotting or immunohistochemistry using antibodies against these proteins, mass spectrometry, intracellular FACS, etc. Patients whose tumors have high level expression of CDK and BCL6 or its homologues will be the target population that would be expected to respond favorably. These patients would be candidates for treatment with a TCIP in accordance with the disclosure, particularly those whose tumor has high levels of BCL6 or another BTB domain containing protein and those whose tumor expresses a target CDK. These levels can be measured by RNA-seq, Western blotting or immunohistochemistry using antibodies against these proteins, mass spectrometry, intracellular FACS, etc. About 70% of patients with small cell lung cancer have distant metastasis at the time of diagnosis. The media survival of this group untreated is about 3 months. With treatment the median survival is 6 to 8 months. Those patients that have metastasis at the time of treatment and whose tumor expressed high levels of a target CDK and BCL6 or another BTB domain containing protein and would be likely to benefit from treatment with a TCIP of the disclosure. A similar approach may be employed to identify appropriate patient populations suffering from other malignancies, e.g., lymphomas, such as DCBLC, such as described above.

AR-BCL6 TCIPs

As reviewed above, in some embodiments, chemical inducers of proximity include a compound of formula I:

AL-L-BC (I)

where:

AL is a ligand that specifically binds to an androgen receptor;

BC is a ligand that specifically binds to B-cell lymphoma 6 (BCL-6) or a BCL6 BTB-domain family member (e.g., functional homologue thereof); and L is a linker (optional), or a pharmaceutically acceptable salt thereof.

Figure 19:
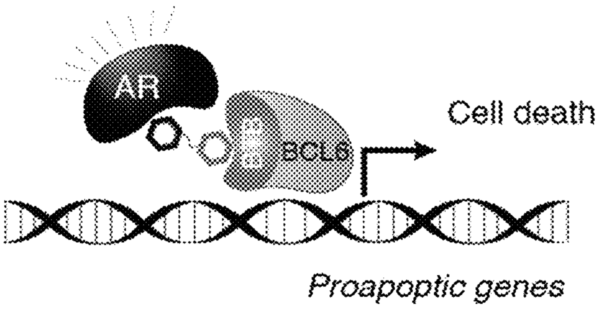
FIG. 19 illustrates the design of a TCIP to hijack BCL-6 to kill androgen receptor (AR) driven prostate cancer cells.
Figure 20:
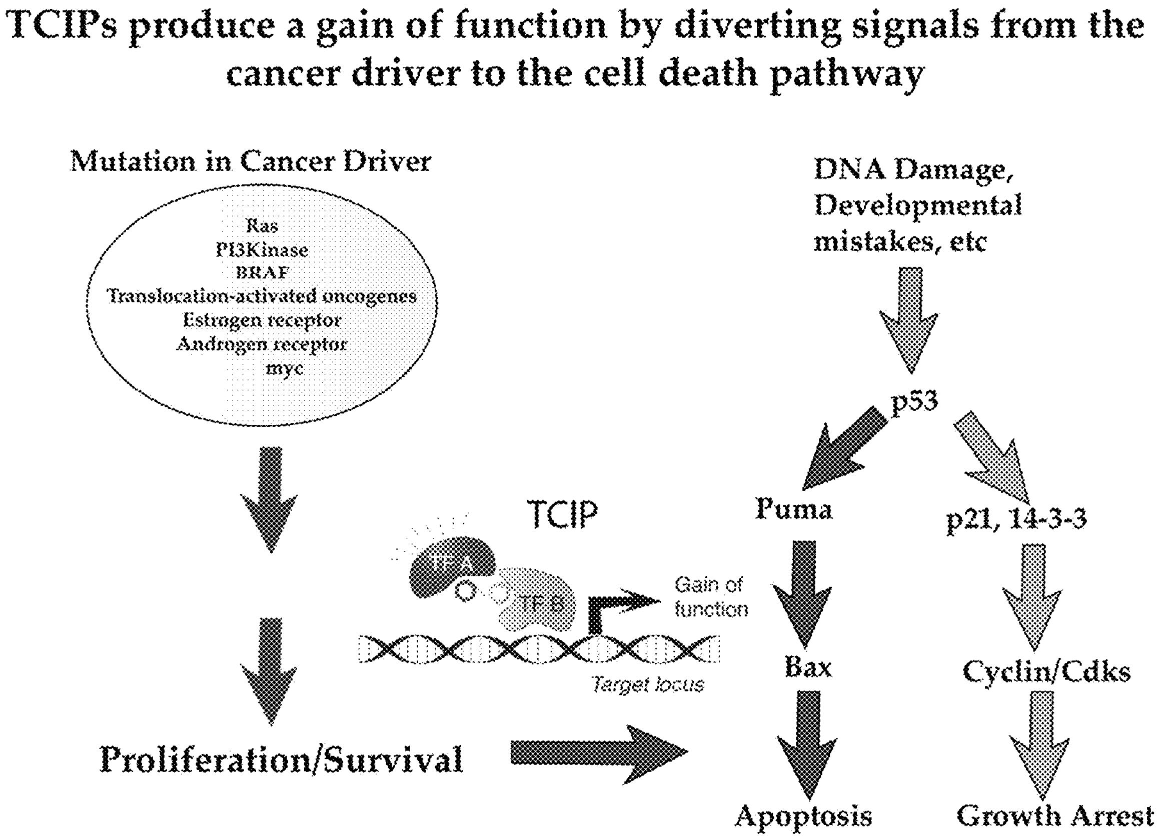
FIG. 20 illustrates an example of a gain-of-function provided by compounds of the disclosure (e.g., TCIPs). Normally the cancer driver promotes the proliferation, spread and survival of the cancer cell. In this example, the TCIP causes the signals from the cancer driver to be diverted to evolutionarily conserved cell death pathways that the cancer driver would not normally engage.
Figure 21:
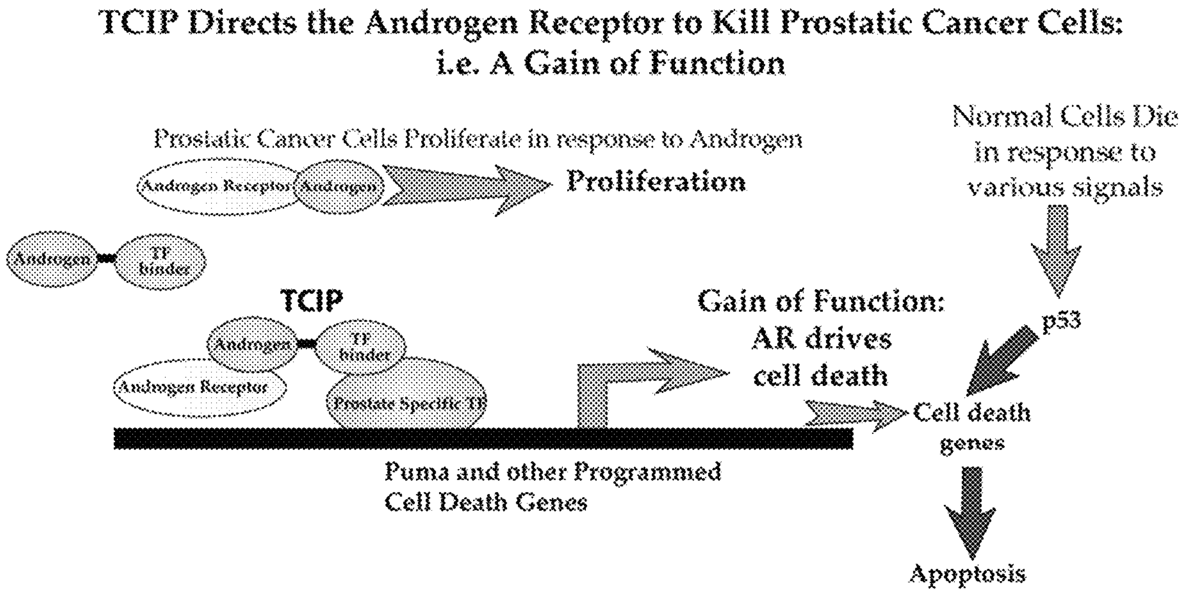
FIG. 21 illustrates a non-limiting example of the way that compounds of the disclosure (e.g., TCIPs, such as those described in FIG. 22) cause the androgen receptor to gain a function that it does not normally have, e.g., cell killing. By engaging the androgen dependent proliferation pathway on one side using the AR moiety and the BCL6 protein or a prostate specific transcription factor controlling cell death genes using the second moiety, proliferative signals are induced to cause cell death.
Figure 22:
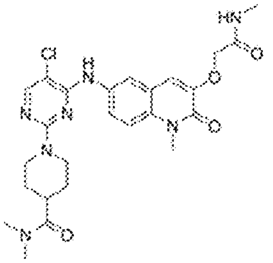
FIG. 22 provides components for the design and synthesis of AR-TCIPs in accordance with embodiments of the disclosure. A. BCL6 BTB Inhibitors and Degraders. These molecules may be used to produce the arm of the AR-TCIP that binds to endogenous BCL6 or its homologues. B. Steroidal and non-steroidal androgen agonist that may be used to form the arm of the AR-TCIP that binds to endogenous androgen receptors in prostatic cancer cells. C. Androgen receptor antagonists that may be used as described in B. D. Linkers that may be used to construct AR-BCL6 TCIPs.
Figure 22:
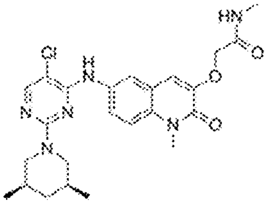
Figure 22:
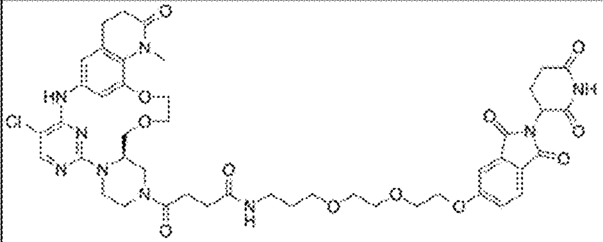
Figure 22:
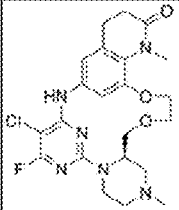
Figure 22:
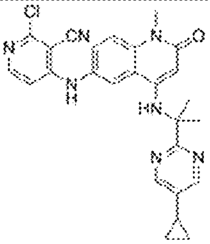
Figure 22:
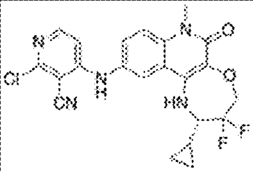
Figure 22:
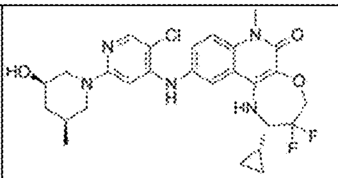
Figure 22:
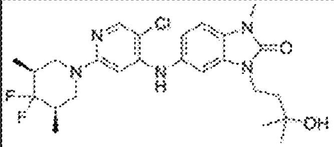
Figure 22:
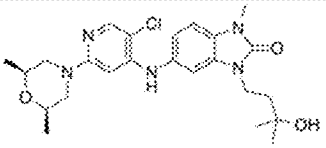
Figure 22:
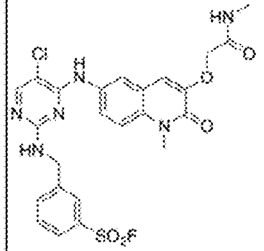
Figure 22:
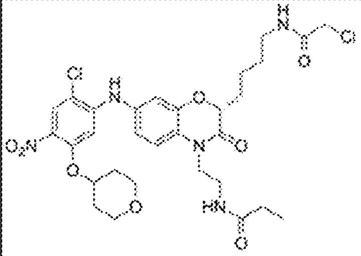
Figure 22:
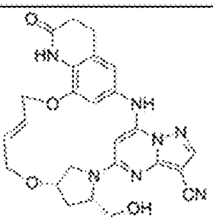
Figure 22:
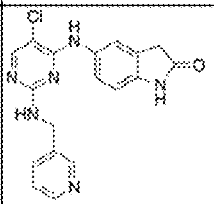
Figure 22:
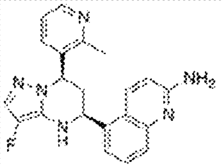
Figure 22:
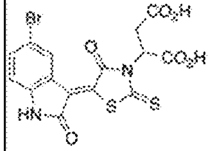
Figure 22:
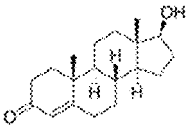
Figure 22:
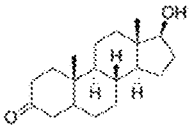
Figure 22:
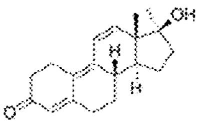
Figure 22:
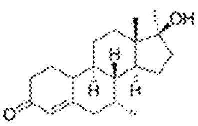
Figure 22:
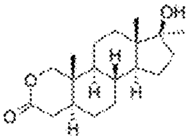
Figure 22:
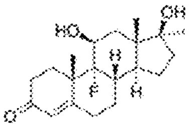
Figure 22:
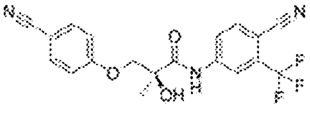
Figure 22:
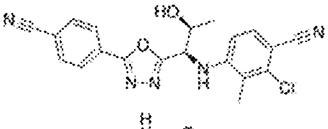
Figure 22:
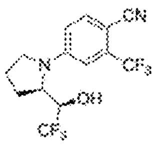
Figure 22:
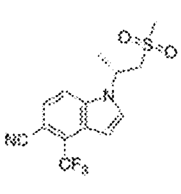
Figure 22:
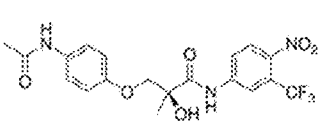
Figure 22:
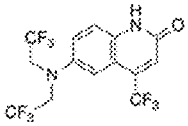
Figure 22:
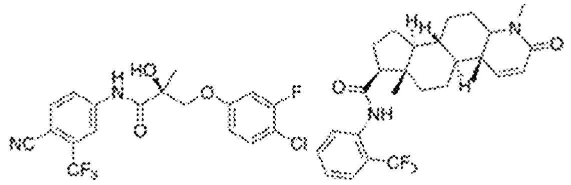
Figure 22:
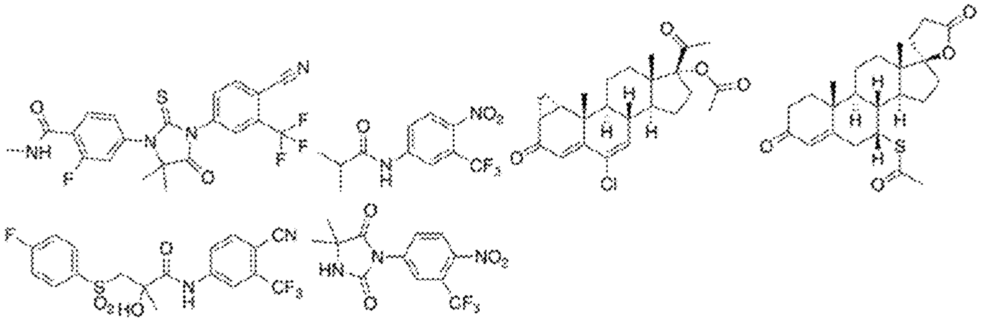
Figure 22:
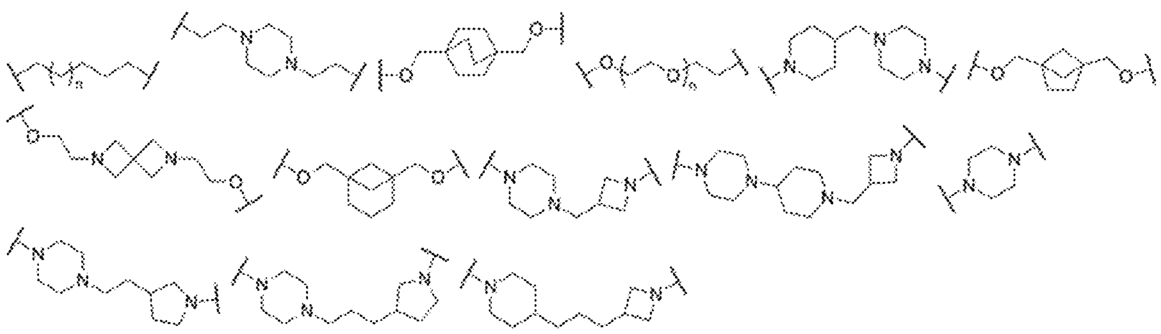
Figure 23:
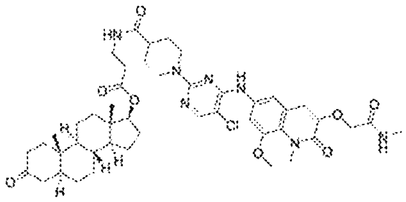
FIG. 23 depicts structures of AR-BCL6 TCIPs in accordance with embodiments of the disclosure synthesized and tested for their ability to kill human prostatic cancers. Each structure includes an androgen receptor binder, a linker and a BCL6 binder/inhibitor, which binds to the conserved BTB domain present in functionally related proteins. Each of the components are shown in the Figure and are examples of TCIPs of embodiments of the disclosure. The molecules labeled RCS-02-075 (AR-BCL6 neg. control 1) and RCS-02-155 (AR-BCL6 neg. control 2) are negative binding controls that have minor, but significant chemical modifications in the AR binding side and the BCL6 binding site, respectively.
Figure 23:
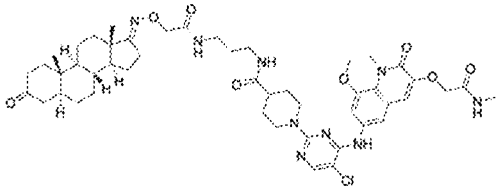
Figure 23:
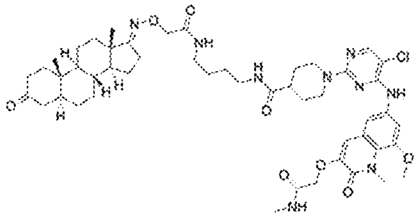
Figure 23:
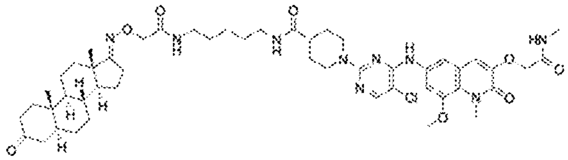
Figure 23:
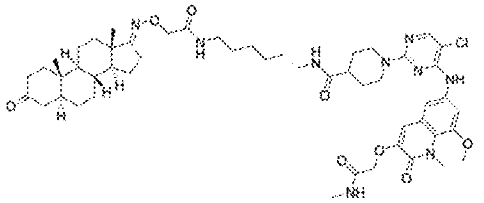
Figure 23:
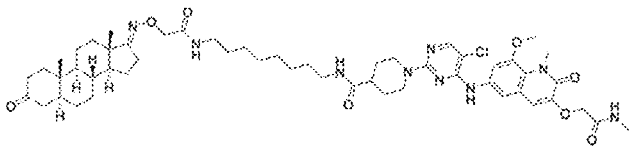
Figure 23:
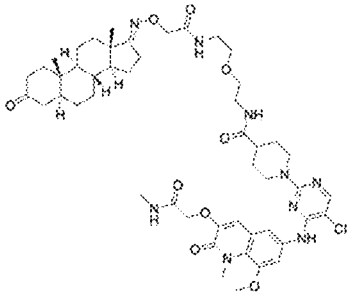
Figure 23:
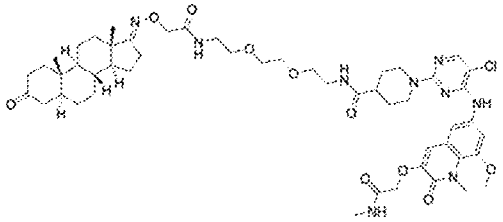
Figure 23:
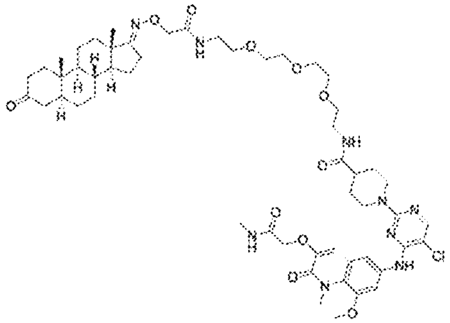
Figure 23:
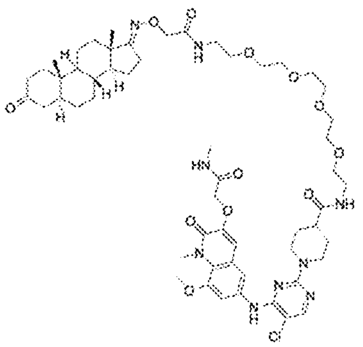
Figure 23:
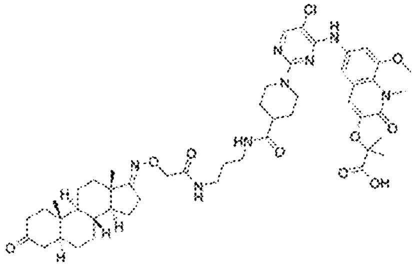
Figure 23:
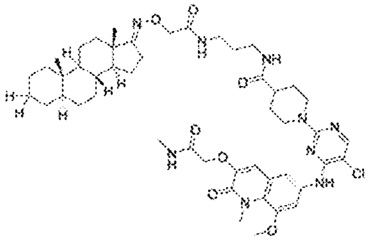
Figure 23:
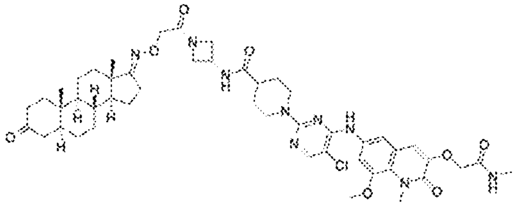
Figure 23:
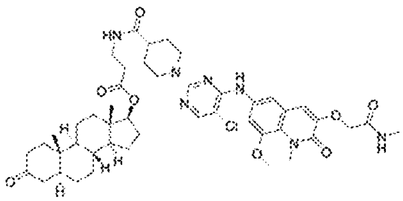
Figure 23:
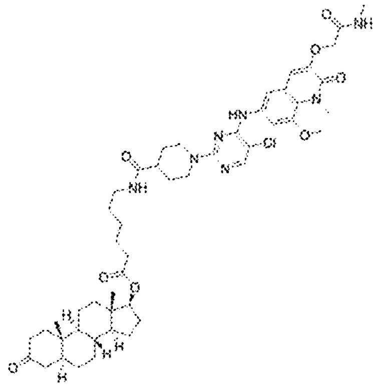
Figure 23:
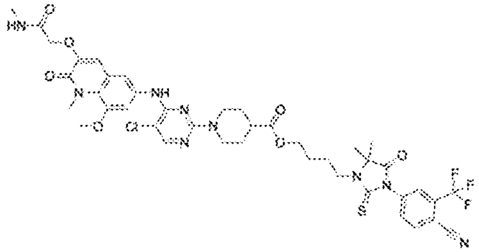
Figure 23:
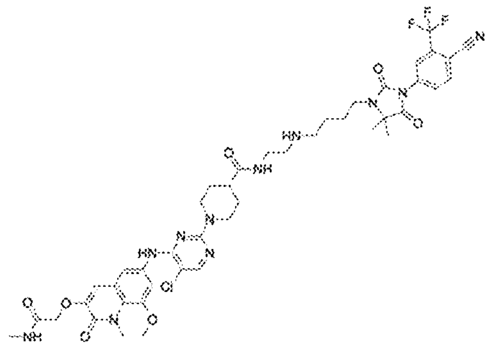

FIG. 19 provides an illustration of how to build a TCIP by rational design using existing components. As shown in FIG. 19, the design of a TCIP configured to hijack BCL6 (and/or a functional homologue thereof) to kill AR-positive prostatic cancer cells is shown. BCL6 is a transcription factor and oncogene that prevents death of a variety of cancer cells, including lymphoma and SCLC cells, by binding the repressors BCOR, NCO and SMRT (PMID:30335946) on the promoters of cell death genes. Several inhibitors of BCL6's repressive function have been produced that prevent the binding of BCOR, NCOR and SMRT to a site formed by the dimeric surface of BCL6 (PMID:18280243) However, these inhibitors have not been sufficiently active to be used therapeutically (PMID:30335946).

Chemical linkage of BCL-6 inhibitors, such as BI-3812 (PMID32275432), to AR ligand compounds, e.g., steroidal or non-steroidal AR agonists or antagonists, that then bind and induce proximity to the cell death (pro-apoptotic) promoters, such as those for TP53, PUMA and BIM, convert the inhibitor of cell death to an activator of cell death in cells having high concentrations of AR, such as prostate cancer cells, e.g., hormone-sensitive prostate cancer cells.

Specific TCIPs finding use in embodiments of the disclosure include, but are not limited to:

BAK-04-083 (C2)

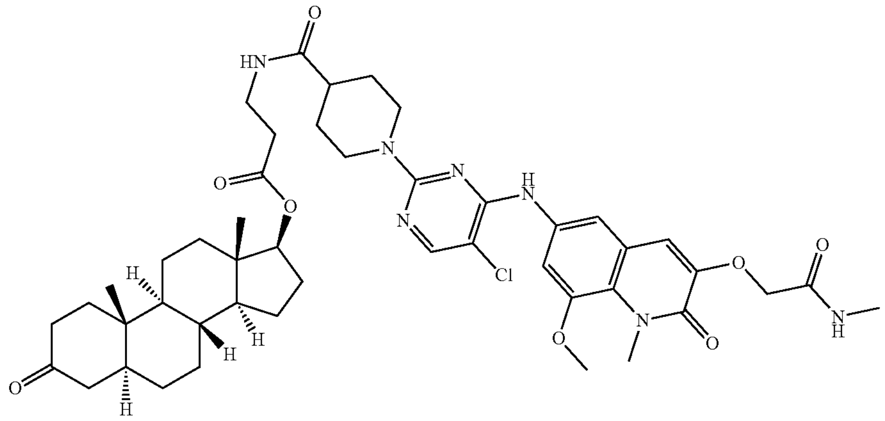

RCS-02-063 (C3)

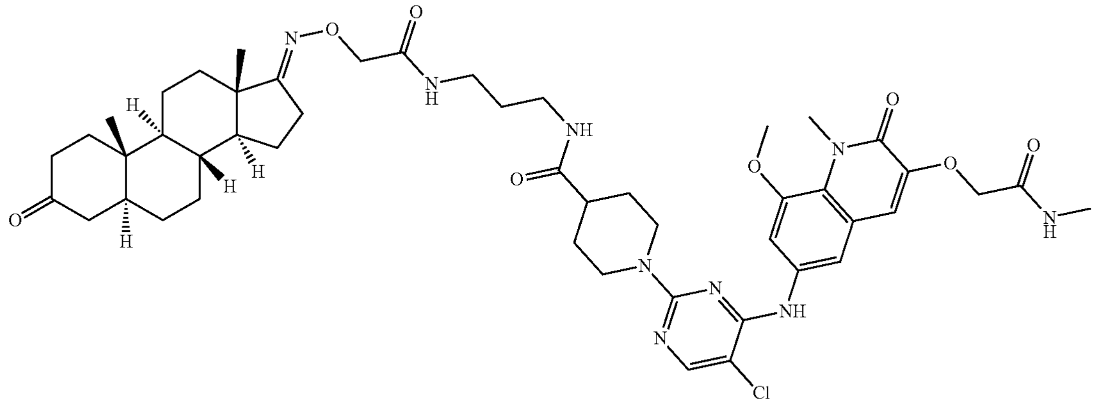

-continued
RCS-02-093 (C4)
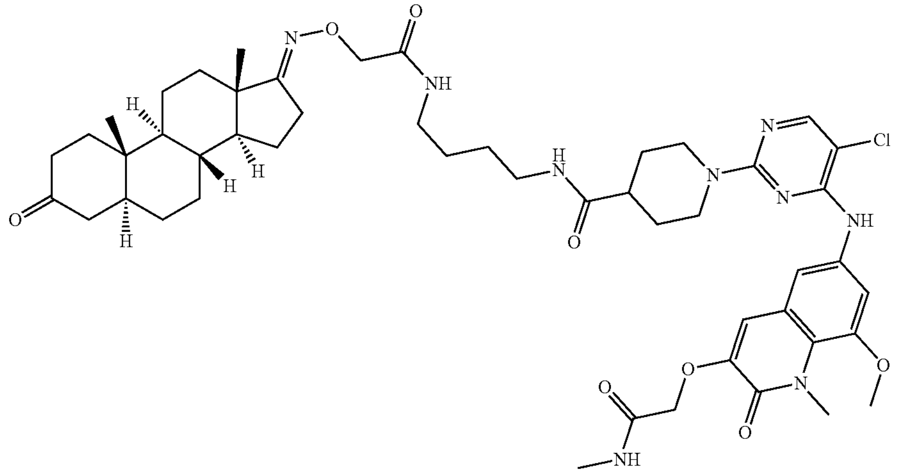
BAK-04-003 (C5)
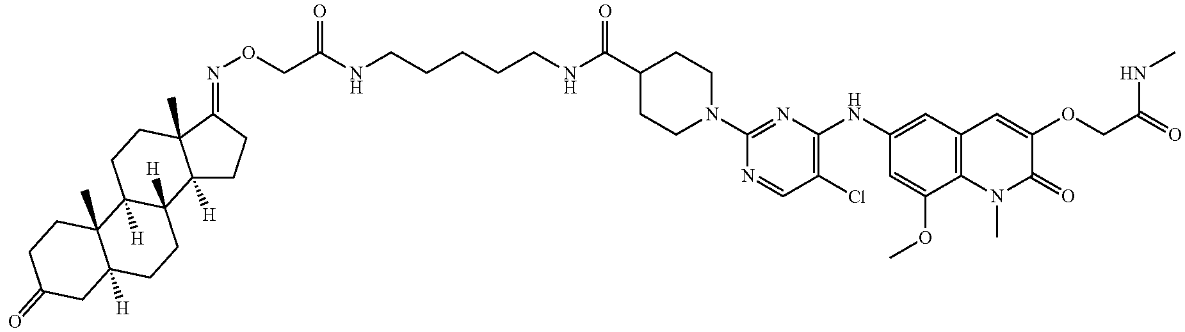
RCS-02-085 (C6)
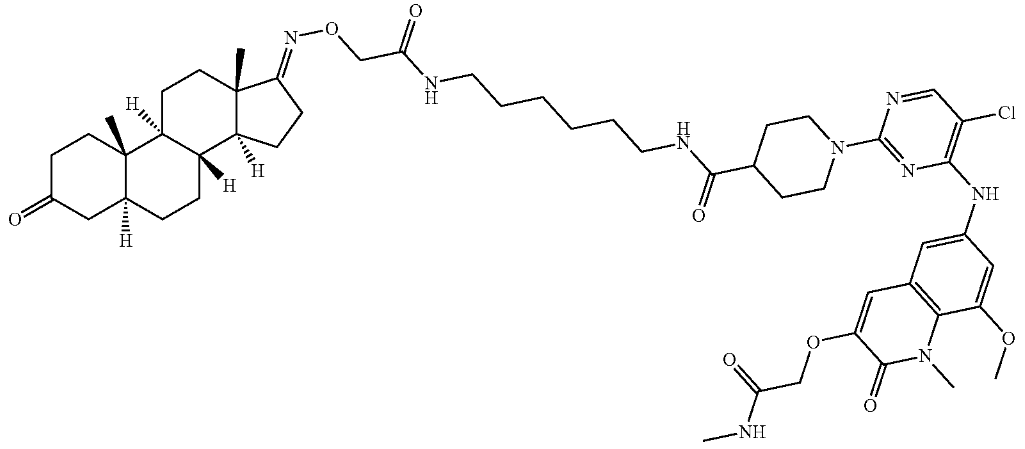
BAK-04-006 (C8)
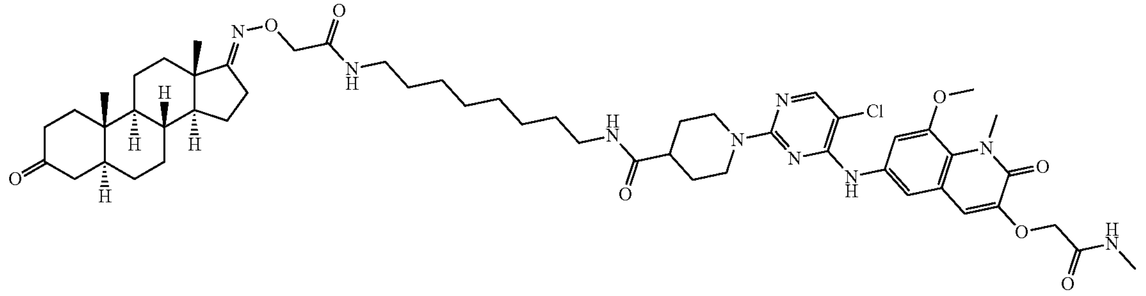

-continued
RCS-02-060 (peg1)
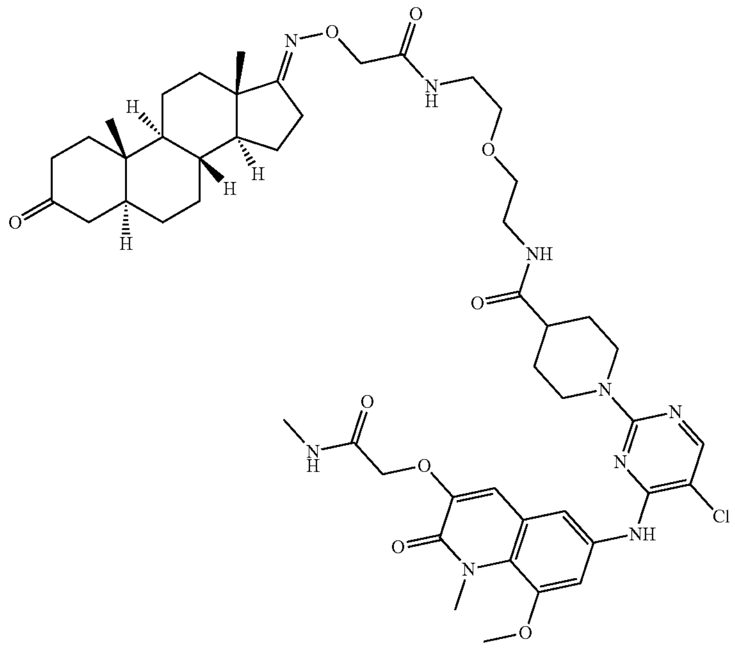
RCS-02-058 (peg2)
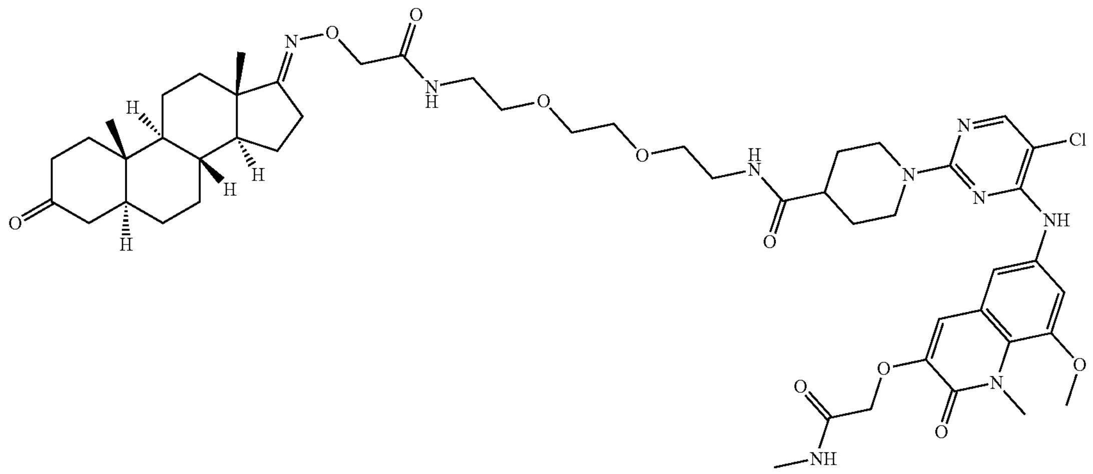

-continued
RCS-02-061 (peg3)
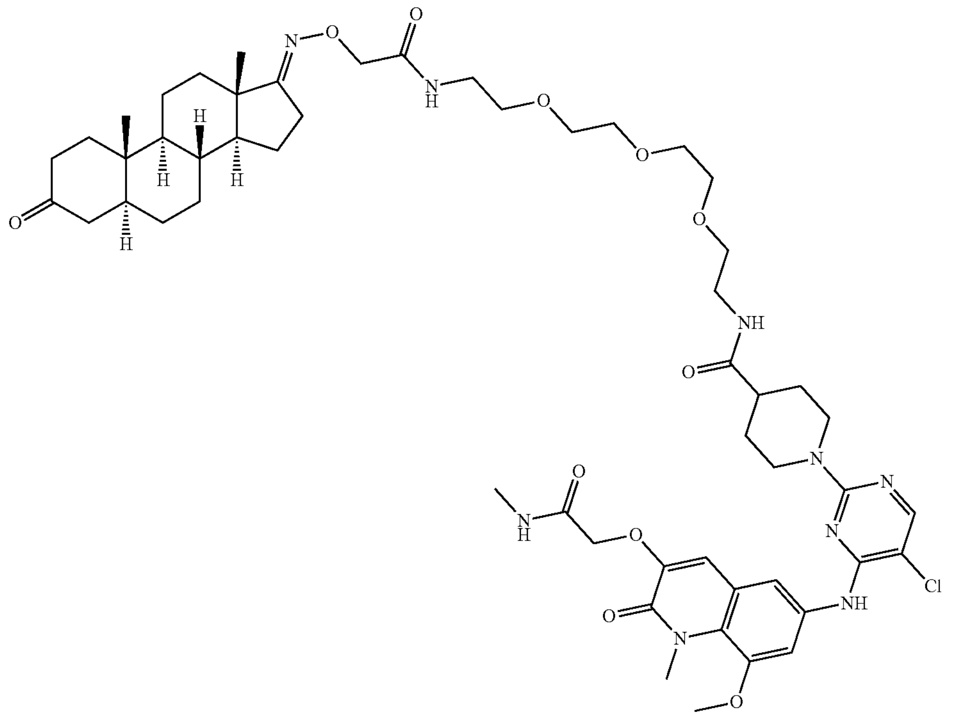
RCS-02-062 (peg4)
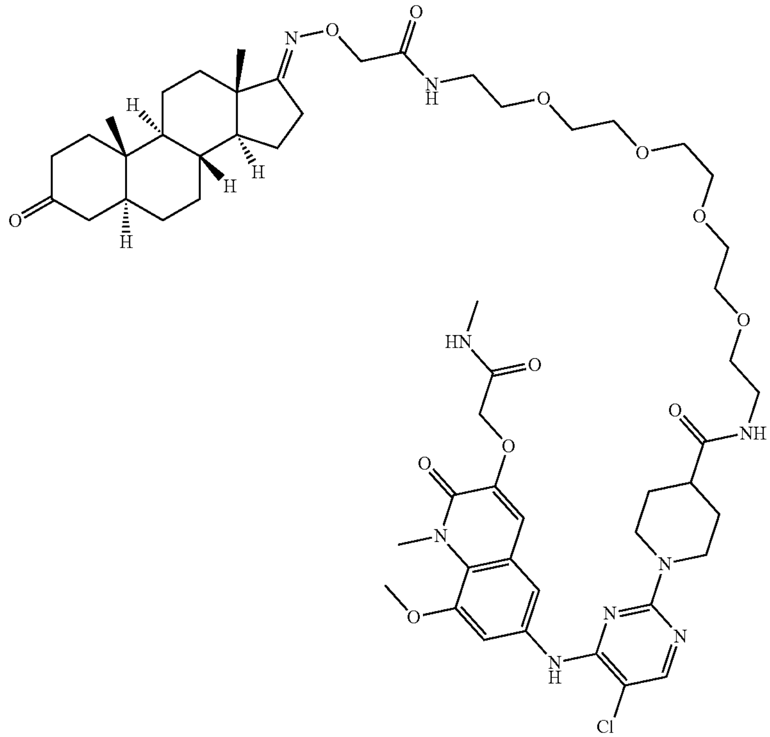

-continued
RCS-02-075 (AR-BCL6 neg. control 1)
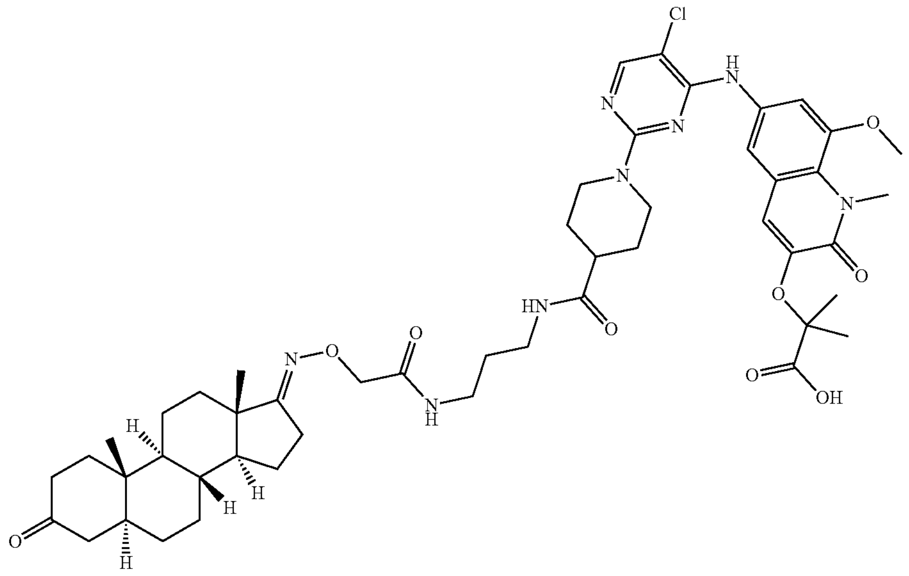
RCS-02-155 (AR-BCL6 neg. control 2)
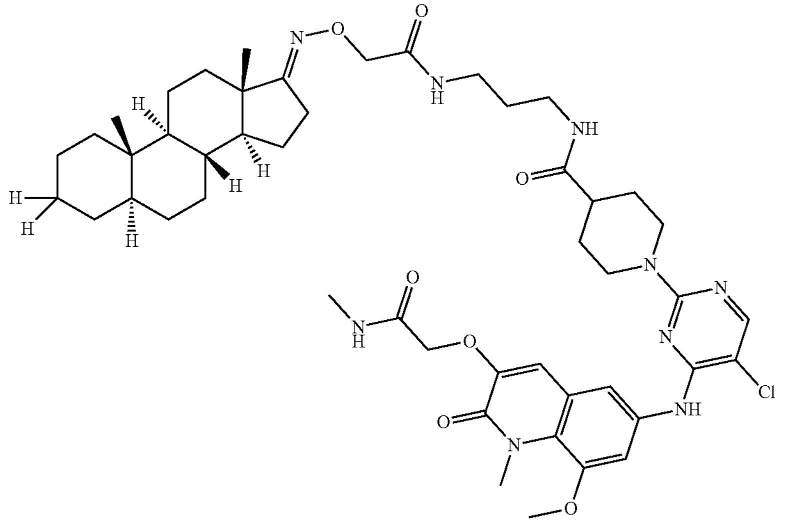
BAK-04-039
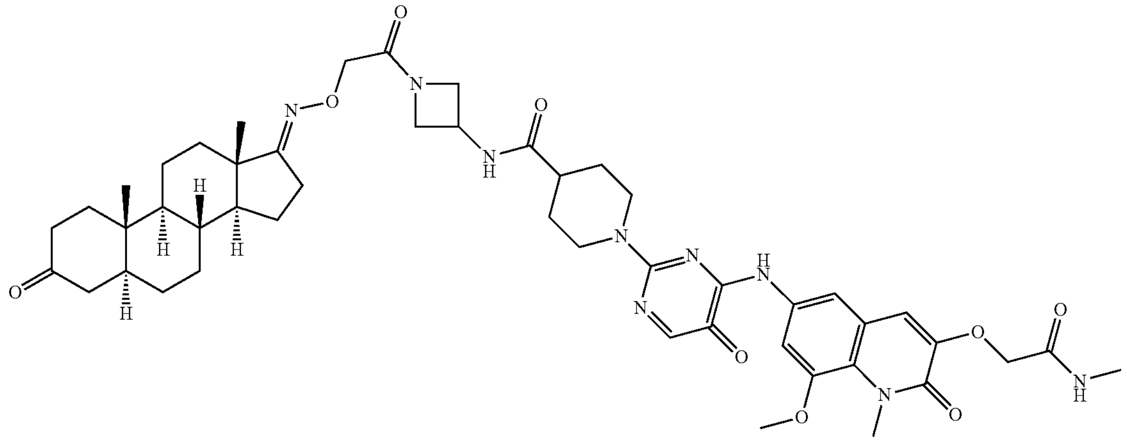

-continued
BAK-04-083
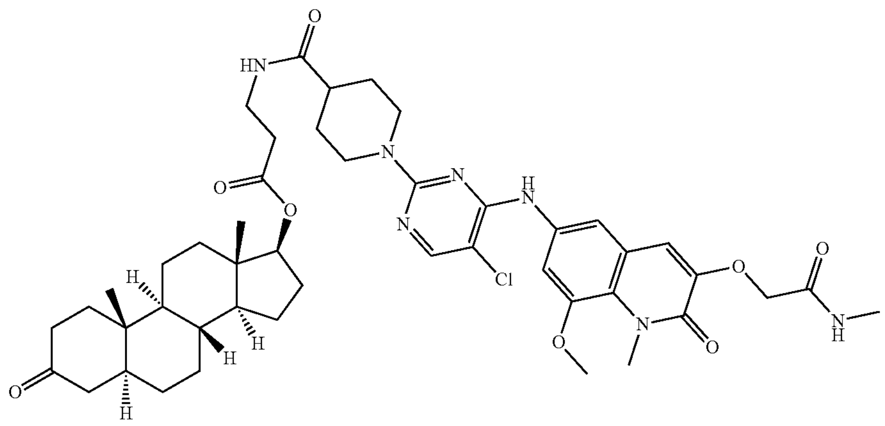
BAK-04-084
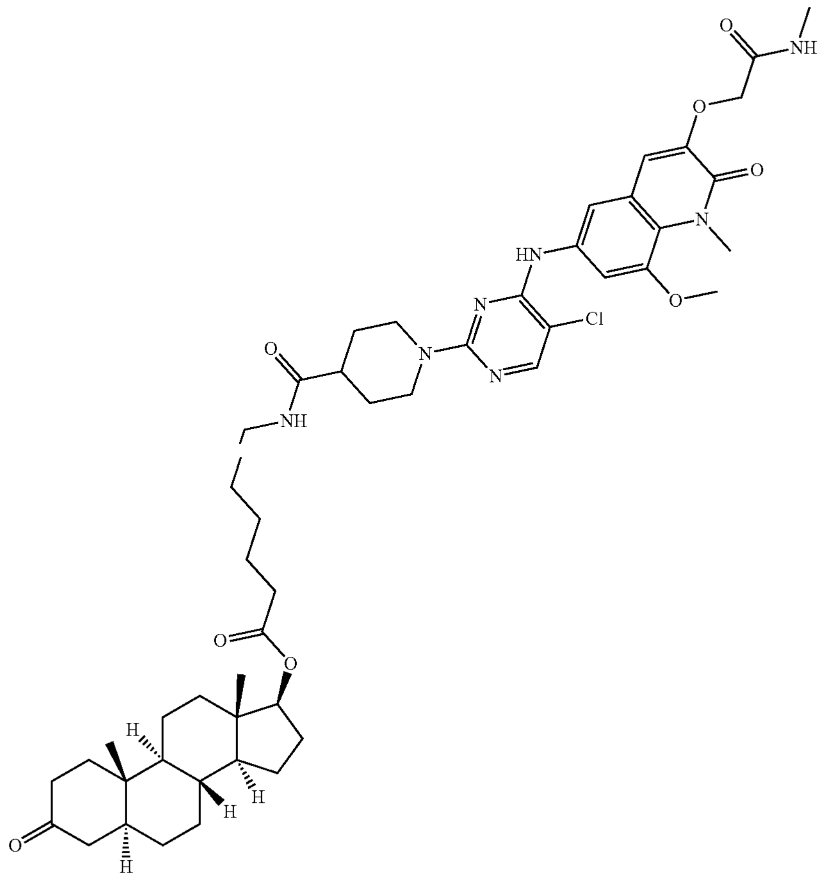

-continued

RCS-02-160

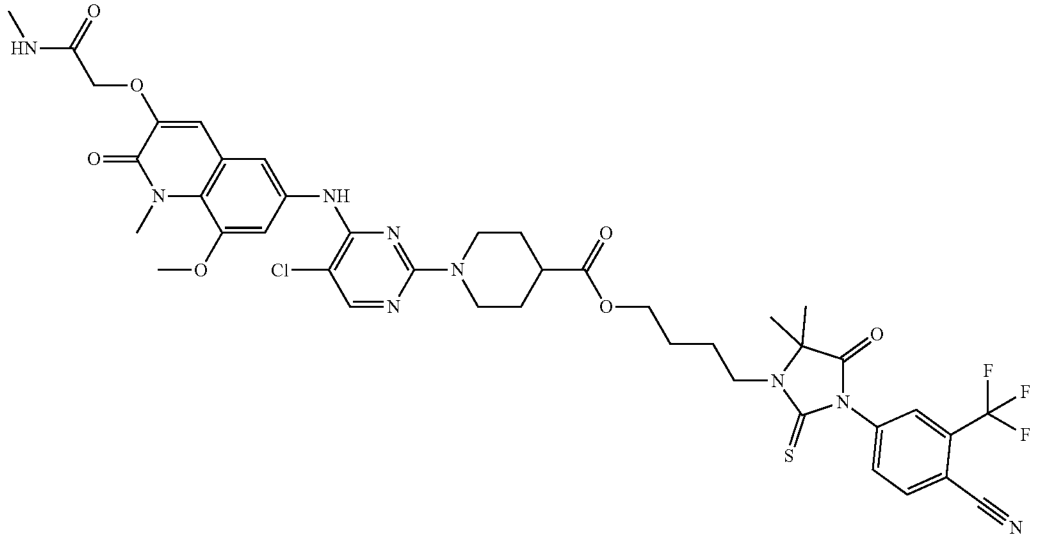

RCS-02-176

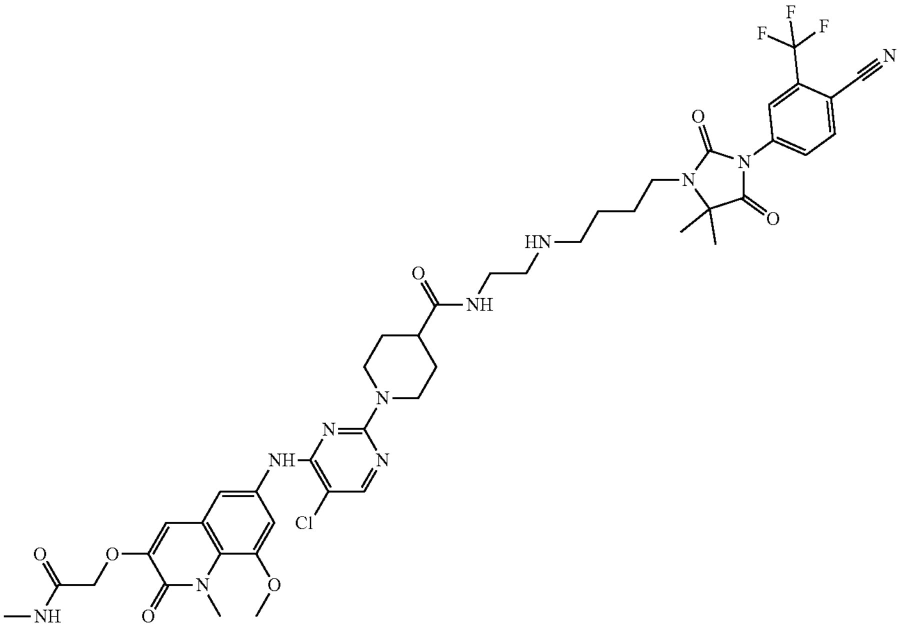

In some instances, the TCIP is not a TCIP disclosed in FIG. 4 of WO 2022/098989.

Methods of enhancing transcription of pro-apoptotic genes, e.g., as described herein, find use in, for example, treatment of malignancies. The target malignancy treated by embodiments of the disclosure may be any malignancy having cells that are susceptible to activity of a TCIP, such as described herein. In some instances, the malignancy is characterized by the presence of malignant cells having elevated levels of BCL6 and/or above normal levels of AR. In some instances, the malignancy is prostate cancer.

Embodiments of the methods may include assessing whether a subject suffering from a neoplastic disease has a particular type of malignancy (i.e., cancer) For examples, embodiments of methods may include assessing whether the subject has a susceptible prostate cancer. For example, the methods may include assessing whether the prostate cancer is hormone responsive prostate cancer, e.g., the prostate cancer has elevated levels of AR, and then employing an appropriate TCIP to treat the particular cancer. For example, if the prostate cancer has elevated levels AR, a CIP having a ligand that binds to AR may be employed. Where the target malignancy is prostate cancer, in some instances the target patient population includes patients with prostate cancer either contained or metastatic at the time of presentation or discovery. Among patients with prostate cancer, those to be treated for prostate cancer can be chosen by measuring the level of expression of BCL6 and/or AR in their tumors. This can be done using any convenient protocol, e.g., by RNA-seq, Western blotting or immunohistochemistry using antibodies against these proteins. Patients whose tumors have high level expression of AR and BCL6 or its homologues will be the target population that would be expected to respond favorably. These patients would be candidates for treatment with a TCIP, particularly those whose tumor has high levels of BCL6 or one of its homologues and those whose tumor expresses AR. These levels can be measured by RNA-seq, Western blotting or immunohistochemistry using antibodies against these proteins, mass spectrometry, intracellular FACS, etc.

Combination Therapy

The present disclosure further comprises combination therapies. In certain embodiments, the subject method includes administering a therapeutically effective amount of one or more additional active agents in combination with the compound (e.g., CIP, TCIP) of the disclosure. The compound can be administered to a subject prior to, simultaneously with, or subsequent to administration of the one or more additional active agents. In some embodiments, by combination therapy is meant that a CIP can be used in a combination with another therapeutic agent to treat a single disease or condition. Alternatively, a second CIP could be used to overcome drug-induced resistance to a first CIP or to boost the apoptotic activity of the first CIP. This could be accomplished by using a ligand to another anchoring transcription factor that binds to one or more of the apoptotic gene promoter/enhancers. In some embodiments, a CIP compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or after administration of another therapeutic agent. The subject compounds can be administered in combination with other therapeutic agents in a variety of therapeutic applications. Therapeutic applications of interest for combination therapy include those applications those described above.

As reviewed above, in some instances the compounds of the disclosure (e.g., CIPS, TCIPs) may be employed for treating neoplastic conditions. In some embodiments, the compounds of the disclosure can be used jointly with any agent or combination of agents useful in the treatment of a neoplastic condition, such as anti-cancer agents: e.g. cancer chemotherapeutic agents, radio-therapy, radio-immunotherapy, biologic response modifiers, monoclonal-antibodies, antibody-drug conjugates (ADCs) and immuno-therapy agents. In some embodiments, an anti-cancer-agent, radioimmunotherapy, biologic response modifiers, monoclonal-antibodies, antibody-drug conjugates (ADCs) and immunotherapy agents is an agent approved by the FDA or similar regulatory agency of a country other than the USA, for treating cancer. In embodiments, an anti-cancer agent, radioimmunotherapy, biologic response modifiers, monoclonal-antibodies, antibody-drug conjugates (ADCs) and immunotherapy agents is an agent with antineoplastic or immunomodulatory properties that has not (e.g., yet) been approved by the FDA or similar regulatory agency of a country other than the USA, for treating cancer. Agents of interest which can be used jointly with the compounds provided herein in such instances include, but are not limited to, Cancer chemotherapeutic agents, Agents that act to reduce cellular proliferation, Antimetabolite agents, Microtubule affecting agents, Hormone modulators and steroids, natural products and biological response modifiers, e.g., as described in greater detail below. Compounds of the present disclosure may be employed in combination with active agent combinations, such as CHOP (a chemotherapy combination consisting of cyclophosphamide, doxorubicin hydrochloride (hydroxydaunorubicin), vincristine sulfate (Oncovin), and prednisone) R-CHOP (an immunochemotherapy regimen consisting of rituximab, cyclophosphamide, hydroxydaunorubicin hydrochloride (doxorubicin hydrochloride), vincristine (Oncovin) and prednisone); and the like.

Cancer chemotherapeutic agents include non-peptidic (i.e., non-proteinaceous) compounds that reduce proliferation of cancer cells and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD). Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™) melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide. Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine. Suitable natural products and their derivatives, (e.g., *vinca* alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like. Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation. Therefore, compounds that bind to the estrogen receptor are used to block this activity. Corticosteroids may inhibit T cell proliferation. Other suitable chemotherapeutic agents include metal complexes, e.g., cisplatin (cis-DDP), carboplatin, etc.; ureas, e.g., hydroxyurea; and hydrazines, e.g., N-methylhydrazine; epidophyllotoxin; a topoisomerase inhibitor; procarbazine; mitoxantrone; leucovorin; tegafur; etc. Other anti-proliferative agents of interest include immunosuppressants, e.g., mycophenolic acid, thalidomide, deoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl) propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*). Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701. Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

In some instances, the compounds of the disclosure may be employed in combination with other targeted anti-cancer therapies such as but not limited to: inhibitors of kinases such as BTK, BCR-ABL, ERK, PI3K, AKT, RTK, RAF, MEK, SYK, MAPK inhibitors of Ras, mTOR, MDM2.

In some instances, the TCIPs of the disclosure are employed in combination with immunotherapy agents. Examples of immunotherapy include anti-PD-1/PD-L1 immunotherapies, such as anti-PD-1/PD-L1 therapeutic antagonists, where such antagonists include but are not limited to e.g., OPDIVO® (nivolumab), KEYTRUDA® (pembrolizumab), Tecentriq™ (atezolizumab), durvalumab (MED14736), avelumab (MSB0010718C), BMS-936559 (MDX-1105), CA-170, BMS-202, BMS-8, BMS-37, BMS-242 and the like. Nivolumab (OPDIVO®) is a humanized IgG4 anti-PD-1 monoclonal antibody used to treat cancer. Pembrolizumab (KEYTRUDA®), formerly known as MK-3475, lambrolizumab, etc., is a humanized antibody used in cancer immunotherapy targeting the PD-1 receptor. Atezolizumab (Tecentriq™) is a fully humanized, engineered monoclonal antibody of IgG1 isotype against the PD-L1 protein. Durvalumab (MedImmune) is a therapeutic monoclonal antibody that targets PD-L1. Avelumab (also known as MSB0010718C; Merck KGaA, Darmstadt, Germany & Pfizer) is a fully human monoclonal PD-L1 antibody of isotype IgG1. BMS-936559 (also known as MDX-1105; Bristol-Myers Squibb) is a blocking antibody that has been shown to bind to PD-L1 and prevent its binding to PD-1 (see e.g., U.S. NIH Clinical Trial No. NCT00729664). CA-170 (Curis, Inc.) is a small molecule PD-L1 antagonist. BMS-202, BMS-8, BMS-37, BMS-242 are small molecule PD-1/PD-L1 complex antagonists that bind PD-1 (see e.g., Kaz et al., (2016) Oncotarget 7(21); the disclosure of which is incorporated herein by reference in its entirety). Anti-PD-L1 antagonists, including e.g., antibodies, useful in the methods described herein include but are not limited to e.g., those described in U.S. Pat. Nos. 7,722,868; 7,794,710; 7,892,540; 7,943,743; 8,168,179; 8,217,149; 8,354,509; 8,383,796; 8,460,927; 8,552,154; 8,741,295; 8,747,833; 8,779,108; 8,952,136; 8,981,063; 9,045,545; 9,102,725; 9,109,034; 9,175,082; 9,212,224; 9,273,135 and 9,402,888; the disclosures of which are incorporated herein by reference in their entirety. Anti-PD-1 antagonists, including e.g., antibodies, useful in the methods described herein include but are not limited to e.g., those described in U.S. Pat. Nos. 6,808,710; 7,029,674; 7,101,550; 7,488,802; 7,521,051; 8,008,449; 8,088,905; 8,168,757; 8,460,886; 8,709,416; 8,951,518; 8,952,136; 8,993,731; 9,067,998; 9,084,776; 9,102,725; 9,102,727; 9,102,728; 9,109,034; 9,181,342; 9,205,148; 9,217,034; 9,220,776; 9,308,253; 9,358,289; 9,387,247 and 9,402,899; the disclosures of which are incorporated herein by reference in their entirety.

Pharmaceutical Preparations

Also provided are pharmaceutical preparations of the TCIP compounds. The TCIP compounds can be incorporated into a variety of formulations for administration to a subject. More particularly, the TCIP compounds of the present disclosure can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including intravenous, oral, buccal, rectal, parenteral, intraperitoneal, intradermal, transdermal, intratracheal, etc., administration. In pharmaceutical dosage forms, the compounds may be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of an oil-in-water emulsions. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The compounds can be utilized in aerosol formulation to be administered via inhalation. The compounds of the present disclosure can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present disclosure can be administered rectally via a suppository. The suppository can include vehicles such as cocoa butter, carbowaxes and polyethylene glycols, which melt at body temperature, yet are solidified at room temperature.

The compounds of this disclosure and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such as buffers, surfactants, antioxidants, viscosity modifying agents, preservatives and the like. Each of these components is well-known in the art. See, for example, U.S. Pat. No. 5,985,310, the disclosure of which is herein incorporated by reference. Other components suitable for use in the formulations of the present disclosure can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy. As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular peptidomimetic compound employed and the effect to be achieved, and the pharmacodynamics associated with each compound in the host.

Kits & Systems

Also provided are kits and systems that find use in practicing embodiments of the methods, such as those described as described above. The term "system" as employed herein refers to a collection of two or more different active agents, present in a single composition or in disparate compositions, that are brought together for the purpose of practicing the subject methods. The term "kit" refers to a packaged active agent or agents. For example, kits and systems for practicing the subject methods may include one or more pharmaceutical formulations. As such, in certain embodiments the kits may include a single pharmaceutical composition, present as one or more unit dosages, where the composition may include one or more expression/activity inhibitor compounds. In yet other embodiments, the kits may include two or more separate pharmaceutical compositions, each containing a different active compound.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. BRD4-BCL6 TCIPs
I. Synthesis and Characterization of TCIPs
A. General Synthesis Protocols
1. General Synthesis 1
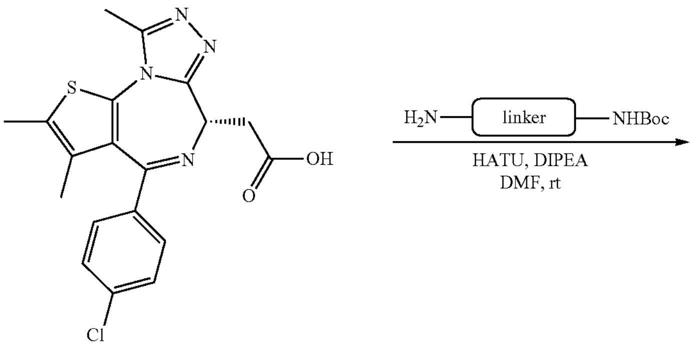
S1
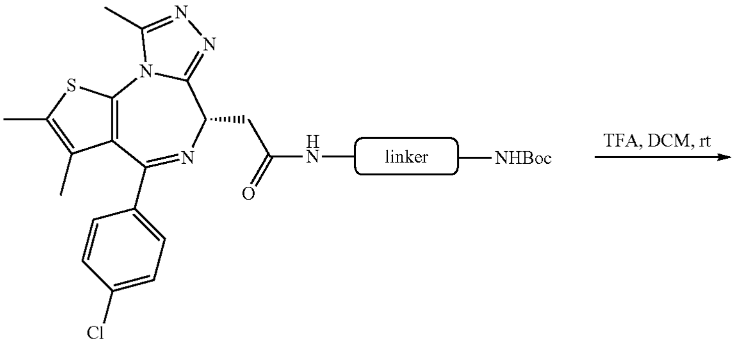
S2
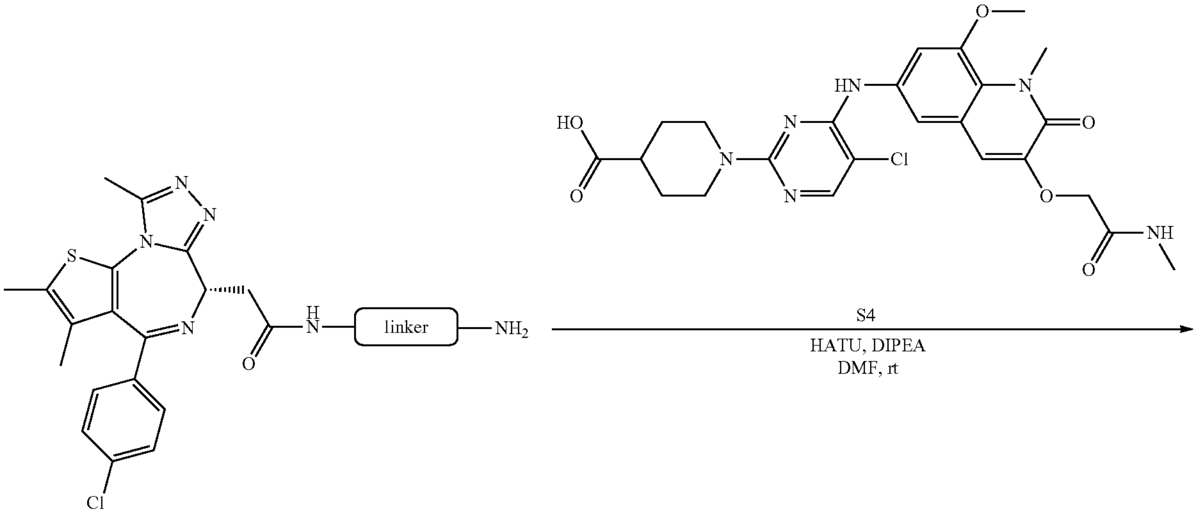
S3

-continued

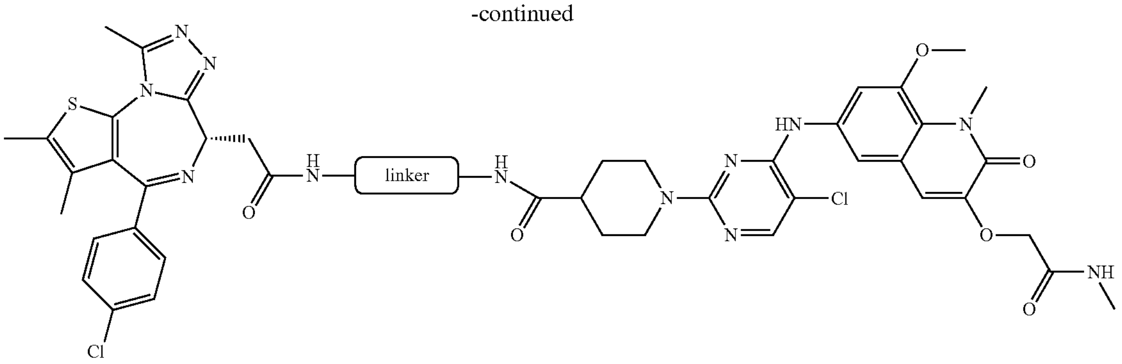

a. Step 1: Synthesis of Intermediate S2

To a mixture of JQ-1 carboxylic acid 1 (1.0 eq) and HATU (1.0 eq) DIPEA (3 eq) in DMF was added linker(1.2 eq), the mixture was stirred at room temperature for 1 hour. LC-MS indicated formation of desired product. The mixture was concentrated and purified via prep-HPLC to afford intermediate S2.

b. Step 2: Synthesis of Intermediate S3

To intermediate S2 was added a solution of DCM/Trifluoroacetic acid (3:1). The mixture was stirred at room temperature for 1 hour. LC-MS indicated formation of desired product. The mixture was concentrated under reduced pressure to give crude product which was used directly without future purification.

c. Step 3: Synthesis of Desired Product

To a mixture of 1-(5-chloro-4-((8-methoxy-1-methyl-3-(2-(methylamino)-2-oxoethoxy)-2-oxo-1,2-dihydroquinolin-6-yl)amino)pyrimidin-2-yl)piperidine-4-carboxylic acid (S4) (1.0 eq), HATU (1.0 eq), DIPEA (3 eq) in DMF was added intermediate S3 (1.2 eq), the mixture was stirred at room temperature for 1 hour. LC-MS indicated formation of desired product. The mixture was concentrated and purified via prep-HPLC to afford desired product.

2. General Synthesis 2

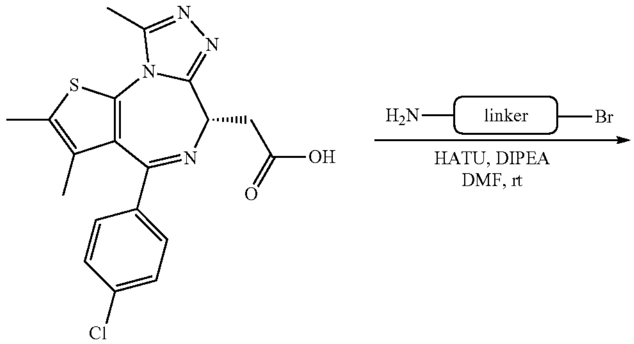

S1

-continued

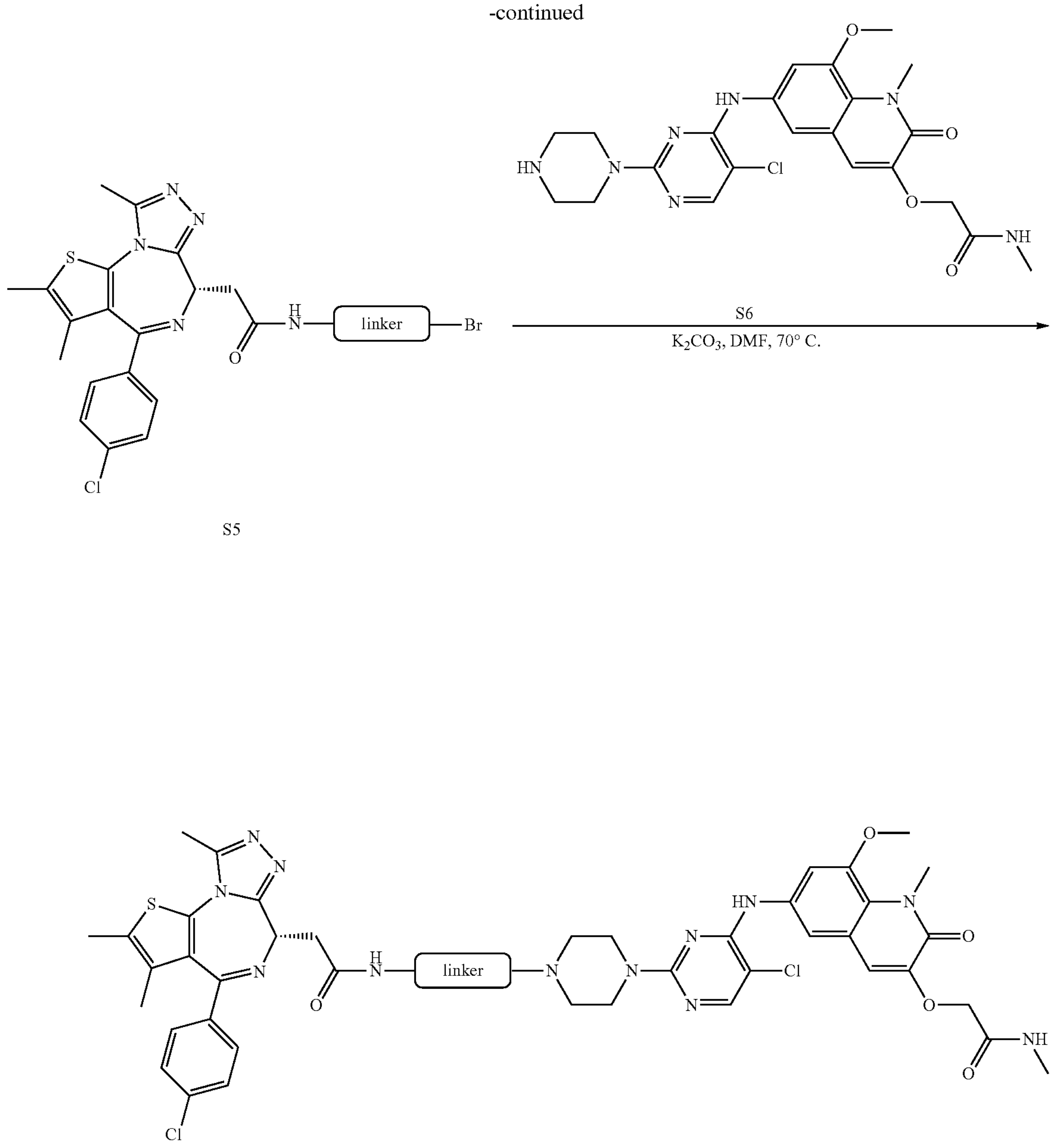

a. Step 1: Synthesis of Intermediate S5

To a mixture of JQ-1 carboxylic acid 1 (1.0 eq) and HATU (1.0 eq) DIPEA (3 eq) in DMF was added linker(1.2 eq), the mixture was stirred at room temperature for 1 hour. LC-MS indicated formation of desired product. The mixture was concentrated and purified via prep-HPLC to afford intermediate S5.

b. Step 2: Synthesis of Desired Product

To a mixture of 2-((6-((5-chloro-2-(piperazin-1-yl)pyrimidin-4-yl)amino)-8-methoxy-1-methyl-2-oxo-1,2-dihydroquinolin-3-yl)oxy)-N-methylacetamide (S6) (1.0 eq), $K_2CO_3$ (3.0 eq) in DMF was added intermediate S5 (1.3 eq), the mixture was stirred at 70° C. for 1 hour. LC-MS indicated formation of desired product. The mixture was concentrated and purified via prep-HPLC to afford desired product.

B. Synthesized Compounds and Characteristics

1. JWZ-7-6

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(6-(2-(4-(4-chlorophenyl)-2,3,9-trimethyl-6H-thieno[3,2-f][1,2,4]triazolo[4,3-a][1,4]diazepin-6-yl)acetamido)hexyl)piperidine-4-carboxamide(JWZ-7-6)

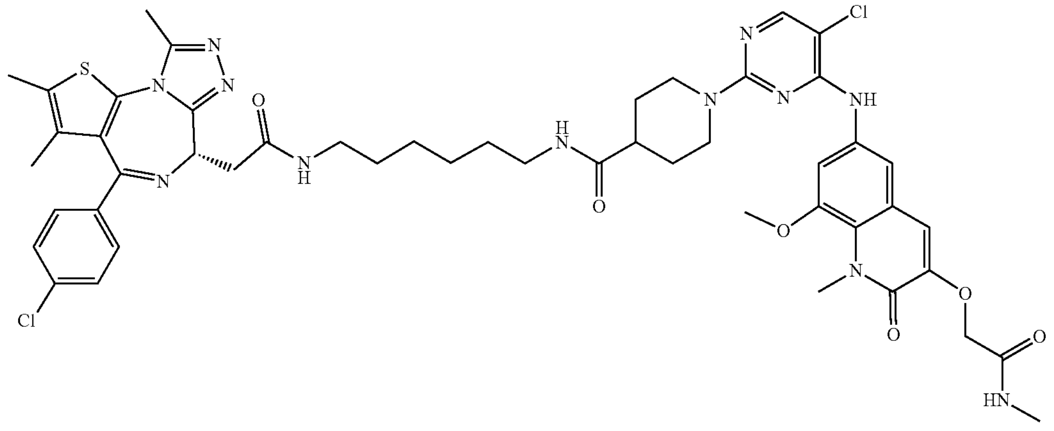

JWZ-7-6

LC-MS (ESI) m/z: 1011.4 $[M+H]^+$.

1H NMR (500 MHz, DMSO-d6) δ 8.98 (s, 1H), 8.09 (t, J=5.8 Hz, 1H), 8.03 (d, J=1.7 Hz, 1H), 7.88 (q, J=4.8 Hz, 1H), 7.71 (t, J=5.7 Hz, 1H), 7.44 (d, J=1.8 Hz, 2H), 7.40 (d, J=7.9 Hz, 2H), 7.36-7.31 (m, 2H), 6.94 (s, 1H), 4.48 (s, 2H), 4.43-4.37 (m, 3H), 3.79 (s, 3H), 3.78 (s, 3H), 3.17 (dd, J=15.0, 8.3 Hz, 1H), 3.13-3.03 (m, 2H), 3.02-2.97 (m, 1H), 2.94 (q, J=6.6 Hz, 2H), 2.85 (t, J=12.6 Hz, 2H), 2.58 (d, J=4.6 Hz, 3H), 2.52 (d, J=1.7 Hz, 3H), 2.32 (s, 3H), 1.64 (d, J=12.9 Hz, 2H), 1.53 (s, 3H), 1.48-1.27 (m, 6H), 1.24-1.16 (m, 4H).

2. JWZ-7-7

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(7-(2-(4-(4-chlorophenyl)-2,3,9-trimethyl-6H-thieno[3,2-f][1,2,4]triazolo[4,3-a][1,4]diazepin-6-yl)acetamido)heptyl)piperidine-4-carboxamide(JWZ-7-7)

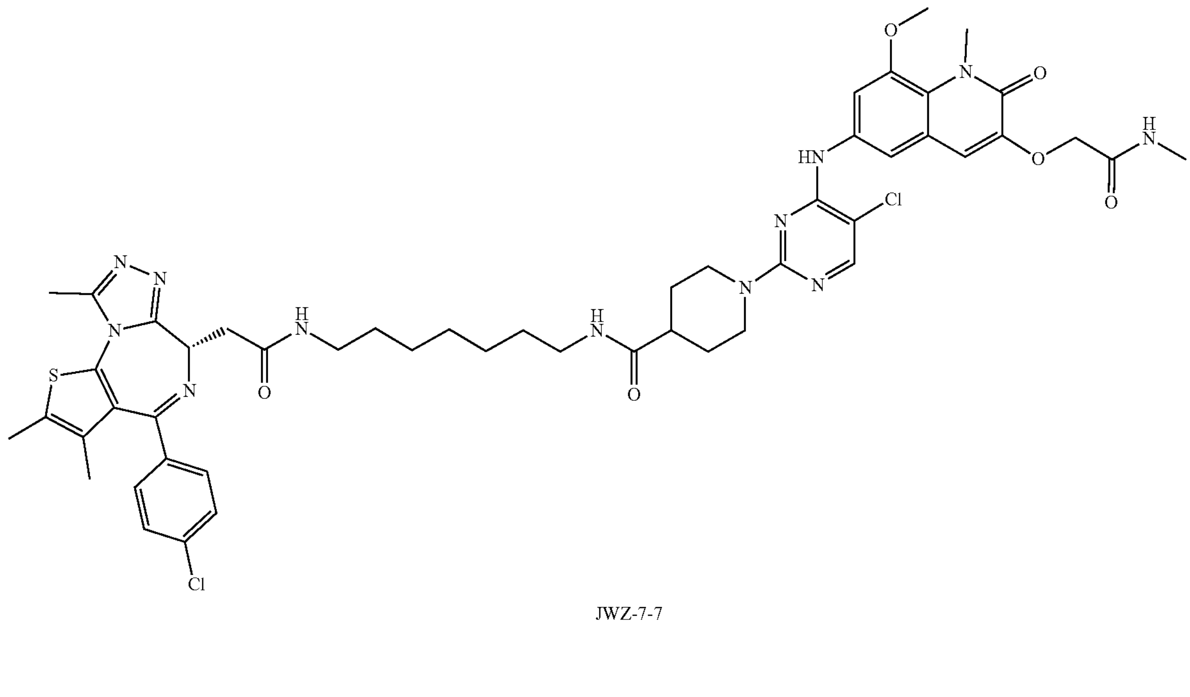

JWZ-7-7

LC-MS (ESI) m/z: 1025.4 $[M+H]^+$.

1H NMR (500 MHz, DMSO-d6) δ 8.96 (s, 1H), 8.09 (t, J=5.7 Hz, 1H), 8.03 (s, 1H), 7.88 (d, J=5.2 Hz, 1H), 7.70 (t, J=5.6 Hz, 1H), 7.44 (s, 2H), 7.41 (d, J=8.2 Hz, 2H), 7.34 (d, J=8.2 Hz, 2H), 6.94 (s, 1H), 4.48 (s, 2H), 4.46-4.35 (m, 3H), 3.79 (s, 3H), 3.77 (s, 3H), 3.14 (qd, J=15.0, 7.1 Hz, 2H), 3.02 (dq, J=13.0, 6.7 Hz, 2H), 2.94 (q, J=6.7 Hz, 2H), 2.84 (t, J=12.5 Hz, 2H), 2.58 (d, J=4.6 Hz, 3H), 2.52 (s, 3H), 2.44 (d, J=3.0 Hz, 8H), 2.33 (s, 3H), 1.64 (d, J=12.8 Hz, 2H), 1.55 (s, 3H), 1.49-1.39 (m, 2H), 1.33 (dt, J=27.4, 6.9 Hz, 4H), 1.18 (p, J=7.7, 6.9 Hz, 6H).

3. JWZ-7-13

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(2-(4-(2-(2-(4-(4-chlorophenyl)-2,3,9-trimethyl-6H-thieno[3,2-f][1,2,4]triazolo[4,3-a][1,4]diazepin-6-yl)acetamido)ethyl)piperazin-1-yl)ethyl)piperidine-4-carboxamide(JWZ-7-13)

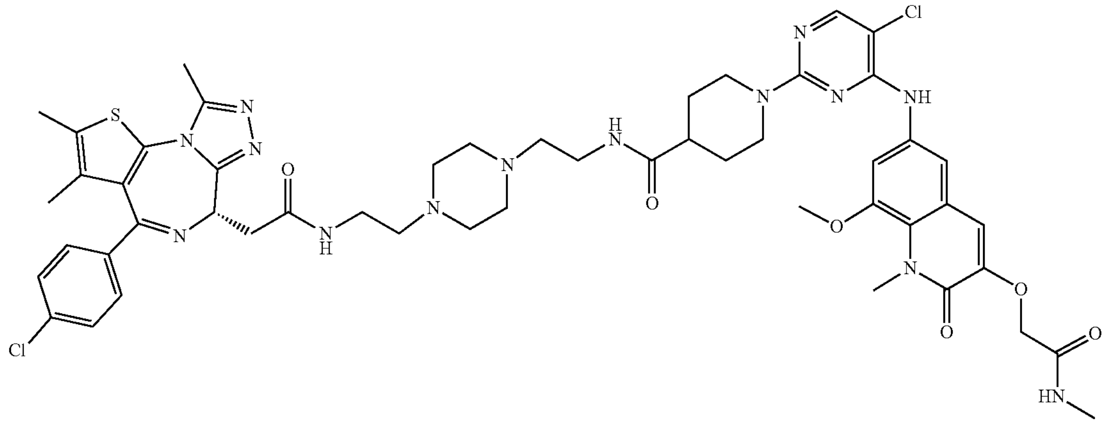

JWZ-7-13

LC-MS (ESI) m/z: 1067.4 $[M+H]^+$.

1H NMR (500 MHz, DMSO-d6) δ 8.90 (s, 1H), 8.34 (s, 1H), 8.02 (s, 1H), 7.96 (s, 1H), 7.90 (q, J=4.4 Hz, 1H), 7.49-7.44 (m, 2H), 7.42 (d, J=8.3 Hz, 2H), 7.35 (d, J=8.2 Hz, 2H), 6.94 (s, 1H), 4.48 (s, 2H), 4.46-4.40 (m, 6H), 3.80 (s, 3H), 3.79 (s, 3H), 3.43-3.15 (m, 10H), 2.97-2.79 (m, 8H), 2.58 (d, J=4.6 Hz, 3H), 2.53 (s, 3H), 2.34 (s, 3H), 1.68 (d, J=12.6 Hz, 2H), 1.55 (s, 3H), 1.43 (q, J=12.1, 11.6 Hz, 2H).

4. JWZ-7-14

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(3-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)propyl)piperidine-4-carboxamide(JWZ-7-14)

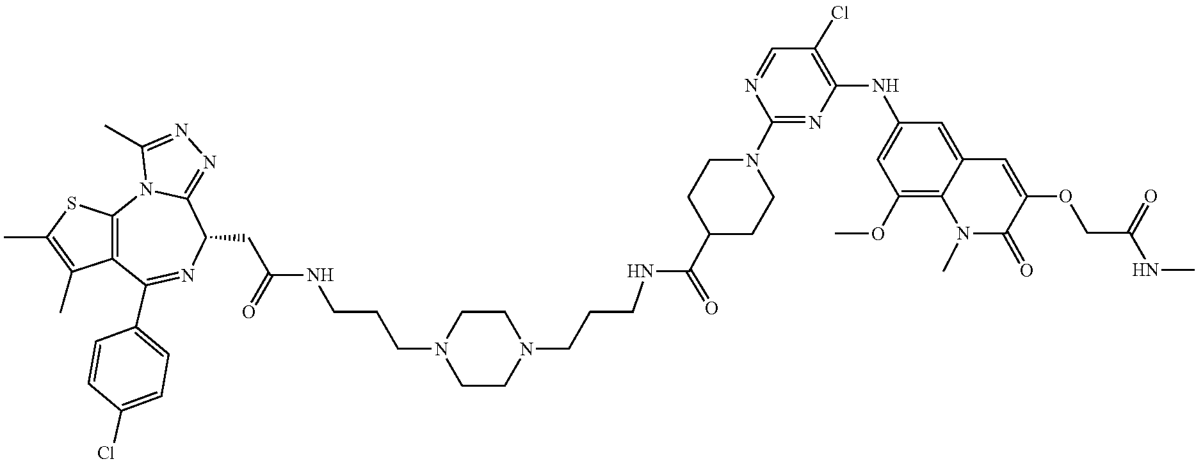

JWZ-7-14

LC-MS (ESI) m/z: 1067.4 $[M+H]^+$.

1H NMR (500 MHz, DMSO-d6) δ 8.83 (s, 1H), 8.27 (d, J=6.4 Hz, 1H), 8.02 (d, J=2.9 Hz, 1H), 7.90 (d, J=5.5 Hz, 2H), 7.49 (d, J=2.4 Hz, 1H), 7.45 (d, J=2.5 Hz, 1H), 7.43 (dd, J=8.6, 2.9 Hz, 2H), 7.38-7.34 (m, 2H), 6.93 (d, J=3.0 Hz, 1H), 4.49 (d, J=2.8 Hz, 2H), 4.47-4.41 (m, 3H), 3.80 (s, 3H), 3.79 (s, 3H), 3.27-3.12 (m, 5H), 3.04 (q, J=6.7, 6.1 Hz, 4H), 2.99-2.79 (m, 8H), 2.58 (d, J=4.5 Hz, 3H), 2.53 (d, J=2.9 Hz, 3H), 2.35 (d, J=2.9 Hz, 3H), 2.30 (s, 1H), 1.75-1.61 (m, 6H), 1.56 (d, J=2.8 Hz, 3H), 1.50-1.37 (m, 3H), 1.23-1.13 (m, 2H).

5. JWZ-7-15

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(9-(2-(4-(4-chlorophenyl)-2,3,9-trimethyl-6H-thieno[3,2-f][1,2,4]triazolo[4,3-a][1,4]diazepin-6-yl)acetamido)nonyl)piperidine-4-carboxamide(JWZ-7-15)

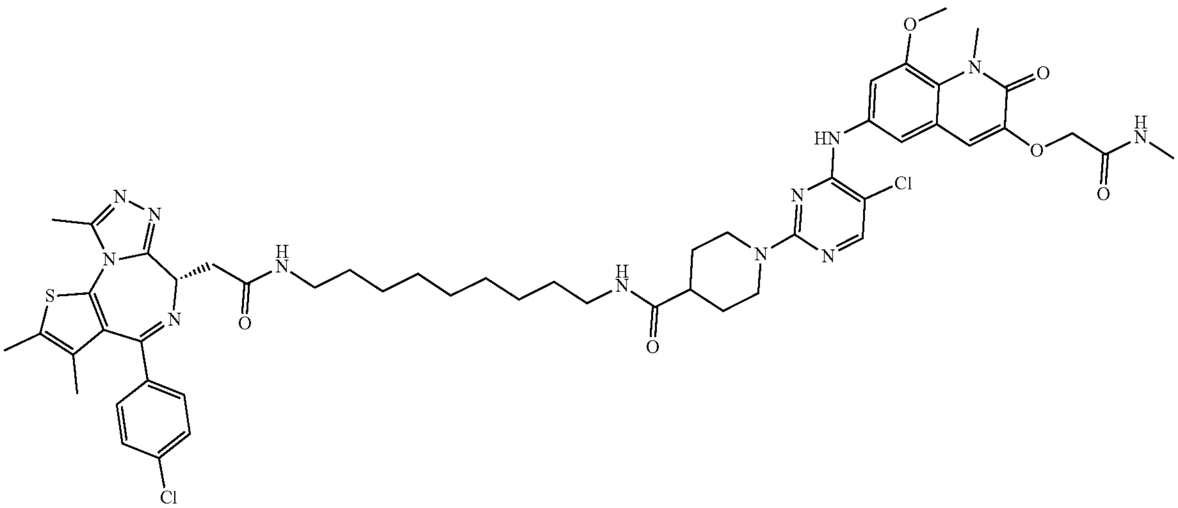

JWZ-7-15

LC-MS (ESI) m/z: 1053.4 $[M+H]^+$.

1H NMR (500 MHz, DMSO-d6) δ 8.86 (s, 1H), 8.08 (t, J=5.7 Hz, 1H), 8.01 (s, 1H), 7.89 (d, J=4.7 Hz, 1H), 7.69 (t, J=5.6 Hz, 1H), 7.46 (s, 2H), 7.40 (d, J=8.8 Hz, 2H), 7.37-7.32 (m, 2H), 6.93 (s, 1H), 4.48 (s, 2H), 4.45-4.39 (m, 3H), 3.80 (s, 3H), 3.78 (s, 3H), 3.22-2.97 (m, 7H), 2.93 (q, J=6.6 Hz, 3H), 2.83 (td, J=12.9, 2.7 Hz, 3H), 2.58 (d, J=4.7 Hz, 3H), 2.52 (s, 3H), 2.33 (s, 3H), 2.30 (dt, J=7.5, 3.7 Hz, 1H), 1.66-1.60 (m, 2H), 1.55 (s, 3H), 1.47-1.26 (m, 8H), 1.22-1.10 (m, 8H).

6. JWZ-7-20

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(10-(2-(4-(4-chlorophenyl)-2,3,9-trimethyl-6H-thieno[3,2-f][1,2,4]triazolo[4,3-a][1,4]diazepin-6-yl)acetamido)decyl)piperidine-4-carboxamide (JWZ-7-20)

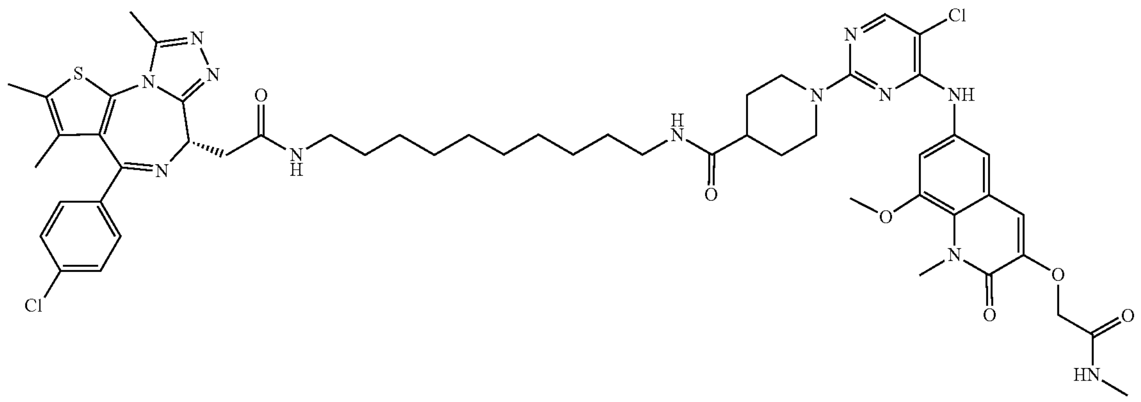

JWZ-7-20

LC-MS (ESI) m/z: 1053.4 $[M+H]^+$.

1H NMR (500 MHz, DMSO-d6) δ 9.02 (s, 1H), 8.16 (t, J=5.7 Hz, 1H), 8.10 (s, 1H), 7.97 (d, J=4.7 Hz, 1H), 7.76 (t, J=5.6 Hz, 1H), 7.53 (s, 2H), 7.50-7.41 (m, 4H), 7.01 (s, 1H), 4.55 (s, 2H), 4.53-4.45 (m, 3H), 3.87 (s, 3H), 3.86 (s, 3H), 3.25 (dd, J=14.9, 8.5 Hz, 2H), 3.20-3.09 (m, 3H), 3.09-2.98 (m, 4H), 2.92 (td, J=13.0, 2.8 Hz, 3H), 2.65 (d, J=4.6 Hz, 3H), 2.60 (s, 3H), 2.41 (s, 3H), 2.39-2.35 (m, 1H), 1.74-1.68 (m, 2H), 1.62 (s, 3H), 1.51 (dd, J=12.1, 3.8 Hz, 3H), 1.43 (t, J=7.1 Hz, 2H), 1.36 (t, J=6.8 Hz, 2H), 1.29-1.16 (m, 11H).

7. JWZ-7-22

(S)-2-((6-((5-chloro-2-(4-(11-(2-(4-(4-chlorophenyl)-2,3,9-trimethyl-6H-thieno[3,2-f][1,2,4]triazolo[4,3-a][1,4]diazepin-6-yl)acetamido)undecyl)piperazin-1-yl)pyrimidin-4-yl)amino)-8-methoxy-1-methyl-2-oxo-1,2-dihydroquinolin-3-yl)oxy)-N-methylacetamide (JWZ-7-22)

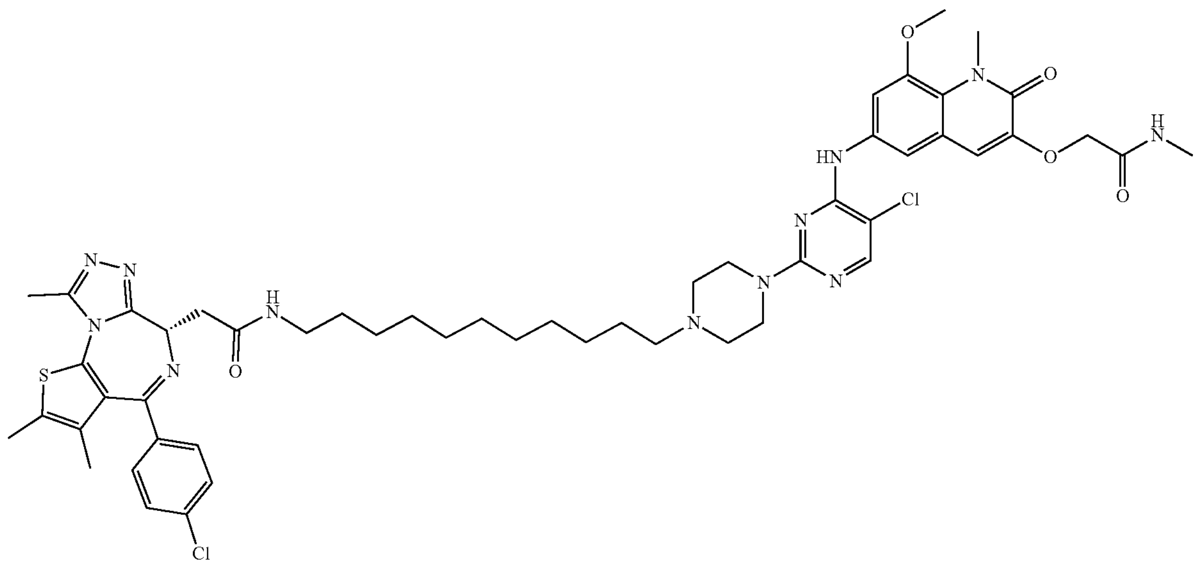

JWZ-7-22

LC-MS (ESI) m/z: 1039.4 $[M+H]^+$.

1H NMR (500 MHz, DMSO-d6) δ 9.66 (s, 1H), 9.01 (s, 1H), 8.16 (d, J=3.2 Hz, 1H), 8.00 (q, J=4.7 Hz, 1H), 7.56 (d, J=2.3 Hz, 1H), 7.48 (d, J=8.7 Hz, 2H), 7.46-7.41 (m, 2H), 7.08 (s, 1H), 4.57 (s, 2H), 4.50 (dd, J=8.3, 5.8 Hz, 3H), 3.88 (s, 3H), 3.87 (s, 3H), 3.32-2.99 (m, 12H), 2.66 (d, J=4.6 Hz, 3H), 2.60 (s, 3H), 2.41 (s, 3H), 1.69-1.64 (m, 2H) 1.63 (s, 3H), 1.44 (t, J=7.0 Hz, 2H), 1.35-1.20 (m, 14H).

8. JWZ-7-23

(S)-2-((6-((5-chloro-2-(4-(8-(2-(4-(4-chlorophenyl)-2,3,9-trimethyl-6H-thieno[3,2-f][1,2,4]triazolo[4,3-a][1,4]diazepin-6-yl)acetamido)octyl)piperazin-1-yl)pyrimidin-4-yl)amino)-8-methoxy-1-methyl-2-oxo-1,2-dihydroquinolin-3-yl)oxy)-N-methylacetamide (JWZ-7-23)

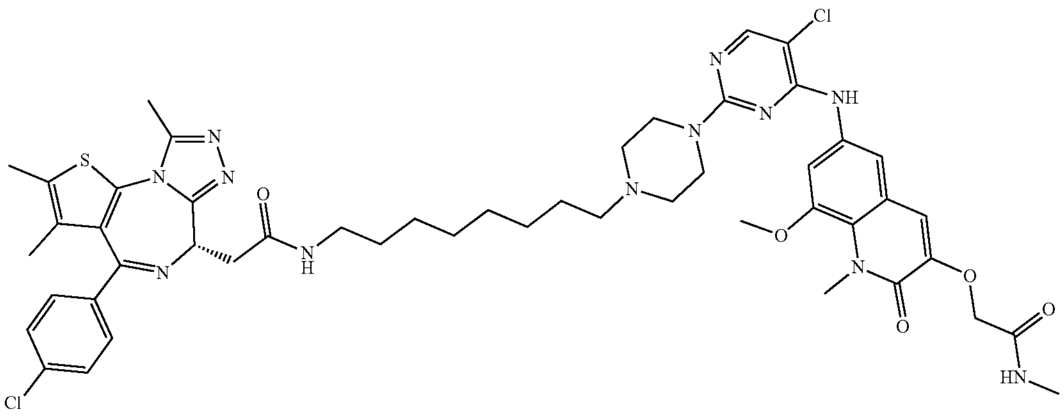

JWZ-7-23

LC-MS (ESI) m/z: 997.4 [M+H]$^+$.

1H NMR (500 MHz, DMSO-d6) δ 9.65 (s, 1H), 8.93 (s, 1H), 8.10 (d, J=5.7 Hz, 1H), 8.08 (s, 1H), 7.91 (q, J=4.6 Hz, 1H), 7.48 (d, J=2.3 Hz, 1H), 7.42 (d, J=1.6 Hz, 1H), 7.40 (s, 1H), 7.38-7.33 (m, 2H), 7.00 (s, 1H), 4.50 (s, 2H), 4.47-4.40 (m, 3H), 3.80 (s, 3H), 3.80 (s, 3H), 3.22-3.10 (m, 6H), 3.06-2.92 (m, 6H), 2.58 (d, J=4.7 Hz, 3H), 2.52 (s, 3H), 2.34 (s, 3H), 1.60 (d, J=9.2 Hz, 2H), 1.55 (s, 3H), 1.36 (d, J=6.4 Hz, 2H), 1.22 (s, 6H), 1.17 (s, 2H).

9. JWZ-7-24

(S)-2-((6-((5-chloro-2-(4-(1-(4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)piperazin-1-yl)pyrimidin-4-yl)amino)-8-methoxy-1-methyl-2-oxo-1,2-dihydroquinolin-3-yl)oxy)-N-methylacetamide (JWZ-7-24)

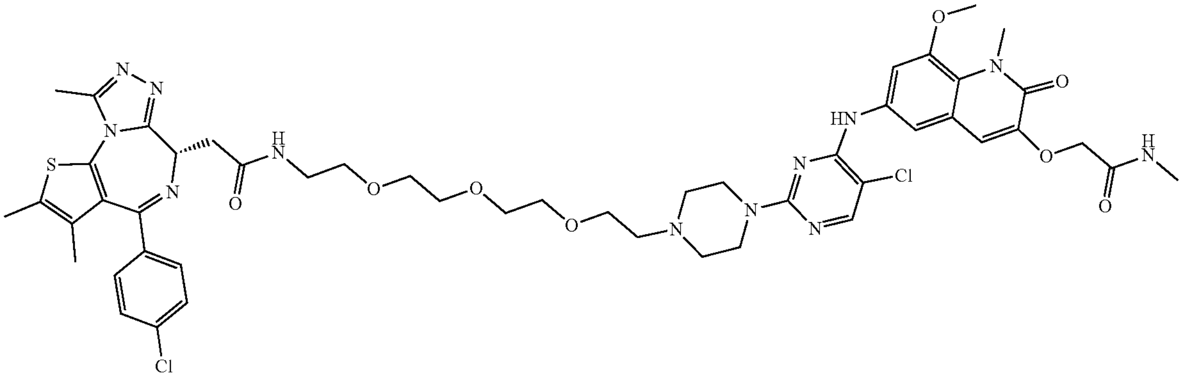

JWZ-7-24

LC-MS (ESI) m/z: 1045.4 [M+H]$^+$.

1H NMR (500 MHz, DMSO-d6) δ 9.85 (s, 1H), 9.00 (s, 1H), 8.25 (t, J=5.7 Hz, 1H), 8.14 (s, 1H), 8.04 (q, J=4.7 Hz, 1H), 7.53 (d, J=2.3 Hz, 1H), 7.48 (d, J=8.8 Hz, 2H), 7.45-7.39 (m, 2H), 7.08 (s, 1H), 4.56 (s, 2H), 4.54-4.47 (m, 3H), 3.88 (s, 3H), 3.87 (s, 3H), 3.79 (t, J=5.0 Hz, 2H), 3.64-3.51 (m, 12H), 3.43 (t, J=5.9 Hz, 2H), 3.34 (t, J=5.1 Hz, 2H), 3.29-3.21 (m, 4H), 2.66 (d, J=4.6 Hz, 3H), 2.59 (s, 3H), 2.40 (s, 3H), 1.61 (s, 3H).

10. JWZ-7-97

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(3-(3-(2-(4-(4-chlorophenyl)-2,3,9-trimethyl-6H-thieno[3,2-f][1,2,4]triazolo[4,3-a][1,4]diazepin-6-yl)acetamido)propoxy)propyl)piperidine-4-carboxamide (JWZ-7-97)

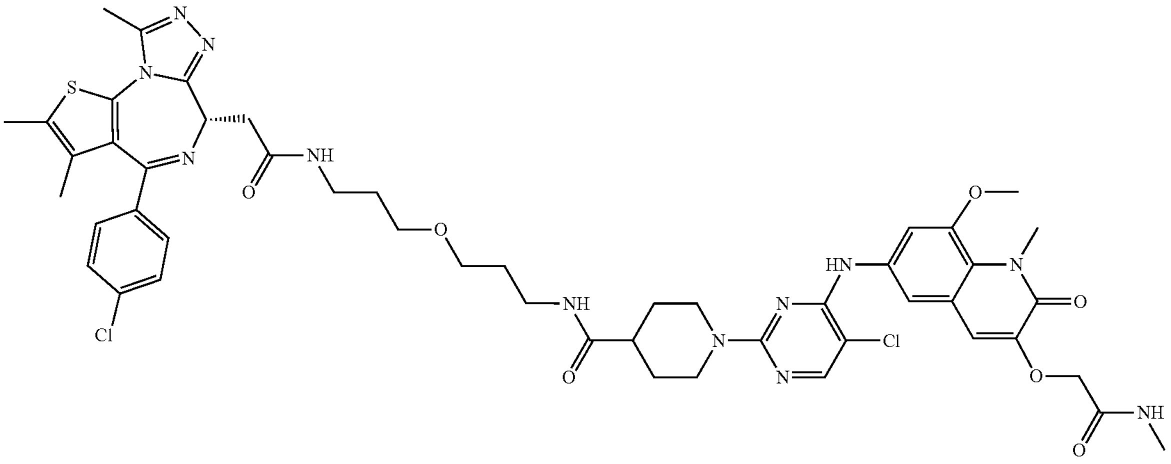

JWZ-7-97

LC-MS (ESI) m/z: 1027.4 $[M+H]^+$.

1H NMR (500 MHz, DMSO-d6) δ 9.10 (s, 1H), 8.15 (t, J=5.7 Hz, 1H), 8.04 (s, 1H), 7.90 (q, J=4.6 Hz, 1H), 7.75 (t, J=5.7 Hz, 1H), 7.43 (d, J=1.5 Hz, 2H), 7.41 (d, J=8.8 Hz, 2H), 7.36-7.32 (m, 2H), 6.95 (s, 1H), 4.48 (s, 2H), 4.44 (dd, J=8.1, 6.2 Hz, 1H), 4.36 (d, J=13.1 Hz, 2H), 3.79 (s, 3H), 3.78 (s, 3H), 3.29 (dt, J=24.4, 6.2 Hz, 4H), 3.22-2.98 (m, 6H), 2.84 (t, J=12.9 Hz, 2H), 2.58 (d, J=4.6 Hz, 3H), 2.52 (s, 3H), 2.32 (s, 3H), 1.67-1.56 (m, 4H), 1.53 (d, J=2.6 Hz, 4H), 1.44 (qd, J=12.5, 4.0 Hz, 2H), 1.16 (s, 1H).

11. JWZ-7-98

(S)-2-((6-((5-chloro-2-(4-(2-(2-(2-(4-(4-chlorophenyl)-2,3,9-trimethyl-6H-thieno[3,2-f][1,2,4]triazolo[4,3-a][1,4]diazepin-6-yl)acetamido)ethyl)-2,7-diazaspiro[3.5]nonane-7-carbonyl)piperidin-1-yl)pyrimidin-4-yl)amino)-8-methoxy-1-methyl-2-oxo-1,2-dihydroquinolin-3-yl)oxy)-N-methylacetamide (JWZ-7-98)

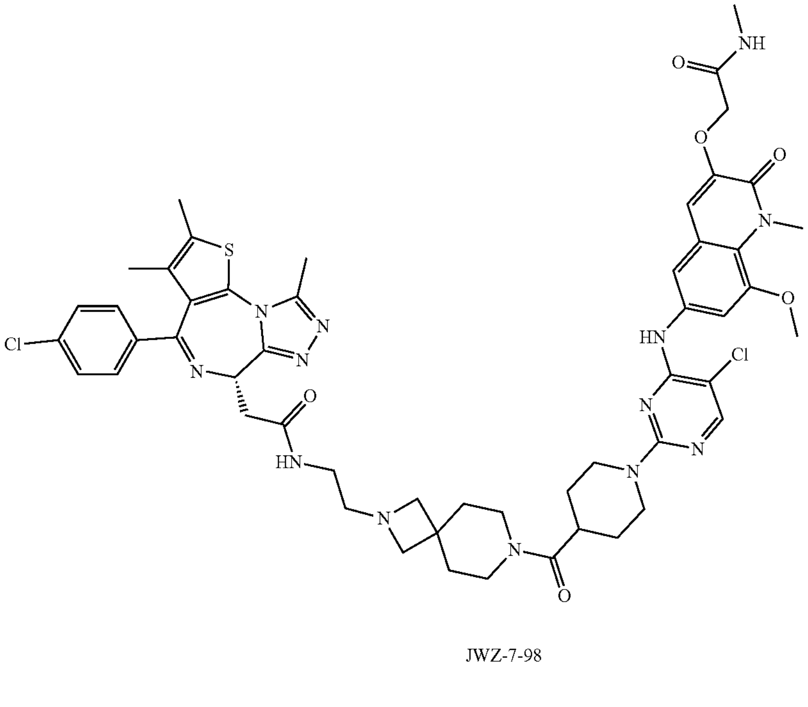 [SMILES: CNC(=O)COc1cc2cc(Nc3nc(N4CCC(C(=O)N5CCC6(CC5)CN(CCNC(=O)C[C@@H]5N=C(c7ccc(Cl)cc7)c7c(sc(C)c7C)-n7c(C)nnc75)C6)CC4)ncc3Cl)cc(OC)c2n(C)c1=O]

JWZ-7-98

LC-MS (ESI) m/z: 1064.4 [M+H]+.

1H NMR (500 MHz, DMSO-d6) δ 9.07 (s, 1H), 8.14 (s, 1H), 8.04 (s, 1H), 7.90 (q, J=4.6 Hz, 1H), 7.75 (t, J=5.7 Hz, 1H), 7.43 (d, J=1.5 Hz, 2H), 7.41 (d, J=8.8 Hz, 2H), 7.36-7.32 (m, 2H), 6.95 (s, 1H), 4.64-4.62 (m, 1H), 4.50-4.44 (m, 1H), 4.40 (d, J=13.3 Hz, 2H), 3.79 (dd, J=8.4, 3.6 Hz, 2H), 3.71 (d, J=6.6 Hz, 1H), 3.58-3.17 (m, 4H), 2.93 (q, J=14.1 Hz, 1H), 2.57 (d, J=4.6 Hz, 3H), 2.52 (d, J=4.9 Hz, 3H), 2.35 (s, 3H), 1.78 (dd, J=50.1, 24.2 Hz, 4H), 1.62-1.52 (m, 6H), 1.44 (q, J=12.6 Hz, 2H).

12. JWZ-7-100

(S)-1-(5-chloro-4-((8-methoxy-1-methyl-3-(2-(methylamino)-2-oxoethoxy)-2-oxo-1,2-dihydroquinolin-6-yl)amino)pyrimidin-2-yl)-N-(3-((3-(2-(4-(4-chlorophenyl)-2,3,9-trimethyl-6H-thieno[3,2-f][1,2,4]triazolo[4,3-a][1,4]diazepin-6-yl)acetamido)propyl)(methyl)amino)propyl)piperidine-4-carboxamide (JWZ-7-100)

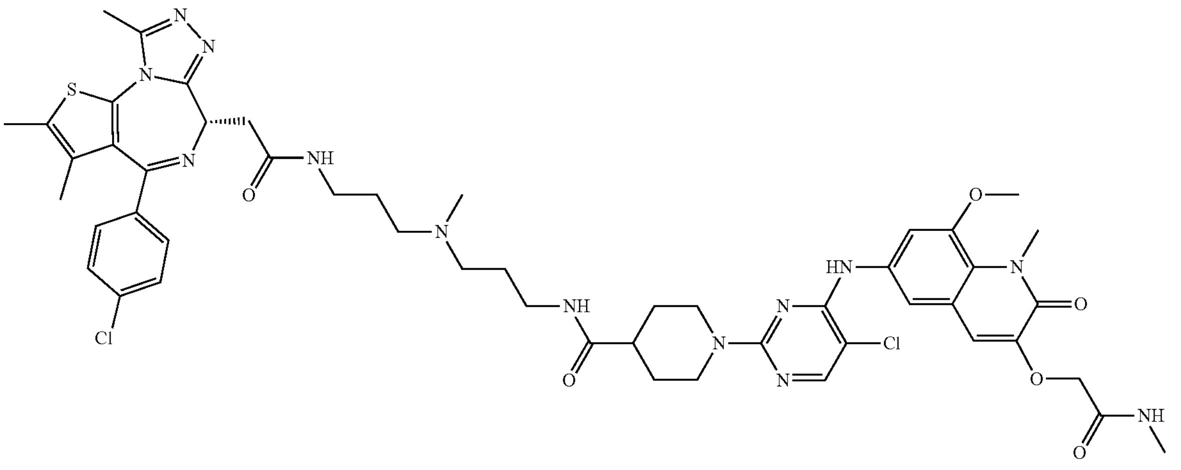

JWZ-7-100

LC-MS (ESI) m/z: 1040.4 [M+H]+.

1H NMR (500 MHz, DMSO-d6) δ 9.47-9.33 (m, 1H), 8.94 (s, 1H), 8.32 (q, J=6.2 Hz, 1H), 8.02 (s, 1H), 7.92 (dq, J=18.7, 5.4, 4.8 Hz, 2H), 7.47-7.40 (m, 4H), 7.35 (d, J=8.3 Hz, 1H), 6.94 (s, 1H), 4.48 (s, 2H), 4.46-4.39 (m, 2H), 3.80 (s, 3H), 3.78 (s, 3H), 3.28-3.11 (m, 4H), 3.09-2.80 (m, 10H), 2.67 (dd, J=7.9, 4.8 Hz, 3H), 2.58 (d, J=4.6 Hz, 3H), 2.53 (s, 3H), 2.32 (d, J=3.6 Hz, 3H), 1.79-1.64 (m, 6H), 1.54 (s, 3H), 1.49-1.38 (m, 2H).

II. JWZ-7-7 Rewires Cancer Drivers to Activate Proapoptotic Genes in DLBCL

Figure 3:
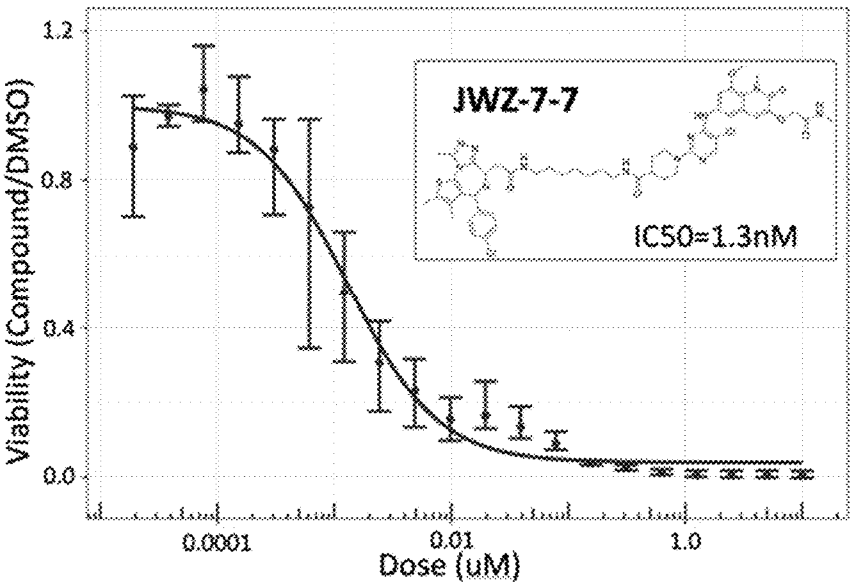
FIG. 3 illustrates that the TCIP JWZ-7-7 kills CHOP-resistant, p53 negative Karpas422 DLBCL at 1.3 nM. Data is the mean of 4 biologic repeats by 3 experimenters.

As shown in FIG. 3, the BRD4-BCL6 TCIP (JWZ-7-7) as illustrated in FIG. 2 and synthesized as described above has a 1.3 nM EC50 for killing DLBCL cells. JWZ-7-7 reprograms the normal negative feedback regulation of BCL6 into a powerful positive feedback loop at 1 nanomolar (FIG. 3). The effectiveness of this molecule was examined in 16 DLBCL cell lines, 4 follicular lymphoma cell lines, 5 breast cancer cell lines, 2 lung adenocarcinoma cell lines and 3 small cell lung cancer cell lines and find that killing is highly correlated with BCL6 expression ($R^2$=0.68). Notably, primary human fibroblasts are not killed at 400 nM, which is 400-fold higher concentration than the effective dose on DLBCL with BCL6 mutation/overexpression. Hence, JWZ-7-7 is a relatively non-toxic, highly potent new therapy for human DLBCL.

IIIA. Dominant Gain of Function Via JWZ-7-7

RNA-seq and Western blotting studies using JWZ-7-7 have demonstrated robust activation of target apoptotic genes (at 24 hours) that are normally repressed by BCL6, including BCL6 itself and the master activator of cell death, FOXO3. See FIGS. 4A & 4B. Using RNA-seq, 60% of BCL6 repressed genes are activated by JWZ-7-7. The activation of these genes is evident within 15 minutes of adding JWZ-7-7 to the media over the cells by the phosphorylation of serine 2 of RNA polymerase II indicating elongating transcription complexes.

Within one hour of adding JWZ-7-7, BRD4 is recruited to the promoters of known BCL6 target genes including the region mutated in BCL6 that is a cluster of BCL6 binding sites normally used for repression. The addition of BRD4 to the promoters of BCL6 target genes increases occupancy of the promoters by about 50%, while about 10% of BRD4 is lost from enhancers and super enhancers over the genome. Therefore, it was concluded that about 10% of total BRD4 is borrowed from enhancers and relocalized to promoters of BCL6 target genes indicating a gain-of-function at the BCL6 promoters.

IIIB. Rewiring the Cancer Driver to Activate Cell Death

Normally BCL6 represses cell death and allows the cancer cell to survive thereby providing a driving force for the survival of the cancer cell. JWZ-7-7 rewires the cancer cell so that BCL6 activates cell death genes by recruiting BRD4 to the BCL6 promoter and activating transcription of BCL6 which in turn activates proapoptotic genes resulting in rapid cell death by a variety of assays including resazurin assay, TUNNEL and Annexin 5. The loss of viability likely leads to the reduction in expression of MYC (FIG. 4B) as the DNA of the cells is fragmented.

IIIC. Effect on Cell Death

It was found that 4 hours exposure to 10 nM JWZ-7-7 followed by washout is sufficient to give robust killing, similar to exposure for 72 hours. It is believed that this reflects either the stability of the ternary complex between BRD4, JWZ-7-7 and BCL6 or the execution point of the induced genes involved in apoptosis. Rescue experiments—It was found that both JQ1 and BI3812 rescue cell death induced by 5 nM JWZ-7-7 as predicted if the ternary complex was essential for killing.

IV. JWZ-7-7 (TCIP1) Selectively Kills SCLC in Tissue Culture

Figure 5:
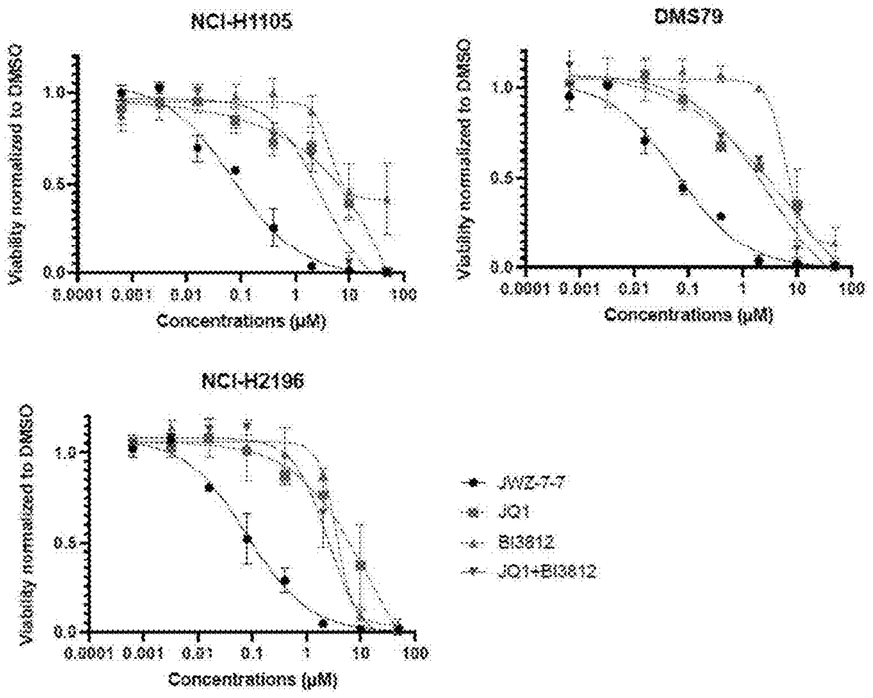
FIG. 5 provides dose response curves of JWZ-7-7, BI-3812, JQ1, and combinations on three small cell lung cancer lines (NCI-H1105, DMS-79, NCI-H2196).

IC50 of JWZ-7-7, BI-3812, JQ1, and combinations were calculated based on a dose response curve on three small cell lung cancer lines (FIG. 5). The dose response curve on viability was performed in technical replicates and biological triplicate after treating cells for 72 hours across a broad range of concentrations via serial dilutions. Viable cells were measured after treatment via a resazurin assay. The signal for viable assays was normalized to the DMSO treated negative control. A four-parameter non-linear fit was performed to fit a curve to calculate the IC50 for each of the cell lines. The table below describes the calculated IC50 across JWZ-7-7, JQ1, BI-3812 and combination of JQ1 and BI-3812 after 72 h treatment in technical replicates and biological triplicates. The table also highlights the expression level of BCL6 and BRD4 in each of the cell lines tested as described in the Cancer Cell Line Encyclopedia. Based on these results, JWZ-7-7 leads to significant loss of viability in the six SCLC cell lines after 72 h treatment.

| Cell Line | BCL6 (TPM) | BRD4 (TPM) | JWZ-7-7 IC50 | JQ1 IC50 | BI-3812 IC50 | JQ1 + BI-3812 IC50 |
|---|---|---|---|---|---|---|
| NCI-H1105 | 100.97 | 75.27 | 0.075 μM | Unstable | 4.3 μM | 3.1 μM |
| DMS-79 | 63.62 | 51.3 | 0.066 μM | 10.05 μM | 6.1 μM | 2.9 μM |
| NCI-H2196 | 62.47 | 46.97 | 0.081 μM | 14.4 μM | 3.5 μM | 2.5 μM |

V. JWZ-7-7 (TCIP) Forms a Ternary Complex with BCL6 and BRD4

Figure 6:
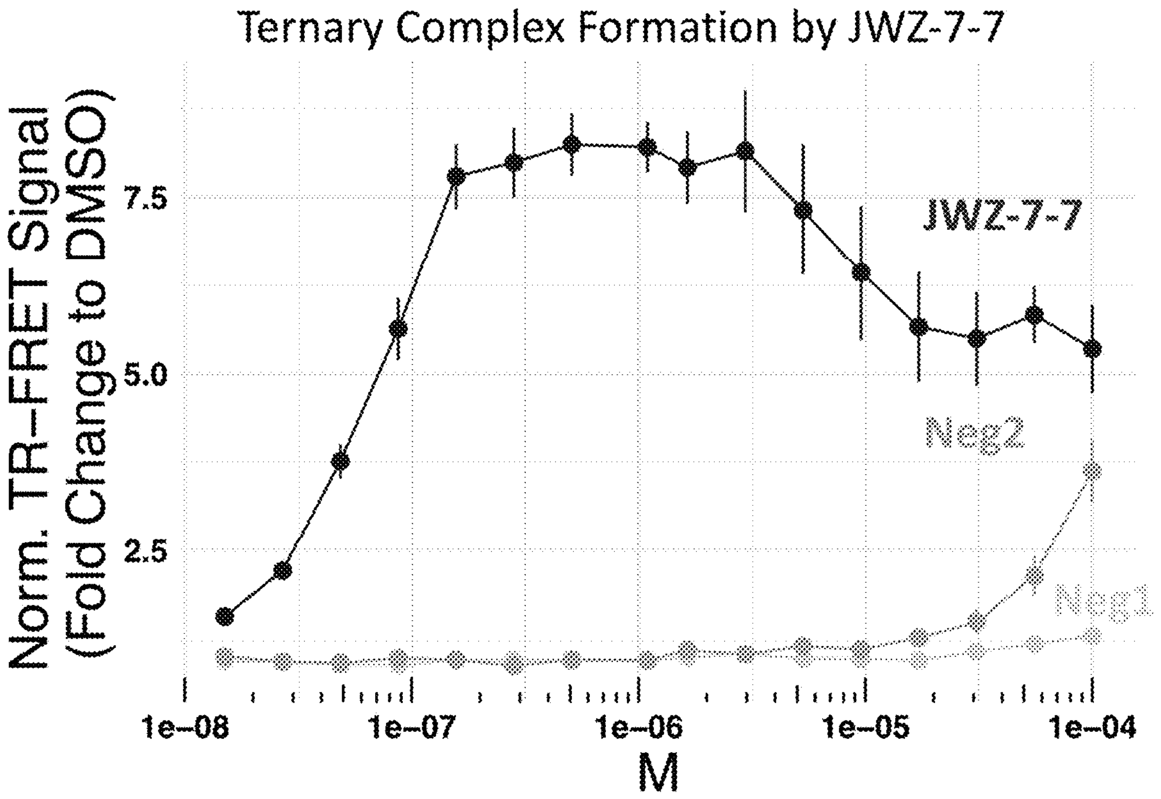
FIG. 6 provides the results of a TR-FRET (Time-Resolved Fluorescence Resonance Energy Transfer) assay to detect ternary complex formation between JWZ-7-7, BRD4 and BCL6.

FIG. 6 illustrates the results of TR-FRET (Time-Resolved Fluorescence Resonance Energy Transfer) assay to detect ternary complex formation between JWZ-7-7, BRD4 and BCL6. The upper curve is the signal generated by the addition of JWZ-7-7 with purified six-histidine-tagged bromodomain 1 of BRD4 and biotinylated BTB domain of BCL6, in combination with a terbium-conjugated anti-histidine antibody and FITC-conjugated streptavidin. Reaction was incubated for 1 hr at room temperature, and subsequently the fluorescence at 520 nm and 490 nm was measured. The 520 nm/490 nm ratio is plotted respective to DMSO control. The two lower curves are performed by addition of Neg1 and Neg2 instead of JWZ-7-7. Compounds other than JWZ-7-7 that showed ternary complex formation are: XFL-03-018, JWZ-7-6, XFL-03-017, JWZ-7-23, JWZ-7-15, JWZ-7-20, JWZ-7-22, XFL-01-186, JWZ-7-97, XFL-01-173, XFL-01-185, JWZ-7-98, JWZ-7-100, JWZ-7-13, and JWZ-7-14. The structure of JWZ-7-7 is provided in FIG. 2 and the structures of Neg1 and Neg2 are provided below:

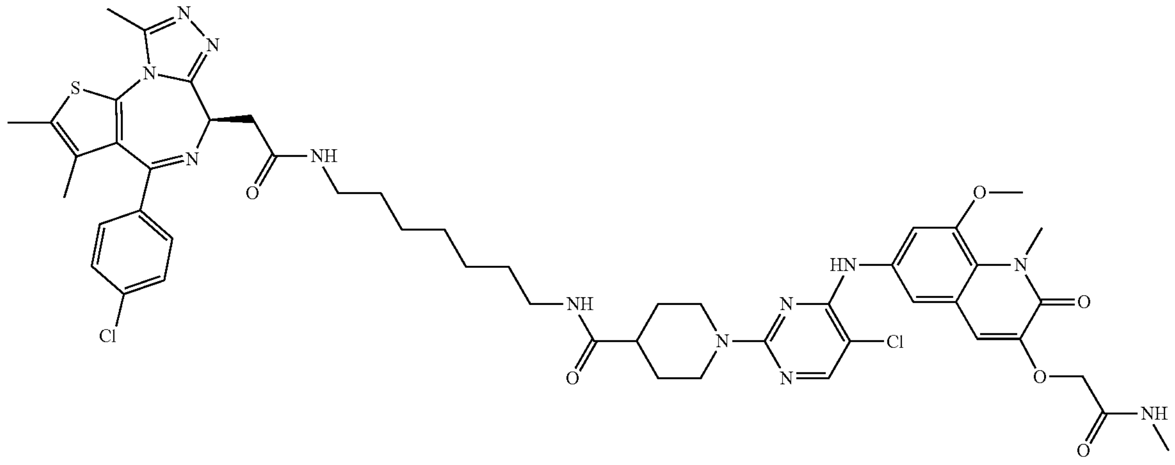

JWZ-7-7-Neg1

-continued

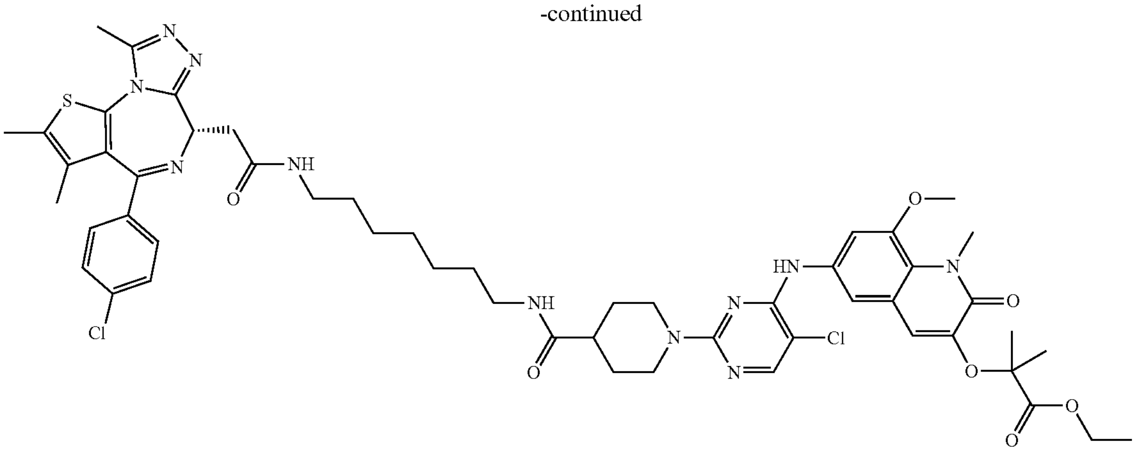

JWZ-7-7-Neg2

VI. In Vivo Target Engagement by JWZ-7-7 (TCIP1)

Figure 7A:
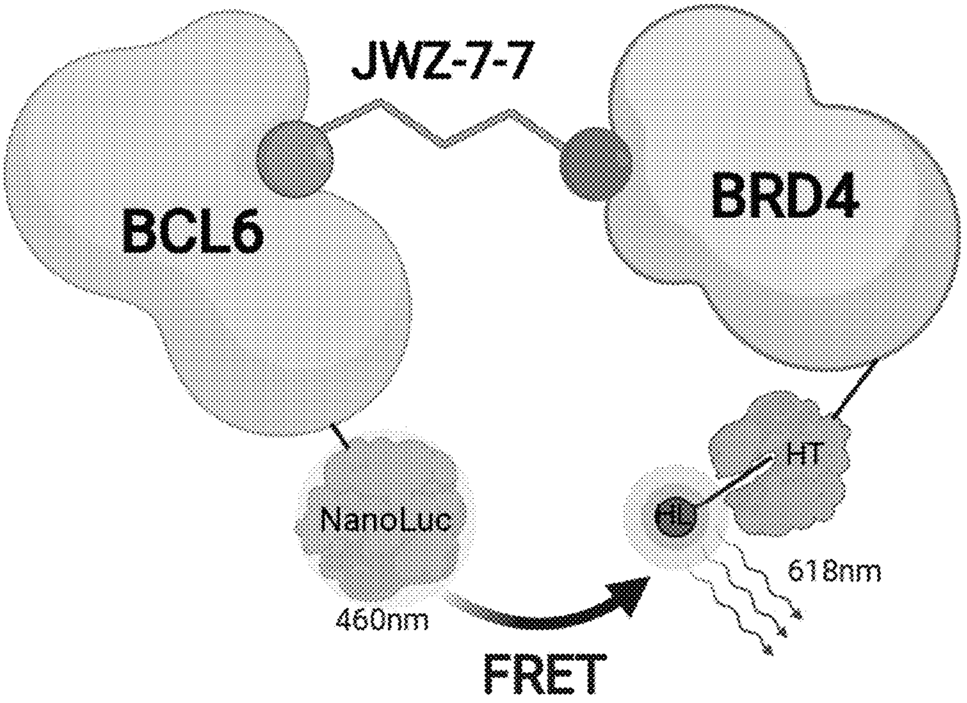
FIGS. 7A and 7B illustrate a nanoBRET assay of JWZ-7-7 and results obtained therefrom, respectively.
Figure 7B:
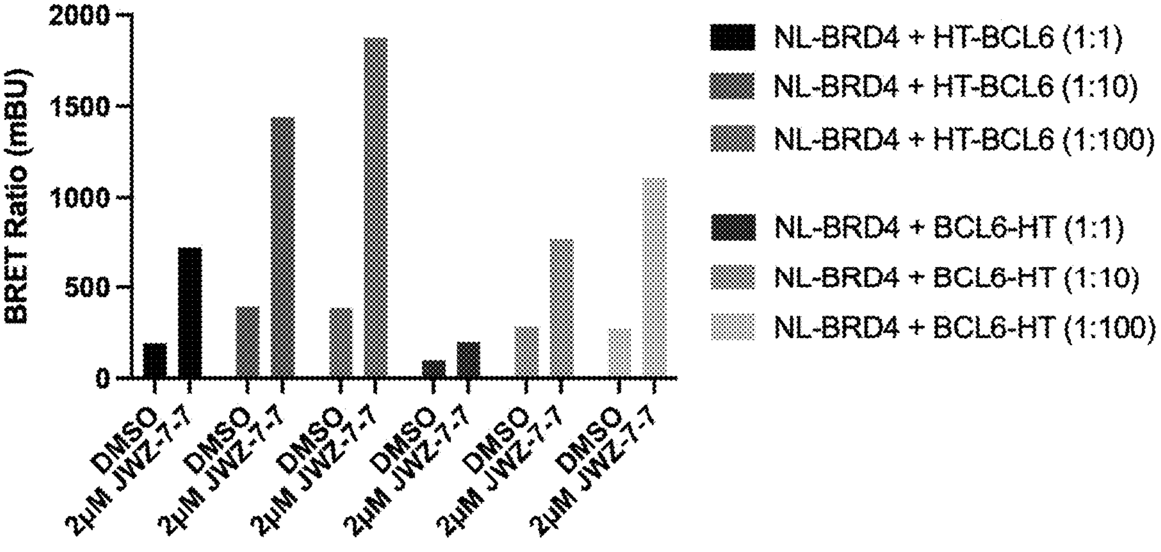
Figure 8:
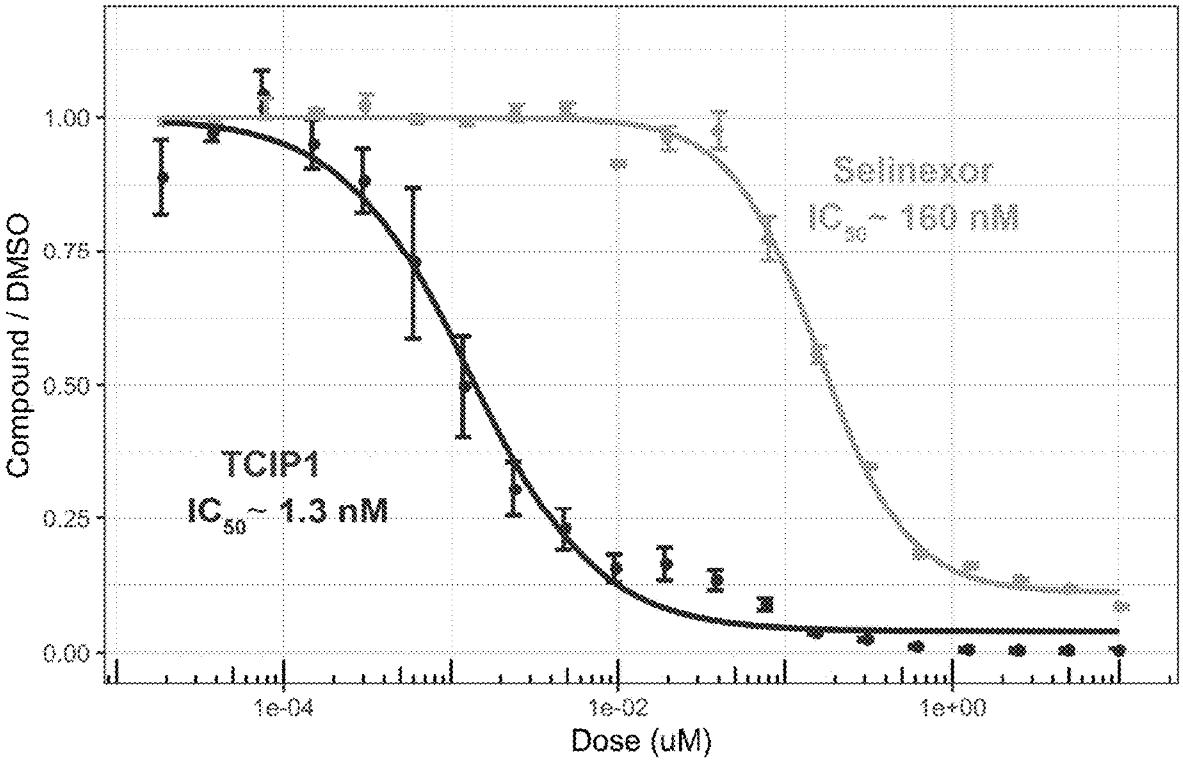
FIG. 8 demonstrates that TCIP1 is 100-fold more potent than the recently FDA-approved Selinexor in DLBCL and is less toxic.

To demonstrate target engagement, the nanoBRET assay in HEK cells was used, as illustrated in FIG. 7A. The conditions and methods for nanoBRET, a well-recognized assay of in vivo target engagement, are described in PMID 26006698. As shown, JWZ-7-7 generated a specific signal of proximity for both C- and N-terminally labeled BCL6 with N-terminally labeled BRD4. See FIG. 7B.

VII. Measurement of Serum Half Life of JWZ-7-7

Tests were performed to determine whether JWZ-7-7 is capable of maintaining sufficiently high blood levels for killing SCLC and DLBCL. Formulations for either IV or IP administration were prepared as follows:

Formulation #1—Used for IV Animals
- Concentration: 0.6 mg/ml
- Composition: 5/5/90 DMSO/Tween80/saline
- Dose: 5 μl/g body weight
- Appearance: clear solution Formulation #2—Used for IP Animals
- Concentration: 1 mg/ml
- Composition: 5/5/90 DMSO/Tween80/saline
- Dose: 10 μl/g body weight
- Appearance: clear solution After either IV or IP injection of 3 mice each with either 3 mg/Kg (IV) or 10 mg/Kg(IP), the levels of JWZ-7-7 were measured at the indicated intervals. The calculated T1/2 is 4.47 hours for IV injection and 5.63 hours for IV injection. The results are summarized in the following the following table:

JWZ-7-7
Dose: 3 mg/Kg IV, 10 mg/Kg IP

| Subject | $T_{1/2}$ hr | $T_{max}$ hr | $C_{max}$ ng/mL | $C_{max}$ μM | $AUC_{last}$ min*ng/mL | $AUC_{last}$ μM · hr | $AUC_{INF\_obs}$ min*ng/mL | AUC % Extrap | Cl_obs mL/min/kg | $MRT_{INF\_obs}$ hr | Vss_obs L/kg |
|---|---|---|---|---|---|---|---|---|---|---|---|
| IV Mouse-1 | 3.74 | 0.08 | 31100 | 30.36 | 744580 | 12.11 | 797713 | 6.66 | 3.8 | 1.59 | 0.36 |
| IV Mouse-2 | 3.93 | 0.08 | 14500 | 14.15 | 402652 | 6.55 | 444167 | 9.35 | 6.8 | 2.39 | 0.97 |
| IV Mouse-3 | 5.73 | 0.08 | 36500 | 35.63 | 891309 | 14.50 | 988029 | 9.79 | 3.0 | 2.14 | 0.39 |
| Avg. | 4.47 | 0.08 | 27367 | 26.71 | 679514 | 11.06 | 743303 | 8.60 | 4.5 | 2.04 | 0.57 |
| Subject | $T_{1/2}$ hr | $T_{max}$ hr | $C_{max}$ ng/mL | $C_{max}$ μM | AUClast min*ng/mL | $AUC_{last}$ μM · hr | $AUC_{INF\_obs}$ min*ng/mL | $AUC_{\% Extrap}$ | Cl_obs mL/min/kg | F % | CL*F |
| IP Mouse-4 | 5.48 | 0.08 | 389 | 0.38 | 100685 | 1.64 | 174254 | 42.22 | 57.4 | | |
| IP Mouse-5 | 6.32 | 0.50 | 805 | 0.79 | 202511 | 3.29 | 349182 | 42.00 | 28.6 | | |
| IP Mouse-6 | 5.08 | 1.00 | 885 | 0.86 | 192976 | 3.14 | 315593 | 38.85 | 31.7 | | |
| Avg. | 5.63 | 0.53 | 693 | 0.68 | 165391 | 2.69 | 279676 | 41.03 | 39.2 | | |

These studies demonstrate that JWZ-7-7 is stable in serum and that concentrations sufficient to kill either SCLC or DLBCL can be obtained in a mouse.
Example 2. ER-BCL6 TCIPs
1. Synthetic Methods for CIPs that Mediate Binding of an Estrogen Receptor to BCL-6
Scheme 1
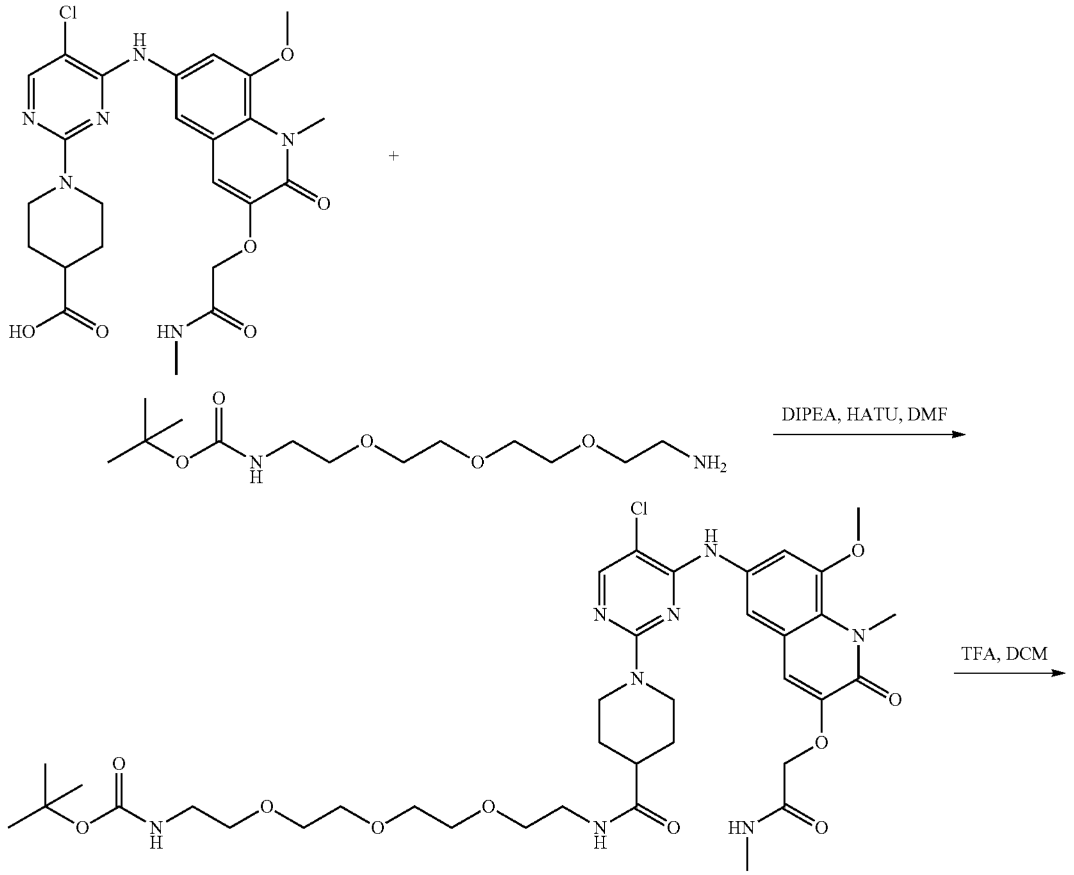
Int-1
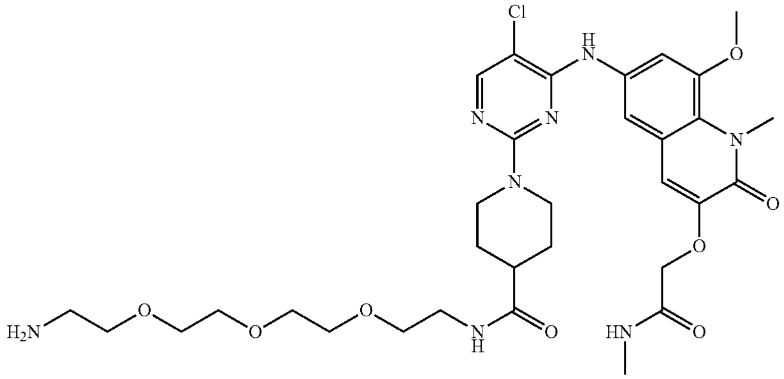

Step 1. Preparation of Int-1

A solution of 1-(5-chloro-4-((8-methoxy-1-methyl-3-(2-(methylamino)-2-oxoethoxy)-2-oxo-1,2-dihydroquinolin-6-yl)amino)pyrimidin-2-yl)piperidine-4-carboxylic acid (10 mg, 0.02 mmol, according to lit.1) t-Boc-N-amido-PEG3-amine and (30 mg, 0.1 mmol), HATU (21 mg, 0.05 mmol) and DIPEA (50 uL, 0.4 mmol) in DMF (0.25 mL) was stirred at room temperature for 1 h. The crude reaction was purified by HPLC to afford compound Int-1 (16 mg, 95%). MS obsd. [(M+H)+]:805.9

Step 2. Preparation of Compound 1

A solution of Int-1 (16 mg, 0.02 mmol) was dissolved in DCM (1 mL) and added TFA 0.2 mL and stirred at room temperature for 0.5 h. The crude reaction was purified by HPLC to afford compound 1, (10 mg, 50%) as white solid. MS obsd. [(M+H)+]:705.8. $^{1}$H NMR (500 MHz, DMSO) δ 8.88 (s, 1H), 8.08 (s, 1H), 7.99 (q, J=4.6 Hz, 1H), 7.89 (t, J=5.7 Hz, 1H), 7.78 (s, 3H), 7.58-7.51 (m, 2H), 7.01 (s, 1H), 4.56 (s, 2H), 4.51 (dt, J=13.2, 3.4 Hz, 2H), 3.80-3.97 (m, 6H), 3.61-3.51 (m, 9H), 3.40 (t, J=6.2 Hz, 2H), 3.20 (q, J=6.0 Hz, 2H), 3.03-2.86 (m, 4H), 2.66 (d, J=4.7 Hz, 3H), 2.42 (tt, J=11.6, 3.9 Hz, 1H), 1.71 (dd, J=13.4, 3.6 Hz, 2H), 1.50 (qd, J=12.4, 4.2 Hz, 2H).

Scheme 2

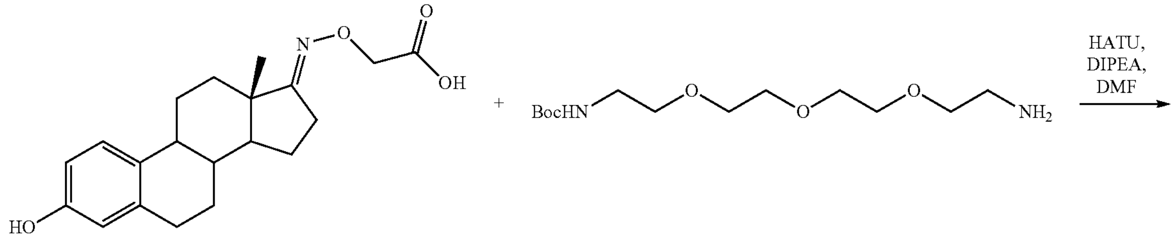

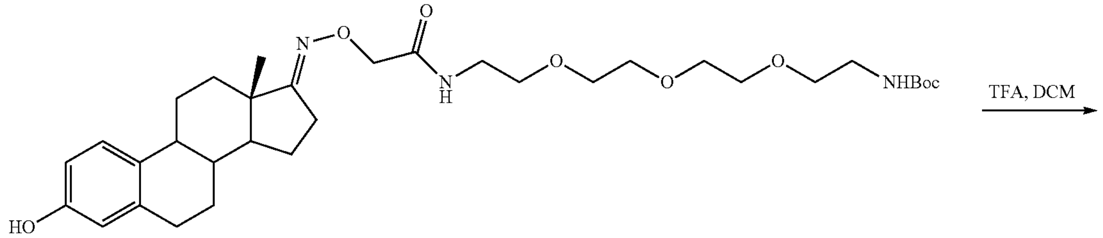

Int-2

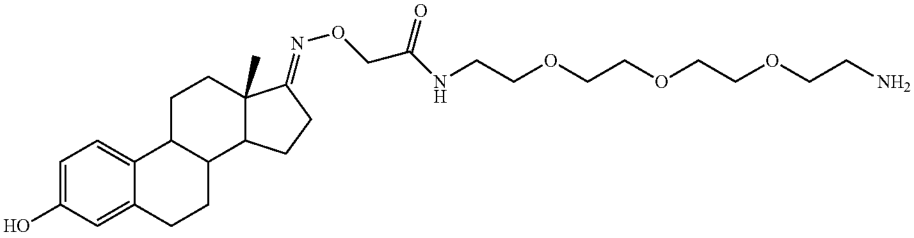

Int-3

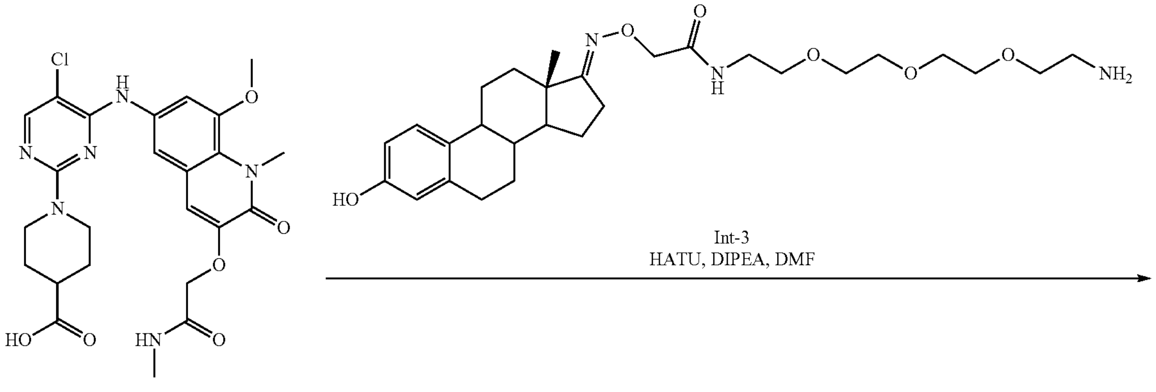

-continued

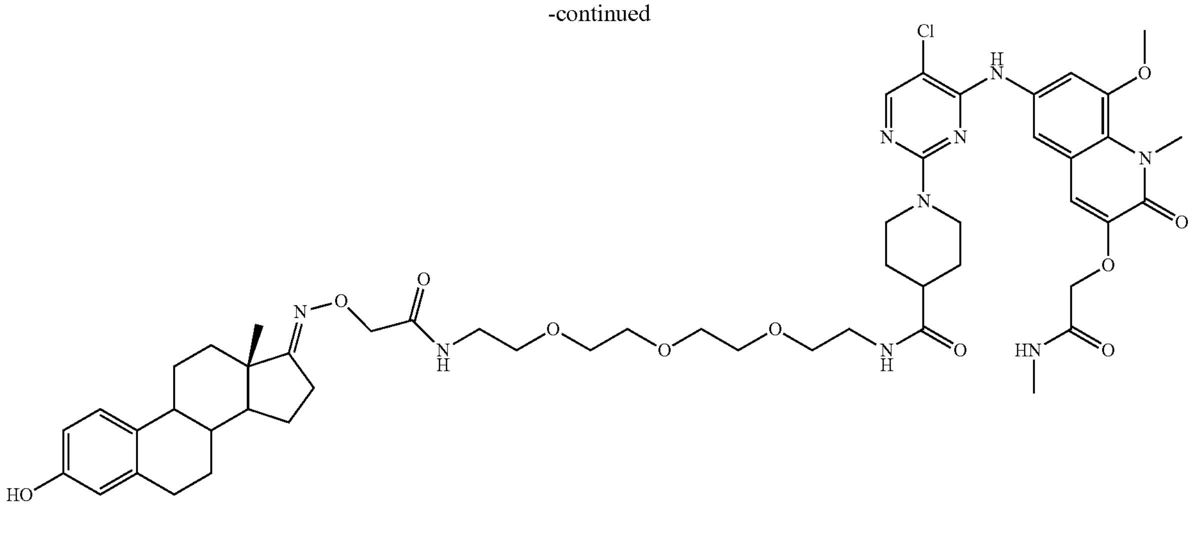

2

Step 1. Preparation of Int-2

A solution of 2-((((13S,E)-3-hydroxy-13-methyl-6,7,8,9,11,12,13,14,15,16-decahydro-17H-cyclopenta[a]phenanthren-17-ylidene)amino)oxy)acetic acid (20 mg, 0.06 mmol, according to lit.1) t-Boc-N-amido-PEG3-amine and (17 mg, 0.06 mmol), HATU (33 mg, 0.09 mmol) and DIPEA (33 uL, 0.2 mmol) in DMF (0.5 mL) was stirred at room temperature for 1 h. The crude reaction was purified by flash chromatography to afford coupling product Int-2 (20 mg, 70%) as white solid Step 2. Preparation of Int-3

Int-3 (60 mg, 0.1 mmol) was dissolved in 1 mL DCM and subjected to 0.2 mL TFA at room temperature for 0.5 h. The crude reaction was purified by HPLC to afford compound Int-3 (30 mg, 60%). MS obsd. [(M+H)+]: 518.7

Step 3. Preparation of Compound 2

A solution of Int-3 (30 mg, 0.06 mmol), and 1-(5-chloro-4-((8-methoxy-1-methyl-3-(2-(methylamino)-2-oxoethoxy)-2-oxo-1,2-dihydroquinolin-6-yl)amino)pyrimidin-2-yl)piperidine-4-carboxylic acid (30 mg, 0.06 mmol, prepared according to WO 2018/108704 A1), HATU (38 mg, 0.1 mmol) and DIPEA (50 uL, 0.3 mmol) in DMF (1 mL) was stirred at room temperature for 1 h. The crude reaction was purified by HPLC to afford compound 2, (10 mg, 50%) as white solid. MS obsd. [(M+H)+]:1031.1. $^1$H NMR (500 MHz, DMSO) δ 9.07 (s, 1H), 9.03 (s, 2H), 8.15-8.08 (m, 1H), 7.94 (q, J=4.1 Hz, 1H), 7.86 (t, J=5.6 Hz, 1H), 7.52 (d, J=1.5 Hz, 2H), 7.41 (q, J=5.7 Hz, 1H), 7.07-6.99 (m, 2H), 6.51 (dq, J=8.2, 2.4 Hz, 1H), 6.44 (q, J=2.5 Hz, 1H), 4.56 (s, 2H), 4.47 (d, J=13.0 Hz, 2H), 4.34 (d, J=2.6 Hz, 2H), 4.02 (s, 1H), 3.91-3.84 (m, 5H), 3.45-3.60 (m, 8H), 3.43 (t, J=6.0 Hz, 2H), 3.39 (ddd, J=7.5, 4.7, 1.8 Hz, 2H), 3.31-3.24 (m, 2H), 3.19 (q, J=5.9 Hz, 2H), 2.97 (m, 3H), 2.74 (m, 1H), 2.65 (dd, J=4.6, 1.2 Hz, 3H), 2.54 (d, J=8.5 Hz, 2H), 2.28 (td, J=8.5, 4.1 Hz, 1H), 2.15 (q, J=4.4 Hz, 1H), 1.91-1.80 (m, 3H), 1.76-1.60 (m, 3H), 1.57-1.45 (m, 2H), 1.20-1.36 (m, 5H), 0.91-0.85 (m, 3H).

Scheme 3

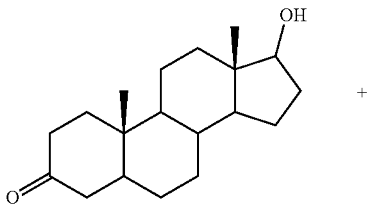

-continued

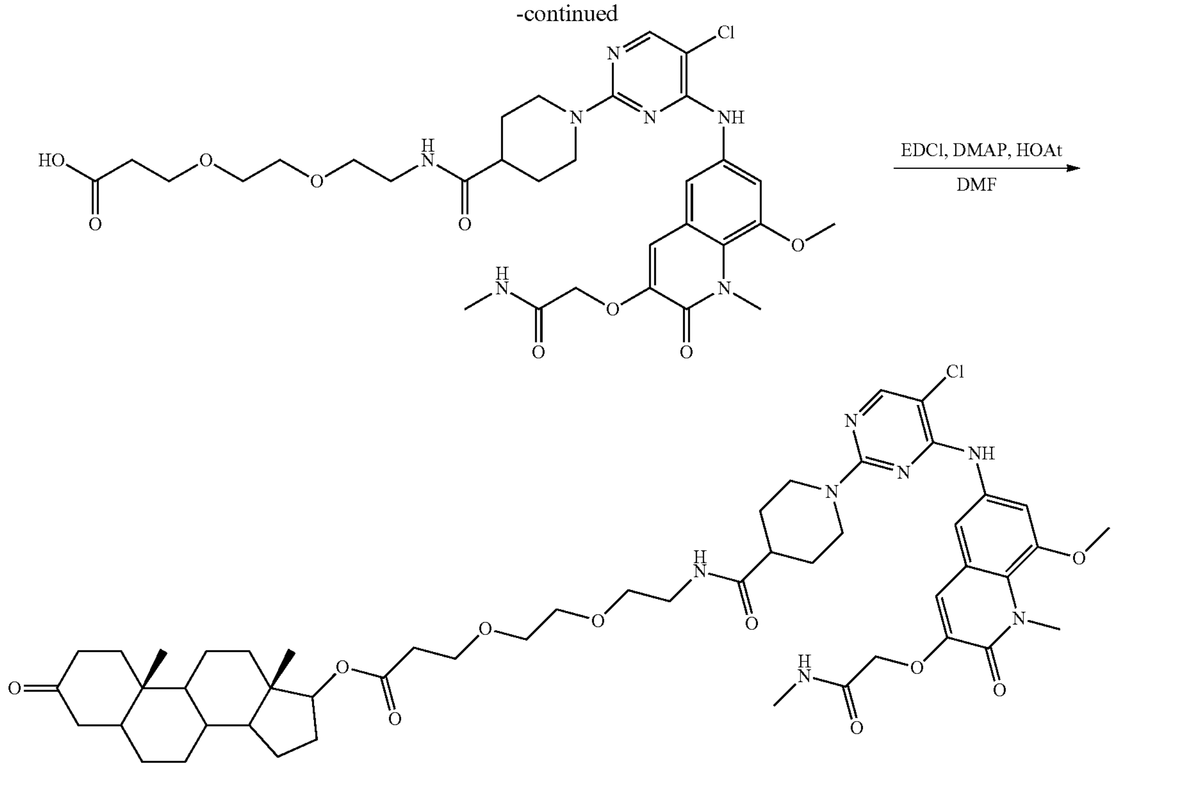

3

A solution of 3-(2-(2-(1-(5-chloro-4-((8-methoxy-1-methyl-3-(2-(methylamino)-2-oxoethoxy)-2-oxo-1,2-dihydroquinolin-6-yl)amino)pyrimidin-2-yl)piperidine-4-carboxamido)ethoxy)ethoxy)propanoic acid (7 mg, 0.009 mmol), DHT (6 mg, 0.018 mmol), EDCl (6 mg, 0.04 mmol), DMAP (5 mg, 0.018), HOAt (5 mg, 0.009 mmol) in 0.25 mL DMF was stirred at room temperature for 1 h. The crude reaction was purified by HPLC to afford compound 3 (2 mg, 30%) as white solid. MS obsd. [(M+H)+]:963.1. $^{1}$H NMR (500 MHz, DMSO) δ 10.84 (s, 1H), 8.82 (s, 1H), 8.06 (s, 1H), 7.98 (s, 1H), 7.84 (q, J=8.3 Hz, 2H), 7.45-7.60 (m, 2H), 7.00 (s, 1H), 4.55 (s, 2H), 4.53-4.45 (m, 3H), 3.87 (d, J=6.7 Hz, 4H), 3.61 (t, J=6.1 Hz, 4H), 3.52-3.47 (m, 9H), 3.24-3.15 (m, 5H), 3.00 (s, 2H), 2.91 (t, J=13.0 Hz, 4H), 2.78 (s, 3H), 2.78-2.75 (m, 4H), 2.66 (d, J=4.7 Hz, 3H), 2.53 (s, 6H), 2.43-1.99 (6H, m), 1.77-0.73 (22H, m).

Compound 4

4

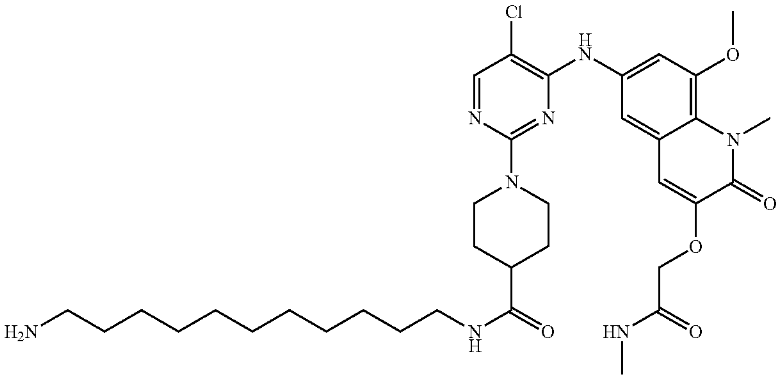

Compound 4 was prepared according to procedure of scheme 1.

MS obsd. [(M+H)+]: 699.8. $^1$H NMR (500 MHz, DMSO) δ 8.76 (s, 1H), 8.00 (s, 1H), 7.92 (q, J=4.5 Hz, 1H), 7.70 (t, J=5.7 Hz, 1H), 7.59 (s, 1H), 7.51-7.44 (m, 2H), 6.93 (s, 1H), 4.50-4.41 (m, 4H), 3.80 (m, 5H), 2.94 (d, J=6.7 Hz, 2H), 2.80-2.90 (m, 2H), 2.60-2.69 (m, 3H), 2.58 (d, J=4.7 Hz, 3H), 2.35-2.26 (m, 2H), 1.62 (dd, J=13.4, 3.7 Hz, 2H), 1.43-1.17 (m, 20H).

Compound 5

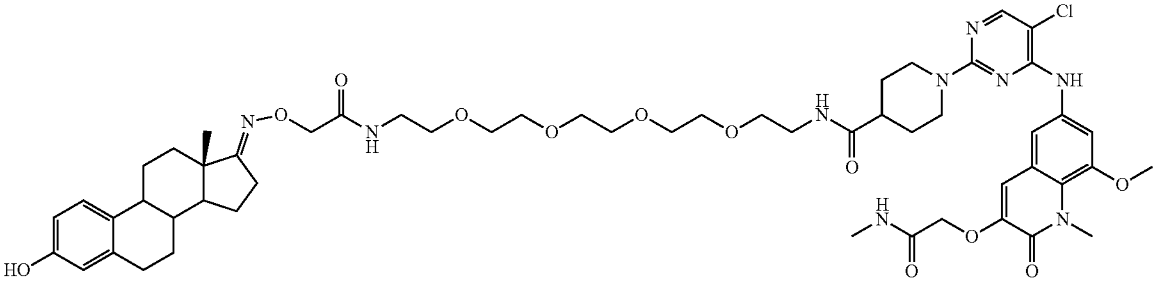

5

Compound 5 was prepared according to procedure of scheme 2.

MS obsd. [(M+H)+]: 1075.2. $^1$H NMR (500 MHz, DMSO) δ 8.93 (s, 1H), 8.81 (s, 1H), 8.00 (s, 1H), 7.89 (d, J=2.3 Hz, 1H), 7.79 (t, J=5.7 Hz, 1H), 7.46 (s, 2H), 7.33 (q, J=5.2 Hz, 1H), 6.90-6.95 (m, 2H), 6.43 (dd, J=8.4, 2.7 Hz, 1H), 6.36 (d, J=2.6 Hz, 1H), 4.48 (s, 2H), 4.42 (dd, J=10.5, 7.0 Hz, 2H), 4.26 (s, 2H), 3.79 (d, J=6.7 Hz, 4H), 3.40-3.50 (m, 12H) 3.20 (m, 2H), 3.11 (q, J=5.9 Hz, 3H), 2.83 (td, J=12.9, 2.8 Hz, 2H), 2.73-2.62 (m, 2H), 2.58 (d, J=4.7 Hz, 3H), 2.53-2.44 (m, 1H), 2.34 (m, 2H), 2.20-2.02 (m, 13H), 1.83-1.70 (m, 3H), 1.67-1.60 (m, 2H), 1.42-1.27 (m, 2H), 0.80 (s, 3H).

Compound 6

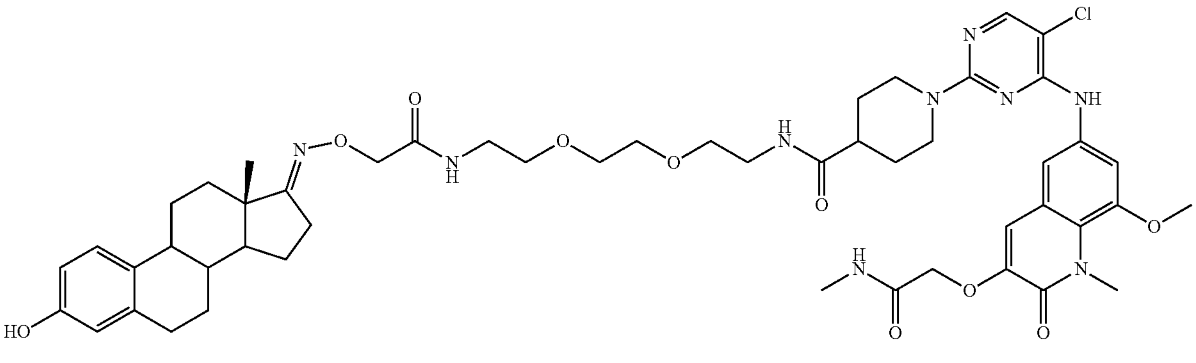

6

Compound 6 was prepared according to procedure of scheme 2.

MS obsd. [(M+H)+]987.1: $^1$H NMR (500 MHz, DMSO) δ 8.93 (s, 1H), 8.80 (s, 1H), 8.00 (s, 1H), 7.89 (d, J=5.3 Hz, 2H), 7.78 (t, J=5.6 Hz, 2H), 7.46 (s, 2H), 7.34 (q, J=9.6 Hz, 2H), 7.00-6.91 (m, 3H), 6.42 (d, J=8.3 Hz, 2H), 6.37 (d, J=7.7 Hz, 2H), 4.45 (d, J=29.5 Hz, 5H), 4.26 (s, 2H), 3.79 (d, J=6.7 Hz, 7H), 3.33 (dt, J=16.2, 5.8 Hz, 11H), 3.19 (q, J=5.9 Hz, 5H), 3.11 (q, J=6.0 Hz, 4H), 2.83 (t, J=12.4 Hz, 4H), 2.73-2.61 (m, 4H), 2.58 (d, J=4.7 Hz, 4H), 2.48 (d, J=9.6 Hz, 4H), 2.38-2.29 (m, 3H), 2.20 (d, J=13.2 Hz, 2H), 2.06 (t, J=11.8 Hz, 2H), 1.82-1.73 (m, 4H), 1.63-1.24 (m, 15H), 1.24-1.15 (m, 4H), 0.79 (s, 3H).

Compound 7

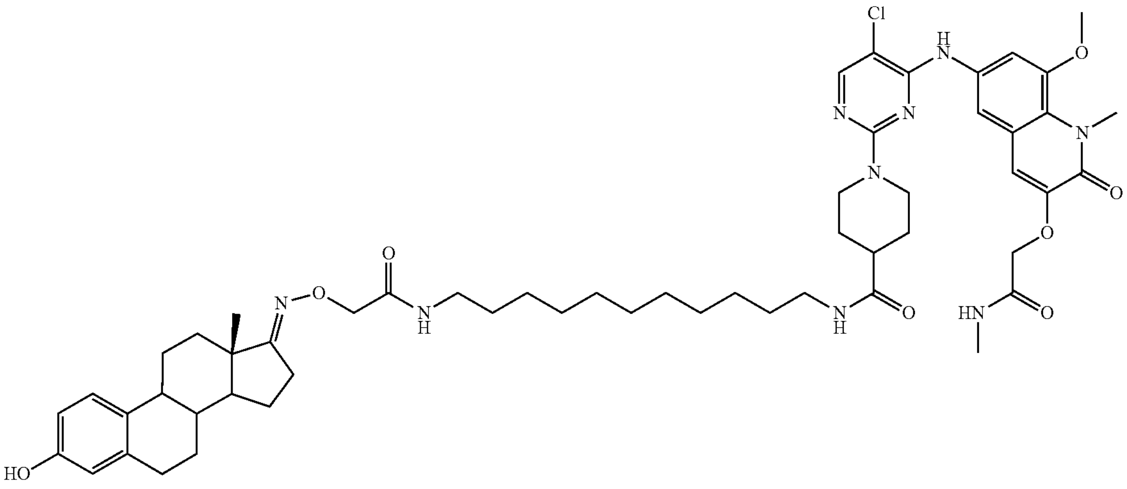

7

Compound 7 was prepared according to procedure of scheme 2.

MS obsd. [(M+H)+]: 1025.3. $^1$H NMR (500 MHz, DMSO) δ 8.95 (br, 2H), 8.76 (s, 1H), 7.99 (s, 1H), 7.92 (s, 1H), 7.68 (t, J=5.8 Hz, 1H), 7.47 (d, J=2.1 Hz, 1H), 7.30 (t, J=5.9 Hz, 1H), 6.98-6.91 (m, 1H), 6.43 (dd, J=8.5, 2.6 Hz, 1H), 6.37 (d, J=2.6 Hz, 1H), 4.49-4.41 (m, 2H), 4.23 (s, 1H), 3.79 (d, J=5.2 Hz, 3H), 3.09-2.95 (m, 4H), 2.92 (d, J=4.2 Hz, 3H), 2.86-2.78 (m, 5H), 2.06 (s, 1H), 1.78 (t, J=14.9 Hz, 3H), 1.62-1.42 (m, 7H), 1.14 (d, J=7.5 Hz, 7H), 0.80 (s, 3H).

Compound 8

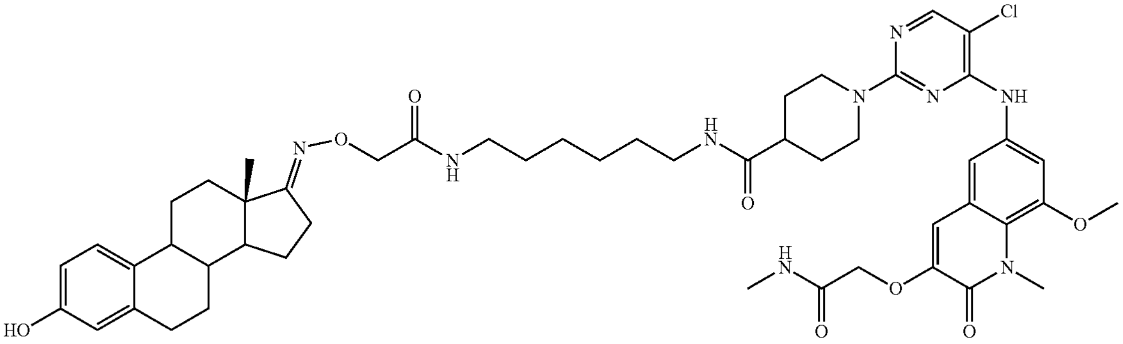

8

Compound 8 was prepared according to procedure of scheme 2.

MS obsd. [(M+H)+]: 955.1. $^1$H NMR (500 MHz, DMSO) δ 8.93 (s, 1H), 8.79 (s, 1H), 8.00 (s, 1H), 7.92 (d, J=5.0 Hz, 1H), 7.69 (t, J=5.6 Hz, 2H), 7.46 (q, J=2.3 Hz, 2H), 7.33 (t, J=6.0 Hz, 2H), 6.95 (d, J=10.7 Hz, 3H), 6.42 (dd, J=8.4, 2.6 Hz, 2H), 6.36 (d, J=2.7 Hz, 2H), 4.47 (s, 2H), 4.44 (d, J=12.6 Hz, 2H), 4.23 (s, 2H), 3.79 (d, J=5.4 Hz, 6H), 3.03 (p, J=6.8 Hz, 4H), 2.93 (q, J=6.5 Hz, 3H), 2.85-2.76 (m, 4H), 2.66 (dd, J=11.1, 6.1 Hz, 3H), 2.64-2.56 (m, 5H), 2.50-2.45 (m, 3H), 2.33-2.24 (m, 3H), 2.23-2.16 (m, 2H), 2.05 (t, J=11.2 Hz, 2H), 1.81-1.70 (m, 5H), 1.65-1.58 (m, 3H), 1.47-1.35 (m, 5H), 1.35-1.13 (m, 17H), 0.79 (s, 3H).

(methylamino)-2-oxoethoxy)-2-oxo-1,2-dihydroquinolin-6-yl)amino)pyrimidin-2-yl)-N-methylpiperidine-4-carboxamide (15 mg, 0.02 mmol, according to scheme 1), HATU (20 mg, 0.05 mmol) and DIPEA (50 uL, 0.3 mmol) in DMF (0.25 mL) was stirred at room temperature for 1 h. The crude reaction was purified by HPLC to yield 9 (2 mg, 15%) as white solid. MS obsd. [(M+H)+]: 1045.2. $^1$H NMR (500 MHz, DMSO) δ 8.94 (s, 2H), 8.76 (s, 1H), 7.99 (d, J=4.6 Hz, 1H), 7.89 (d, J=6.2 Hz, 1H), 7.50-7.43 (m, 2H), 7.31 (q, J=6.3 Hz, 1H), 7.00-6.91 (m, 3H), 6.43 (td, J=8.2, 2.5 Hz, 2H), 6.37 (dd, J=8.5, 2.5 Hz, 2H), 4.55 (s, 1H), 4.47 (d, J=1.8 Hz, 2H), 4.26 (d, J=2.2 Hz, 2H), 3.79 (dd, J=5.7, 2.1 Hz, 5H), 3.47 (s, 2H), 3.46-3.36 (m, 8H), 3.35 (s, 11H), Scheme 4.

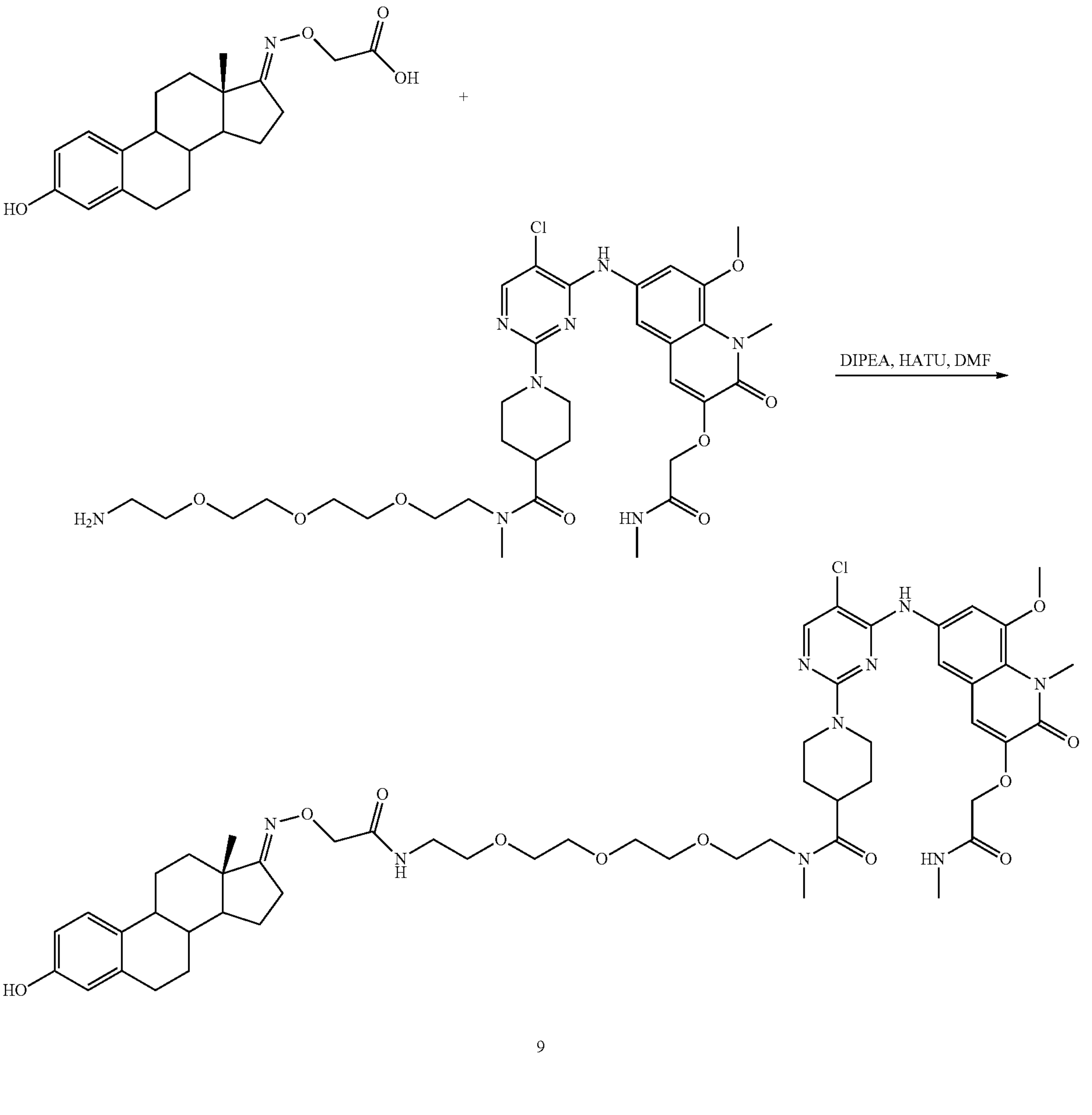

9

A solution of 2-((((13S,E)-3-hydroxy-13-methyl-6,7,8,9,1 1,12,13,14,15,16-decahydro-17H-cyclopenta[a]phenanthren-17-ylidene)amino)oxy)acetic acid (15 mg, 0.06 mmol, according to lit.1N-(2-(2-(2-(2-aminoethoxy)ethoxy)ethoxy)ethyl) -1-(5-chloro-4-((8-methoxy-1-methyl-3-(2-

3.23-3.14 (m, 1H), 2.99 (d, J=17.6 Hz, 2H), 2.93-2.79 (m, 4H), 2.74 (d, J=3.1 Hz, 2H), 2.71-2.61 (m, 1H), 2.65 (s, 3H), 2.58 (d, J=4.7 Hz, 3H), 2.38 (dd, J=18.3, 9.5 Hz, 1H), 2.21 (t, J=13.5 Hz, 2H), 2.08 (d, J=11.9 Hz, 2H), 1.80 (td, J=11.2, 3.4 Hz, 2H), 1.76 (s, 4H), 1.59 (d, J=10.5 Hz, 2H), 1.45-1.37

(m, 4H), 1.35-1.27 (m, 3H), 1.27 (s, 9H), 1.25 (d, J=12.0 Hz, 1H), 1.19 (dd, J=13.2, 6.2 Hz, 2H), 0.80 (s, 3H).

II. Testing of bifunctional CIPs which recruit the estrogen receptor (ER) to the BCL6 transcription factor.

To identify genes that when over expressed can kill a cancer cell an unbiased screen of the 13 proapoptotic genes that have been shown to be transcriptionally controlled was performed (Strasser, A., O'Connor, L. & Dixit, V. M. Apoptosis signaling. Annu Rev Biochem 69, 217-245 (2000)). As predicted from the literature, induction of these genes in breast cancer, lymphoma and lung SCC lines induced 12 to 60% cell death after 48 hr of induction with Dox. As expected, Bim was most effective in lymphoma (Faber, A. C., Ebi, H., Costa, C. & Engelman, J. A. Apoptosis in targeted therapy responses: the role of BIM. Adv Pharmacol 65, 519-542, doi:10.1016/B978—O—12-397927-8.00016-6 (2012)). It was noted that 8 of these genes are reported to be BCL6-repressed or FOXO3-activated. To test our hypothesis that providing additional transcriptional activation to derepressed BCL6 would activate cell death genes and lead to apoptosis, it was made use of the fact that about 10% of DLBCL overexpress the estrogen receptor (ER) including the CHOP-resistant Karpas422 line (Dyer, M. J., Fischer, P., Nacheva, E., Labastide, W. & Karpas, A. A new human B-cell non-Hodgkin's lymphoma cell line (Karpas 422) exhibiting both t (14; 18) and t(4; 11) chromosomal translocations. Blood 75, 709-714 (1990)).

Bifunctional CIPs were synthesized that link the BCL6 inhibitor, B13812 to estrone, an estrogen analogue using a series of linkers of different lengths. FIG. 9, Panel A provides the structures of molecules synthesized to test the effect of the linkers on estrone and on B13812, as well as negative controls not binding ER (XFL-01-190 and 106)) or BCL6 (XFL-03-004).

Figure 4A:
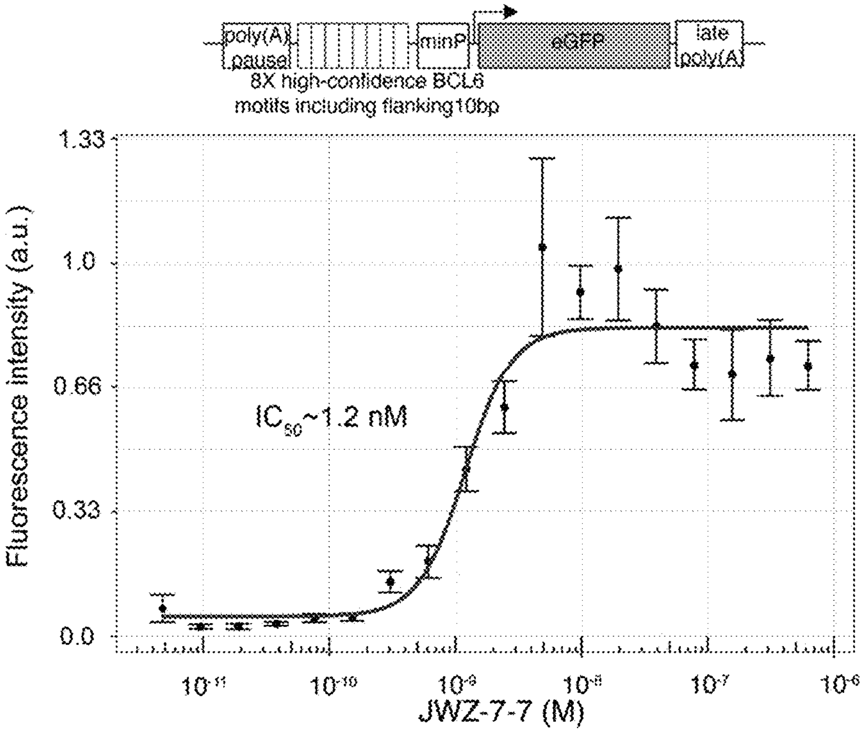
FIG. 4A shows that the TCIP JWZ-7-7 uses endogenous BCL6 and BRD4 levels to rapidly upregulate gene expression in DLBCL cells. Karpas 422 cells were transfected with a GFP reporter containing high-confidence BCL6 binding sites, and treated with JWZ-7-7 for 8 hrs.
Figure 4B:
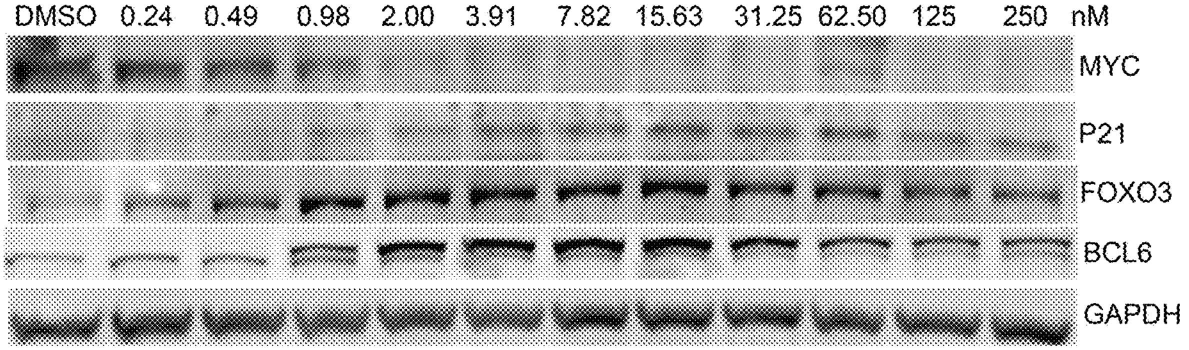
FIG. 4B shows that the TCIP JWZ-7-7 rapidly and specifically regulates genes critical for DLBCL at <1 NM. Karpas 422 cells were treated with JWZ-7-7 at the indicated concentrations for 24 hours and extracts prepared and Western-blotted. BCL6 (long isoform) is the upper band, the short isoform is the lower band. Note "hook effect" (reduction in activity at higher concentrations) characteristic of ternary complex formation.
Figure 10:
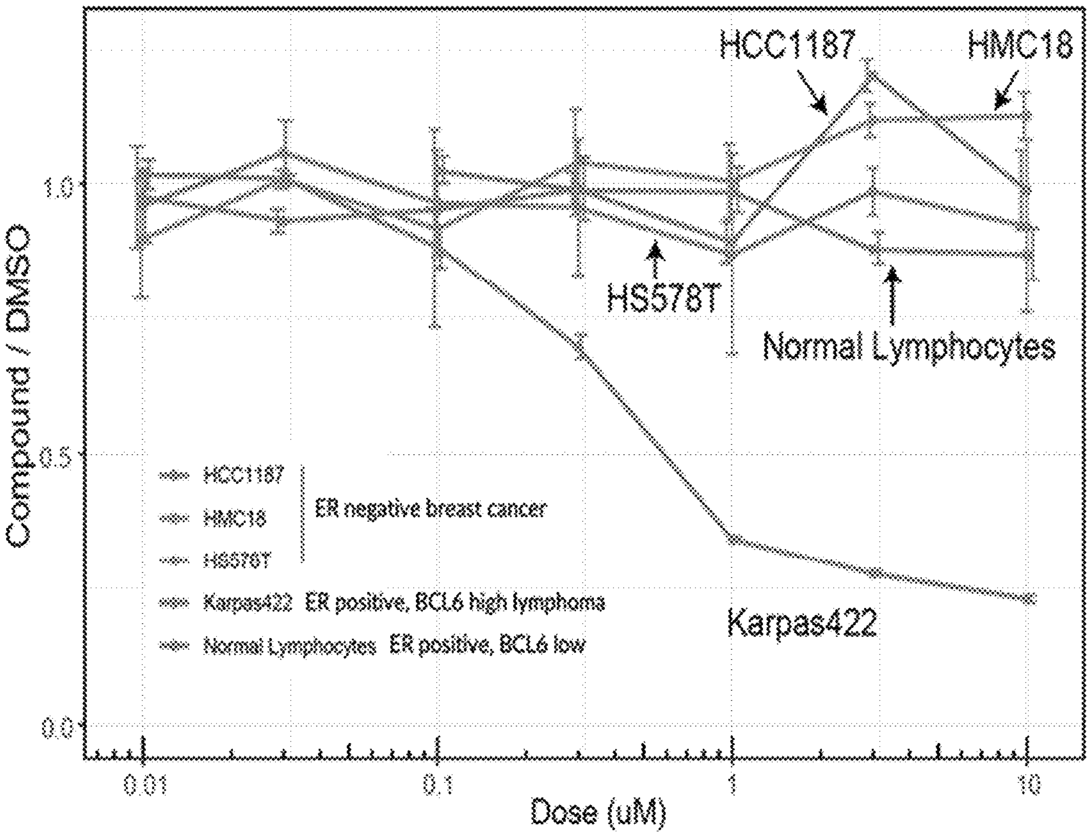
FIG. 10 demonstrates that XFL-01-92 specifically kills DLBCL cells. Shown are dose-response curves for lymphocytes and three breast cancer cell lines that do not overexpress BCL6.
Figure 11:
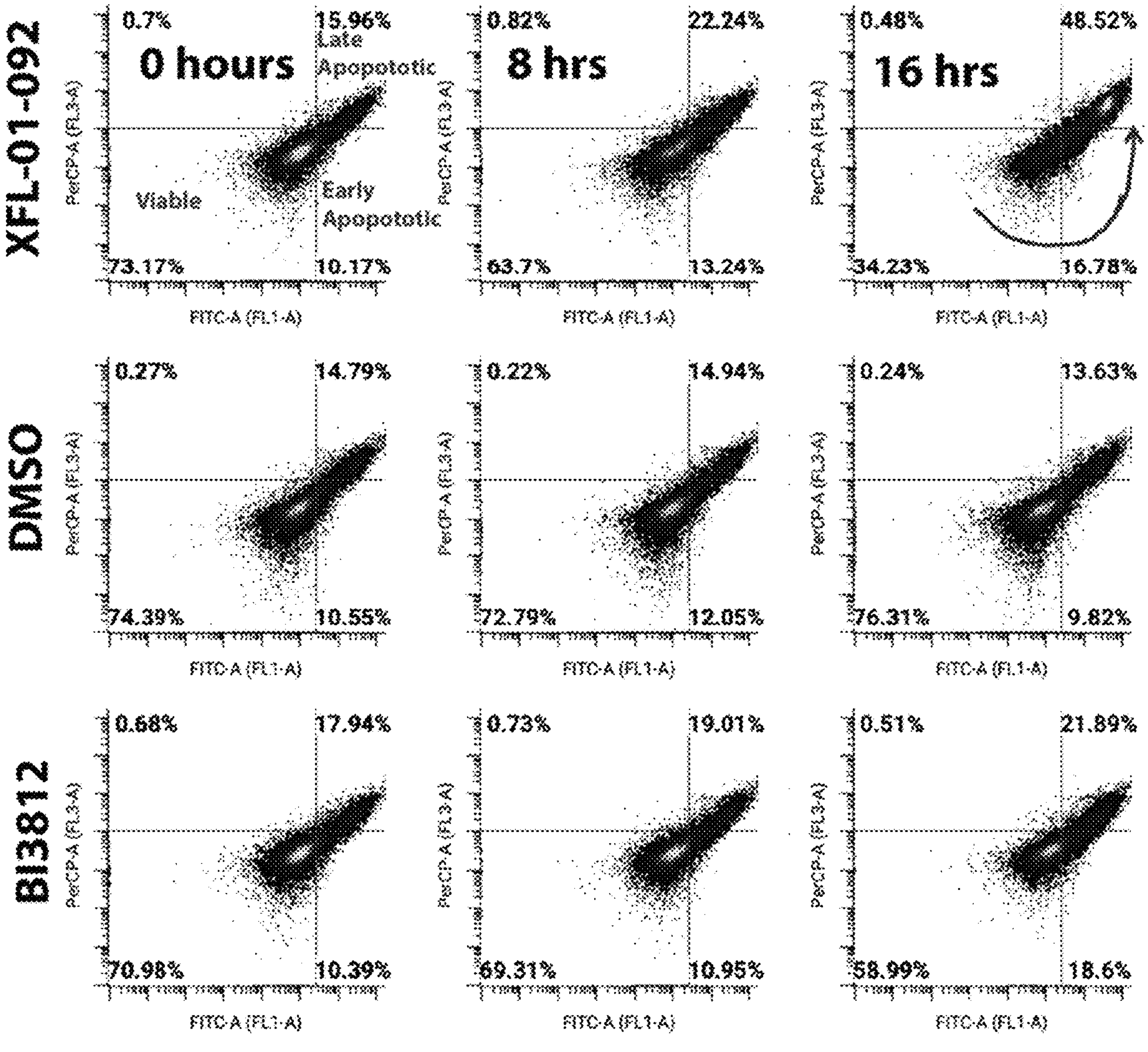
FIG. 11 demonstrates that CIP-induced apoptosis is rapid and robust. XFL-01-92 induces apoptosis within 8 hours of addition to Karpas 422 cells. Annexin V and 7AAD staining identify early and late apoptosis.

Several of these molecules produced far more active cell death of the CHOP-resistant Karpas422 cell line than either B13812 or estrone alone or added together (FIG. 9, Panel B and data not shown). In FIG. 9, Panel B, viability of Karpas DLBCL 48 hours after adding estrone, B13812, B13802 (BCL6 degrader) and XFL-01-92. Note that XFL-01-92 is far more active at specifically killing these cells which over express ER as well as BCL6 than either parent compound. The androgen (XFL-01-108) or linker compounds as well as the two negative control compounds were all inactive. Furthermore, these TCIPs had no effect on normal lymphocytes and several other cell lines not over-expressing either ER or BCL6 (FIG. 3). FIG. 10 shows the dose-response curves for lymphocytes and three breast cancer cell lines that do not over-express BCL6. To date, 12 other lines have been tested and killing has not been observed of any cells not over-expressing both targets. In addition, the cells die by apoptosis beginning 8 hours after addition of drug (FIG. 11). In FIGS. 4A-4B, XFL-01-92 induces apoptosis within 8 hours of addition to Karpas 422 cells. Annexin V and 7AAD staining identify early and late apoptosis. These studies indicate that the ER-BCL6-CIP is specific for cells over-expressing both ER and BCL6 and that sensitivity is predictable.

Example 3. CDK9-BCL6 TCIPs

I. Synthesis and Characterization of TCIPs

General Procedure

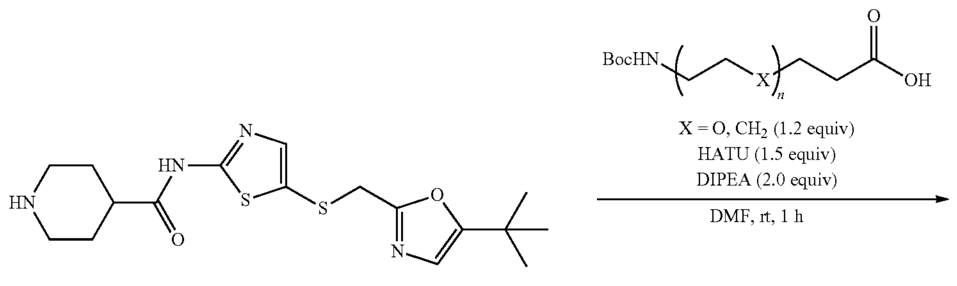

-continued

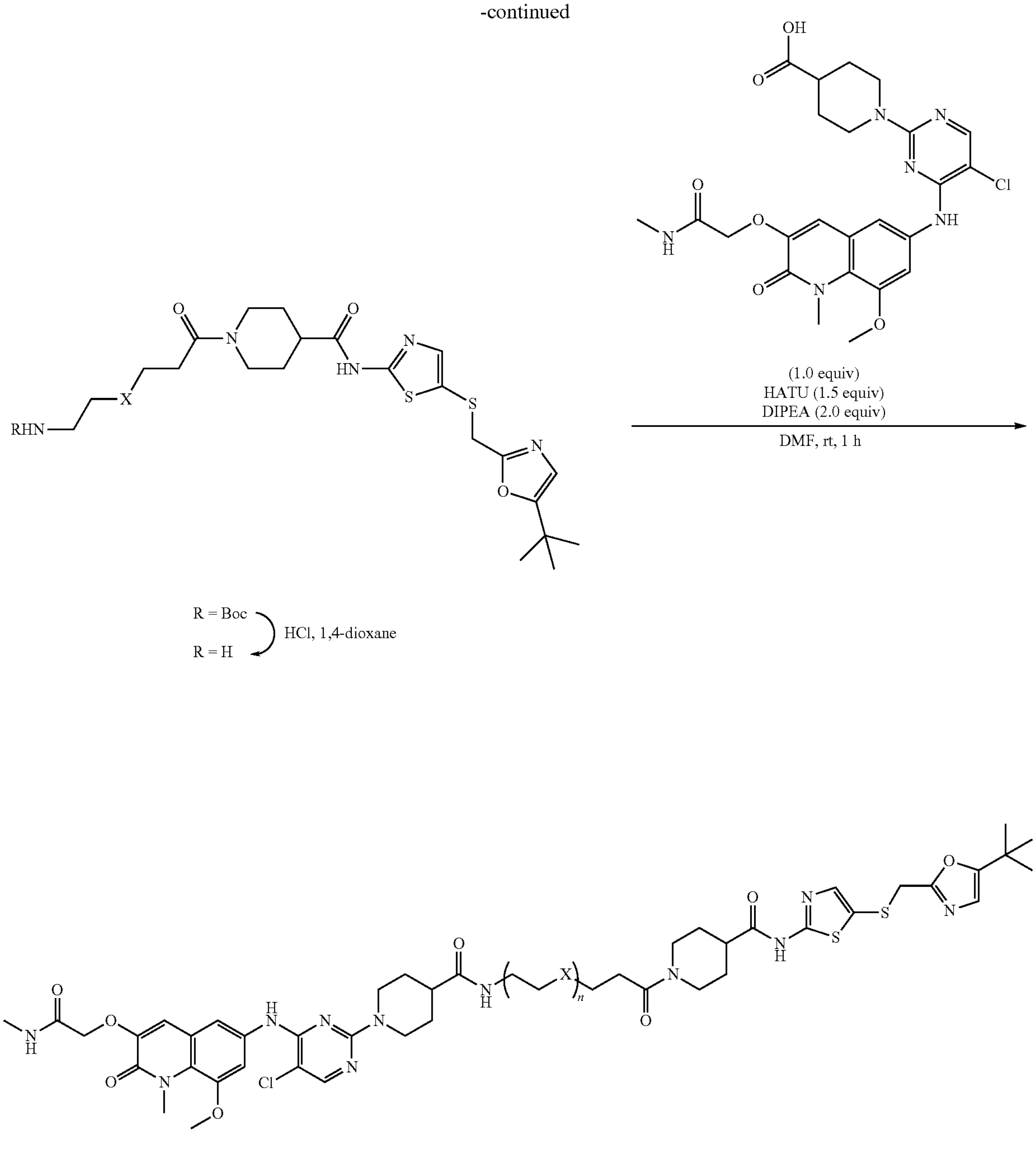

To a solution of SNS-032 (0.010 g, 0.02 mmol, 1.0 equiv) in DMF (0.2 mL) was added N-Boc-carboxylic acid linker (1.2 equiv), HATU (12 mg, 0.03 mmol, 1.5 equiv), and DIPEA (0.01 mL, 0.04 mmol, 2.0 equiv) and the resulting yellow solution was stirred at ambient temperature until UPLC-MS analysis indicated full conversion of starting material. The reaction mixture was diluted with EtOAc and water was added. The aqueous layer was extracted with EtOAc and the combined organic extracts washed with brine, dried over $Na_2SO_4$, and concentrated under reduced pressure. The resulting residue was taken up in 1,4-dioxane (0.2 mL) and HCl (0.2 mL, 4.0 M in 1,4-dioxane) was added. The mixture was stirred until UPLC-MS analysis indicated complete removal of the Boc protecting group, upon which all volatiles were removed under reduced pressure. The obtained residue was taken up in DMF (0.2 mL) and B12356 (0.010 g, 0.021 mmol, 1.0 equiv), HATU (0.012 g, 0.03 mmol, 1.5 equiv), and DIPEA (0.01 mL, 0.04 mmol, 2.0 equiv) were added. The reaction mixture was stirred at ambient temperature until full consumption of starting material was observed by UPLC-MS and the reaction mixture was purified without work-up by preparative, reverse-phase high-performance liquid chromatography (RP-HPLC).

BAK-04-014
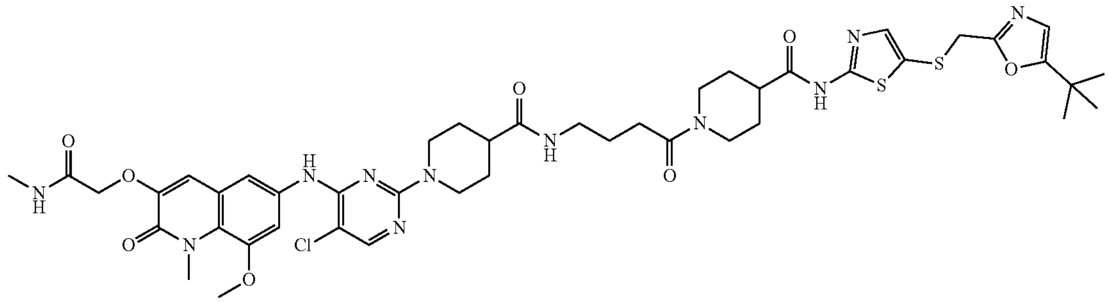
BAK-04-014
$^1$H NMR (500 MHz, DMSO-$d_6$) δ=12.29 (s, 1H), 9.20 (s, 1H), 8.13 (s, 1H), 7.95 (d, J=4.9 Hz, 1H), 7.83 (t, J=5.6 Hz, 1H), 7.50 (s, 2H), 7.38 (d, J=1.8 Hz, 1H), 7.02 (s, 1H), 6.70 (s, 1H), 4.55 (s, 2H), 4.44 (d, J=13.1 Hz, 2H), 4.37 (d, J=13.0 Hz, 1H), 4.04 (s, 2H), 3.86 (d, J=7.2 Hz, 6H), 3.12-2.91 (m, 4H), 2.76-2.68 (m, 1H), 2.65 (d, J=4.7 Hz, 3H), 2.58 (t, J=12.8 Hz, 1H), 2.43-2.35 (m, 10H), 2.30 (q, J=7.4 Hz, 1H), 1.84-1.71 (m, 1H), 1.61 (t, J=7.2 Hz, 1H), 1.58-1.49 (m, 2H), 1.16 (s, 9H). MS $(M)^+$=978.58
BAK-04-015
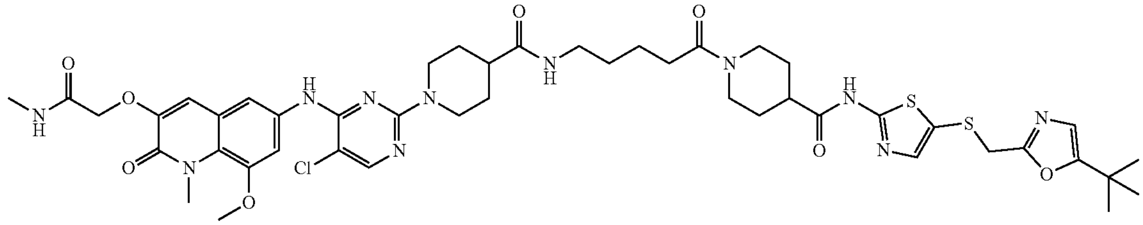
BAK-04-015
$^1$H NMR (500 MHz, DMSO-$d_6$) δ=12.29 (s, 1H), 8.98 (s, 1H), 8.09 (s, 1H), 7.95 (d, J=4.8 Hz, 1H), 7.80 (t, J=5.7 Hz, 1H), 7.54-7.50 (m, 2H), 7.38 (s, 1H), 7.01 (s, 1H), 6.70 (s, 1H), 4.55 (s, 2H), 4.48 (d, J=13.0 Hz, 2H), 4.37 (d, J=13.2 Hz, 1H), 4.04 (s, 2H), 3.86 (d, J=7.4 Hz, 6H), 3.03 (q, J=7.0 Hz, 3H), 2.92 (t, J=12.6 Hz, 2H), 2.76-2.67 (m, 1H), 2.65 (d, J=4.6 Hz, 3H), 2.57 (t, J=12.5 Hz, 1H), 2.43-2.35 (m, 1H), 2.30 (q, J=7.1 Hz, 2H), 1.85-1.75 (m, 2H), 1.71 (d, J=12.7 Hz, 2H), 1.58-1.32 (m, 9H), 1.16 (s, 9H). MS (M)+=992.54.
BAK-04-016
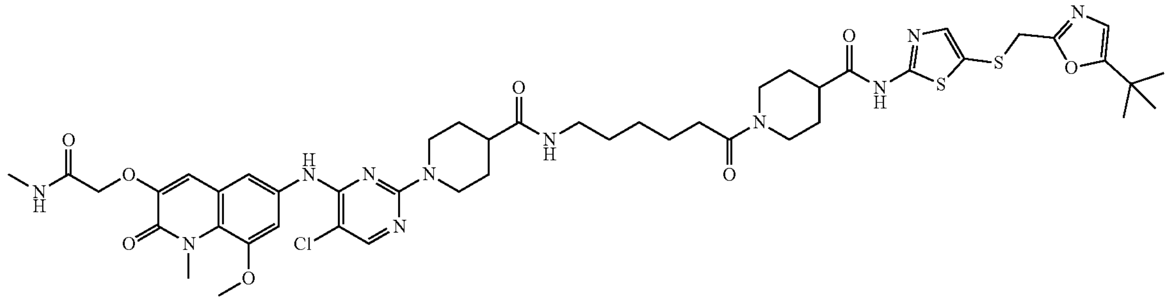
BAK-04-016

$^1$H NMR (500 MHz, DMSO-$d_6$) δ=12.29 (s, 1H), 9.00 (s, 1H), 8.09 (s, 1H), 7.96 (d, J=5.0 Hz, 1H), 7.78 (t, J=5.6 Hz, 1H), 7.52 (d, J=1.2 Hz, 2H), 7.38 (d, J=1.3 Hz, 1H), 7.01 (s, 1H), 6.71 (d, J=1.4 Hz, 1H), 4.55 (s, 2H), 4.48 (d, J=13.1 Hz, 2H), 4.37 (d, J=13.2 Hz, 1H), 4.05 (d, J=1.4 Hz, 2H), 3.86 (dd, J=7.5, 1.3 Hz, 6H), 3.02 (q, J=7.1 Hz, 3H), 2.92 (t, J=12.7 Hz, 2H), 2.71 (t, J=11.1 Hz, 1H), 2.65 (dd, J=4.6, 1.3 Hz, 3H), 2.57 (t, J=12.0 Hz, 1H), 2.38 (t, J=11.5 Hz, 1H), 2.34-2.21 (m, 2H), 1.84-1.75 (m, 3H), 1.71 (d, J=12.5 Hz, 2H), 1.48 (dd, J=18.5, 10.3 Hz, 5H), 1.38 (d, J=8.0 Hz, 3H), 1.26 (dt, J=15.0, 6.8 Hz, 3H), 1.17 (d, J=1.3 Hz, 9H). MS $(M)^+$=1006.59.

BAK-04-021

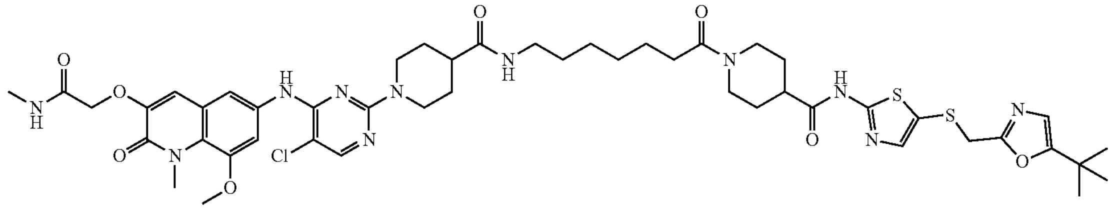

BAK-04-021

$^1$H NMR (500 MHz, DMSO-$d_6$) δ=12.29 (s, 1H), 8.92 (s, 1H), 8.08 (s, 1H), 7.97 (d, J=4.9 Hz, 1H), 7.77 (t, J=5.6 Hz, 1H), 7.52 (s, 2H), 7.38 (s, 1H), 7.00 (s, 1H), 6.71 (s, 1H), 4.55 (s, 2H), 4.49 (d, J=13.1 Hz, 2H), 4.37 (d, J=13.2 Hz, 1H), 4.04 (s, 2H), 3.86 (d, J=7.3 Hz, 6H), 3.01 (q, J=7.2 Hz, 2H), 2.90 (t, J=12.5 Hz, 2H), 2.75-2.67 (m, OH), 2.65 (d, J=4.6 Hz, 3H), 2.58 (d, J=12.5 Hz, 1H), 2.43-2.33 (m, 1H), 2.28 (td, J=7.4, 4.8 Hz, 2H), 1.80 (t, J=11.5 Hz, 2H), 1.70 (d, J=12.6 Hz, 2H), 1.57-1.42 (m, 5H), 1.37 (t, J=7.0 Hz, 3H), 1.31-1.21 (m, 5H), 1.16 (s, 9H). MS $(M)^+$=1020.64

BAK-04-022

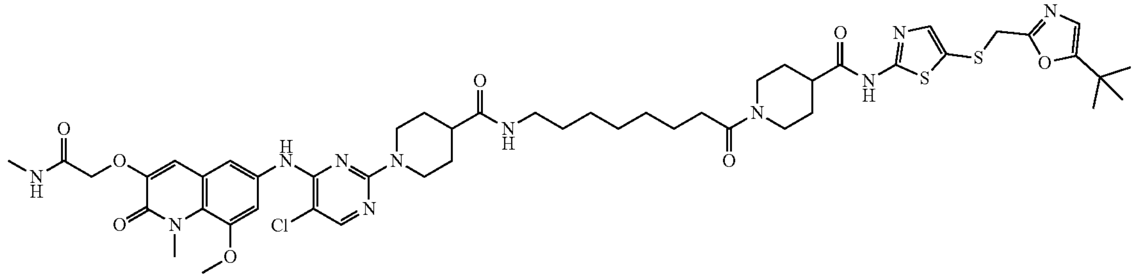

BAK-04-022

$^1$H NMR (500 MHz, DMSO) δ 12.38 (s, 1H), 8.79 (s, 1H), 8.17 (d, J=4.9 Hz, 1H), 8.05 (s, 1H), 7.89 (t, J=5.7 Hz, 1H), 7.56 (q, J=2.3 Hz, 2H), 7.37 (s, 1H), 6.99 (s, 1H), 6.70 (s, 1H), 4.57 (s, 2H), 4.51 (d, J=12.6 Hz, 2H), 4.36 (d, J=12.7 Hz, 1H), 4.04 (s, 2H), 3.86 (d, J=7.6 Hz, 6H), 3.00 (q, J=7.1 Hz, 3H), 2.87 (t, J=12.6 Hz, 2H), 2.79-2.73 (m, 1H), 2.64 (d, J=4.6 Hz, 3H), 2.56 (s, 1H), 2.43-2.35 (m, 1H), 2.30-2.24 (m, 1H), 1.79 (t, J=12.5 Hz, 2H), 1.70 (d, J=12.6 Hz, 2H), 1.48 (d, J=12.1 Hz, 5H), 1.37 (s, 2H), 1.23 (d, J=7.0 Hz, 9H), 1.16 (s, 9H). MS $(M)^+$=1034.55.

BAK-04-023
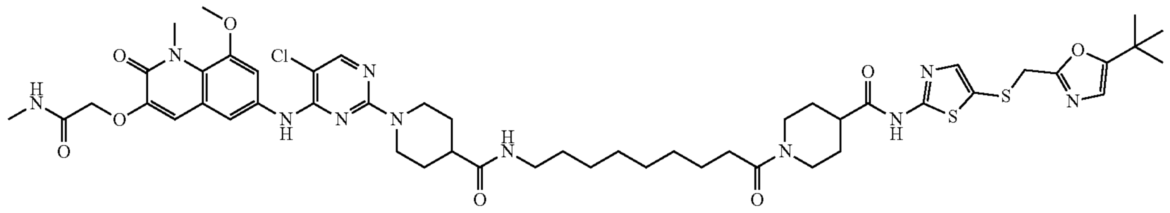
BAK-04-023
$^1$H NMR (500 MHz, DMSO-$d_6$) δ=13.62 (s, 1H), 10.40 (s, 1H), 9.44 (s, 1H), 9.29 (d, J=4.8 Hz, 1H), 9.10 (t, J=5.6 Hz, 1H), 8.85 (s, 2H), 8.72 (s, 1H), 8.35 (s, 1H), 8.04 (s, 1H), 5.88 (s, 2H), 5.79 (d, J=13.1 Hz, 2H), 5.71 (d, J=13.1 Hz, 1H), 5.38 (s, 2H), 5.20 (d, J=6.7 Hz, 6H), 4.34 (q, J=7.0 Hz, 2H), 4.26 (t, J=12.5 Hz, 2H), 4.04 (ddt, J=11.4, 7.7, 3.7 Hz, 1H), 3.98 (d, J=4.6 Hz, 3H), 3.94-3.87 (m, 1H), 3.76-3.68 (m, 1H), 3.61 (q, J=7.1 Hz, 2H), 3.18-3.09 (m, 2H), 3.04 (d, J=12.7 Hz, 2H), 2.90-2.77 (m, 2H), 2.71 (d, J=7.5 Hz, 1H), 2.58 (s, 9H), 2.50 (s, 9H). MS $(M)^+$=1048.63.
BAK-04-028
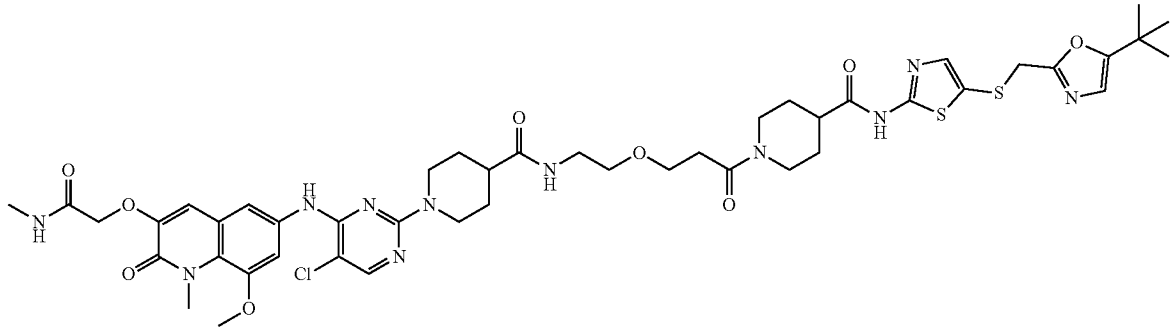
BAK-04-028
$^1$H NMR (500 MHz, DMSO-$d_6$) δ=12.29 (s, 1H), 8.99 (s, 1H), 8.09 (s, 1H), 7.94 (d, J=4.8 Hz, 1H), 7.83 (t, J=5.6 Hz, 1H), 7.52 (s, 2H), 7.38 (s, 1H), 7.00 (s, 1H), 6.70 (s, 1H), 4.55 (s, 2H), 4.47 (d, J=13.1 Hz, 2H), 4.37 (d, J=13.1 Hz, 1H), 4.04 (s, 2H), 3.91 (d, J=13.7 Hz, 1H), 3.86 (d, J=7.7 Hz, 6H) 3.61 (t, J=6.5 Hz, 2H), 3.38 (t, J=5.9 Hz, 2H), 3.18 (q, J=6.0 Hz, 2H), 3.02 (t, J=12.4 Hz, 1H), 2.93 (d, J=12.7 Hz, 1H), 2.74-2.68 (m, 1H), 2.65 (d, J=4.7 Hz, 3H), 2.61-2.52 (m, 2H), 2.46-2.37 (m, 1H), 1.83-1.75 (m, 2H), 1.72 (d, J=12.8 Hz, 2H), 1.51 (qd, J=13.0, 5.5 Hz, 3H), 1.44-1.34 (m, 1H), 1.16 (s, 9H). MS (M)+=1008.52.
BAK-04-029
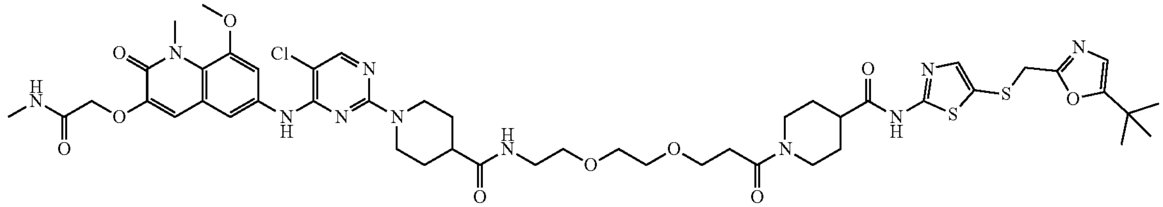
BAK-04-029

$^1$H NMR (500 MHz, DMSO-de) 6=12.28 (s, 1H), 8.95 (s, 1H), 8.08 (s, 1H), 7.95 (d, J=4.8 Hz, 1H), 7.86 (t, J=5.7 Hz, 1H), 7.52 (s, 2H), 7.38 (s, 1H), 7.00 (s, 1H), 6.70 (s, 1H), 4.55 (s, 2H), 4.48 (d, J=13.1 Hz, 2H), 4.36 (d, J=13.1 Hz, 1H), 4.04 (s, 2H), 3.91 (d, J=13.6 Hz, 1H), 3.86 (d, J=7.4 Hz, 6H), 3.61 (t, J=6.7 Hz, 2H), 3.49 (s, 4H), 3.39 (t, J=5.9 Hz, 2H), 3.18 (q, J=5.9 Hz, 2H), 3.01 (t, J=12.7 Hz, 1H), 2.91 (t, J=12.6 Hz, 2H), 2.71 (ddd, J=11.4, 7.5, 3.8 Hz, 1H), 2.62-2.52 (m, 2H), 2.46-2.39 (m, 1H), 1.83-1.75 (m, 1H), 1.71 (d, J=12.8 Hz, 2H), 1.51 (ddd, J=20.6, 13.4, 9.5 Hz, 2H), 1.44-1.34 (m, 1H), 1.16 (s, 9H).

MS $(M)^+$=1052.29.

BAK-04-030

Example 4. AR-BCL6 TCIPs

I. Synthesis of AR TCIPs

Synthesis of Oxime Intermediate 3

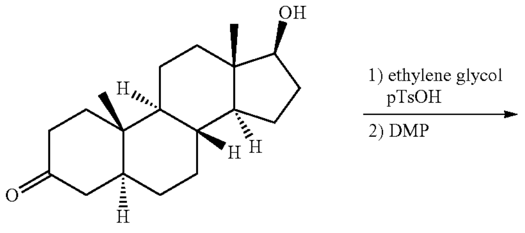

1

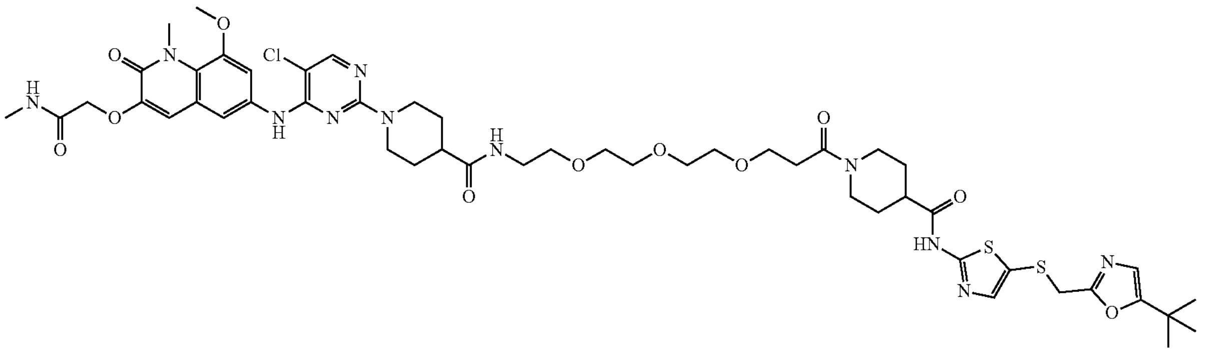

BAK-04-030

$^1$H NMR (500 MHz, DMSO-$d_6$) δ=12.28 (s, 1H), 9.21 (s, 1H), 8.13 (s, 1H), 7.95 (d, J=4.8 Hz, 1H), 7.87 (t, J=5.7 Hz, 1H), 7.50 (s, 2H), 7.38 (s, 1H), 7.02 (s, 1H), 6.70 (s, 1H), 4.55 (s, 2H), 4.42 (d, J=13.2 Hz, 2H), 4.36 (s, 1H), 4.04 (s, 2H), 3.92 (d, J=13.8 Hz, 1H), 3.86 (d, J=5.8 Hz, 6H), 3.60 (t, J=6.7 Hz, 2H), 3.54-3.45 (m, 8H), 3.39 (t, J=5.9 Hz, 2H), 3.18 (q, J=5.9 Hz, 2H), 3.06-2.92 (m, 3H), 2.71 (ddd, J=11.4, 7.5, 3.7 Hz, 1H), 2.65 (d, J=4.7 Hz, 3H), 2.62-2.53 (m, 2H), 2.47-2.40 (m, 1H), 1.83-1.75 (m, 1H), 1.72 (d, J=12.8 Hz, 2H), 1.60-1.47 (m, 3H), 1.39 (q, J=11.2 Hz, 1H), 1.16 (s, 9H). MS (M)+=1096.58.

II. Activity of TCIPS

Figure 14:
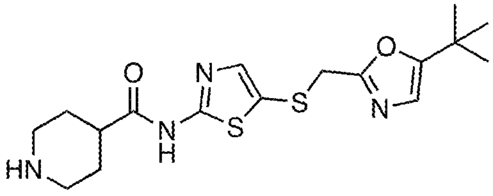
FIG. 14 provides the structure of the CDK9 inhibitor SNS-032 (A), the structures of BCL6 binders (B) and TCIPs prepared from these ligands (C); in accordance with embodiments of the disclosure.
Figure 14:
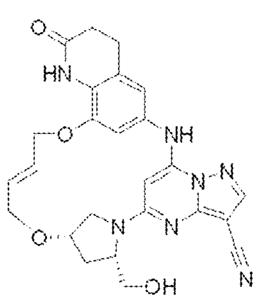
Figure 14:
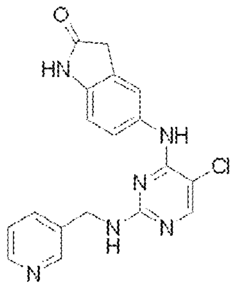
Figure 14:
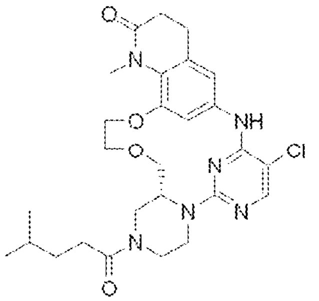
Figure 14:
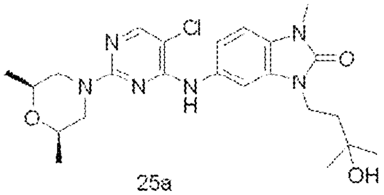
Figure 14:
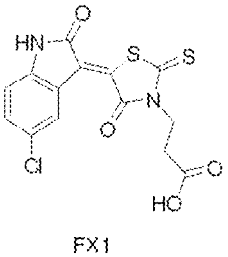
Figure 14:
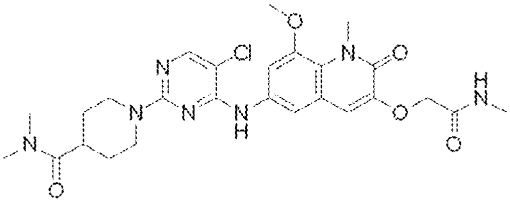
Figure 14:
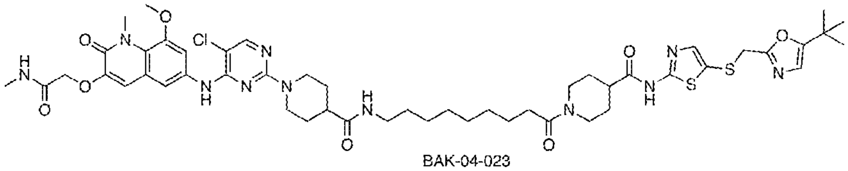
Figure 14:
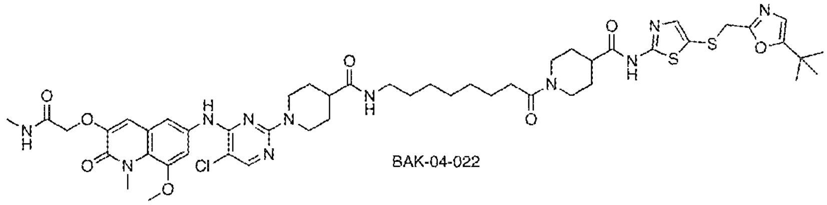
Figure 14:
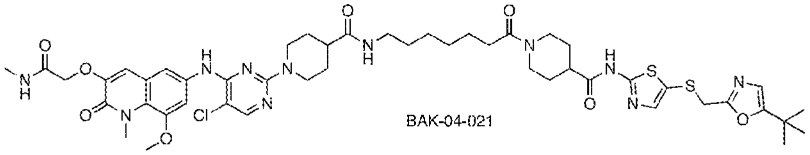
Figure 14:
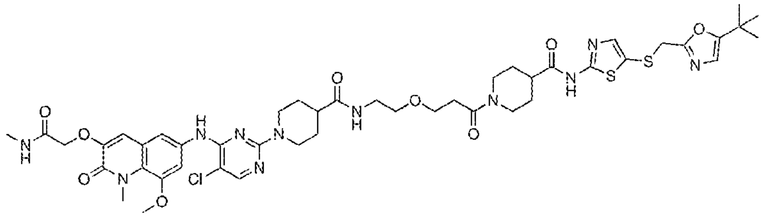
Figure 14:
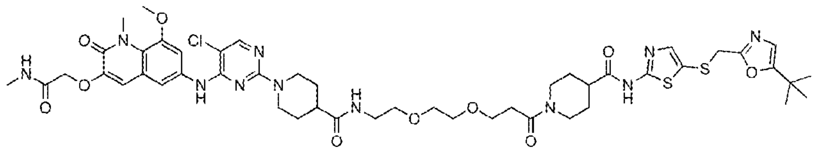
Figure 14:
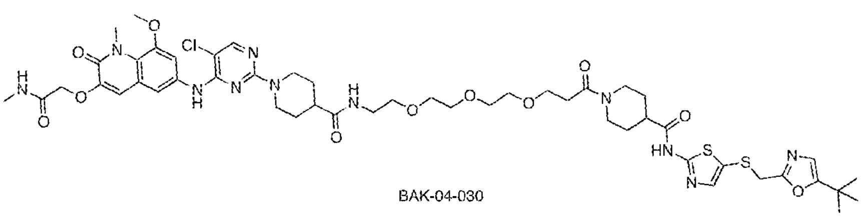
Figure 14:
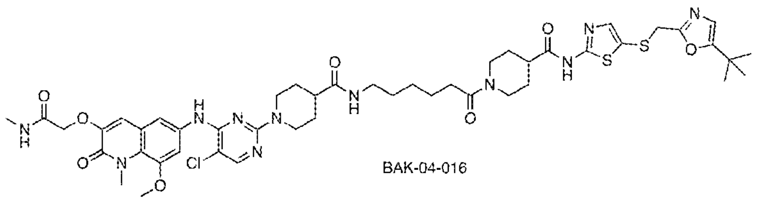
Figure 14:
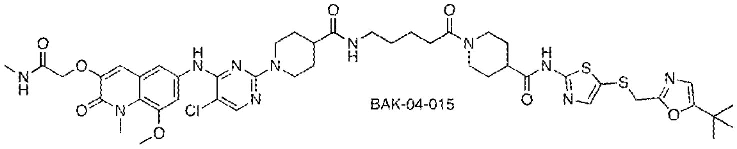
Figure 14:
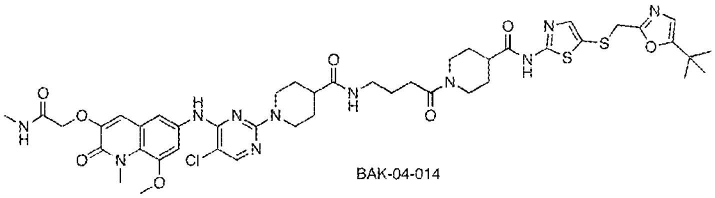
Figure 15:
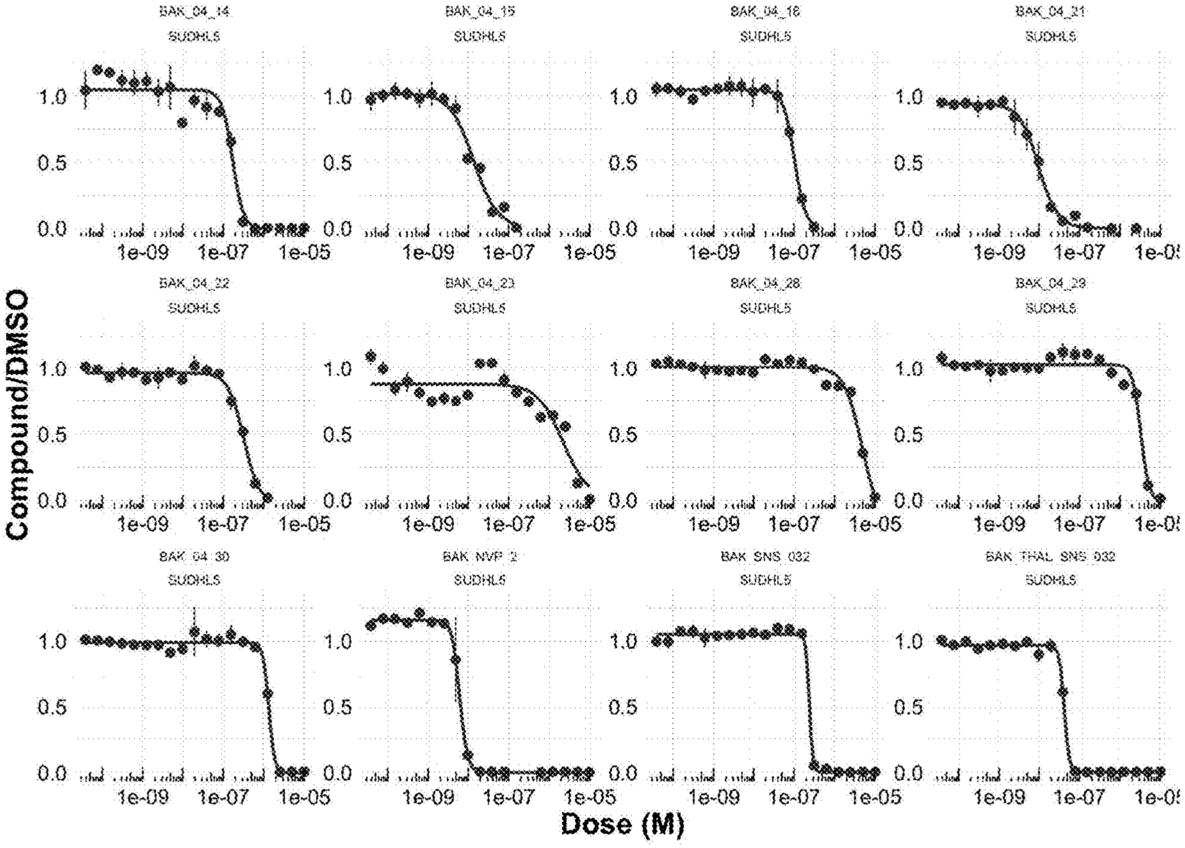
FIG. 15 demonstrates that CDK9-BCL6 TCIPs effectively kill human lymphomas. The molecules shown in FIG. 14 were used at the indicated concentrations to treat different lymphoma cell lines, such as SUDHL5 shown here. Death was recorded 72 hours later. Additional data is provided in FIG. 26 with controls.

FIG. 15 CDK9-BCL6 TCIPs Effectively Kill Human Lymphomas. The molecules shown in FIG. 14 were used at the indicated concentrations to treat different lymphoma cell lines, such as SUDHL5 shown here. Death was recorded 72 hours later.

Figure 16:
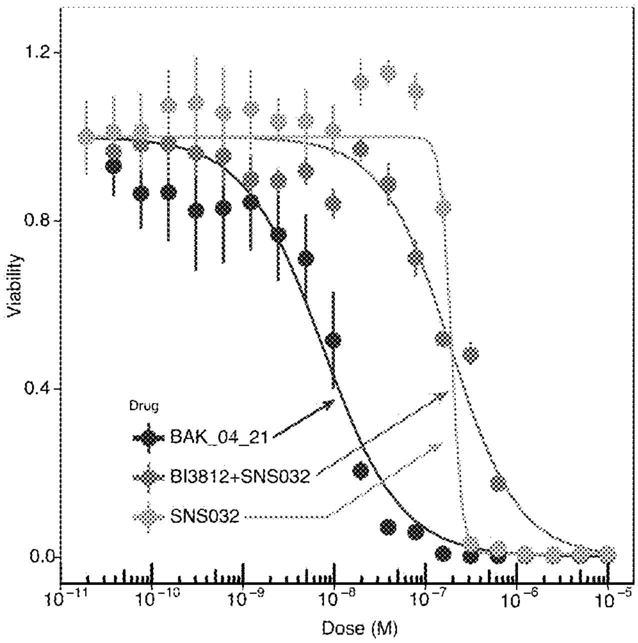
FIG. 16 demonstrates that CDK9-BCL6 TCIP (BAK_04_21) is more effective at killing lymphoma cells than component molecules and competitor molecules.

FIG. 16 CDK9-BCL6 TCIPs are more effective at killing lymphoma cells than component molecules and competitor molecules.

Figure 17:
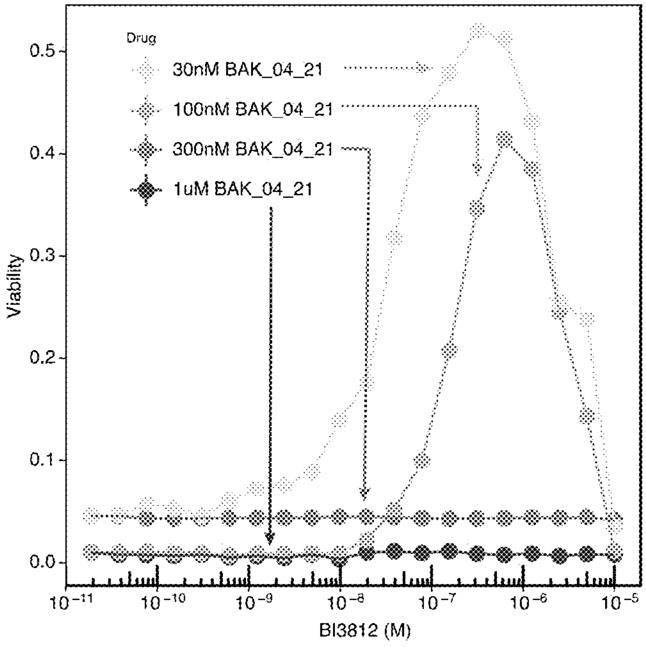
FIG. 17 demonstrates that CDK9-BCL6 TCIP BAK04-21 forms a ternary complex in cells that can be competed with the BCL6 inhibitor. Cell death was recorded 72 hours after adding TCIP BAK04-21 with increasing concentrations of the BCL6 inhibitor BI3812, shown on the X axis.
Figure 18A:
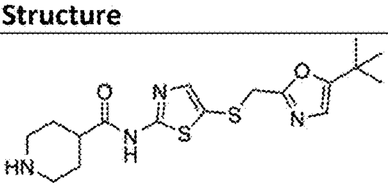
FIG. 18A provides the structures of CDK ligands that may be employed in TCIPs in accordance with embodiments of the disclosure, while FIG. 18B provides the structures of additional BCL6 ligands that may be employed TCIPs in accordance with embodiments of the disclosure.
Figure 18A:
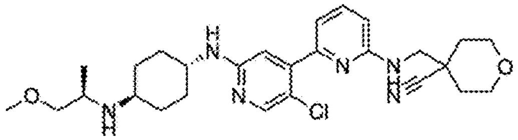
Figure 18A:
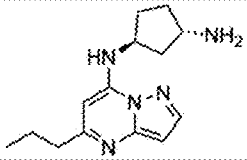
Figure 18A:
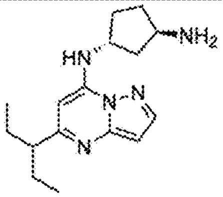
Figure 18A:
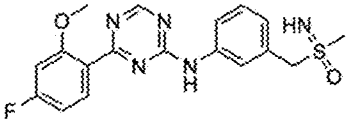
Figure 18A:
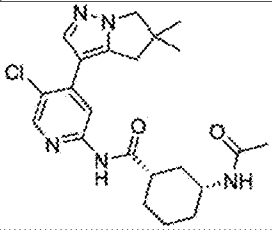
Figure 18A:
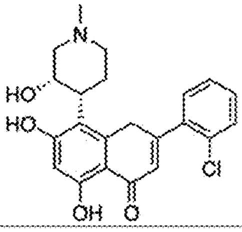
Figure 18A:
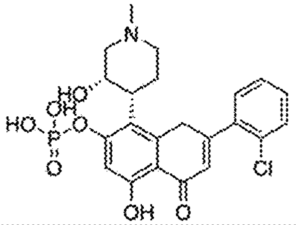
Figure 18A:
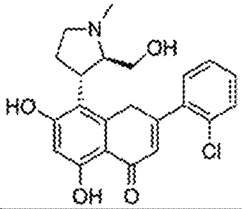
Figure 18A:
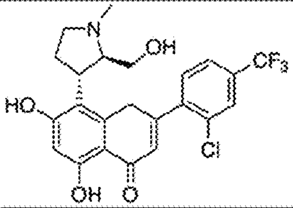
Figure 18A:
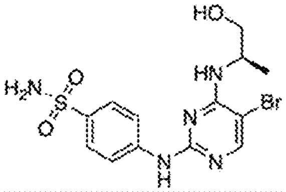
Figure 18A:
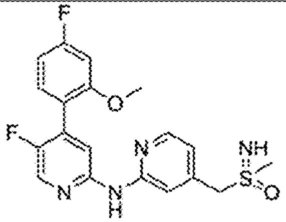
Figure 18A:
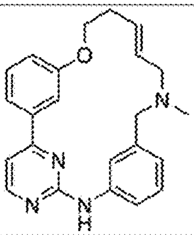
Figure 18A:
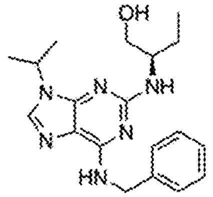
Figure 18A:
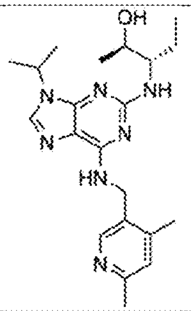
Figure 18A:
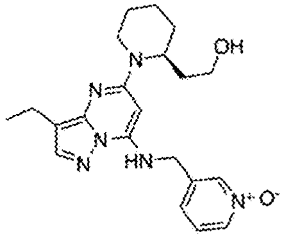
Figure 18A:
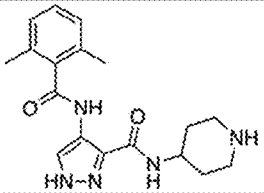
Figure 18A:
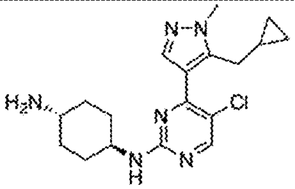
Figure 18A:
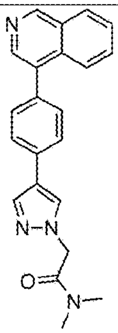
Figure 18A:
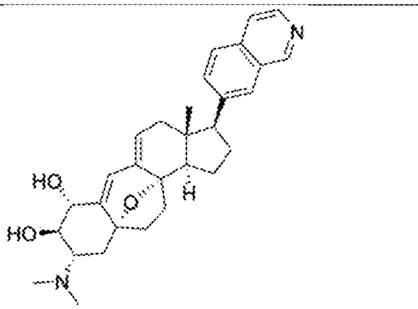
Figure 18A:
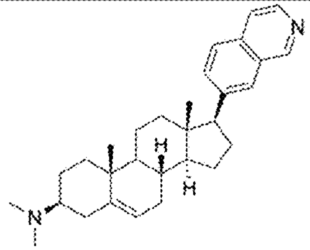
Figure 18A:
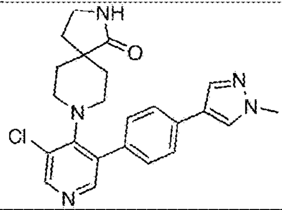
Figure 18A:
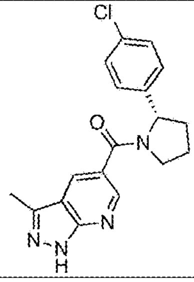
Figure 18A:
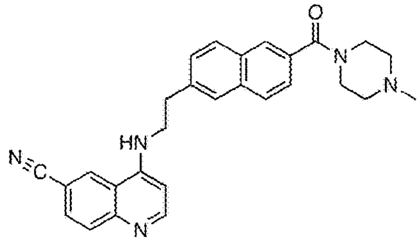
Figure 18A:
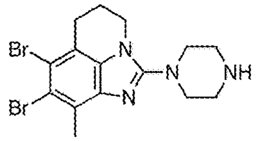
Figure 18A:
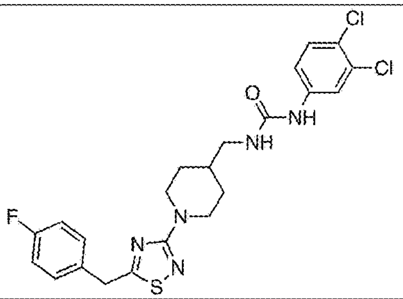
Figure 18A:
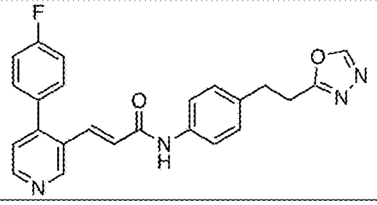
Figure 18A:
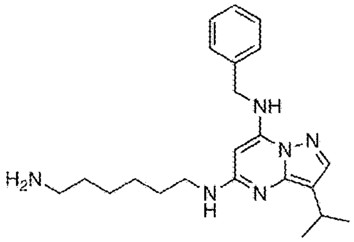
Figure 18A:
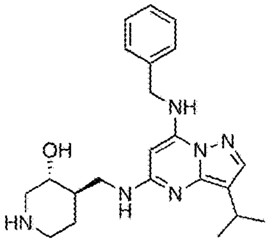
Figure 18A:
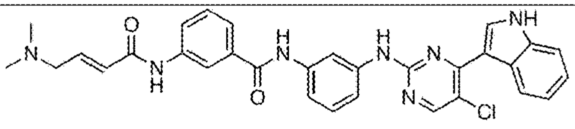
Figure 18A:
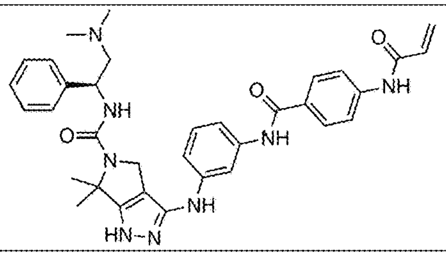
Figure 18B:
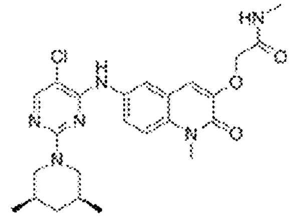
Figure 18B:
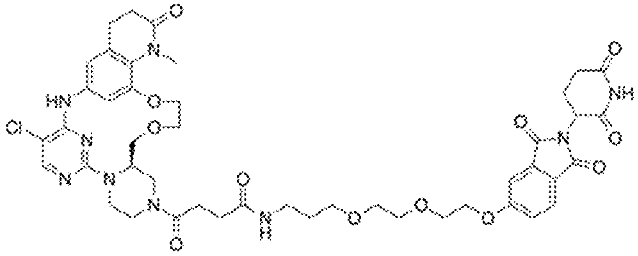
Figure 18B:
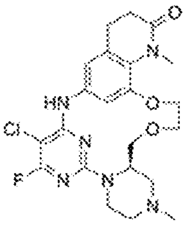
Figure 18B:
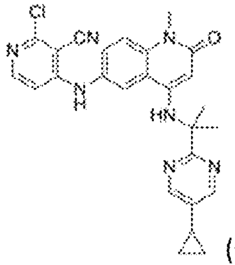
Figure 18B:
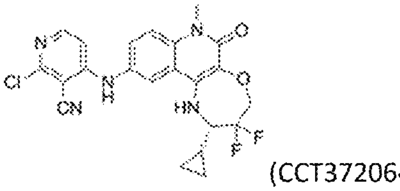
Figure 18B:
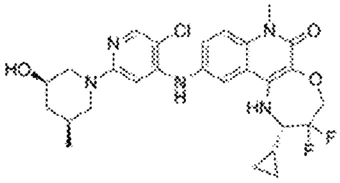
Figure 18B:
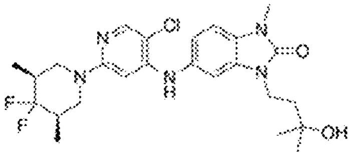
Figure 18B:
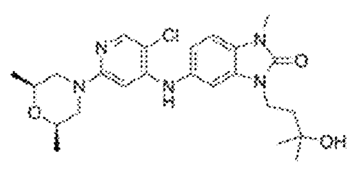
Figure 18B:
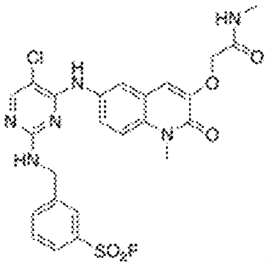
Figure 18B:
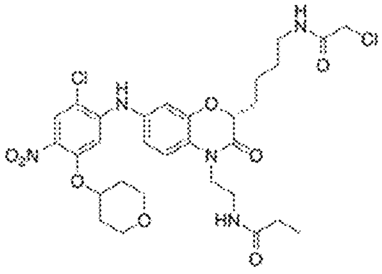
Figure 18B:
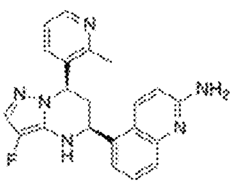
Figure 18B:
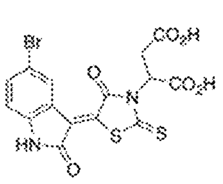

FIG. 17 CDK9-BCL6 TCIP BAK04-21 forms a ternary complex in cells that can be competed with the BCL6 inhibitor. Cell death was recorded 72 hours after adding TCIP BAK04-21 with increasing concentrations of the BCL6 inhibitor B13812, shown on the X axis.

-continued

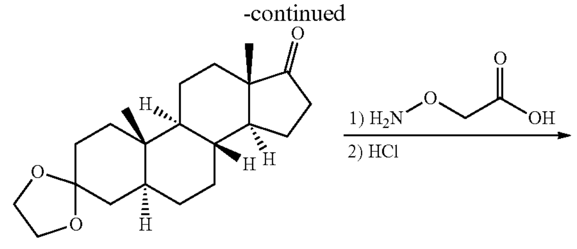

2

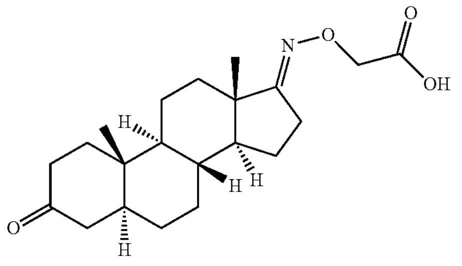

3

To a solution of dihydrotestosterone (DHT, 1, 0.50 g, 1.7 mmol, 1.0 equiv) in toluene (6 mL) was added ethylene glycol (3.4 mL) and para-toluenesulfonic acid monohydrate (0.33 g, 1.7 mmol, 1.0 equiv) and the resulting mixture was stirred at 80° C. for 1 h. The reaction mixture was cooled to ambient temperature and all volatiles were concentrated under reduced pressure. The residue was partitioned between $CH_2Cl_2$ and aq. sat. sodium bicarbonate and the aqueous layer was extracted with $CH_2Cl_2$. The combined organic extracts were washed with brine, dried, and concentrated under reduced pressure to afford a white solid, which was taken up in $CH_2Cl_2$ (10 mL) and KOAc (0.20 g, 2.0 mmol, 1.2 equiv) and PCC (0.73 g, 3.4 mmol, 2.0 equiv) were added. The dark suspension was stirred at ambient temperature for 2 h, after which it was diluted with diethyl ether and filtered over a plug of celite. The filtrate was concentrated to afford 2 as a white solid (0.57 g, quantitative yield). Intermediate 2 (0.16 g, 0.47 mmol, 1.0 equiv) was dissolved in pyridine (5 mL) and 2-(aminooxy)acetic acid hydrochloride (0.17 g, 1.3 mmol, 2.8 equiv) was added. The reaction mixture was stirred at ambient temperature until TLC analysis indicated full consumption of starting material. The mixture was poured on 10% aqueous HCl and the water phase was extracted with EtOAc. The combined organic extracts were washed with brine and concentrated under reduced pressure. The resulting residue was taken up in acetone (4 mL) and 2 M HCl (2 mL) and the solution was stirred for 2 h. The aqueous layer was extracted with $CH_2Cl_2$ and the organic extracts were concentrated to afford intermediate 3 as white solid (0.17 g, quantitative yield).

$^1H$ NMR (500 MHz, $CDCl_3$) δ=4.57 (d, J=1.8 Hz, 2H), 2.63-2.46 (m, 2H), 2.44-2.23 (m, 3H), 2.10 (ddd, J=15.0, 4.0, 2.2 Hz, 1H), 2.02 (ddd, J=13.2, 6.5, 2.3 Hz, 2H), 1.95-1.88 (m, 1H), 1.88-1.73 (m, 3H), 1.68 (ddd, J=9.1, 3.9, 2.5 Hz, 1H), 1.59-1.49 (m, 2H), 1.47-1.32 (m, 6H), 1.28-1.18 (m, 2H), 1.03 (s, 3H), 0.99 (dd, J=12.5, 5.0 Hz, 1H), 0.94 (s, 3H), 0.87-0.77 (m, 2H).

-continued

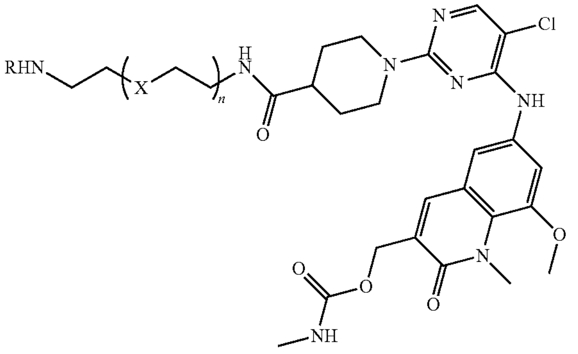

5: R = Boc

HCl, 1,4-dioxane

6: R = H

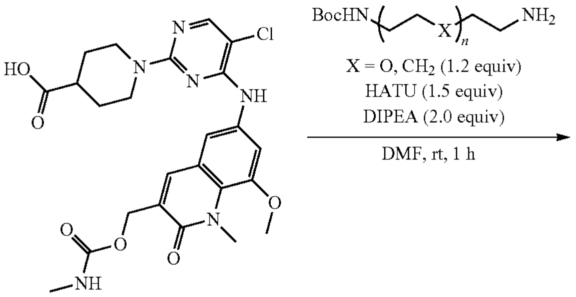

4

To a solution of 4 (11 mg, 0.016 mmol, 1.0 equiv) in DMF (0.3 mL) was added N-Boc-bis amine linker (1.2 equiv), HATU (12 mg, 0.031 mmol, 2.0 equiv) and DIPEA (4.2 μL, 0.024 mmol, 1.5 equiv) and the resulting yellow-brown solution was stirred at ambient temperature for 2 h. The solvent was removed under reduced pressure and high vacuum and the material was taken up in 1,4-dioxane (0.2 mL) and 4 M HCl in 1,4-dioxane (0.2 mL) and stirred at ambient temperature for 30 min. The volatiles were removed under reduced pressure and the residue was used in the subsequent step without further purification.

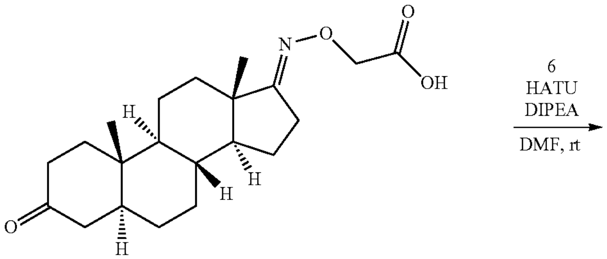

3

-continued

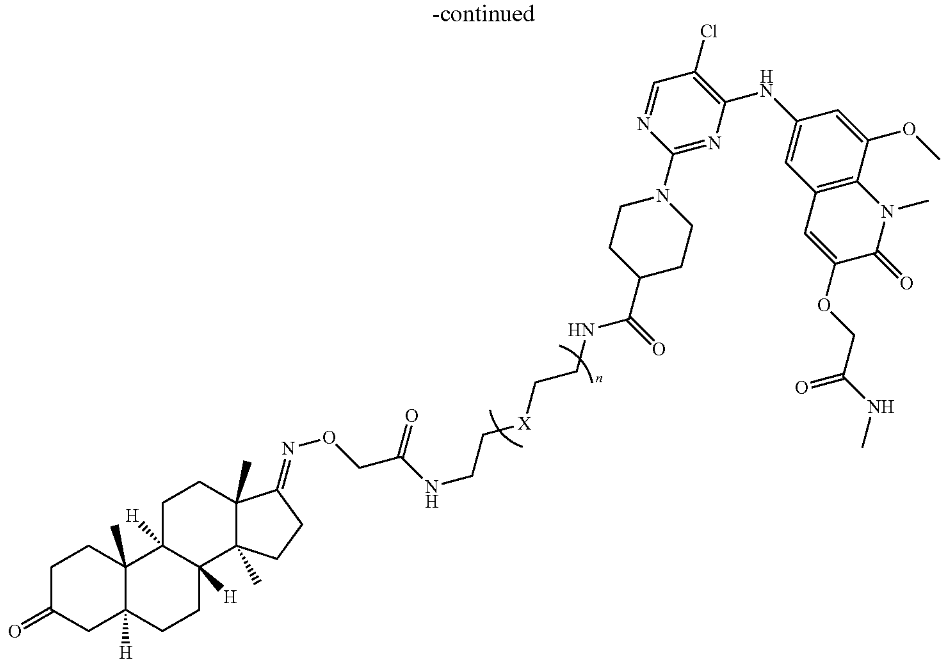

Intermediate 3 (6.4 mg, 0.018 mmol, 1.1 equiv)) and 6 (1.0 equiv) were dissolved in DMF (0.3 mL) and HATU (9.1 mg, 0.024 mmol, 1.5 equiv) and DIPEA (8.4 μL, 0.048 mmol, 2.0 equiv) were added. The resulting yellow solution was stirred at ambient temperature until LCMS analysis indicated completion of the reaction. The solution was directly purified by RP-HPLC.

RCS-02-058

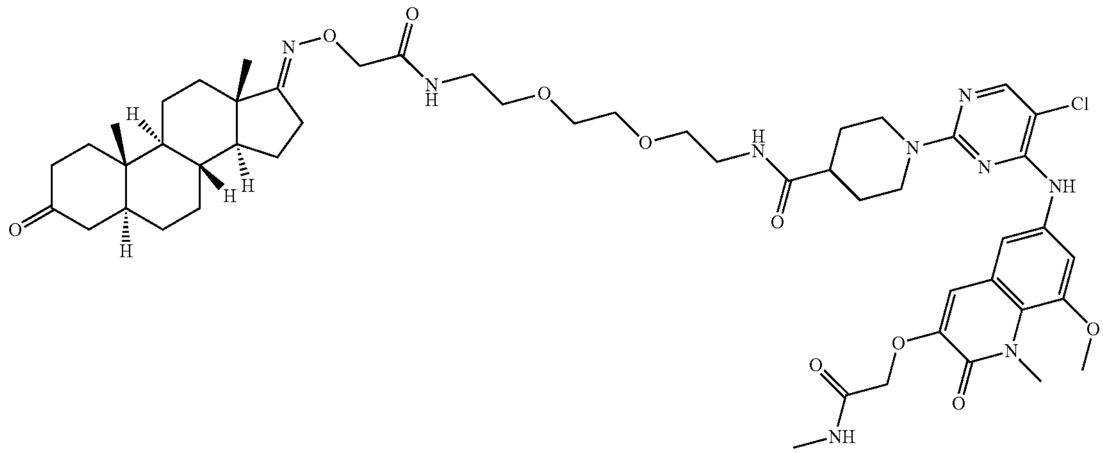 [SMILES: CNC(=O)COc1cc2cc(Nc3nc(N4CCC(C(=O)NCCOCCOCCNC(=O)CO/N=C5\CC[C@H]6[C@@H]7CC[C@H]8CC(=O)CC[C@]8(C)[C@H]7CC[C@]56C)CC4)ncc3Cl)cc(OC)c2n(C)c1=O]

MS $(M)^+$=1004.62.

$^1$H NMR (500 MHz, DMSO) δ=9.07 (s, 1H), 8.11 (s, 1H), 7.95 (d, J=4.9 Hz, 1H), 7.88 (d, J=5.7 Hz, 1H), 7.53 (s, 2H), 7.38 (t, J=5.9 Hz, 1H), 7.01 (s, 1H), 4.55 (s, 2H), 4.47 (d, J=13.1 Hz, 2H), 4.31 (s, 2H), 3.90-3.81 (m, 6H), 3.50 (s, 4H), 3.40 (dt, J=11.7, 5.9 Hz, 4H), 3.26 (q, J=5.9 Hz, 2H), 3.19 (q, J=5.6 Hz, 2H), 2.95 (t, J=12.6 Hz, 2H), 2.66 (d, J=4.6 Hz, 3H), 2.48-2.35 (m, 3H), 2.28 (t, J=14.4 Hz, 1H), 2.10-2.03 (m, 1H), 1.92-1.83 (m, 2H), 1.78-1.63 (m, 4H), 1.58-1.41 (m, 4H), 1.36-1.19 (m, 6H), 1.08 (td, J=11.9, 5.9 Hz, 1H), 0.96 (s, 3H), 0.93-0.85 (m, 1H), 0.84 (s, 3H), 0.72 (t, J=12.0 Hz, 1H).

RCS-02-060
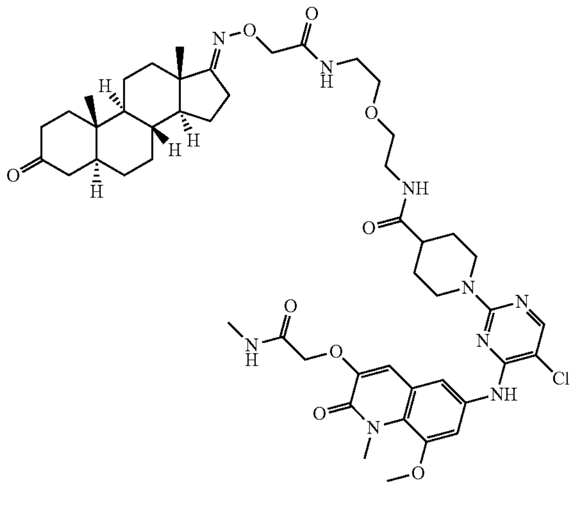 [SMILES: CNC(=O)COc1cc2cc(Nc3nc(N4CCC(C(=O)NCCOCCNC(=O)CO/N=C5\CC[C@H]6[C@@H]7CC[C@H]8CC(=O)CC[C@]8(C)[C@H]7CC[C@]56C)CC4)ncc3Cl)cc(OC)c2n(C)c1=O]
MS $(M)^{+}$=960.57.
$^{1}$H NMR (500 MHz, DMSO) δ=9.07 (s, 1H), 8.11 (s, 1H), 7.94 (d, J=4.9 Hz, 1H), 7.83 (t, J=5.6 Hz, 1H), 7.58-7.50 (m, 2H), 7.38 (t, J=5.8 Hz, 1H), 7.01 (s, 1H), 4.54 (s, 2H), 4.46 (d, J=13.2 Hz, 2H), 4.30 (s, 2H), 3.86 (d, J=6.2 Hz, 6H), 3.39 (q, J=5.7 Hz, 4H), 3.25 (q, J=5.9 Hz, 2H), 3.18 (q, J=5.8 Hz, 2H), 3.00-2.83 (m, 2H), 2.65 (d, J=4.7 Hz, 3H), 1.90-1.81 (m, 2H), 1.76-1.61 (m, 5H), 1.57-1.37 (m, 4H), 1.26 (tq, J=19.3, 13.0 Hz, 5H), 1.11-1.02 (m, 1H), 0.95 (s, 3H), 0.92-0.84 (m, 1H), 0.82 (s, 3H), 0.70 (t, J=11.3 Hz, 1H).
RCS-02-061
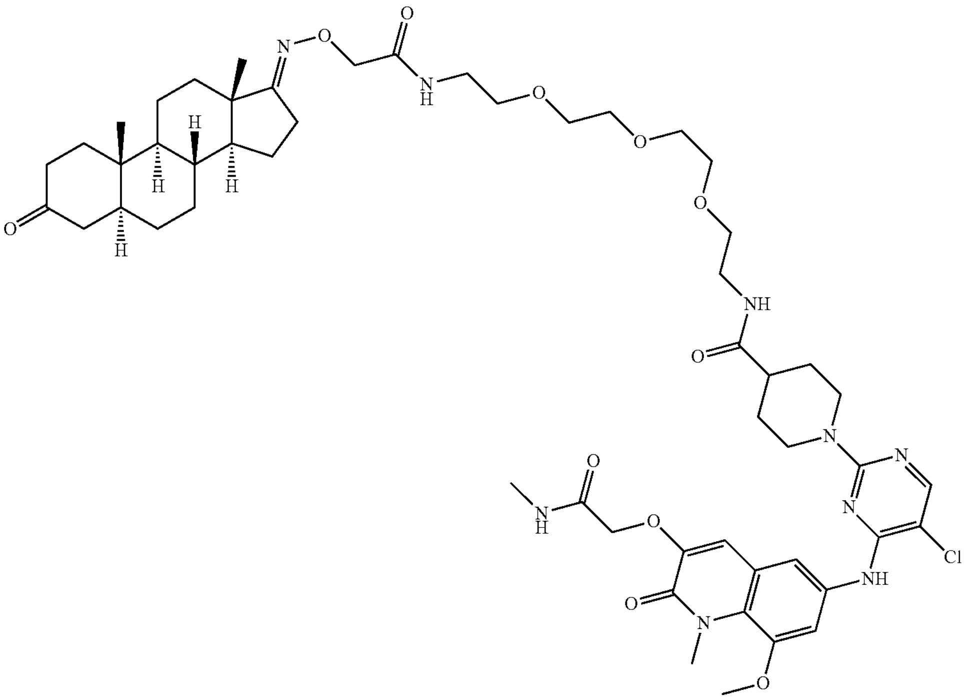

MS $(M)^+$=1048.68.
$^1$H NMR (500 MHz, DMSO-d6) δ=7.66 (d, J=2.2 Hz, 1H), 7.13 (d, J=2.2 Hz, 1H), 6.86 (t, J=5.0 Hz, 1H), 6.65 (q, J=4.9 Hz, 1H), 6.51 (t, J=5.3 Hz, 1H), 4.75 (s, 2H), 4.71 (s, 2H), 3.89 (d, J=9.5 Hz, 6H), 3.77 (ddd, J=15.5, 9.4, 6.8 Hz, 2H), 3.71-3.55 (m, 14H), 3.37 (dt, J=5.0, 4.2 Hz, 2H), 3.30 (dt, J=5.4, 4.6 Hz, 2H), 2.84 (d, J=4.9 Hz, 3H), 2.59-2.25 (m, 9H), 2.05 (m, 2H), 1.84-1.44 (m, 11H), 1.41-1.27 (m, 3H), 1.19-1.09 (m, 1H), 1.07 (s, 3H), 1.02 (s, 3H), 0.90 (m, 1H).
RCS-02-062
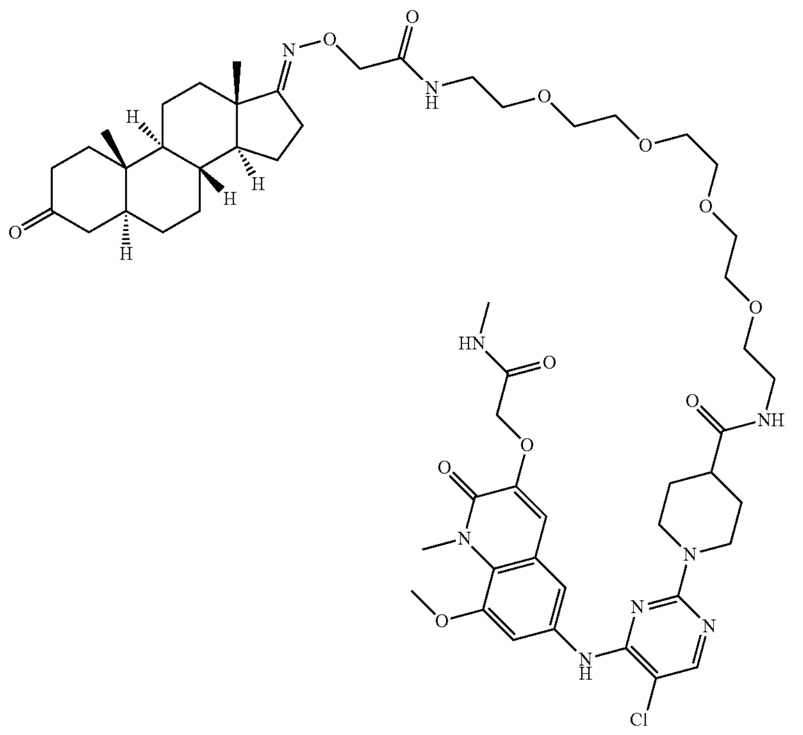 [SMILES: CNC(=O)COc1cc2cc(Nc3nc(N4CCC(C(=O)NCCOCCOCCOCCOCCNC(=O)CO/N=C5\CC[C@H]6[C@@H]7CC[C@H]8CC(=O)CC[C@]8(C)[C@H]7CC[C@]56C)CC4)ncc3Cl)cc(OC)c2n(C)c1=O]
MS $(M)^+$=1092.73.
$^1$H NMR (500 MHz, DMSO-d6) δ=9.18 (s, 1H), 8.26 (s, 1H), 7.66 (d, J=2.2 Hz, 1H), 7.13 (d, J=2.2 Hz, 1H), 6.86 (t, J=5.0 Hz, 1H), 6.65 (q, J=4.9 Hz, 1H), 6.51 (t, J=5.3 Hz, 1H), 4.75 (s, 2H), 4.71 (s, 2H), 3.89 (d, J=9.5 Hz, 6H), 3.77 (ddd, J=15.5, 9.4, 6.8 Hz, 2H), 3.72-3.61 (m, 14H), 3.59 (dt, J=7.0, 4.4 Hz, 4H), 3.37 (dt, J=5.0, 4.2 Hz, 2H), 3.30 (dt, J=5.3, 4.6 Hz, 2H), 2.84 (d, J=4.9 Hz, 3H), 2.59-2.25 (m, 9H), 2.05 (dddd, J=13.2, 9.4, 6.8, 5.3 Hz, 2H), 1.84-1.44 (m, 11H), 1.41-1.27 (m, 3H), 1.19-1.09 (m, 1H), 1.07 (s, 3H), 1.02 (s, 3H), 0.94-0.86 (m, 1H).

RCS-02-063

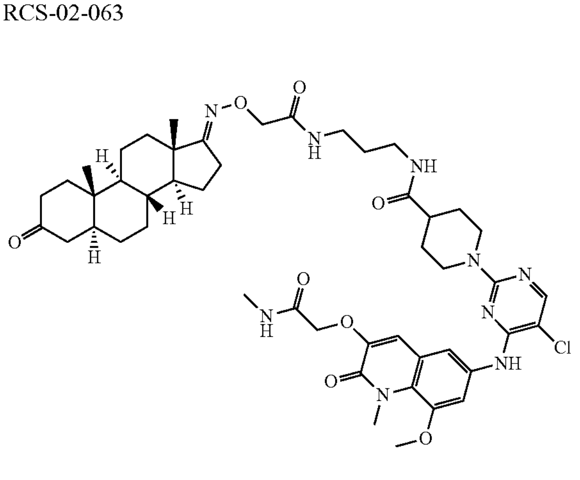

MS $(M)^+$=930.54.

$^1$H NMR (500 MHz, DMSO-d6d) δ=9.18 (s, 1H), 8.26 (s, 1H), 7.66 (d, J=2.2 Hz, 1H), 7.52 (t, J=4.9 Hz, 1H), 7.13 (d, J=2.2 Hz, 1H), 6.65 (q, J=4.9 Hz, 1H), 6.44 (t, J=5.3 Hz, 1H), 4.75 (s, 2H), 4.71 (s, 2H), 3.89 (d, J=9.5 Hz, 6H), 3.77 (ddd, J=15.5, 9.4, 6.8 Hz, 2H), 3.64 (ddd, J=15.4, 9.4, 6.8 Hz, 2H), 3.16 (m, 4H), 2.84 (d, J=4.9 Hz, 3H), 2.59-2.25 (m, 9H), 2.05 (m, 2H), 1.84-1.62 (m, 6H), 1.62-1.55 (m, 4H), 1.55-1.52 (m, 2H), 1.52-1.44 (m, 2H), 1.41-1.27 (m, 3H), 1.19-1.09 (m, 1H), 1.07 (s, 3H), 1.02 (s, 3H), 0.94-0.86 (m, 1H).

Figure 24:
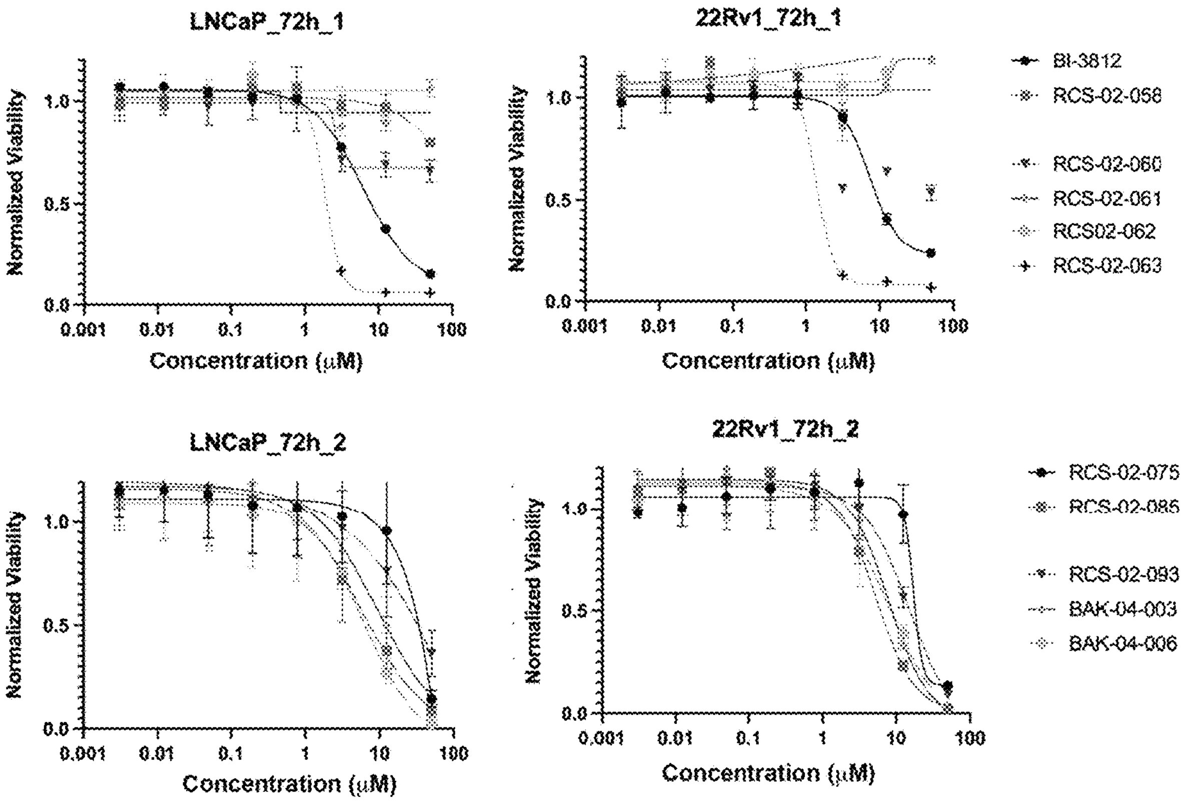
FIG. 24 demonstrates that AR-TCIPs rapidly and robustly kill human prostatic cancer cell lines. Four different cell lines were used that are androgen-dependent. The AR-TCIPs were added at the indicated concentrations and viable cell counts were determined after 72 hours of exposure. RCS-02-063 shows effective killing of prostate cancer cell lines with an IC50 of about 1.5 μM.

II. AR TCIPs Rewire Cancer Drivers to Activate Proapoptotic Genes in Prostatic Cancer Cells The AR-BCL6 TCIPs synthesized in I above were tested for their ability to kill prostate cancer cell lines as an indication of their ability to treat human prostatic cancer. The results are shown in FIG. 24. AR-TCIPs rapidly and robustly kill human prostatic cancer cell lines. Four different cell lines were used that are androgen-dependent. The drugs were added at the indicated concentrations and viable cell counts determined after 72 hours of exposure. RCS-02-063 shows effective killing of each prostate cancer cell lines. The EC50 is shown in each case. TCIP RCS-02-063 shows effective killing with an IC50 of about 1 μM.

III. Activity of RCS-02-063

Figure 25:
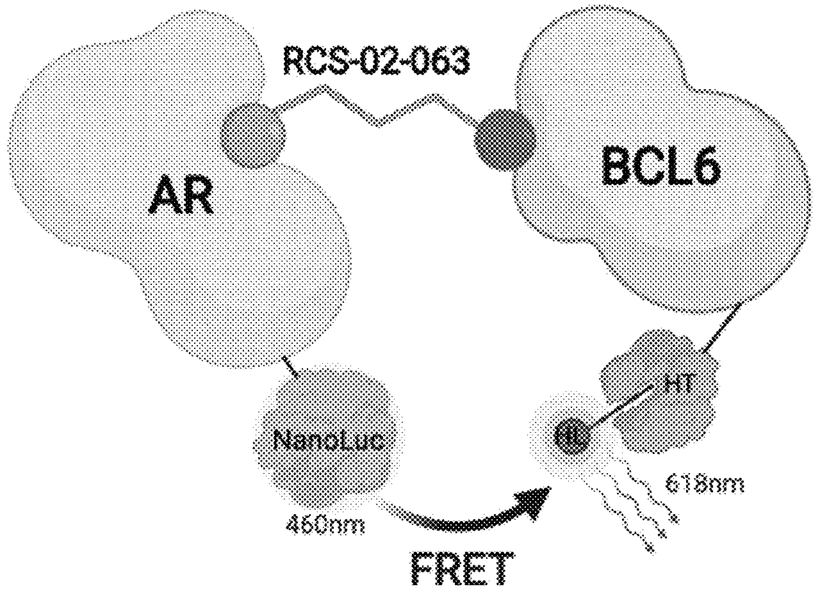
FIG. 25 (Panels A-B) depict target engagement in vivo by TCIP RCS-02-063. The nanoBRET assay was constructed using nanoluc-labeled AR and Halotag-labeled BCL6. A BRET signal was then detected after excitation at 460 nm of HEK293 cells infected with the labeled fusion proteins. TCIP RCS-02-063 induces a robust BRET signal indicating in vivo target engagement.
Figure 25:
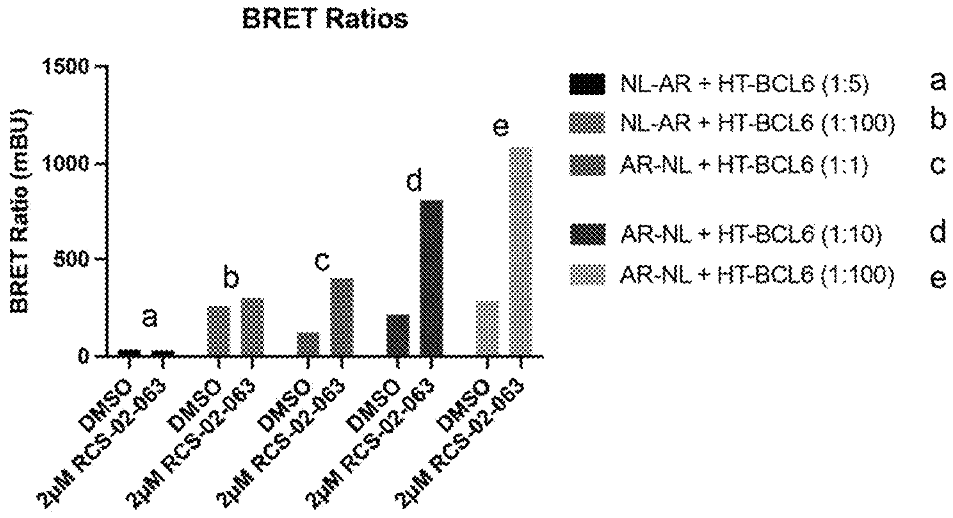

To ascertain activity of TCIP RCS-02-063 as schematically illustrated in FIG. 1, w a BRET assay was developed to detect in vivo target engagement and ternary complex formation. FIG. 25 (Panels A-B) provides an illustration of the assay as wells the results obtained therefrom. As shown, the nanoBRET assay was constructed using long-wavelength fluorophore (HaloTag) HT-labeled AR and an extremely bright luciferase (Nanoluc)-labeled BCL6. A BRET signal at 618 nm was then detected after excitation at 460 nm of HEK293 cells infected with the labeled fusion proteins. The results show that TCIP RCS-02-063 induces a robust BRET signal indicating in vivo target engagement. The results indicate that, within the cell, TCIP RCS-02-063 induces proximity of the labeled BCL6 and labeled AR.

Figure 26:
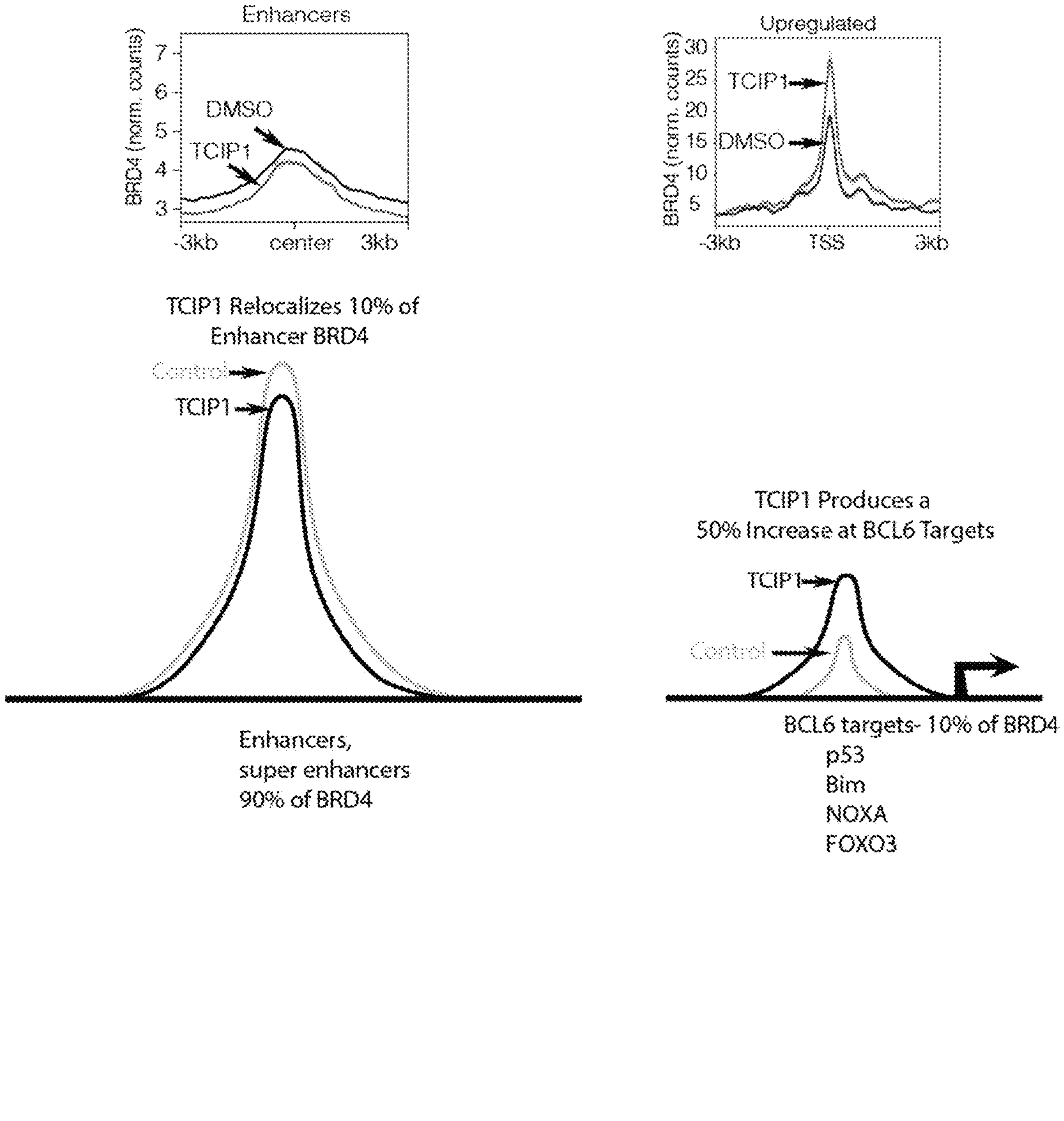
FIG. 26 demonstrates a gain-of-function (e.g., regulation of expression of a target gene that would otherwise not be achieved in the absence of formation of a ternary complex between a first endogenous protein, a second endogenous protein, and a compound of the disclosure) as described herein is achieved by recruiting a fraction of the available second endogenous protein present in the cell and thereby avoids mechanism-based toxicity. In this example, less than 10% of BRD4 was recruited to the promoters of cell death genes by a compound disclosed herein (e.g., TCIP1 compound) to activate pro-apoptotic BCL6 targets. The gain-of-function is the activation of the proapoptotic pathways by BCL6, rather than suppressing them, which is its normal role.

Example 5. A Compound of the Disclosure Activates Proapoptotic BCL6 Targets by Recruiting Less than 10% of the Amount of BRD4 Present in a Target Cell Karpas 422 cells were treated for one hour with TCIP1 and then CHIP-seq was carried out with antibodies to BRD4. As shown in FIG. 26 (upper left panel), TCIP1 produces a small reduction in the amount of BRD4 over genomic enhancers. In contrast, the upper right panel of FIG. 26 shows that TCIP1 treatment results in a 50% increase in BRD4 over genomic BCL6 sites near upregulated BCL6 target genes. The bottom panel of FIG. 26 is a reconstruction of this experiment taking into account that 90% of BRD4 is bound to enhancers genome wide and shows the degree of relocalization of about 10% of BRD4 from enhancers that have most of the cell's BRD4 to the BCL6 target genes, where there is a 50% increase with TCIP treatment.

Example 6. Rewiring Cancer Drivers to Activate Apoptosis

Genes that drive the proliferation, survival, invasion and metastasis of malignant cells have been identified for many human cancers. Independent studies have identified cell death pathways that eliminate cells for the good of the organism.

This example describes a new class of molecules: TCIPs (Transcriptional/Epigenetic Chemical Inducers of Proximity) that recruit the endogenous cancer driver, or a downstream transcription factor, to the promoters of cell death genes, thereby activating their expression. To develop this concept, this example focuses on diffuse large B cell lymphoma (DLBCL), in which the transcription factor BCL6 (B-cell lymphoma 6) is deregulated. BCL6 binds to the promoters of cell death genes and epigenetically suppresses their expression. The first TCIPs were produced by chemically linking BCL6 inhibitors to small molecules that bind transcriptional activators, such as BRD4. TCIP1 reduces binding of BRD4 at enhancers by 10%, while increasing its binding by 50% over genomic BCL6 binding sites, producing Pol II serine 2 phosphorylation and transcriptional elongation of proapoptotic BCL6 targets within 15 minutes. TCIP1 kills DLBCL lines, including chemotherapy-resistant, TP53-mutant lines with an $EC_{50}$ of 1.3 nM in 72 hrs, reflecting a dominant gain-of-function mechanism. TCIP1 captures the combinatorial specificity inherent to transcription and operates at low target occupancy explaining its relative lack of toxicity to normal cells and mice. The general TCIP concept has applications in elimination of senescent cells, enhancing expression of therapeutic genes, treatment of diseases produced by haploinsufficiency, and activation of immunogens for immunotherapy.

Figure 27:
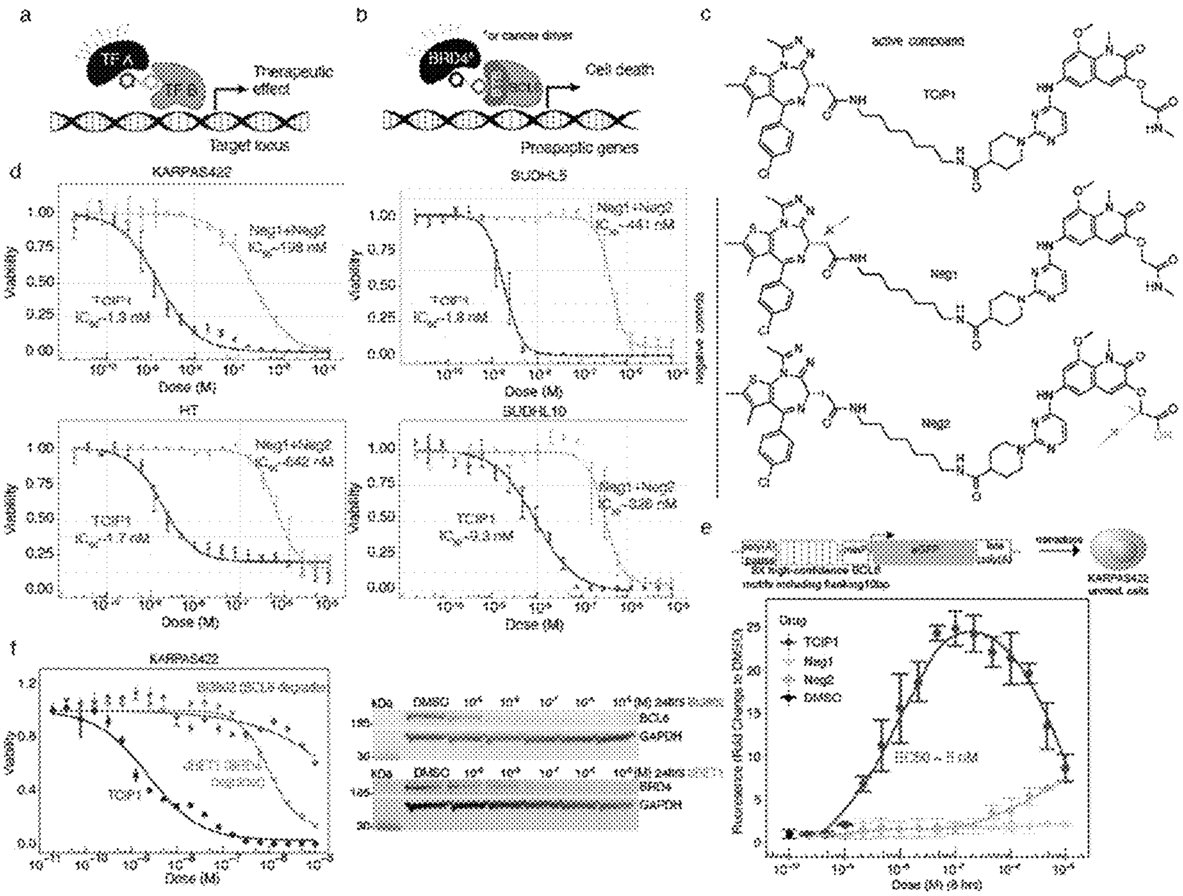
FIG. 27 (Panels A-F) depict non-limiting examples of production of compounds of the disclosure, and data related thereto.

To rewire transcriptional circuits within a genetically unmodified cell or organism, small molecules were developed that allow the recruitment of transcriptional or epigenetic regulators to the regulatory regions of target therapeutic genes. The general features of the concept and design of a TCIP is illustrated in FIG. 27, Panel A and involves synthesis of small molecules that bind a specific transcriptional or epigenetic regulator on one side, and on the other side, a transcription factor that binds to a target therapeutic gene. 1. 1. Cell Culture Lymphoma and leukemia cells were cultured in RPMI-1640 (ATCC 30-2001)+10% FBS with antibiotics (100× PenStrep GIBCO #15140122). Primary human fibroblasts were obtained from ATCC (#CRL2522), cultured in DMEM+10% FBS with antibiotics and used at passages 3-5. Primary human tonsillar lymphocytes were a kind gift from M. M. Davis. Cells were routinely checked for *mycoplasma* and immediately checked upon suspicion. No cultures tested positive.

2. Cell Viability Measurements 30,000 cells were plated in 100 μL media per well of a 96 well plate and treated with drug for indicated times and doses. A resazurin-based indicator of cell health (PrestoBlue, ThermoFisher #P50200) was added for 1.5 hours after which the fluorescence ratio at 560/590 nm was recorded. The background fluorescence was subtracted and the signal was normalized to DMSO-treated cells. $EC_{50}$ measurements on cell lines were done with 4 biological repeats by separate cell passages maintained by 3 independent investigators. Fit of dose-response curves to data and statistical analysis was performed using drc package in R using the four-parameter log-logistic function.

3. PRISM Cell Proliferation Assay

The PRISM cell proliferation assay was carried out as previously described (Yu et al., Nature Biotechnology (2016) 34:419-423).

4. Chemical Synthesis

Unless otherwise noted, all reagents were purchased from commercial suppliers and used without further purification unless otherwise noted. Reactions were monitored using a Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=85% A at 0 min, 1% A at 1.7 min; solvent A=0.1% formic acid in water; solvent B=0.1% formic acid in Acetonitrile; flow rate: 0.6 mL/min. Analytical thin layer chromatography (TLC) was performed on Merck silica gel 60 F254 TLC glass plates and analytes were visualized by fluorescence quenching (using 254 nm light) and stained by potassium permanganate solution (KMnO4 (3 g), $K_2CO_3$ (20 g), 5% aq. NaOH (5 mL), water (300 mL)) followed by heating. Purification of reaction products was carried out by flash column chromatography using CombiFlash® Rf with Teledyne Isco RediSep® normal-phase silica flash columns (4 g, 12 g, 24 g, 40 g or 80 g) or preparative RP-HPLC using Waters SunFire™ Prep C18 column (19×100 mm, 5 μm particle size) using a gradient of 10-90% methanol in water containing 0.05% trifluoroacetic acid (TFA) over 40 min (45 min run time) at a flow of 40 mL/min. Assayed compounds were isolated and tested as TFA salts and purities of assayed compounds were in all cases greater than 95%, as determined by reverse-phase UPLC analysis. NMR spectra were acquired on a 500 MHz Bruker Avance Ill spectrometer, operating at the denoted spectrometer frequency given in MHz for the specified nucleus. All experiments were acquired at 298.0 K with a calibrated Bruker Variable Temperature Controller unless otherwise noted. The chemical shifts are reported in parts per million (ppm) and coupling constants (J) are given in Hertz (Hz). $^1H$ NMR spectra are reported with the solvent resonance as the reference unless noted otherwise ($CDCl_3$ at 7.26 ppm, $CD_3OD$ at 3.31 ppm, DMSO-$d^6$ at 2.50 ppm). Peaks are reported as (s=singlet, d=doublet, t=triplet, q=quartet, m=multiplet or unresolved, br=broad signal, coupling constant(s) in Hz, integration). 5. Protein Expression and Purification The construct for 6×His-TEV-BRD4$^{BD1}$ was described in Filippakopoulos et al. (Nature (2010) 468: 1067-1073) and was a gift from Nicola Burgess-Brown (Addgene plasmid #38943; n2t.net/addgene:38943; RRID: Addgene_38943). The construct for BCL6BTB_AviTag was based off previously designed BCL6 constructs used for TR-FRET assays, as reported in multiple papers including (Kerres et al., Cell Rep (2017) 20: 2860-2875; McCoull et al., ACS Chem Biol (2018) 13: 3131-3141), and contains amino acids 5-129 with three mutations, C8Q, C67R, C84N, that enhance stability but have no difference on backbone structure with the wild-type version (Stead et al., Acta Crystallographica Section F Structural Biology and Crystallization Communications (2008) 64: 1101-1104). A Trx-6×His-HRV3C-BCL6BTB construct without the AviTag was produced similarly for ITC studies where the tag was cleaved by addition of HRV3C.

6. TR-FRET

Each reaction contained 100 nM BRD4$^{BD1}$, 100 nM BCL6BTB-Avi-Biot, 20 nM Streptavidin-FITC (Thermo #SA1001), and 1:400 anti-6×His terbium antibody (PerkinElmer #61H12TLF) in 10 μL of buffer containing 20 mM HEPES, 150 mM NaCl, 0.1% BSA, 0.1% NP-40, and 1 mM TCEP in a 384-well plate. Protein was incubated with drug digitally dispensed (Tecan D300e) for 1 hour in the dark at room temperature before excitation at 337 nm and measurement of emission at 520 nm (FITC) and 490 nm (terbium) with a PHERAstar FS plate reader (BMG Labtech). The ratio of signal at 520 nm to 490 nm was calculated and normalized to DMSO-treated conditions, and plotted.

7. Isothermal Calorimetry (ITC)

Tag-cleaved version of BCL6$^{BTB}$ and BRD4$^{BD1}$ were used for experiments, in a VP-ITC machine. For binary assays with TCIP1, 400 μM BCL6$^{BTB}$ or BRD4$^{BD1}$ were titrated from the syringe into a cell containing 40 μM TCIP1. For the binary protein-protein ITC, 330 μM $BCL_6^{BTB}$ was titrated into 68 μM BRD4$^{BD1}$. For binary assays with JQ1 or Bl3812, 100 μM BCL6$^{BTB}$ or 350 μM BRD4$^{BD1}$ was titrated from the syringe into a cell containing 5 μM Bl3812 or 20 μM JQ1. For the ternary complex assays, 200 μM BRD4$^{BD1}$ was incubated with 10 μM TCIP1 in the cell (20-fold excess, to drive saturation of the binary complex), and 100 μM BCL6$^{BTB}$ was titrated from the syringe, at 310 rpm stirring at 25° C. in a buffer containing 10 mM HEPES pH 7.5, 200 mM NaCl, 5% glycerol, 1 mM TCEP, and matched DMSO % (never more than 0.4%) in the syringe and the cell. The first one or two injections and outliers from instrument noise were routinely excluded. Data was fit to a one-site model using MicroCal LLC Origin software.

8. Biolayer Interferometry (BLI)

The tag-cleaved version of BRD4$^{BD1}$ and biotinylated BCL6$^{BTB}$ were used for experiments, in a Gator Bio BLI machine. 50 μM of BRD4$^{BD1}$ was added to each well containing titrations of TCIP1 from 5.5 nM to 12 μM so that BRD4$^{BD1}$ would be in excess and drive binary BRD4$^{BD1}$: TCIP1 complex formation. 100 nM BCL6$^{BTB}$ was loaded on the tip. Experiments were carried out at 25° C. After loading, association was carried out for 300s, dissociation for 300s, and a baseline for 30s. A TCIP1-only control was carried out for each concentration confirming that there was no binding between $BCL_6^{BTB}$ and TCIP1 on its own. A BRD4$^{BD1}$-only control was carried out similarly confirming that BCL6$^{BTB}$ and BRD4$^{BD1}$ do not interact on their own. Data was analyzed in GraphPad Prism with the association curves fit to the model "One-phase association" and the dissociation curves to the model "One-phase decay" to obtain kinetic parameters. The $K_D$ was obtained by fitting a "One-site binding" curve to the Span of each association curve vs. concentration of drug.

9. Flow Cytometry

For annexin V assays, 500,000 cells plated at 1 M/mL treated with drug for indicated timepoints and doses were harvested on ice and washed twice in 2.5% FBS/PBS. 2.5 μL of 7-AAD and 2.5 μL of FITC-Annexin V (Biolegend #640922) were added. Cells were incubated for 15 minutes at RT, then immediately measured on a BD Accuri. Gates were drawn based off single-stain and no-stain controls. For cell cycle and TUNEL analysis, cells plated at 1 M/mL were treated with drug for indicated timepoints and doses and pulsed with 10 μM ethynyl-EdU (Thermo #C10424) for 2 hours prior to harvesting on ice. 1 M cells were counted and washed in 2.5% FBS/PBS. Cells were resuspended at 10 M/mL and fixed in 4% PFA, washed, and permeabilized in 0.5% Triton-X100/PBS. Fixed and permeabilized cells were washed and labeled with BrdUTP using terminal deoxynucleotidyl transferase (TdT, BD #556405) for 60 minutes at 37° C., rinsed, and then labeled with AlexaFluor 647-azide (Thermo #C10424) for 30 minutes at RT in the dark. After washes, the sample was incubated with 2 μL 7-AAD and 5 μL RNAseA for 30 minutes at RT in the dark, washed, and measured on a BD Accuri. Gates were drawn based off single-stain and no-stain controls and kept constant across conditions.

10. BCL6 Reporter Assay

KARPAS422 cells were lentivirally transduced with a construct containing the reporter. After selection, cells were plated and treated with indicated amount of TCIP1 for 8 hours. Cells were washed in 2.5% FBS/PBS, 1:250 v/v of 7-AAD was added to distinguish live from dead cells, and harvested for flow cytometry on a BD Accuri. The GFP-positive gate were drawn off non-transduced cells and normalized to cells treated with DMSO.

11. BCL6-BRD4 nanoBRET Assay

HEK293T cells were transfected with 1 μg of a construct with an N-terminal fusion of HaloTag to full-length BCL6 and 1 μg of a construct with an N-terminal fusion of nanoLuc (nano-luciferase) to full-length BRD4 (Promega #N169A). A 12-point dose-response curve with 3 technical replicates for each TCIP was carried out and corrected BRET ratios were calculated according to manufacturer assay protocol (Promega #TM439). Data was fit using the R package drc using the four-parameter log-logistic function. $EC_{50}$ values graphed in FIG. 29, Panel G were "left-side" $EC_{50}$s as curves displayed the characteristic hook effect of a bifunctional molecule.

12. RNA Extraction, qPCR, and Sequencing Library Preparation Cells were plated at 1 M/mL and harvested in TRIsure (Bioline #38033). RNA was extracted using Direct-zol RNA MicroPrep columns (Zymo #$R^{2062}$) treated with DNAseI. cDNA was prepared for RT-qPCR using the SensiFAST cDNA preparation kit according to manufacturer instructions (Bioline #65054). 1 μL of cDNA was used per RT-qPCR reaction prepared with SYBR Lo-ROX (Bioline #94020). For sequencing library preparation, polyA-containing transcripts were enriched for (NEB #E7490S) and prepared into paired-end libraries (NEB #E7760S). Libraries were sequenced on an Illumina NovaSeq (Novogene).

13. Western Blots

Cells were plated at 1 M/mL and treated with drug at indicated timepoints and doses. 2 M Cells were harvested on ice in RIPA buffer (50 mM Tris-HCl pH 8, 150 mM NaCl, 1% NP-40, 0.1% DOC, 1% SDS, protease inhibitor cocktail (homemade), 1 mM DTT) and 1:200 benzonase (Sigma #E1014) was added and incubated for 20 minutes. After 10 minute centrifugation at 14,000 g and 4° C., the supernatant was collected and protein concentration was measured by Bradford. Antibodies used for immunoblots are: BCL6 (Cell Signaling #D65C10), BRD4 (Abcam ab243862), BCL2 (Cell Signaling 15071), TP53 (Santa Cruz DO-1), c-MYC (Cell Signaling D84C12), FOXO3 (Cell Signaling 75D8), p21 (Cell Signaling 12D1), GAPDH (Santa Cruz 6C5).

14. RNA-Seq Analysis

Raw Reads were Checked for Quality Using Fastqc (www.bioinformatics.babraham.ac.uk/projects/fastqc/) and trimmed from adapters using cutadapt (Martin, M., EMBnet.journal (2011) 17: 10) using parameters cutadapt—a AGATCGGAAGAGCACACGTCTGAACTCCAGTCA -b (SEQ ID NO:01) AGATCGGAAGAGCGTCGTGTAGG-GAAAGAGTGT (SEQ ID NO:02) -nextseq-trim=20-minimum-length 1. Transcripts were quantified using kallisto (Bray et al., Nature Biotechnology (2016) 34: 525-527) against the human Gencode v33 indexed transcriptome and annotations. Differential gene analysis was performed using DESeq2 (Love et al., Genome Biol (2014) 15: 550) using apeglm (Zhu et al., Bioinformatics (2019) 35: 2084-2092) to shrink $log_2$FoldChanges and pathway and enrichment analyses using Enrichr (Chen et al., BMC bioinformatics (2013) 14: 128) and ChIP-Atlas (Zou et al., Nucleic Acids Research (2022). For analysis of BCL6 binding at ±1 kb from the TSS of differentially regulated genes, BCL6 peaks were reconstructed from OCILY1 DLBCL cells as deposited in (Hatzi et al., Cell Reports (2013) 4: 578-588), using macs2 (Zhang et al., Genome Biology (2008) 9: $R^{137}$), callpeak with a score cutoff ≥100, and overlap was calculated.

15. ChIP-Seq Experiment and Library Preparation 30 million cells were treated with TCIP1 or DMSO for indicated timepoints. Cells were washed in PBS and crosslinked for 12 minutes in CiA Fix Buffer (50 mM HEPES pH 8.0, 1 mM EDTA, 0.5 mM EGTA, 100 mM NaCl) with addition of formaldehyde to a final concentration of 1%. The crosslinking reaction was quenched by glycine added at 0.125 M final concentration. Crosslinked cells were centrifuged at 1,000×g for 5 minutes. Nuclei were prepared by 10 minute incubation of resuspended pellet in CiA NP-Rinse 1 buffer (50 mM HEPES pH 8.0, 140 mM NaCl, 1 mM EDTA, 10% glycerol, 0.5% IPEGAL CA-630, 0.25% Triton X100) followed by wash in CIA NP-Rinse 2 buffer (10 mM Tris pH 8.0, 1 mM EDTA, 0.5 mM EGTA, 200 mM NaCl). The pellet was resuspended in CiA Covaris Shearing Buffer (0.1% SDS, 1 mM EDTA pH 8.0, 10 mM Tris HCl pH 8.0) with 1000× protease inhibitors (Roche) and sonicated for 20 minutes with Covaris E220 sonicator (Peak Power 140, Duty Factor 5.0, Cycles/Burst 200). The distribution of fragments was confirmed with agarose gel. 300 μL of chromatin per ChIP was used with anti-BRD4 antibodies (Cell Signaling E2A7X). 50 μg of chromatin was used with anti-Pol II ser 2 phos (Abcam ab5095) and anti-Pol II ser 5 phos (ActiveMotif 3E8) antibodies. 25 μg of chromatin was used with anti-H3K27ac (Abcam ab4729). For each Pol II ser 2 phos, Pol II ser 5 phos, and H3K27ac ChIP, exactly 20 ng (for Pol II ser 2 phos and ser 5 phos) or 50 ng (for H3K27ac) *Drosophila* chromatin (ActiveMotif #53083) was spiked-in with 2 μL spike-in-chromatin-specific antibody (ActiveMotif #61686). After overnight incubation at 4° C. in IP buffer (50 mM HEPES pH 7.5, 300 mM NaCl, 1 mM EDTA, 1% Triton X100, 0.1% sodium deoxycholic acid salt (DOC), 0.1% SDS), Ips were washed twice with IP buffer, once with DOC buffer (10 mM Tris pH 8, 0.25 M LiCl, 0.5% IPEGAL CA-630, 0.5% sodium deoxycholic acid salt (DOC), 1 mM EDTA), and, once with 10 mM Tris/1 mM EDTA buffer (TE) pH 8. Ips and inputs were reverse-crosslinked in TE/0.5% SDS/0.5 μg/μL proteinase K for 55° C./3 hours then 65° C./18 hours, then DNA was purified using a PCR cleanup spin column (Takara #74609). The sequencing library preparation was performed using NEBNext Ultra II DNA kit (#E7645S). Libraries were sequenced on an Illumina NovaSeq (Novogene).

16. ChIP-Seq Analysis

The data quality was checked using fastqc. The raw reads were trimmed from adapters with trim_galore (parameters:

—paired—255 Ilumine) and raw reads were aligned to hg38 human genome assembly and the dm6 fly genome assembly using bowtie2 (parameters: —local—maxins 1000). Low quality reads, duplicated reads and reads with multiple alignments were removed using samtools (Li et al., Bioinformatics (2009) 25: 2078-2079) and Picard (broadinstitute-.github.io/picard/). Macs2 was used to map position of peaks with FDR cutoff of 0.05. Bedtools (Quinlan et al, Bioinformatics (2010) 26: 841-842) was used to find consensus set of peaks by merging peaks across multiple conditions (bedtools merge), count number of reads in peaks (bedtools intersect—c) and generate genome coverage (bedtools genomecov-bga). deepTools (Ramirez et al., Nucleic Acids Research (2016) 44: W160-W165). Was used to generate coverage densities across multiple experimental conditions (deeptools computeMatrix and deeptools plotProfile) and to generate bigwig files (deeptools bamCoverage), where reads mapping to ENCODE blacklist regions were excluded (Amemiya, Scientific Reports (2019) 9. Normalization was performed as suggested by manufacturer protocol (ActiveMotif #61686 and #53083) where the human-genome-mapped unique reads in each ChIP were downsampled proportional to a normalization factor calculated by: i) counting the unique reads in each sample that align to the fly genome; ii) identifying the sample containing the least amount of mapped fly genome reads; and iii) computing the normalization factor for each sample as (reads mapping to fly genome in sample with minimum mapped fly reads)/(reads mapping to fly genome in current sample). This procedure was carried out on a per-antigen basis (i.e., the H3K27ac ChIPs were treated separately from the Pol II ser 2 phos ChIPs which were separate from the Poll II ser 5 phos ChIPs). The average percentage of reads in each sample that mapped to the fly genome was 1.8±1.4% (mean±s.d.). All browser tracks and metaprofiles shown were calculated with spike-in normalized and input-subtracted data. The peak differential analysis and PCA analysis was performed using DESeq2[82]. The SRX4609168 public dataset was used to extract positions of BCL6 summits for FIG. 35, Panel D. Enhancers and super-enhancers used in FIGS. 35F, 39D, and 39E were classified using the ROSE[58] algorithm by stitching together H3K27ac peaks in untreated cells within 12.5 kb but excluding regions within 2 kb of a TSS unless within a larger H3K27ac domain. Data from Bal et al (Nature (2022) 607: 808-815) was used to cross-check the analysis and annotate the BCL6 intronic hyper-mutated super enhancer.

17. Mouse Tolerability and Pharmacokinetic Study 10 mg/kg of TCIP1 was injected intraperitoneally into C57BL/6 male mice (n=3 in treatment and n=3 in vehicle conditions) using a 25-29 gauge needle to deliver 10 μL/g body weight of a formulation of 1 mg/mL TCIP1 in 5% DMSO, 5% Tween-80, and 80% Saline. Vehicle was the same formulation (5/5/80 DMSO/Tween-80/Saline). The formulation was checked to be a clear solution and after administration, the animal was put back in its cage. For PK properties, plasma levels were measured at 0, 5, 15, 30, 60, 120, 240, 360, and 480 mins after drug administration. For tolerability work, bodyweights and observation of animal health were recorded each day through 5 days of dosing once daily. After 5 days, tissues were collected 8 hours after the last drug administration and split into one part for RNA-seq, homogenized in TRIzoI (Thermo #15596026), another part for histology, snap-frozen, and another part for measurement of drug levels where molar concentrations were recorded with the assumption of 1 g tissue ~1 mL. FFPE blocks (on snap-frozen tissue) and H & E staining were done by the Stanford Histology/Pathology Service Core, by Prof. Hannes Vogel, MD and Pauline Chu.

18. Data Reporting: No Statistical Methods were Used to Predetermine Sample Size.

Experiments were not randomized and investigators were not blinded.

II.

1. TCIP1 Selectively Kills DLBCL Cells at Low Nanomolar Concentrations

To design the first TCIPs, DLBCL was targeted and made use of small molecules that bind to the BTB (BR-C, ttk, and bab) domain of BCL6 and prevent the binding of NCOR (nuclear receptor corepressor), BCOR (BCL6 corepressor) and SMRT (silencing mediator of retinoic acid and thyroid hormone receptor), which epigenetically suppress some BCL6 targets including pro-apoptotic, cell cycle arrest and DNA-damage response genes, such as TP53, by binding HDACs and Polycomb Repressive Complexes (PRC), as well as by other repressive mechanisms (FIG. 27, Panel B). To provide additional transcriptional activation of proapoptotic genes, over simple derepression, the BTB inhibitor BI3812 was linked covalently to the BET (bromodomain-and-extraterminal) protein family binder JQ1, which binds comparably to both bromodomains of BRD4 and slightly less potently to the bromodomains of BRD2 and BRD3. These bromodomain proteins are involved in transcription and contribute a driving function to several tumors by facilitating MYC activation. A series of molecules with linkers of different lengths and flexibility was synthesized including TCIP1 (FIG. 27, Panel C).

These molecules were tested for their effect on viability of the chemotherapy (CHOP, or cyclophosphamide, hydroxydaunorubicin, Oncovin, and prednisone)-resistant DLBCL cell line, KARPAS422. This line has biallelic inactivation of TP53 and was chosen for its high level of expression of BCL6, and the fact that it was derived from a tumor that had become resistant to CHOP therapy and has multiple drivers. TCIP1 rapidly and robustly killed KARPAS422 with an $EC_{50}$ of 1.3 nM, 72 hours after addition of drug. Cell killing was essentially complete at 72 hours (FIG. 27, Panel D).

Three other DLBCL lines with high levels of BCL6 (FIG. 27, Panel D) were also rapidly and robustly killed by TCIP1. Adding JQ1 and BI3812 separately or together showed 100-fold to 1000-fold less effective cell killing (FIG. 28, Panel A), excluding the possibility that TCIP1 acts by simply delivering two inhibitors into the cell. Negative chemical controls, Neg1 and Neg2, were also synthesized having the same linker structure as TCIP1 but having modifications known to mitigate binding to BRD4 or BCL6, respectively. Neg1 and Neg2 had greater than 100-fold less effect on cell viability compared to TCIP1, even in combination (FIG. 27, Panel D), indicating that binding both proteins in proximity is required for effective killing. It was noted that neither BI3812 nor JQ1 produced complete loss of cell viability (FIG. 28, Panel A) leaving a resistant population of cells as has been previously reported.

Figure 28:
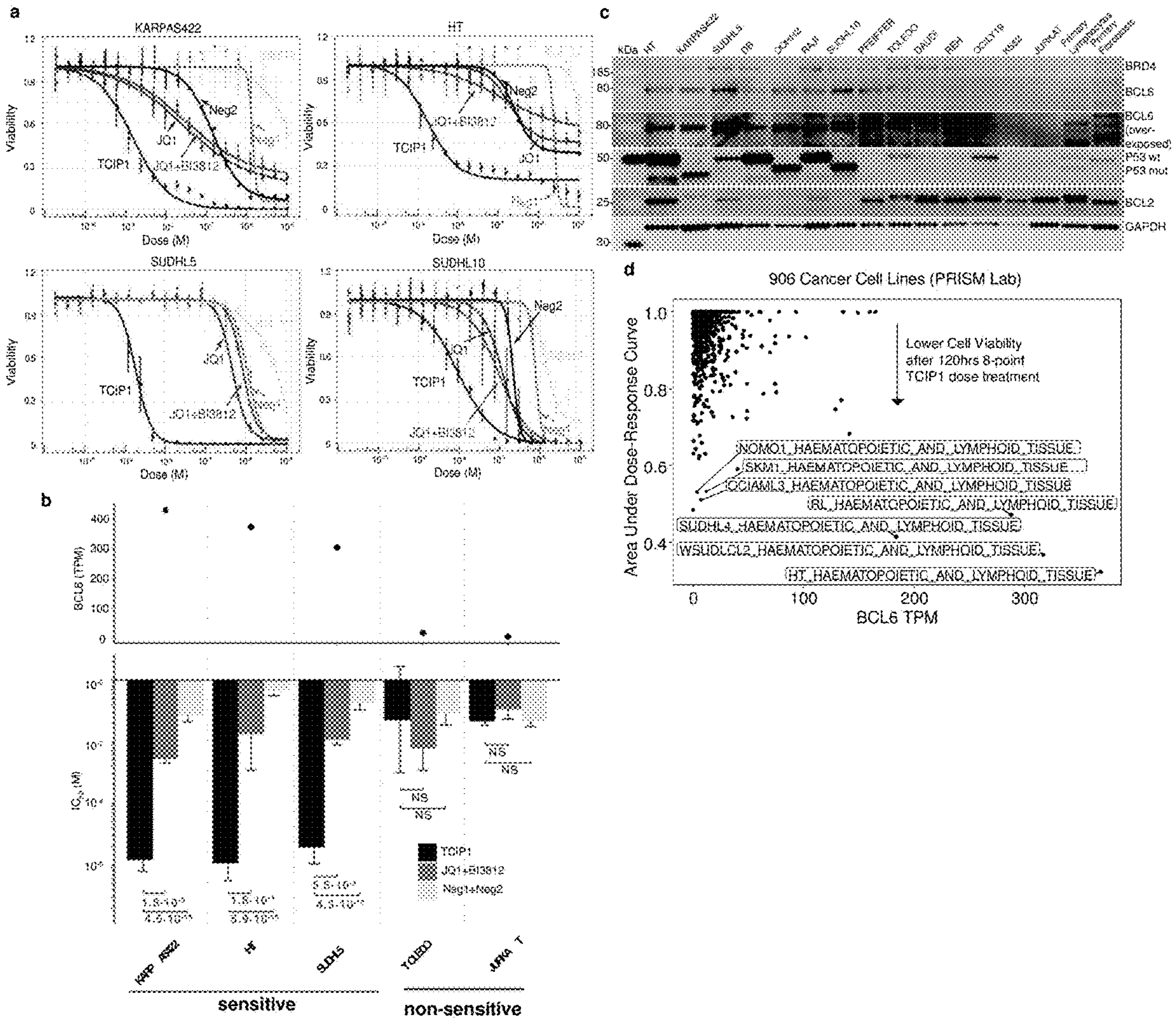
FIG. 28 (Panels A-D) depict data demonstrating potency of a compound of the disclosure in cancer cell lines and correlation with BCL6 levels.

A panel of 14 lymphoma and other blood cancer cell lines expressing different levels of BCL6 was tested. As expected, killing as measured by $EC_{50}$ was correlated with BCL6 levels and BCL6 mRNA levels were predictive of sensitivity to TCIP1 (FIG. 28, Panel B). Some DLBCL cell lines such as OCILY19, with no detectable level of BCL6 (FIG. 28, Panel B), showed little or no response compared to controls. The level of expression of BCOR, NCOR and SMRT, which engage PRC and HDACs to produce epigenetic suppression of target genes varied among the cell lines and could also contribute to the variation in sensitivity. Protein levels of p53, BCL6, BRD4, and BCL2 in the cell lines were confirmed and are consistent with previous data on their gene expression (FIG. 28, Panel C). Among the cell lines tested there was no evidence that killing required TP53, nor was there evidence of repression of killing by endogenous BCL2 levels (FIG. 28, Panel B). Finally, to examine the potency of TCIP1 among diverse cancer types, an unbiased screen was carried out of the effect of TCIP1 on the viability of 906 cancer cell lines (PRISM[37]) originating from various lineages. The most sensitive cancer cells were those that both originated from hematopoietic and/or lymphoid tissues and had high BCL6 levels (FIG. 28, Panel D).

To test if TCIP1 derepresses BCL6-regulated gene expression using endogenous levels of BCL6 and BRD4, a BCL6 reporter was designed from known BCL6 binding sites at promoters of cell death genes such as TP53 and CASP8, based on ChIP-seq data in DLBCL cells, including the flanking 10 bp to capture any endogenous transcription factors co-binding (FIG. 27, Panel E). Transduction of KARPAS422 cells with the reporter and subsequent addition of TCIP1 revealed a dose-dependent activation of about 25-fold at 8 hours, with an $EC_{50}$ of 5 nM, similar to the $EC_{50}$ of cell viability in these same cells (FIG. 27, Panel D). Reporter activation also featured the characteristic "hook effect," reflecting competition among bifunctional molecules for limited endogenous proteins, and the controls Neg1 and Neg2 did not activate the reporter. It was also noted that TCIP1 was >1000-fold as potent in killing DLBCL cells compared to degradation of BRD4 by dBET1[38] or degradation of BCL6 by BI3802[39] (FIG. 27, Panel F), indicating that simple sequestration of these proteins is not the primary contributor to the potency of TCIP1. Taken together, the data show that TCIP1 is a potent activator of BCL6-regulated transcription and is relatively specific in its antiproliferative potency to BCL6-overexpressing lymphoma cells.

2. Lymphoma Cell Killing Requires Formation of a Ternary Complex

The 1000-fold increase in potency of TCIP1 over BRD4 or BCL6 degradation suggested the formation of a gain-of-function ternary complex between BRD4, BCL6, and TCIP1 similar to that initially seen with FK1012. Hence, chemical rescue experiments were carried out in which increasing concentrations of either JQ1 or BI3812 were titrated to multiple DLBCL cell lines, against constant concentrations of TCIP1 that kill 50 to 95% of cells within 72 hours. Increasing concentrations of either JQ1 or BI3812 prevented death by TCIP1, indicating that both the BRD4 binding side and the BCL6 binding side of TCIP1 are essential for effective killing (FIGS. 29A, 29B). Examination of other DLBCL lines indicated that rescue was most prominent in sensitive cell lines and that death of cell lines with little or no BCL6 could not be rescued (FIGS. 30A-30C). Indeed, in low-BCL6 cell lines, the potency of TCIP1 was comparable with Neg2, which contains a functional BRD4 inhibitor but an inactivated BCL6 inhibitor, suggesting that the effects of TCIP1 in lines without BCL6 are due to simple BRD4 inhibition, but at a much higher concentration (FIGS. 30D, 30E).

Figure 29:
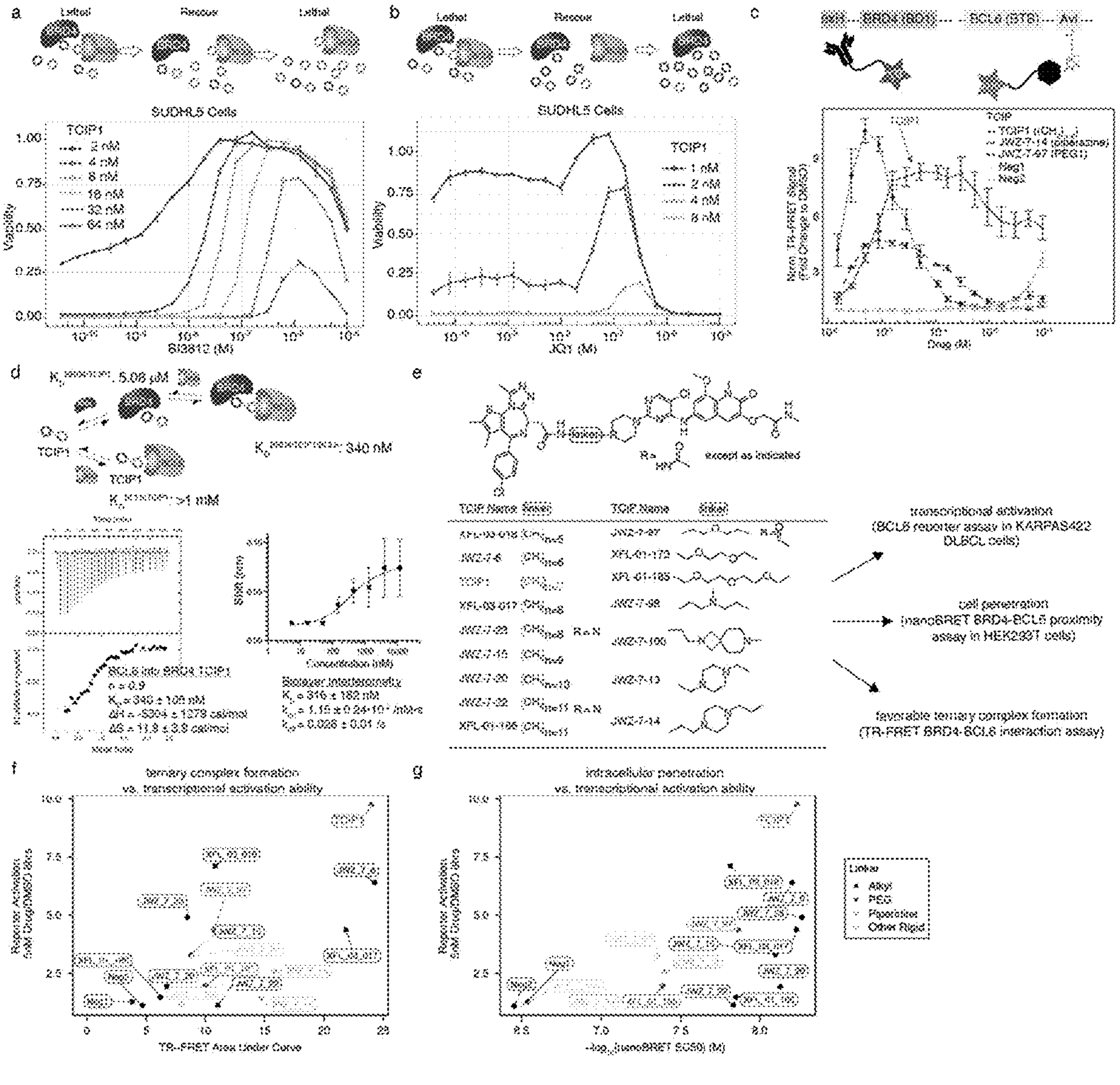
FIG. 29 (Panels A-G) depict data demonstrating that a compound of the disclosure functions by inducing ternary complex formation.
Figure 32:
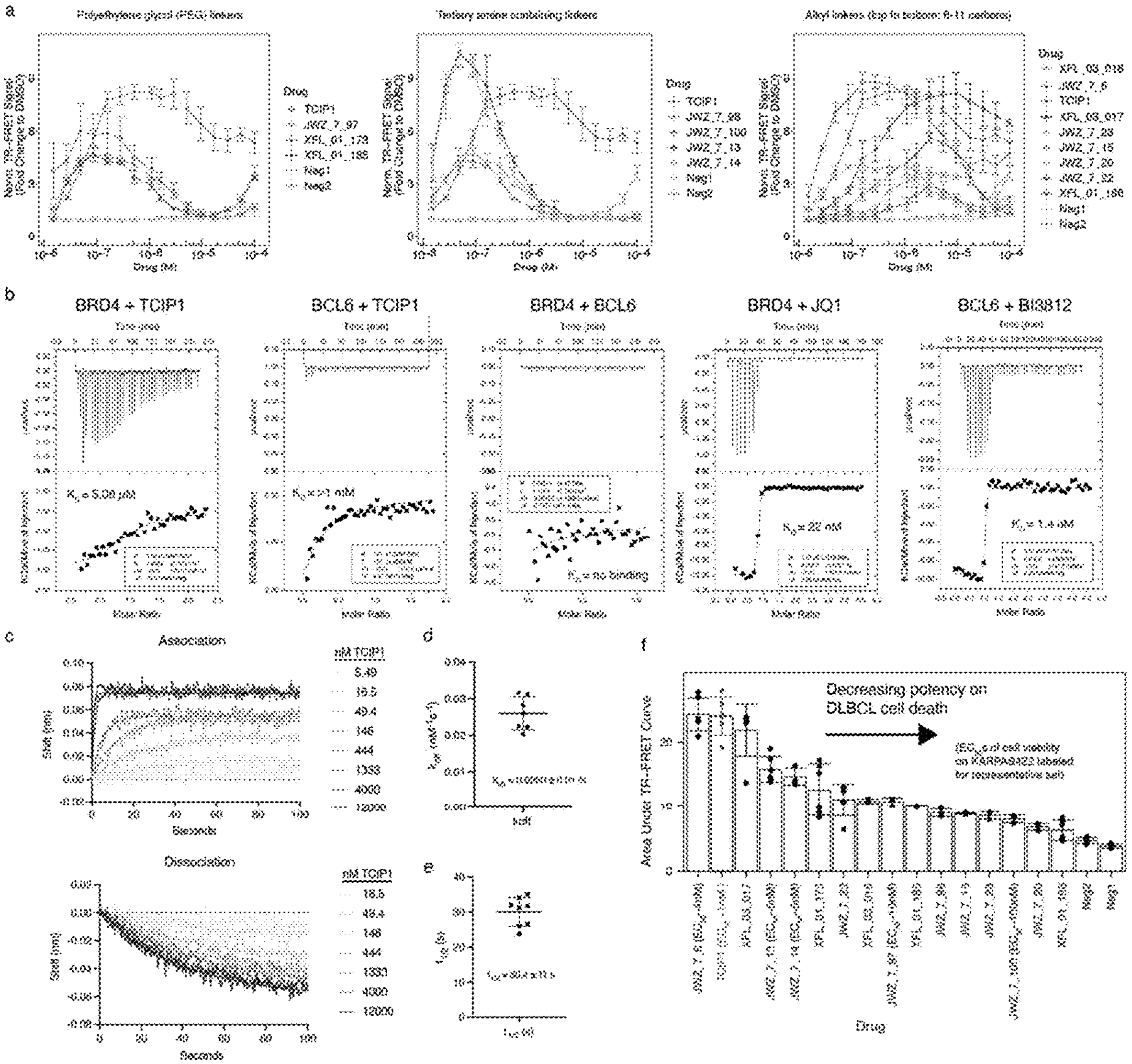
FIG. 32 (Panels A-F) depict biochemical studies of ternary complex binding affinities of compounds of the disclosure.

To gain evidence of a directly induced proximity interaction between TCIP1, BRD4, and BCL6, a TR-FRET assay was developed based on the proximity of the BTB domain of BCL6 labeled with FITC to bromodomain 1 of BRD4 detected with an anti-histidine-tag, terbium-conjugated antibody (FIG. 29, Panel C). Formation of a ternary complex in vitro, related to TR-FRET peak height and area under the curve, was detected using TCIP1 as well as multiple TCIP molecules shown in FIG. 29, Panel E. More flexible or longer linkers reduced ternary complex formation and increased the concentration required for the signal to peak (FIG. 32, Panel A). Of note was the fact that the signal shows a skewed "hook" and does not return to zero at high levels of TCIP1, as well as in other TCIPs that were of similar linker structure and potency in cells (for example see JWZ-7-6 or XFL-03-017, (FIGS. 32A, 32C, and 29E).

One reason for a broadening of the hook effect is the formation of cooperative protein-protein interactions induced by the drug, such as a molecular glue. Hypothesizing that TCIP1 may induce a molecular glue interaction important for potency, isothermal calorimetry (ITC) binary and ternary titrations of TCIP1, $BRD4^{BD1}$, and $BCL6^{BTB}$ were carried out. Strikingly, both binary interactions of BCL6:TCIP1 BRD4:TCIP1 were weak ($K_D^{BRD4:TCIP1}$=5.08 μM; $K_D^{BCL6:TCIP1}$>1 mM, (FIG. 30, Panel B), but the ternary complex affinity was $K_D^{BRD4:TCIP1:BCL6}$=340±108 nM (mean±s.d. of 3 replicates) (FIG. 29, Panel D, left). Using an orthogonal method, biolayer interferometry (BLI), a similar affinity of $K_D^{BRD4:TCIP1:BCL}$=316±182 nM was obtained (FIG. 29, Panel D, right) and confirmed that there was little interaction between TCIP1 and $BCL6^{BTB}$. The published affinities of JQ1 to BRD4 and BI3812 to BCL6 were verified using ITC and that the protein domains do not interact on their own (FIG. 32, Panel B). BLI measurements also revealed that the ternary complex has a slow off-rate of 26 milliseconds with a half-life of 30 seconds (FIGS. 32C-32E). Taken together, the data show that TCIP1 induces a stable, cooperative protein-protein interaction between bromodomain 1 of BRD4 and the BTB domain of BCL6, that could be documented in future structural studies.

In selecting TCIP1, a small library of related TCIPs employing different linkers (FIG. 29, Panel E) was first synthesized. TCIP1 was the most potent in cell killing. However, the calculated affinity of the ternary complex (340 nM by ITC) was less than the $EC_{50}$ for cell death in the most sensitive DLBCL cell lines. This disparity may reflect the fact that small fragments of the two proteins was used for in vitro binding studies, but in the cell, there may be a contribution of regions of the two proteins outside these fragments, such as the second bromodomain of BRD4. To better understand the relationship between TCIP molecular structure and cellular activity, the relationship between BCL6 reporter transactivation in DLBCL cells, favorable ternary complex formation in vitro by TR-FRET (FIG. 29, Panel F), and ternary complex formation inside the cell by nanoBRET, a bioluminescence-based assay that measures proximity between full length BRD4 and BCL6 inside HEK293T cells (FIG. 29, Panel G) were analyzed. The total area under the TR-FRET curve was correlated with BCL6 reporter activation (FIG. 29, Panel F); potency in cell killing among the different TCIPs also was positively correlated with the total area under the TR-FRET curve, with TCIP1 giving the most robust killing among those tested (FIG. 32, Panel F). The most potent TCIPs at activating the BCL6 reporter had the highest affinity ternary complex formation inside the cell as measured by nanoBRET (FIG. 29, Panel G), with TCIP1 again standing out as the most potent. From these experiments it was concluded that activation of BCL6-dependent genes requires an intracellular ternary complex of BRD4, TCIP1 and BCL6 and that this ternary complex likely has a gain-of-function mechanism accounting for the greatly increased potency over BRD4 or BCL6 degraders (FIG. 27, Panel F).

3. TCIP1 Activates Apoptosis at Each Stage of the Cell Cycle

Figure 31:
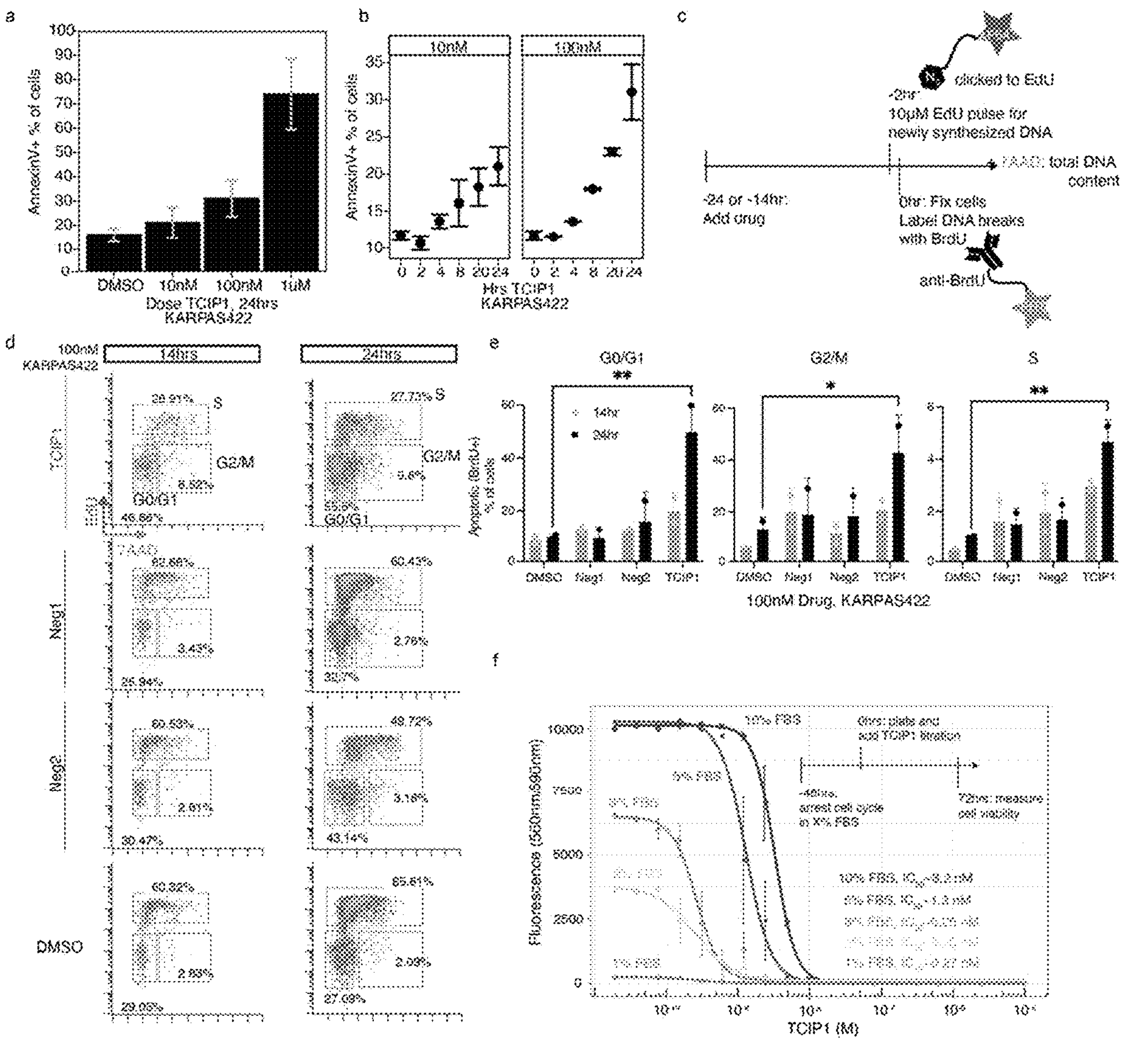
FIG. 31 (Panels A-F) depict data demonstrating that a compound of the disclosure induces apoptosis at every stage of the cell cycle.

To characterize the cell death observed with TCIP1, cells that have externalized phosphatidylserine by staining with annexin V were quantified. A dose-dependent increase in annexin-positive cells was observed, at 10 nM TCIP1, at 24 hours (FIG. 31, Panel A). TCIP1 induced detectable apoptosis by 4-8 hours (FIG. 31, Panel B).

Figure 34:
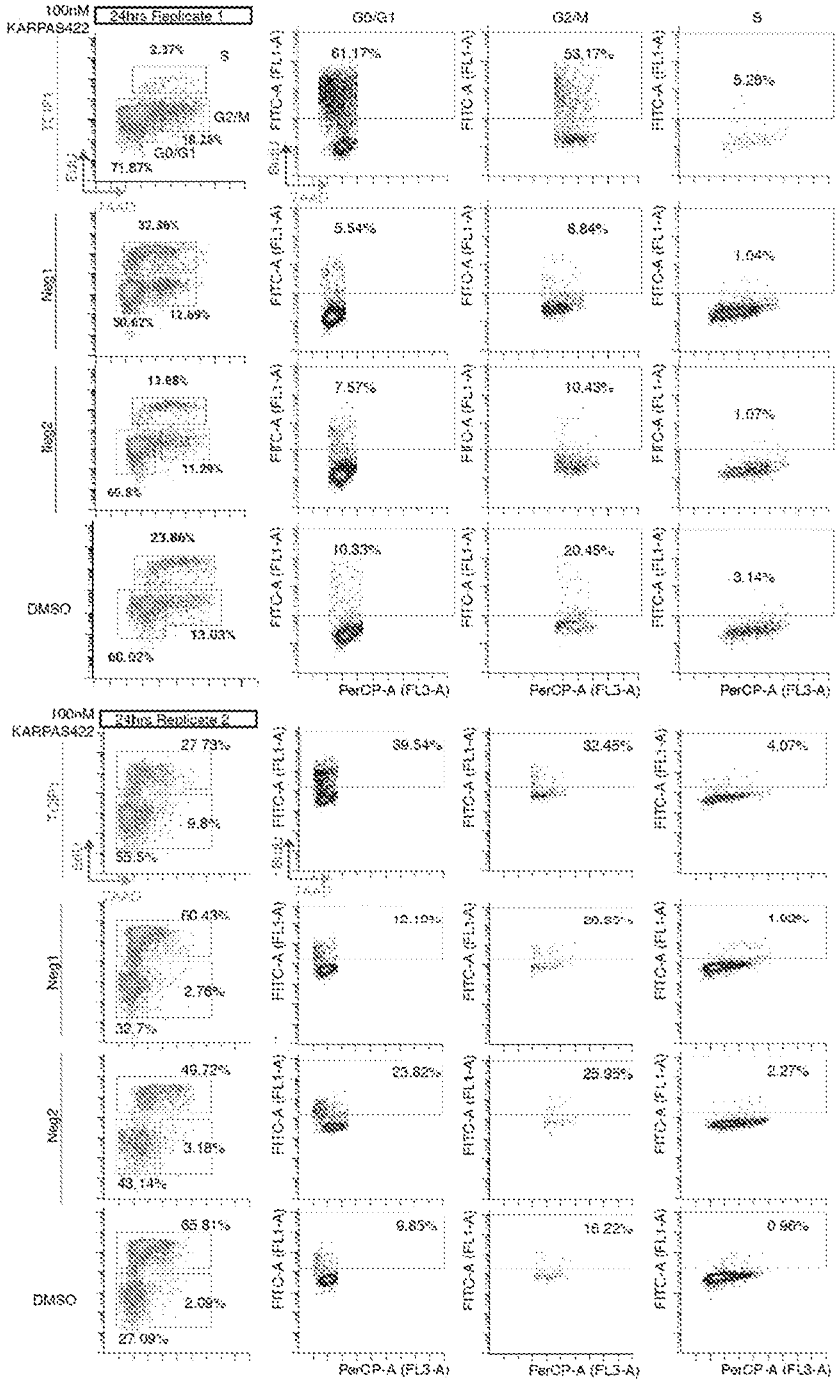
FIG. 34 depicts cell-cycle block and apoptosis induction by a compound of the disclosure.

Cancers can evade cell killing by many chemotherapeutics that function only during a specific stage of the cell cycle. To investigate the cell-cycle dependence of the apoptosis caused by TCIP1, cell cycle analysis in concert with TUNEL staining was performed, which measures DNA fragmentation (FIG. 31, Panel C). The assay allows the analysis of the percentage of apoptotic cells in each cell population: G0/G1, G2/M, and S phase cells (FIG. 34). First, the cell cycle analysis revealed that TCIP1 induced both a G1/S and G2/M block in the cell cycle (FIGS. 31D and 34). By then examining DNA cleavage with the TUNEL assay, cell death was found to occur during all phases of the cell cycle (FIG. 31, Panel E). To further examine the mechanism of cell death by TCIP1, serum starvation was used to arrest the cell cycle in G0/G1. Surprisingly, the cells became even more sensitive to TCIP1 after serum deprivation, exhibiting an $EC_{50}$ of 250 µM compared to 1.1 nM without arrest (FIG. 31, Panel F). The finding implies that unlike many conventional chemotherapeutics, BRD4-BCL6-TCIPs could kill cancer cells without periods of potential insensitivity. This observation is consistent with the total loss of cell viability produced by TCIP1 compared to the inhibitors or degraders (FIGS. 27F and 28A) and also suggests that TCIP1 produces cell death by activating more than a single cell death pathway.

4. TCIP1 Represses MYC and its Target Genes while Activating Proapoptotic Genes

Figure 33:
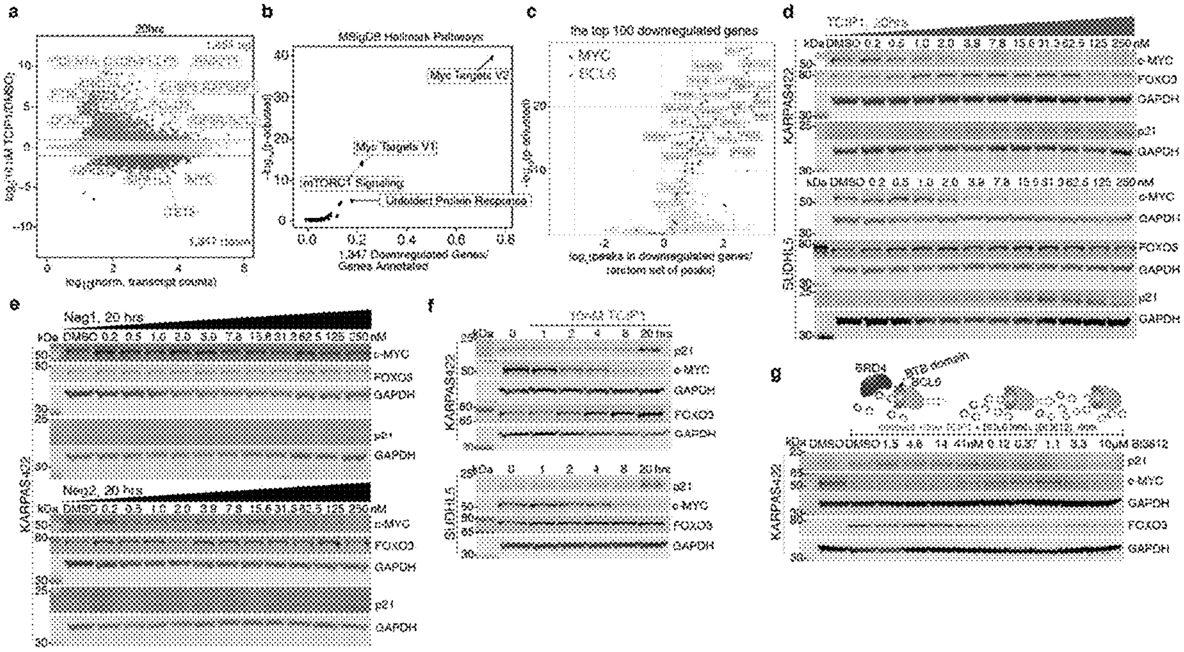
FIG. 33 (Panels A-G) depict data demonstrating that a compound of the disclosure represses MYC and its targets while activating pro-apoptotic genes.
Figure 36:
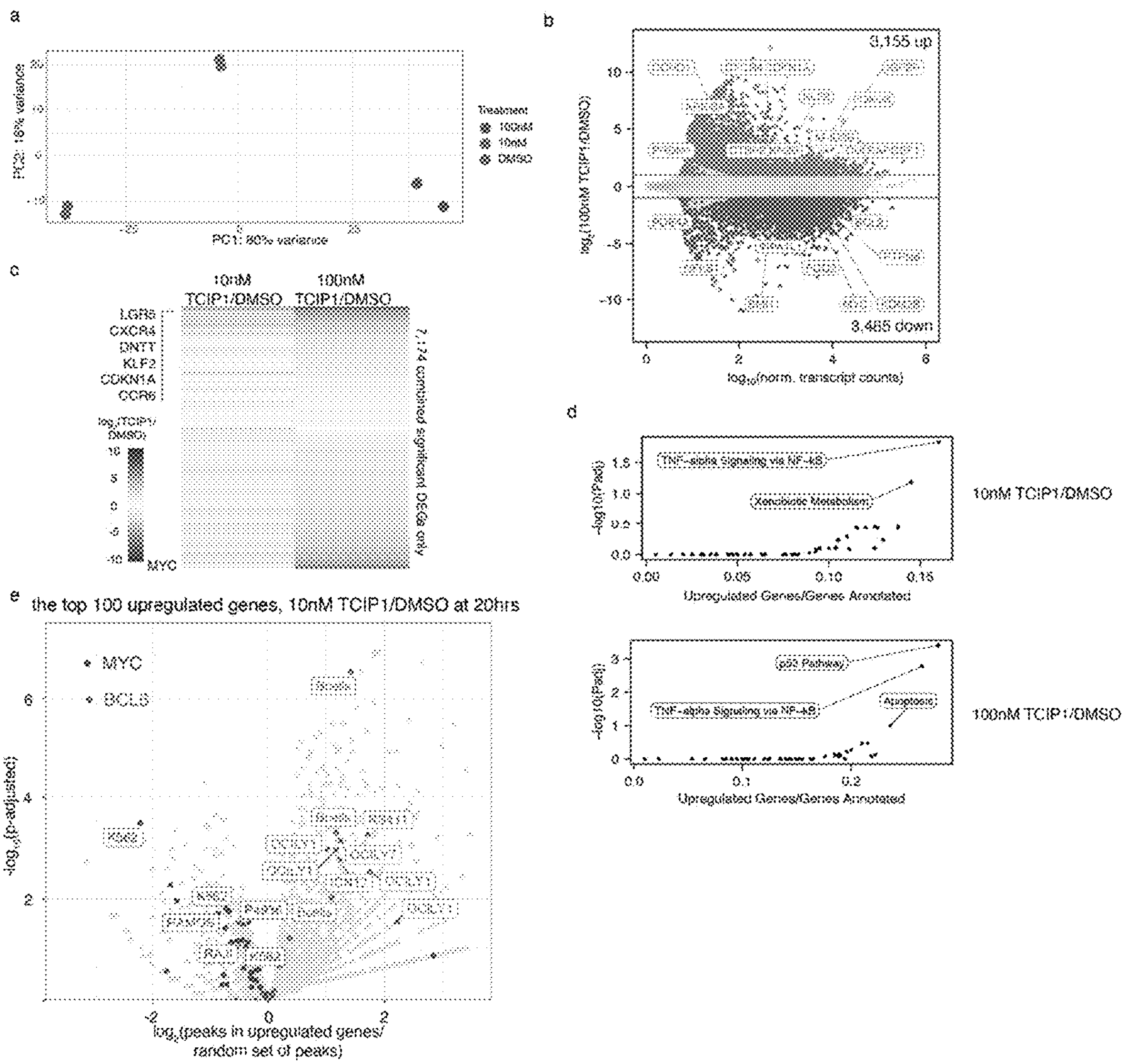
FIG. 36 (Panels A-E) depict robust and dose-dependent gene regulation by a compound of the disclosure.

To define the genes involved in induction of apoptosis by TCIP1, RNA-seq studies were carried out 20 hours after adding drug at 10 or 100 nM, when apoptosis was beginning and the critical genes were likely to be executing their function(s). Principal component analysis indicated that repeats were highly correlated and drug concentration determined most of the variation within the samples (FIG. 36, Panel A). At just 10 nM TCIP1, 1,674 genes were increased in expression, while 1,364 were reduced (FIG. 33, Panel A). Because a high percentage of the TCIP1-treated cells contain fragmented DNA by TUNEL assay at 24 hours (FIG. 31, Panel E), many of the "reduced genes" could reflect DNA fragmentation as part of the apoptotic process and digestion to mononucleosomes. Among the group of genes whose expression was most reduced were MYC and its targets (FIGS. 33B, 36C). The top 100 most TCIP1-reduced genes were examined using ChIP-seq data of human transcription factors in blood cancer cell lines, and found the promoters of TCIP1-inhibited genes highly enriched for MYC binding in multiple datasets (FIG. 33, Panel C). This is significant since many DLBCLs are considered to be MYC-dependent. Examination of MYC protein levels upon TCIP1 addition showed that MYC levels were reduced starting at less than 1 nM TCIP1 and within 2 hours of drug addition (FIG. 33, Panel D, and FIG. 33, Panel F). The chemical controls Neg1 and Neg2, containing a functional BCL6 or BRD4 inhibitor, respectively, did not affect MYC levels at comparable concentrations (FIG. 33, Panel E). BET/BRD4 inhibitors such as JQ1 are known to reduce expression of MYC[32], but at much higher levels of drug (500 nM) than TCIP1. Taken together, the data indicate that the repression seen could not be due to TCIP1 acting as a BRD4 inhibitor alone or synergistically with the BCL6 inhibitor Bl3812. Hence, the data supports a gain-of-function for the ternary complex formed by TCIP1.

Genes activated by TCIP1 were enriched for known BCL6 targets which are normally repressed by BCL6 (FIGS. 33A, 36D, and 36E). For example, CDKN1A (p21) increased by about 64-fold, while FOXO3 and PMAIP1/NOXA, pro-apoptotic genes in lymphocytes, were also induced. Along with the p53 and apoptosis pathways, TCIP1 also induces the TNFα pathway (FIG. 36, Panel D). Signaling via NF-kB is known to be repressed by BCL6. Gene expression changes at 100 nM TCIP1 echoed those at 10 nM, but increased in magnitude (FIGS. 36B, 36C). These changes in mRNA levels were paralleled by dose- and time-dependent changes in protein expression of known BCL6 targets in two different DLBCL cell lines, SUDHL5 and KARPAS422, and no effect of the chemical controls Neg1 and Neg2 at comparable drug concentrations (FIGS. 33D, 33E). For example, p21, which is normally negatively regulated by BCL6, is induced by low nanomolar concentrations of TCIP1 (FIG. 33, Panel D). Of particular interest is the observation that FOXO3 is activated by 0.5 nM TCIP1 (FIG. 33, Panel D) and within two hours by 10 nM TCIP1 (FIG. 33, Panel F). The activation of FOXO3 also displayed a hook effect (FIG. 33, Panel D), characteristic of a ternary complex, as seen in the BCL6 reporter activation (FIG. 27, Panel E). FOXO3 is a master pro-apoptotic gene with a BCL6 binding site at its promoter, it is often activated downstream of TP53. However, TP53, another known BCL6 target often upstream of p21 and other pro-apoptotic genes, is biallelically inactivated in KARPAS422 and several of the other CHOP-resistant DLBCL that are robustly killed by TCIP1 (FIGS. 28B, 28C). These studies indicate that TCIP1 can effectively rewire the transcriptional circuitry of DLBCLs such that cell killing is produced by a pathway that normally represses apoptosis.

Finally, to clarify the role of ternary complex formation for the gene expression and protein level changes observed, binding of TCIP1 to BCL6 was blocked by titrating the $BCL6^{BTB}$ inhibitor Bl3812 against a constant 10 nM TCIP1 (FIG. 33, Panel G). Titration of Bl3812 reversed p21 upregulation, FOXO3 upregulation, and MYC downregulation (FIG. 33, Panel G). The results indicate that both activation of these BCL6 targets and repression of MYC are mediated by the formation of a ternary complex between BRD4, TCIP1, and BCL6, and support the evidence in FIGS. 29A-29G that the active biological entity is the ternary complex. The potency of TCIP1 relative to BRD4 and BCL6 degraders (FIGS. 27A-27F) also supports a gain-of-function for the TCIP1 ternary complex.

Figure 35:
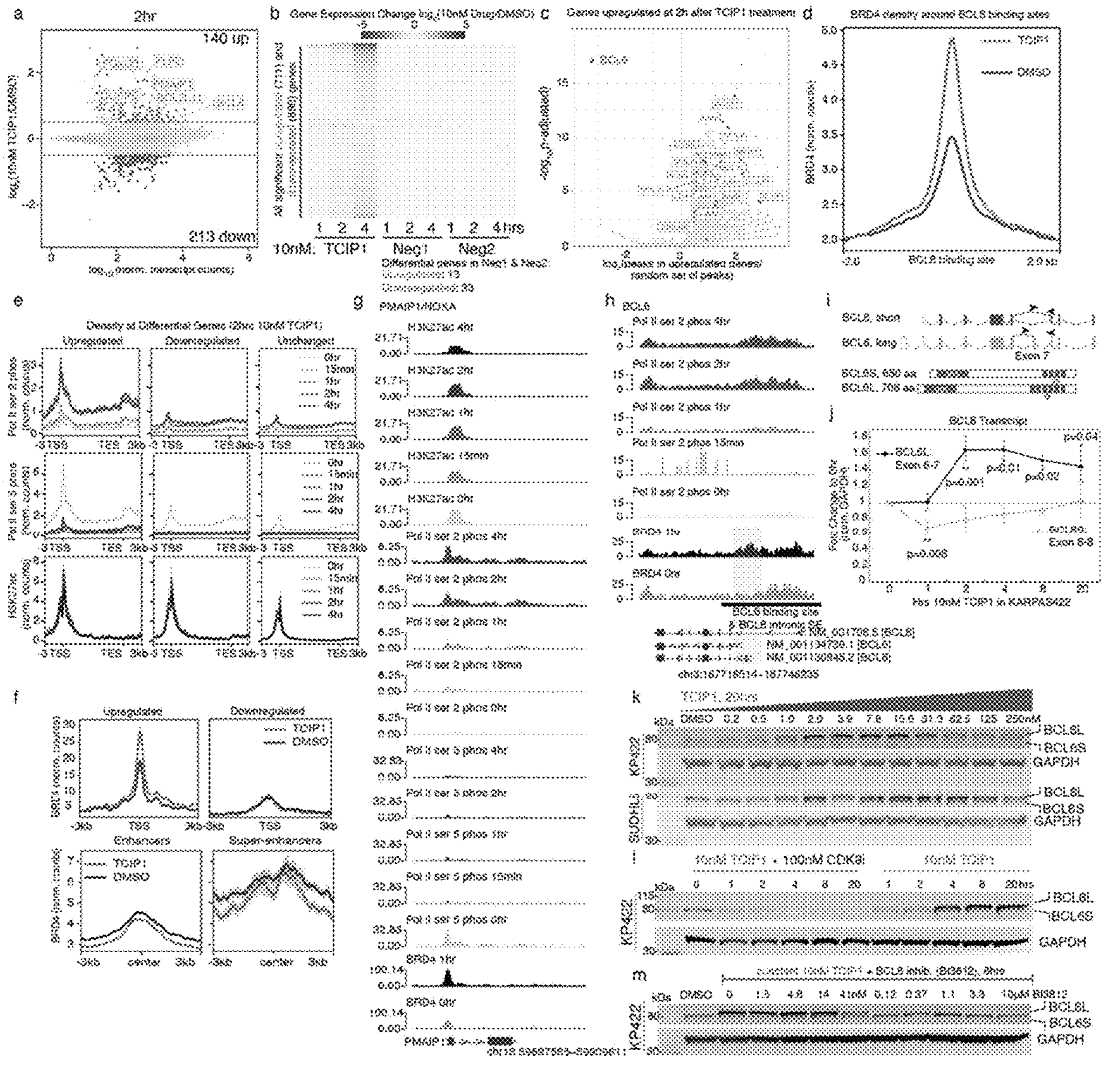
FIG. 35 (Panels A-M) depict rapid activation of BCL6-target genes by recruitment of BRD4.

5. Identification of Direct Targets of TCIP1 by Short Timepoint RNA- and ChIP-Seq To identify direct targets of TCIP1, a short time-course RNA-seq was carried out with 10 nM TCIP1 in KARPAS422 cells for 1 hour, 2 hours, and 4 hours along with negative controls (FIGS. 35A, 35B). A selective set of only 140 genes, including well-characterized BCL6-repressed targets such as the apoptotic regulators BCL2L11/BIM, FOXO3, and BCL6, were activated at 2 hours and likely represent direct transcriptional targets of TCIP1 (FIG. 35, Panel A). This indicates that multiple cell death pathways are activated consistent with the ability of TCIP1 to induce cell death throughout the cell cycle (FIGS. 31A-31F). Almost all differential genes were increasingly activated at 4 hours compared to negligible effects of the control molecules Neg1 and Neg2 (FIG. 35, Panel B). Consistent with protein kinetic data (FIG. 33, Panel F), TNFα signaling and p53 pathways began to be upregulated at 1 and 2 hours, but MYC targets only began to be repressed at 4 hours (FIG. 38, Panel C) while MYC protein was reduced at 2 hours (FIG. 33, Panel F). Although a number of genes showed reduced expression in TCIP1-treated cells at the early 1 and 2 hours timepoints, in contrast to the upregulated genes they were not statistically significantly enriched for any particular biological pathway (FIG. 38, Panel C) and could represent general stress from the onset of DNA fragmentation. Analysis of BCL6 binding data using published BCL6 ChIP-seq in the DLBCL line OCILY1 at the promoters of genes upregulated at 1, 2, and 4 hours showed that 53%, 57%, and 55% respectively of them had BCL6 enriched within 1 kilobase of their transcription start site (TSS). Further analysis using ChIP-seq data of human transcription factors in blood cancer cell lines, revealed that the promoters of these TCIP1-activated genes were statistically significantly enriched for BCL6 binding in multiple datasets (FIG. 35, Panel C). These studies indicate that TCIP1 specifically activates BCL6-target genes.

ChIP-seq studies of BRD4 after 1 hour of drug addition revealed that TCIP1 produced a consistent, modest -1.5-fold increase in BRD4 recruitment to BCL6 sites over the genome (FIG. 35, Panel D). This was surprising because TCIP1 rapidly and robustly activated many genes normally repressed by BCL6. This observation could indicate that TCIP1 needs to recruit only small amounts of BRD4 to produce activation of BCL6 targets, and/or that the two other BET proteins expressed in these cells, BRD2 and BRD3, also mediate its effects. BRD4 and other BET proteins have previously been implicated largely in transcriptional elongation, particularly in mediating P-TEFb/CDK9 activation of RNA Polymerase II (Pol 1) elongation activity by phosphorylation of serine 2 of the C-terminal domain (CTD) of Pol II (Pol 1 ser 2 phos). The major other CTD modification of Pol II is serine 5 phosphorylation (Pol 1 ser 5 phos), which marks paused polymerase ready to initiate transcription. These serines are actively phosphorylated and dephosphorylated during the cycle of transcription. To closely examine the consequences of TCIP1 addition on transcription, short timepoint ChIP-seq experiments were carried out with antibodies specific to Pol II ser 2 phos (elongation) and Pol II ser 5 phos (paused) after 10 nM TCIP1 addition for 15 mins, 1 hour, 2 hours, and 4 hours. In parallel acetylation of lysine 27 on histone H3 (H3K27ac) was examined, a mark associated with active enhancers and promoters. These studies were all carried out with a known amount of *Drosophila* chromatin spiked-in to the ChIP, to allow for consistent normalization and accurate quantification of absolute changes genome-wide.

Figure 38:
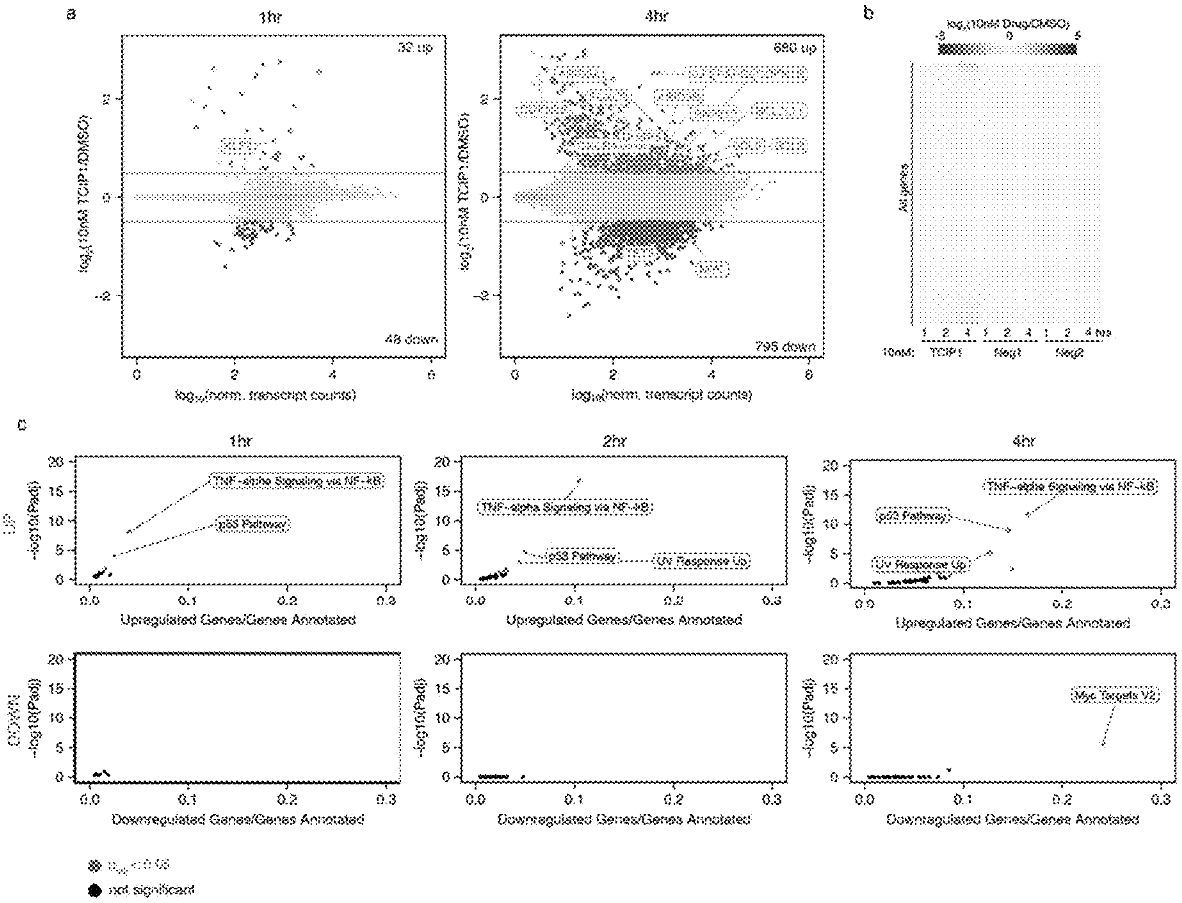
FIG. 38 (Panels A-C) depict specific activation of gene expression by a compound of the disclosure but not related controls.

It was found that just 15 minutes of drug addition increased Pol II ser 2 phosphorylation, further increasing over 1, 2, and 4 hours, reflecting immediate transcriptional elongation, at well-characterized BCL6 target proapoptotic genes including PMAIP1/NOXA, FOXO3, BCL2L11/BIM, and BCL6 itself (FIGS. 35E, 35G, 35H, 39A, and 39B). Effects at downregulated genes were similar to those at unchanged genes and could reflect background or a stress response (FIG. 35, Panel E, top row), given that downregulated genes at this 2 hours timepoint appeared to be a collection of various genes that were not significantly enriched for any particular biological pathway and may be related to DNA fragmentation (FIG. 38, Panel C). Accompanying this immediate elongation effect was a loss of Pol II ser 5 phos, reflecting paused polymerase, at both upregulated and downregulated genes as well as in unchanged genes (FIG. 35, Panel E, middle row). This loss is both in the spike-in normalized (metaprofiles shown) as well as "reads in peaks" (i.e., relative log expression or "RLE") normalized ChIP-seq data (volcano plots in FIG. 39, Panel C). Again, the changes at downregulated genes were similar to that at unchanged genes (FIGS. 35E, 35G). It was further ascertained that BRD4 increases at the promoters of upregulated genes selectively, -150% after just 1 hour of TCIP1 addition (FIG. 35, Panel F, top row), consistent with its increase at BCL6 binding sites genome-wide (FIG. 35, Panel D). The loss of paused polymerase could reflect a redistribution effect and/or a switch from pausing to productive elongation, especially at TCIP1-upregulated genes.

Figure 39:
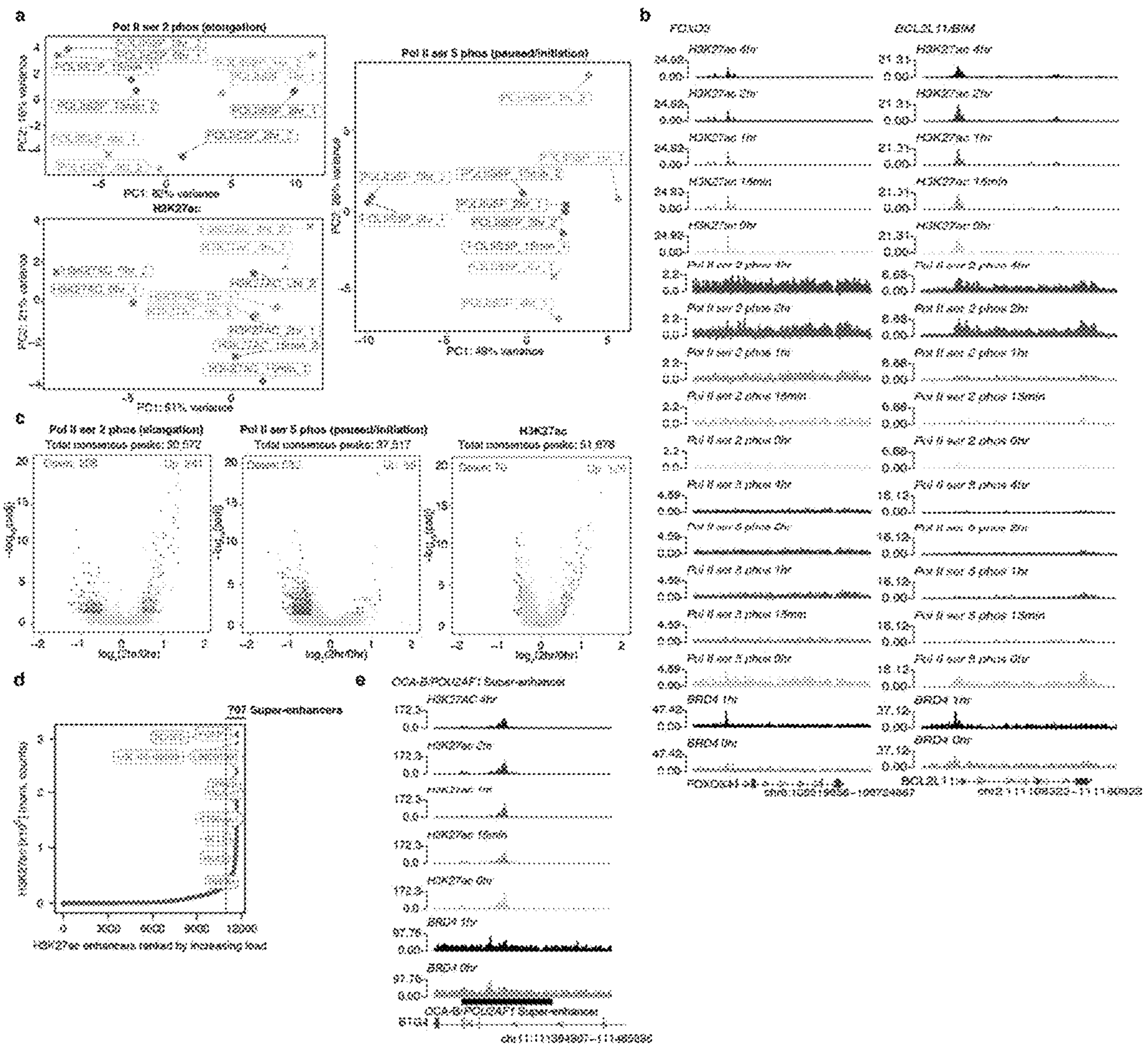
FIG. 39 (Panels A-E) depict ChIP-seq analyses of BRD4, H3K27ac, and RNA Pol II in response to a compound of the disclosure.

To examine the consequences at regulatory regions, as BCL6 also regulates enhancer repression, active enhancers and super-enhancers in the DLBCL cell line, KARPAS422, was mapped using H3K27ac ChIP-seq data. The concurrent decrease of BRD4 from active enhancers, and super-enhancers where there is a 20× higher cumulative load of BRD4 is only ~10% (FIG. 35, Panel F, bottom row; genome track of OCA-B super-enhancer in FIG. 39, Panel E). Also, there were negligible changes in H3K27ac genome-wide: after 2 hours, only 126 peaks increased while 70 peaks decreased ($\log_2$FoldChange ≥0.5, $p_{adj}$≤0.05) out of 51,678 total consensus peaks reconstructed (FIGS. 39A, 39C). Statistically significant changes in H3K27ac at gene promoters of upregulated or downregulated genes or unchanged genes was also not observed (FIG. 35, Panel E). This is consistent with the genetic studies of Melnick and colleagues, that point to a competition model underlying repression. Taken together, the data supports a model whereby TCIP1 borrows a fraction of the total BRD4, recruits it to BCL6 binding sites and BCL6-regulated genes, and rapidly activates transcriptional elongation and the expression of these target genes.

6. TCIP1 Rewires the BCL6 Negative Feedback Pathway to a Positive Feedback Loop

Figure 40:
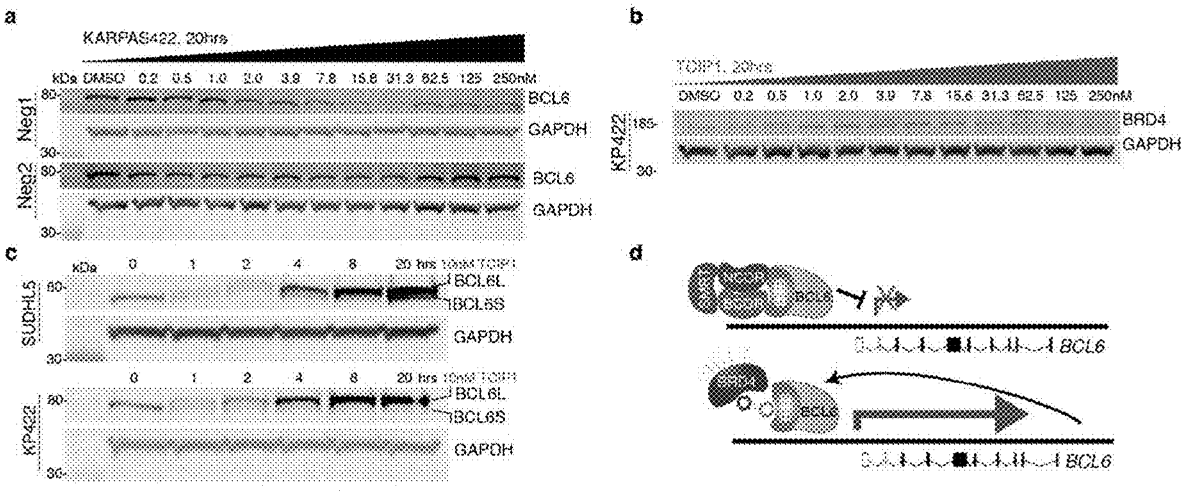
FIG. 40 (Panels A-D) depict conversion of BCL6 autoinhibitory pathway to feedforward loop.

BCL6 is overexpressed in several cancers either through mutation or other means, apparently to protect the cancer cell from programmed cell death induced by TP53 and other pathways inhibited by BCL6. BCL6 expression is subject to negative autoregulation that originates from BCL6 binding sites in the $1^{st}$ intron of the BCL6 gene, which are often deleted or mutated in DLBCL, providing protection from cell death. The TCIPs that were designed and synthesized should convert this negative feedback pathway to a positive feedback pathway, by replacing the epigenetic repression that BCL6 provides with transcriptional activation by BRD4. To determine if this prediction is correct, BCL6 mRNA levels after treatment with TCIP1 were examined and it was found that within 1-2 hours of 10 nM TCIP1 addition, the long isoform of BCL6 is upregulated at the expense of its short isoform, due to transcription of and alternative splicing of exon 7 in the BCL6 gene (FIGS. 351, 35J). Analysis of protein levels of BCL6 after TCIP1 addition showed that BCL6 protein was significantly increased in a dose-dependent manner, also showing a hook effect in two different DLBCL cell lines (FIG. 35, Panel K). Simultaneous addition of a nanomolar CDK9 inhibitor, NVP2, to block elongation of transcription, prevented upregulation of BCL6 protein levels (FIG. 35, Panel L). The chemical controls Neg1 and Neg2 also did not affect BCL6 (FIG. 40, Panel A). The kinetics of BCL6 induction were similar in two separate TCIP1-sensitive DLBCL cell lines (SUDHL5 and KARPAS422) (FIG. 40, Panel C); in addition, BRD4 protein levels did not change substantially (FIG. 40, Panel B). Because the primary transcript of BCL6 is 24 kilobases and RNA polymerase II moves at 2-3 kilobases per minute, it could be transcribed, spliced and translated in 50 to 74 minutes. It was therefore hypothesized that transcription of the autoregulated long form of BCL6 must start almost immediately after addition of TCIP1. Indeed, in the ChIP-seq data, it was observed that elongation of polymerase measured by Pol II ser 2 phos starts to increase, at exon-intron junctions, at just 15 minutes, and continues to spread through the gene body at 1, 2, and 4 hours after 10 nM TCIP1 addition (FIG. 35, Panel H). BRD4 density increases modestly by 1 hour at the known intronic BCL6 binding site and super-enhancer that is also hypermutated in patient DLBCL tumors. Finally, as in FIG. 33, Panel G, to clarify the role of ternary complex formation for the BCL6 upregulation observed, the $BCL6^{BTB}$ inhibitor BI3812 was titrated against a constant 10 nM TCIP1 and could reverse the upregulation of BCL6 observed (FIG. 35, Panel M). The data indicate that BCL6 is itself a direct target of TCIP1. Thus, TCIPs can rewire a repressive negative feedback pathway into a positive feedback pathway, amplifying the potency of the molecule in killing cancer cells (model in FIG. 40, Panel D).

7. TCIP1 Appears to be Relatively Non-Toxic in Primary Human Cells and Mice

Figure 37:
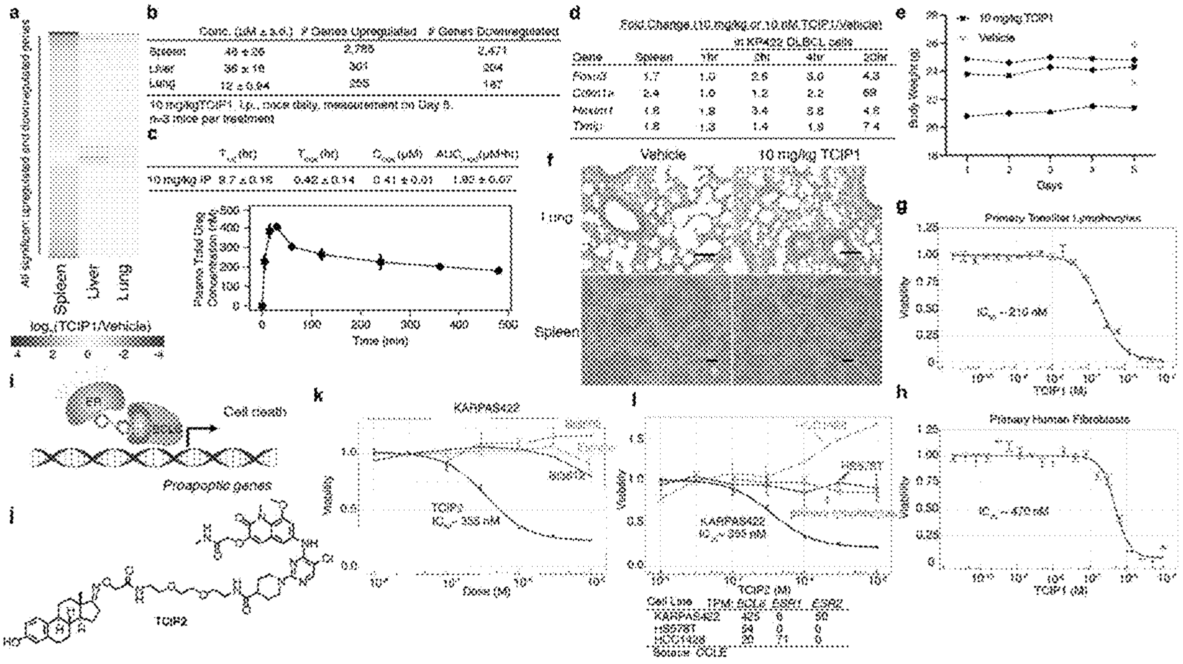
FIG. 37 (Panels A-L) depict toxicity of a compound of the disclosure in mice and primary human cells and generalization to ER-positive cancers.

Cell death by TCIPs requires the coincident expression of both targets and hence, therapeutic effects might be more precisely targeted to the cancer cell rather than normal cells. BCL6 mutant mice die of a complex inflammatory reaction that has been elegantly dissected to specific regions of the protein. Because TCIP operates at a concentration that would occupy only a fraction of the total BCL6 molecules (unlike a degrader or inhibitor), the potential toxicity of TCIP1 to mice was examined. The tolerability, pharmacokinetic properties, and target engagement of TCIP1 in wild-type C57BL/6 mice was evaluated, treated for 5 days with 10 mg/kg TCIP1 once daily by intraperitoneal injection. After treatment, mouse tissue was harvested for RNA-seq and histology. TCIP1 induced dramatic transcriptomic changes in the spleen (2,785 genes upregulated, 2,471 genes downregulated) compared to the liver and lung (255 and 301 genes upregulated, 167 and 204 genes downregulated, respectively), despite comparable tissue concentrations of drug (FIGS. 37A, 37B). Serum concentrations after 8 hours were -100 to 400-fold higher than therapeutic doses (FIG. 37, Panel C). Notable genes upregulated in DLBCL cells, such as FOXO3, CDKN1A, or HEXIM1, were also upregulated in the spleen as well as other known BCL6 targets in lymphocytes (FIG. 37, Panel D), suggesting engagement of BCL6 target genes. Despite the large transcriptomic changes in the spleen, TCIP1 was well-tolerated with no adverse effects noticed and no significant changes in mouse body weight (FIG. 37, Panel E). H & E staining and examination (by H.V.) also did not reveal noticeable abnormalities such as inflammatory infiltrates or apoptotic cells (FIG. 37, Panel F). primary human cells including fibroblasts and lymphocytes (FIGS. 37G, 37H) were further examined. T and B lymphocytes are particularly germane because they have among the highest levels of BCL6. While there is killing of both fibroblasts ($EC_{50}$~470 nM) and lymphocytes ($EC_{50}$ 210 nM) by TCIP1 (FIGS. 37G, 37H), the levels required are at least 200-fold higher than that required for killing of DLBCL overexpressing BCL6, suggesting the existence of a substantial therapeutic window. The data supports the cellular evidence that TCIP1 acts in a context- and tissue-specific manner dependent on coincident expression of BRD4 and BCL6.

8. Generality of the TCIP Strategy

The generality and predictability of the TCIP approach was explored by designing and synthesizing a series of molecules predicted to borrow the transcriptional activity of estrogen hormone receptor protein to activate derepressed BCL6 target genes and produce cell death (FIG. 37, Panel 1). The synthetic estrogen, estrone, was used for these studies, which has somewhat lower affinity for the estrogen receptor (ER) than natural estradiol (FIG. 37, Panel J). Several of the ER-BCL6 TCIPs, such as TCIP2 (FIG. 37, Panel J), showed strong anti-proliferative activity with an $EC_{50}$ of 355 nM (FIG. 37, Panel K). As predicted, killing was most robust in DLBCL lines such as KARPAS422 having higher expression of both ER and BCL6 (FIG. 37, Panel K). Interestingly, several ER-positive human breast cancer cells with low levels of BCL6 showed enhanced proliferation and survival, indicating that the estrone was active and that TCIPs are not intrinsically toxic in cells lacking BCL6 (FIG. 37, Panel L). In contrast, triple negative breast cancer cell lines with neither detectable BCL6 nor ER were not affected by the ER-BCL6 TCIP2 (FIG. 37, Panel L). These studies show that other transcriptional activators could be predictably hijacked or rewired to facilitate transcription of proapoptotic genes in DLBCL cells with high ER levels.

FIG. 27 (Panels A-F) depict production of Transcriptional Chemical Inducers of Proximity (TCIPs). FIG. 27, Panel A: An endogenous target gene is activated or repressed using a bifunctional molecule binding one endogenous transcription factor or epigenetic regulator on one side chemically linked to a moiety that binds a second transcription factor binding the regulatory region of a target gene which might induce production of a therapeutic gene. FIG. 27, Panel B: A specific TCIP that recruits a transcriptional activator (BRD4) or cancer driver to the BCL6 repressor on cell death genes, thereby derepressing transcription and inducing transcription driven by BCL6. FIG. 27, Panel C: Chemical structures of the most potent BCL6/BRD4 TCIP, TCIP1, and negative controls Neg1 (BRD4 non-binding) and Neg2 (BCL6 non-binding). FIG. 27, Panel D: TCIP1 effect on cell viability of the CHOP-resistant, TP53-mutant diffuse large B-cell lymphoma cell (DLBCL) line, KARPAS422, as well as 3 other DLBCL cell lines with high levels of BCL6. n=4 biological repeats, mean±s.d.

FIG. 27, Panel E: Design and activation of a BCL6 reporter with TCIP1 in KARPAS422 cells at 8 hours after drug addition. n=4 biological repeats, mean±s.d. FIG. 27, Panel F: Comparison of TCIP1 effect on cell viability to effect of BRD4 or BCL6 degraders (n=3 technical repeats, mean±s.d). Viability curves in FIG. 27, Panel D and FIG. 27, Panel F are after 72 hours drug treatment.

FIG. 28 (Panels A-D) depicts potency of TCIP1 in cancer cell lines and correlation with BCL6 level. FIG. 28, Panel A: Comparison of TCIP1 effect on cell viability to effect of negative controls Neg1 and Neg2, or single-sided molecules JQ1 and BI3812, or the additive effect of JQ1+BI3812. Mean±s.d., 72 hours drug treatment. FIG. 28, Panel B: TCIP1 $EC_{50}$ of cell viability is anti-correlated with BCL6 content across 14 different cancer cell lines, n=3 biological repeats, mean±s.d., 72 hours drug treatment. FIG. 28, Panel C: Unbiased screen of the effect of TCIP1 on the viability of 906 barcoded cancer cell lines (PRISM). Drug was dosed for 120 hours in triplicate (Methods). FIG. 28, Panel D: Measurement of P53 or BCL2 status of DLBCL cell lines ranked from left to right from high to low-BCL6 protein content.

FIG. 29 (Panels A-G) demonstrate that TCIP1 functions by inducing ternary complex formation. FIG. 29, Panel A: Competitive titration of BI3812 against TCIP1. TCIP1 was added at concentrations from 2-64 nM that killed 90% of SUDHL5 DLBCL cells at the same time as addition of the indicated concentrations of BI3812. n=3 biological repeats, mean±s.d., 72 hours drug treatment. FIG. 29, Panel B: Competitive titration of JQ1 against TCIP1. n=3 biological repeats, mean±s.d. FIG. 29, Panel C: TR-FRET assay to measure molecule-dependent ternary complex formation between BRD4$^{BD1}$ and BCL6BTB. Plotted are a representative set of TCIPs that were the most potent (in cell viability assays) within each category of linker structure. TCIP1 had the highest potency of all designed molecules. n=2 independent repeats with different batches of protein with n=3 technical repeats each, mean±s.e. FIG. 29, Panel D: Analysis of cooperative binding induced by TCIP1 and BRD4$^{BD1}$ and BCL6BTB domains. Representative ternary complex KD measurement by isothermal calorimetry (ITC) shown, for binary measurements see FIG. 30, Panel D. n=3 independent repeats, mean±s.d. ITC parameters shown with 20:1 BRD4$^{BD1}$:TCIP1 in the cell and titration of BCL6BTB. For biolayer interferometry (BLI) measurements were with 50 μM excess BRD4$^{BD1}$ in the well, nanomolar titrations of TCIP1, and biotinylated BCL6BTB on the tip, n=2 independent repeats, mean±s.d. FIG. 29, Panel E: Multiple BRD4-BCL6 TCIPs synthesized with different linkers to test structure-activity relationship. FIG. 29, Panel F: Effect of favorable in vitro ternary complex formation (represented by TR-FRET Area Under Curve) on transcriptional activation of BCL6 reporter in DLBCL cells. FIG. 29, Panel G: Effect of favorable intracellular ternary complex formation (represented by nanoBRET EC50) on transcriptional activation of BCL6 reporter in DLBCL cells.

Figure 30:
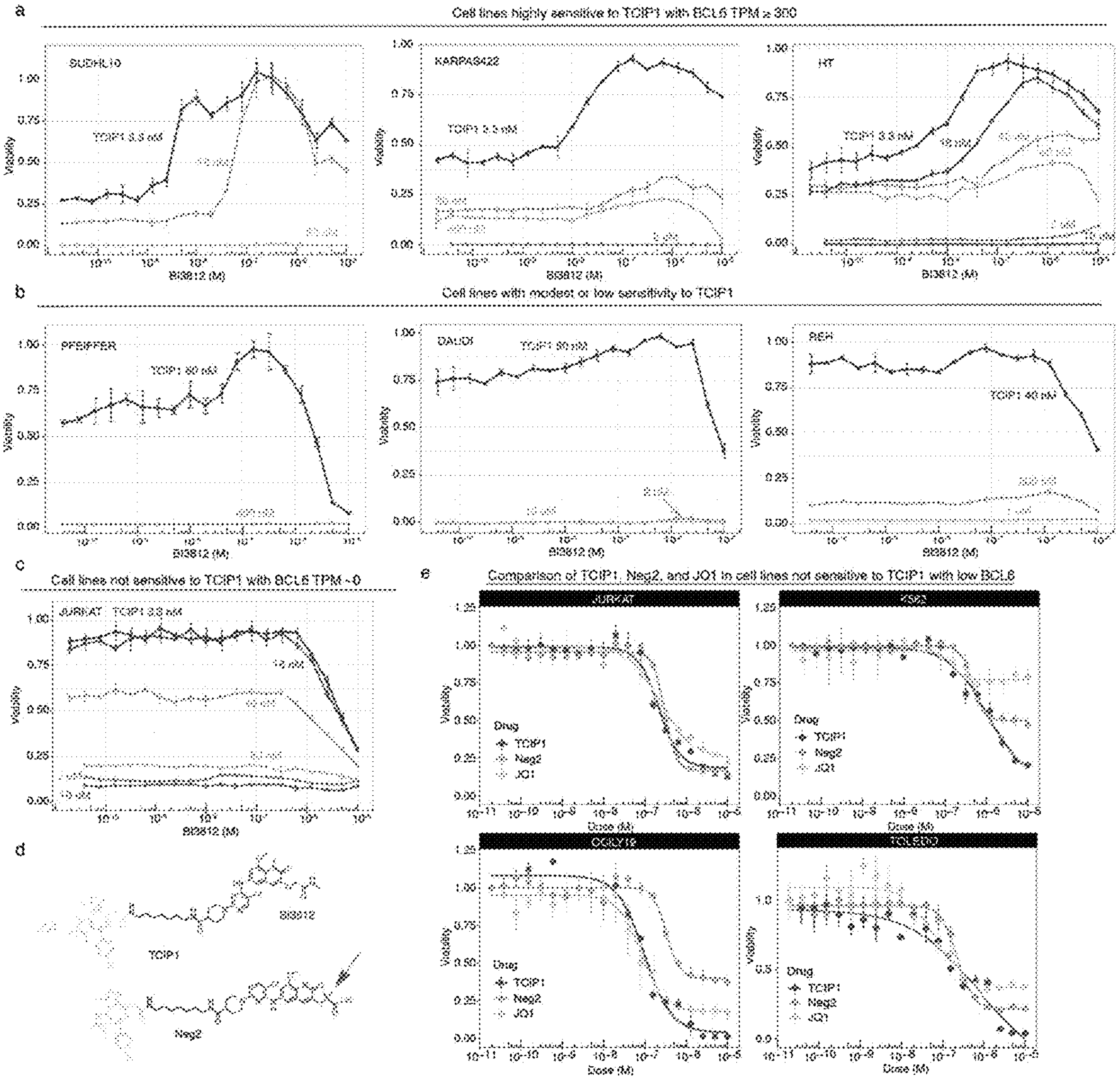
FIG. 30 (Panels A-E) depict data demonstrating rescue of cell death induced by a compound of the disclosure by competitive titration of BCL6 inhibitors.

FIG. 30 (Panels A-E) depict rescue of TCIP1-induced cell death by competitive titration of BCL6 inhibitors. FIG. 30, Panel A: Rescue of TCIP1-induced cell death across cancer cell lines that are highly sensitive to TCIP1, FIG. 30, Panel B: moderately sensitive, or FIG. 30, Panel C: not at all sensitive. n=3 biological repeats, mean±s.d. FIG. 30, Panel D: Comparison of JQ1, TCIP1, and Neg2, which contains a functional BRD4 inhibitor but very low-affinity BCL6 binder (K$_D$~10 μM) in FIG. 30, Panel E: cell lines that have low or no BCL6. n=3 biological repeats, mean±s.d. Viability curves in FIG. 30, Panel A, FIG. 30, Panel B, FIG. 30, Panel C, and FIG. 30, Panel E are after 72 hours drug treatment.

FIG. 31 (Panels A-F) demonstrate that TCIP1 induces apoptosis at every stage of the cell cycle. FIG. 31, Panel A: Dose-dependent induction of apoptosis at 24 hours by TCIP1 as measured by AnnexinV-positive cells (n=4 biological repeats (6 for DMSO), mean±s.d.). FIG. 31, Panel B: Kinetics of TCIP1-induced apoptosis in KARPAS422 cells (n=3 biological repeats for 10 nM, 2 for 100 nM). FIG. 31, Panel C: Design of assay to measure cell cycle progression simultaneously with apoptosis using Terminal deoxynucleotidyl transferase dUTP nick end labeling (TUNEL) staining. FIG. 31, Panel D: TCIP1 induction of cell cycle arrest compared to controls, representative of n=2 biological repeats. FIG. 31, Panel E: 100 nM TCIP1 induction of apoptosis as measured by DNA fragmentation at each stage of the cell cycle (n=2 biological repeats, mean±s.d. *: p≤0.05; **: p50.01; per phase, two-way ANOVA followed by Fishers LSD test on each sample per time point compared only to DMSO, with Dunnet's multiple hypothesis correction). FIG. 31, Panel F: Measurement of cell viability after cell cycle arrest in G0/G1 by serum starvation in KARPAS422 cells and TCIP1 addition (n=3 biological repeats, mean±s.d.).

FIG. 32 (Panels A-F) depict biochemical studies of ternary complex binding affinities of TCIPs. FIG. 32, Panel A: Ternary complex formation by TCIPs with related chemistries. TCIP1 and Neg1 and Neg2 controls are plotted on every graph. n=3 repeats, mean±s.e. FIG. 32, Panel B:

Isothermal calorimetry experiments to measure binary affinities of TCIP1 to BRD4 (BD1), BCL6 (BTB), and associated controls. Representative data from n=2 shown. FIG. 32, Panel C: Representative biolayer interferometry measurements (BLI) of ternary complex kinetics from n=2 repeats shown with biotinylated BCL6 (BTB) on the tip and excess BRD4 in the well with titration of TCIP1. FIG. 32, Panel D: Off-rate and FIG. 32, Panel E: half-life of TCIP1 calculated from BLI measurements. FIG. 32, Panel F: Area under curve of TR-FRET correlates with potency of TCIPs on cell death (KARPAS422 cells, viability at 72 hours). Representative cellular EC$_{50}$s labeled.

FIG. 33 (Panels A-G) demonstrate that TCIP1 represses MYC and its targets while activating pro-apoptotic genes. FIG. 33, Panel A: Gene activation (median change: 4-fold up) and repression after 10 nM TCIP1 addition in KARPAS422 cells for 20 hours, with well-known BCL6 targets labeled. Significance cutoffs were p$_{adj}$≤0.05 and |log$_2$(Drug/DMSO)|21), n=2 biological repeats. FIG. 33, Panel B: Downregulated genes are significantly enriched for MYC targets (MSigDB Hallmark Pathways). FIG. 33, Panel C: Analysis of transcription factor binding at the top downregulated genes in over 4,500 public transcription factor ChIP-seq datasets from blood-lineage cells. FIG. 33, Panel D: Dose-dependent changes in protein levels of target genes selected from the RNA-seq results in two separate DLBCL cell lines, KARPAS422 and SUDHL5. FIG. 33, Panel E: Negligible effect of negative controls Neg1 and Neg2 on protein levels of TCIP1 targets. FIG. 33, Panel F: Kinetics of protein changes in MYC, CDKN1A/p21, and FOXO3 in DLBCL cell lines after 10 nM TCIP1 treatment. FIG. 33G: Rescue of p21 and FOXO3 upregulation, and MYC downregulation, by competitive titration of the BTB binder Bl3812 against constant 10 nM TCIP1 for 8 hours.

FIG. 34 depicts 100 nM TCIP1 addition at 24 hours and simultaneous measurement of cell cycle block and apoptosis in KARPAS422 cells, two separate experiments on different passages of cells shown. Gates were set based on no-stain controls.

FIG. 35 (Panels A-M) depict rapid activation of BCL6-target genes by recruitment of BRD4. FIG. 35, Panel A: Gene expression changes by RNA-seq after 10 nM TCIP1 addition for 2 hours in KARPAS422 cells, with well-known BCL6 targets labeled. Significance cutoffs were p$_{adj}$≤0.05 and |log$_2$(Drug/DMSO)|≤0.5, n=3 biological repeats. FIG. 35, Panel B: Time-dependent changes in gene expression after 1,2, and 4 hours 10 nM TCIP1 compared to Neg1 and Neg2. Only significant gene expression changes are shown. FIG. 35, Panel C: Enrichment analysis of promoters of genes at 2 hours for transcription factor peaks in over 4,500 public transcription factor ChIP-seq datasets in blood cancer cells. FIG. 35, Panel D: BRD4 ChIP-seq peaks in KARPAS422 cells at BCL6 summits after 1 hour 100 nM TCIP1 addition. FIG. 35, Panel E: Time-dependent analysis by ChIP-seq of the average density of Pol II ser 2 phos (elongating), Pol II ser 5 phos (paused/initiating), and H3K27ac (mark of active transcription) along gene bodies ±3 kb after 10 nM TCIP1 addition for the indicated timepoints, at TCIP1-upregulated, TCIP1-downregulated, and unchanged genes identified by the 2 hours 10 nM TCIP1 RNA-seq in FIG. 35, Panel A. Metaprofiles are averaged from spike-in normalized data. FIG. 35, Panel F: BRD4 average density at upregulated and downregulated genes, as in FIG. 35, Panel E, as well as at enhancers and super-enhancers identified by H3K27ac peaks and the ROSE algorithm (Methods). Shading in FIG. 35, Panel E and FIG. 35, Panel F represents standard error. FIG. 35, Panel G: Genome browser track of Pol II ser 2, Pol 11 ser 5, H3K27ac, and BRD4 at each time point of 10 nM TCIP1 addition at known the BCL6 target and TCIP1-upregulated proapoptotic gene PMAIP1/NOXA. FIG. 35, Panel H: Genome browser track of Pol II ser 2 (elongating) and BRD4 at the BCL6 locus with the BCL6 transcripts specific to each isoform shown, and the known BCL6 intronic binding site that also contains a super-enhancer (SE) highlighted. All tracks in FIG. 35, Panel G and FIG. 35, Panel H are spike-in normalized and input-subtracted. FIG. 35, Panel I: BCL6 isoform structure. FIG. 35, Panel J: mRNA levels measured by RT-qPCR of the long and short isoforms of BCL6, with primers specific to exon-exon junctions unique to each isoform (shown by arrows in FIG. 35, Panel 1). n=3 biological repeats, mean±s.d. Statistical significance calculated by Students' t-Test, two-tailed, unpaired, *: p≤0.05; : p≤0.01. FIG. 35, Panel K: Induction of the long isoform of BCL6 protein starting at 0.5 to 1 nM TCIP1. FIG. 35, Panel L: Simultaneous treatment of 10 nM TCIP1 and 100 nM CDK9 inhibitor NVP2 to block transcriptional elongation and measurement of BCL6 protein isoforms. FIG. 35**, Panel M: Reversal of BCL6 upregulation by competitive titration of the BTB binder BI3812 against constant 10 nM TCIP1.

FIG. 36 (Panels A-E) depict robust and dose-dependent gene regulation by TCIP1. FIG. 36, Panel A: Principal component analysis of RNA-seq data after addition of TCIP1 for 20 hours in 2 biological replicates of KARPAS422 cells. FIG. 36, Panel B: Gene expression changes after addition of 100 nM TCIP1 for 20 hours in KARPAS422 cells. Significance cutoffs were $p_{adj}$≤0.05 and $|\log_2$(Drug/DMSO)|≥1), n=2 biological repeats. FIG. 36, Panel C: Dose-dependent change in gene expression. FIG. 36, Panel D: Enrichment analysis of upregulated genes (MSigDB Hallmark Pathways). FIG. 36, Panel E: Analysis of TF binding at the top upregulated genes in over 4,500 public transcription factor ChIP-seq datasets from blood-lineage cells.

FIG. 37 (Panels A-L) depict toxicity of TCIP1 in mice and primary human cells and generalization to ER-positive cancers. FIG. 37, Panel A: Tissue-specific transcriptomic effects of TCIP1, treated at 10 mg/kg IP q.d. for 5 days. n=3 mice each for treatment and vehicle. Only significant gene expression changes are shown. FIG. 37, Panel B: Quantification of transcriptome changes in the liver, lung, and spleen and associated accumulated tissue concentrations of TCIP1. FIG. 37, Panel C: Pharmacokinetic parameters of TCIP1. FIG. 37, Panel D: Comparison of key gene targets upregulated by TCIP1 in both cultured DLBCL cells (KARPAS422 a.k.a KP422) and in the Spleen. FIG. 37, Panel E: Body weight of treated mice. No adverse effects or behavioral abnormalities were noticed. FIG. 37, Panel F: H & E staining of lung and spleen from representative vehicle and drug-treated mice; scale bar: 50 μm in lung images, 100 μm in spleen images. FIG. 37, Panel G: Effect of TCIP1 on cell viability of primary human tonsillar lymphocytes. FIG. 37, Panel H: Effect of TCIP1 on cell viability of primary fibroblasts. n=3 biological repeats, mean±s.d. FIG. 37, Panel I: ER-BCL6 TCIP2 designed to induce cell death in estrogen-positive, BCL6-over-expressing DLBCLs. FIG. 37, Panel J: Chemical structure of TCIP2. FIG. 37, Panel K: Effect on cell viability of TCIP2 compared controls: estrone, BI3812 ($BCL6^{BTB}$ inhibitor), and BI3802 (BCL6 degrader) in KARPAS422 cells with high ERβ (ESR2) levels, n=3 biological repeats, mean±s.d. FIG. 37, Panel L: Measurement of selective effect on cell viability by TCIP2 in DLBCL cells with coincident overexpression of ER and BCL6 (KARPAS422) compared to primary human lymphocytes, a triple-negative breast cancer cell line (HS578T), and ER-driven but BCL6-low breast cancer cells (HCC1428). n=3 biological repeats, mean±s.d. Viability curves in FIG. 37, Panel G, FIG. 37, Panel H, FIG. 37, Panel K, and FIG. 37, Panel L are after 72 hours drug treatment.

FIG. 38 (Panels A-C) depict specific activation of gene expression by TCIP1 but not related controls. FIG. 38, Panel A: Gene expression changes after 1 hour or 4 hours addition of 10 nM TCIP1 in KARPAS422 cells. 2 hours was shown in FIG. 35, Panel A. Significance cutoffs were $p_{adj}$≤0.05 and $|\log_2$(Drug/DMSO)|>0.5), n=3 biological repeats. FIG. 38, Panel B: Specific effects of TCIP1 across transcriptome. For Neg1 and Neg2, n=2 biological repeats. For TCIP1, n=3 biological repeats. FIG. 38, Panel C: Enrichment analysis of upregulated and downregulated genes (MSigDB Hallmark Pathways).

FIG. 39 (Panels A-E) depict ChIP-seq analyses of BRD4, H3K27ac, and RNA Pol II in response to TCIP1. FIG. 39, Panel A: PCA plots of each ChIP-seq experiment at indicated timepoints of 10 nM TCIP1 addition: 0 hr (DMSO), 15 minutes, 1 hour, 2 hours, and 4 hours. FIG. 39, Panel B: Browser tracks of Pol II ser 2 phos, Pol II ser 5 phos, H3K27ac, and BRD4 at BCL6-target genes and TCIP1-upregulated genes FOXO3 and BCL2L11/BIM. All tracks are spike-in normalized and input-subtracted. FIG. 39, Panel C: Volcano plots of Pol II ser 2 phos, Pol II ser 5 phos, and H3K27ac after 2 hours 10 nM TCIP1 addition. Peaks were classified as differential after reads in peaks-based RLE normalization and cutoffs $p_{adj}$≤0.05 and $|\log_2$(Drug/DMSO)|≥0.5. FIG. 39, Panel D: Enhancer and super-enhancer classification in KARPAS422 cells based on H3K27ac ChIP-seq and the ROSE algorithm (Methods). FIG. 39, Panel E: BRD4 and H3K27ac ChIP-seq track at the known OCA-B super-enhancer after TCIP1 addition for indicated timepoints.

FIG. 40 (Panels A-D) depict conversion of BCL6 auto-inhibitory pathway to feedforward loop. FIG. 40, Panel A: Control Neg1 and Neg2 effect on BCL6 protein levels at 20 hours treatment in KARPAS422 cells. FIG. 40, Panel B: Effect on BRD4 levels at 20 hours treatment with TCIP1 in KARPAS422 cells. FIG. 40, Panel C: Kinetics of BCL6 upregulation in two separate DLBCL cell lines, KARPAS422 and SUDHL5, after addition of 10 nM TCIP1. FIG. 40, Panel D: Model for conversion of BCL6 auto-inhibitory circuit to a positive feedback loop.

III.

Both functional and structural studies have shown that the exquisite specificity of transcriptional outcomes is based upon combinatorial interactions. TCIPs are designed to use this fundamental mechanism requiring coincident expression of both regulators to modulate expression of therapeutic genes such as cell death genes. In this way, TCIPs can theoretically make use of the vast combinatorial interactions among transcription factors to produce highly selective patterns of therapeutic use while reducing off-target effects.

Existing approaches to targeted cancer chemotherapy rely upon inhibiting or degrading a protein or preventing its synthesis by RNAi or CRISPR(i). These approaches require complete or near complete removal of the driver function. However, TCIPs rewire these drivers to cell death pathways, and only use a fraction of the total driver molecules per cell. This assertion is supported by the fact that 10 nM TCIP1 produces only a -1.5-fold increase in BRD4 at BCL6 sites over the genome (FIG. 35, Panel D) and less than 10% loss at enhancers, despite robust gene activation and cell killing. It is noted that other BET proteins of homology to BRD4, such as BRD2 and BRD3, could also have affinity to TCIP1, although the global inhibition of transcription that others have seen when degrading or inhibiting the BET proteins was not observed with TCIP1. This mechanism could also explain the far more robust cell killing seen with substantially lower concentrations of TCIP1 when compared to the weaker anti-proliferative effects of conventional small molecule inhibitors or degraders of BCL6 or BET proteins, which act by "occupancy-driven" pharmacology requiring binding to almost all copies of their cognate protein. The effective use of TCIP1 at nanomolar concentrations also likely limits off-target events. As a consequence, TCIPs may avoid mechanism-based toxicity in off target tissues that almost inevitably occurs when one reduces the expression or activity of an essential protein, like BRD4.

Genomic studies demonstrate that cancers often have more than a single driver that may independently contribute to proliferation, survival, invasion, and metastasis and thereby complicate therapeutic approaches. By making use of the cancer cell's own intrinsic driving pathways and rewiring them to activate pathways of cell death, this example introduces an approach to cancer chemotherapy that is analogous to a dominant, gain-of-function mutation in genetics. The TCIP strategy also can engage genomic information specific to the tumor and its stage of development. In conventional chemotherapy multiple drivers are a distinct disadvantage and can produce resistance to single agents. In contrast, the dominant gain-of-function produced by TCIPs could allow the killing of cancer cells with any number of independent drivers, provided the identification of a chemical binder (not necessarily inhibitor) to that driving protein. The experiments developing TCIPs rely only on endogenous transcription factors and epigenetic modifiers with their intrinsic biologic specificity.

Embodiments

Notwithstanding the appended embodiments, the disclosure is also defined by the following embodiments:

BRD4 Ligand Embodiments

1. A compound of formula I:

BR-L-BC (I)

wherein:

BR is a ligand that specifically binds to bromodomain-containing protein 4 (BRD4);

BC is a ligand that specifically binds to B-cell lymphoma 6 (BCL-6) (or a homologue thereof); and L is a linker, or a pharmaceutically acceptable salt thereof.

2. The compound according to Embodiment 1, wherein BR is of formula IA:

(IA)

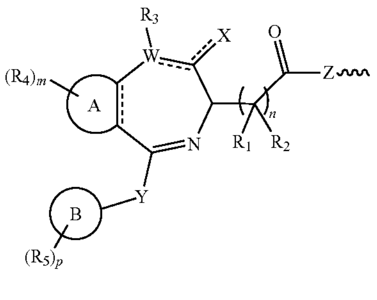

wherein:

n is an integer from 0 to 12;

m is an integer from 0 to 5;

p is an integer from 0 to 5;

A is a 5-8 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

B is a 3-12 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

W is C, N, O or S;

X is oxygen or sulfur, or: $R^3$ and X are taken together with their intervening atoms to form an optionally substituted 5-6 membered cycloalkyl, substituted cycloalkyl, heterocycloalkyl, substituted heterocycloalkyl, aryl, substituted aryl, heteroaryl, substituted heteroaryl, heteroarylalkyl, and substituted heteroarylalkyl;

Y is a covalent bond, alkyl, substituted alkyl, alkenyl, substituted alkenyl, alkynyl, substituted alkynyl, or a substituted bivalent C(1-6) hydrocarbon chain wherein one or more methylene units is optionally replaced by —NR'—, —N(R')C(O)—, —C(O)N(R, —N(R')$SO_2$—, —$SO_2N(R)$—, —O—, —C(O)—, —OC(O)—, —C(O)O—, —S—, —SO— or —$SO_2$—;

Z is —$CH_2$,—NH,—O— or —S—

---- represents a single or double bond;

∿∿∿ represents a bond to the linker;

each of $R_1$, $R_2$, $R_3$, $R_4$ and $R_5$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine and substituted sulfoximine.

3. The compound according to Embodiment 2, wherein $R^3$ and X are taken together with their intervening atoms to form a heteroaryl ring having 1-4 heteroatoms independently selected from nitrogen, oxygen, or sulfur.

4. The compound according to any one of Embodiments 1-3, wherein A is a 5-membered fused heteroaryl ring having 2-3 heteroatoms independently selected from nitrogen, oxygen, or sulfur, or a 6-membered fused heteroaryl ring having 2-3 nitrogen atoms.

5. The compound according to any one of Embodiments 1-4, wherein B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur.

6. The compound according to any one of Embodiments 1-5, wherein each one of $R_1$ and $R_2$ is independently selected from hydrogen, halogen, optionally substituted C(1-6) aliphatic, —OR, —SR, —CN, —$N(R')_2$, —C(O)R, —C(S)R, —$CO_2R$, —C(O)N(R')$_2$, —C(O)SR, —C(O)C(O)R, —C(O)CH$_2$C(O)R, —C(S)N(R')$_2$, —C(S)OR, —S(O)R, —$SO_2R$, —$SO_2N(R')_2$, —N(R')C(O)R, —N(R')C(O)N(R')$_2$, —N(R')C(S)N(R')$_2$, —N(R')$SO_2R$, —N(R')$SO_2N(R')_2$, —N(R')N(R')$_2$, —N(R')C(=N(R'))N(R')$_2$, —C=NN(R')$_2$, -C=NOR, —C(=N(R'))N(R')$_2$, —OC(O)R, —OC(O)N(R')$_2$, or —$(CH_2)_qR^x$ wherein q is 0-3 and $R^x$ is halogen, optionally substituted C(1-6) aliphatic, —OR, -SR, —CN, —N(R')$_2$, —C(O)R, —C(S)R, —$CO_2R$, —C(O)N(R')$_2$, —C(O)SR, —C(O)C(O)R, —C(O)CH$_2$C(O)R, —C(S)N(R')$_2$, —C(S)OR, —S(O)R, —$SO_2R$, —$SO_2N(R')_2$, —N(R')C(O)R, —N(R')C(O)N(R')$_2$, —N(R')C(S)N(R')$_2$, —N(R')$SO_2R$, —N(R')$SO_2N(R')_2$, —N(R')N(R')$_2$, —N(R')C(=N(R'))N(R')$_2$, —C=NN(R')$_2$, -C=NOR, —C(=N(R'))N(R')$_2$, —OC(O)R or —OC(O)N(R')$_2$.

7. The compound according to any one of Embodiments 1-6, wherein each of $R^4$ and $R^5$ is independently —R, halogen, —OR, —SR, —N(R')$_2$, —CN, —$NO_2$, —C(O)R, —C(S)R, —$CO_2R$, —C(O)N(R')$_2$, —C(O)SR, —C(O)C(O)R, —C(O)CH$_2$C(O)R, —C(S)N(R')$_2$, —C(S)OR, —S(O)R, —$SO_2R$, —$SO_2N(R')_2$, —N(R')C(O)R, —N(R')C(O)N(R')$_2$, —N(R')C(S)N(R')$_2$, —N(R')$SO_2R$, —N(R')$SO_2N(R')_2$, —N(R')N(R')$_2$, —N(R')C(=N(R'))N(R')$_2$, —C=NN(R')$_2$, -C=NOR, —C(=N(R'))N(R')$_2$, —OC(O)R, or —OC(O)N(R')$_2$.

8. The compound according to any one of Embodiments 1-7, wherein A is pyrimidino, pyrazino, or pyridazino.

9. The compound according to any one of Embodiments 1-7, wherein A is a 5-membered fused heteroaryl ring having 2 heteroatoms independently selected from nitrogen, oxygen, or sulfur.

10. The compound according to Embodiment 9, wherein A is isothiazolo.

11. The compound according to any one of Embodiments 1-10, wherein B is phenyl.

12. The compound according to any one of Embodiments 1-11, wherein Ring B is a 5-6 membered monocyclic heteroaryl ring having 1-3 heteroatoms independently selected from nitrogen, oxygen, and sulfur.

13. The compound according to any one of Embodiments 1-12, wherein Y is a covalent bond.

14. The compound according to any one of Embodiments 1-13, wherein $R^3$ and X are taken together with their intervening atoms to form an optionally substituted triazolyl ring.

15. The compound according to any one of Embodiments 1-14, wherein BR is of formula IA1:

(IA1)

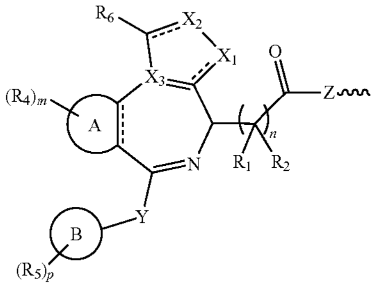

wherein:

$X_1$ is from C, N, O or S;

$X_2$ is from C, N, O or S;

$X_3$ is C or N;

---- represents a single or double bond; and $R_6$ is hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

16. The compound according to Embodiment 15, wherein:

$X_1$ is N or O;

$X_2$ is N; and $X_3$ is C or N.

17. The compound according to Embodiment 15, wherein:

$X_1$ is N;

$X_2$ is N; and $X_3$ is N.

18. The compound according to Embodiment 15, wherein:

$X_1$ is O;

$X_2$ is N; and $X_3$ is C.

19. The compound according to any one of Embodiments 15-18, wherein $R_6$ is hydrogen or a C(1-6) alkyl.

20. The compound according to Embodiment 19, wherein $R_6$ is selected from methyl, ethyl, n-propyl, isopropyl, n-butyl, iso-butyl or tert-butyl.

21. The compound according to Embodiment 20, wherein $R_6$ is methyl.

22. The compound according to any one of Embodiments 1-21, wherein:

n is an integer from 1-4; and each of $R_1$ and $R_2$ are independently selected from hydrogen and a C(1-6) alkyl.

23. The compound according to Embodiment 22, wherein each of $R_1$ and $R_2$ are independently selected from methyl, ethyl, n-propyl, isopropyl, n-butyl, iso-butyl or tert-butyl.

24. The compound according to any one of Embodiments 1-23, wherein:

n is 1; and each of $R_1$ and $R_2$ are hydrogen.

25. The compound according to any one of Embodiments 1-14, wherein BR is of formula IA2:

(IA2)

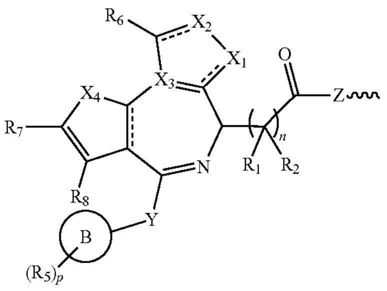

wherein:

$X_1$ is from C, N, O or S;

$X_2$ is from C, N, O or S;

$X_3$ is C or N;

$X_4$ is from $CH_2$, NH, O or S;

---- represents a single or double bond; and each of $R_6$, $R_7$ and $R_8$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

26. The compound according to Embodiment 25, wherein $X_4$ is S.

27. The compound according to any one of Embodiments 25-26, wherein:

$X_1$ is N or O;

$X_2$ is N; and $X_3$ is C or N.

28. The compound according to any one of Embodiments 25-26, wherein:

$X_1$ is N;

$X_2$ is N; and $X_3$ is N.

29. The compound according to any one of Embodiments 25-28, wherein each of $R_6$, $R_7$ and $R_8$ is independently selected from hydrogen or a C(1-6) alkyl.

30. The compound according to Embodiment 29, wherein each of $R_6$, $R_7$ and $R_8$ is independently selected from methyl, ethyl, n-propyl, isopropyl, n-butyl, iso-butyl or tert-butyl.

31. The compound according to Embodiment 30, wherein each of $R_6$, $R_7$ and $R_8$ is methyl.

32. The compound according to any one of Embodiments 25-31, wherein ---- represents a double bond.

33. The compound according to any one of Embodiments 1-14, wherein BR is of formula IA3:

(IA3)

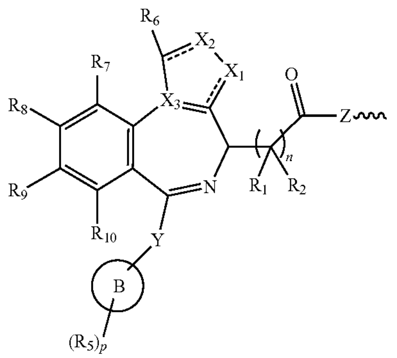

wherein:

$X_1$ is from C, N, O or S;

$X_2$ is from C, N, O or S;

$X_3$ is C or N;

---- represents a single or double bond; and each of $R_6$, $R_7$, $R_8$, $R_9$ and $R_{10}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

34. The compound according to Embodiment 33, wherein:

$X_1$ is N or O;

$X_2$ is N; and $X_3$ is C or N.

35. The compound according to Embodiment 33, wherein:

$X_1$ is N;

$X_2$ is N; and $X_3$ is N.

36. The compound according to Embodiment 33, wherein:

$X_1$ is O;

$X_2$ is N; and $X_3$ is C.

37. The compound according to any one of Embodiments 33-36, wherein each of $R_6$, $R_7$, $R_8$, $R_9$ and $R_{10}$ is independently selected from hydrogen or a C(1-6) alkyl.

38. The compound according to any one of Embodiment 37, wherein $R_6$ is selected from methyl, ethyl, n-propyl, isopropyl, n-butyl, iso-butyl or tert-butyl.

39. The compound according to Embodiment 38, wherein $R_6$ is methyl.

40. The compound according to any one of Embodiments 37-39, wherein each of $R_7$, $R_8$, $R_9$ and $R_{10}$ is hydrogen.

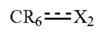

represents a double bond; and

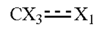

represents a single bond.

42. The compound according to any one of Embodiments 1-14, wherein BR is of formula IA4:

(IA4)

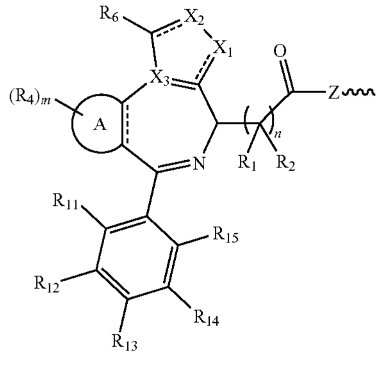

wherein:

n is an integer from 0 to 12;

m is an integer from 0 to 5;

$X_1$ is from C, N, O or S;

$X_2$ is from C, N, O or S;

$X_3$ is C or N;

---- represents a single or double bond;

∿∿∿ represents a bond to the linker; and each of $R_1$, $R_2$, $R_4$, $R_6$, $R_{11}$, $R_{12}$, $R_{13}$, $R_{14}$ and $R_{15}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

43. The compound according to Embodiment 42, wherein:

$X_1$ is N or O;

$X_2$ is N; and $X_3$ is C or N.

44. The compound according to Embodiment 42, wherein:

$X_1$ is N;

$X_2$ is N; and $X_3$ is N.

45. The compound according to Embodiment 42, wherein:

$X_1$ is O;

$X_2$ is N; and $X_3$ is C.

46. The compound according to any one of Embodiments 42-45, wherein $R_6$ is hydrogen or a C(1-6) alkyl.

47. The compound according to Embodiment 46, wherein $R_6$ is selected from methyl, ethyl, n-propyl, isopropyl, n-butyl, iso-butyl or tert-butyl.

48. The compound according to Embodiment 47, wherein $R_6$ is methyl.

49. The compound according to any one of Embodiments 42-48, wherein each one of $R_{11}$, $R_{12}$, $R_{13}$, $R_{14}$ and $R_{15}$ is independently selected from hydrogen, halogen or a C(1-6) alkyl.

50. The compound according to Embodiment 49, wherein:

each one of $R_{11}$, $R_{12}$, $R_{14}$ and $R_{15}$ is independently selected from hydrogen or a C(1-6) alkyl; and $R_{13}$ is halogen.

51. The compound according to Embodiment 50, wherein each one of $R_{11}$, $R_{12}$, $R_{14}$ and $R_{15}$ is hydrogen.

52. The compound according to any one of Embodiments 50-51, wherein $R_{13}$ is selected from fluorine, chlorine, bromine and iodine.

53. The compound according to Embodiment 52, wherein $R_{13}$ is chlorine.

54. The compound according to any one of Embodiments 1-53, wherein BR is selected from:

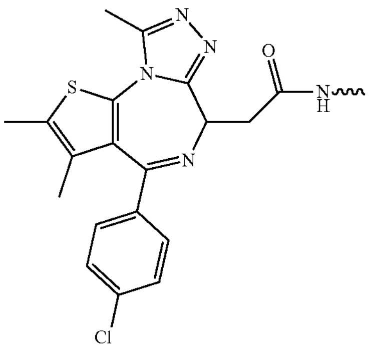

or

-continued

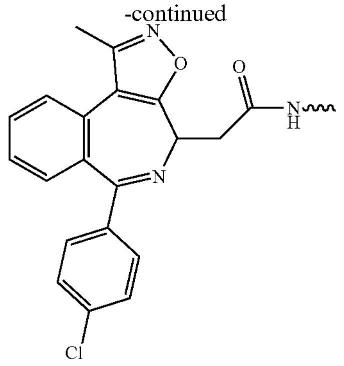

wherein ∿∿ represents a bond to the linker.

55. The compound according to Embodiment 1, wherein BR is of formula IA5:

(IA5)

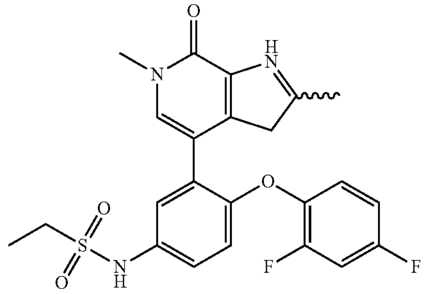

wherein ∿∿ represents a bond to the linker.

57. The compound according to Embodiment 1, wherein BR is selected from:

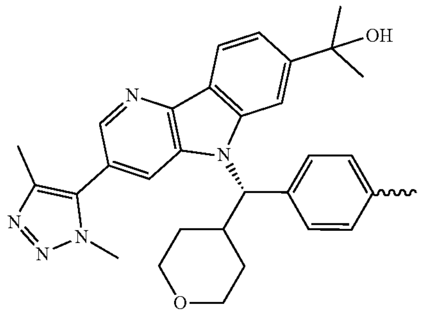

or

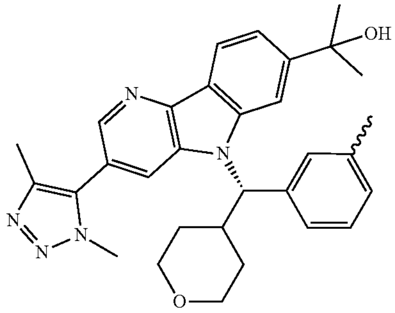

wherein ∿∿ represents a bond to the linker.

57. The compound according to Embodiment 1, wherein BR is selected from:

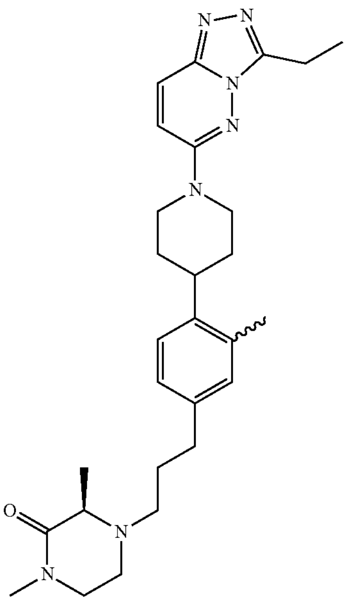
or
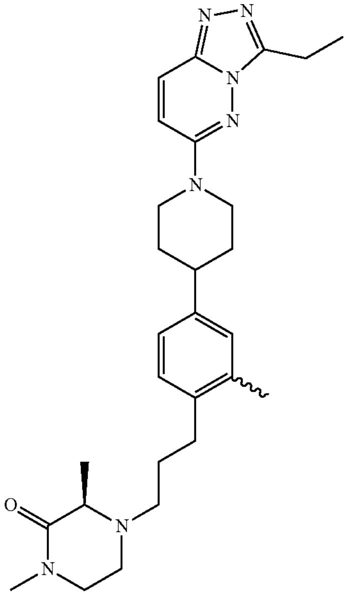
wherein ~~~ represents a bond to the linker.
58. The compound according to Embodiment 1, wherein BR is selected from:
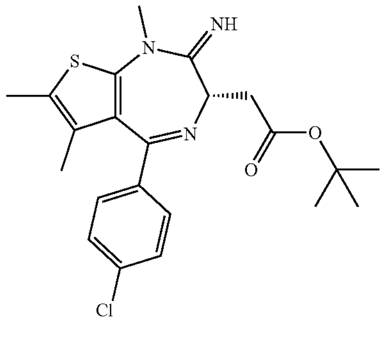
-continued
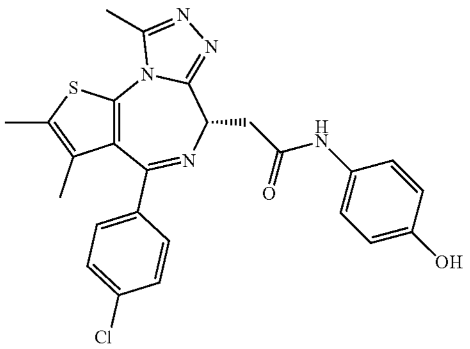
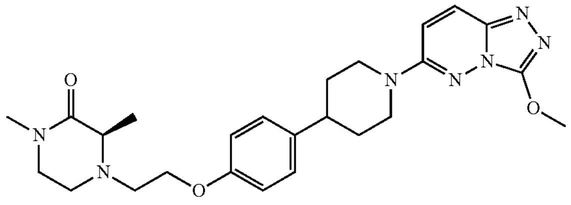
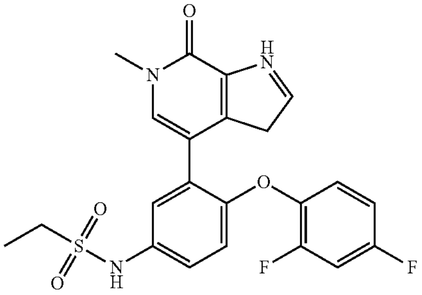
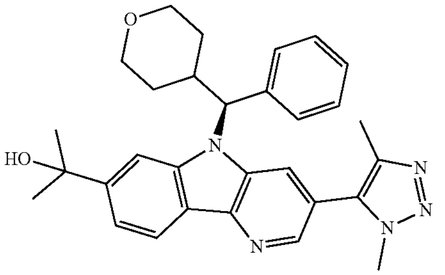
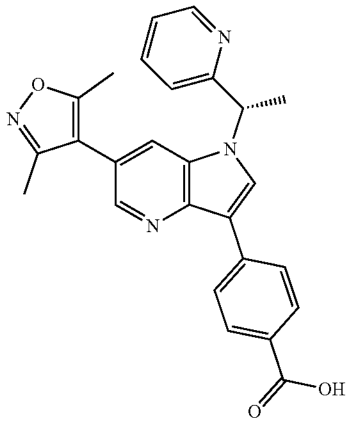

-continued
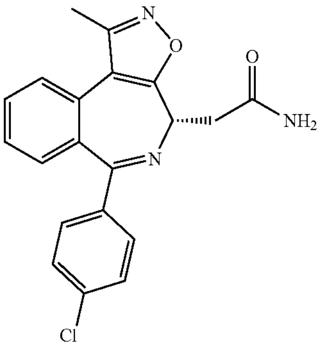
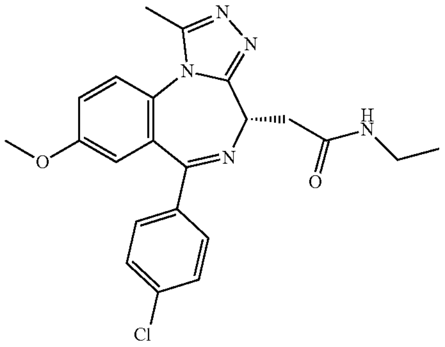
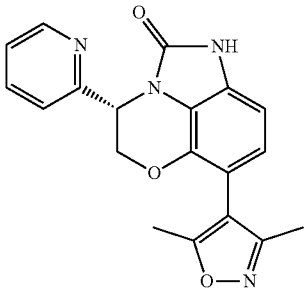
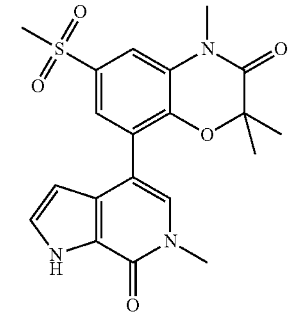
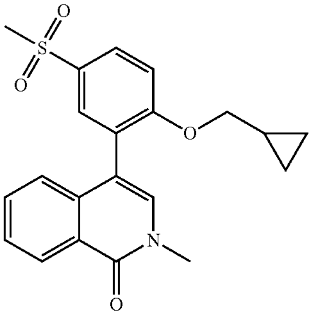
-continued
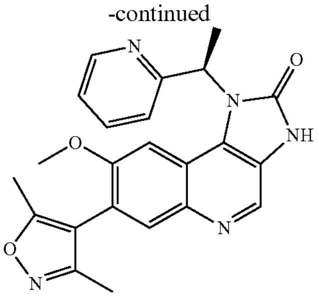
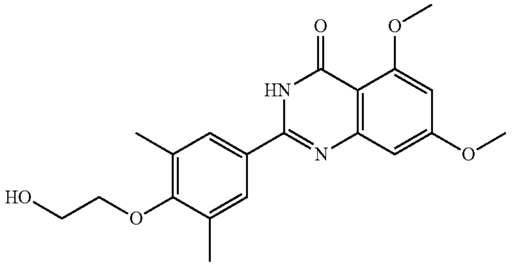
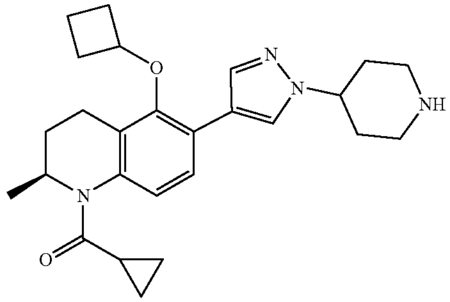
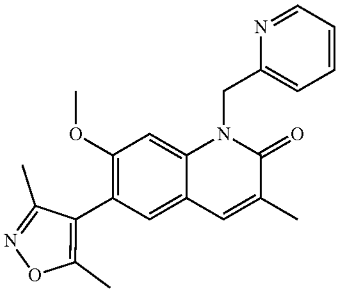
59. The compound according to any one of Embodiments 1-58, wherein BC is of formula IB:
(IB)
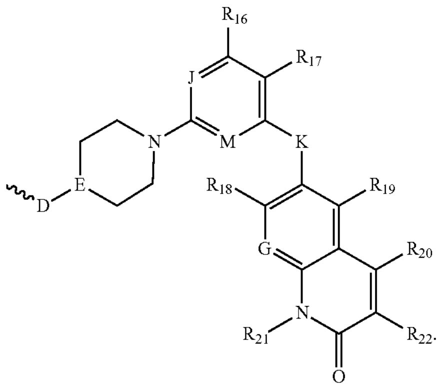

wherein:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from the group consisting of hydrogen, —C(1-4) alkyl, —O—C(1-14) alkyl, —O—C(1-4) haloalkyl, —C(1-4) haloalkyl and halogen;

J is —CH or nitrogen;

M is —CH or nitrogen;

K is —$CH_2$, O, S or —NH;

represents a bond to the linker; and each of $R_{16}$, $R_{17}$, $R_{18}$, $R_{19}$, $R_{20}$, $R_{21}R_{22}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

60. The compound according to Embodiment 59, wherein D is a C(1-6) alkyl.

61. The compound according to Embodiment 59, wherein D is an amide.

62. The compound according to any one of Embodiments 59-61, wherein E is nitrogen.

63. The compound according to any one of Embodiments 59-61, wherein E is —CH.

64. The compound according to any one of Embodiments 59-63, wherein $R_{16}$ is hydrogen.

65. The compound according to any one of Embodiments 59-63, wherein $R_{17}$ is halogen.

66. The compound according to Embodiment 65, wherein $R_{17}$ is chlorine, fluorine, bromine or iodine.

67. The compound according to E66, wherein $R_{17}$ is chlorine.

68. The compound according to any one of Embodiments 59-67, wherein $R_{18}$ is hydrogen, —C(1-4) alkyl, —O—C (1-4) alkyl and halogen.

69. The compound according to any one of Embodiments 59-68, or a salt thereof, wherein G is $CR_{23}$ and $R_{23}$ is selected from the group consisting of hydrogen, C(1-4) alkyl, —O—C(1-4) alkyl, —O—C(1-4) haloalkyl, and halogen.

70. The compound according to Embodiment 69, or a salt thereof, wherein $R_{23}$ is selected from the group consisting of hydrogen, —O—$CH_3$.

71. The compound according to Embodiment 70, wherein $R_{23}$ is —O—$CH_3$.

72. The compound according to any one of Embodiments 59-71, wherein $R_{21}$ is selected from the group consisting of hydrogen, —C(1-6) alkyl optionally substituted with one group selected from —OH, —$NH_2$, —O—$C_1$-alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl.

73. The compound according to any one of Embodiments 59-72, or a salt thereof, wherein $R_{21}$ is selected from the group consisting of —C(1-4) alkyl, optionally substituted with one group selected from —OH, —C(3-6) cycloalkyl and —N($C_{1-4}$ alkyl)$_2$.

74. The compound according to Embodiment 73, or a salt thereof, wherein $R_{21}$ is selected from the group consisting of —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$.

75. The compound according to Embodiment 74, wherein $R_{21}$ is hydrogen or a C(1-6) alkyl.

76. The compound according to Embodiment 75, wherein $R_{21}$ is selected from methyl, ethyl, n-propyl, isopropyl, n-butyl, iso-butyl or tert-butyl.

77. The compound according to Embodiment 76, wherein $R_{21}$ is methyl.

78. The compound according to any one of Embodiments 59-77, wherein $R_{20}$ is hydrogen.

79. The compound according to any one of Embodiments 59-78, wherein $R_{22}$ is $-L-C(R_{24}R^{2}{}_{5})$—$R_{26}$ or —CH═CH—$R_{26}$ wherein $L_1$ is —O— or —S—; $R_{24}$ is hydrogen or C(1-4) alkyl; $R_{25}$ is hydrogen or C(1-4) alkyl; or $R_{24}$ and $R_{25}$ taken together form a —C(3-5) cycloalkyl; $R_{26}$ is —COOH, —$CONH_2$, —C(O)$R_{27}$, —C(O)O$R_{27}$, —C(O)N$R_{27}R_{28}$, —S(O)—$C_{1-6}$ alkyl, —S(O)$_2$—C(1-6) alkyl, —P(O)—($C_{1-6}$ alkyl)$_2$, —C(NH)$NH_2$, $R_{27}$ is a 3-6 membered heterocyclyl or —C(1-4) alkyl optionally substituted by one or more, identical or different groups selected from —OH, —$CF_3$, —N($C_{1-4}$ alkyl)$_2$, —C(3-6) cycloalkyl, 3-6 membered heterocyclyl, —C(2-4) alkenyl, —$C_{2-4}$alkynyl; and $R_{28}$ is hydrogen or C(1-4) alkyl.

80. The compound according to Embodiment 79, wherein $R_{22}$ is selected from the group consisting of:

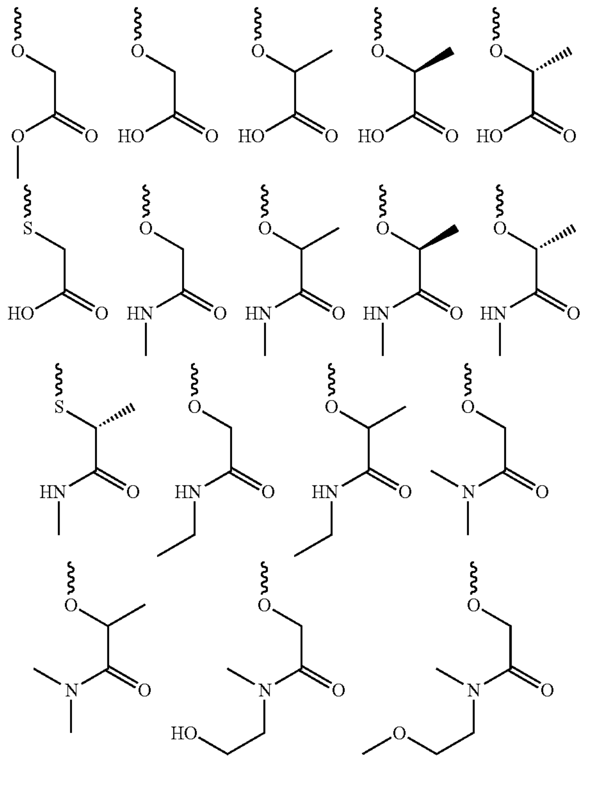

-continued

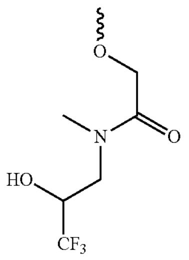

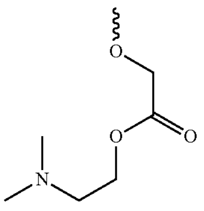

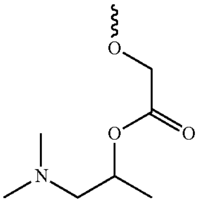

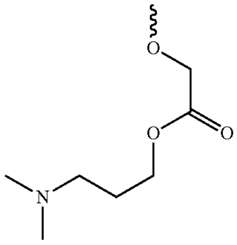

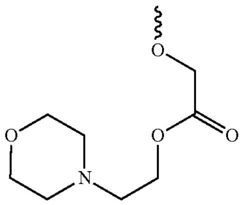

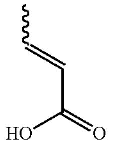

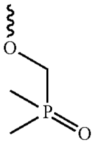

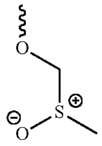

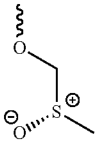

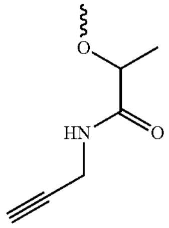

81. The compound according to Embodiment 80, wherein $R_{22}$ is:

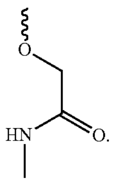

82. The compound according to any one of Embodiments 59-81, wherein BC is of Formula IB1:

(IB1)

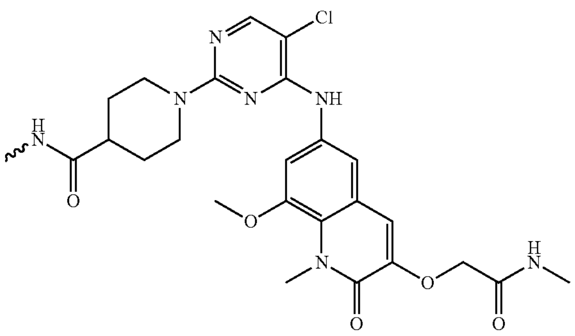

83. The compound according to any one of Embodiments 59-81, wherein BC is of Formula IB2:

(IB2)

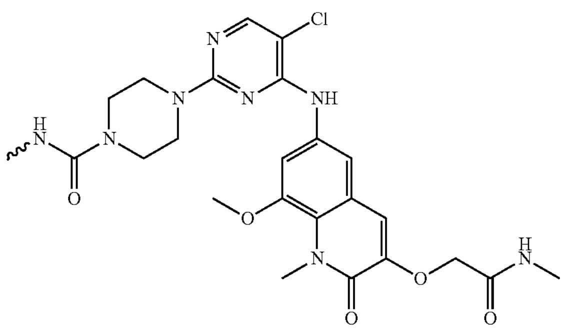

84. The compound according to any one of Embodiments 59-81, wherein BC is of Formula IB3:

(IB3)

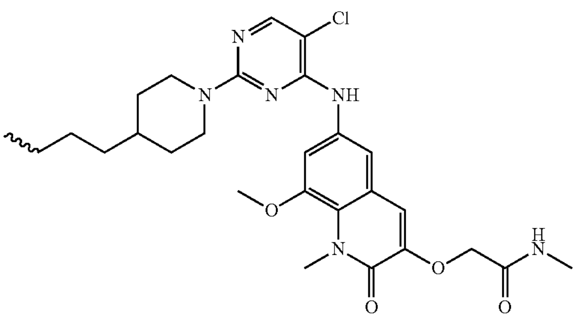

85. The compound according to any one of Embodiments 59-81, wherein BC is of Formula IB4:

(IB4)

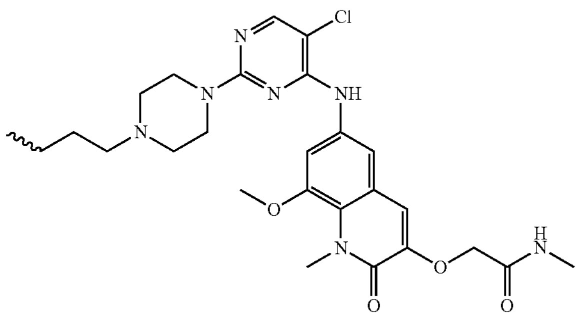

86. The compound according to any one of Embodiments 1-58, wherein BC is of formula IB5:

(IB5)

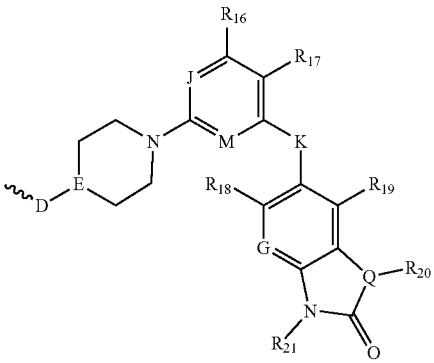

wherein:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from the group consisting of hydrogen, —C(1-4) alkyl, —O—C (1-14) alkyl, -—O—C(1-4) haloalkyl, —C(1-4) haloalkyl and halogen;

J is —CH or nitrogen;

M is —CH or nitrogen;

Q is —CH or nitrogen;

K is —$CH_2$, O, S or NH;

∿∿∿ represents a bond to the linker; and each of $R_{16}$, $R_{17}$, $R_{18}$, $R_{19}$, $R_{20}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

87. The compound according to Embodiment 86, wherein D is a C(1-6) alkyl.

88. The compound according to Embodiment 86, wherein D is an amide.

89. The compound according to any one of Embodiments 86-88, wherein E is nitrogen.

90. The compound according to any one of Embodiments 86-88, wherein E is —CH.

91. The compound according to any one of Embodiments 86-90, wherein $R_{16}$ is hydrogen.

92. The compound according to any one of Embodiments 86-91, wherein $R_{17}$ is halogen.

93. The compound according to Embodiment 92, wherein $R_{17}$ is chlorine, fluorine, bromine or iodine.

94. The compound according to Embodiment 92, wherein $R_{17}$ is chlorine.

95. The compound according to any one of Embodiments 86-94, wherein $R_{18}$ is hydrogen, —C(1-4) alkyl, —O—C (1-4) alkyl and halogen.

96. The compound according to any one of Embodiments 86-95, or a salt thereof, wherein G is $CR_{23}$ and $R_{23}$ is selected from the group consisting of hydrogen, C(1-4) alkyl, —O—C(1-4) alkyl, —O—C(1-4) haloalkyl, and halogen.

97. The compound according to Embodiment 96, or a salt thereof, wherein $R_{23}$ is selected from the group consisting of hydrogen, —O—$CH_3$.

98. The compound according to Embodiment 97, wherein $R_{23}$ is —O—$CH_3$.

99. The compound according to any one of Embodiments 86-98, wherein $R_{21}$ is selected from the group consisting of hydrogen, —C(1-6) alkyl optionally substituted with one group selected from —OH, —$NH_2$, —O—$C_{1-4}$ alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl.

100. The compound according to any one of Embodiments 86-99, or a salt thereof, wherein $R_{21}$ is selected from the group consisting of —C(1-4) alkyl, optionally substituted with one group selected from —OH, —C(3-6) cycloalkyl and —N($C_4$ alkyl)$_2$.

101. The compound according to Embodiment 100, or a salt thereof, wherein $R_{21}$ is selected from the group consisting of —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$.

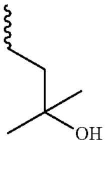

102. The compound according to Embodiment 100, wherein $R_{21}$ is OH

103. The compound according to any one of Embodiments 86-102, wherein $R_{20}$ is hydrogen or a C(1-6) alkyl.

104. The compound according to Embodiment 103, wherein $R_{20}$ is selected from methyl, ethyl, n-propyl, iso-propyl, n-butyl, iso-butyl or tert-butyl.

105. The compound according to Embodiment 104, wherein $R_{20}$ is methyl.

106. The compound according to any one of Embodiments 86-105, wherein BC is of formula IB6:

(IB6)

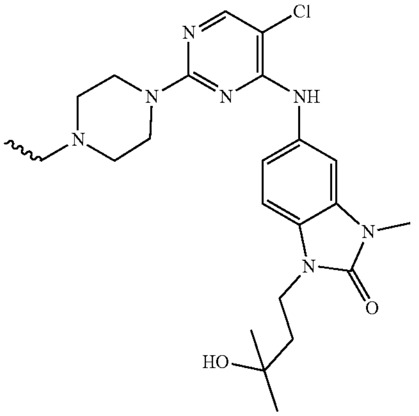

represents a bond to the linker.

107. The compound according to any one of Embodiments 1-58, wherein BC is of formula IB7:

(IB7)

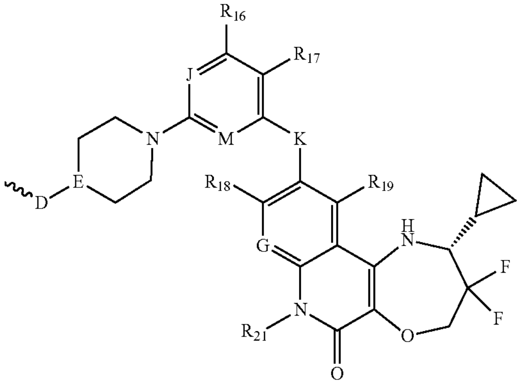

wherein:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from the group consisting of hydrogen, —C(1-4) alkyl, —O—C (1-14) alkyl, —O—C(1-4) haloalkyl, —C(1-4) haloalkyl and halogen;

J is —CH or nitrogen;

M is —CH or nitrogen;

K is —$CH_2$, O, S or NH;

represents a bond to the linker; and each of $R_{16}$, $R_{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

108. The compound according to Embodiment 107, wherein D is a C(1-6) alkyl.

109. The compound according to Embodiment 107, wherein D is an amide.

110. The compound according to any one of Embodiments 107-109, wherein E is nitrogen.

111. The compound according to any one of Embodiments 107-109, wherein E is —CH.

112. The compound according to any one of Embodiments 107-111, wherein $R_{16}$ is hydrogen.

113. The compound according to any one of Embodiments 107-112, wherein $R_{17}$ is halogen.

114. The compound according to Embodiment 113, wherein $R_{17}$ is chlorine, fluorine, bromine or iodine.

115. The compound according to Embodiment 114, wherein $R_{17}$ is chlorine.

116. The compound according to any one of Embodiments 107-115, wherein $R_{18}$ is hydrogen, —C(1-4) alkyl, —O—C(1-4) alkyl and halogen.

117. The compound according to any one of Embodiments 107-116, or a salt thereof, wherein G is $CR_{23}$ and $R_{23}$ is selected from the group consisting of hydrogen, C(1-4) alkyl, —O—C(1-4) alkyl, —O—C(1-4) haloalkyl, and halogen.

118. The compound according to Embodiment 117, or a salt thereof, wherein $R_{23}$ is selected from the group consisting of hydrogen, —O—$CH_3$.

119. The compound according to Embodiment 118, wherein $R_{23}$ is —O—$CH_3$.

120. The compound according to any one of Embodiments 107-119, wherein $R_{21}$ is selected from the group consisting of hydrogen, —C(1-6) alkyl optionally substituted with one group selected from —OH, —$NH_2$, —O—$C_1$-4 alkyl, —NH—C(1-4) alkyl, —N($C_{1-4}$ alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl.

121. The compound according to any one of Embodiments 107-120, or a salt thereof, wherein $R_{21}$ is selected from the group consisting of —C(1-4) alkyl, optionally substituted with one group selected from —OH, —C(3-6) cycloalkyl and —N($C_4$ alkyl)$_2$.

122. The compound according to Embodiment 121, or a salt thereof, wherein $R_{21}$ is selected from the group consisting of —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$.

123. The compound according to Embodiment 122, wherein $R_{21}$ is hydrogen or a C(1-6) alkyl.

124. The compound according to Embodiment 122, wherein $R_{21}$ is selected from methyl, ethyl, n-propyl, iso-propyl, n-butyl, iso-butyl or tert-butyl.

125. The compound according to Embodiment 124, wherein $R_{21}$ is methyl.

126. The compound according to any one of Embodiments 107-125, wherein BC is of formula IB8:

(IB8)

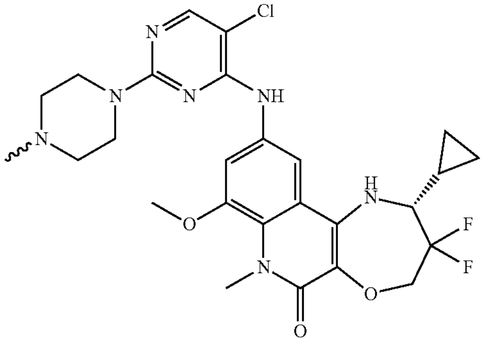

wherein ~~~ represents a bond to the linker.

127. The compound according to any one of Embodiments 1-58, wherein BC is of formula IB9:

(IB9)

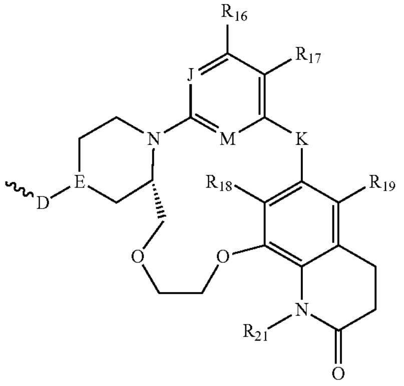

wherein:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

J is —CH or nitrogen;

M is —CH or nitrogen;

K is —$CH_2$, O, S or NH;

~~~ represents a bond to the linker; and each of $R_{16}$, $R_{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

128. The compound according to Embodiment 127, wherein D is a C(1-6) alkyl.

129. The compound according to Embodiment 127, wherein D is an amide.

130. The compound according to any one of Embodiments 127-129, wherein E is nitrogen.

131. The compound according to any one of Embodiments 127-129, wherein E is —CH.

132. The compound according to any one of Embodiments 127-131, wherein $R_{16}$ is hydrogen.

133. The compound according to any one of Embodiments 127-132, wherein $R_{17}$ is halogen.

134. The compound according to Embodiment 133, wherein $R_{17}$ is chlorine, fluorine, bromine or iodine.

135. The compound according to Embodiment 134, wherein $R_{17}$ is chlorine.

136. The compound according to any one of Embodiments 127-135, wherein $R_{18}$ is hydrogen, —C(1-4) alkyl, —O—C(1-4) alkyl and halogen.

137. The compound according to any one of Embodiments 127-136, wherein $R_{21}$ is selected from the group consisting of hydrogen, —C(1-6) alkyl optionally substituted with one group selected from —OH, —$NH_2$, —O—$C_1$-alkyl, —NH—C(1-4) alkyl, —N(C-alkyl)$_2$, —C(3-6) cycloalkyl and 4 to 7 membered heterocyclyl, wherein each cycloalkyl and heterocyclyl group is optionally and independently substituted by one group selected from —C(1-3) alkyl or $R_{21}$ is —C(3-6) cycloalkyl, 4 to 7 membered heterocyclyl, wherein each group is optionally substituted by one group selected from —C(1-3) alkyl.

138. The compound according to any one of Embodiments 126-136, or a salt thereof, wherein $R_{21}$ is selected from the group consisting of —C(1-4) alkyl, optionally substituted with one group selected from —OH, —C(3-6) cycloalkyl and —N($C_{1-4}$ alkyl)$_2$.

139. The compound according to Embodiment 138, or a salt thereof, wherein $R_{21}$ is selected from the group consisting of —$CH_3$, —$CH_2CH_3$, —$CH_2CH_2CH_3$, —$CH(CH_3)_2$, —$(CH_2)_3OH$, —$(CH_2)_2(CH_3)_2$, —$CH_2$-cyclopropyl and —$(CH_2)_2N(CH_3)_2$.

140. The compound according to Embodiment 139, wherein $R_{21}$ is hydrogen or a C(1-6) alkyl.

141. The compound according to Embodiment 140, wherein $R_{21}$ is selected from methyl, ethyl, n-propyl, isopropyl, n-butyl, iso-butyl or tert-butyl.

142. The compound according to Embodiment 141, wherein $R_{21}$ is methyl.

143. The compound according to any one of Embodiments 126-142, wherein BC is of formula IB10:

(IB10)

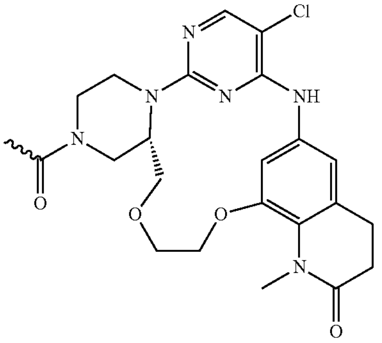

wherein ~~~ represents a bond to the linker.

144. The compound according to any one of Embodiments 1-143, wherein the linker comprises a C(1-16) alkyl chain.

145. The compound according to any one of Embodiments 1-143, wherein the linker comprises a C(1-16) alkyl chain, wherein one or more of the methylene groups is replaced by NH or $CH_3$—N.
~~~

146. The compound according to any one of Embodiments 1-143, wherein the linker comprises a C(1-16) alkoxy chain.

147. The compound according to any one of Embodiments 1-143, wherein the linker comprises a C(1-16) alkoxy chain, wherein one or more of the methylene groups is replaced by NH or $CH_3$—N.

148. The compound according to any one of Embodiments 1-143, wherein the linker comprises a $L^1$-Cyclo-$L^2$, $L^1$-HeteroCyclo-$L^2$, $L^1$-Ar-$L^2$ or $L^1$-Het-$L^2$, where $L^1$ and $L^2$ can be a bond, alkenyl, alkynyl, alkynyloxy, alkenyloxy, alkoxy, or alkyl chain, wherein:

cyclo is a C(3-8) cycloalkyl or substituted C(3-8) cycloalkyl;

heterocyclo is a C(3-8) heterocycloalkyl or substituted C(3-8) heterocycloalkyl;

Ar is an aryl group or substituted aryl group; and

Het is a heteroaryl group or substituted heteroaryl group.

149. The compound according to any one of Embodiments 144-148, wherein the linker is selected from:

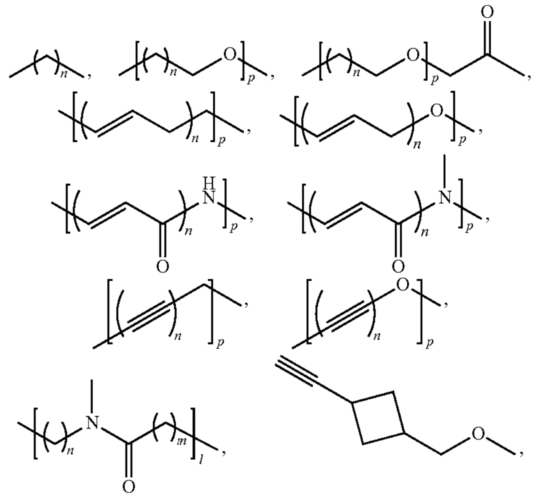

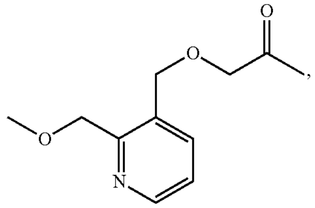

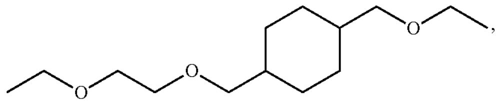

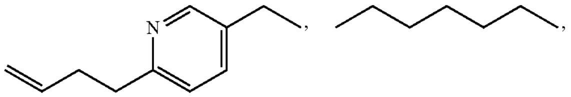

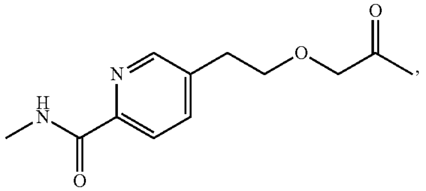

-continued

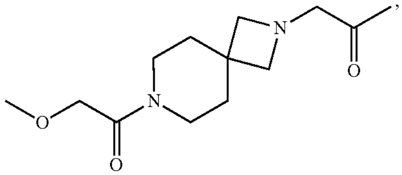

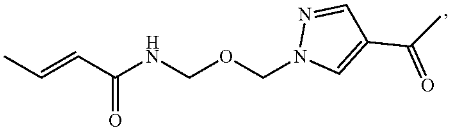

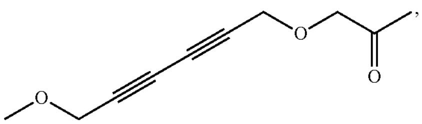

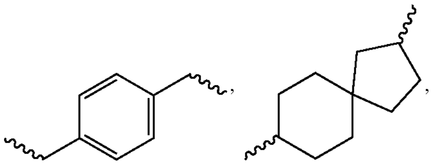

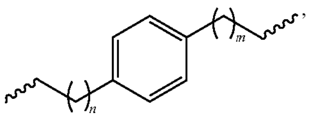

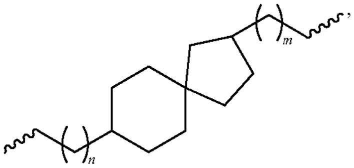

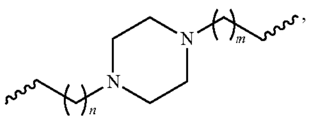

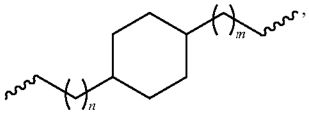

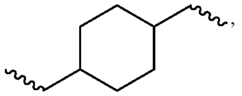

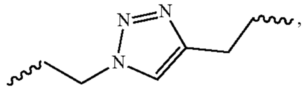

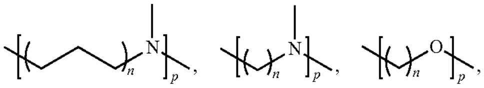

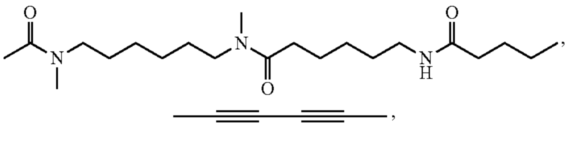

wherein m, n and p are independently selected from 0 or an integer of from 1-12.

150. The compound according to any one of Embodiments 1-149, wherein the linker is selected from linkers 1 to 628 listed above.

151. The compound according to any one of Embodiments 1-150, wherein the compound is selected from:
Compound I-1
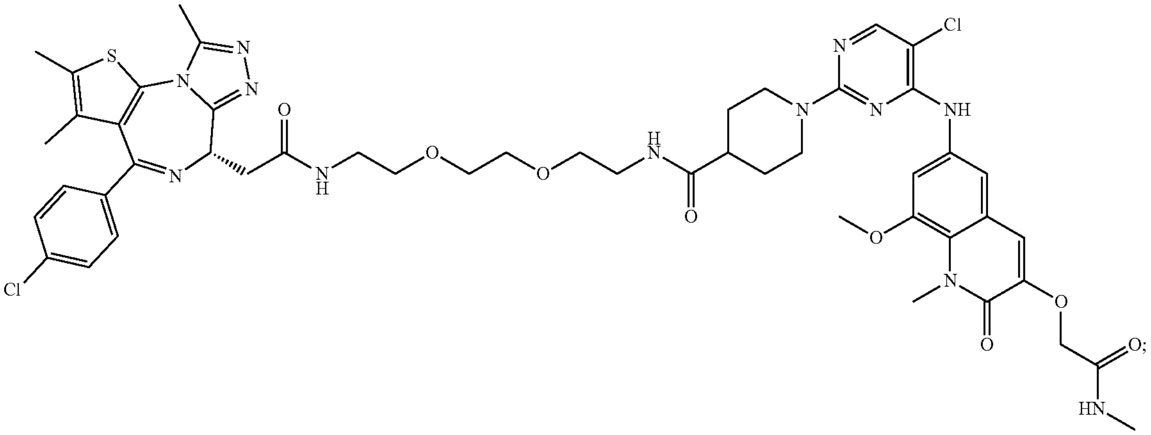
;
Compound I-2
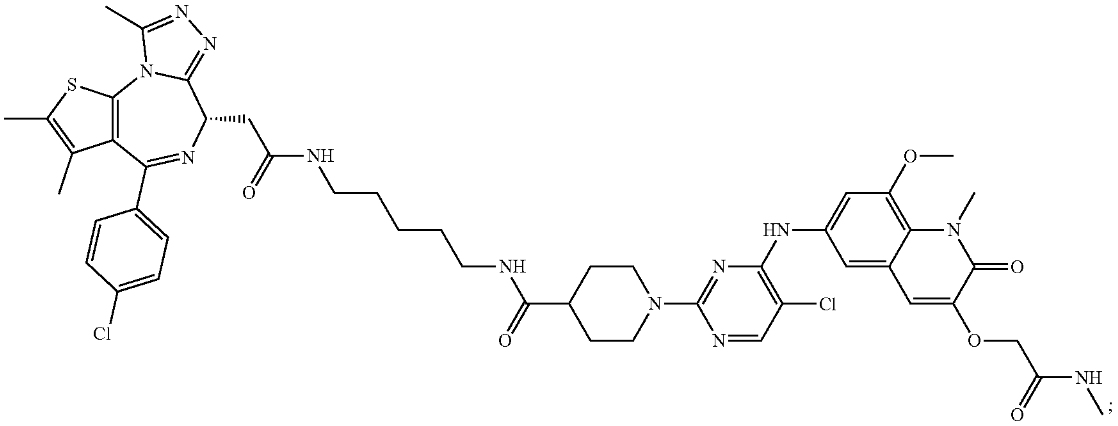
;
Compound I-3
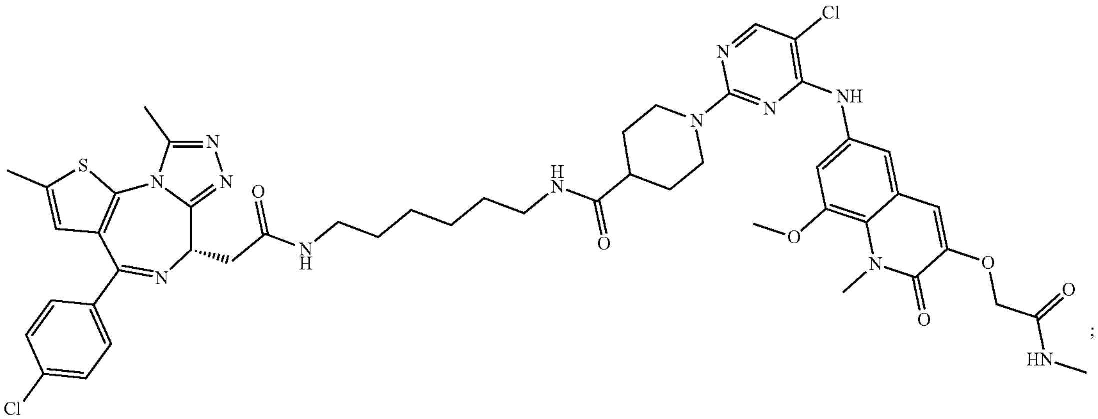
;

-continued
Compound I-4
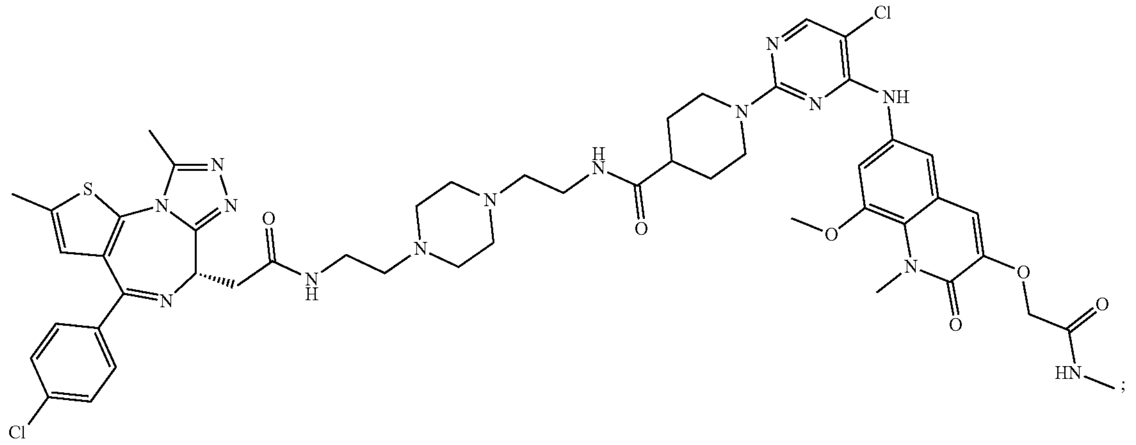
Compound I-5
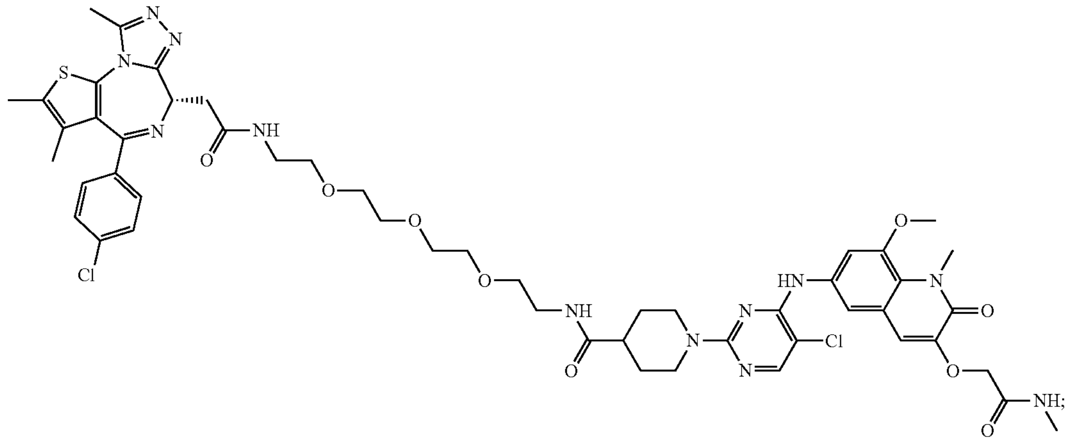
Compound I-6
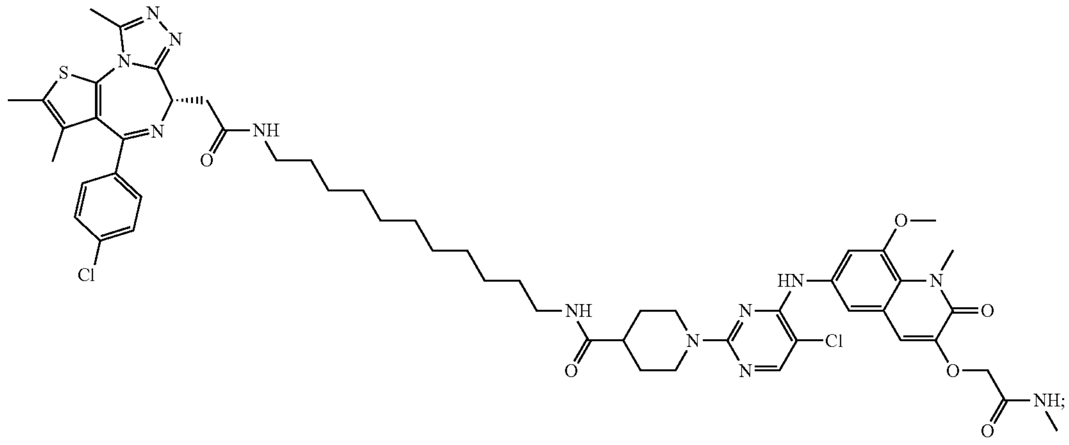

-continued
Compound I-7
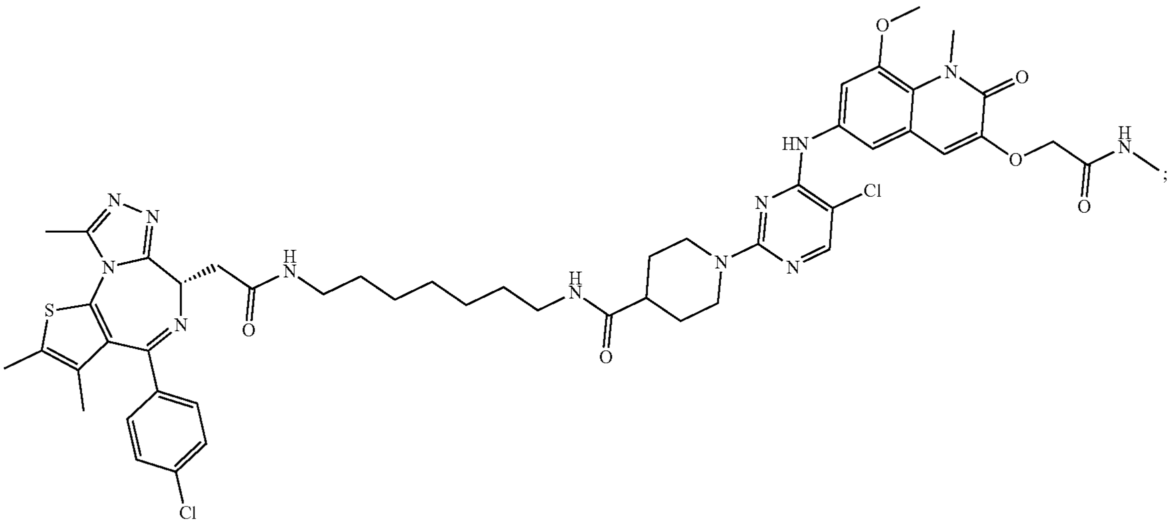
Compound I-8
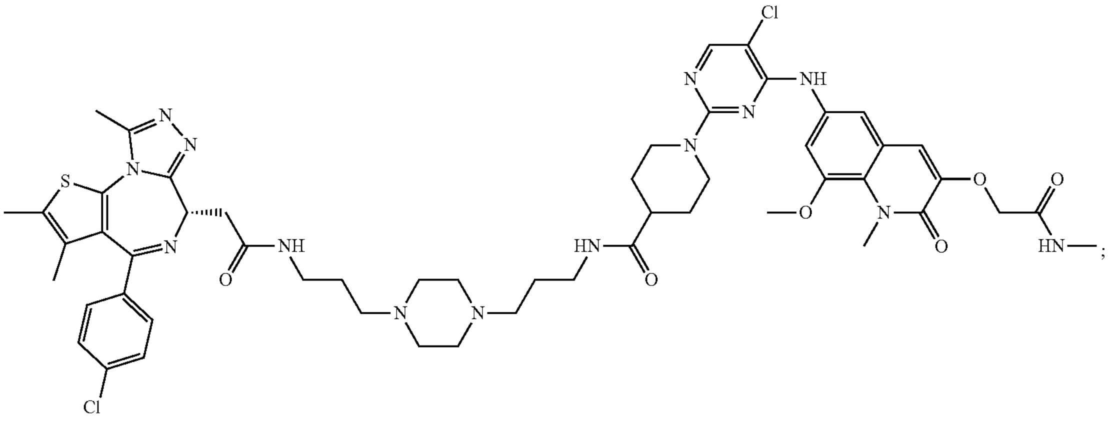
Compound I-9
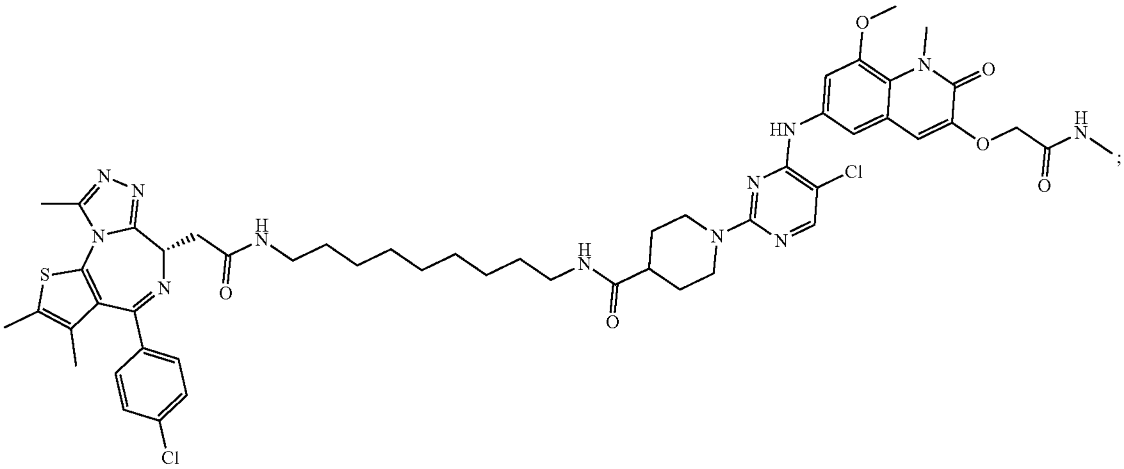

-continued
Compound I-10
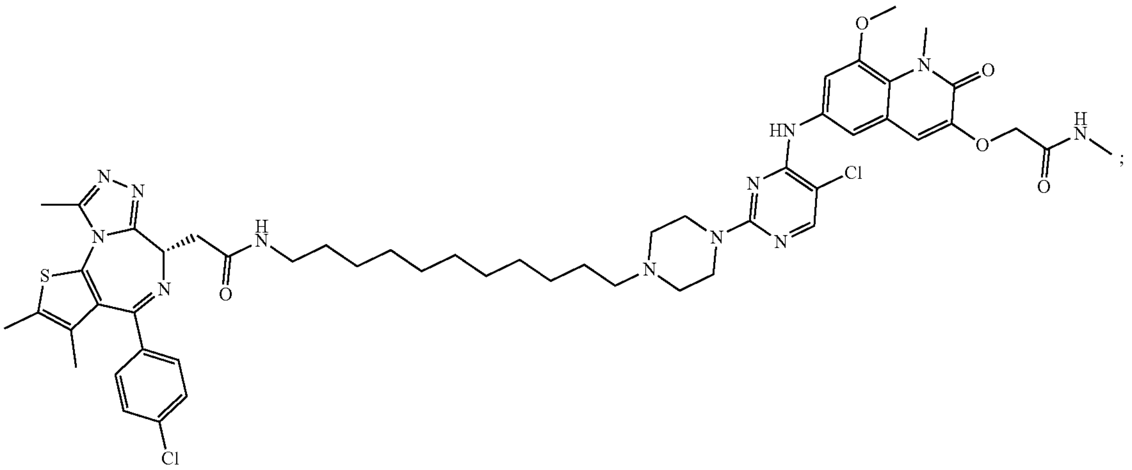
Compound I-11
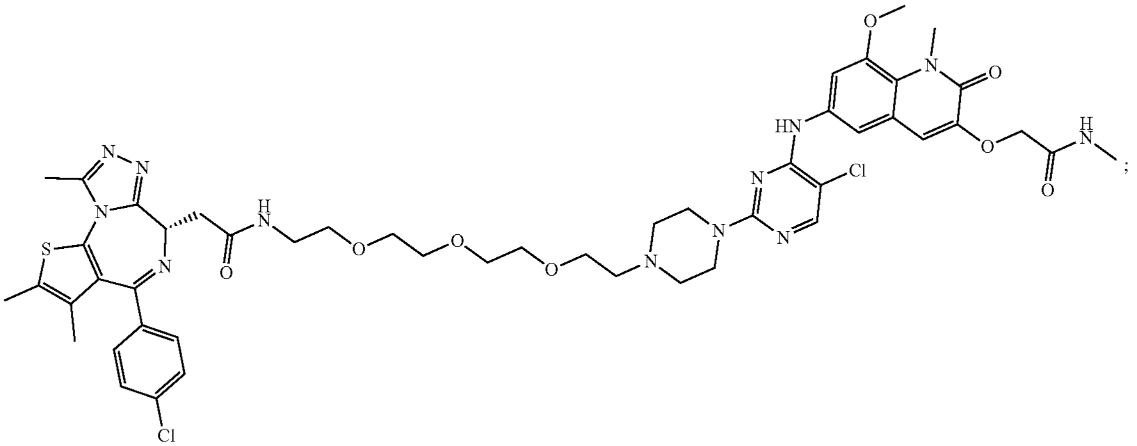
Compound I-12
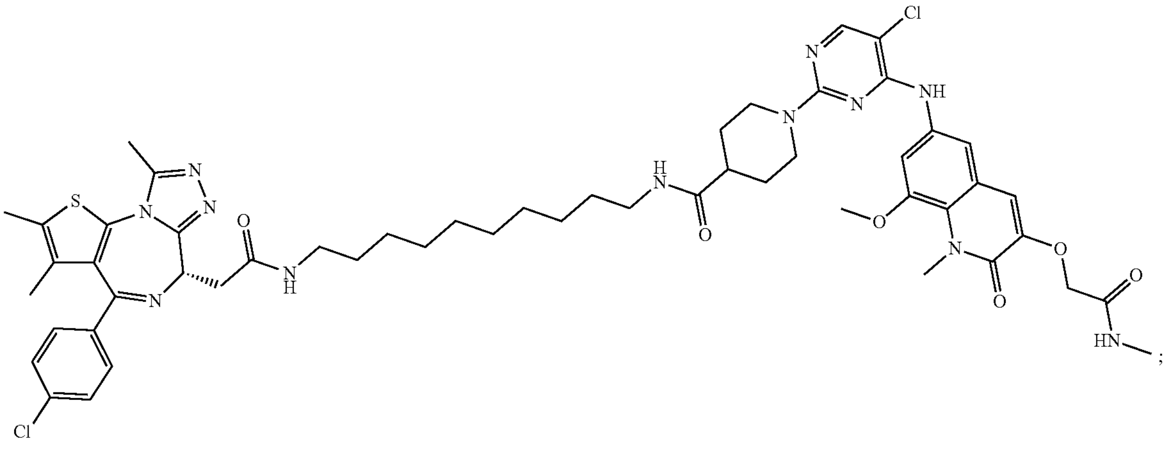

-continued
Compound I-13
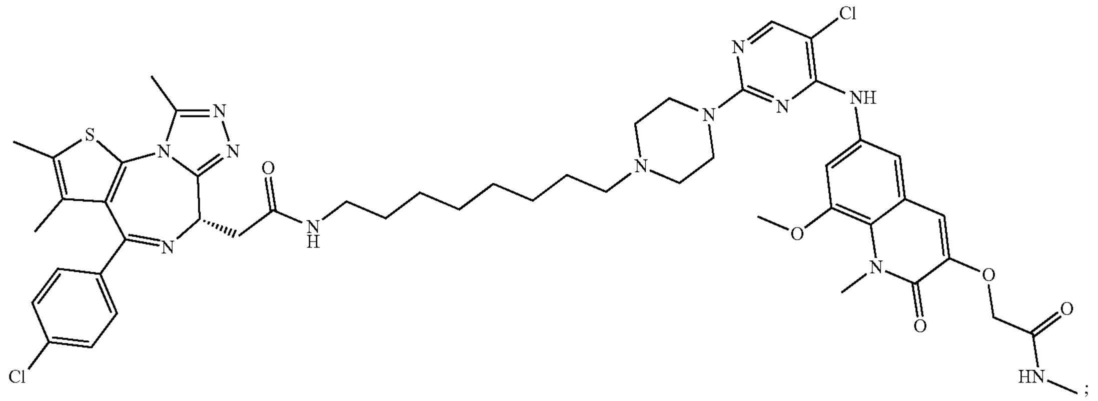
Compound I-14
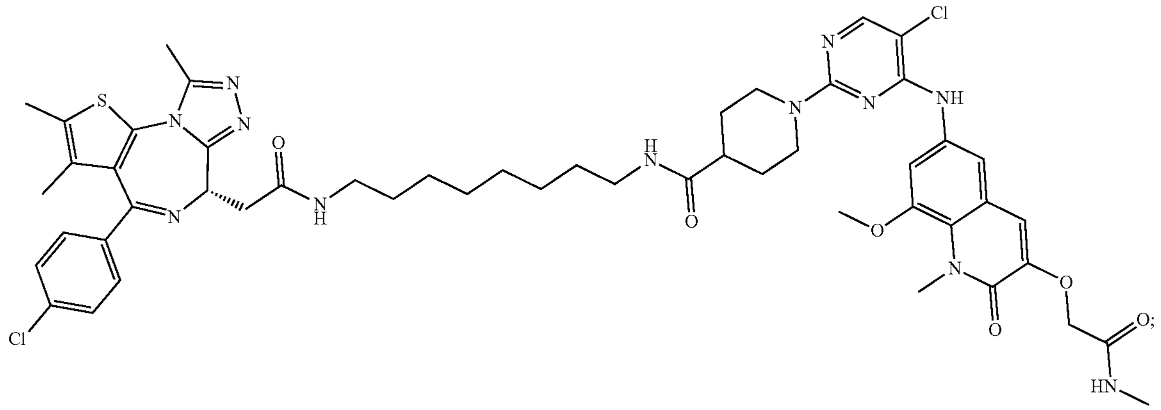
Compound I-15
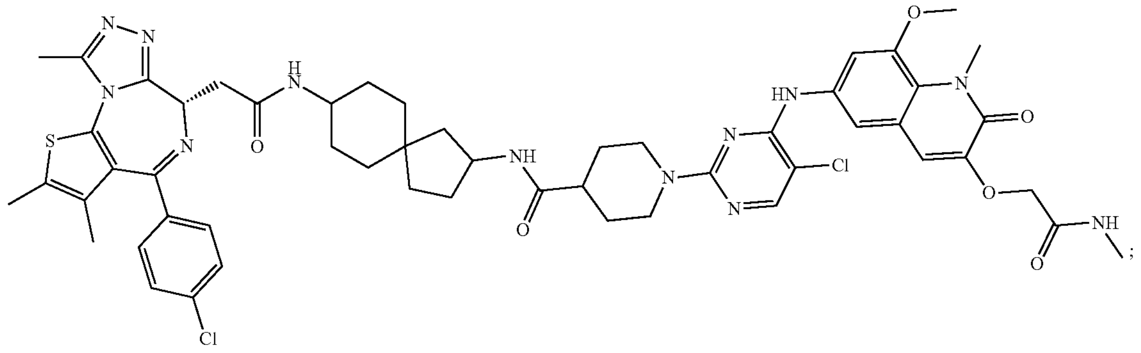

-continued
Compound I-16
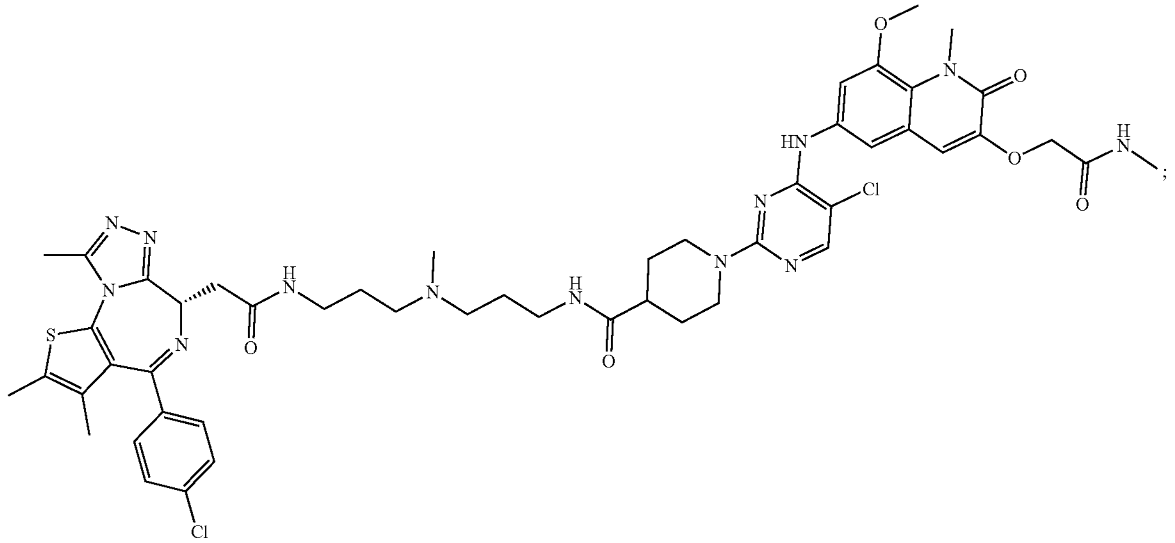
Compound I-17
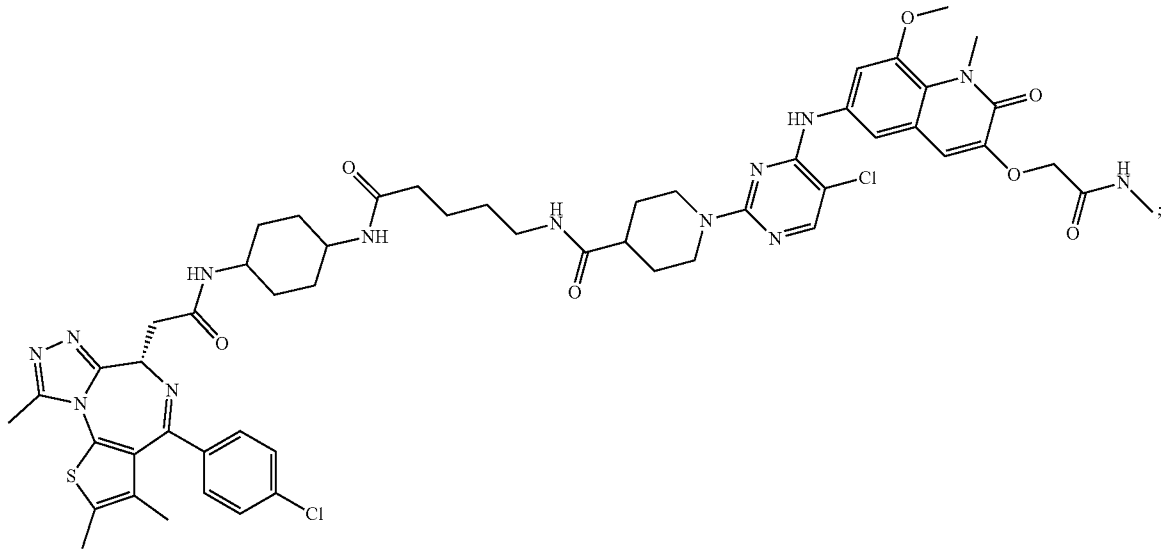

-continued
Compound I-18
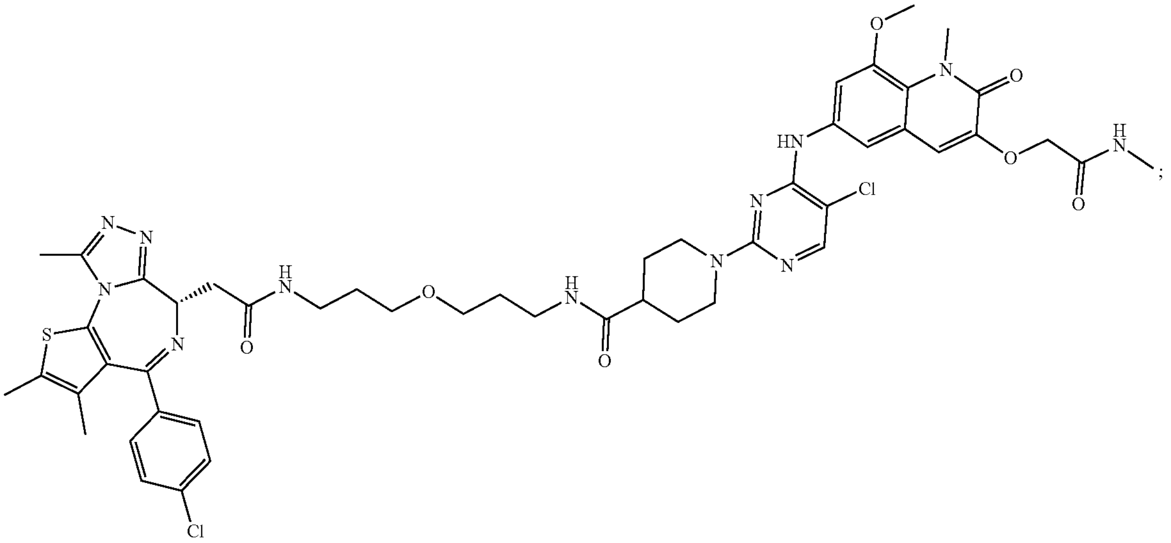
Compound I-19
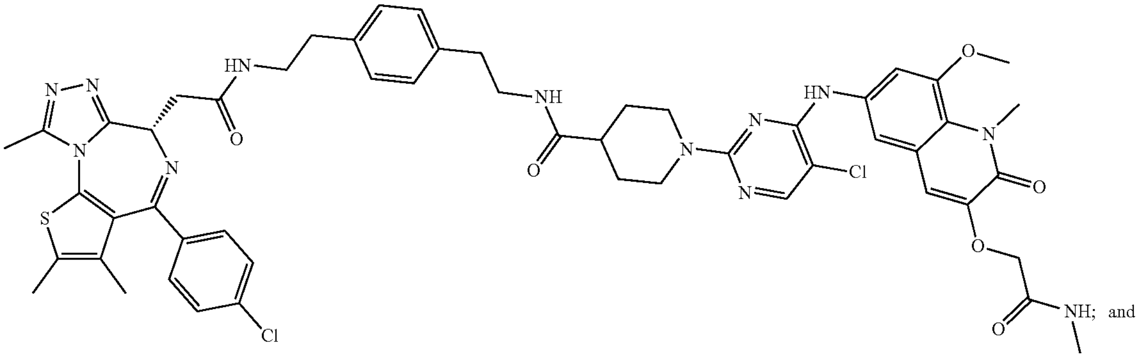
NH; and
Compound I-20
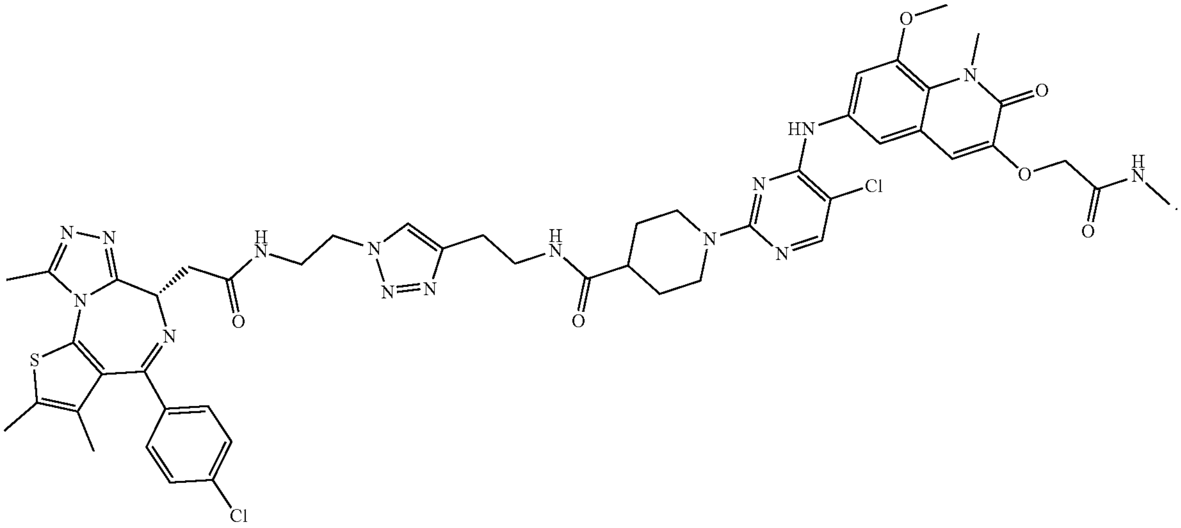
.

152. A method of treating a subject for a malignancy, the method comprising:

administering to the subject an effective amount of a transcriptional chemical inducer of proximity (TCIP) which links BCL-6 and BRD4 to treat the subject for the malignancy.

153. The method according to Embodiment 152, wherein the TCIP is a compound according to any of Embodiments 1 to 151.

154. The method according to any of Embodiments 152 and 153, wherein administration of the CIP activates transcription of a proapoptotic gene to treat the subject for the malignancy.

155. The method according to Embodiment 154, wherein the proapoptotic gene is selected from the group consisting of TP53, PUMA (BBC3), BIM (BCL2L11), BID, BAX, BAK, BOK, BAD, HRK, BIK, BMF, and NOXA.

156. The method according to any of Embodiments 152 to 155, wherein the malignancy is characterized by elevated levels of BCL6.

157. The method according to any of Embodiments 152 to 156, wherein the malignancy is Small Cell Lung Cancer (SCLC).

158. The method according to any of Embodiments 152 to 156, wherein the malignancy is Diffuse Large B-Cell Lymphoma (DLBCL).

159. The method according to Embodiment 158, wherein the DLBCL is refractory DLBCL.

160. The method according to Embodiment 159, wherein the refractory DLBCL is CHOP-resistant DLBCL.

161. The method according to any of Embodiments 152 to 160, wherein the subject is a mammal.

162. The method according to Embodiment 161, wherein the mammal is human.

163. The method according to any of Embodiments 152 to 162, wherein the method further comprises assessing the subject to determine whether the malignancy is susceptible to treatment with the TCIP.

164. The method according to Embodiment 163, wherein the assessing comprises measuring the level of at least one of BRD4 and BCL6 in malignant cells.

165. The method according to Embodiment 164, wherein the assessing comprises measuring the level of BRD4 and BCL6 in malignant cells.

166. The method according to any of Embodiments 164 and 165, wherein the measuring comprises one or more of RNA-seq, Western blotting, immunohistochemistry, mass spec, and intracellular FACS.

167. A pharmaceutical composition comprising:

transcriptional chemical inducer of proximity (TCIP) for treating malignancy, the TCIP comprising a first ligand that specifically binds to BCL-6 and a second ligand that specifically binds to BRD4; and delivery vehicle.

168. The pharmaceutical composition according to Embodiment 167, wherein the TCIP is a compound according to any of Embodiments 1 to 151.

169. The pharmaceutical composition according to any of Embodiments 167 and 168, wherein the pharmaceutical composition is configured for intravenous delivery.

ER Ligand Embodiments

1. A method of treating a subject for Diffuse Large B-Cell Lymphoma (DLBCL), the method comprising:

administering to the subject an effective amount of a chemical inducer of proximity (CIP) which links BCL-6 and an estrogen receptor treat the subject for DLBCL.

2. The method according to Embodiment 1, wherein the CIP comprises a first ligand that specifically binds to BCL-6 covalently linked to a second ligand that specifically binds to the estrogen receptor.

3. The method according to Embodiment 2, wherein binding of the second ligand to the estrogen receptor does not substantially reduce the transcription-activating activity of BCL-6.

4. The method according to Embodiment 3, wherein the first ligand is selected from the group consisting of:

11

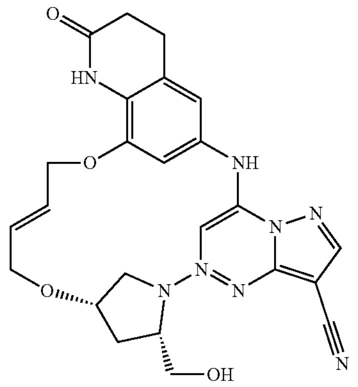

7

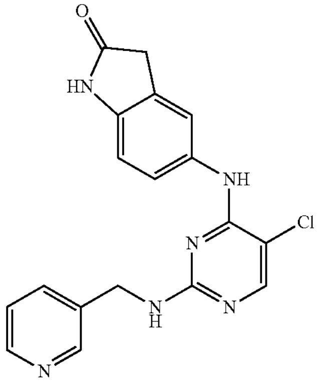

14

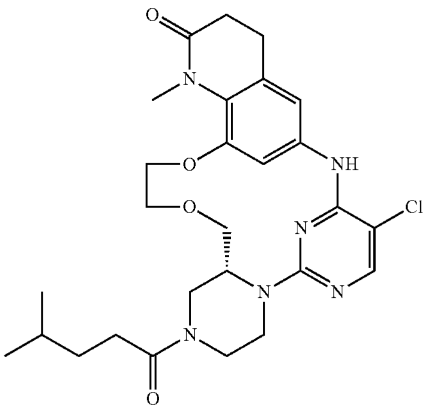

-continued
25a
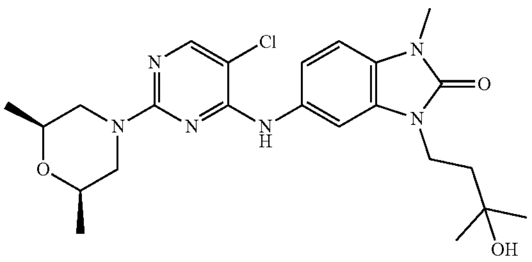
FX1
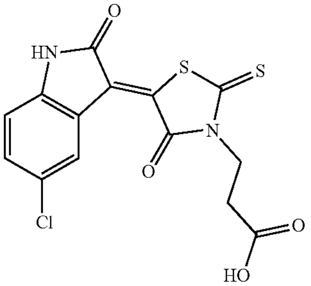
-continued
BI-3812
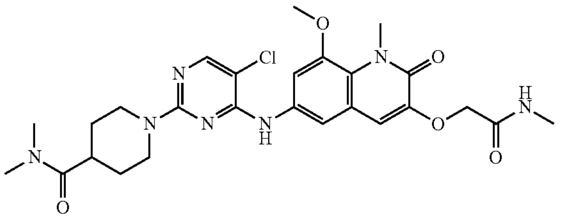
5. The method according to any of Embodiments 2 and 3, wherein the second ligand is selected from the group consisting of:
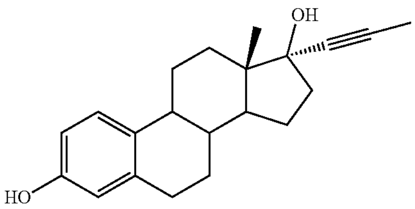
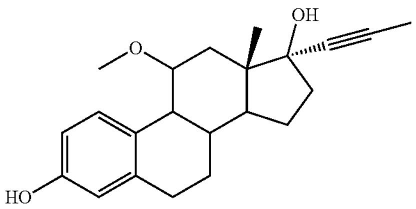
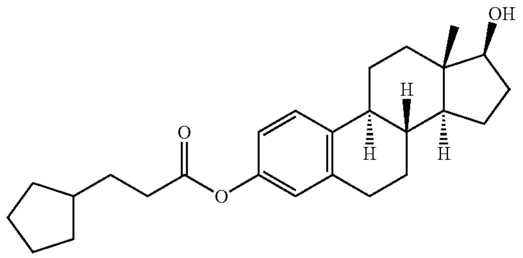
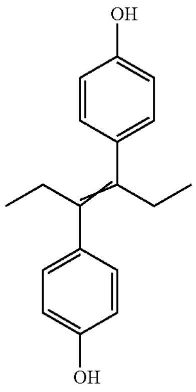
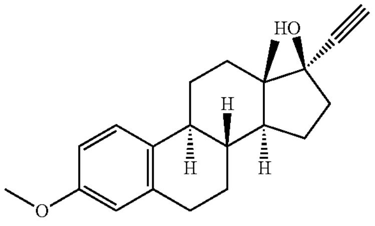
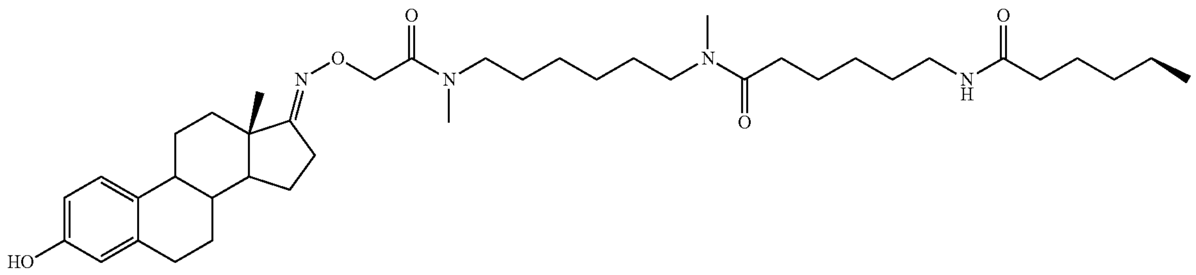

-continued
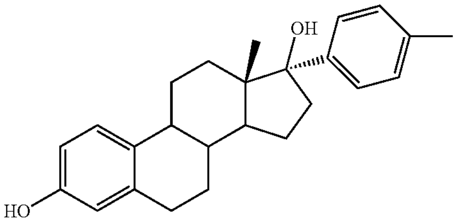
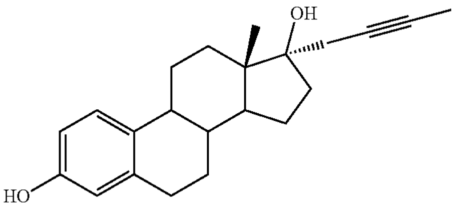
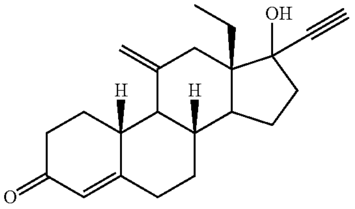
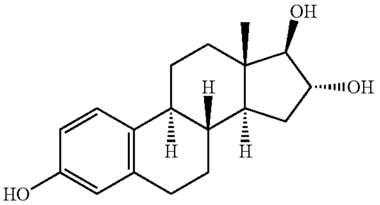
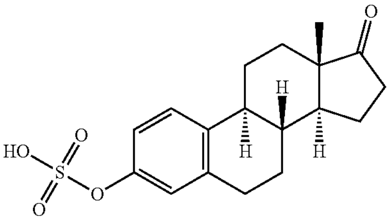
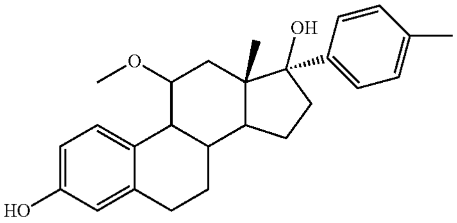
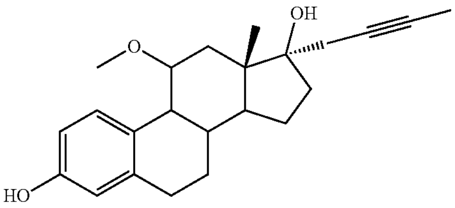
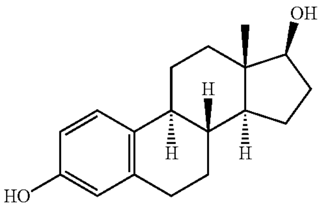
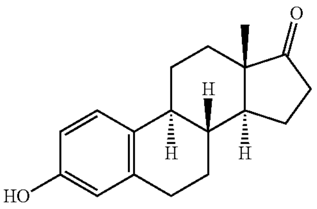
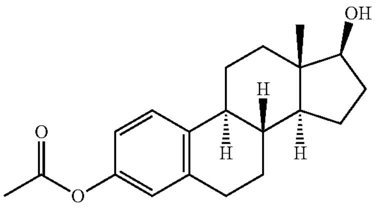
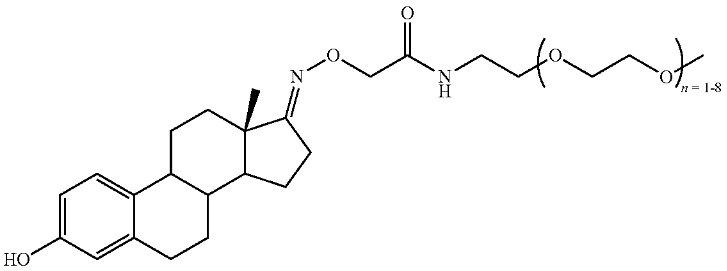
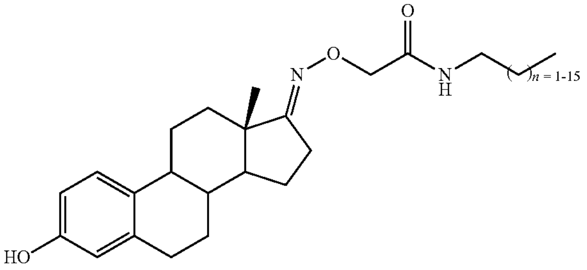
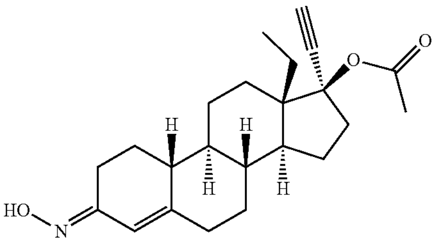
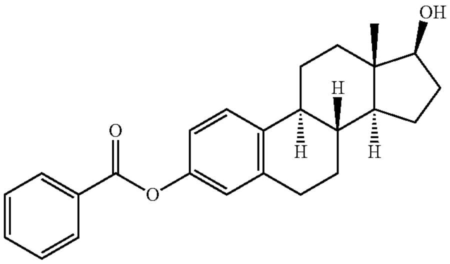
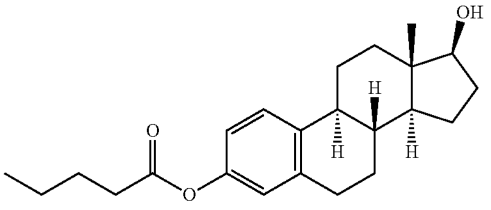

-continued

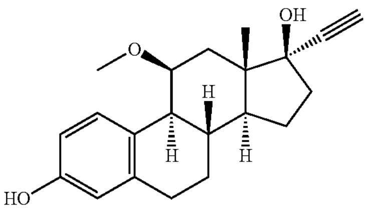

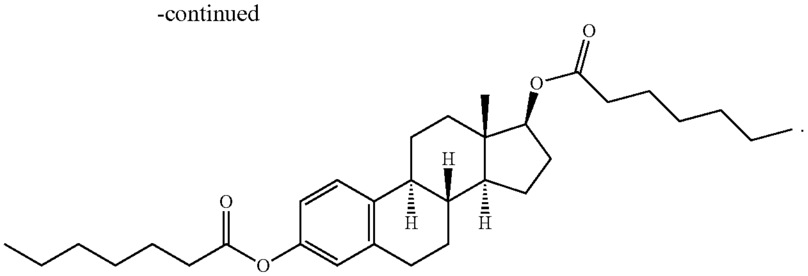

6. The method according to any of Embodiments 2 to 5, wherein the first ligand and second ligand are linked to each other by a linker.

7. The method according to Embodiment 6, wherein the linker comprises an alkyl chain.

8. The method according to Embodiment 6, wherein the linker comprises a polyalkylene glycol chain.

9. The method according to any of the preceding embodiments, wherein administration of the CIP activates transcription of a proapoptotic gene to treat the subject for DLBCL.

10. The method according to Embodiment 9, wherein the proapoptotic gene is selected from the group consisting of TP53, PUMA (BBC3), BIM (BCL2L11), BID, BAX, BAK, BOK, BAD, HRK, BIK, BMF, and NOXA.

11. The method according to any of the preceding embodiments, wherein the DLBCL is refractory DLBCL.

12. The method according to Embodiment 11, wherein the refractory DLBCL is CHOP-resistant DLBCL.

13. The method according to any of the preceding embodiments, wherein the subject is a mammal.

14. The method according to Embodiment 13, wherein the mammal is human.

15. A chemical inducer of proximity (CIP) for treating DLBCL, the CIP comprising a first ligand that specifically binds to BCL-6 joined by a linker to a second ligand that specifically binds to an estrogen receptor.

16. The CIP according to Embodiment 15, wherein the first ligand is selected from the group consisting of:

11

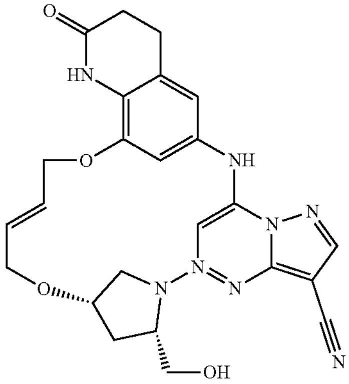

-continued

7

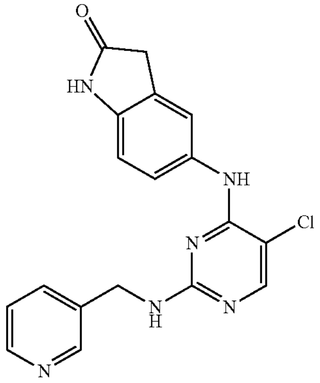

14

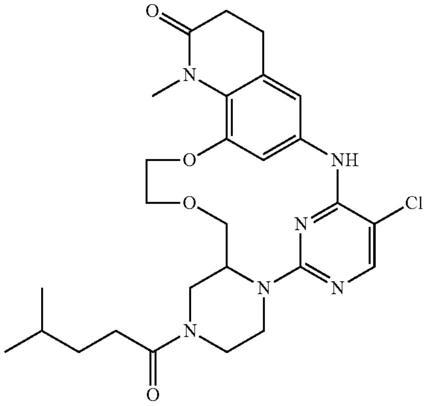

25a

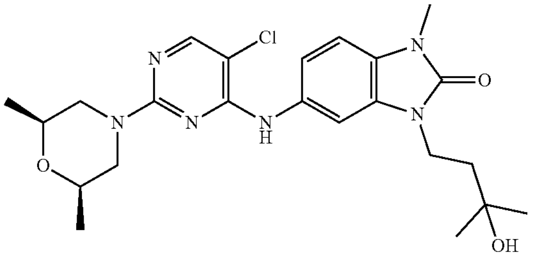

-continued
FX1
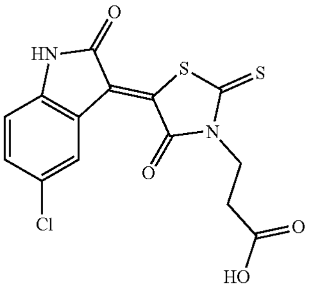
-continued
BI-3812
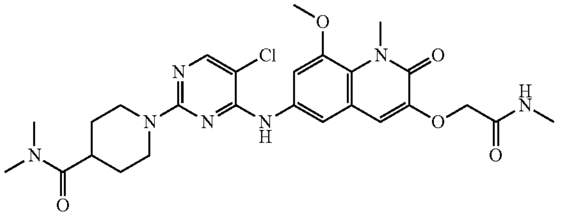
17. The CIP according to any of Embodiments 15 and 16, wherein the second ligand is selected from the group consisting of:
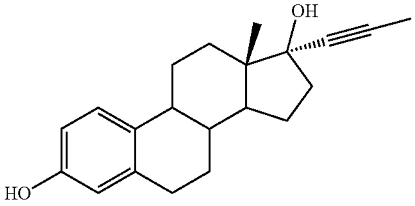
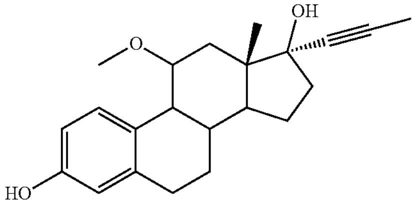
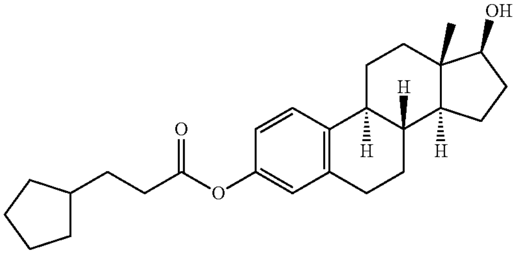
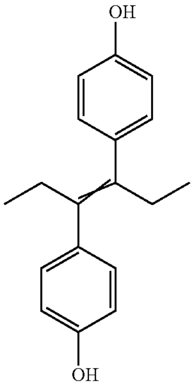
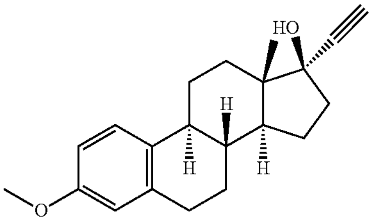
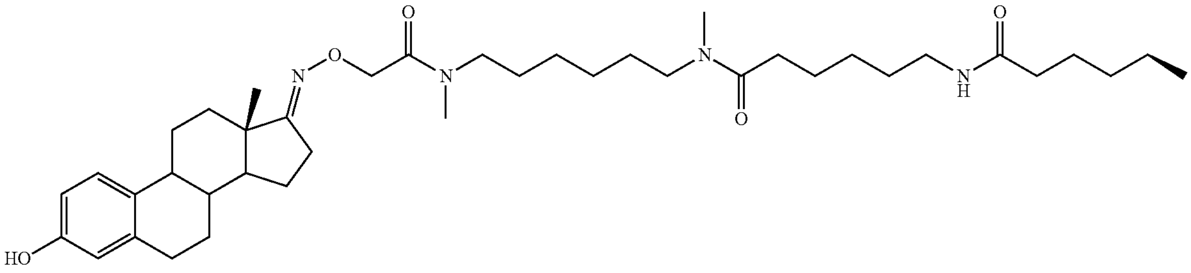
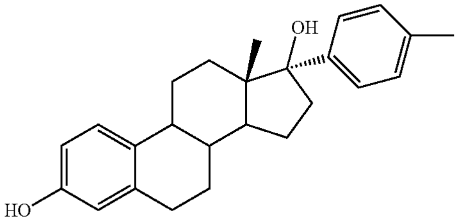
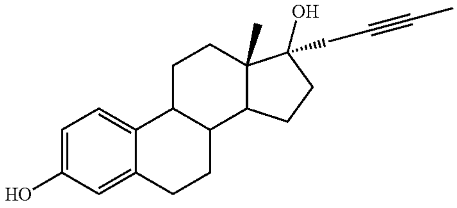

-continued
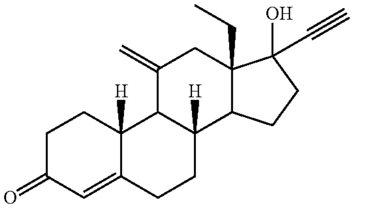
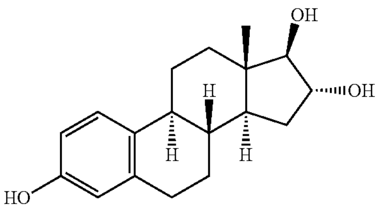
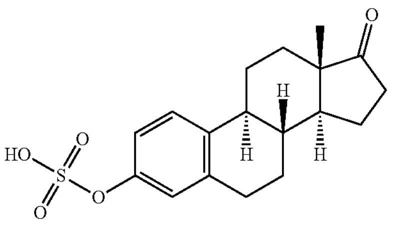
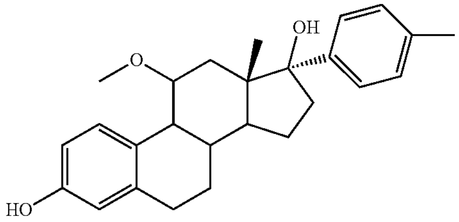
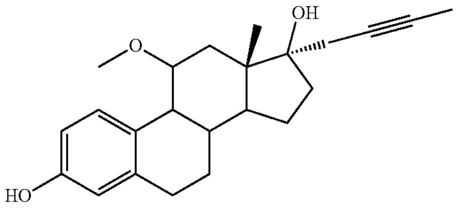
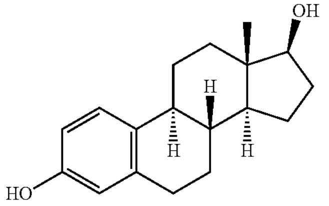
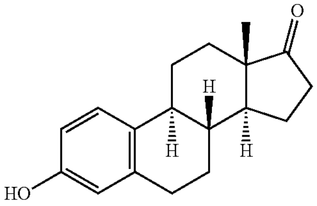
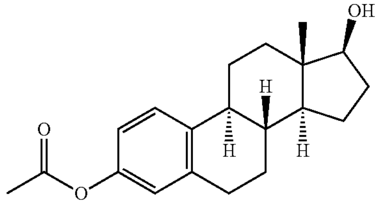
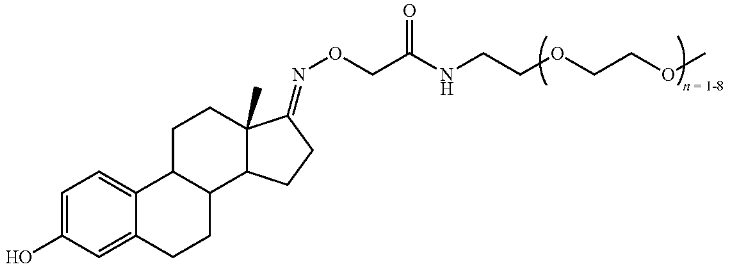
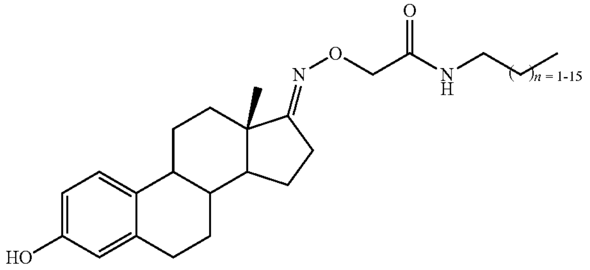
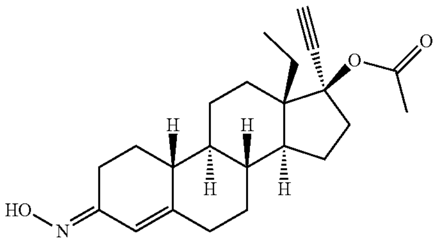
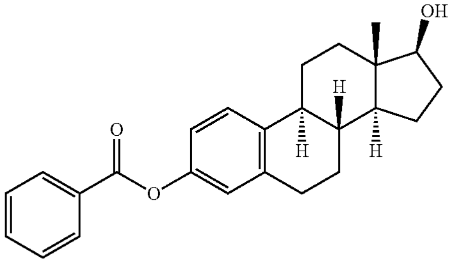
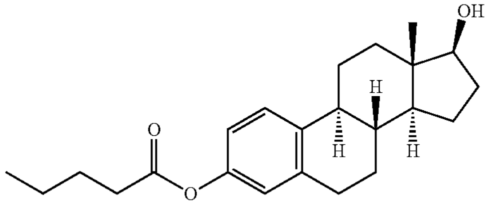
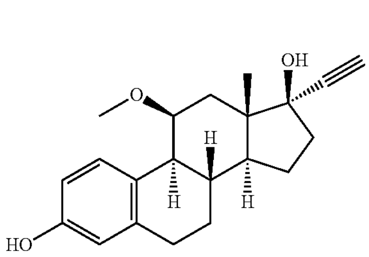
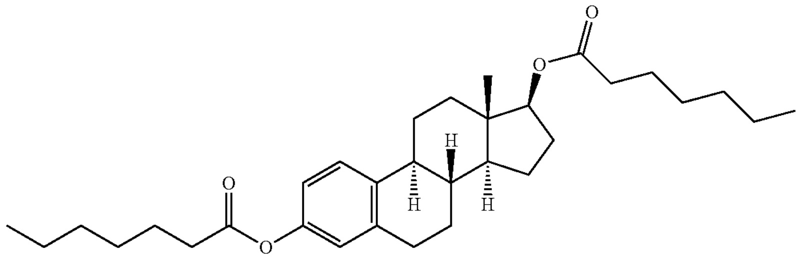
.

18. The CIP according to any of Embodiments 15 to 17, wherein the linker comprises an alkyl chain.

19. The CIP according to any of Embodiments 15 to 17, wherein the linker comprises a polyalkylene glycol chain.

20. The CIP according to any of Embodiments 15 to 19, wherein the CIP has a molecular weight ranging from 300 to 1200 g/mole.

21. A pharmaceutical composition comprising:

chemical inducer of proximity (CIP) for treating DLBCL, the CIP comprising a first ligand that specifically binds to BCL-6 joined by a linker to a second ligand that specifically binds to an estrogen receptor; and delivery vehicle.

22. The pharmaceutical composition according to Embodiment 21, wherein the first ligand is selected from the group consisting of:

11

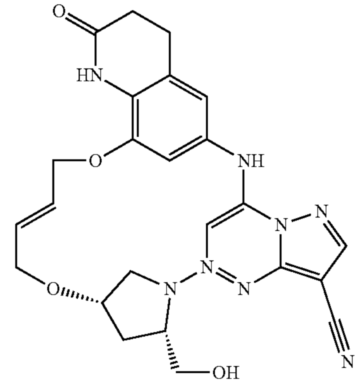

7

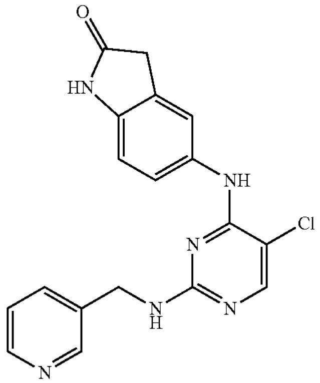

-continued

14

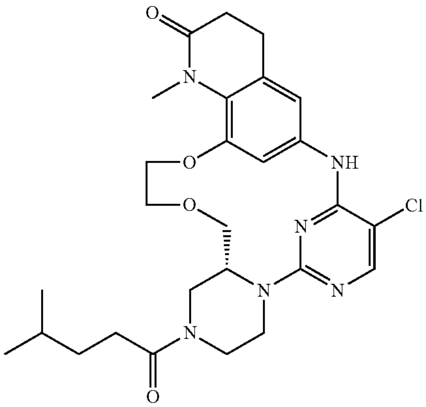

25a

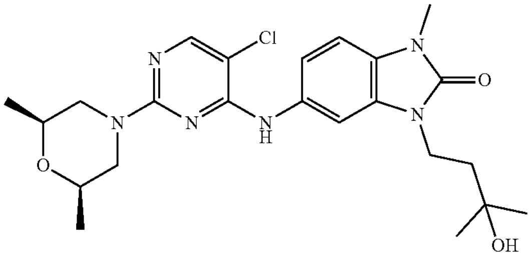

FX1

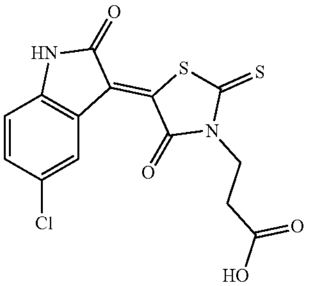

BI-3812

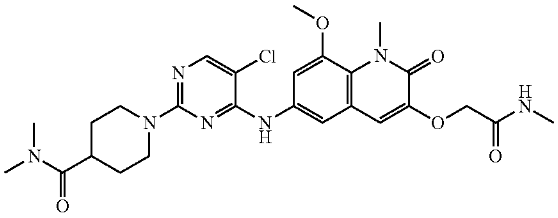

23. The pharmaceutical composition according to any of Embodiments 21 and 22, wherein the second ligand is selected from the group consisting of:

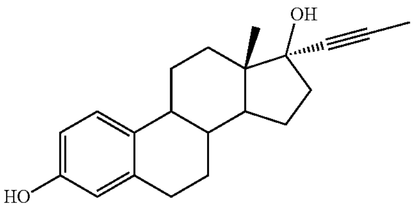
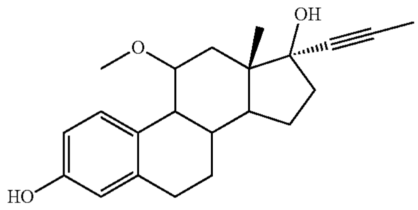
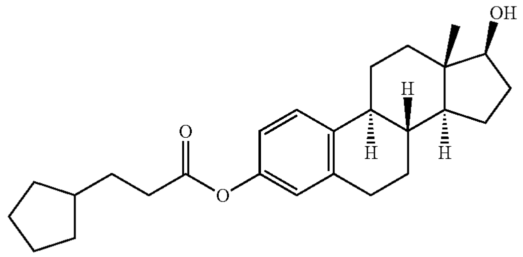
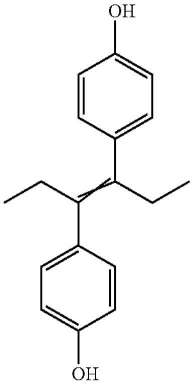
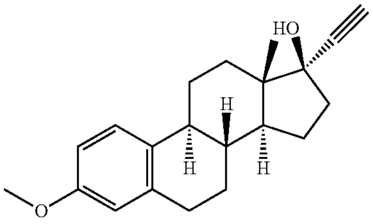
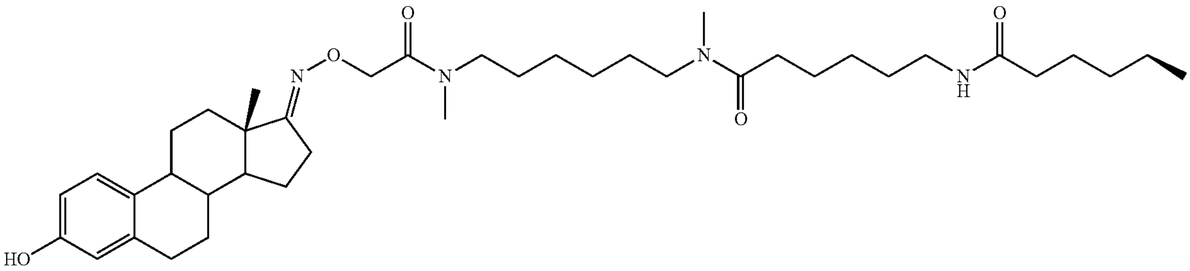
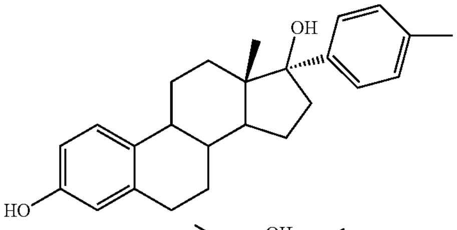
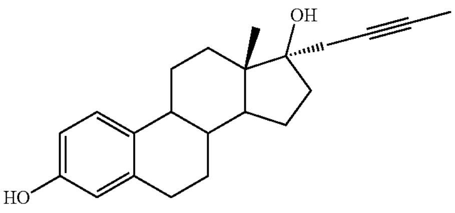
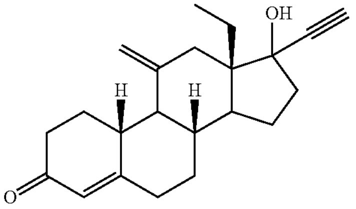
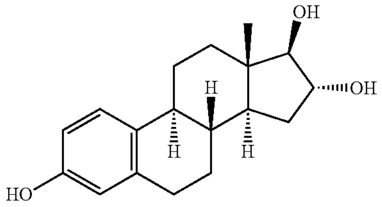
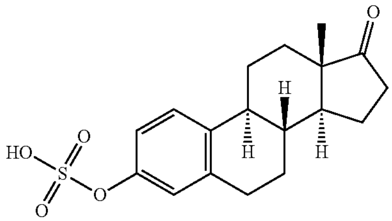
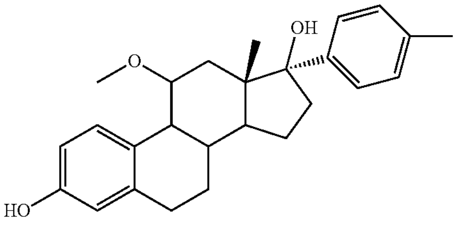
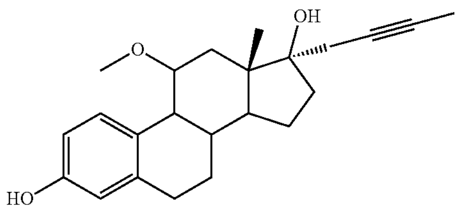
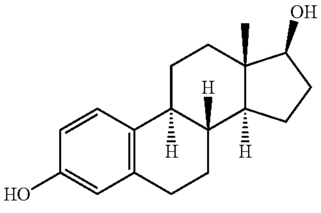
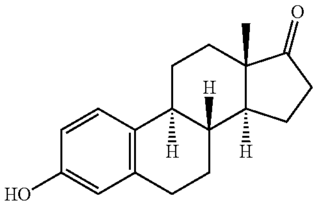
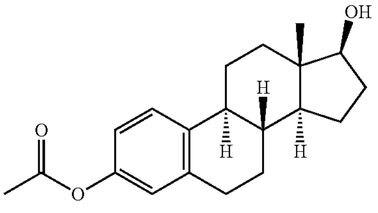

-continued

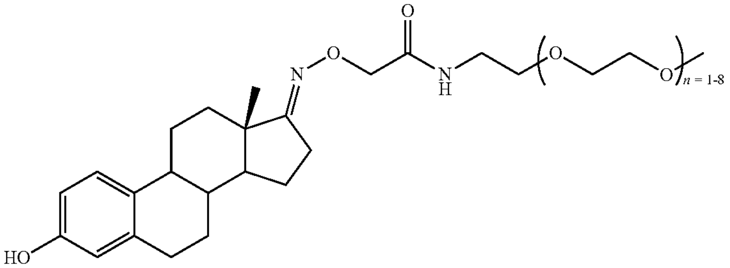

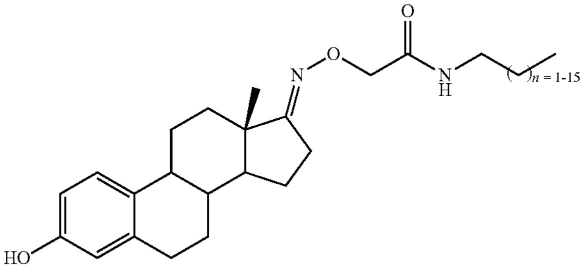

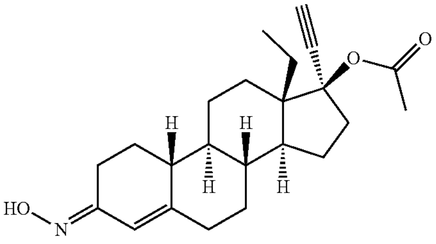

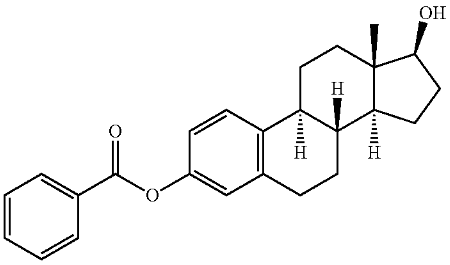

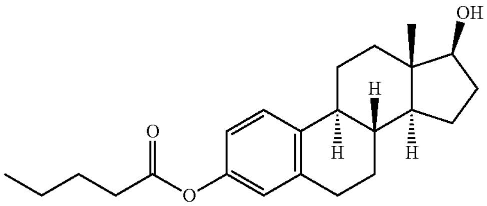

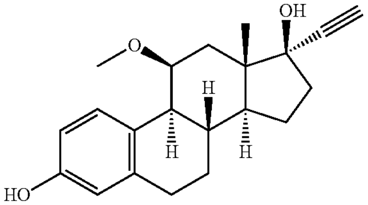

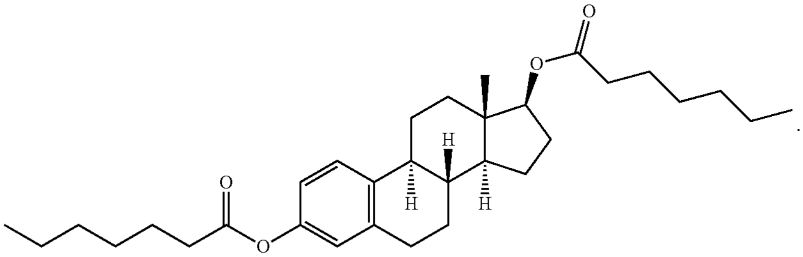

24. The pharmaceutical composition according to any of Embodiments 21 to 23, wherein the linker comprises an alkyl chain.

25. The pharmaceutical composition according to any of Embodiments 21 to 23, wherein the linker comprises a polyalkylene glycol chain.

26. The pharmaceutical composition according to any of Embodiments 21 to 25, wherein the CIP has a molecular weight ranging from 300 to 1200 g/mole.

27. The pharmaceutical composition according to any of Embodiments 21 to 26, wherein the pharmaceutical composition is configured for intravenous delivery.

CDK Ligand Embodiments

1. A method of treating a subject for a malignancy, the method comprising: administering to the subject an effective amount of a transcriptional chemical inducer of proximity (TCIP) which links BCL-6 (or a homologue thereof) and cyclic dependent kinase to treat the subject for the malignancy.

2. The method according to Embodiment 1, wherein the TCIP comprises a first ligand that specifically binds to BCL-6 (or a homologue thereof) covalently linked, directly or via a linker, to a second ligand that specifically binds to a CDK.

3. The method according to Embodiment 2, wherein binding of the second ligand to the CDK does not substantially reduce the transcription-activating activity of BCL-6 (or a homologue thereof).

4. The method according to Embodiment 3, wherein the first ligand is selected from the group consisting of:

11
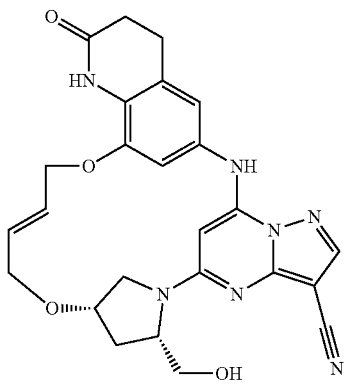
7
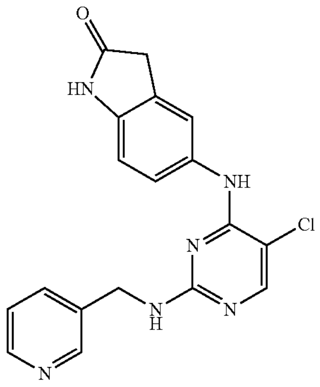
14
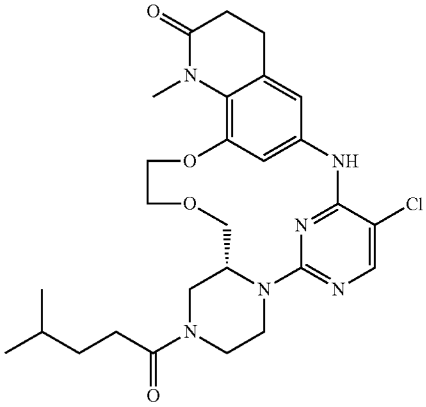
25a
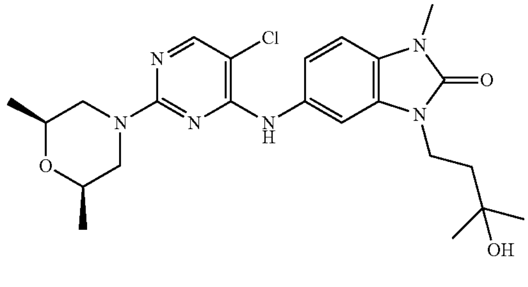
-continued
FX1
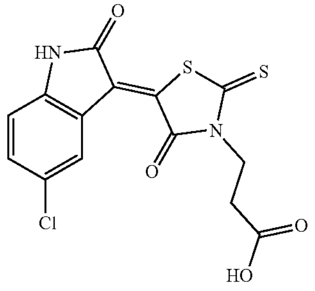
BI-3812
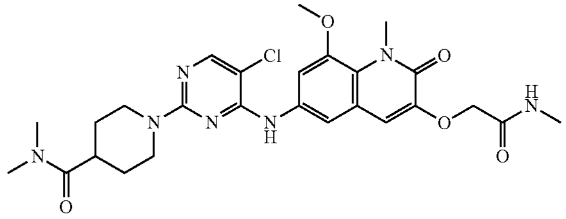
(BI-3802)
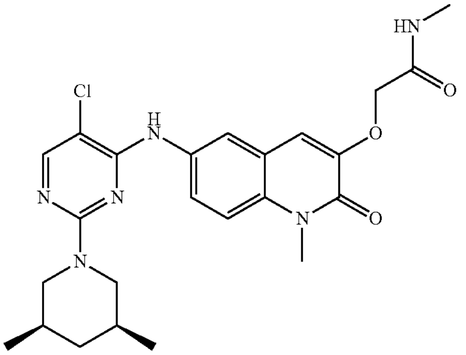
(6)
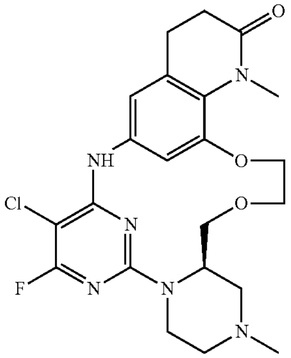

-continued (CCT369347)

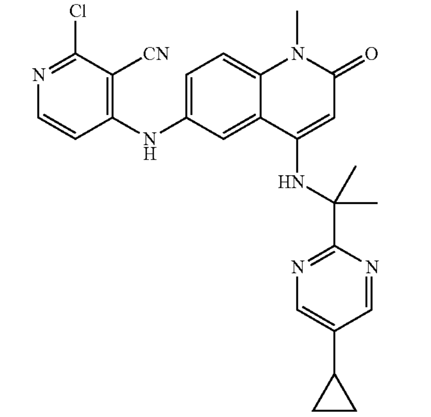

(CCT372064)

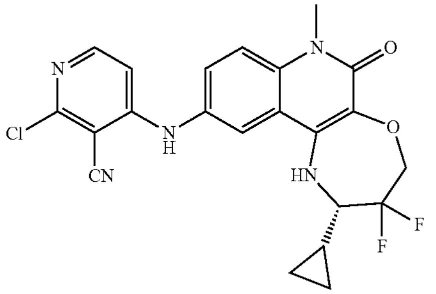

(CCT37566)

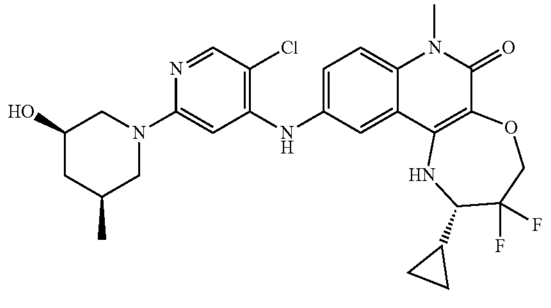

(CCTT369260)

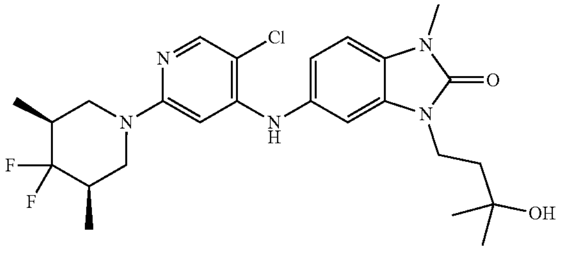

(26c)

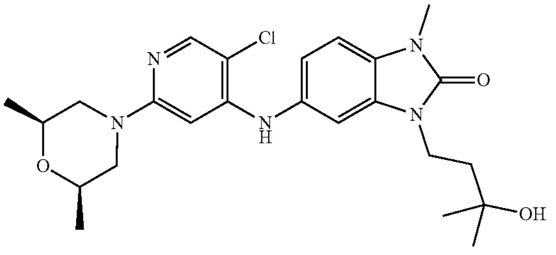

-continued (TMX-2164)

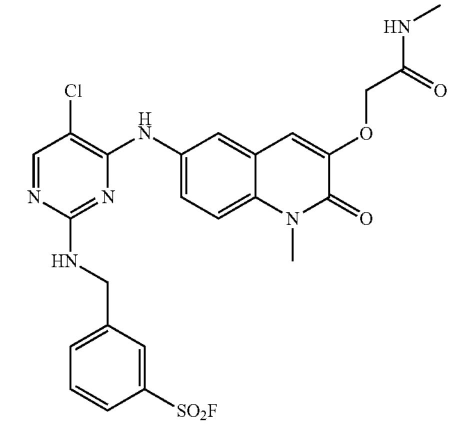

(BCl-1)

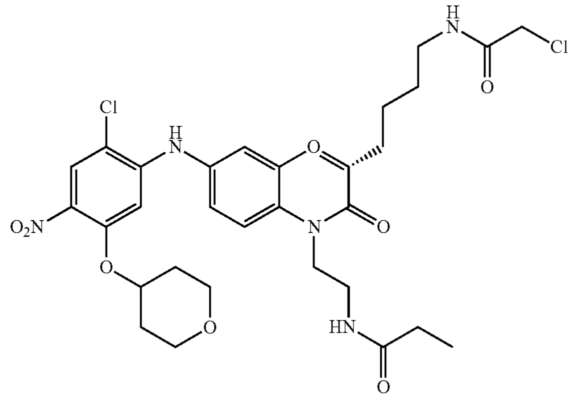

(GSK-137)

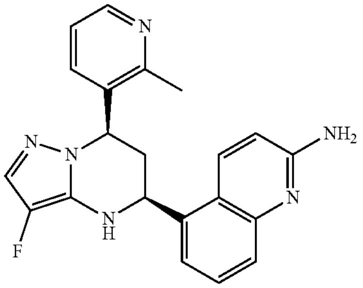

(79-6)

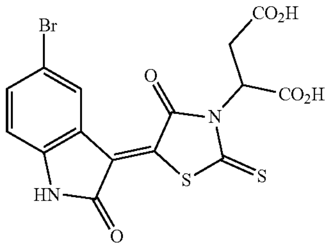

5. The method according to any of Embodiments 2 to 4, wherein the second ligand is selected from the group consisting of a CDK9 ligand, a CDK8 ligand and a CDK7 ligand.

6. The method according to Embodiment 5, wherein the second ligand is a CDK9 ligand.

7. The method according to Embodiment 6, wherein the CDK 9 ligand is selected from the group consisting of:

| Name | Structure |
|---|---|
| SNS-032 | 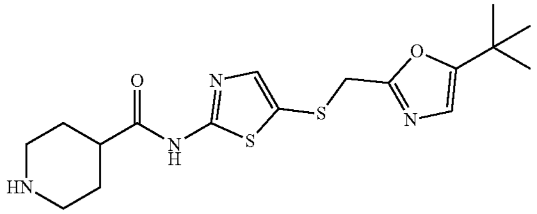 [SMILES: CC(C)(C)c1cnc(CSc2cnc(NC(=O)C3CCNCC3)s2)o1] |
| NVP-2 | 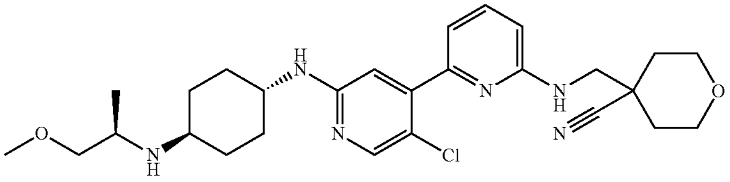 [SMILES: COC[C@@H](C)N[C@H]1CC[C@H](Nc2cc(-c3cccc(NCC4(C#N)CCOCC4)n3)c(Cl)cn2)CC1] |
| KI-ARv-03 | 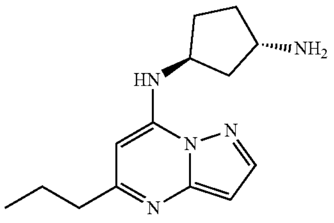 [SMILES: CCCc1cc(N[C@H]2CC[C@H](N)C2)n2nccc2n1] |
| KB-0742 | 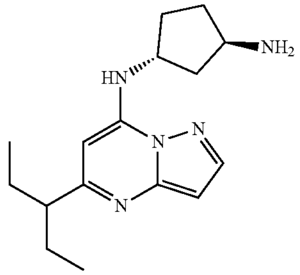 [SMILES: CCC(CC)c1cc(N[C@@H]2CC[C@@H](N)C2)n2nccc2n1] |
| BAY-1143572 | 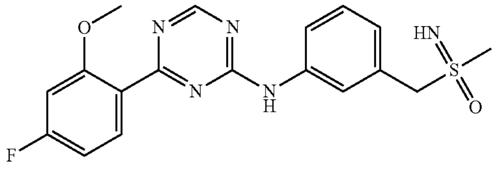 [SMILES: COc1cc(F)ccc1-c1ncnc(Nc2cccc(CS(C)(=N)=O)c2)n1] |
| AZD-4573 | 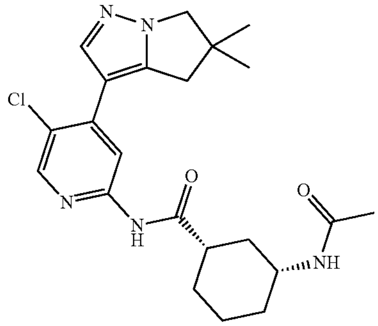 [SMILES: CC(=O)N[C@@H]1CCC[C@H](C(=O)Nc2cc(-c3cnn4c3CC(C)(C)C4)c(Cl)cn2)C1] |

-continued
| Name | Structure |
|---|---|
| Alvocidib | 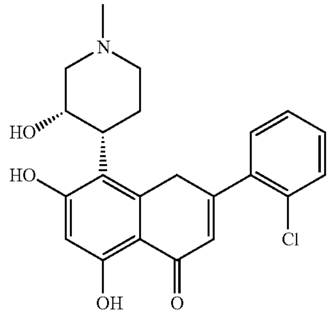 [SMILES: CN1CC[C@H](c2c(O)cc(O)c3c2CC(c2ccccc2Cl)=CC3=O)[C@H](O)C1] |
| TP-1287 | 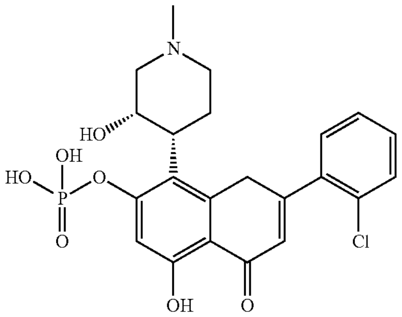 [SMILES: CN1CC[C@H](c2c(OP(=O)(O)O)cc(O)c3c2CC(c2ccccc2Cl)=CC3=O)[C@H](O)C1] |
| Riviciclib | 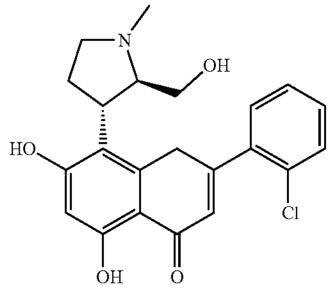 [SMILES: CN1CC[C@@H](c2c(O)cc(O)c3c2CC(c2ccccc2Cl)=CC3=O)[C@@H]1CO] |
| Voruciclib | 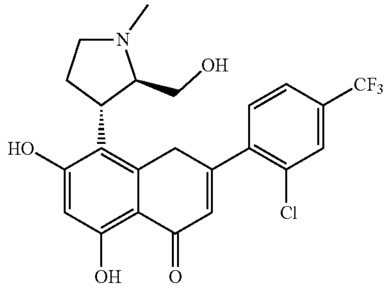 [SMILES: CN1CC[C@@H](c2c(O)cc(O)c3c2CC(c2ccc(C(F)(F)F)cc2Cl)=CC3=O)[C@@H]1CO] |
| ZK-304709 | 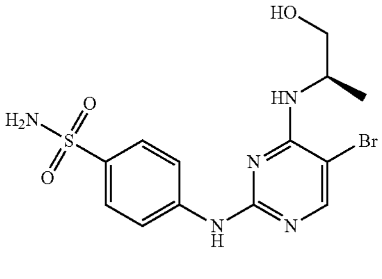 [SMILES: C[C@H](CO)Nc1nc(Nc2ccc(S(N)(=O)=O)cc2)ncc1Br] |

-continued
| Name | Structure |
|---|---|
| BAY-1251152 | 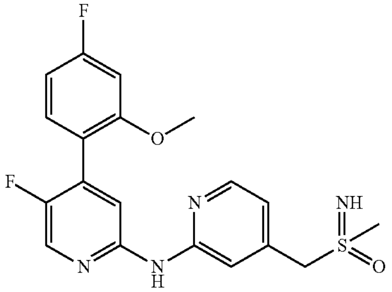 [SMILES: COc1cc(F)ccc1-c1cc(Nc2cc(CS(C)(=N)=O)ccn2)ncc1F] |
| Zotiraciclib (TG-02) | 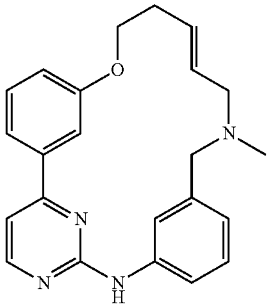 [SMILES: CN1C/C=C/CCOc2cccc(c2)-c2ccnc(n2)Nc2cccc(c2)C1] |
| Seliciclib | 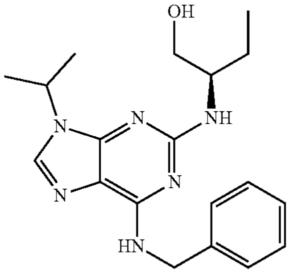 [SMILES: CC[C@H](CO)Nc1nc(NCc2ccccc2)c2ncn(C(C)C)c2n1] |
| Fadraciclib | 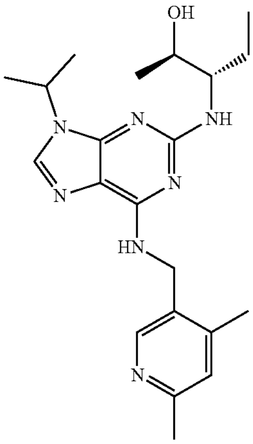 [SMILES: CC[C@H](Nc1nc(NCc2cnc(C)cc2C)c2ncn(C(C)C)c2n1)[C@@H](C)O] |

-continued
| Name | Structure |
| --- | --- |
| Dinaciclib | 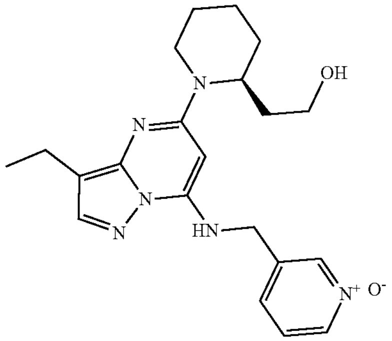 |
| AT7519 | 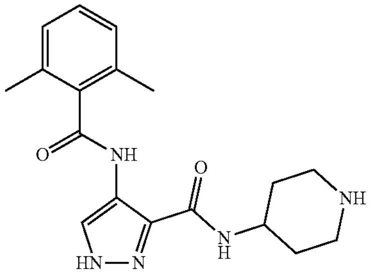 [SMILES: Cc1cccc(C)c1C(=O)Nc1c[nH]nc1C(=O)NC1CCNCC1] |
| BTX-A51 | 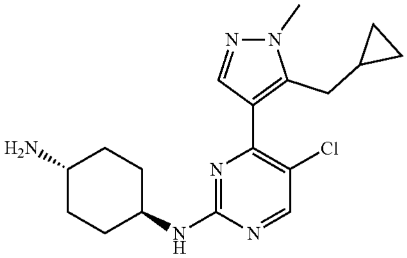 [SMILES: Cn1ncc(-c2nc(N[C@H]3CC[C@H](N)CC3)ncc2Cl)c1CC1CC1] |
| LY2857785 | 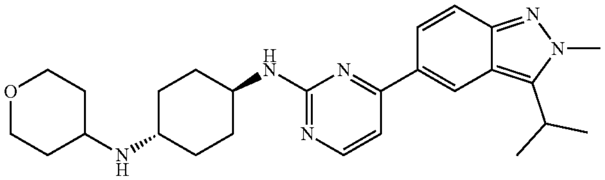 |

8. The method according to Embodiment 5, wherein the second ligand is a CDK8 ligand.
9. The method according to Embodiment 8, wherein the CDK8 ligand is selected from the group consisting of:
| Name | Structure |
| --- | --- |
| BI-1347 | 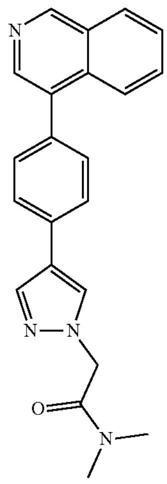 [SMILES: CN(C)C(=O)Cn1cc(-c2ccc(-c3cncc4ccccc34)cc2)cn1] |
| Cortistatin A | 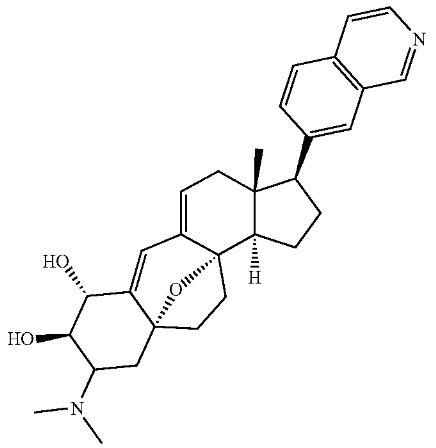 [SMILES: CN(C)C1C[C@@]23CC[C@@]4(O2)C(=CC[C@]2(C)[C@@H](c5ccc6ccncc6c5)CC[C@H]24)C=C3[C@@H](O)[C@@H]1O] |
| JH-VIII-49 | 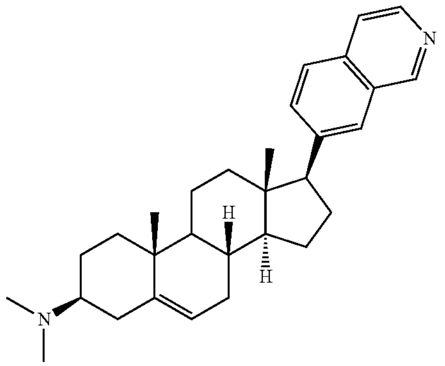 |

-continued
| Name | Structure |
|---|---|
| CCT251545 | 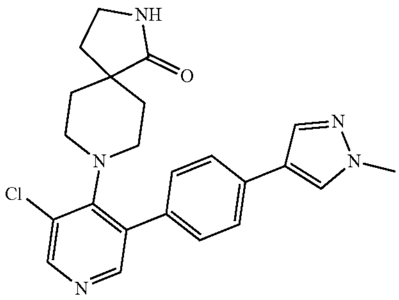 [SMILES: Cn1cc(-c2ccc(-c3cncc(Cl)c3N3CCC4(CCNC4=O)CC3)cc2)cn1] |
| MSC253818 | 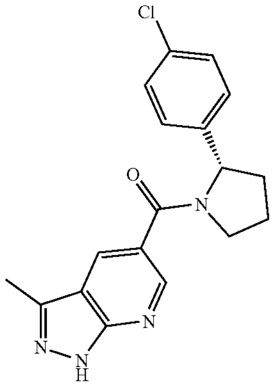 [SMILES: Cc1n[nH]c2ncc(C(=O)N3CCC[C@H]3c3ccc(Cl)cc3)cc12] |
| Senexin C | 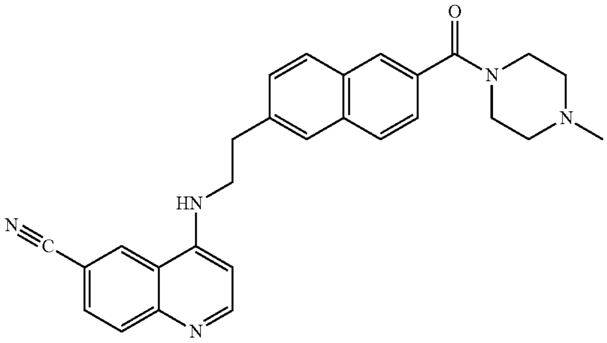 [SMILES: CN1CCN(C(=O)c2ccc3cc(CCNc4ccnc5ccc(C#N)cc45)ccc3c2)CC1] |
| Sel 120-34A | 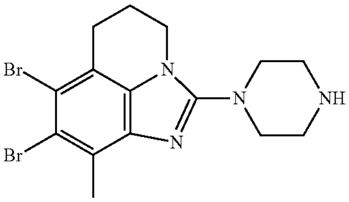 [SMILES: Cc1c(Br)c(Br)c2c3c1nc(N1CCNCC1)n3CCC2] |

-continued
| Name | Structure |
| --- | --- |
| W-34 | 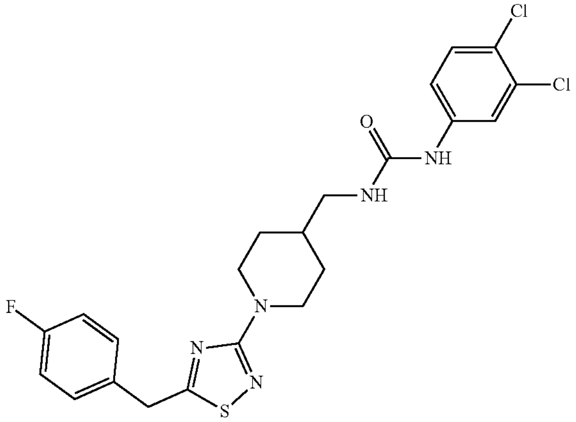 [SMILES: O=C(NCC1CCN(c2nsc(Cc3ccc(F)cc3)n2)CC1)Nc1ccc(Cl)c(Cl)c1] |
| T-814 | 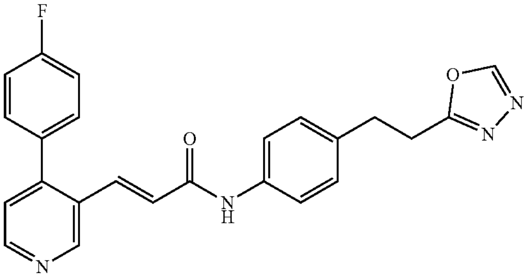 [SMILES: O=C(/C=C/c1cnccc1-c1ccc(F)cc1)Nc1ccc(CCc2nnco2)cc1] |
10. The method according to Embodiment 5, wherein the second ligand is a CDK7 ligand.
11. The method according to Embodiment 10, wherein the CDK7 ligand is selected from the group consisting of:
| Name | Structure |
| --- | --- |
| BS-181 | 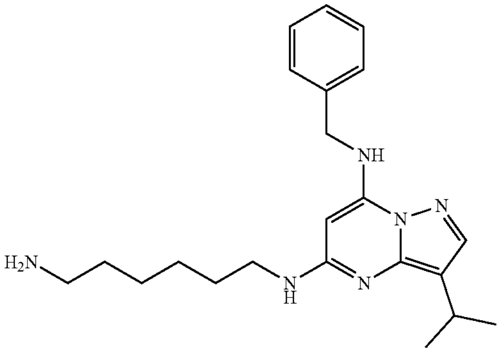 [SMILES: CC(C)c1cnn2c(NCc3ccccc3)cc(NCCCCCCN)nc12] |
| CT7001 | 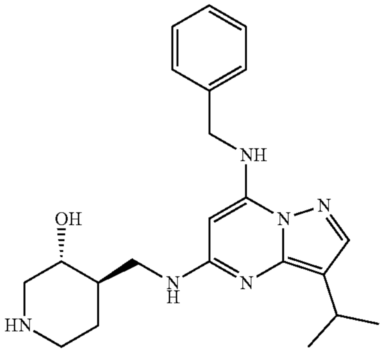 [SMILES: CC(C)c1cnn2c(NCc3ccccc3)cc(NC[C@H]3CCNC[C@@H]3O)nc12] |

-continued
| Name | Structure |
| --- | --- |
| THZ2 | 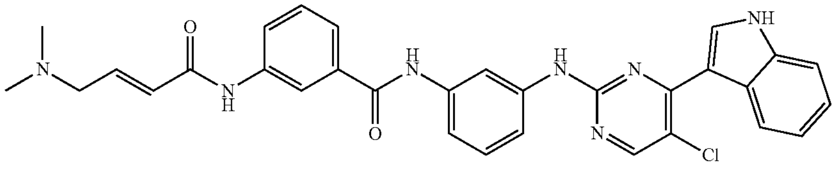 [SMILES: CN(C)C/C=C/C(=O)Nc1cccc(C(=O)Nc2cccc(Nc3ncc(Cl)c(-c4c[nH]c5ccccc45)n3)c2)c1] |
| THZ2 reversible compound | 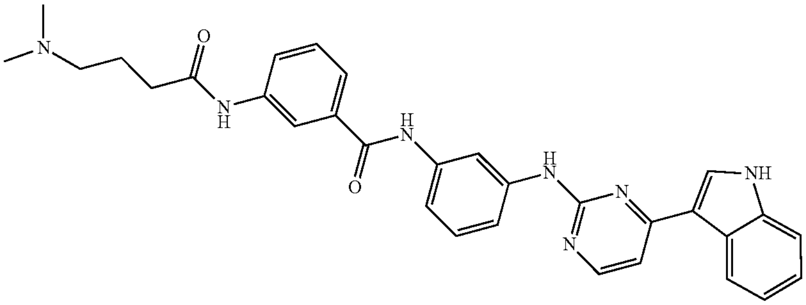 [SMILES: CN(C)CCCC(=O)Nc1cccc(C(=O)Nc2cccc(Nc3nccc(-c4c[nH]c5ccccc45)n3)c2)c1] |
| YKL-1-116 | 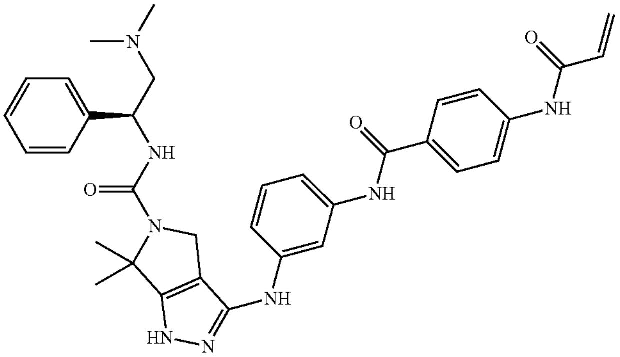 [SMILES: C=CC(=O)Nc1ccc(C(=O)Nc2cccc(Nc3n[nH]c4c3CN(C(=O)N[C@H](CN(C)C)c3ccccc3)C4(C)C)c2)cc1] |
| YKL-5-124 | 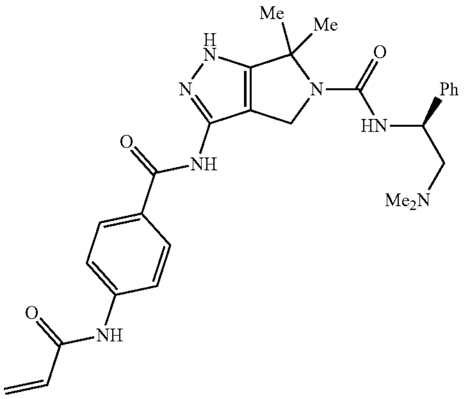 [SMILES: C=CC(=O)Nc1ccc(C(=O)Nc2n[nH]c3c2CN(C(=O)N[C@H](CN(C)C)c2ccccc2)C3(C)C)cc1] |

-continued
| Name | Structure |
|---|---|
| YKL-5-124 Reversible compound | 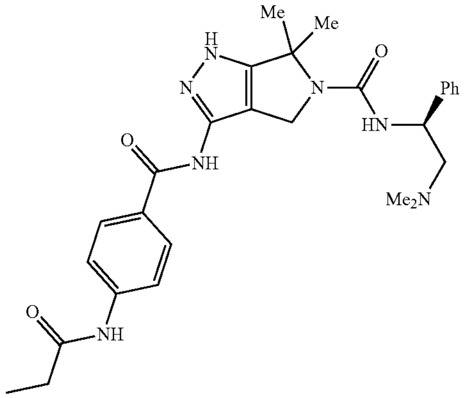 [SMILES: CCC(=O)Nc1ccc(C(=O)Nc2n[nH]c3c2CN(C(=O)N[C@H](CN(C)C)c2ccccc2)C3(C)C)cc1] |
| SY-1365 and the reversible compound thereof (structure not shown) | 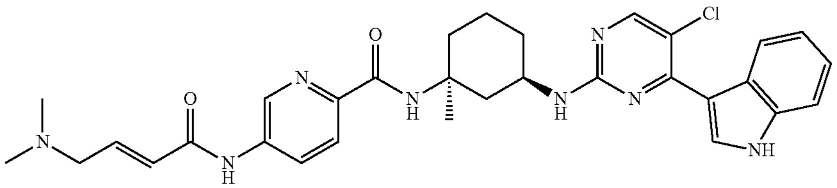 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)nc1] |
| SY5609 | 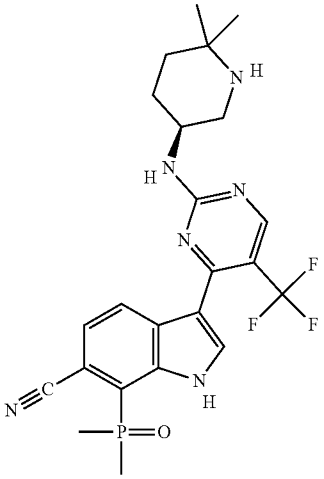 |
| LY3405105 and the reversible compound thereof (structure no shown) | 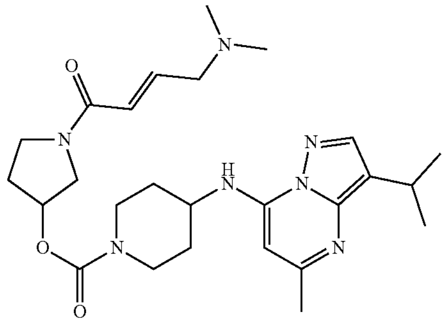 [SMILES: Cc1cc(NC2CCN(C(=O)OC3CCN(C(=O)/C=C/CN(C)C)C3)CC2)n2ncc(C(C)C)c2n1] |

-continued
| Name | Structure |
| --- | --- |
| LDC4279 | 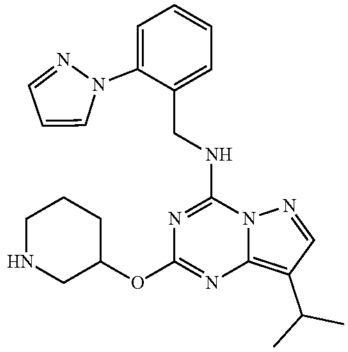 [SMILES: CC(C)c1cnn2c(NCc3ccccc3-n3cccn3)nc(OC3CCCNC3)nc12] |
12. The method according to any of Embodiments 2 to 11, wherein the first ligand and second ligand are linked to each other by a linker.
13. The method according to Embodiment 12, wherein the linker is selected from the group consisting of:
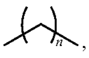, 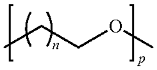, 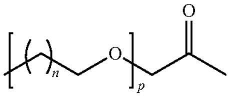,
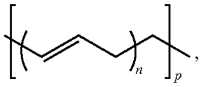, 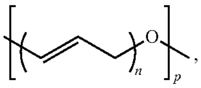,
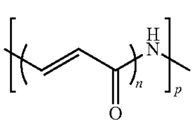, 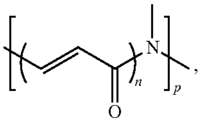,
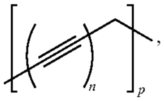, 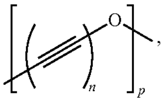,
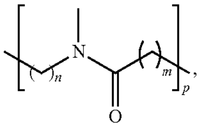, 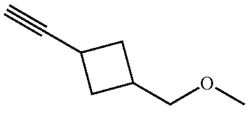,
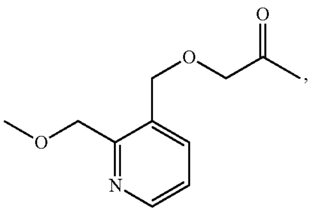,
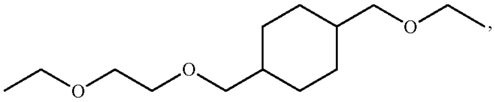,
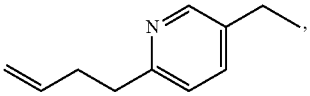, 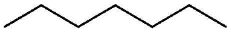,
-continued
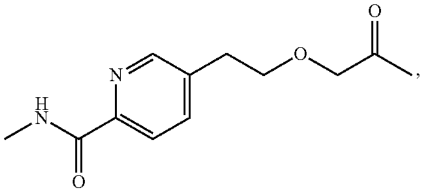,
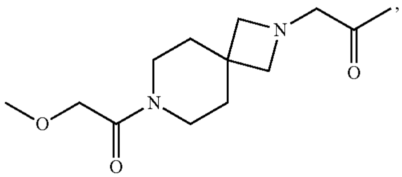,
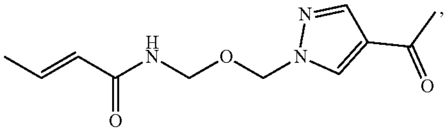,
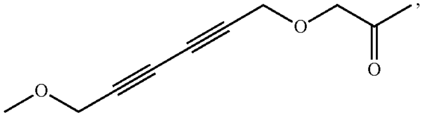,
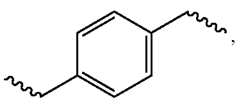, 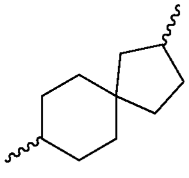,
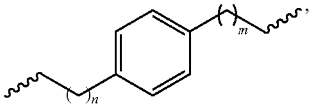,
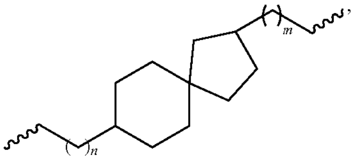

-continued
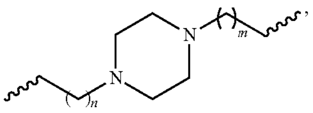
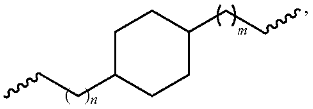
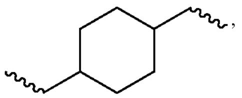
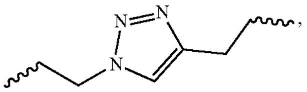
-continued
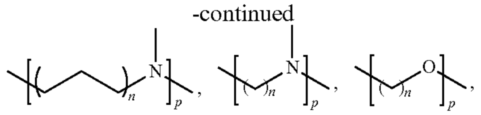
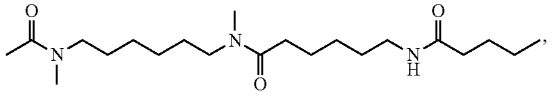
where m, n and p are independently selected from 0 or an integer of from 1-12.
14. The method according to Embodiment 13, wherein TCIP is selected from the group consisting of:
BAK-04-023
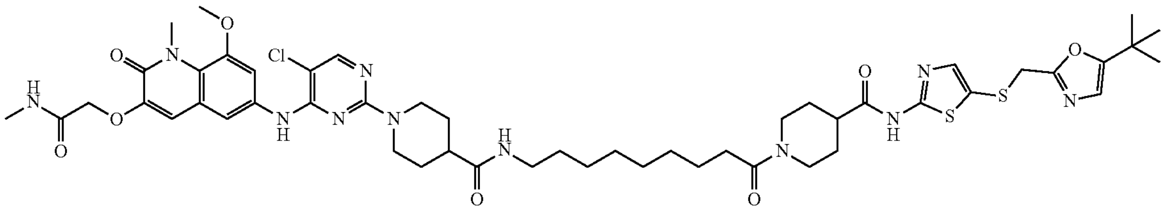
BAK-04-022
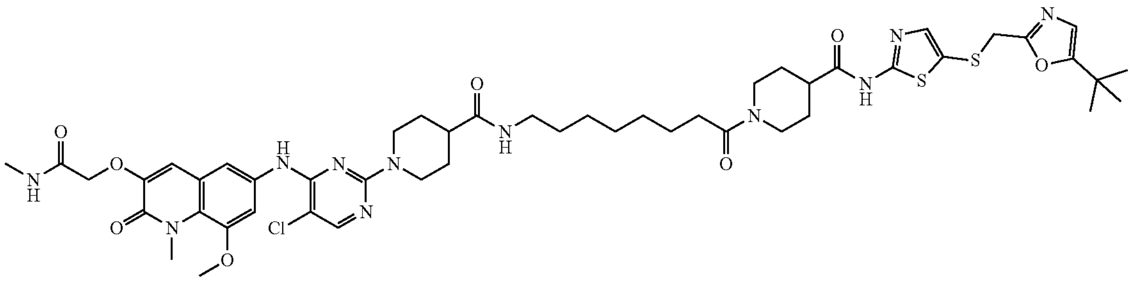
BAK-04-021
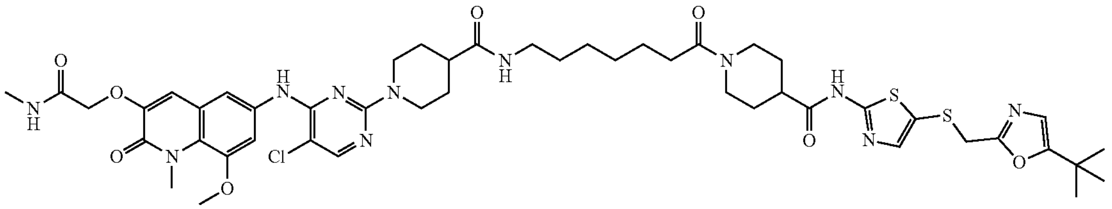
BAK-04-028
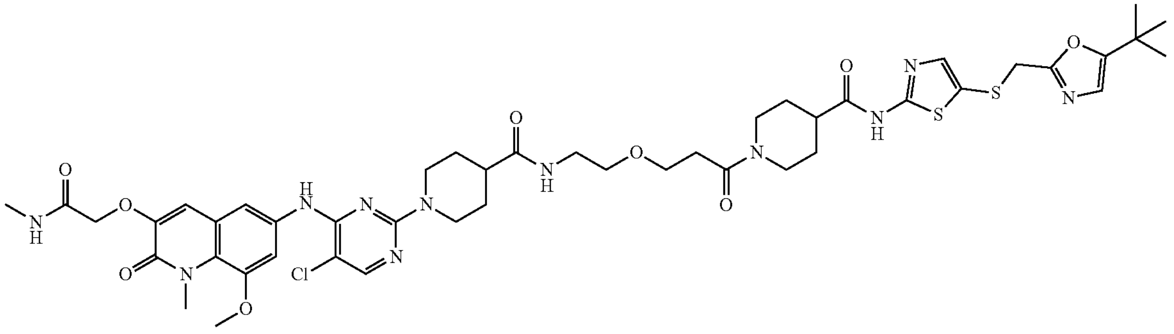

-continued
BAK-04-029
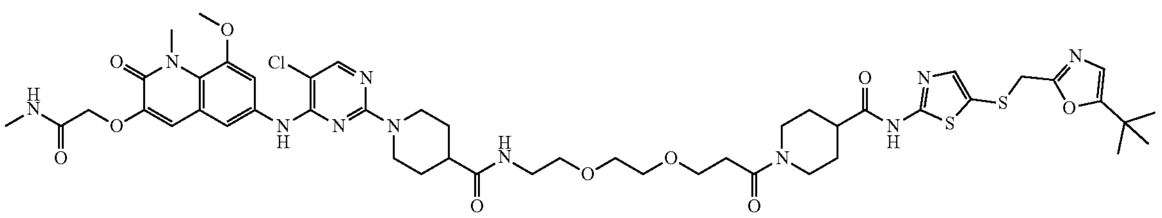
BAK-04-030
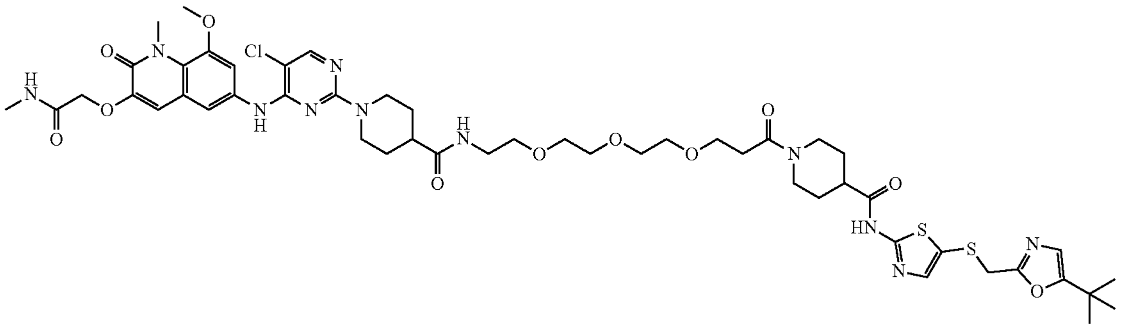
BAK-04-016
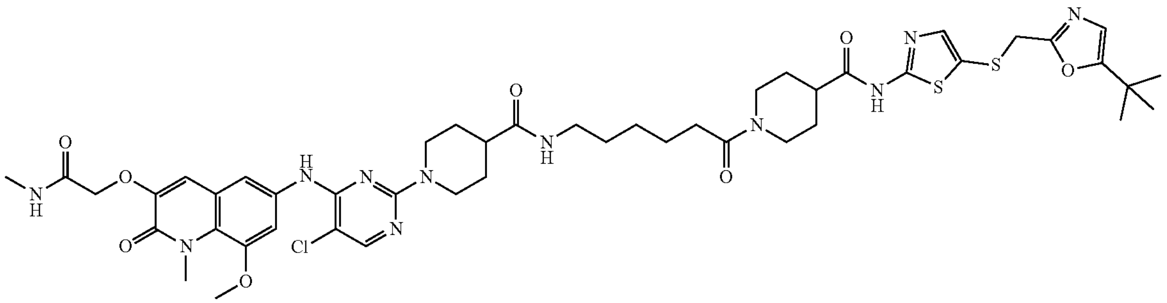
BAK-04-015
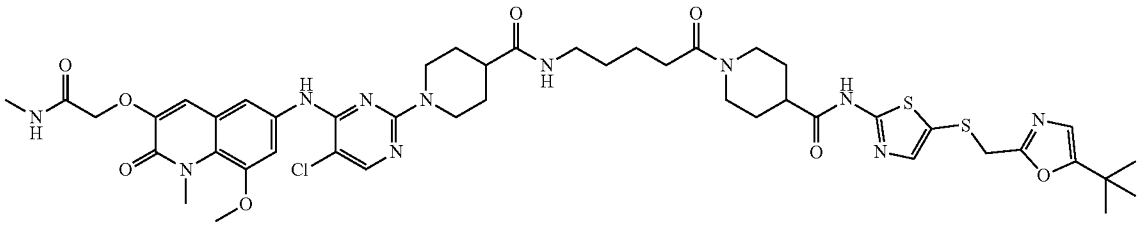
BAK-04-014
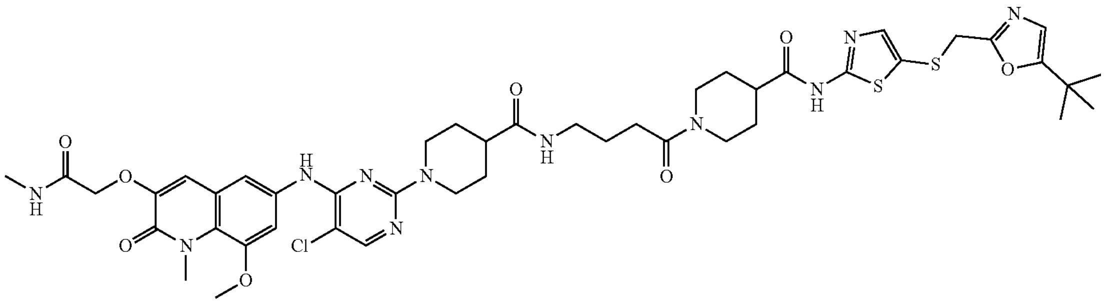

-continued
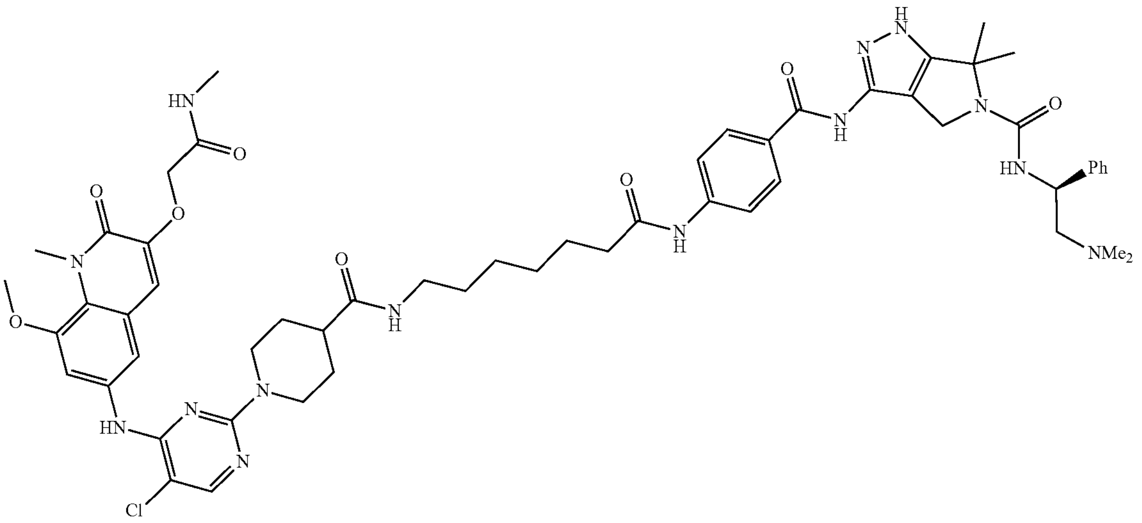
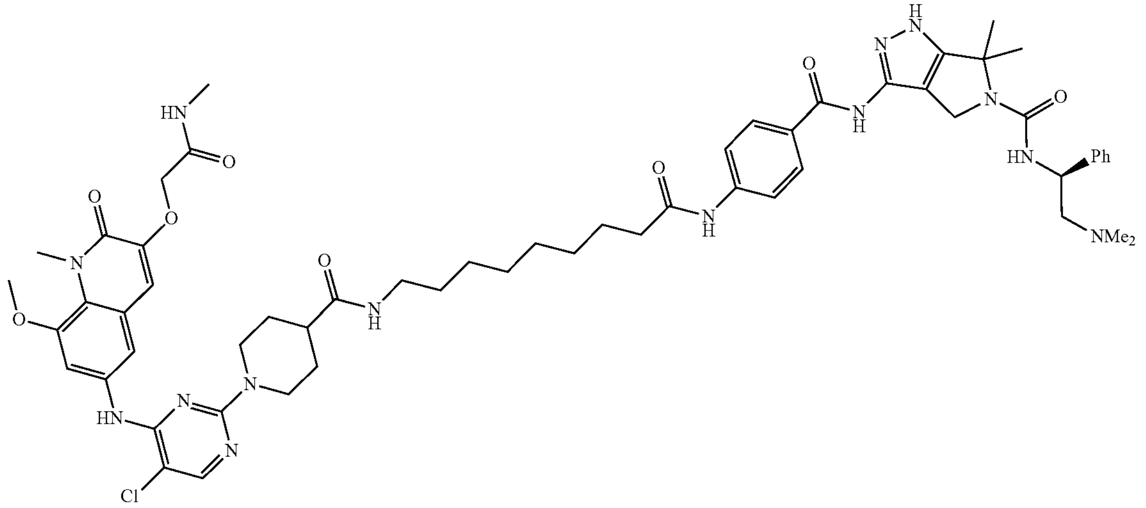
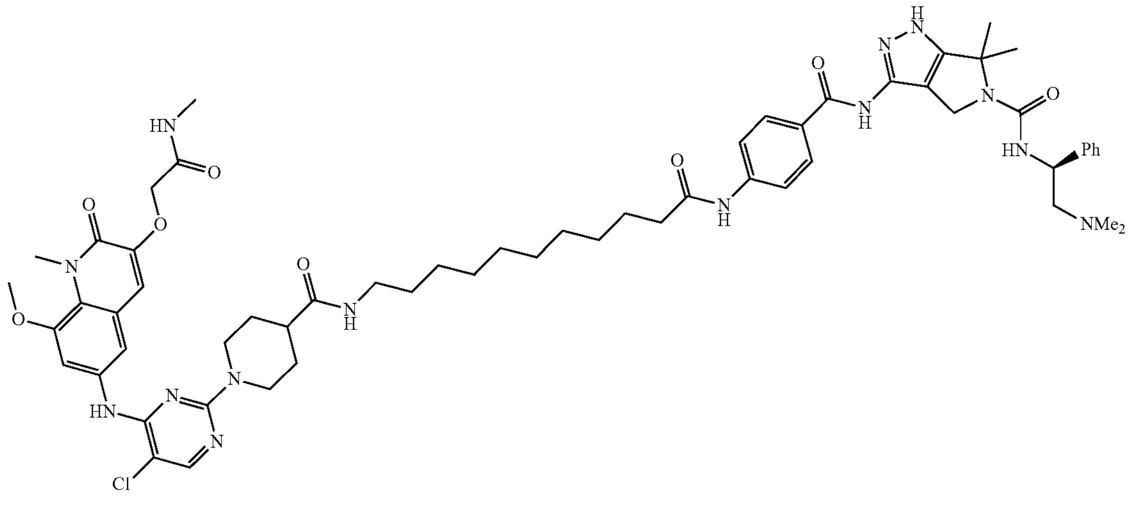

-continued
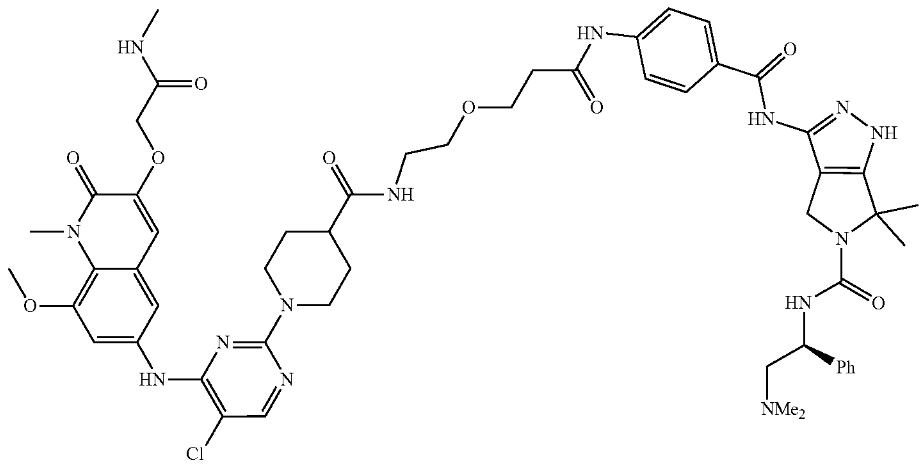
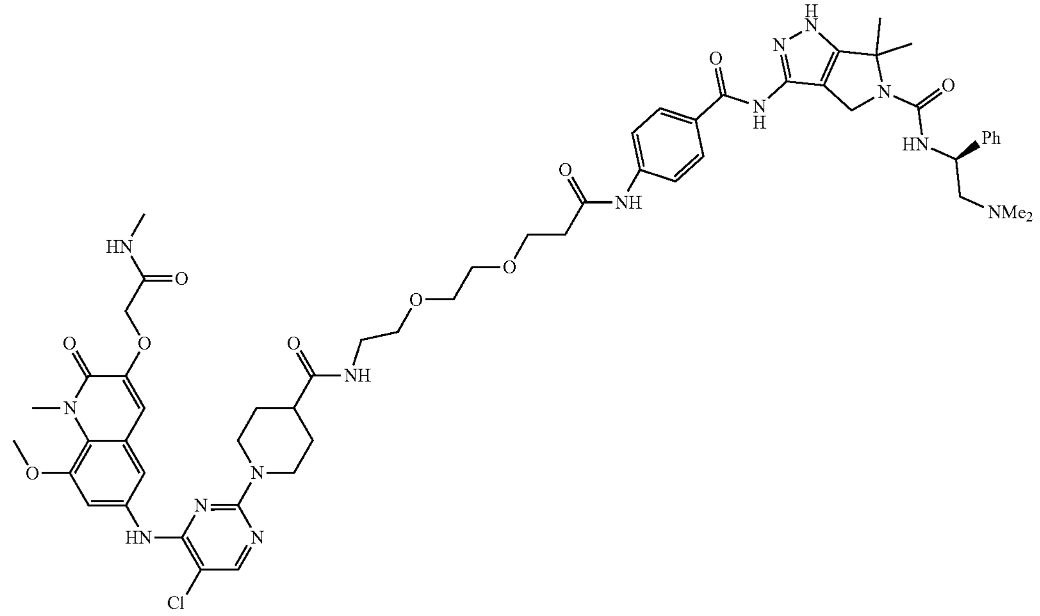
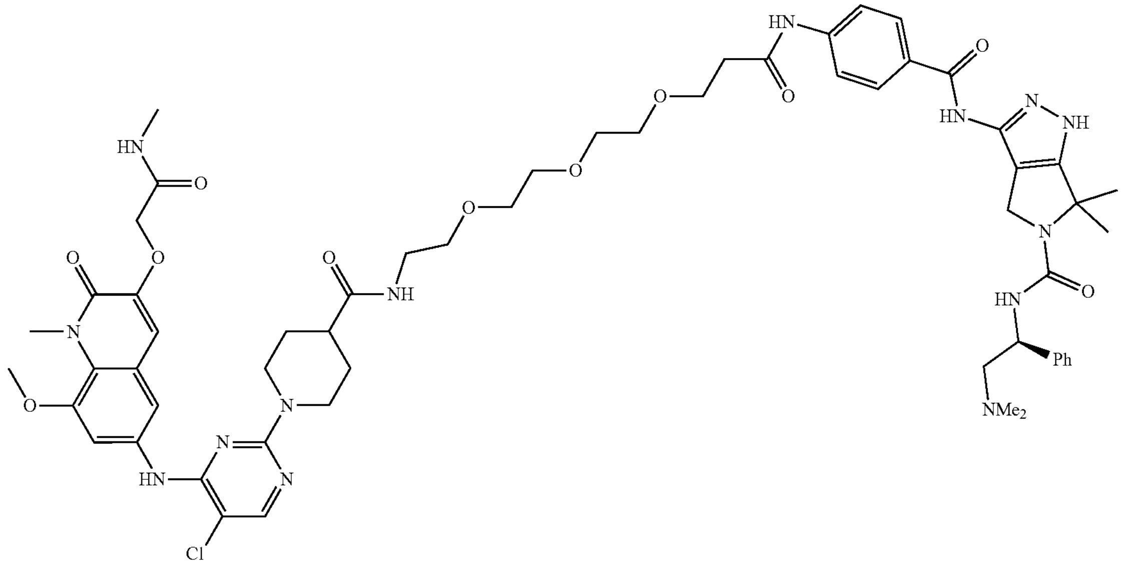

-continued
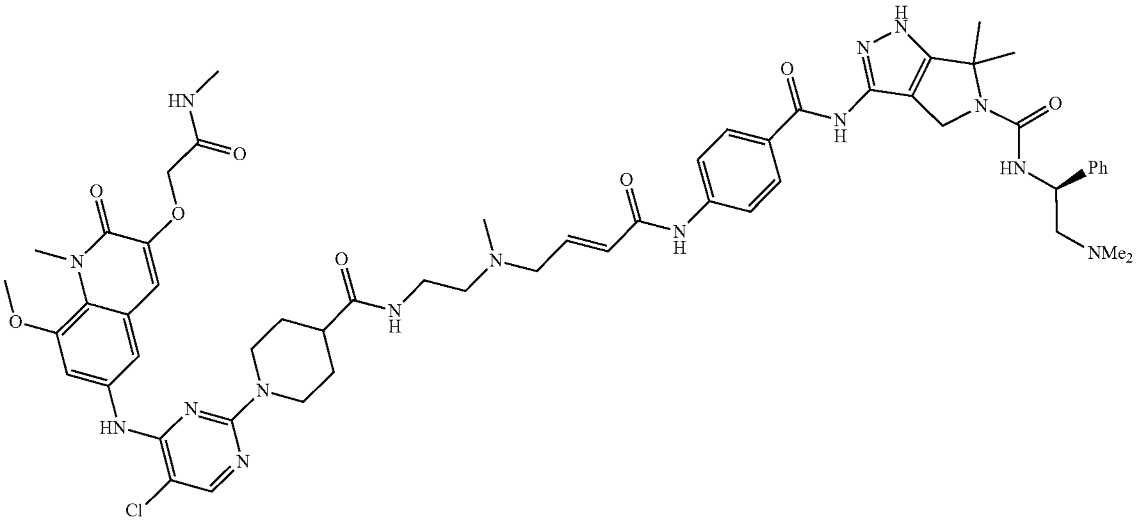
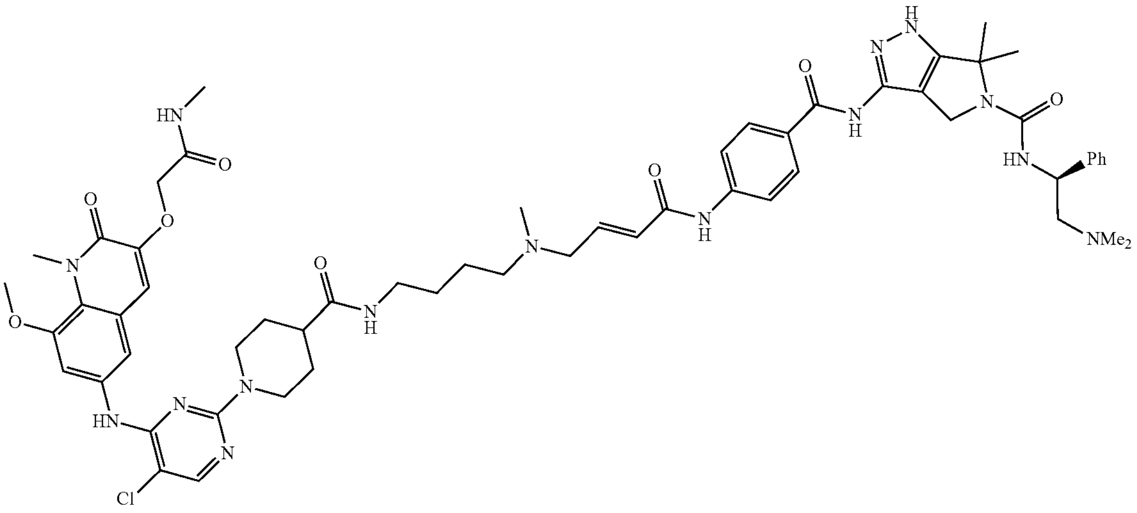
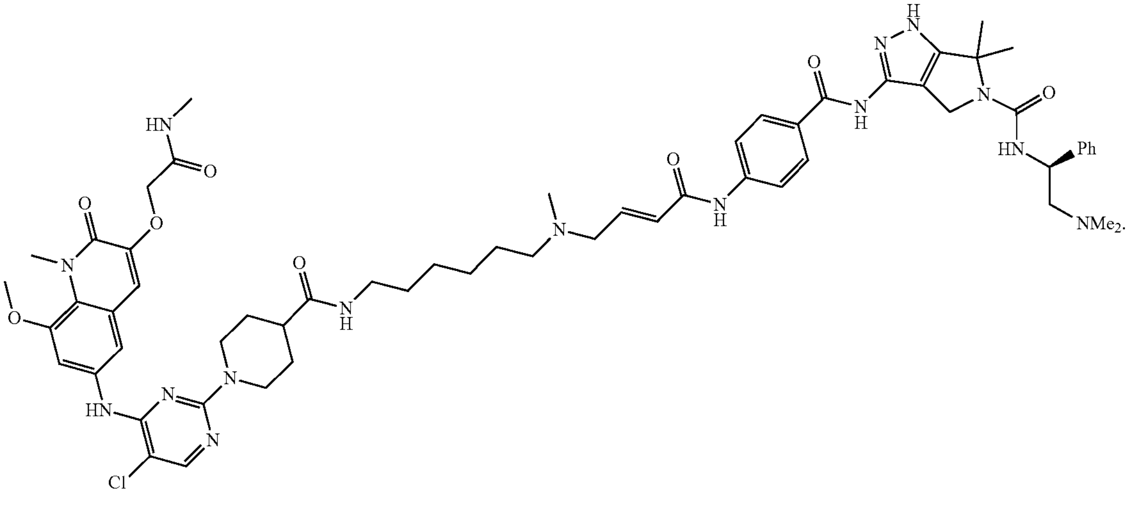

15. The method according to any of the preceding embodiments, wherein administration of the CIP activates transcription of a proapoptotic gene to treat the subject for the malignancy.

16. The method according to Embodiment 15, wherein the proapoptotic gene is selected from the group consisting of TP53, PUMA (BBC3), BIM (BCL2L11), BID, BAX, BAK, BOK, BAD, HRK, BIK, BMF, and NOXA.

17. The method according to any of the preceding embodiments, wherein the malignancy is characterized by elevated levels of BCL6 (or a homologue thereof).

18. The method according to any of the preceding embodiments, wherein the malignancy is Small Cell Lung Cancer (SCLC).

19. The method according to any of Embodiments 1 to 17, wherein the malignancy is Diffuse Large B-Cell Lymphoma (DLBCL).

20. The method according to Embodiment 19, wherein the DLBCL is refractory DLBCL.

21. The method according to Embodiment 20, wherein the refractory DLBCL is CHOP-resistant DLBCL.

22. The method according to any of Embodiments 1 to 17, wherein the malignancy is breast cancer.

23. The method according to any of the preceding embodiments, wherein the subject is a mammal.

24. The method according to Embodiment 23, wherein the mammal is human.

25. The method according to any of the preceding embodiments, wherein the method further comprises assessing the subject to determine whether the malignancy is susceptible to treatment with the TCIP.

26. The method according to Embodiment 25, wherein the assessing comprises measuring the level of at least one of a CDK and BCL6 in malignant cells.

27. The method according to Embodiment 26, wherein the assessing comprises measuring the level of a CDK and BCL6 (or a homologue thereof) in malignant cells.

28. The method according to any of Embodiments 26 and 27, wherein the measuring comprises one or more of RNA-seq, Western blotting, immunohistochemistry, mass spec, and intracellular FACS.

29. A transcriptional chemical inducer of proximity (TCIP) for treating malignancy, the TCIP comprising a first ligand that specifically binds to BCL-6 (or a homologue thereof) and a second ligand that specifically binds to a CDK.

30. The TCIP according to Embodiment 29, wherein the TCIP comprises a first ligand that specifically binds to BCL-6 covalently linked to a second ligand that specifically binds to a CDK.

31. The TCIP according to Embodiment 30, wherein binding of the second ligand to the CDK does not substantially reduce the transcription-activating activity of BCL-6 or its functional homologue.

32. The TCIP according to Embodiment 31, wherein the first ligand is selected from the group consisting of:

11

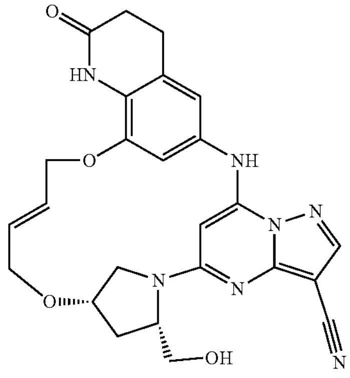

7

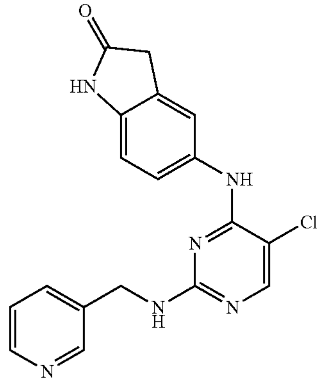

14

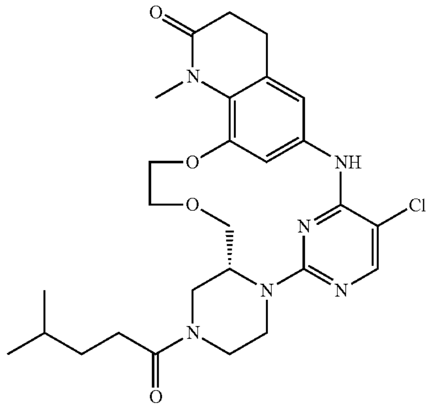

25a

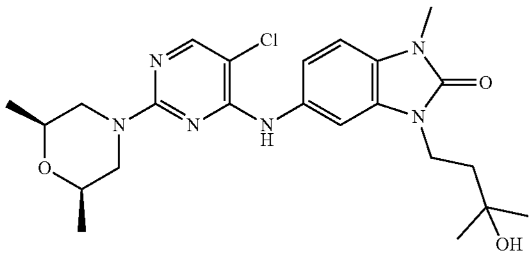

-continued
FX1
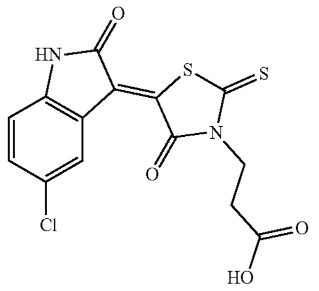
BI-3812
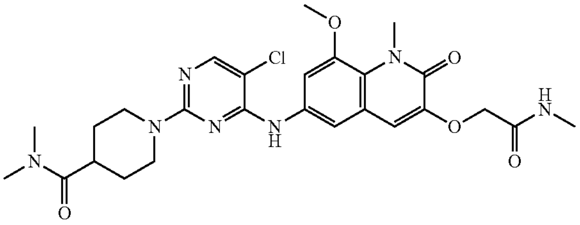
(BI-3802)
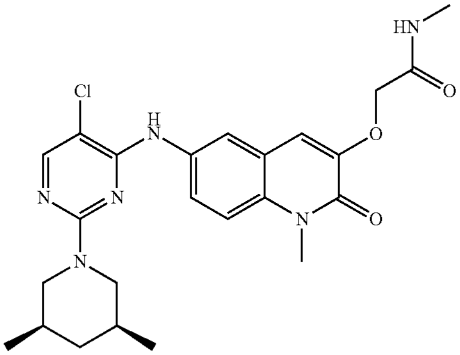
(6)
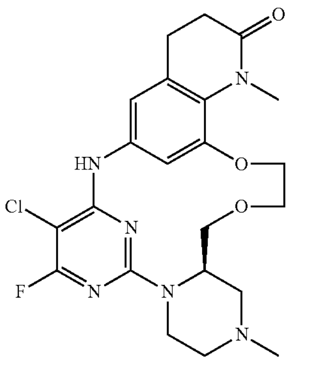
-continued
(CCT369347)
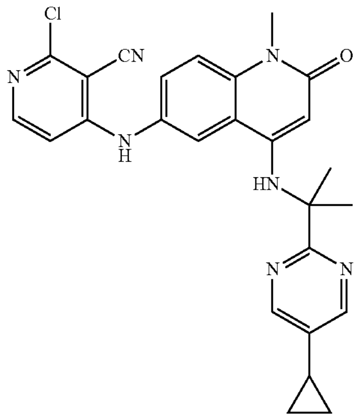
(CCT372064)
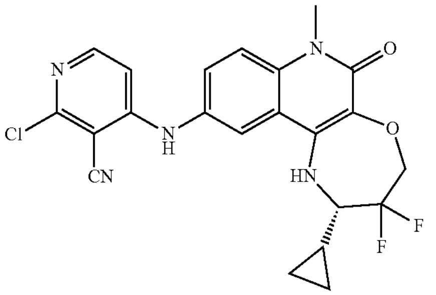
(CCT37566)
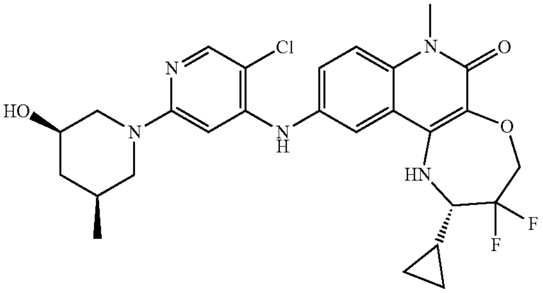
(CCTT369260)
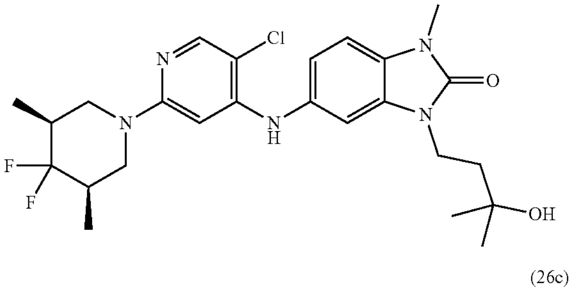
(26c)
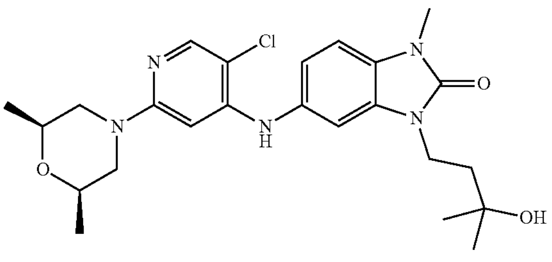

-continued (TMX-2164)

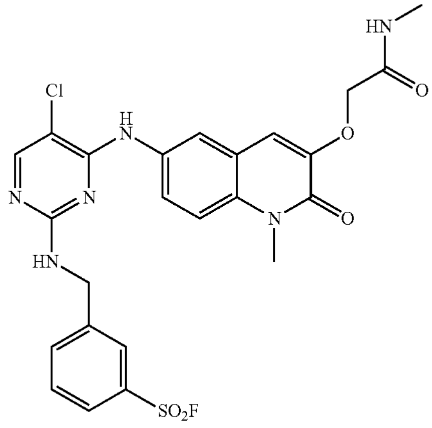

(BC1-1)

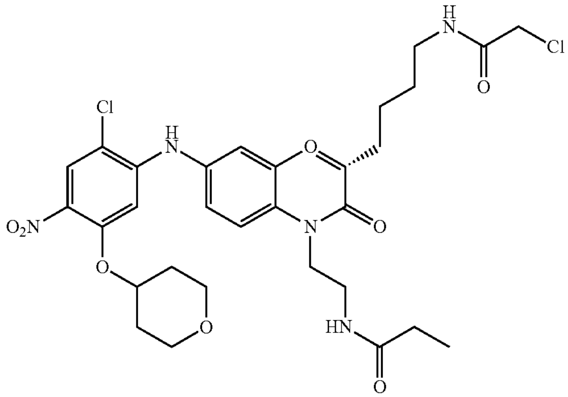

-continued (GSK-137)

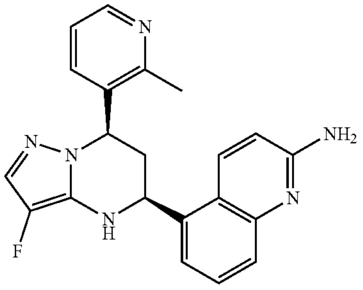

(79-6)

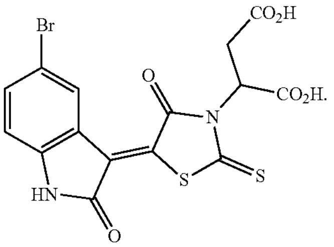

33. The TCIP according to any of Embodiments 29 to 32, wherein the second ligand is selected from the group consisting of a CDK9 ligand, a CDK8 ligand and a CDK7 ligand.

34. The TCIP according to Embodiment 33, wherein the second ligand is a CDK9 ligand.

35. The TCIP according to Embodiment 34, wherein the CDK9 ligand is selected from the group consisting of:

| Name | Structure |
|---|---|
| SNS-032 | 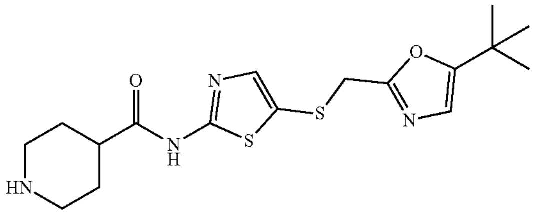 [SMILES: CC(C)(C)c1cnc(CSc2cnc(NC(=O)C3CCNCC3)s2)o1] |
| NVP-2 | 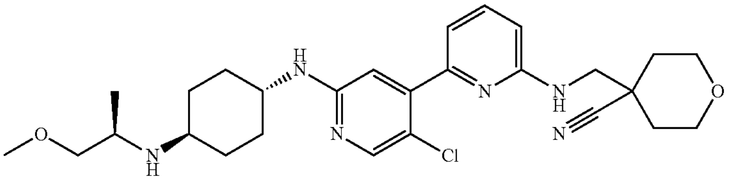 [SMILES: COC[C@@H](C)N[C@H]1CC[C@H](Nc2cc(-c3cccc(NCC4(C#N)CCOCC4)n3)c(Cl)cn2)CC1] |
| KI-ARv-03 | 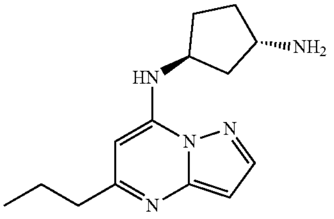 [SMILES: CCCc1cc(N[C@H]2CC[C@H](N)C2)n2nccc2n1] |

-continued
| Name | Structure |
| --- | --- |
| KB-0742 | 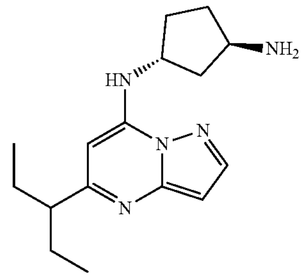 [SMILES: CCC(CC)c1cc(N[C@@H]2CC[C@@H](N)C2)n2nccc2n1] |
| BAY-1143572 | 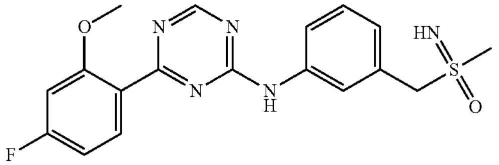 [SMILES: COc1cc(F)ccc1-c1ncnc(Nc2cccc(CS(C)(=N)=O)c2)n1] |
| AZD-4573 | 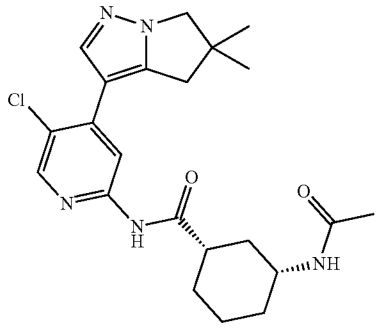 [SMILES: CC(=O)N[C@@H]1CCC[C@H](C(=O)Nc2cc(-c3cnn4c3CC(C)(C)C4)c(Cl)cn2)C1] |
| Alvocidib | 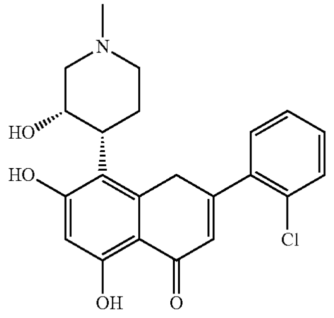 [SMILES: CN1CC[C@H](c2c(O)cc(O)c3c2CC(c2ccccc2Cl)=CC3=O)[C@H](O)C1] |
| TP-1287 | 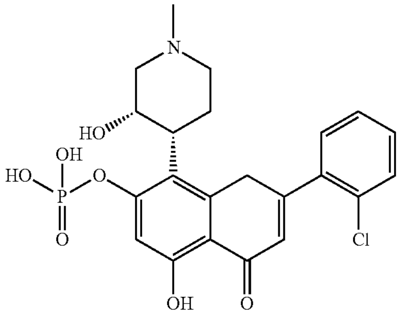 [SMILES: CN1CC[C@H](c2c(OP(=O)(O)O)cc(O)c3c2CC(c2ccccc2Cl)=CC3=O)[C@H](O)C1] |

-continued
| Name | Structure |
|---|---|
| Riviciclib | 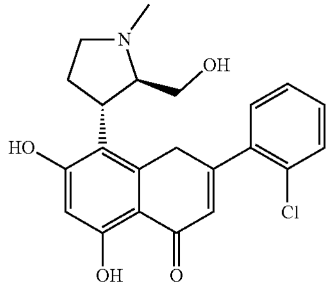 [SMILES: CN1CC[C@@H](c2c(O)cc(O)c3c2CC(c2ccccc2Cl)=CC3=O)[C@@H]1CO] |
| Voruciclib | 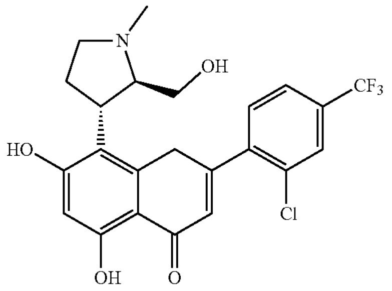 [SMILES: CN1CC[C@@H](c2c(O)cc(O)c3c2CC(c2ccc(C(F)(F)F)cc2Cl)=CC3=O)[C@@H]1CO] |
| ZK-304709 | 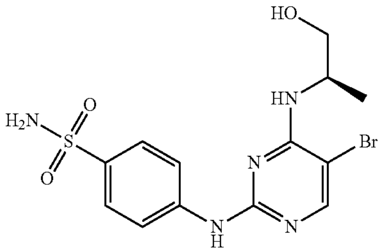 [SMILES: C[C@H](CO)Nc1nc(Nc2ccc(S(N)(=O)=O)cc2)ncc1Br] |
| BAY-1251152 | 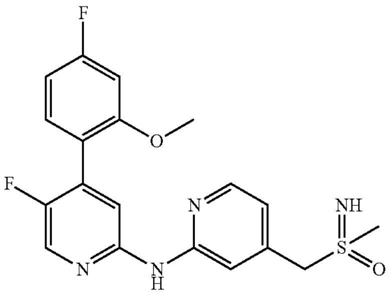 [SMILES: COc1cc(F)ccc1-c1cc(Nc2cc(CS(C)(=N)=O)ccn2)ncc1F] |
| Zotiraciclib (TG-02) | 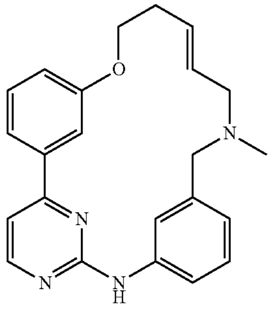 [SMILES: CN1C/C=C/CCOc2cccc(c2)-c2ccnc(n2)Nc2cccc(c2)C1] |

-continued
| Name | Structure |
|---|---|
| Seliciclib | 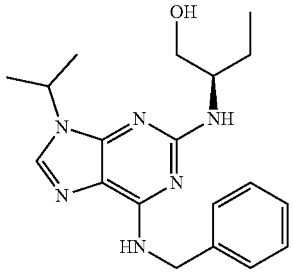 [SMILES: CC[C@H](CO)Nc1nc(NCc2ccccc2)c2ncn(C(C)C)c2n1] |
| Fadraciclib | 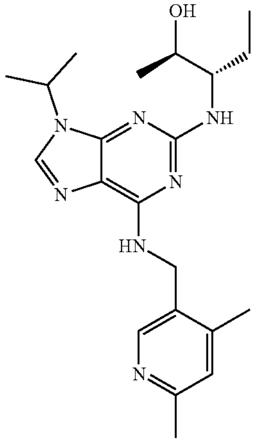 [SMILES: CC[C@H](Nc1nc(NCc2cnc(C)cc2C)c2ncn(C(C)C)c2n1)[C@@H](C)O] |
| Dinaciclib | 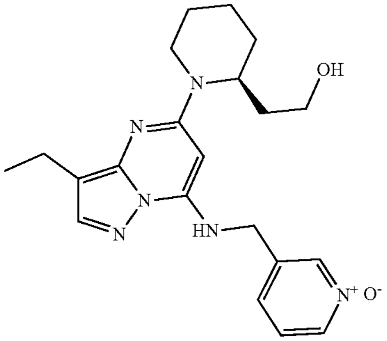 |
| AT7519 | 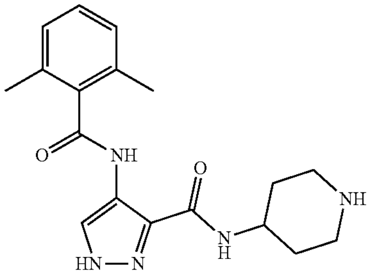 [SMILES: Cc1cccc(C)c1C(=O)Nc1c[nH]nc1C(=O)NC1CCNCC1] |

-continued
| Name | Structure |
|---|---|
| BTX-A51 | 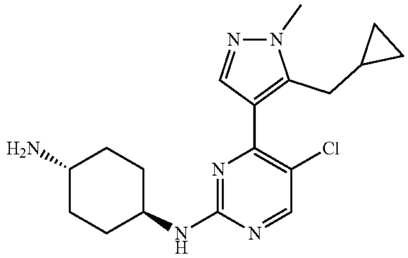 [SMILES: Cn1ncc(-c2nc(N[C@H]3CC[C@H](N)CC3)ncc2Cl)c1CC1CC1] |
| LY2857785 | 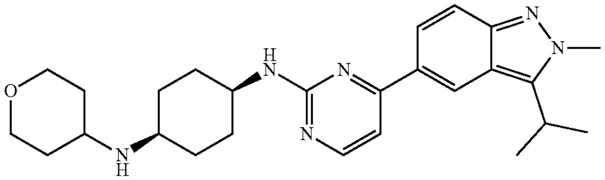 [SMILES: CC(C)c1c2cc(-c3ccnc(N[C@H]4CC[C@@H](NC5CCOCC5)CC4)n3)ccc2nn1C] |
36. The TCIP according to Embodiment 33, wherein the second ligand is a CDK8 ligand.
37. The TCIP according to Embodiment 36, wherein the CDK8 ligand is selected from the group consisting of:
| Name | Structure |
|---|---|
| BI-1347 | 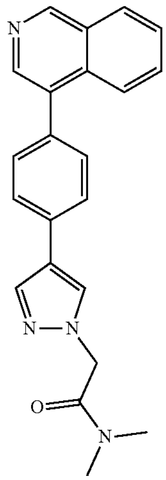 [SMILES: CN(C)C(=O)Cn1cc(-c2ccc(-c3cncc4ccccc34)cc2)cn1] |
| Cortistatin A | 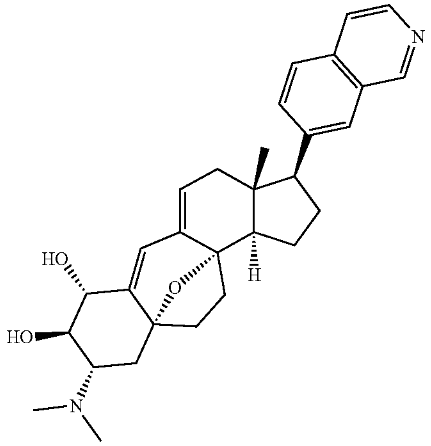 [SMILES: CN(C)[C@H]1C[C@@]23CC[C@@]4(O2)C(=CC[C@]2(C)[C@@H](c5ccc6ccncc6c5)CC[C@H]24)C=C3[C@@H](O)[C@@H]1O] |

-continued
| Name | Structure |
|---|---|
| JH-VIII-49 | 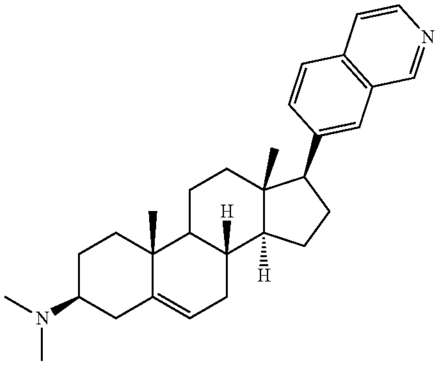 |
| CCT251545 | 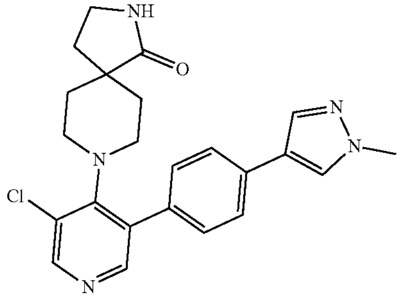 [SMILES: Cn1cc(-c2ccc(-c3cncc(Cl)c3N3CCC4(CCNC4=O)CC3)cc2)cn1] |
| MSC253818 | 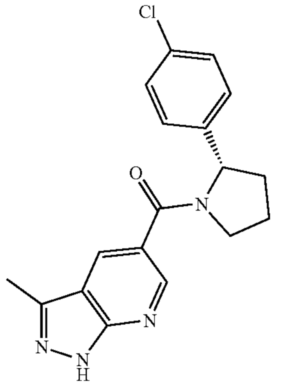 [SMILES: Cc1n[nH]c2ncc(C(=O)N3CCC[C@H]3c3ccc(Cl)cc3)cc12] |
| Senexin C | 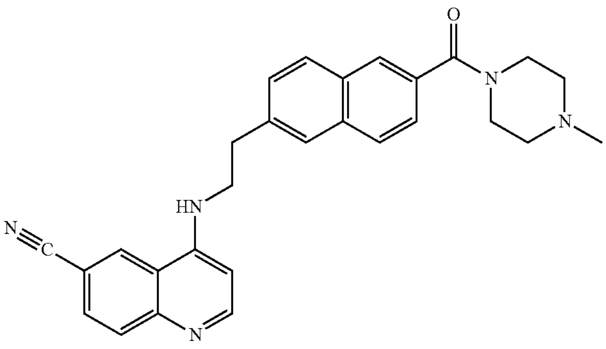 [SMILES: CN1CCN(C(=O)c2ccc3cc(CCNc4ccnc5ccc(C#N)cc45)ccc3c2)CC1] |

-continued
| Name | Structure |
| --- | --- |
| Sel 120-34A | 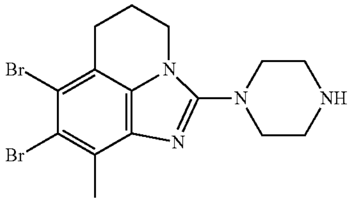 [SMILES: Cc1c(Br)c(Br)c2c3c1nc(N1CCNCC1)n3CCC2] |
| W-34 | 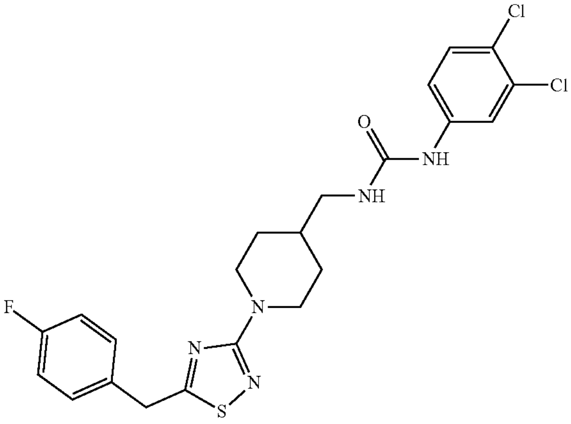 [SMILES: O=C(NCC1CCN(c2nsc(Cc3ccc(F)cc3)n2)CC1)Nc1ccc(Cl)c(Cl)c1] |
| T-814 | 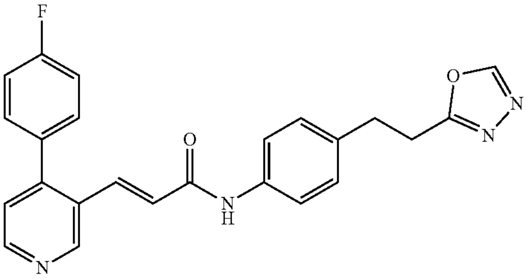 [SMILES: O=C(/C=C/c1cnccc1-c1ccc(F)cc1)Nc1ccc(CCc2nnco2)cc1] |
38. The TCIP according to Embodiment 33, wherein the second ligand is a CDK7 ligand.
39. The TCIP according to Embodiment 38, wherein the CDK7 ligand is selected from the group consisting of:
| Name | Structure |
| --- | --- |
| BS-181 | 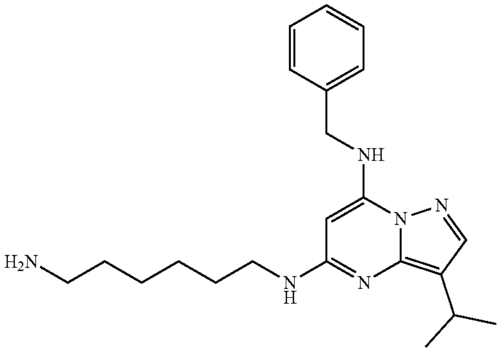 [SMILES: CC(C)c1cnn2c(NCc3ccccc3)cc(NCCCCCCN)nc12] |

-continued
| Name | Structure |
| --- | --- |
| CT7001 | 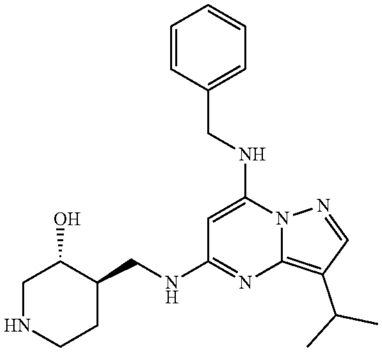 [SMILES: CC(C)c1cnn2c(NCc3ccccc3)cc(NC[C@H]3CCNC[C@@H]3O)nc12] |
| THZ2 | 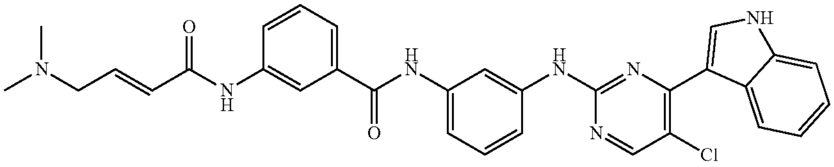 [SMILES: CN(C)C/C=C/C(=O)Nc1cccc(C(=O)Nc2cccc(Nc3ncc(Cl)c(-c4c[nH]c5ccccc45)n3)c2)c1] |
| THZ2 reversible compound | 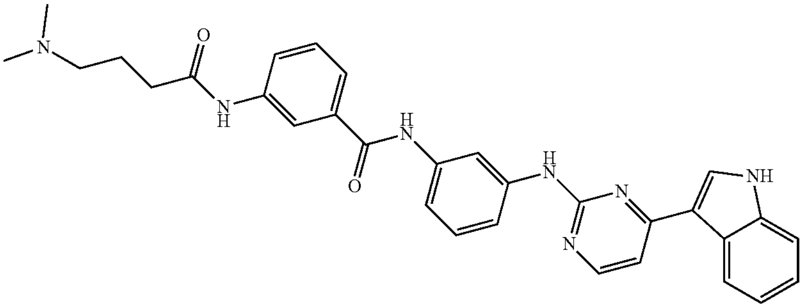 [SMILES: CN(C)CCCC(=O)Nc1cccc(C(=O)Nc2cccc(Nc3nccc(-c4c[nH]c5ccccc45)n3)c2)c1] |
| YKL-1-116 | 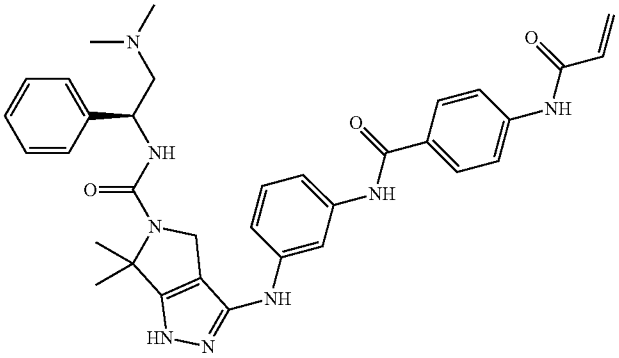 [SMILES: C=CC(=O)Nc1ccc(C(=O)Nc2cccc(Nc3n[nH]c4c3CN(C(=O)N[C@H](CN(C)C)c3ccccc3)C4(C)C)c2)cc1] |

-continued
| Name | Structure |
| --- | --- |
| YKL-5-124 | 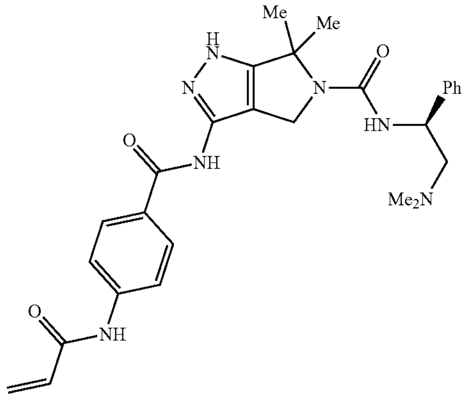 [SMILES: C=CC(=O)Nc1ccc(C(=O)Nc2n[nH]c3c2CN(C(=O)N[C@H](CN(C)C)c2ccccc2)C3(C)C)cc1] |
| YKL-5-124 Reversible compound | |
| SY-1365 and the reversible compound thereof (structure not shown) | 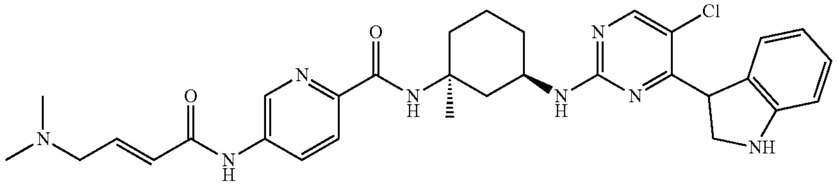 [SMILES: CN(C)C/C=C/C(=O)Nc1ccc(C(=O)N[C@@]2(C)CCC[C@@H](Nc3ncc(Cl)c(C4CNc5ccccc54)n3)C2)nc1] |
| SY5609 | 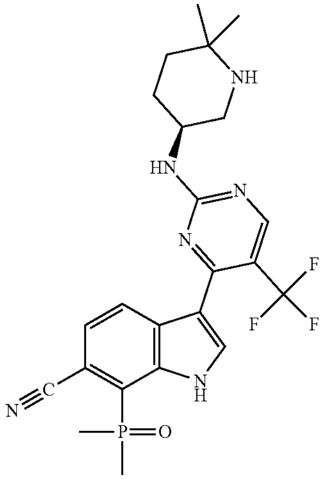 [SMILES: CC1(C)CC[C@H](Nc2ncc(C(F)(F)F)c(-c3c[nH]c4c(P(C)(C)=O)c(C#N)ccc34)n2)CN1] |
| LY3405105 and the reversible compound thereof (structure no shown) | 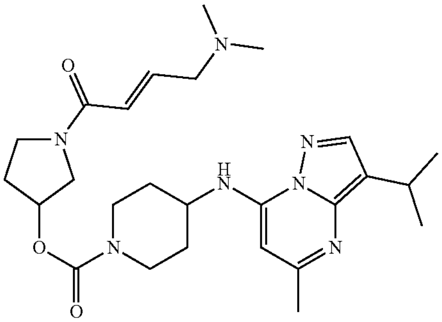 [SMILES: Cc1cc(NC2CCN(C(=O)OC3CCN(C(=O)/C=C/CN(C)C)C3)CC2)n2ncc(C(C)C)c2n1] |

-continued
| Name | Structure |
| --- | --- |
| LDC4279 | 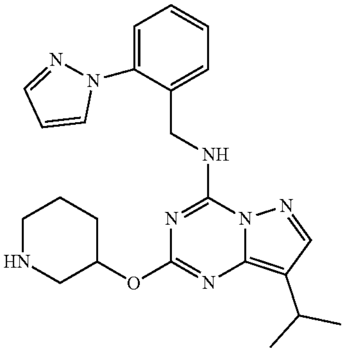 [SMILES: CC(C)c1cnn2c(NCc3ccccc3-n3cccn3)nc(OC3CCCNC3)nc12] |
40. The TCIP according to any of Embodiments 29 to 39, wherein the first ligand and second ligand are linked to each other by a linker.
41. The TCIP according to Embodiment 40, wherein the linker is selected from the group consisting of:
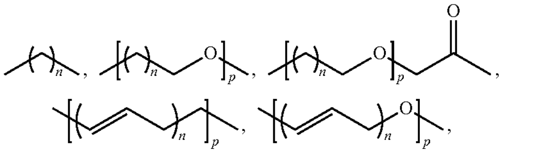
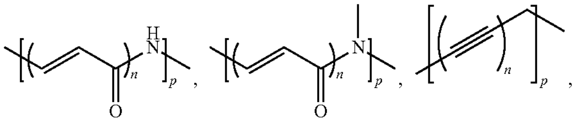
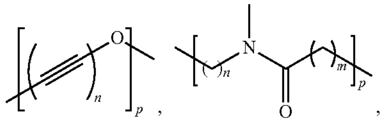
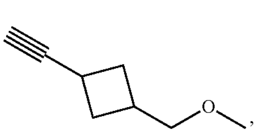
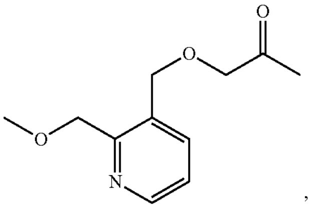
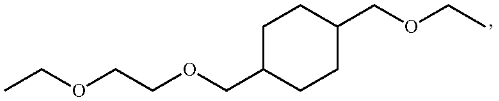
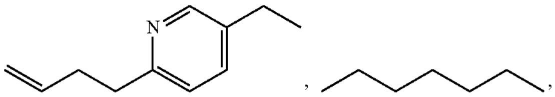
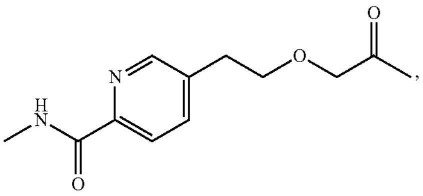
-continued
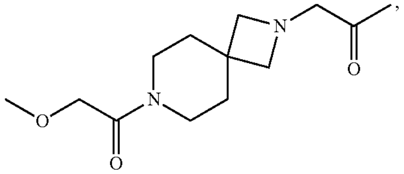
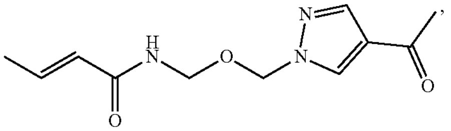
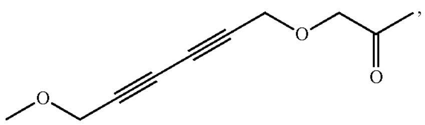
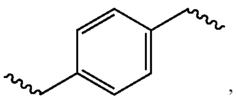
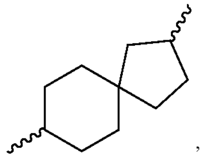
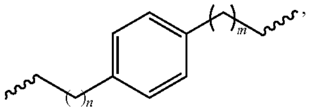
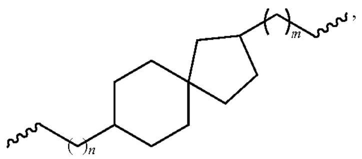
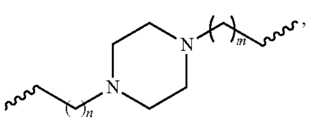
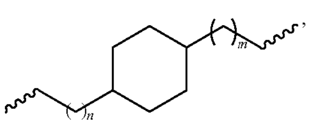

-continued
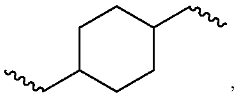
,
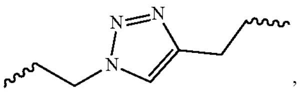
,
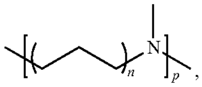
,
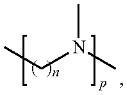
,
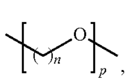
,
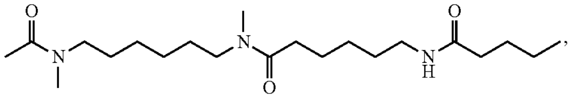
,
-continued
,
where m, n and p are independently selected from 0 or an integer of from 1-12.
42. The TCIP according to any of Embodiments 29 to 41, wherein the TCIP has a molecular weight ranging from 300 to 1200 g/mole.
43. The TCIP according to Embodiment 42, wherein TCIP is selected from the group consisting of:
BAK-04-023
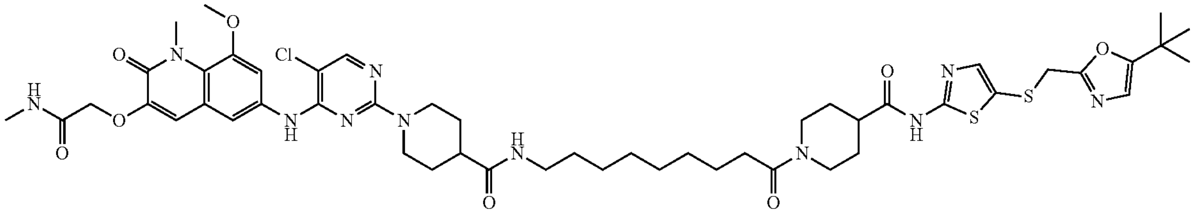
BAK-04-022
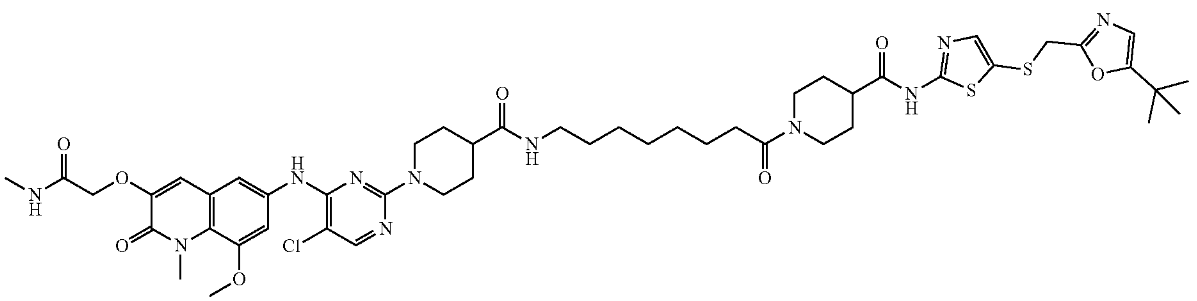
BAK-04-021
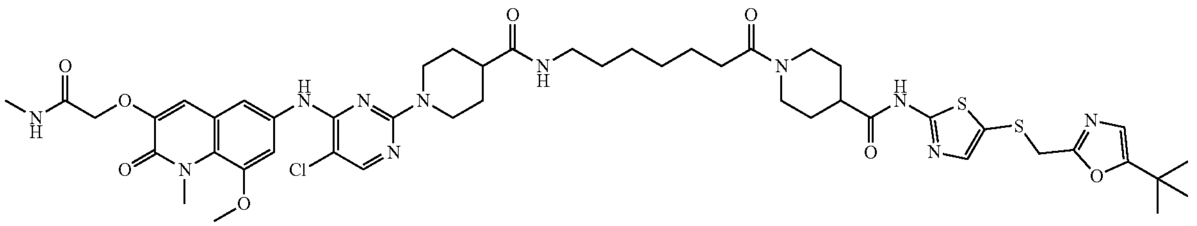
BAK-04-028
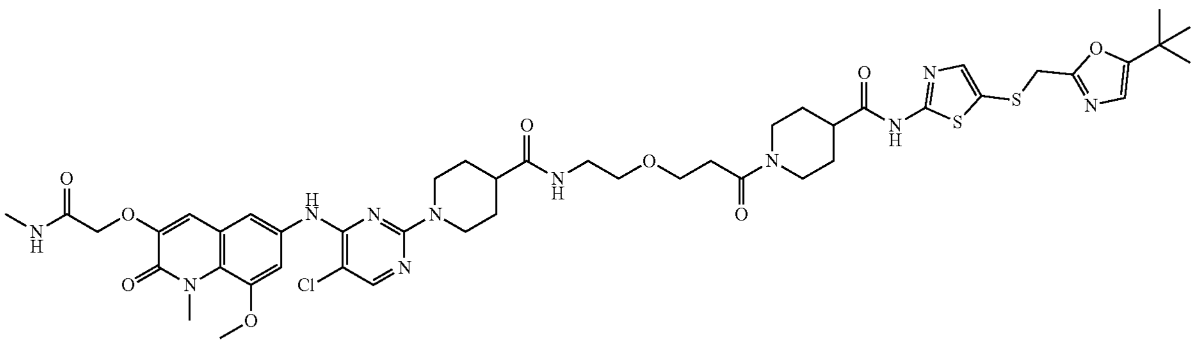

-continued
BAK-04-029
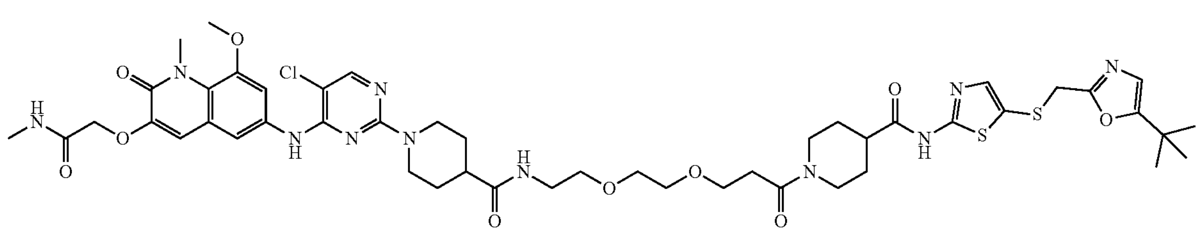
BAK-04-030
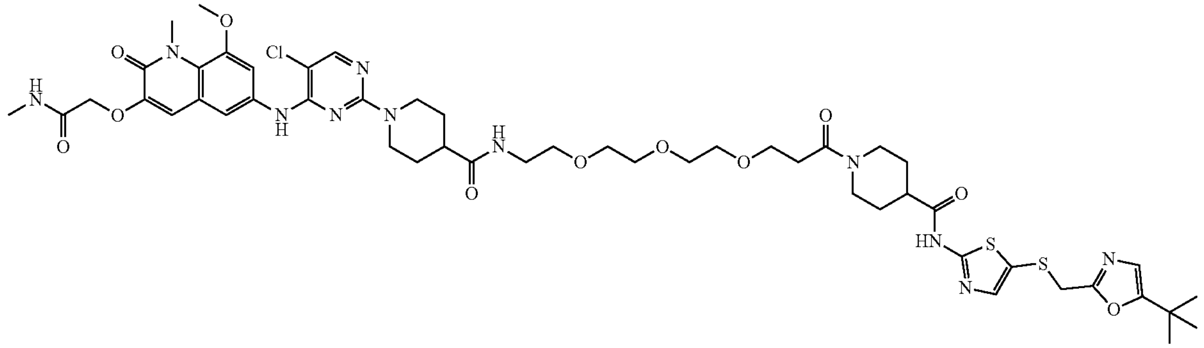
BAK-04-016
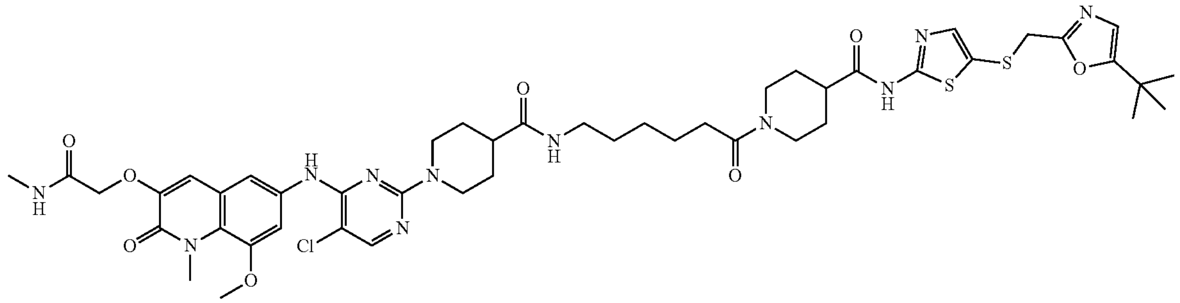
BAK-04-015
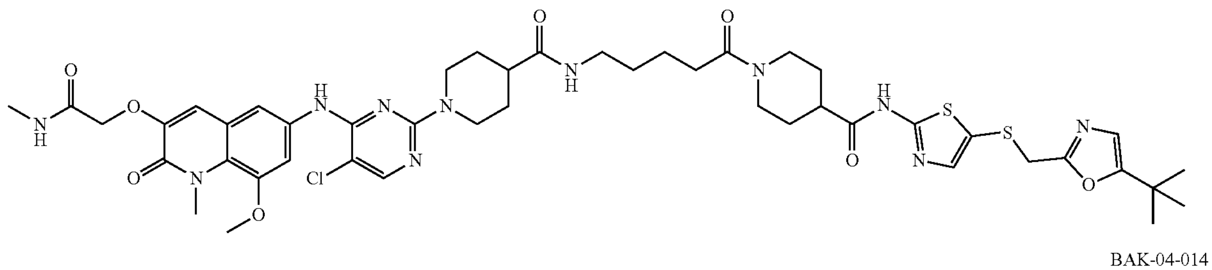
BAK-04-014
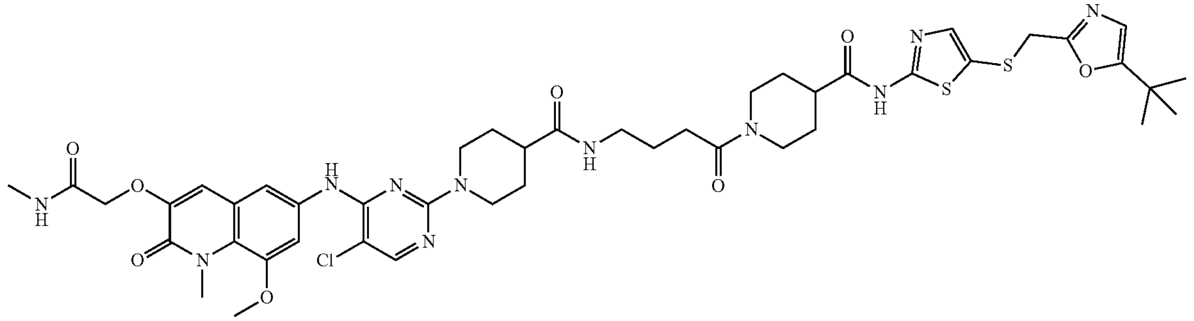

-continued
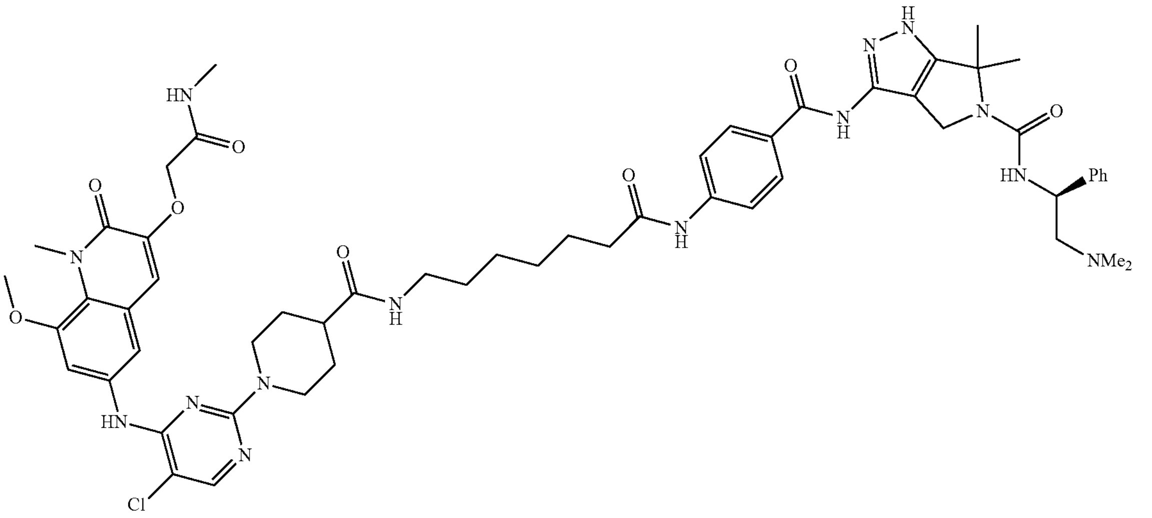
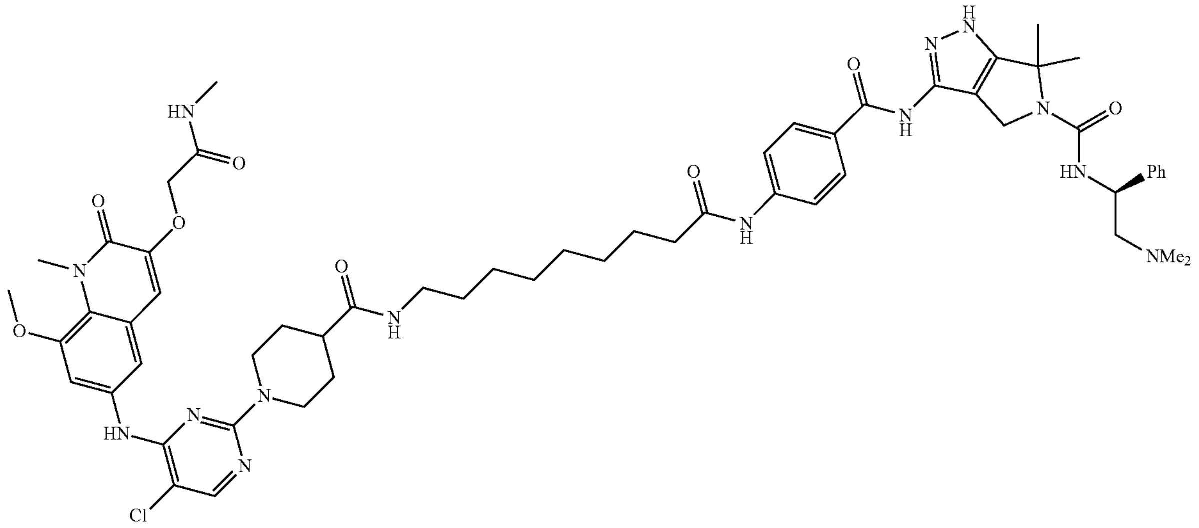
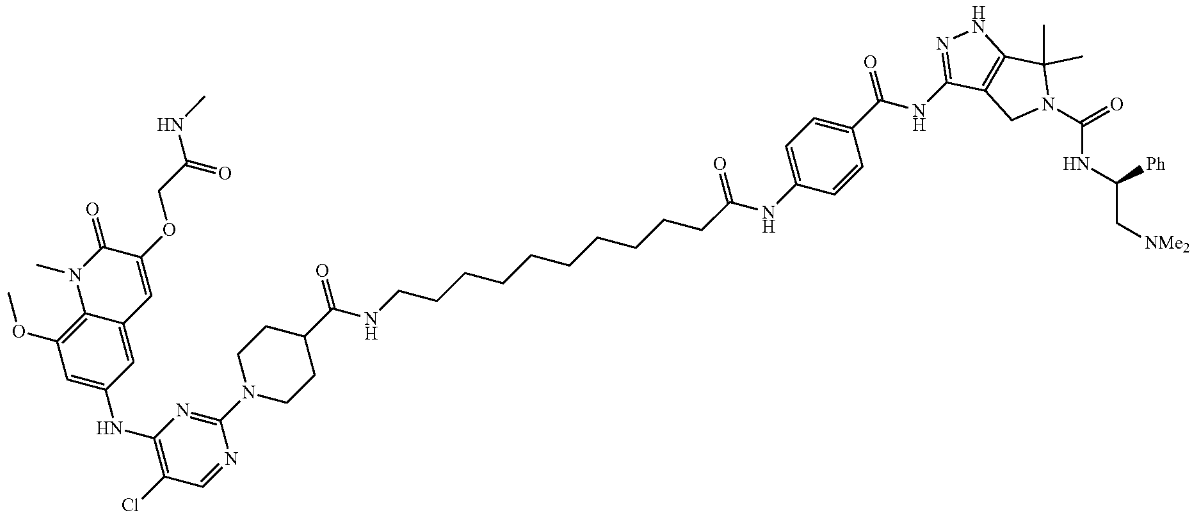

-continued
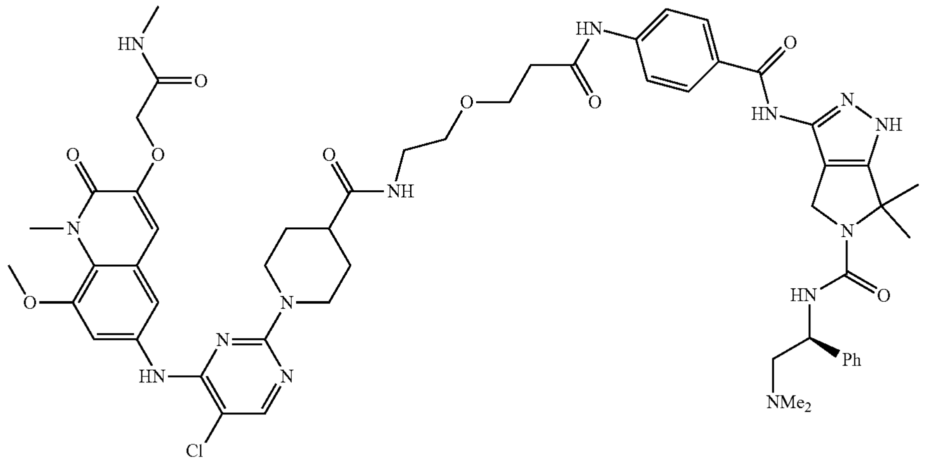
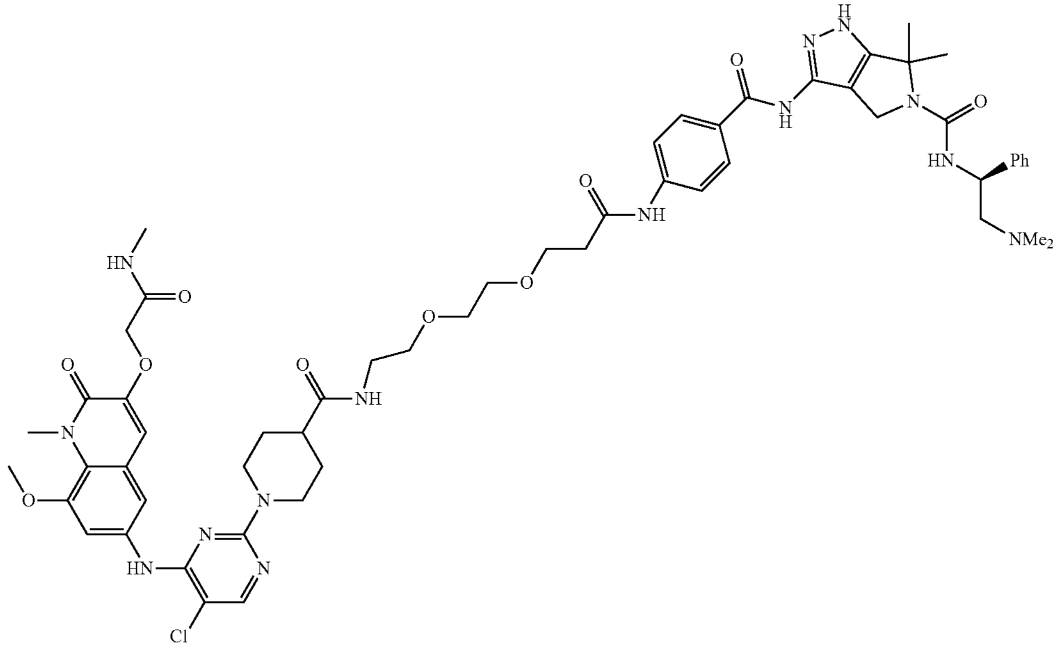
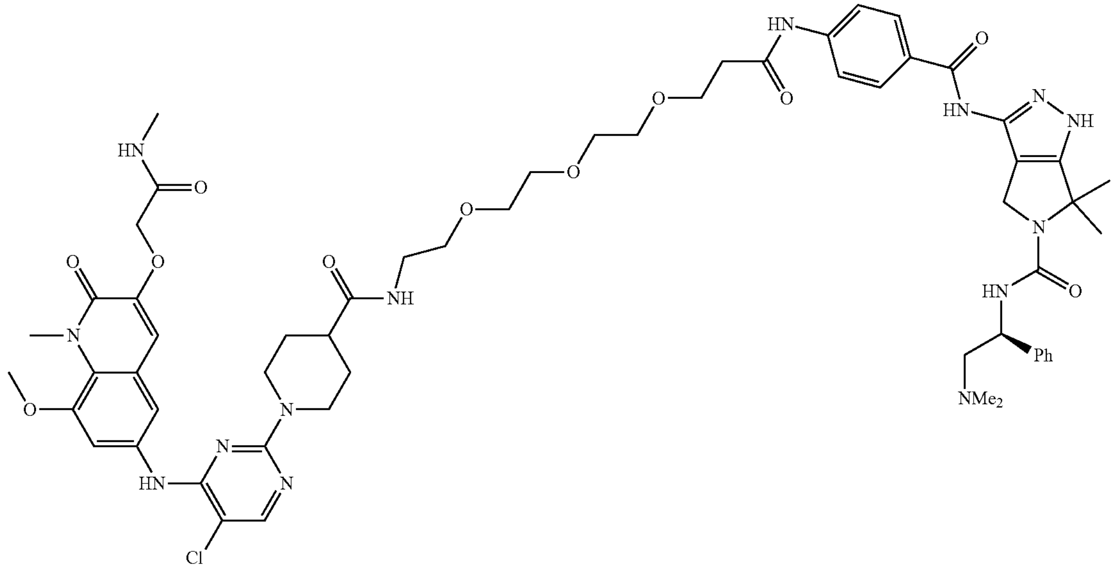

-continued
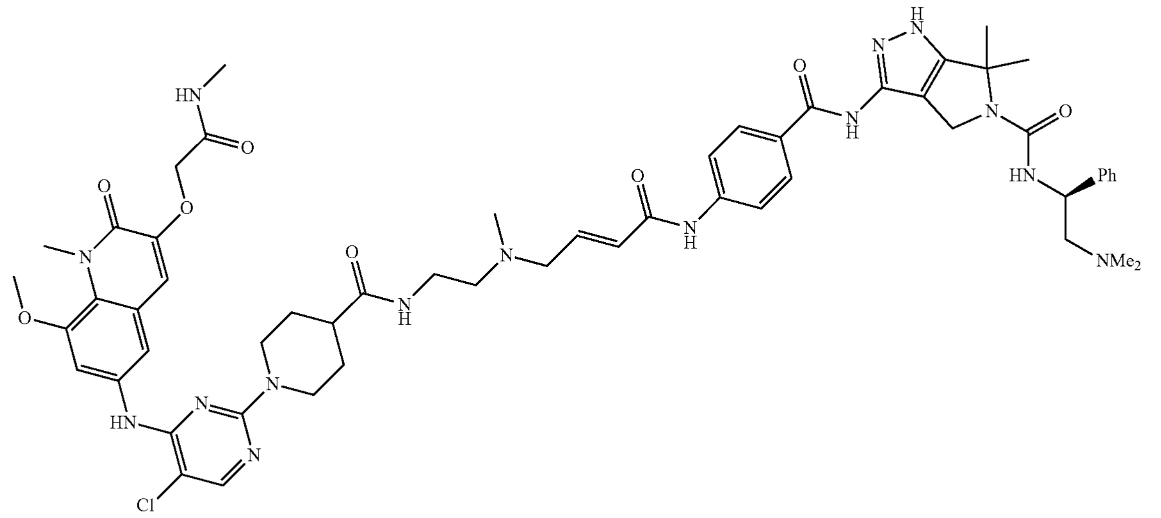
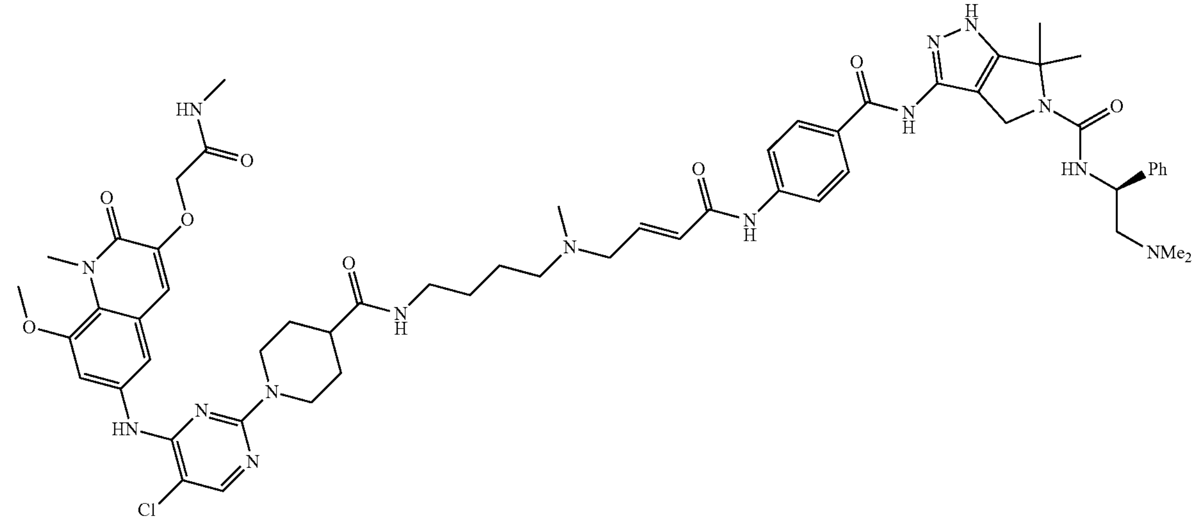
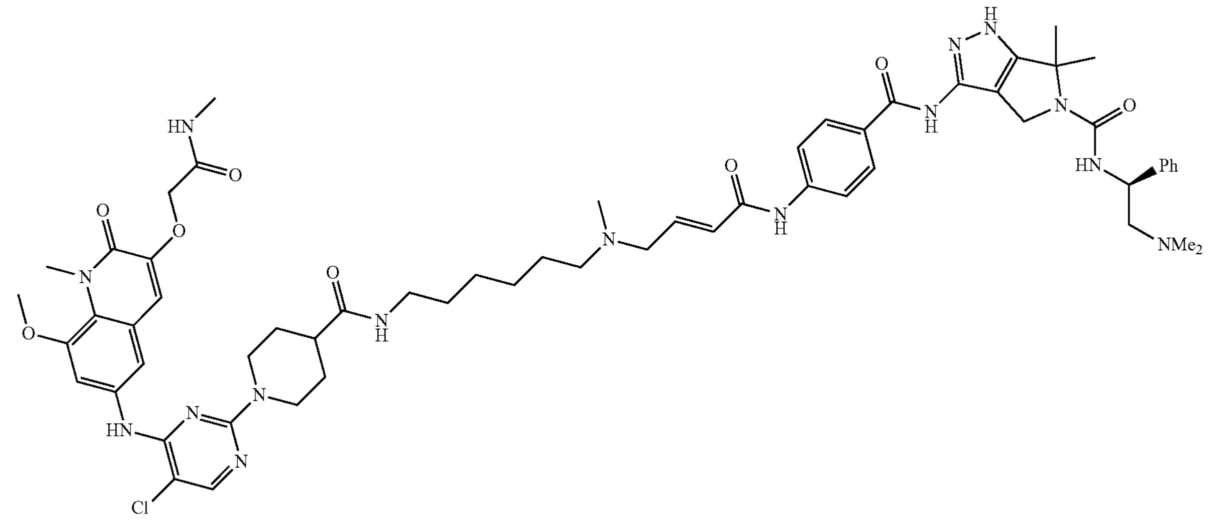

44. A pharmaceutical composition comprising:

transcriptional chemical inducer of proximity (TCIP) for treating malignancy, the TCIP comprising a first ligand that specifically binds to BCL-6 (or a homologue thereof) and a second ligand that specifically binds to a CDK; and delivery vehicle.

45. The pharmaceutical composition according to Embodiment 44, wherein the TCIP comprises a first ligand that specifically binds to BCL-6 (or a homologue thereof) covalently linked to a second ligand that specifically binds to a CDK.

46. The pharmaceutical composition according to Embodiment 45, wherein binding of the second ligand to the CDK does not substantially reduce the transcription-activating activity of BCL-6.

47. The pharmaceutical composition according to Embodiment 46, wherein the first ligand is selected from the group consisting of:

11

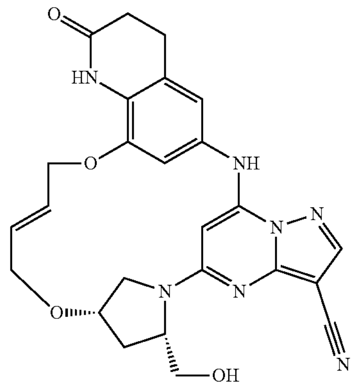

7

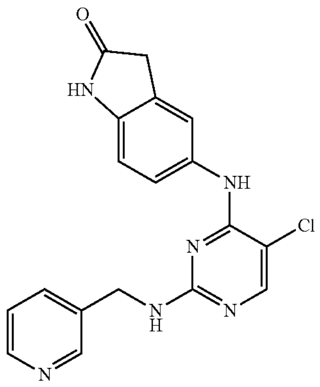

-continued

14

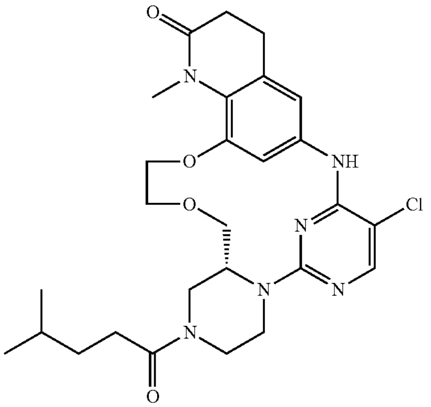

25a

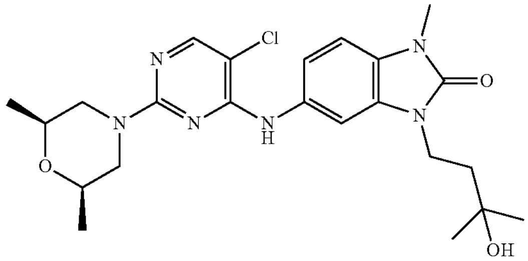

FX1

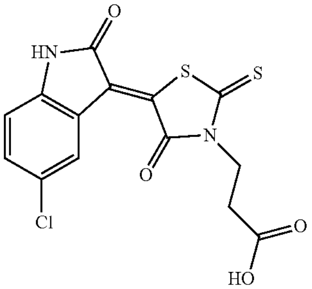

BI-3812

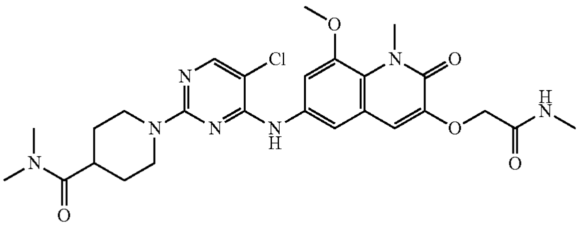

(BI-3802)

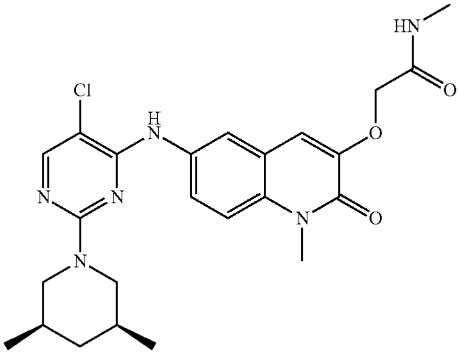

-continued
(6)
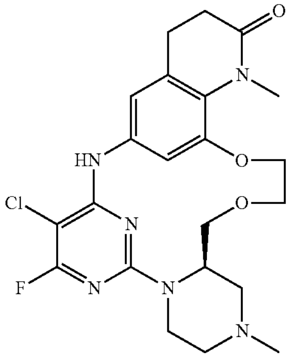
(CCT369347)
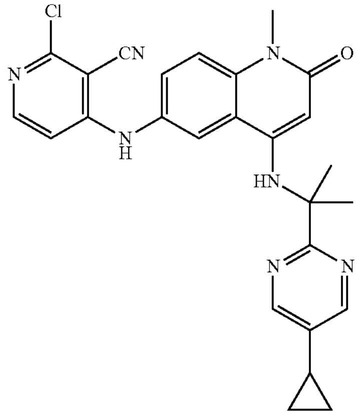
(CCT372064)
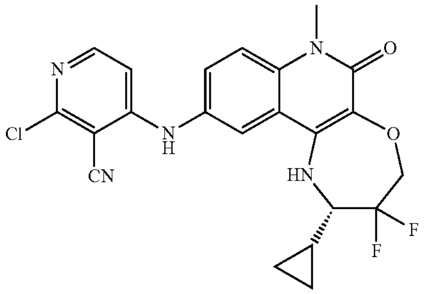
(CCT37566)
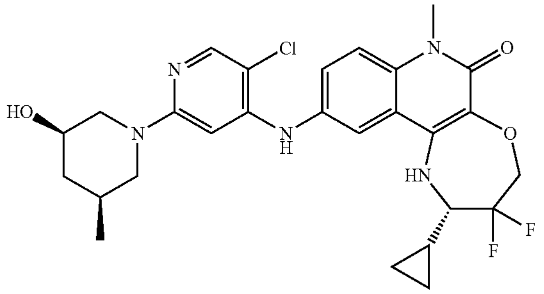
-continued
(CCTT369260)
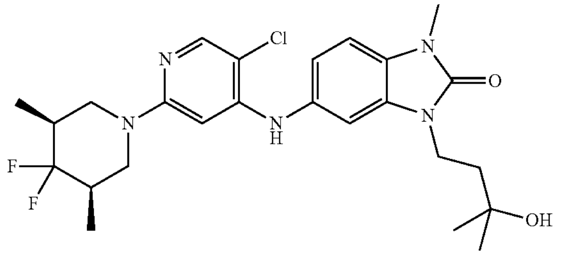
(26c)
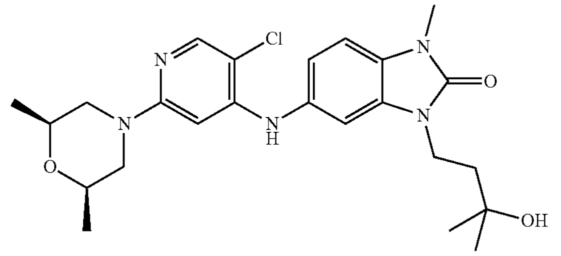
(TMX-2164)
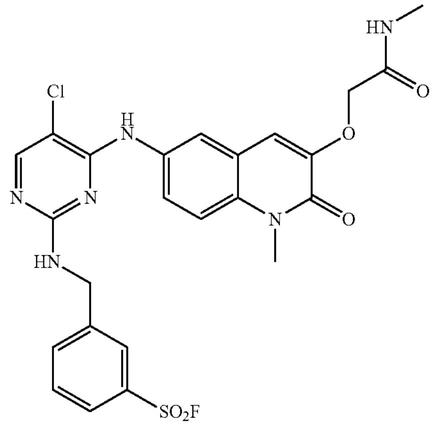
(BC1-1)
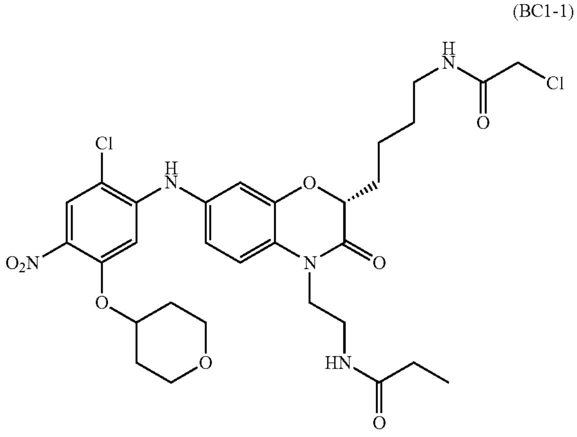

-continued (GSK-137)

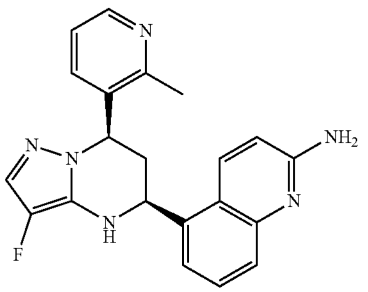

-continued (79-6)

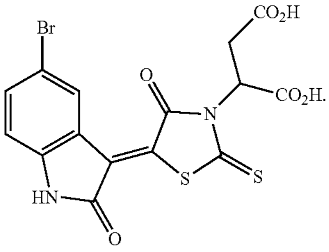

48. The pharmaceutical composition according to any of Embodiments 44 to 47, wherein the second ligand is selected from the group consisting of a CDK9 ligand, a CDK8 ligand and a CDK7 ligand.

49. The pharmaceutical composition according to Embodiment 48, wherein the second ligand is a CDK9 ligand.

50. The TCIP according to Embodiment 49, wherein the CDK9 ligand is selected from the group consisting of:

| Name | Structure |
|---|---|
| SNS-032 | 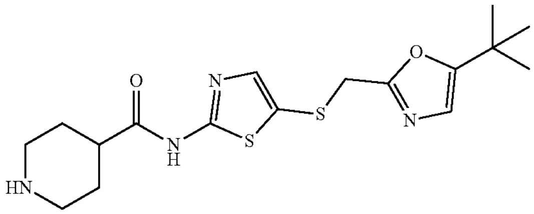 [SMILES: CC(C)(C)c1cnc(CSc2cnc(NC(=O)C3CCNCC3)s2)o1] |
| NVP-2 | 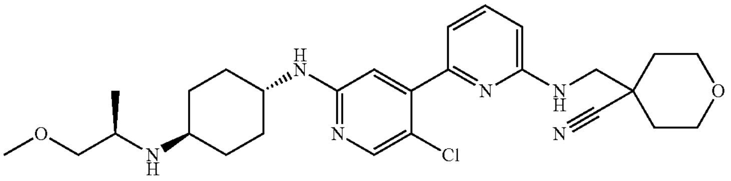 [SMILES: COC[C@@H](C)N[C@H]1CC[C@H](Nc2cc(-c3cccc(NCC4(C#N)CCOCC4)n3)c(Cl)cn2)CC1] |
| KI-ARv-03 | 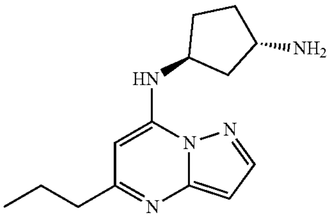 [SMILES: CCCc1cc(N[C@H]2CC[C@H](N)C2)n2nccc2n1] |
| KB-0742 | 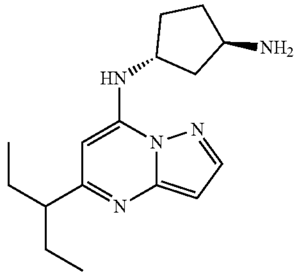 [SMILES: CCC(CC)c1cc(N[C@@H]2CC[C@@H](N)C2)n2nccc2n1] |

-continued
| Name | Structure |
| --- | --- |
| BAY-1143572 | 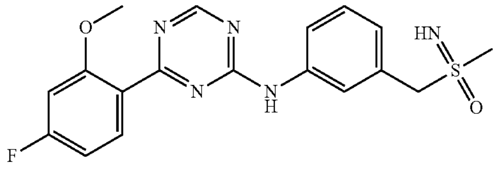 [SMILES: COc1cc(F)ccc1-c1ncnc(Nc2cccc(CS(C)(=N)=O)c2)n1] |
| AZD-4573 | 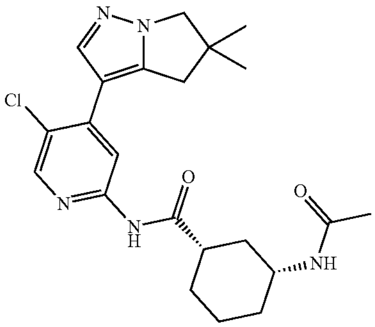 [SMILES: CC(=O)N[C@@H]1CCC[C@H](C(=O)Nc2cc(-c3cnn4c3CC(C)(C)C4)c(Cl)cn2)C1] |
| Alvocidib | 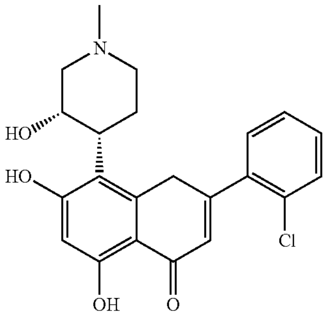 [SMILES: CN1CC[C@H](c2c(O)cc(O)c3c2CC(c2ccccc2Cl)=CC3=O)[C@H](O)C1] |
| TP-1287 | 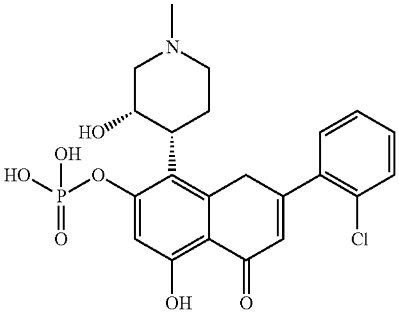 [SMILES: CN1CC[C@H](c2c(OP(=O)(O)O)cc(O)c3c2CC(c2ccccc2Cl)=CC3=O)[C@H](O)C1] |
| Riviciclib | 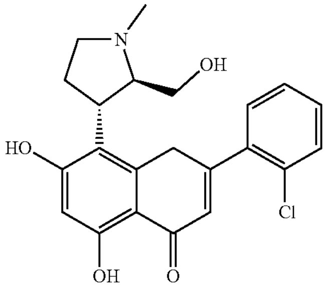 [SMILES: CN1CC[C@@H](c2c(O)cc(O)c3c2CC(c2ccccc2Cl)=CC3=O)[C@@H]1CO] |

-continued
| Name | Structure |
| --- | --- |
| Voruciclib | 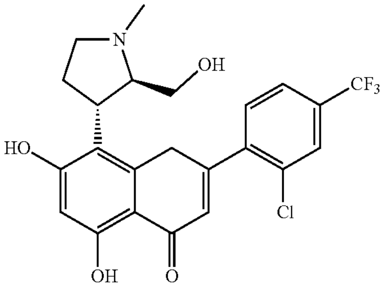 [SMILES: CN1CC[C@@H](c2c(O)cc(O)c3c2CC(c2ccc(C(F)(F)F)cc2Cl)=CC3=O)[C@@H]1CO] |
| ZK-304709 | 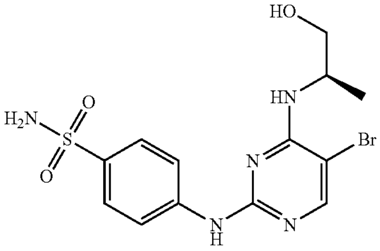 [SMILES: C[C@H](CO)Nc1nc(Nc2ccc(S(N)(=O)=O)cc2)ncc1Br] |
| BAY-1251152 | 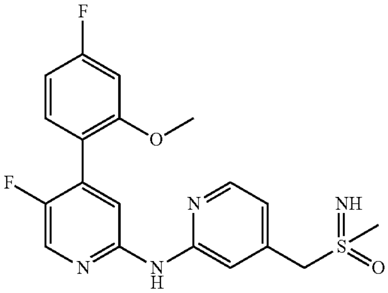 [SMILES: COc1cc(F)ccc1-c1cc(Nc2cc(CS(C)(=N)=O)ccn2)ncc1F] |
| Zotiraciclib (TG-02) | 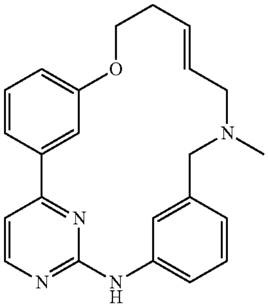 [SMILES: CN1C/C=C/CCOc2cccc(c2)-c2ccnc(n2)Nc2cccc(c2)C1] |
| Seliciclib | 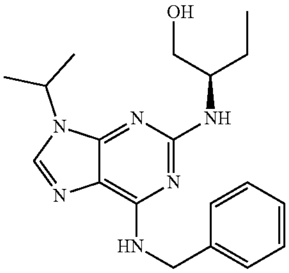 [SMILES: CC[C@H](CO)Nc1nc(NCc2ccccc2)c2ncn(C(C)C)c2n1] |

-continued
| Name | Structure |
|---|---|
| Fadraciclib | 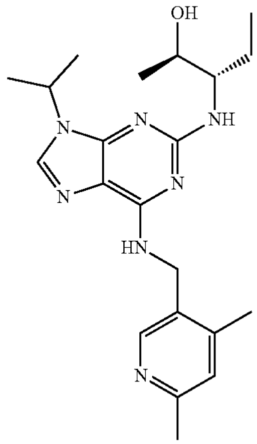 [SMILES: CC[C@H](Nc1nc(NCc2cnc(C)cc2C)c2ncn(C(C)C)c2n1)[C@@H](C)O] |
| Dinaciclib | 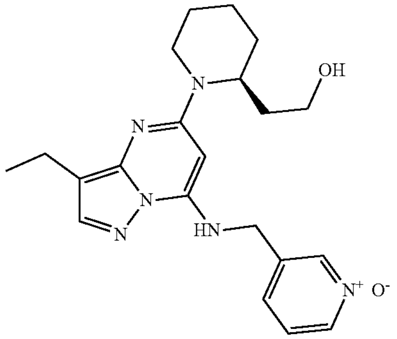 |
| AT7519 | 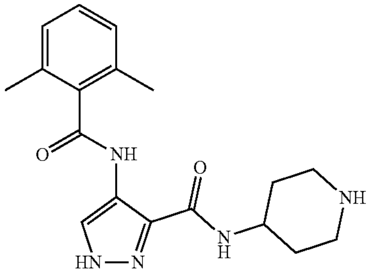 [SMILES: Cc1cccc(C)c1C(=O)Nc1c[nH]nc1C(=O)NC1CCNCC1] |
| BTX-A51 | 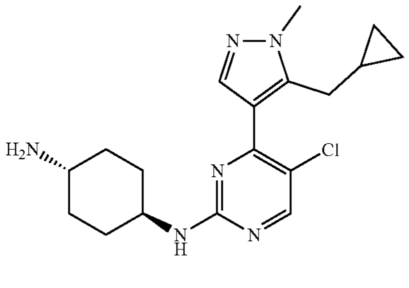 [SMILES: Cn1ncc(-c2nc(N[C@H]3CC[C@H](N)CC3)ncc2Cl)c1CC1CC1] |
| LY2857785 | 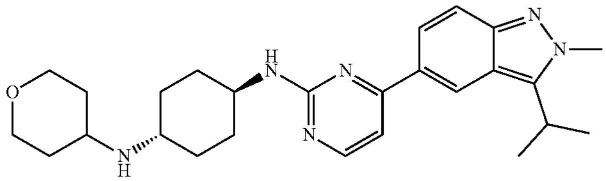 |

51. The pharmaceutical composition according to Embodiment 48, wherein the second ligand is a CDK8 ligand.
52. The pharmaceutical composition according to Embodiment 51, wherein the CDK8 ligand is selected from the group consisting of:
| Name | Structure |
|---|---|
| BI-1347 | 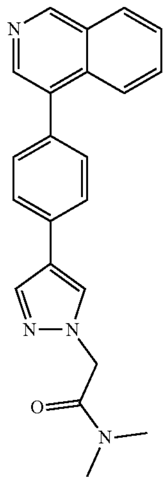 [SMILES: CN(C)C(=O)Cn1cc(-c2ccc(-c3cncc4ccccc34)cc2)cn1] |
| Cortistatin A | 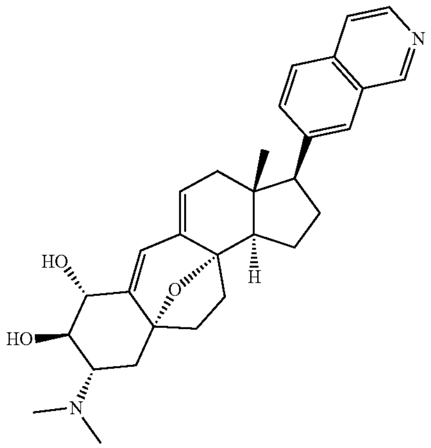 [SMILES: CN(C)[C@H]1C[C@@]23CC[C@@]4(O2)C(=CC[C@]2(C)[C@@H](c5ccc6ccncc6c5)CC[C@H]24)C=C3[C@@H](O)[C@@H]1O] |
| JH-VIII-49 | 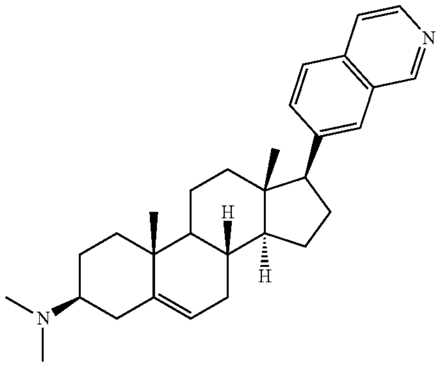 |

-continued
| Name | Structure |
|---|---|
| CCT251545 | 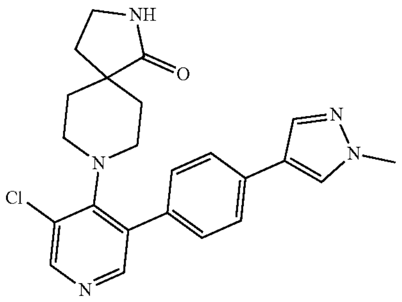 [SMILES: Cn1cc(-c2ccc(-c3cncc(Cl)c3N3CCC4(CCNC4=O)CC3)cc2)cn1] |
| MSC253818 | 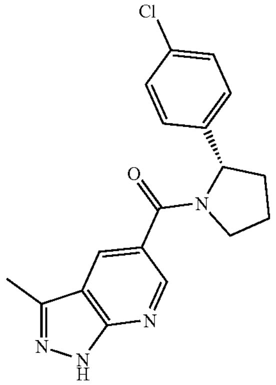 [SMILES: Cc1n[nH]c2ncc(C(=O)N3CCC[C@H]3c3ccc(Cl)cc3)cc12] |
| Senexin C | 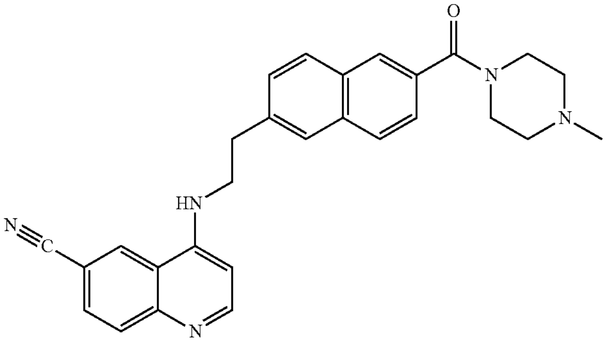 [SMILES: CN1CCN(C(=O)c2ccc3cc(CCNc4ccnc5ccc(C#N)cc45)ccc3c2)CC1] |
| Sel 120-34A | 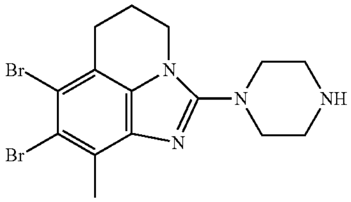 [SMILES: Cc1c(Br)c(Br)c2c3c1nc(N1CCNCC1)n3CCC2] |

-continued
| Name | Structure |
| --- | --- |
| W-34 | 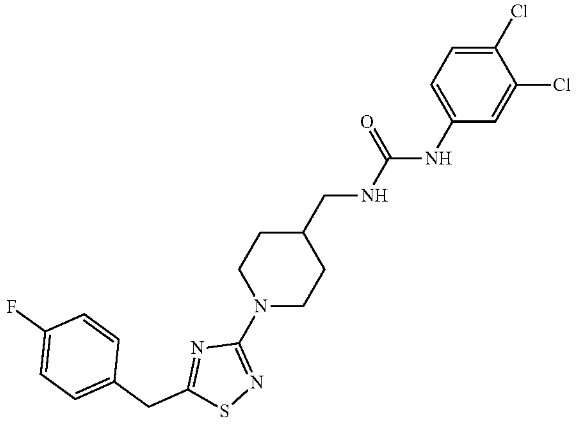 [SMILES: O=C(NCC1CCN(c2nsc(Cc3ccc(F)cc3)n2)CC1)Nc1ccc(Cl)c(Cl)c1] |
| T-814 | 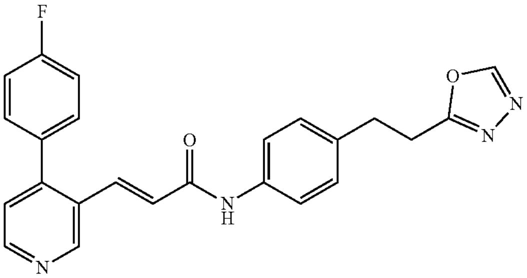 [SMILES: O=C(/C=C/c1cnccc1-c1ccc(F)cc1)Nc1ccc(CCc2nnco2)cc1] |
53. The pharmaceutical composition according to Embodiment 48, wherein the second ligand is a CDK7 ligand.
54. The pharmaceutical composition according to Embodiment 53, wherein the CDK7 ligand is selected from the group consisting of:
| Name | Structure |
| --- | --- |
| BS-181 | 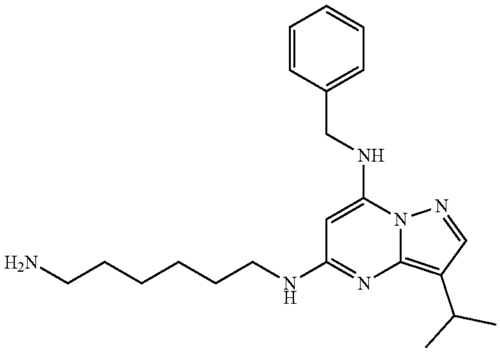 [SMILES: CC(C)c1cnn2c(NCc3ccccc3)cc(NCCCCCCN)nc12] |

-continued
| Name | Structure |
| --- | --- |
| CT7001 | 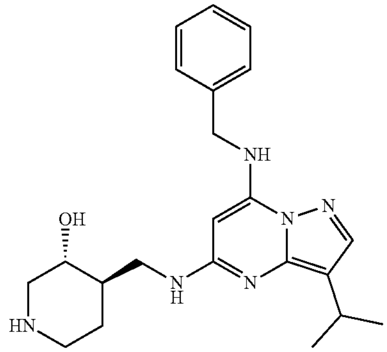 [SMILES: CC(C)c1cnn2c(NCc3ccccc3)cc(NC[C@H]3CCNC[C@@H]3O)nc12] |
| THZ2 | 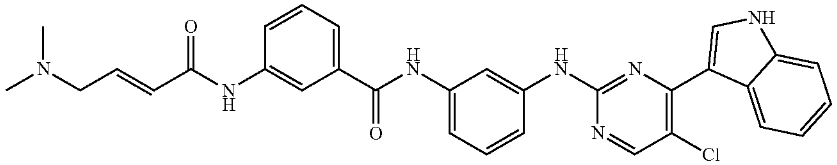 [SMILES: CN(C)C/C=C/C(=O)Nc1cccc(C(=O)Nc2cccc(Nc3ncc(Cl)c(-c4c[nH]c5ccccc45)n3)c2)c1] |
| THZ2 reversible compound | 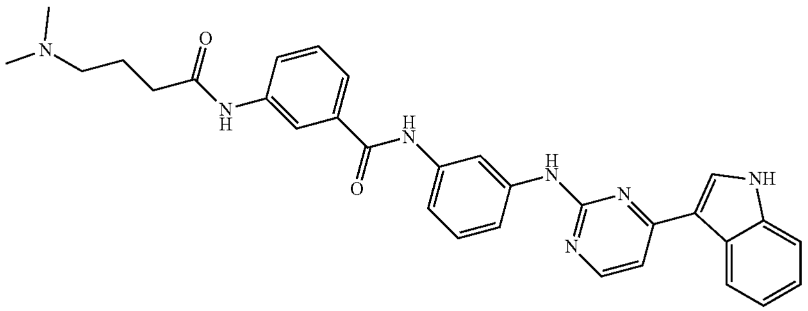 [SMILES: CN(C)CCCC(=O)Nc1cccc(C(=O)Nc2cccc(Nc3nccc(-c4c[nH]c5ccccc45)n3)c2)c1] |
| YKL-1-116 | 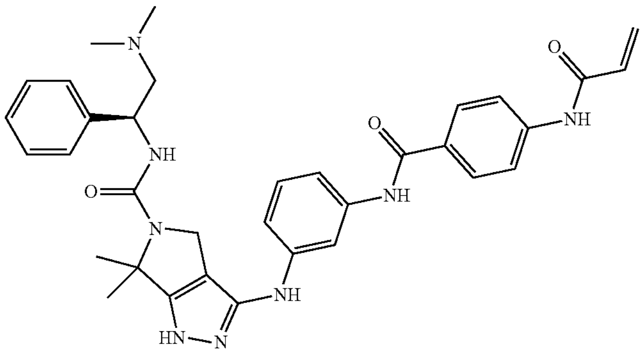 [SMILES: C=CC(=O)Nc1ccc(C(=O)Nc2cccc(Nc3n[nH]c4c3CN(C(=O)N[C@H](CN(C)C)c3ccccc3)C4(C)C)c2)cc1] |
| YKL-5-124 | |
| YKL-5-124 Reversible compound | |
| SY-1365 and the reversible compound thereof (structure not shown) | 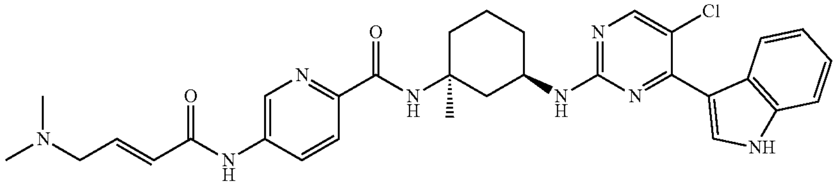 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)nc1] |

-continued
| Name | Structure |
| --- | --- |
| SY5609 | 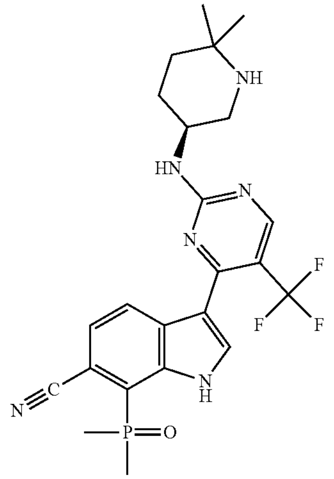 [SMILES: CC1(C)CC[C@H](Nc2ncc(C(F)(F)F)c(-c3c[nH]c4c(P(C)(C)=O)c(C#N)ccc34)n2)CN1] |
| LY3405105 and the reversible compound thereof (structure no shown) | 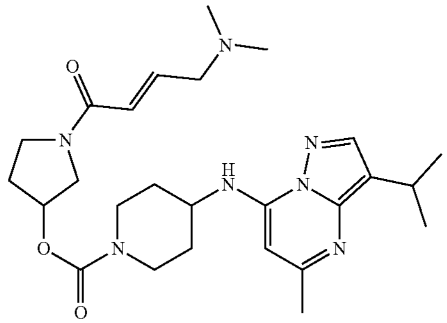 [SMILES: Cc1cc(NC2CCN(C(=O)OC3CCN(C(=O)/C=C/CN(C)C)C3)CC2)n2ncc(C(C)C)c2n1] |
| LDC4279 | 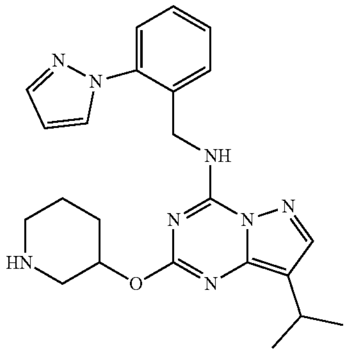 [SMILES: CC(C)c1cnn2c(NCc3ccccc3-n3cccn3)nc(OC3CCCNC3)nc12] |
55. The pharmaceutical composition according to any of Embodiments 44 to 54, wherein the first ligand and second ligand are linked to each other by a linker.
56. The pharmaceutical composition according to Embodiment 55, wherein the linker is selected from the group consisting of:
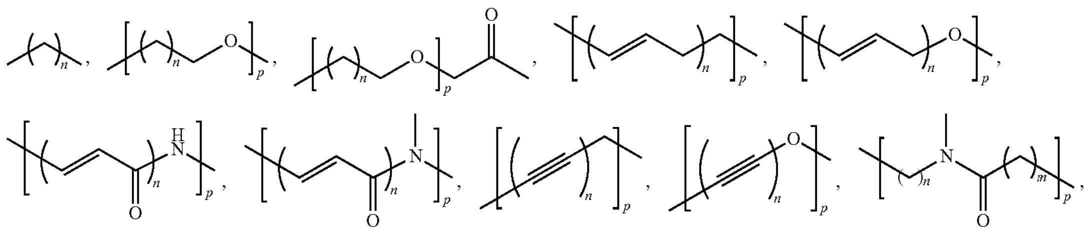

-continued
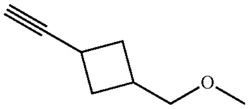,
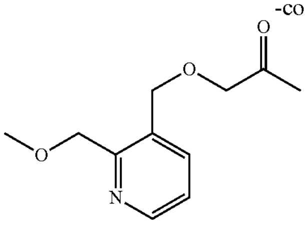,
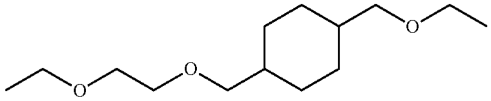,
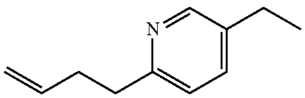,
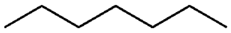,
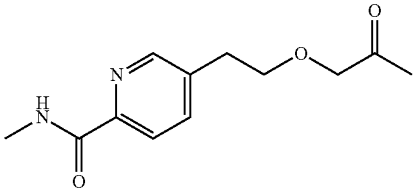,
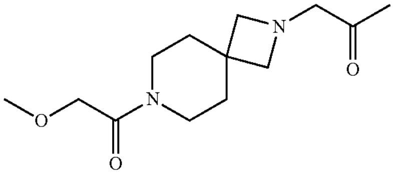,
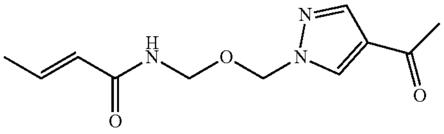,
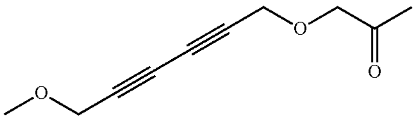,
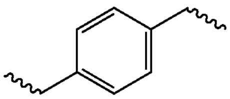,
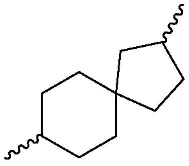,
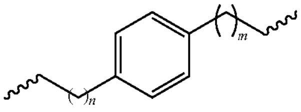,
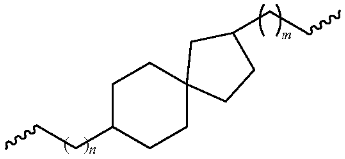,
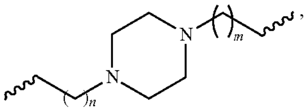,
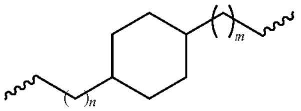,
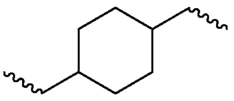,
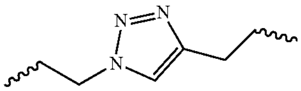,
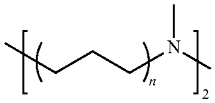,
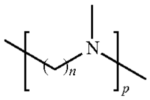,
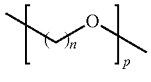,
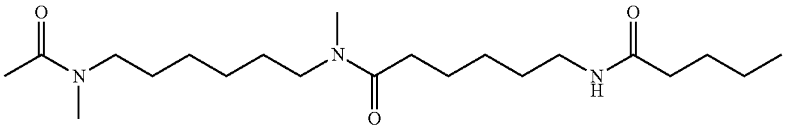,
,
where m, n and p are independently selected from 0 or an integer of from 1-12. 57. The pharmaceutical composition according to any of Embodiments 44 to 56, wherein the TCIP has a molecular weight ranging from 300 to 1200 g/mole. 58. The pharmaceutical composition according to Embodiment 57, wherein TCIP is selected from the group consisting of:
BAK-04-023
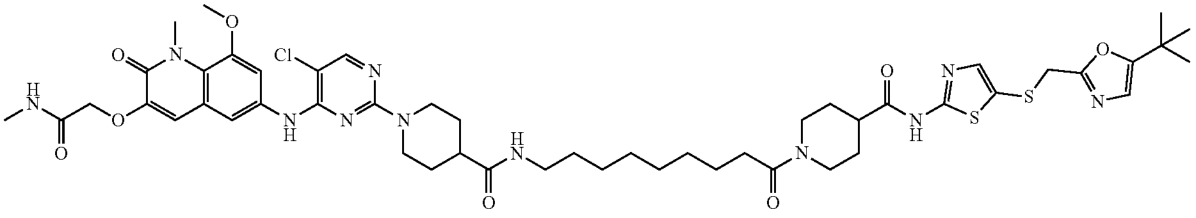

-continued
BAK-04-022
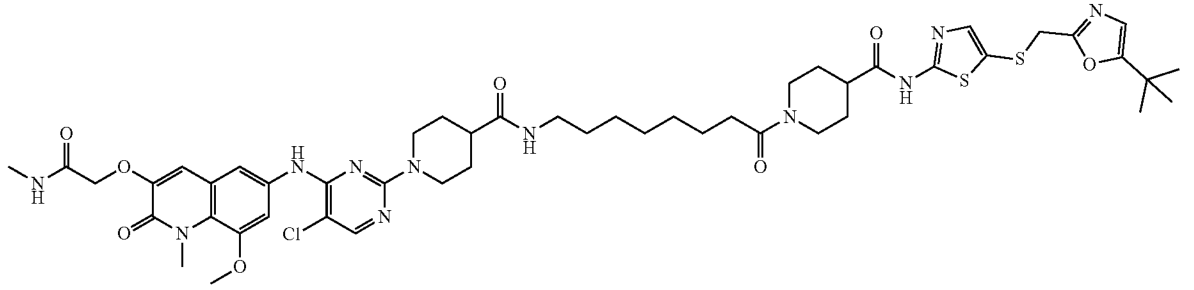
BAK-04-021
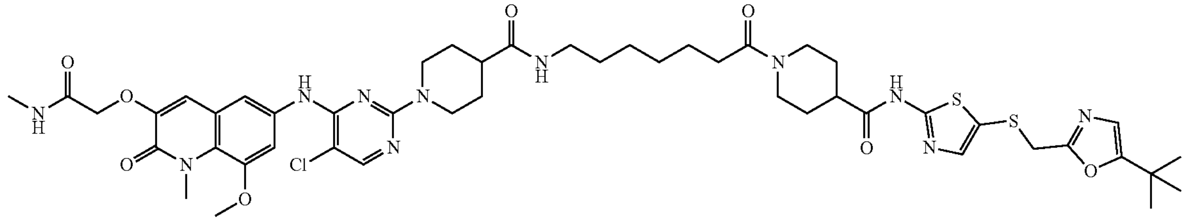
BAK-04-028
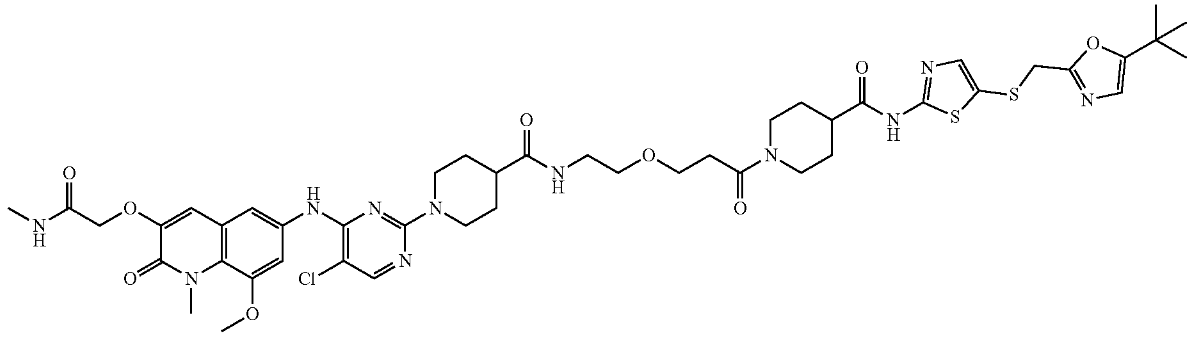
BAK-04-029
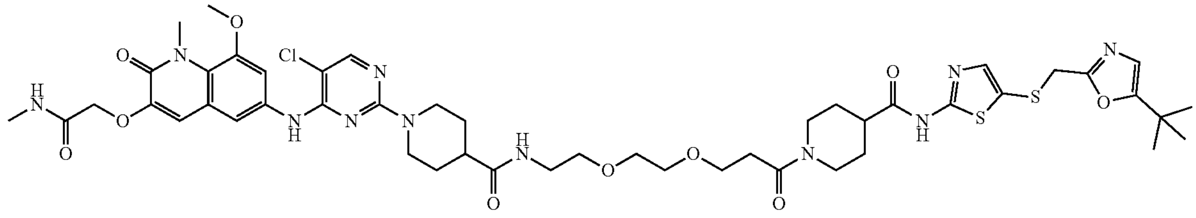
BAK-04-030
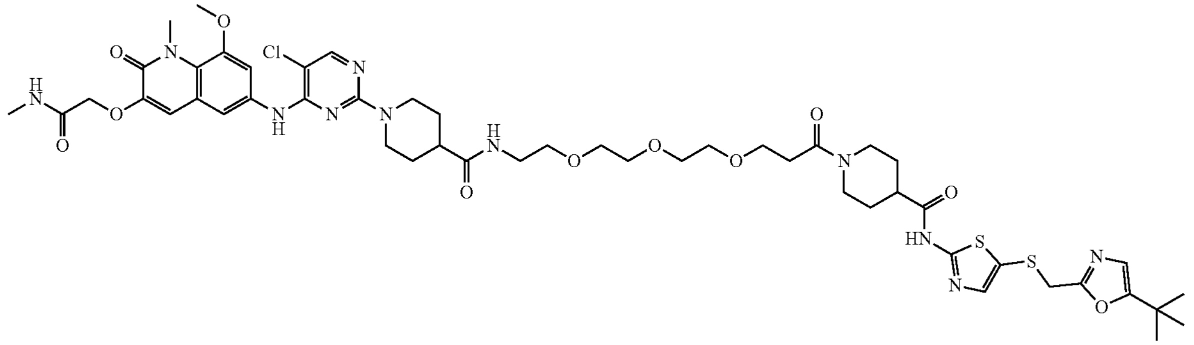

-continued
BAK-04-016
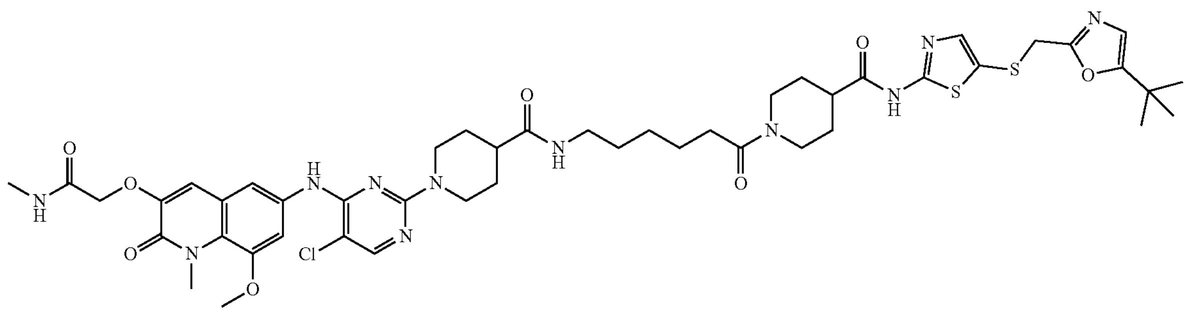
BAK-04-015
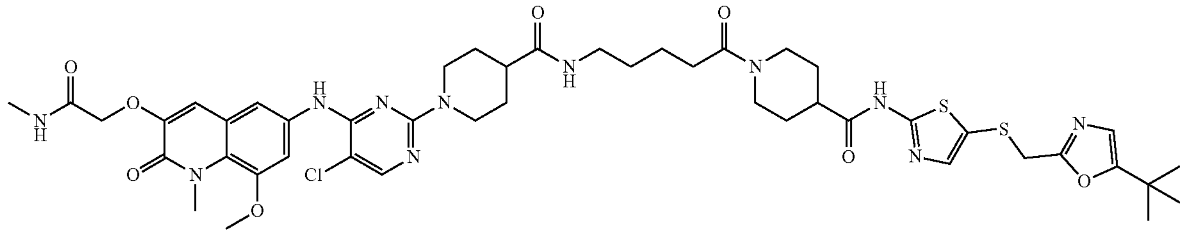
BAK-04-014
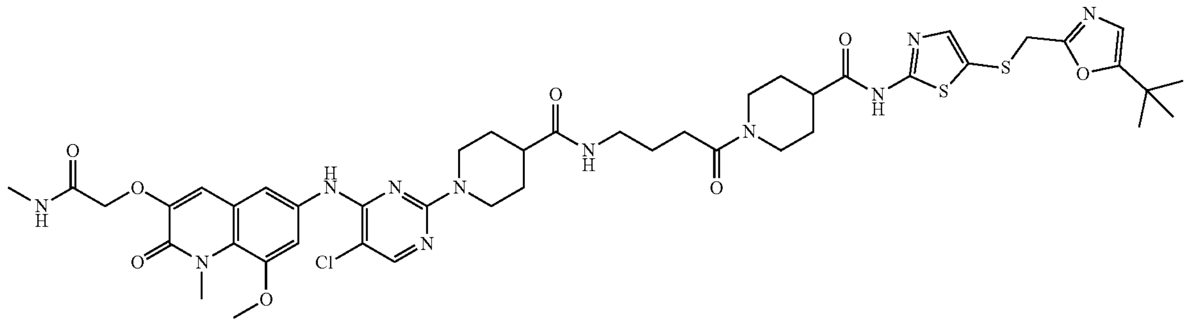
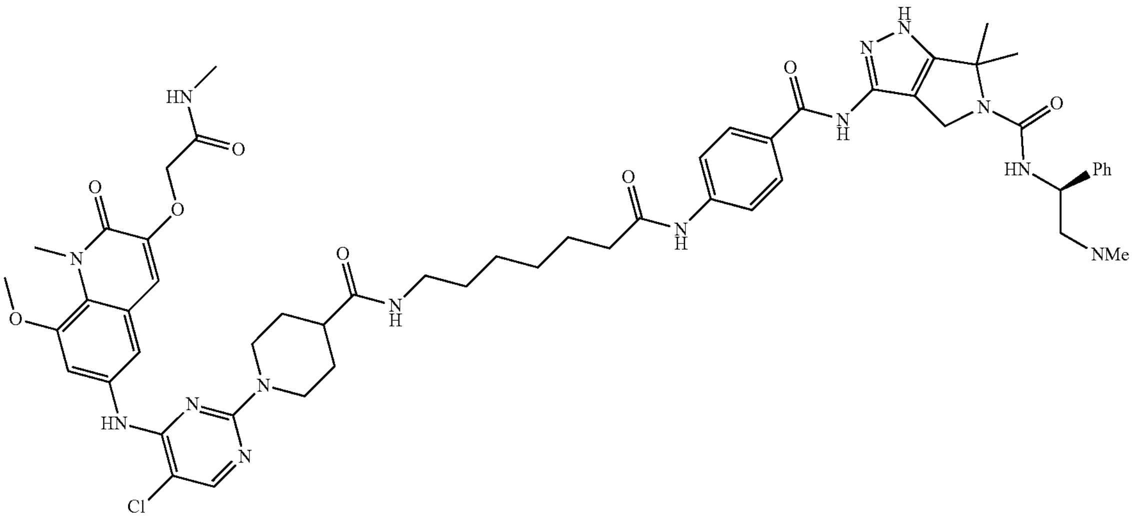

-continued
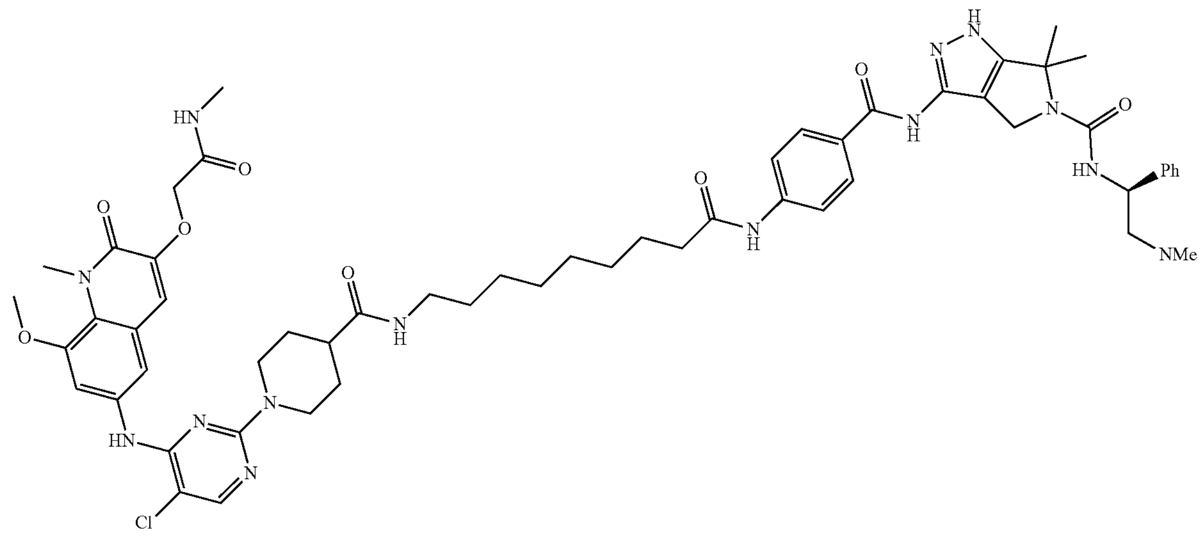
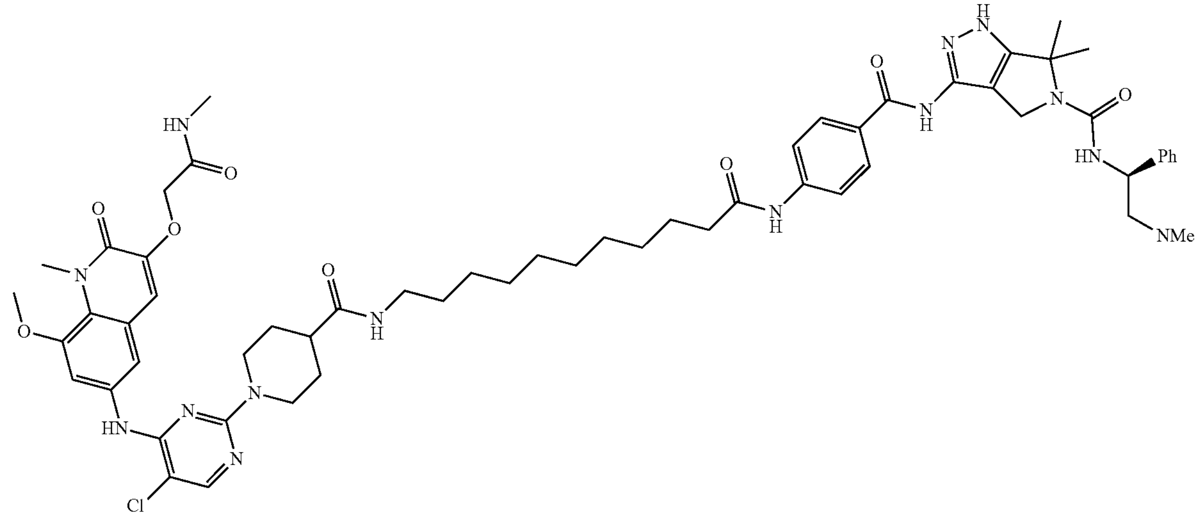
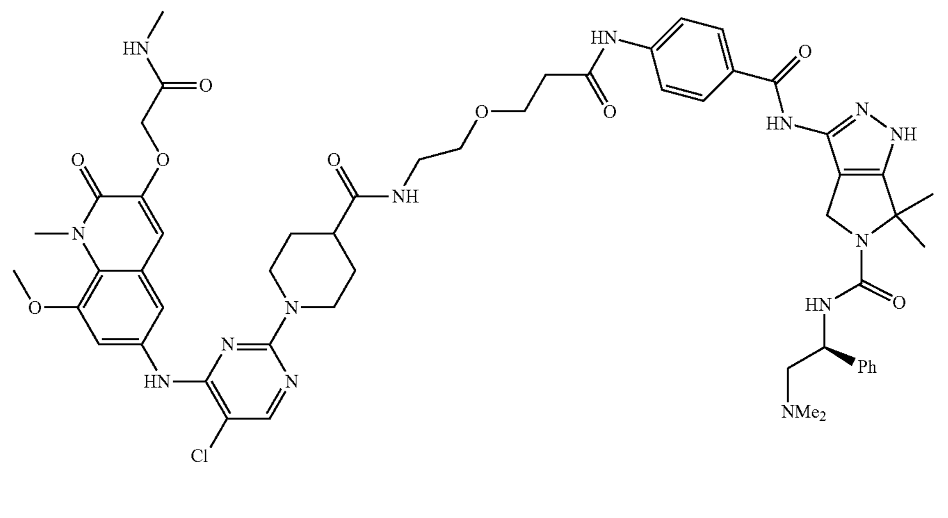

-continued
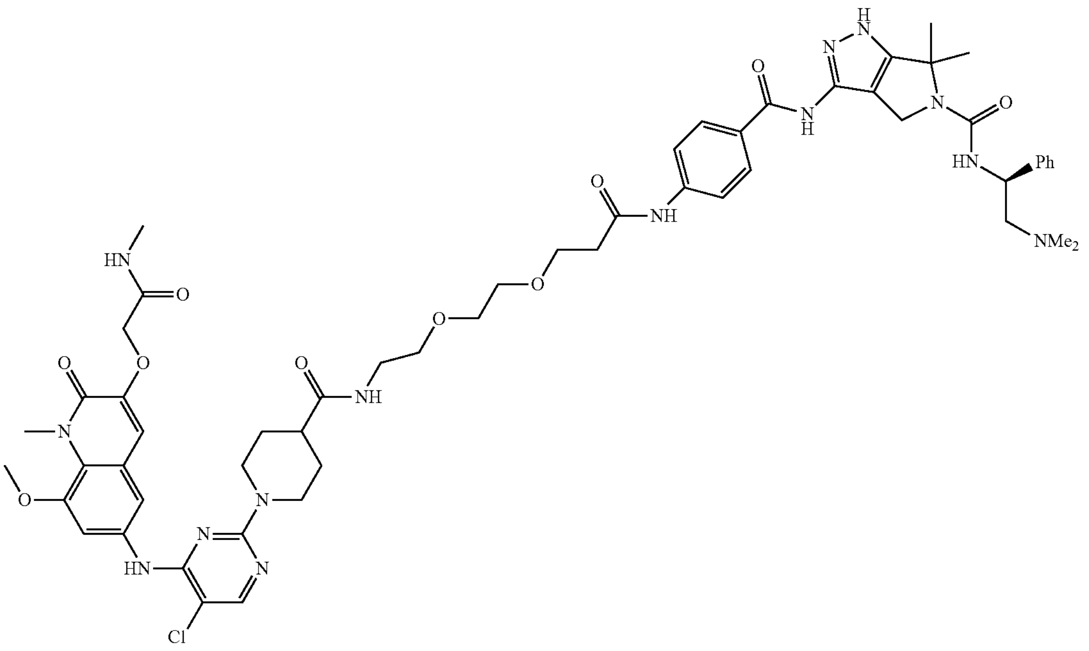
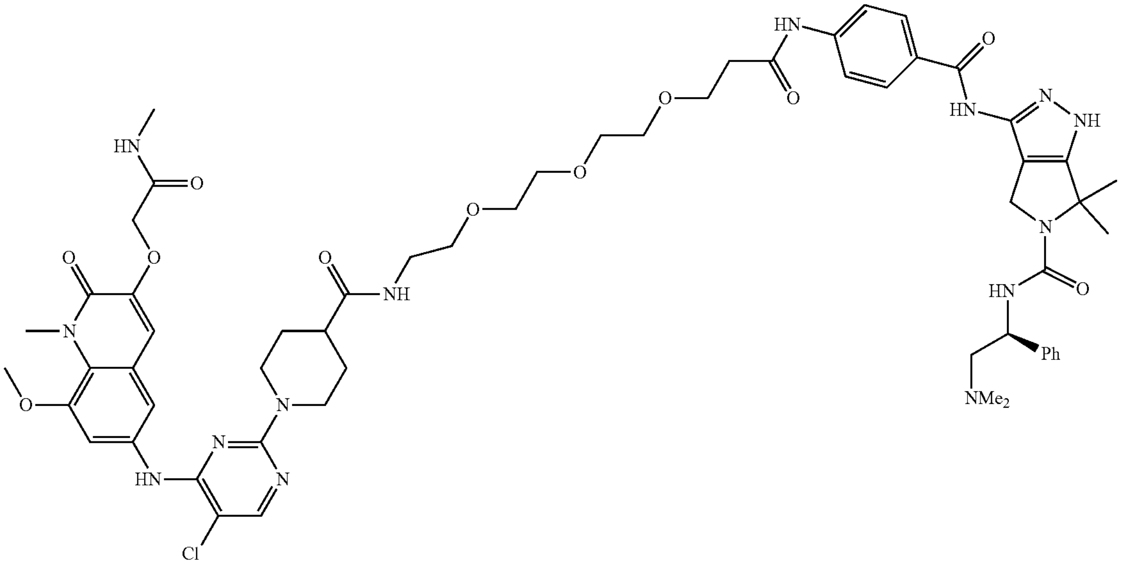
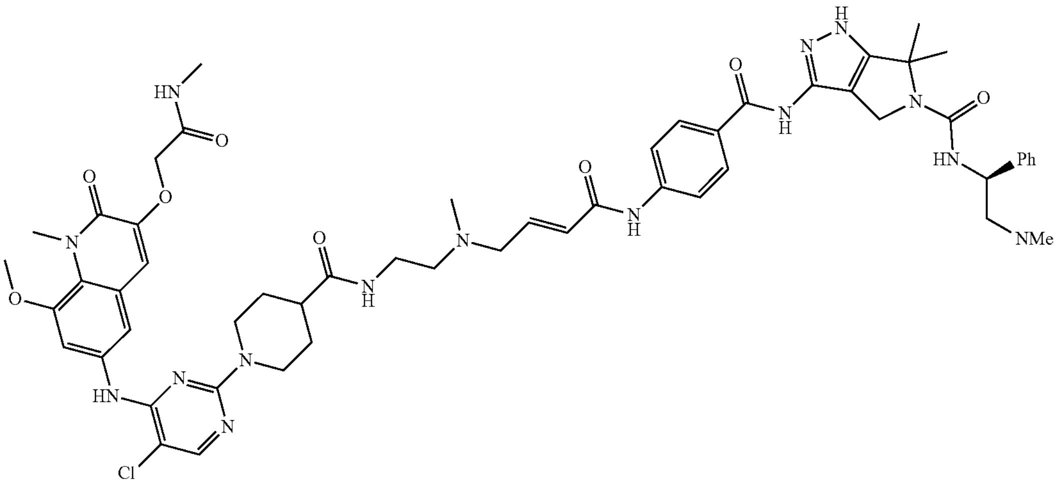

-continued

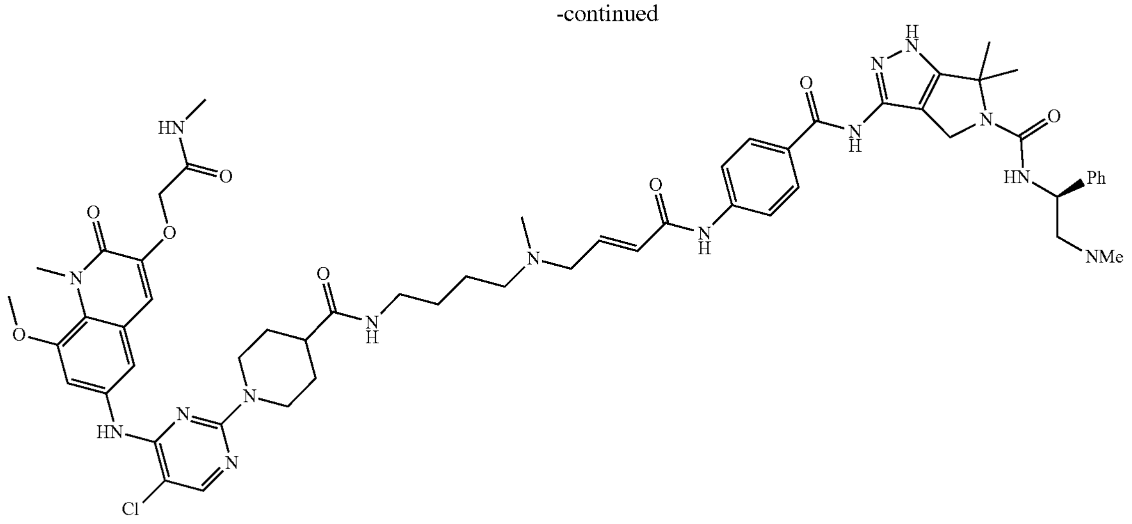

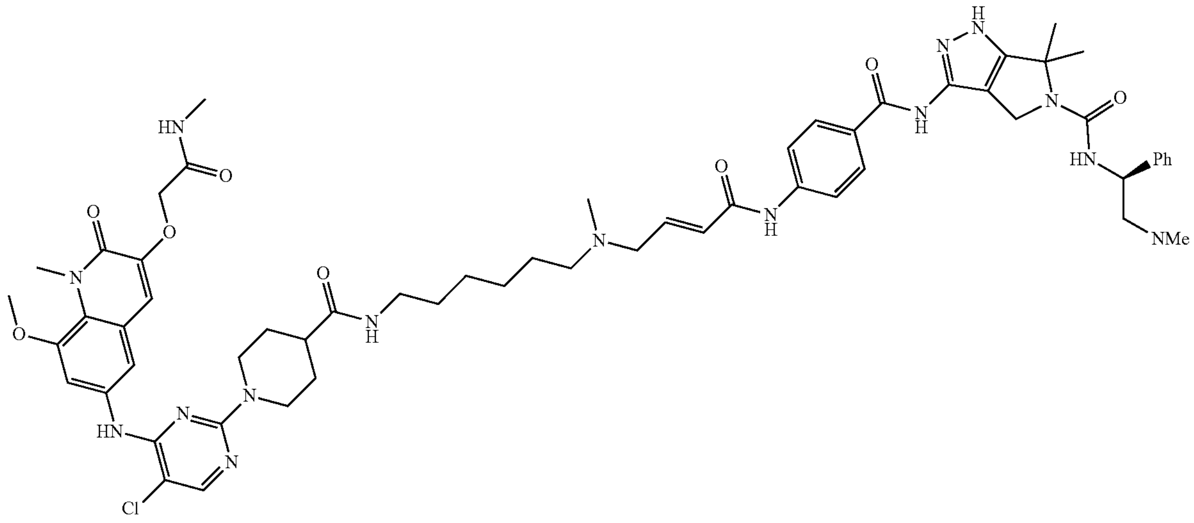

59. The pharmaceutical composition according to any of Embodiments 44 to 58, wherein the pharmaceutical composition is configured for intravenous delivery.

AR Ligand Embodiments

1. A method of treating a subject for a malignancy, the method comprising:
   administering to the subject an effective amount of a transcriptional chemical inducer of proximity (TCIP) which links BCL-6 (or a homologue thereof) and an androgen receptor (AR) to treat the subject for the malignancy.

2. The method according to Embodiment 1, wherein the TCIP comprises a first ligand that specifically binds to BCL-6 (or a homologue thereof) covalently linked to a second ligand that specifically binds to an AR.

3. The method according to Embodiment 2, wherein binding of the second ligand to the AR does not substantially reduce the transcription-activating activity of BCL-6 (or a homologue thereof).

4. The method according to Embodiment 3, wherein the first ligand is selected from the group consisting of:

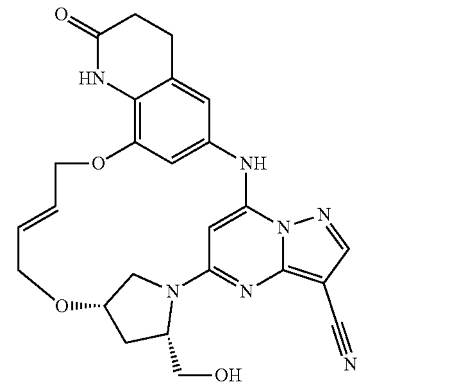
11
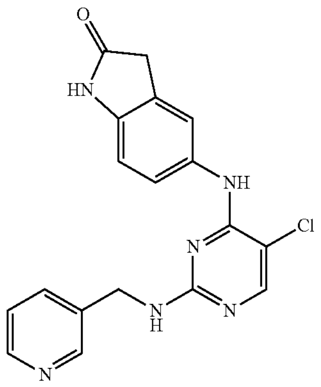
7
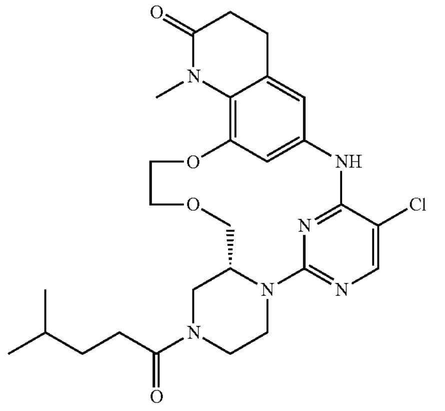
14
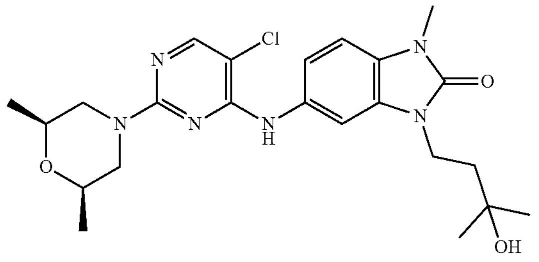
25a
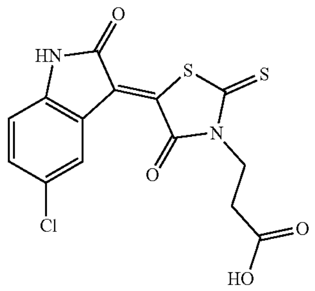
FX1
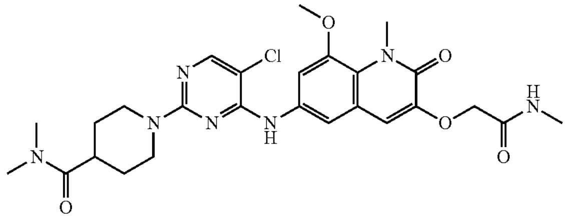
BI-3812
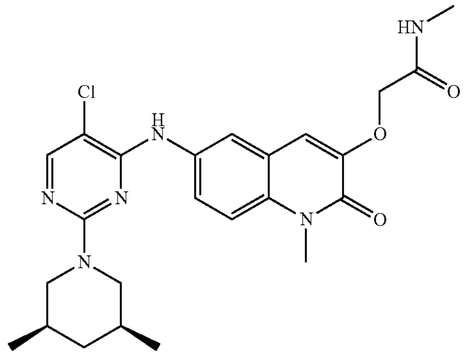
(BI-3802)

-continued
(14)
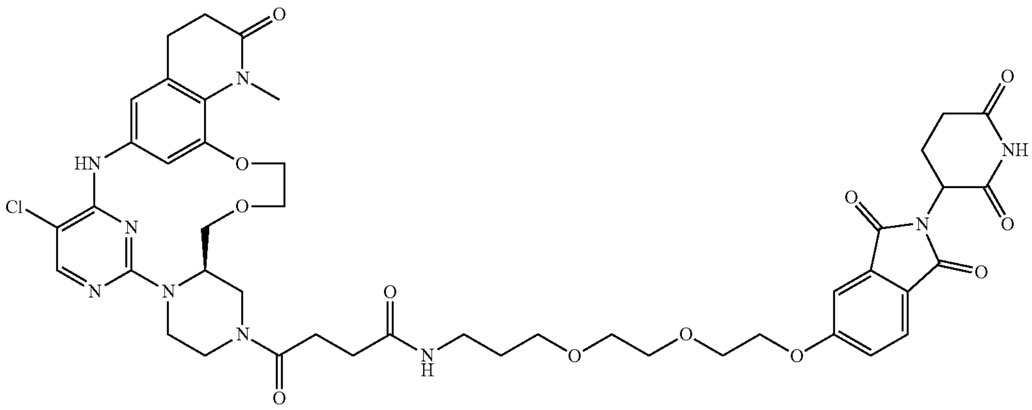
(6)
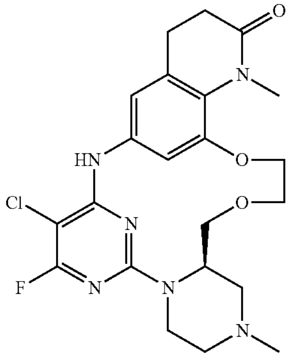
(CCT369347)
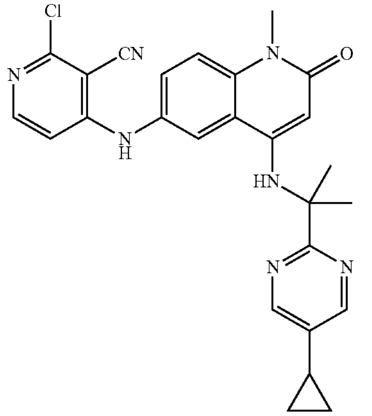
(CCT372064)
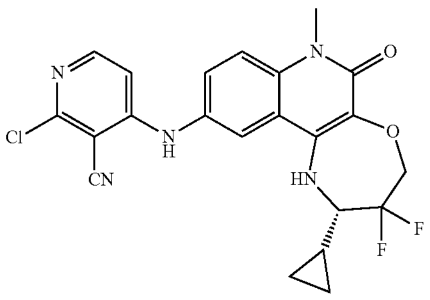
(CCT37566)
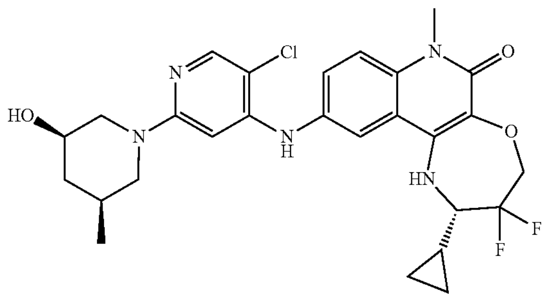
(CCTT369260)
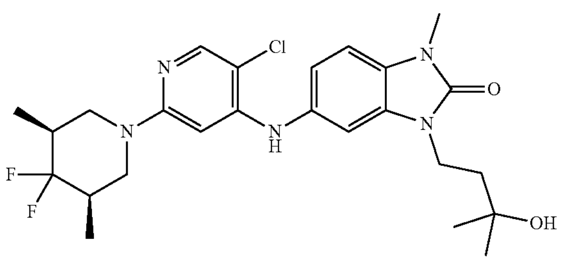
(26c)
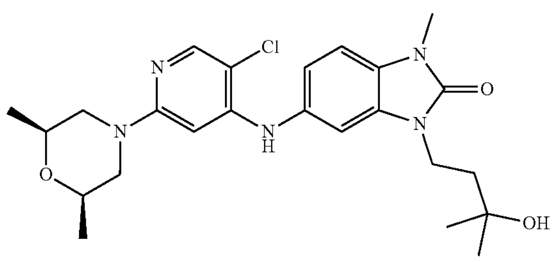

-continued (TMS-2164)

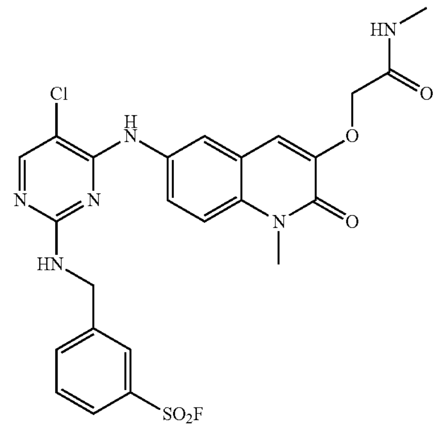

(BC1-1)

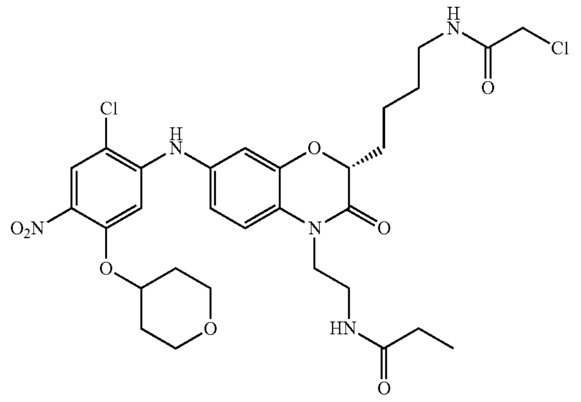

(GSK-137)

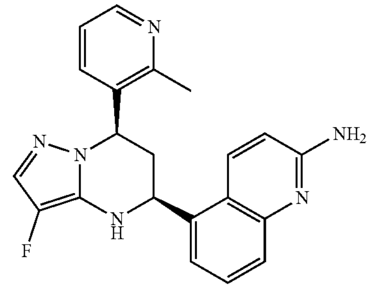

(79-6)

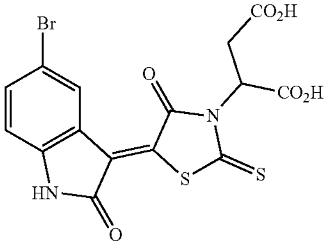

5. The method according to any of Embodiments 2 to 4, wherein the second ligand comprises an AR agonist.

6. The method according to Embodiment 5, wherein the AR agonist comprises a steroidal AR agonist.

7. The method according to Embodiment 6, wherein the steroidal AR agonist is selected from the group consisting of:

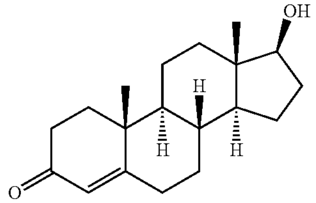

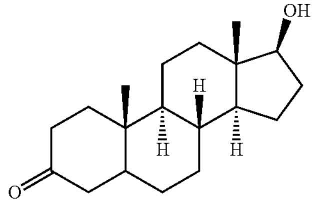

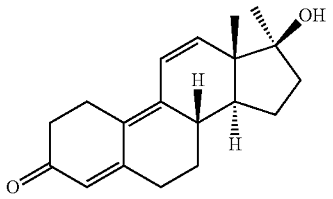

-continued

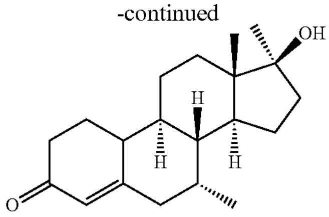

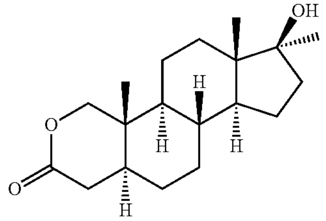

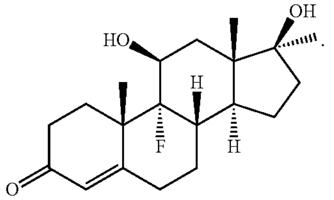

8. The method according to Embodiment 5, wherein the AR agonist comprises a non-steroidal agonist.

9. The method according to Embodiment 8, wherein the AR agonist is selected from the group consisting of:

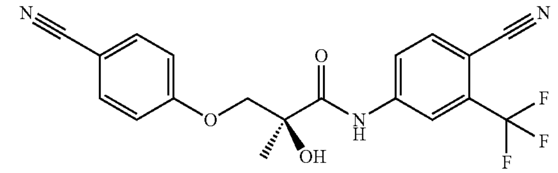

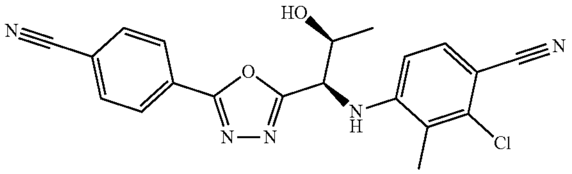

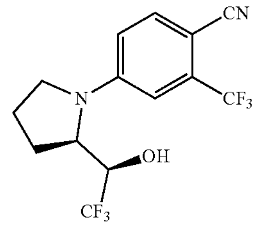

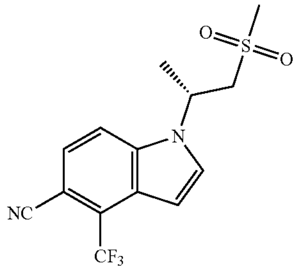

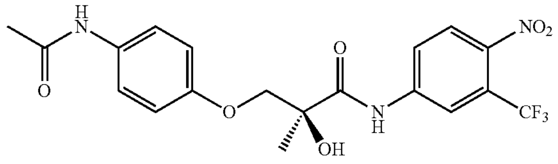

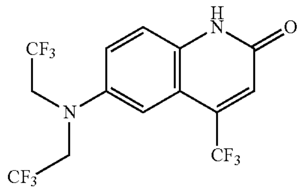

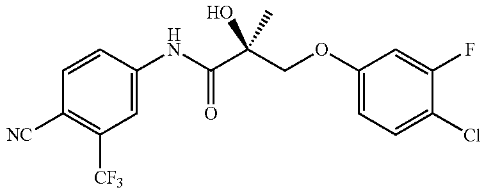

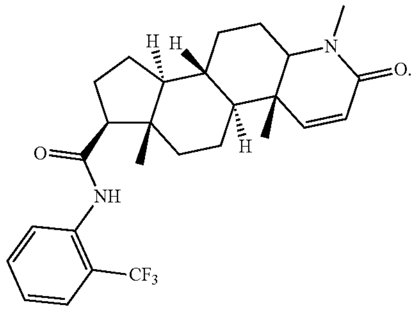

10. The method according to Embodiments 2 to 4, wherein the second ligand comprises an AR antagonist.

11. The method according to Embodiment 10, wherein the AR antagonist comprises a non-steroidal AR antagonist.

12. The method according to Embodiment 11, wherein the non-steroidal AR antagonist is selected from the group consisting of:

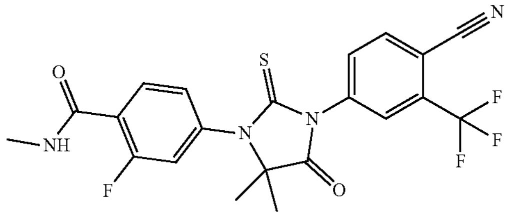

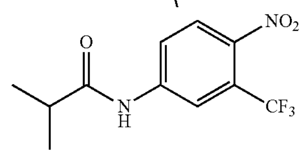

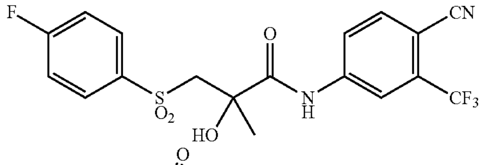

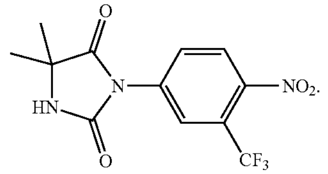

13. The method according to Embodiment 10, wherein the AR antagonist comprises a steroidal AR antagonist.

14. The method according to Embodiment 13, wherein the steroidal AR antagonist is selected from the group consisting of:

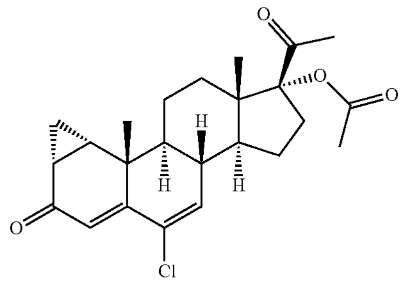

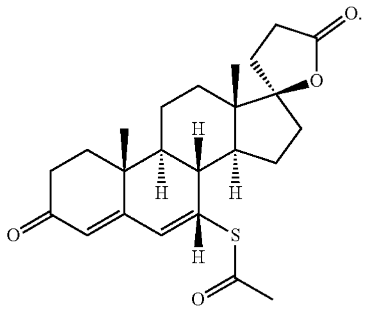

15. The method according to any of Embodiments 2 to 14, wherein the first ligand and second ligand are linked to each other by a linker.

16. The method according to Embodiment 15, wherein the linker is selected from the group consisting of:

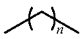, 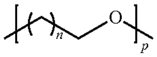, 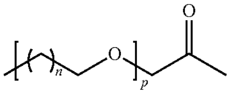, 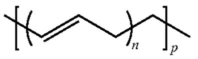, 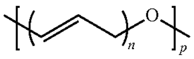,
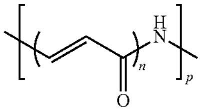, 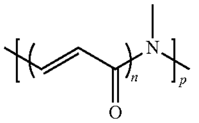, 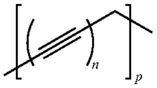, 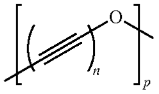, 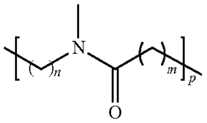,
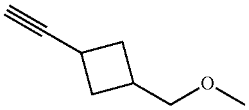, 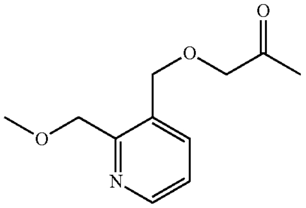, 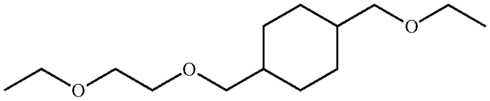,
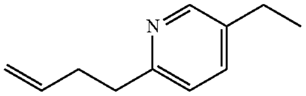, 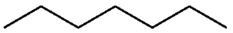, 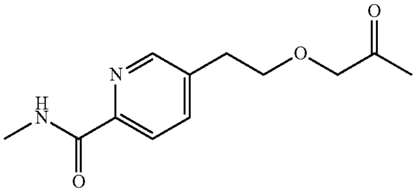,
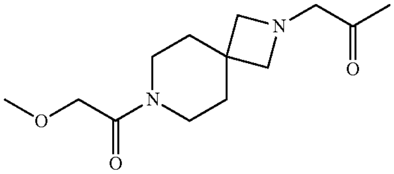, 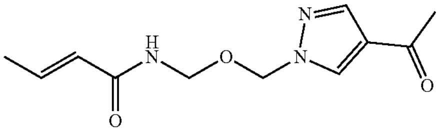,
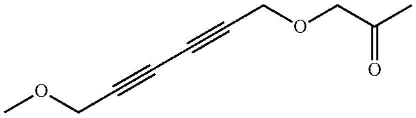, 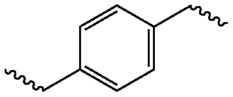, 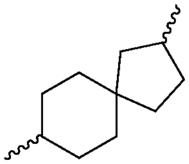,
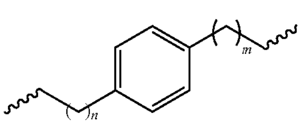, 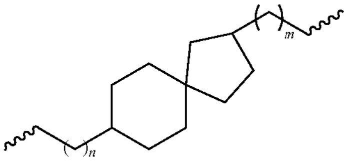, 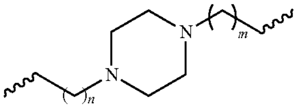,
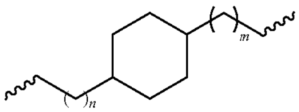, 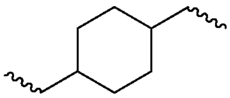, 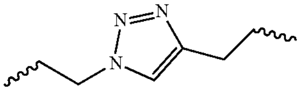, 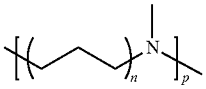,
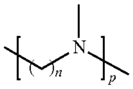, 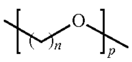, 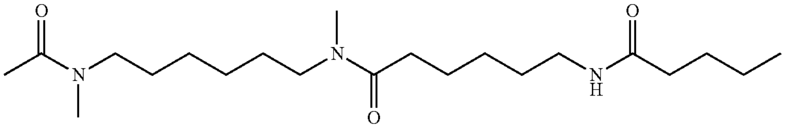,
,
where m, n and p are independently selected from 0 or an integer of from 1-12.
17. The method according to any of the preceding embodiments, wherein the TCIP is selected from the group consisting of:

BAK-04-083 (C2)
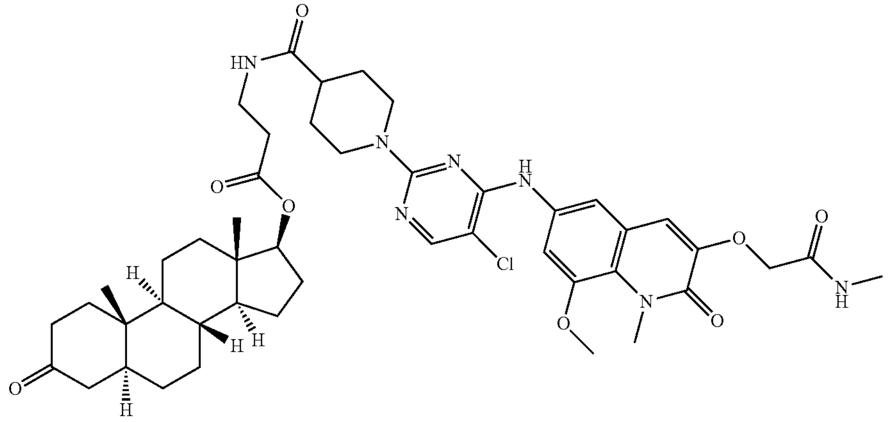
RCS-02-063 (C3)
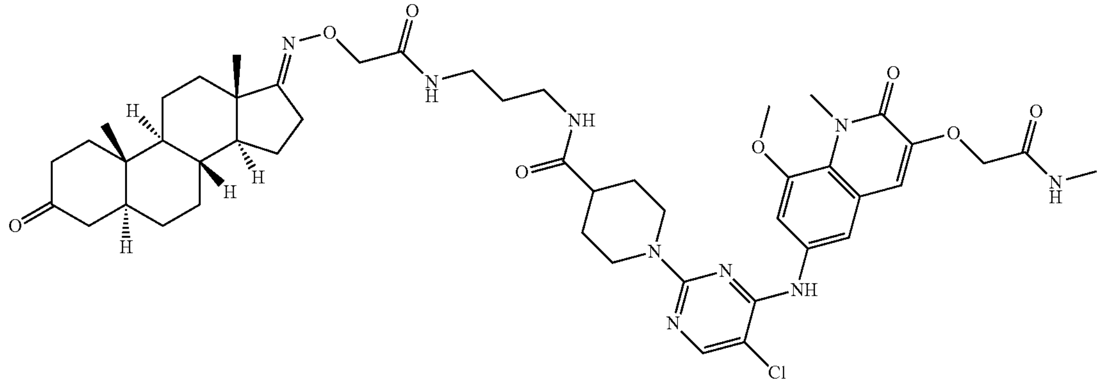
RCS-02-093 (C4)
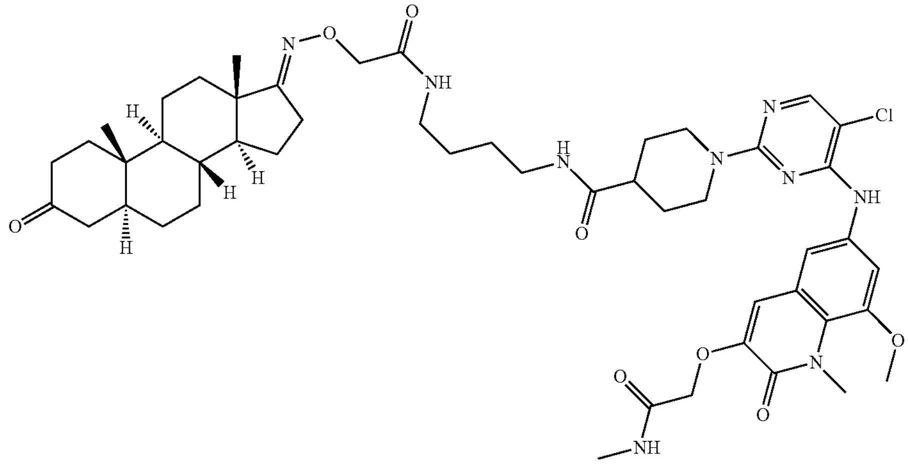
BAK-04-003 (C5)
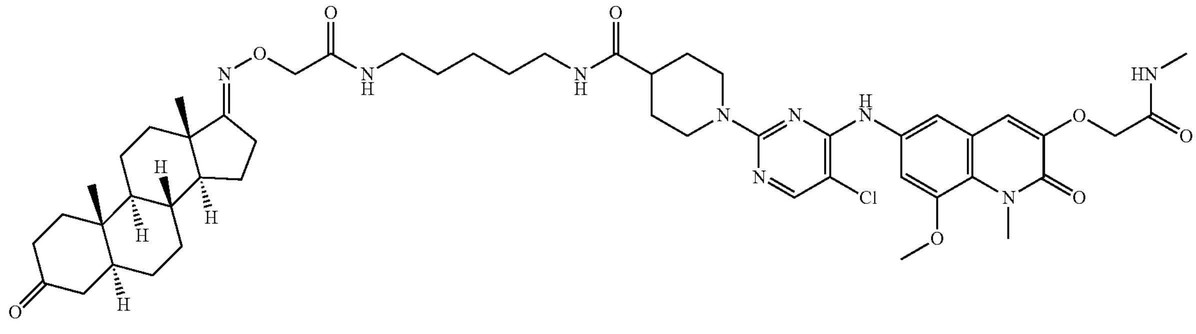

-continued
RCS-02-085 (C6)
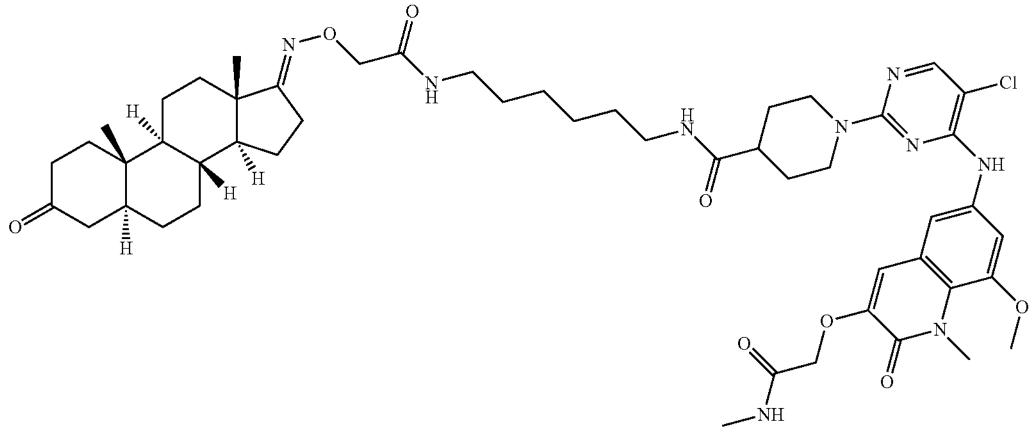
BAK-04-006 (C8)
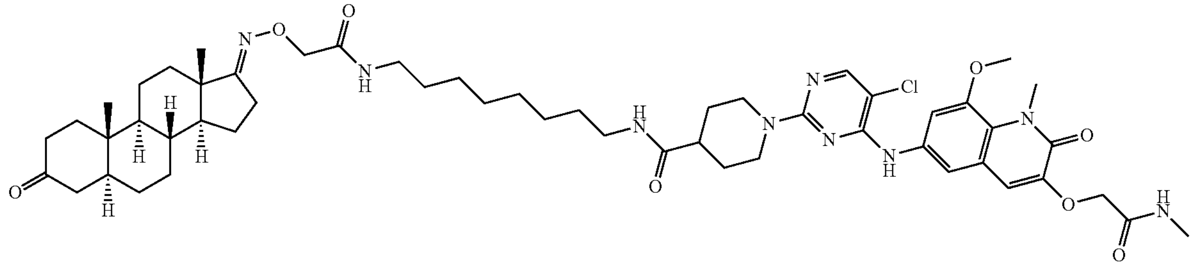
RCS-02-060 (peg1)
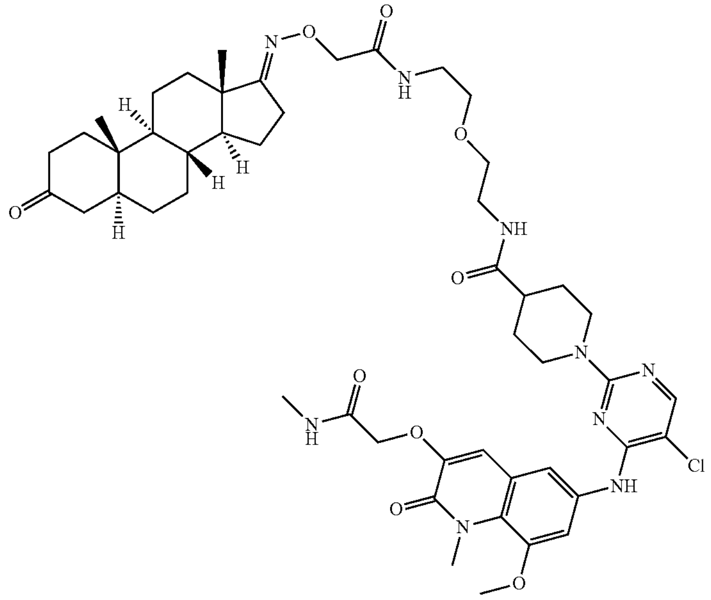

-continued
RCS-02-058 (peg2)
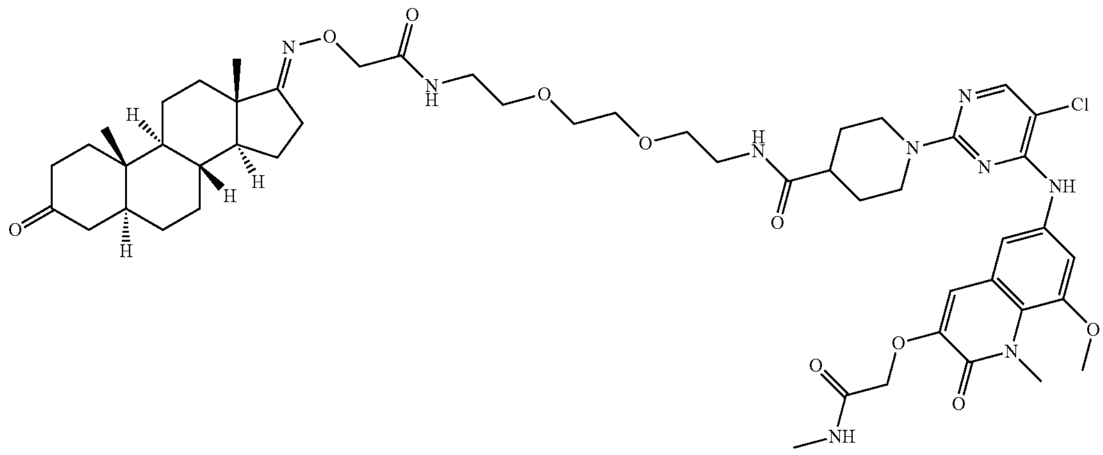
RCS-02-061 (peg3)
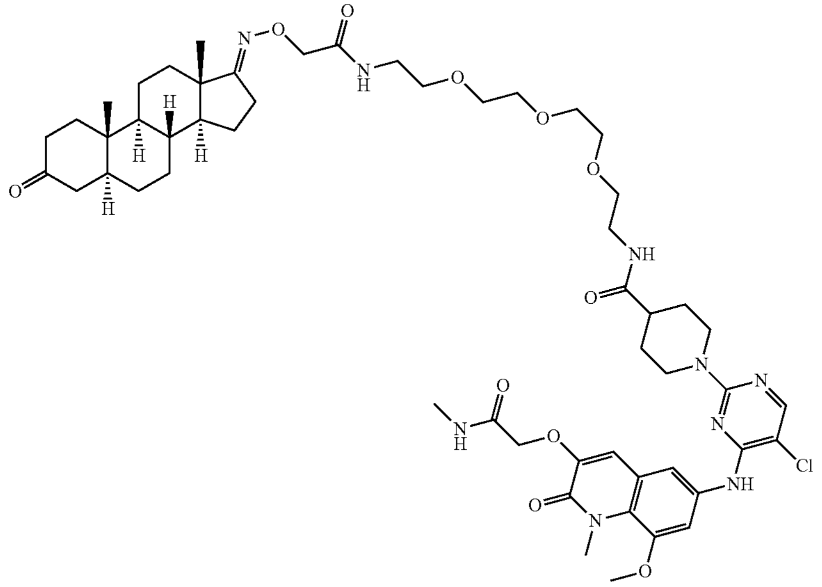
RCS-02-062 (peg4)
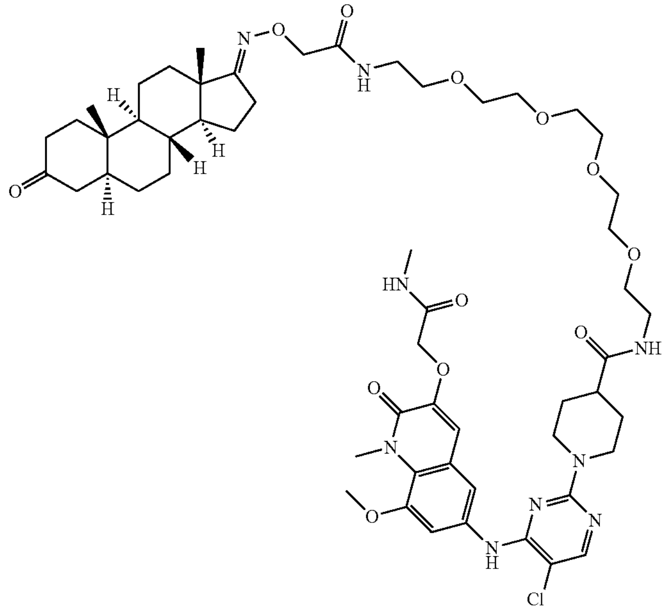

-continued
BAK-04-039
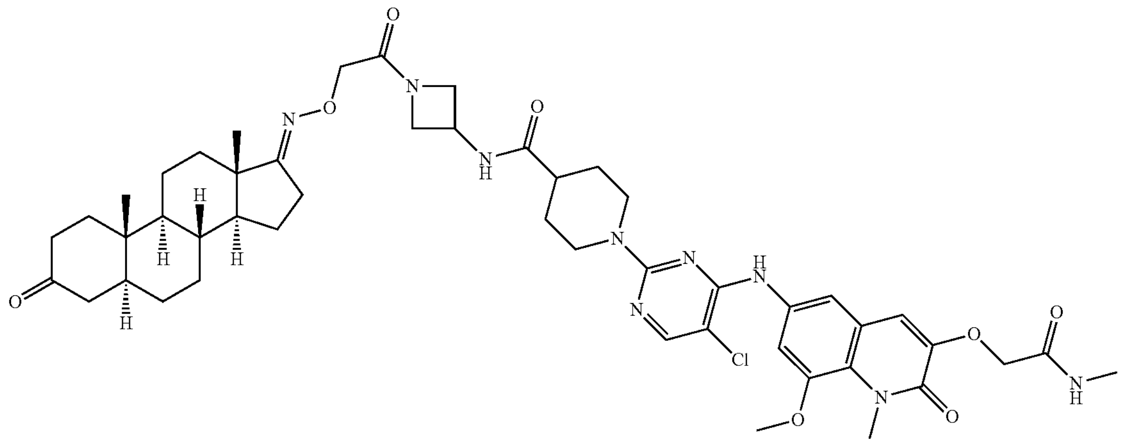
BAK-04-083
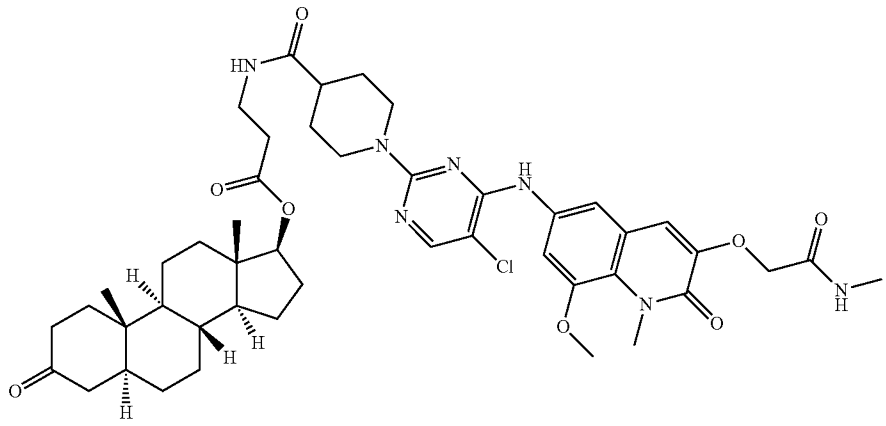
BAK-04-084
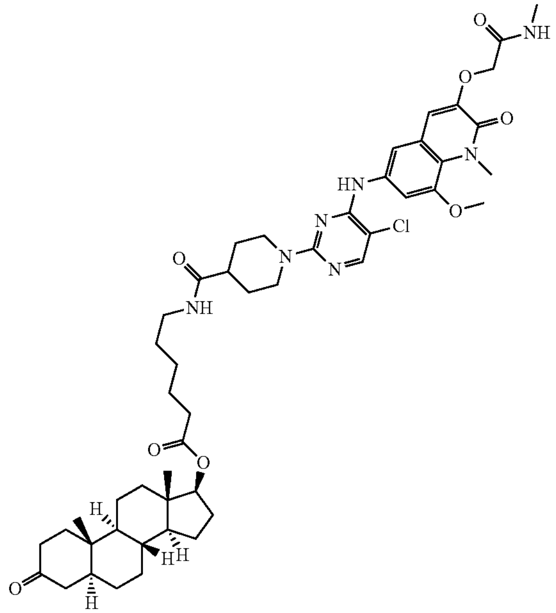

-continued

RCS-02-160

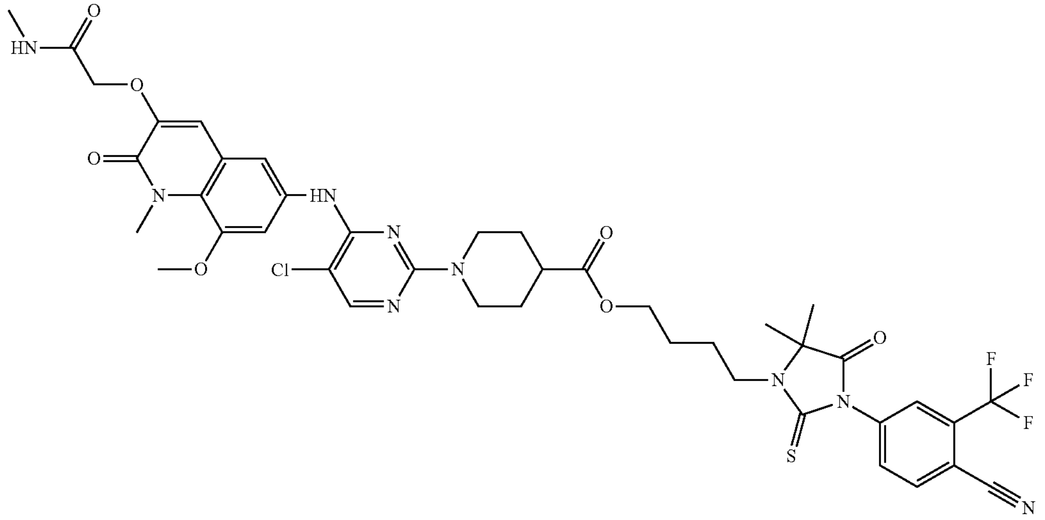

RCS-02-176

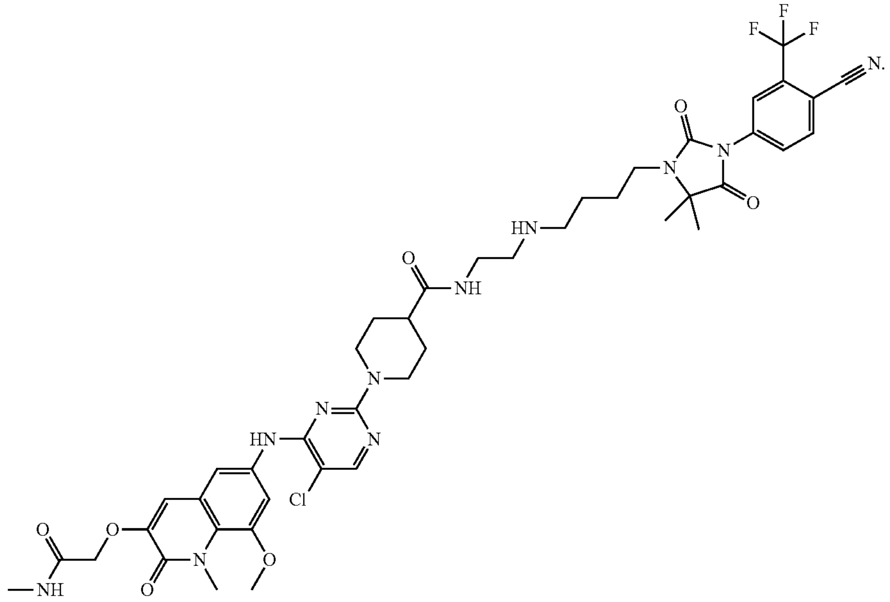

18. The method according to any of the preceding embodiments, wherein administration of the CIP activates transcription of a proapoptotic gene to treat the subject for the malignancy.

19. The method according to Embodiment 18, wherein the proapoptotic gene is selected from the group consisting of TP53, PUMA (BBC3), BIM (BCL2L11), BID, BAX, BAK, BOK, BAD, HRK, BIK, BMF, and NOXA.

20. The method according to any of the preceding embodiments, wherein the malignancy is characterized by elevated levels of AR.

21. The method according to any of the preceding embodiments, wherein the malignancy is characterized by elevated levels of BCL6 (or a homologue thereof).

22. The method according to any of the preceding embodiments, wherein the malignancy is prostate cancer.

23. The method according to any of the preceding embodiments, wherein the subject is a mammal.

24. The method according to Embodiment 23, wherein the mammal is human.

25. The method according to any of the preceding embodiments, wherein the method further comprises assessing the subject to determine whether the malignancy is susceptible to treatment with the TCIP.

26. The method according to Embodiment 25, wherein the assessing comprises measuring the level of at least one of AR and BCL6 in malignant cells.

27. The method according to Embodiment 26, wherein the assessing comprises measuring the level of AR and BCL6 (or a homologue thereof) in malignant cells.

28. The method according to any of Embodiments 26 and 27, wherein the measuring comprises one or more of RNA-seq, Western blotting, immunohistochemistry, mass spec, and intracellular FACS.

29. A transcriptional chemical inducer of proximity (TCIP) for treating malignancy, the TCIP comprising a first ligand that specifically binds to BCL-6 (or a homologue thereof) joined by a linker to a second ligand that specifically binds to an AR.

30. The TCIP according to Embodiment 29, wherein the TCIP has a molecular weight ranging from 300 to 1200 g/mole.
31. The TCIP according to Embodiments 29 to 30, wherein the first ligand is selected from the group consisting of:
11
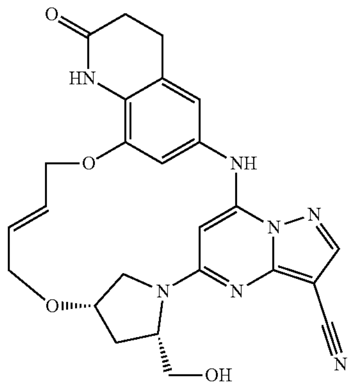
7
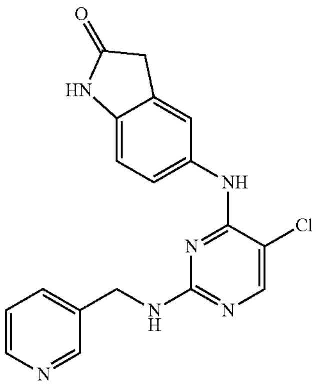
14
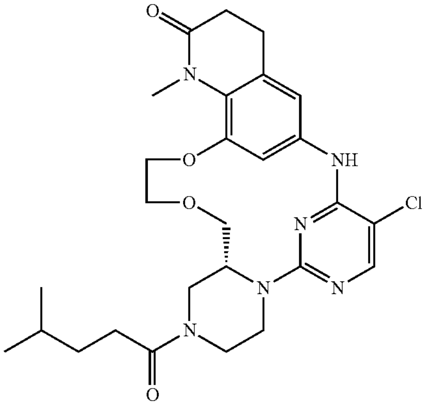
25a
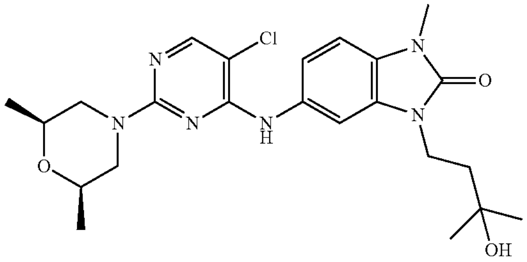
FX1
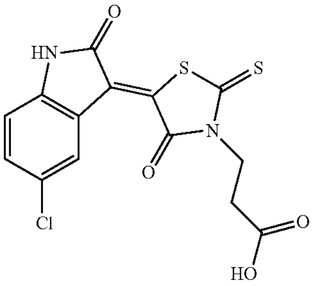
BI-3812
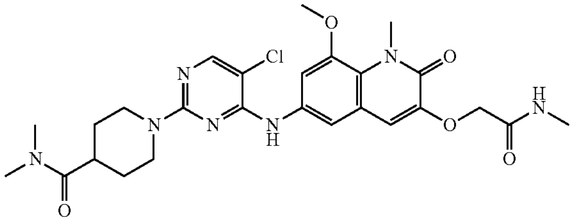
(BI-3802)
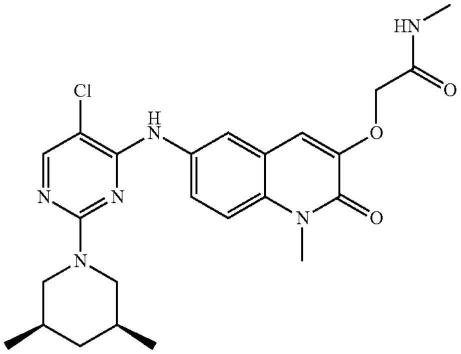

-continued
(14)
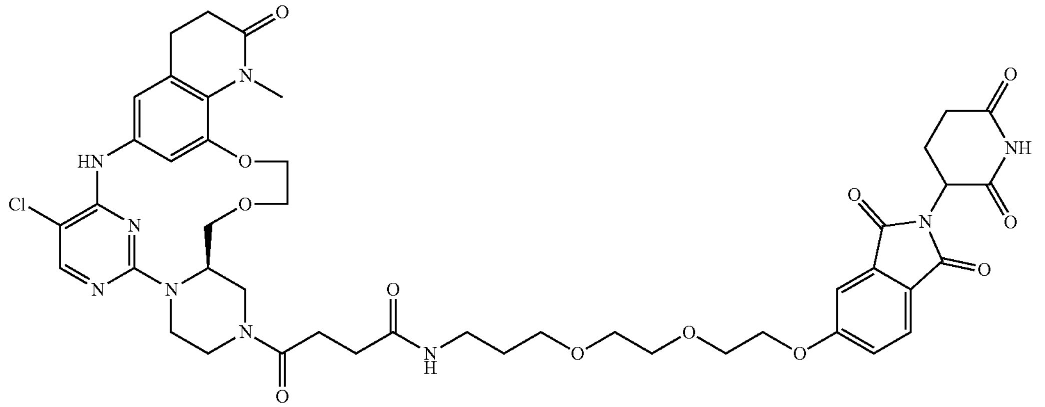
(6)
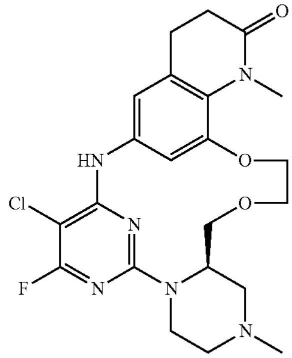
(CCT369347)
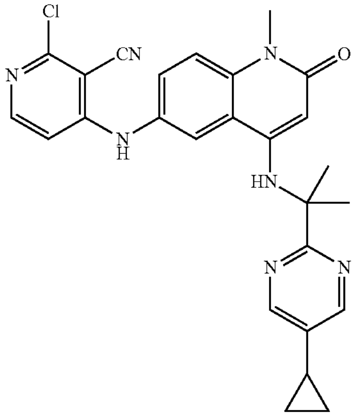
(CCT372064)
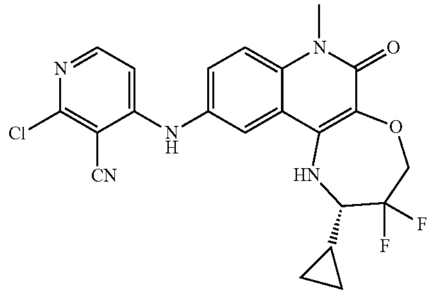
(CCT37566)
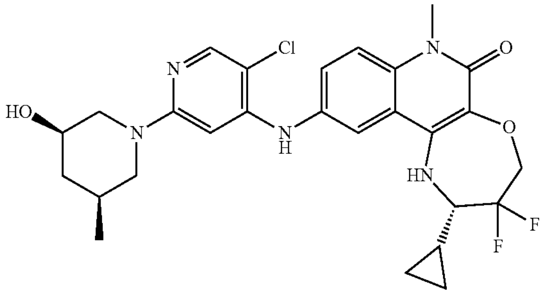
(CCTT369260)
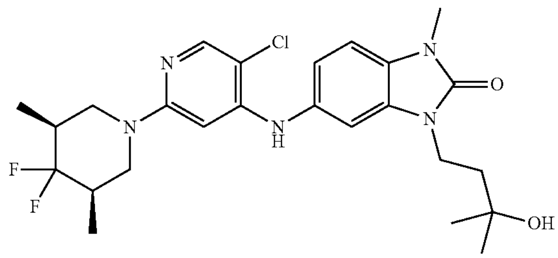
(26c)
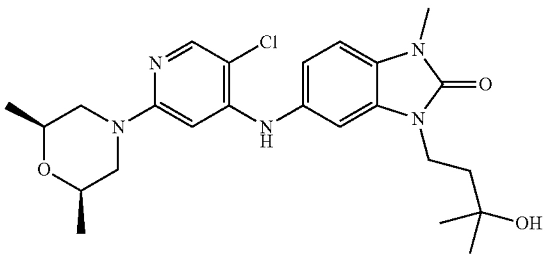

-continued (TMX-2164)

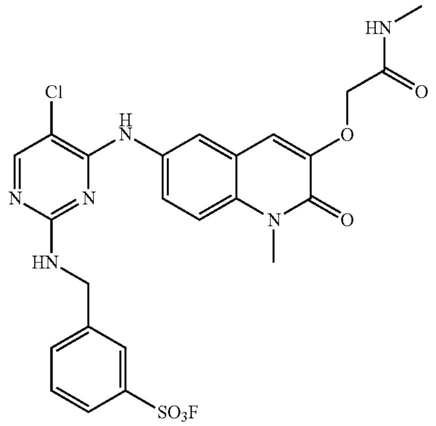

(BCl-1)

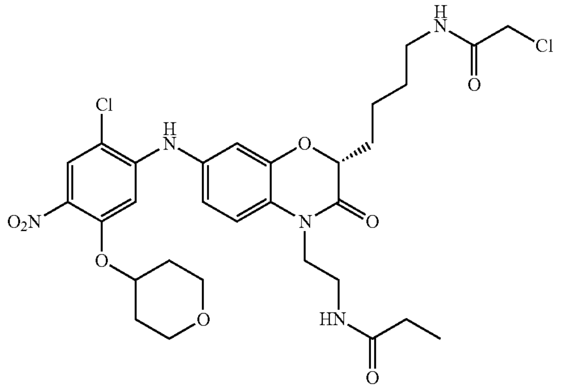

(GSK-137)

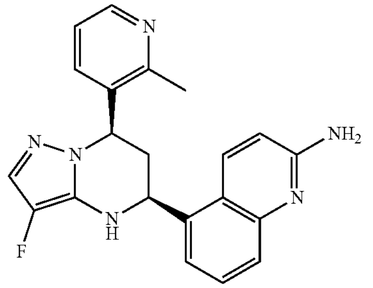

(79-6)

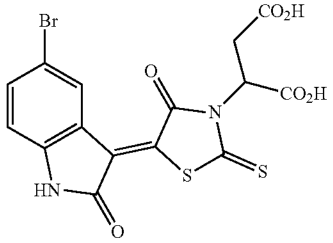

32. The TCIP according to any of Embodiments 29 to 31, wherein the second ligand comprises an AR agonist.

33. The TCIP according to Embodiment 32, wherein the AR agonist comprises a steroidal AR agonist.

34. The TCIP according to Embodiment 33, wherein the steroidal AR agonist is selected from the group consisting of:

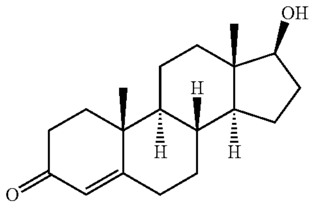

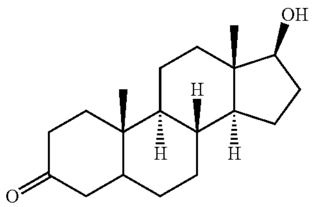

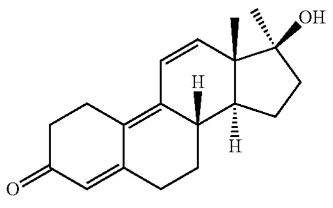

-continued

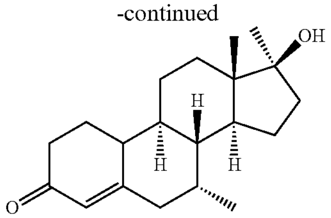

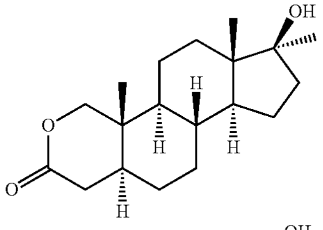

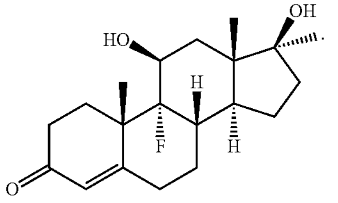

35. The TCIP according to Embodiment 32, wherein the AR agonist comprises a non-steroidal agonist.

36. The TCIP according to Embodiment 35, wherein the AR agonist is selected from the group consisting of:

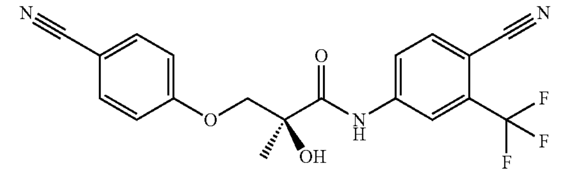

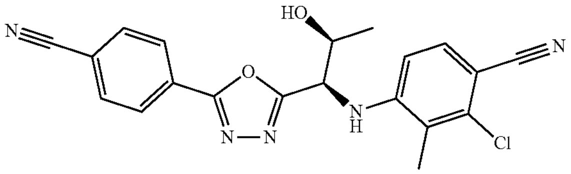

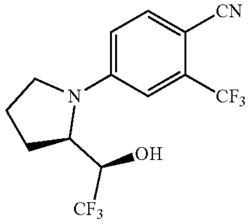

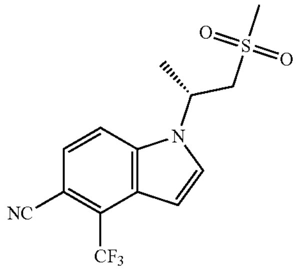

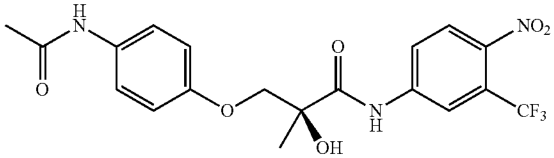

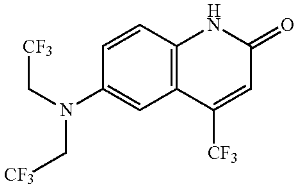

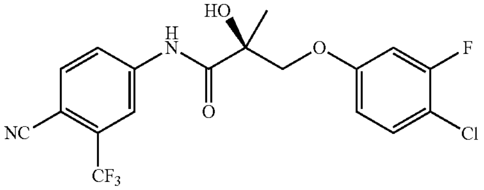

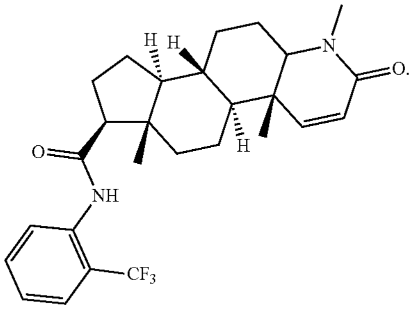

37. The TCIP according to Embodiments 29 to 31, wherein the second ligand comprises an AR antagonist.

38. The TCIP according to Embodiment 37, wherein the AR antagonist comprises a non-steroidal AR antagonist.

39. The TCIP according to Embodiment 38, wherein the non-steroidal AR antagonist is selected from the group consisting of:

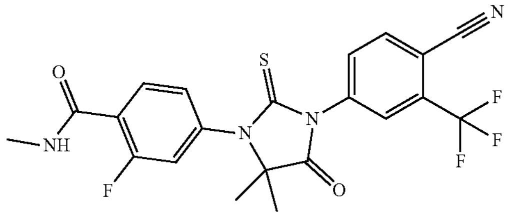

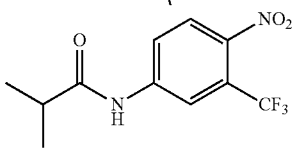

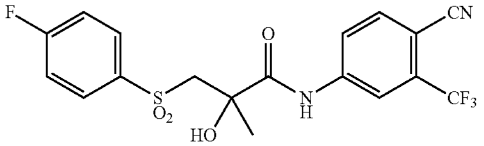

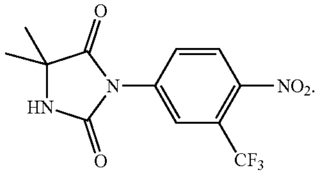

40. The TCIP according to Embodiment 37, wherein the AR antagonist comprises a steroidal AR antagonist.

41. The TCIP according to Embodiment 40, wherein the steroidal AR antagonist is selected from the group consisting of:

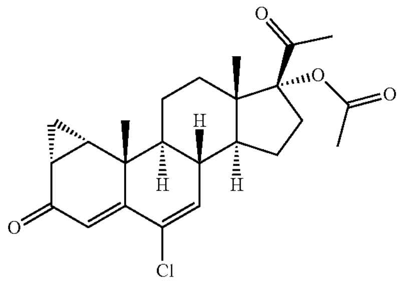

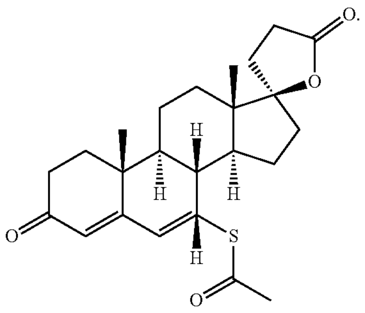

42. The TCIP according to any of Embodiments 29 to 41, wherein the linker is selected from the group consisting of:

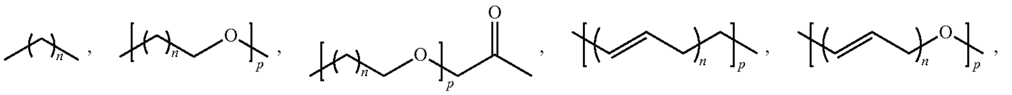
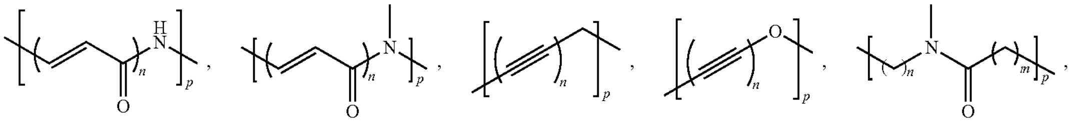
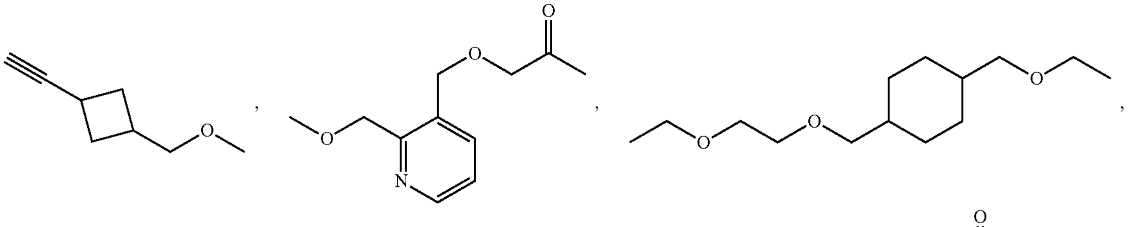
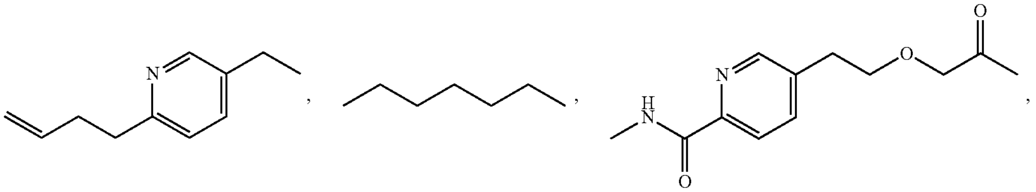
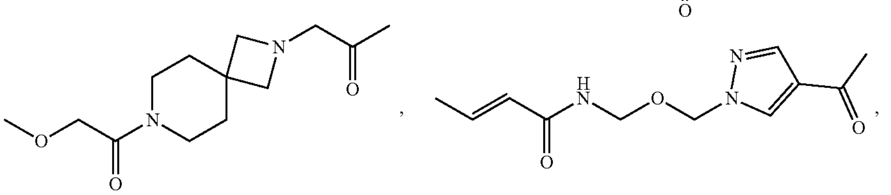
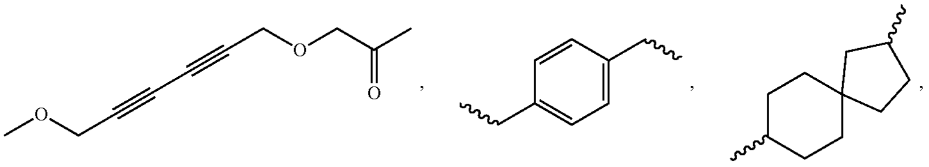
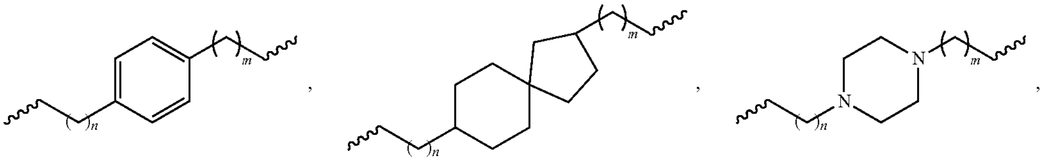
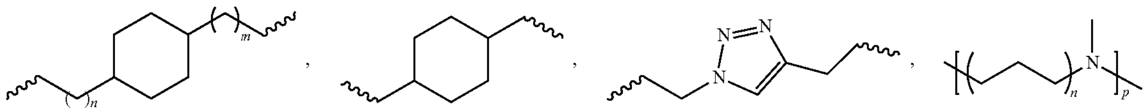
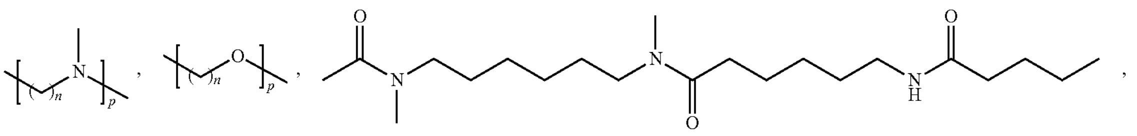
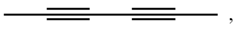
where m, n and p are independently selected from 0 or an integer of from 1-12.
43. The TCIP according to any of the preceding embodiments, wherein the TCIP is selected from the group consisting of:

BAK-04-083 (C2)
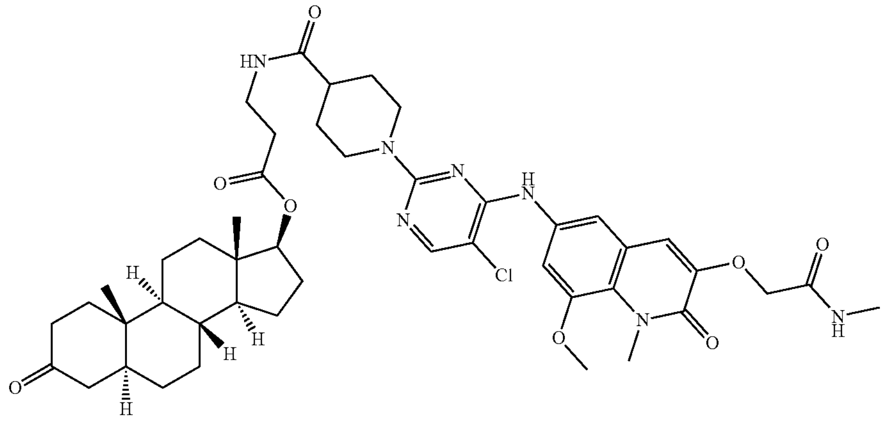
RCS-02-063 (C3)
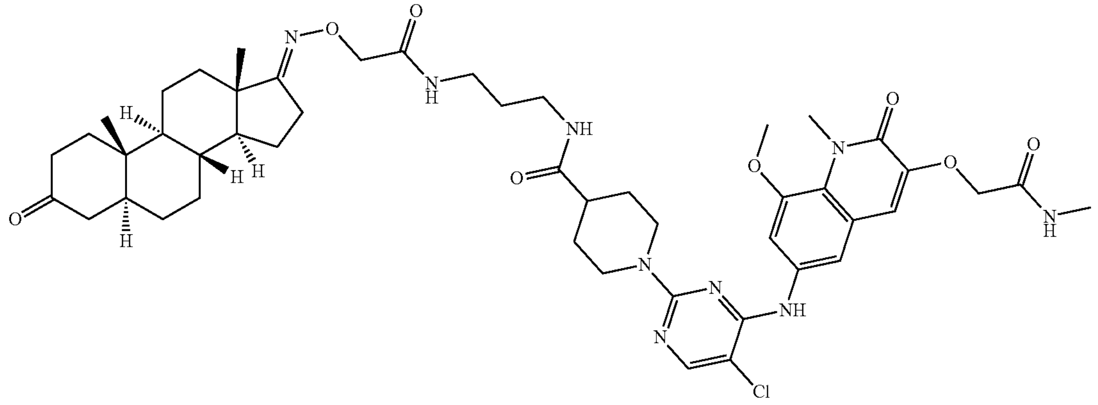
RCS-02-093 (C4)
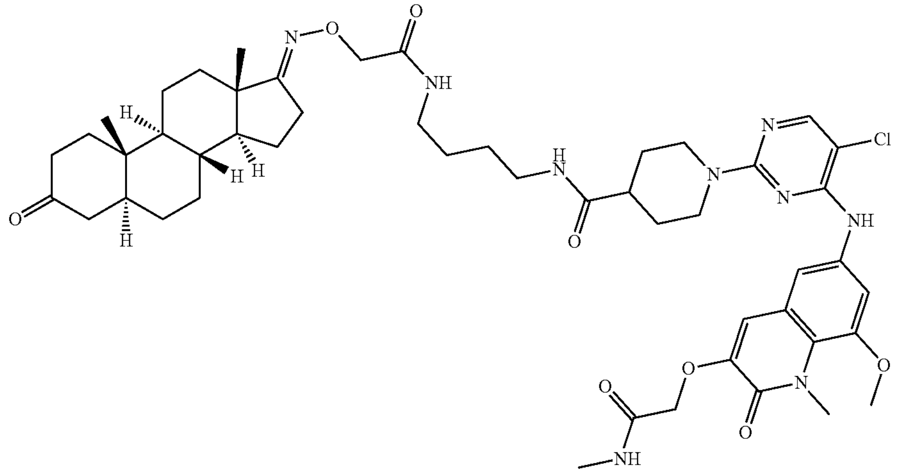

-continued
BAK-04-003 (C5)
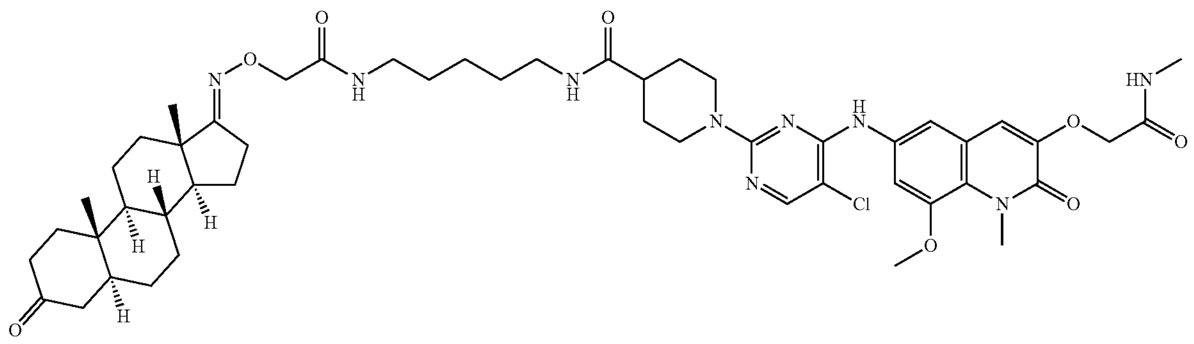
RCS-02-085 (C6)
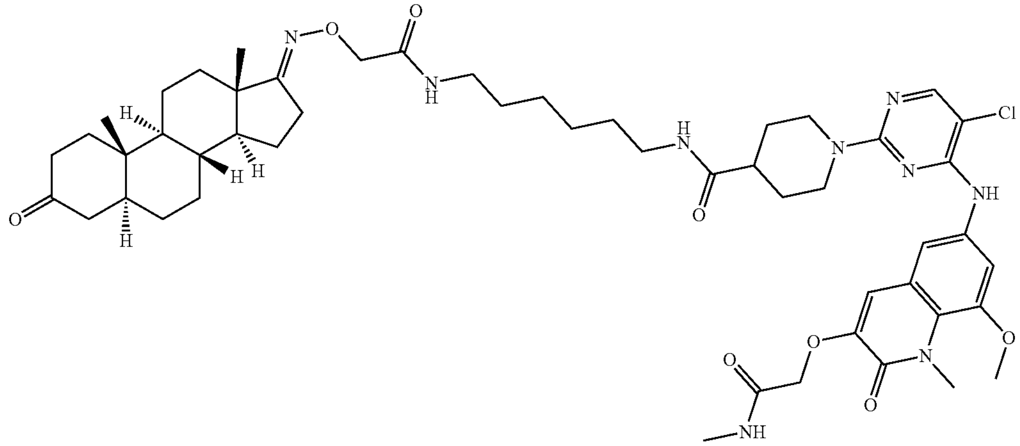
BAK-04-006 (C8)
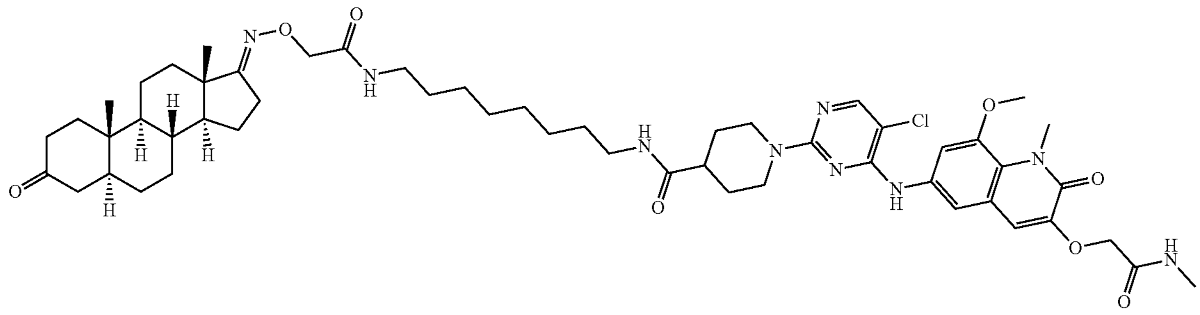

-continued
RCS-02-060 (peg1)
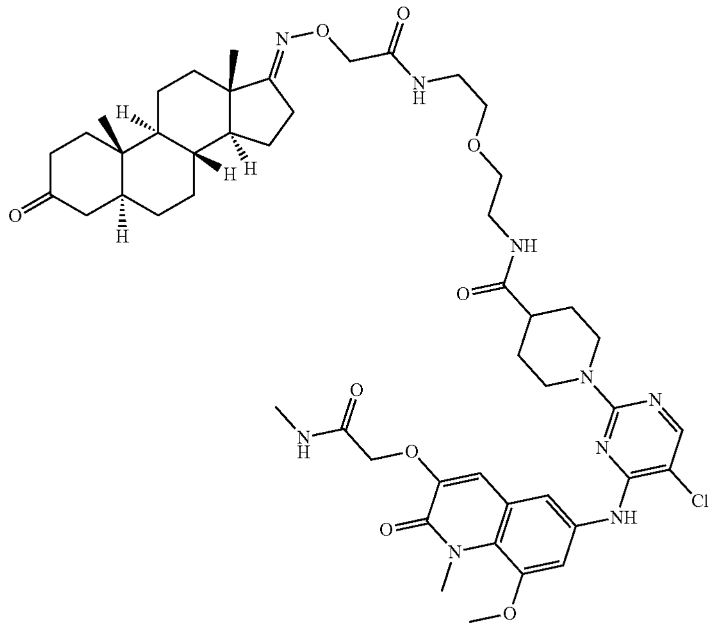
RCS-02-058 (peg2)
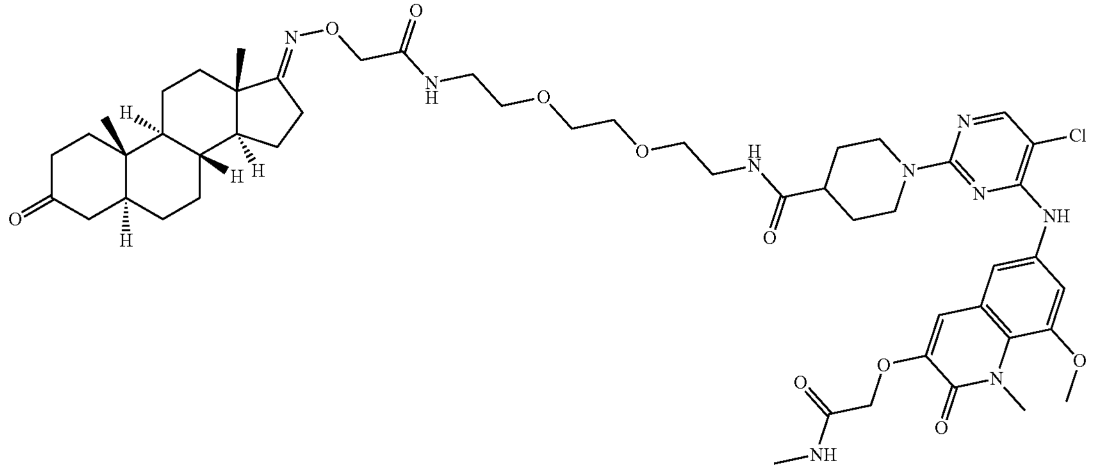

-continued
RCS-02-061 (peg3)
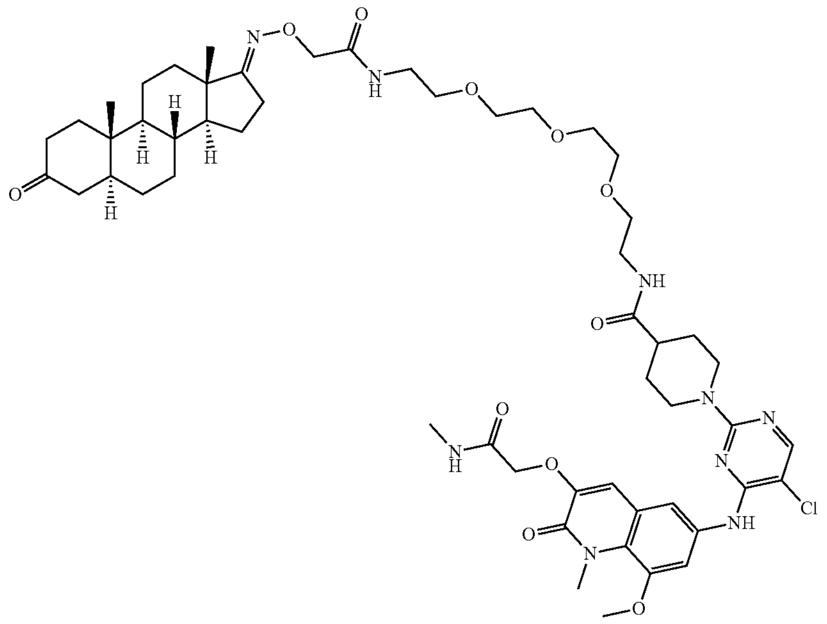
RCS-02-062 (peg4)
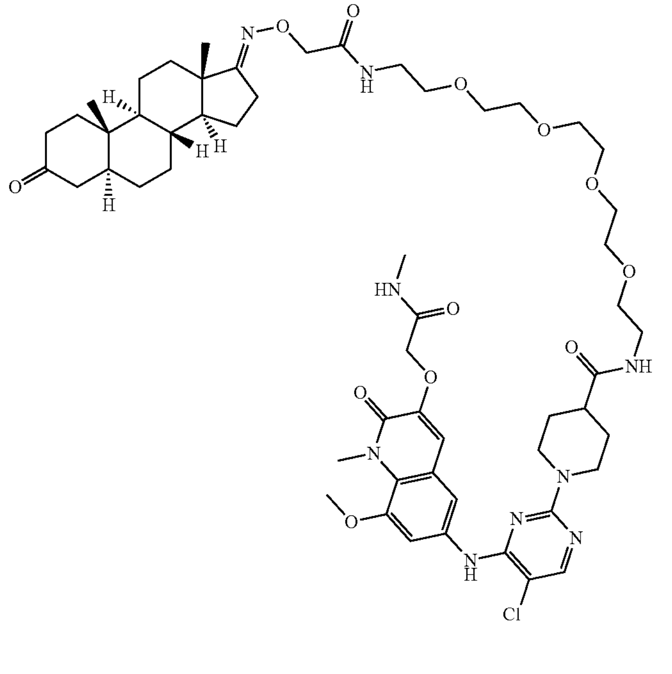

-continued
BAK-04-039
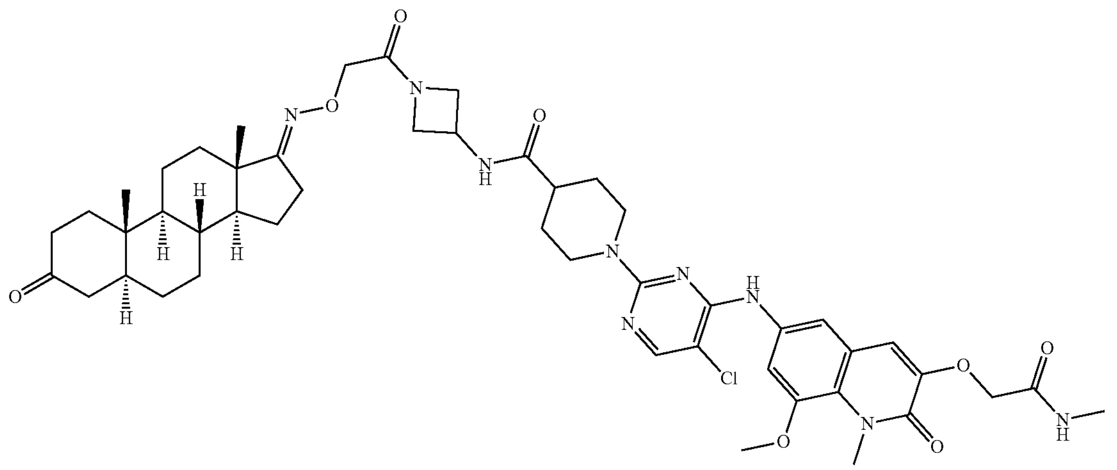
BAK-04-083
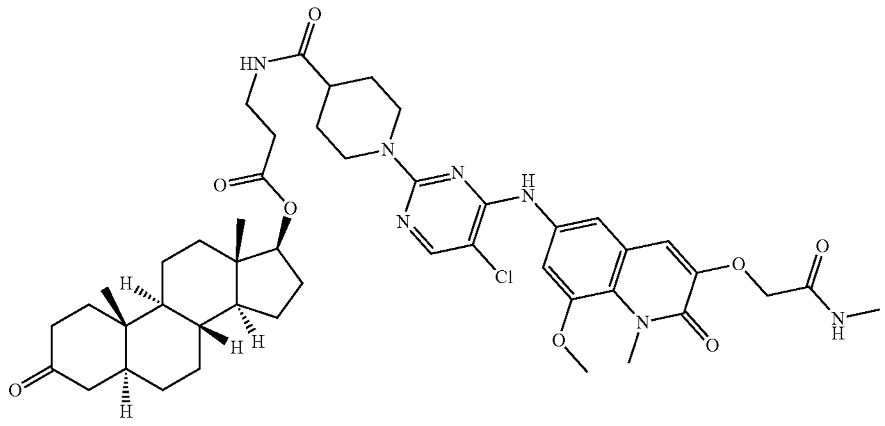
BAK-04-084
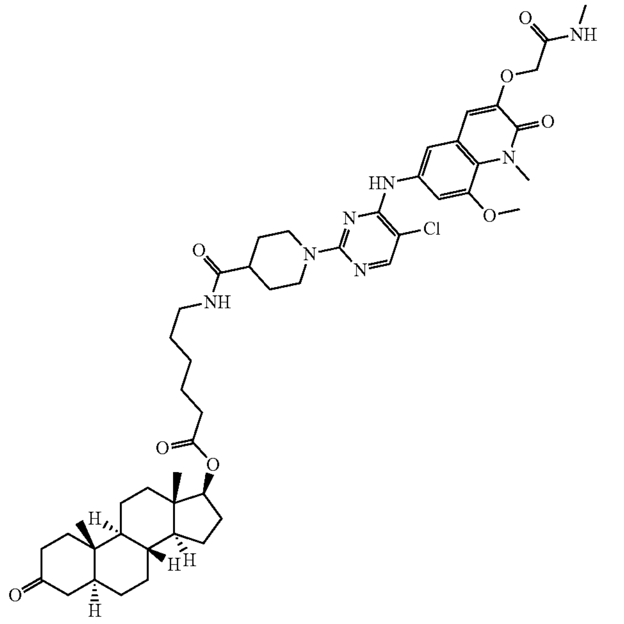

-continued

RCS-02-160

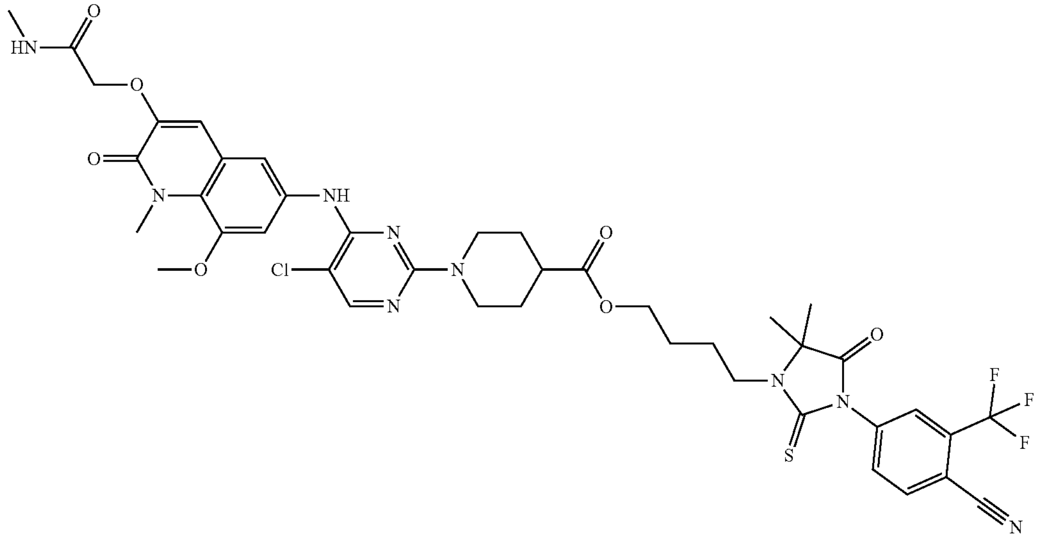

RCS-02-176

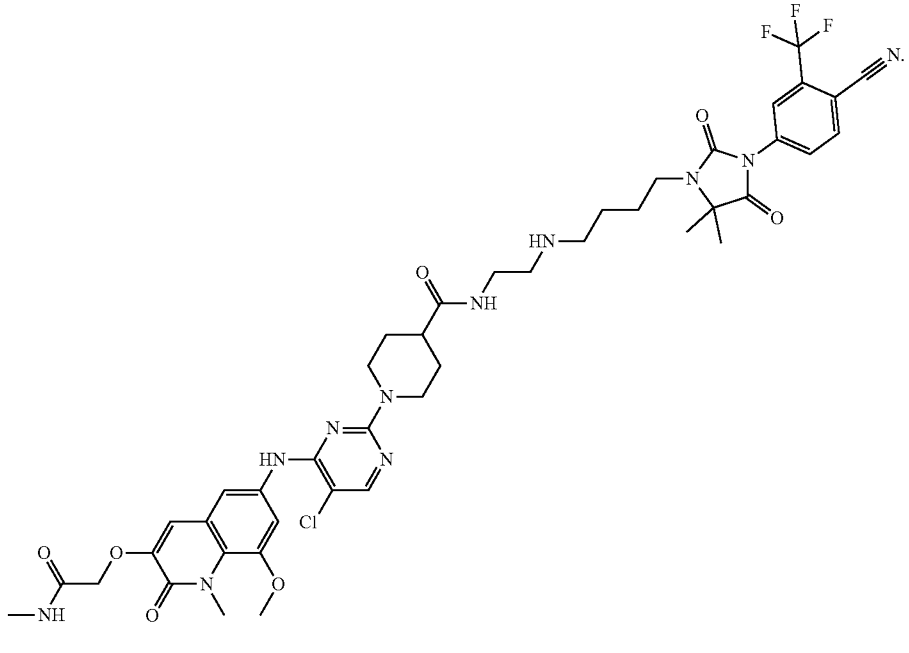

44. A pharmaceutical composition comprising:

transcriptional chemical inducer of proximity (TCIP) for treating malignancy, the TCIP comprising a first ligand that specifically binds to BCL-6 (or a homologue thereof) joined by a linker to a second ligand that specifically binds to an AR; and delivery vehicle.

45. The pharmaceutical composition according to Embodiment 44, wherein the TCIP has a molecular weight ranging from 300 to 1200 g/mole.

46. The pharmaceutical composition according to Embodiments 44 to 45, wherein the first ligand is selected from the group consisting of:

11
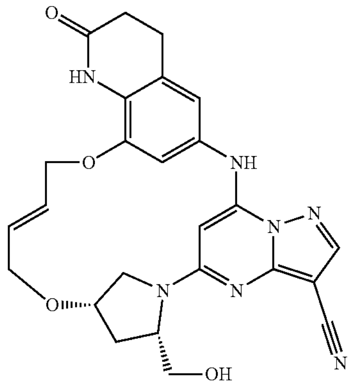
7
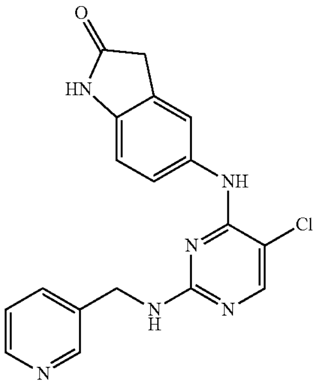
14
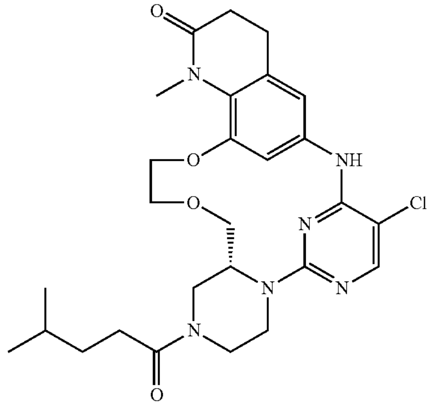
25a
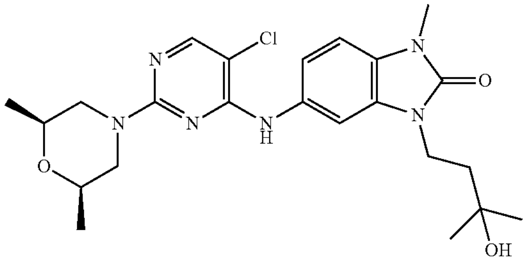
FX1
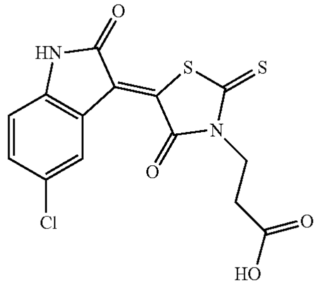
BI-3812
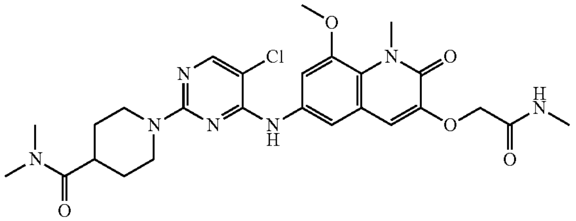
(BI-3802)
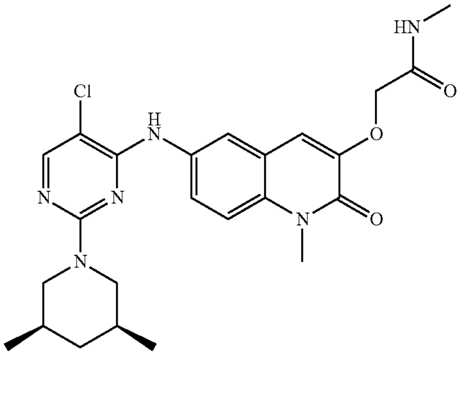

-continued
(14)
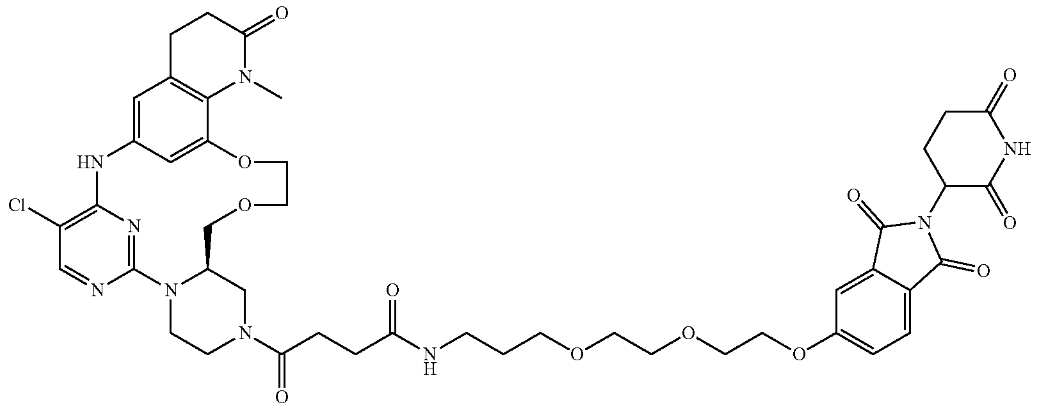
(6)
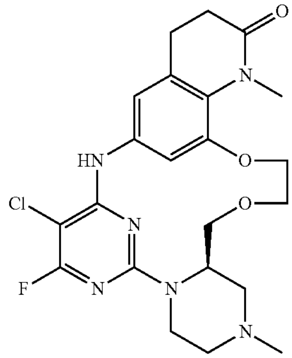
(CCT369347)
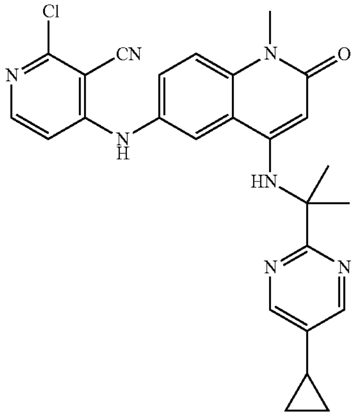
(CCT372064)
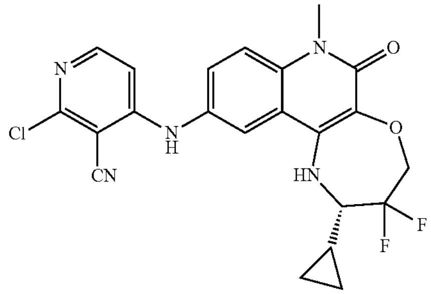
(CCT37566)
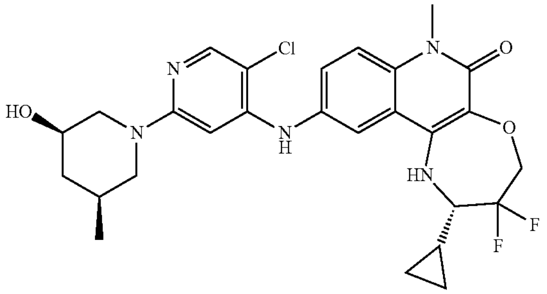
(CCTT369260)
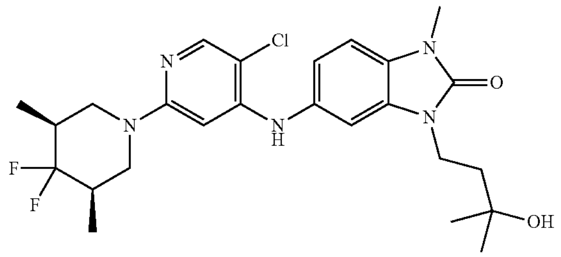
(26c)
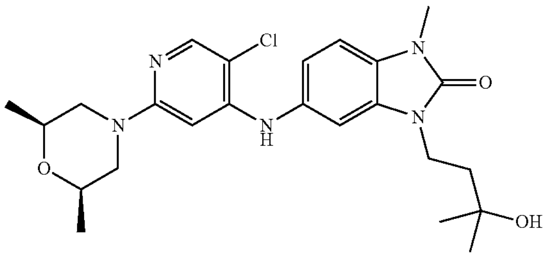

-continued (TMX-2164)

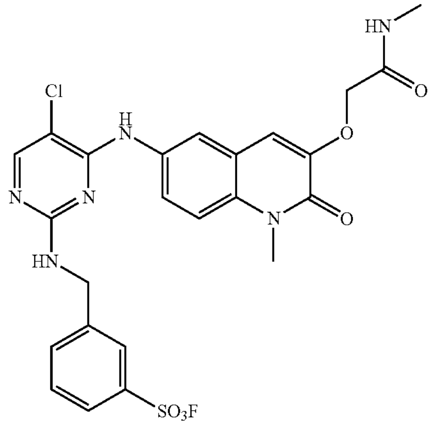

(BCl-1)

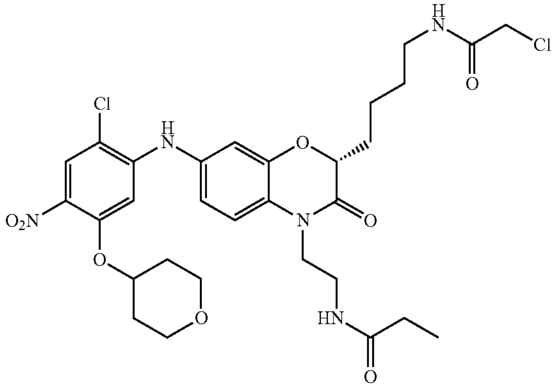

(GSK-137)

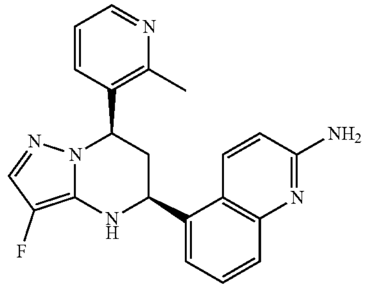

(79-6)

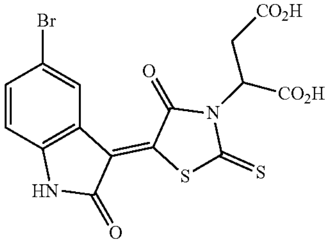

47. The pharmaceutical composition according to any of Embodiments 44 to 46, wherein the second ligand comprises an AR agonist.

48. The pharmaceutical composition according to Embodiment 47, wherein the AR agonist comprises a steroidal AR agonist.

49. The pharmaceutical composition according to Embodiment 48, wherein the steroidal AR agonist is selected from the group consisting of:

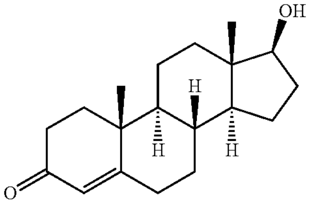

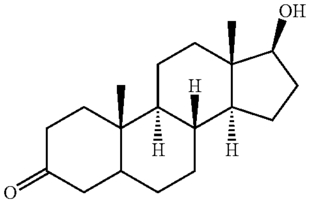

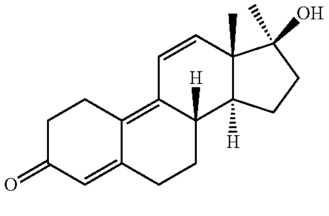

-continued

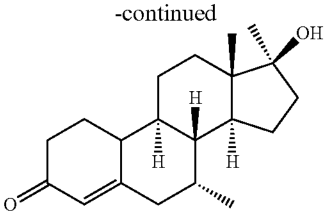

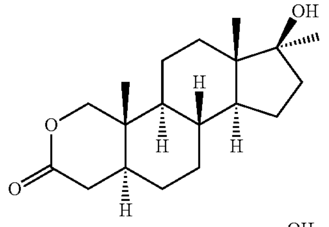

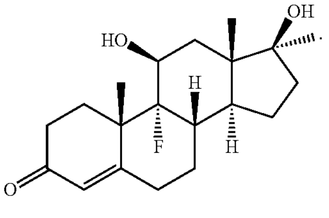

50. The pharmaceutical composition according to Embodiment 47, wherein the AR agonist comprises a non-steroidal agonist.

51. The pharmaceutical composition according to Embodiment 50, wherein the AR agonist is selected from the group consisting of:

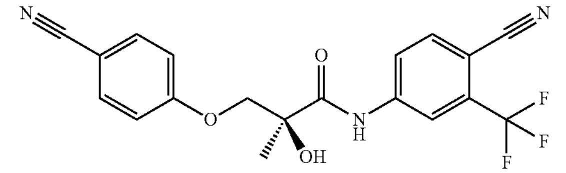

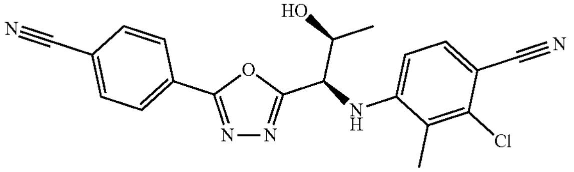

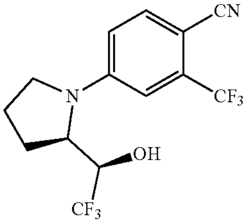

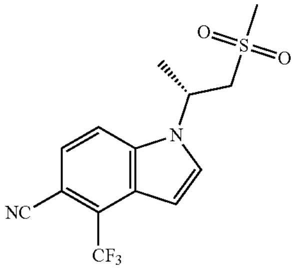

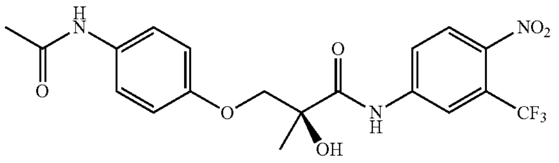

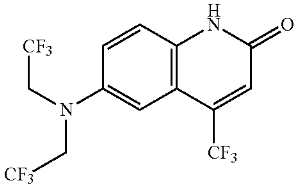

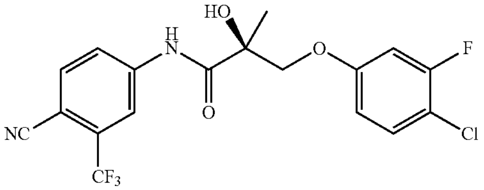

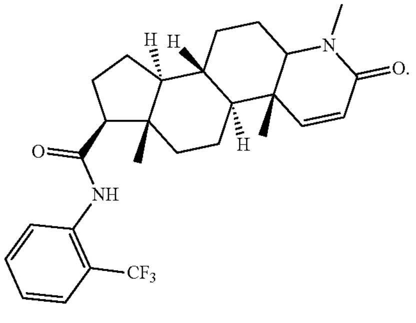

52. The pharmaceutical composition according to Embodiments 44 to 46, wherein the second ligand comprises an AR antagonist.

53. The pharmaceutical composition according to Embodiment 52, wherein the AR antagonist comprises a non-steroidal AR antagonist.

54. The pharmaceutical composition according to Embodiment 53, wherein the non-steroidal AR antagonist is selected from the group consisting of:

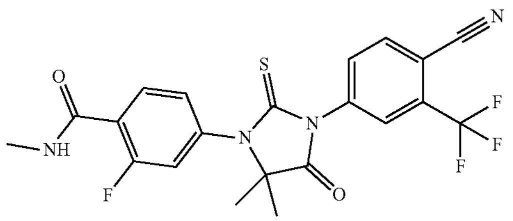

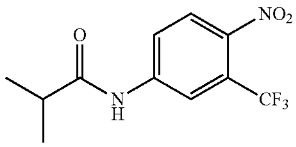

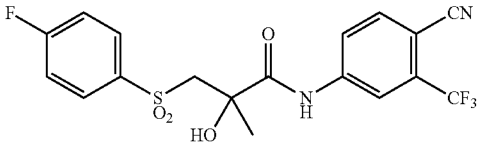

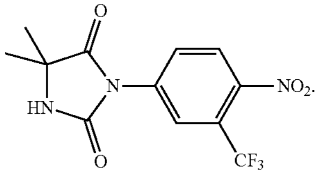

55. The pharmaceutical composition according to Embodiment 54, wherein the AR antagonist comprises a steroidal AR antagonist.

56. The pharmaceutical composition according to Embodiment 55, wherein the steroidal AR antagonist is selected from the group consisting of:

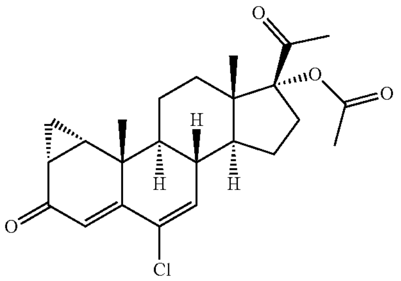

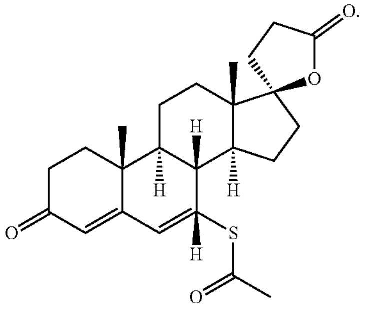

57. The TCIP according to any of Embodiments 44 to 56, wherein the linker is selected from the group consisting of:

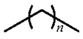, 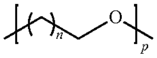, 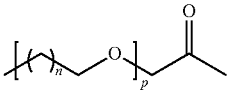, 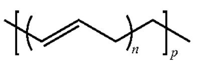, 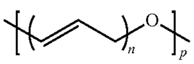,
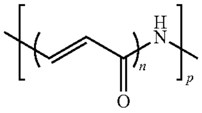, 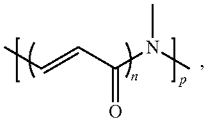, 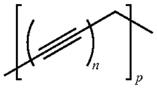, 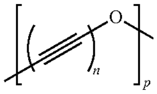, 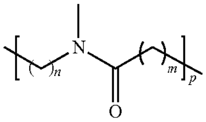,
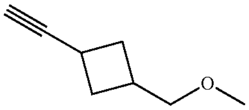, 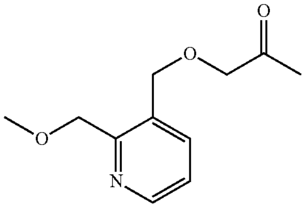, 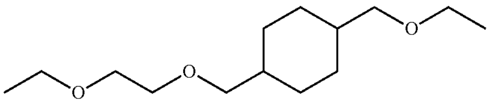,
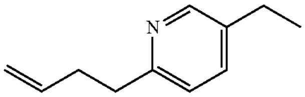, 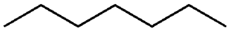, 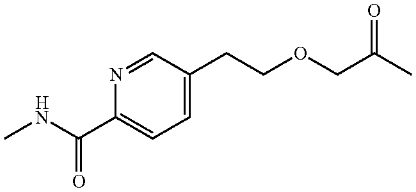,
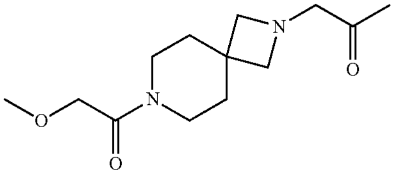, 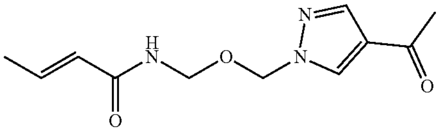,
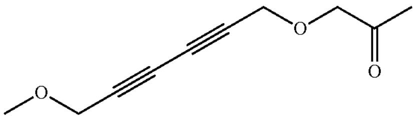, 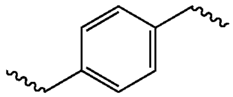, 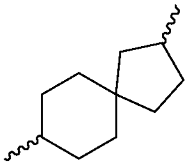,
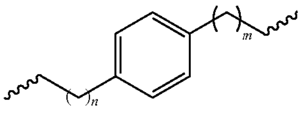, 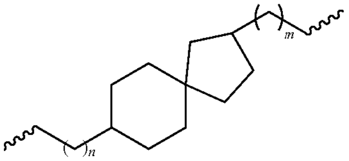, 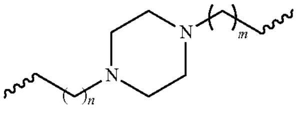,
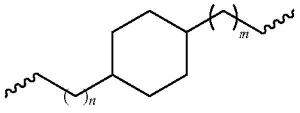, 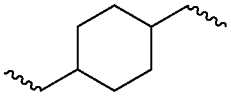, 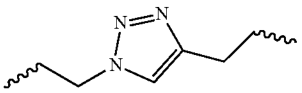, 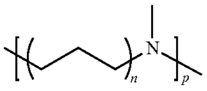,
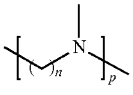, 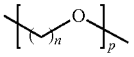, 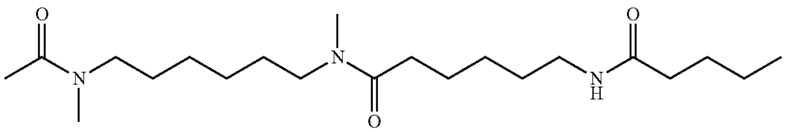,
,
where m, n and p are independently selected from 0 or an integer of from 1-12.
58. The pharmaceutical composition according to any of the preceding embodiments, wherein the TCIP is selected from the group consisting of:

BAK-04-083 (C2)
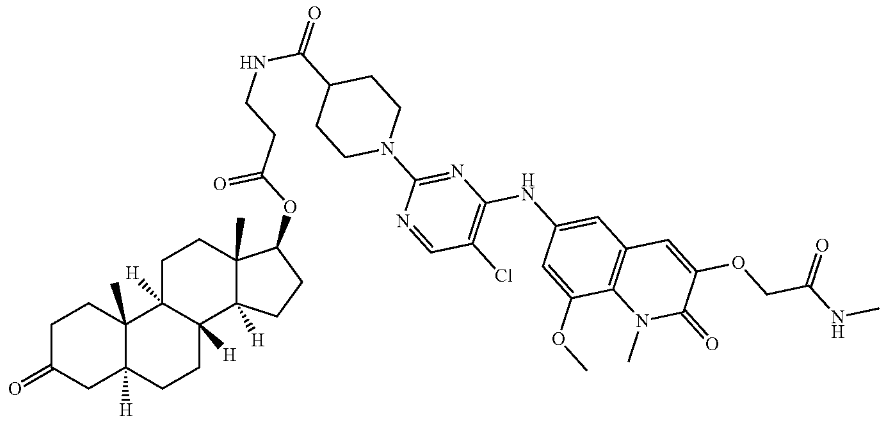
RCS-02-063 (C3)
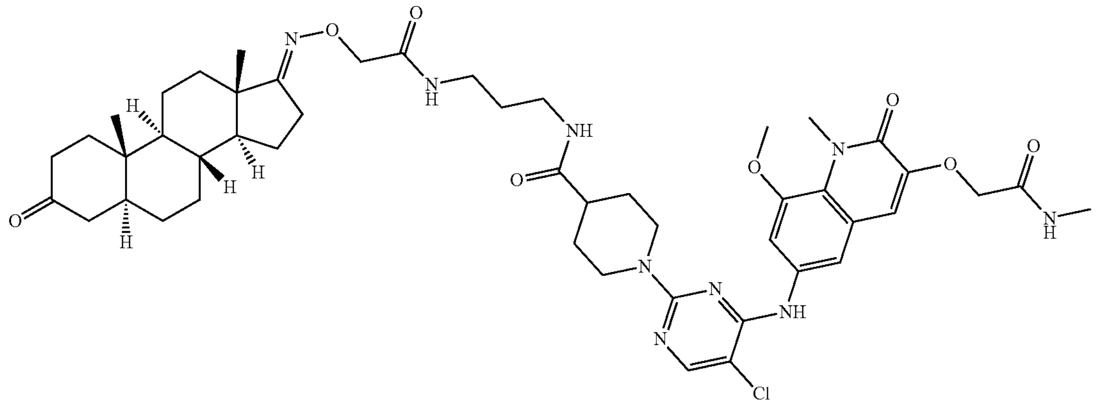
RCS-02-093 (C4)
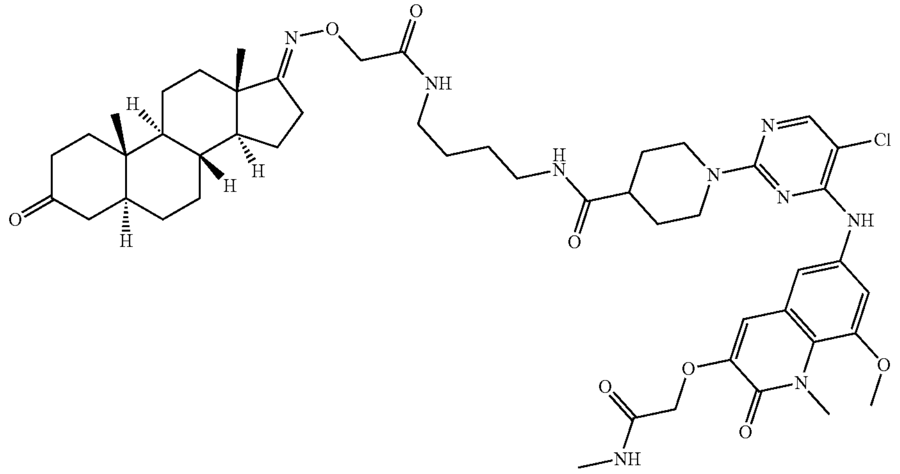

-continued
BAK-04-003 (C5)
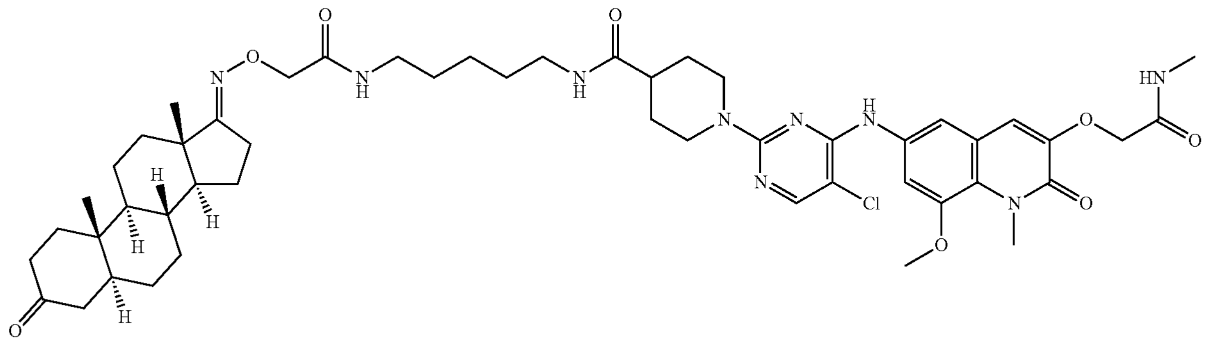
RCS-02-085 (C6)
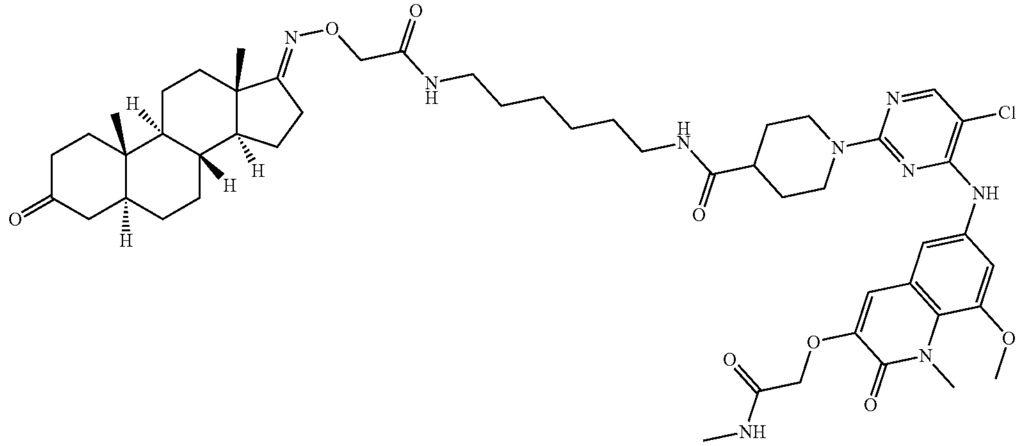
BAK-04-006 (C8)
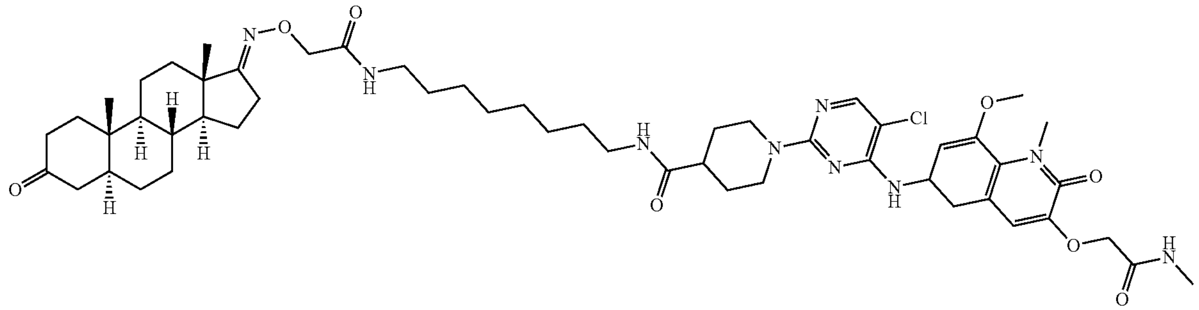

-continued
PCS-02-060 (peg1)
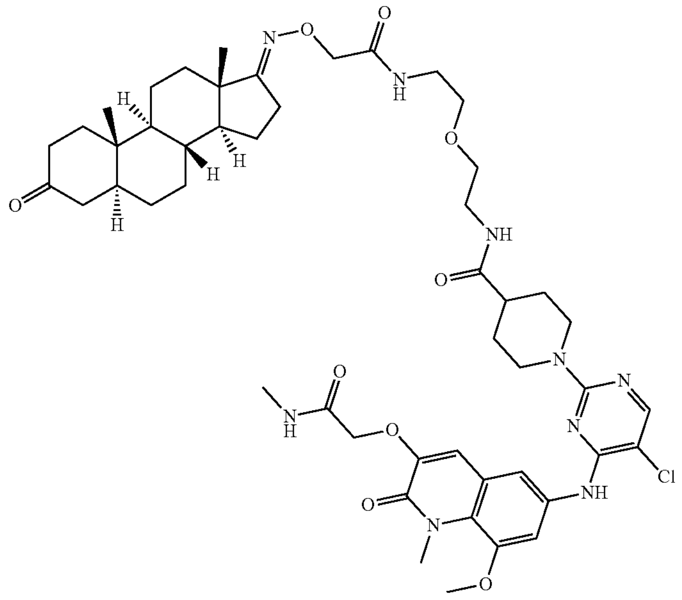
RCS-02-058 (peg2)
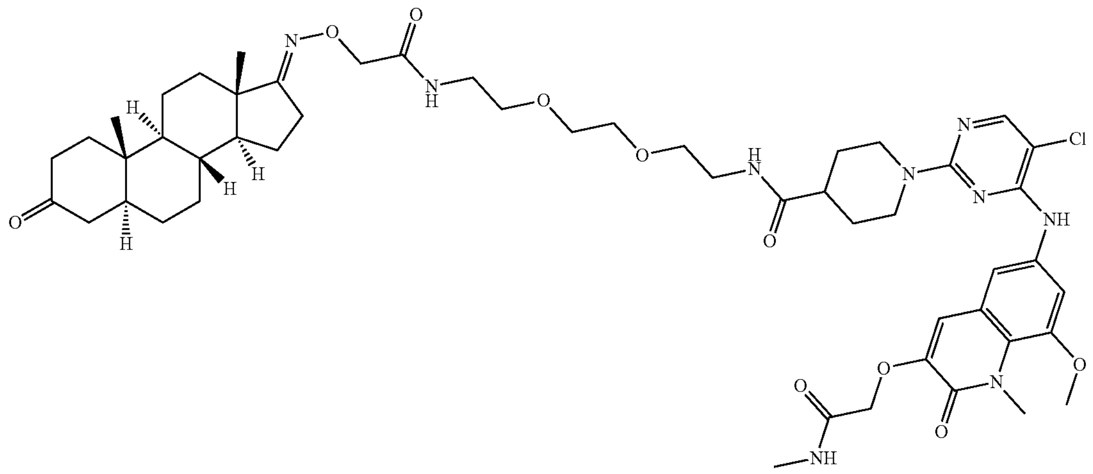

-continued
RCS-02-061 (peg3)
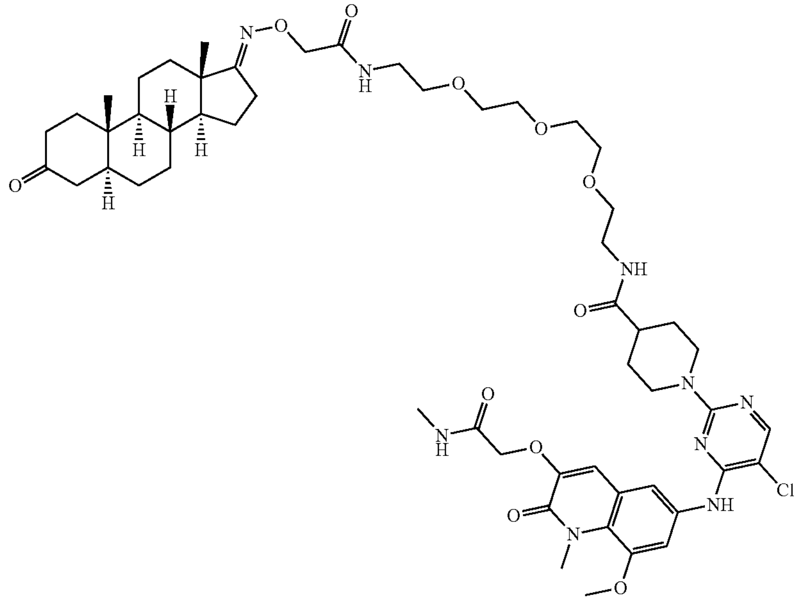
RCS-02-062 (peg4)
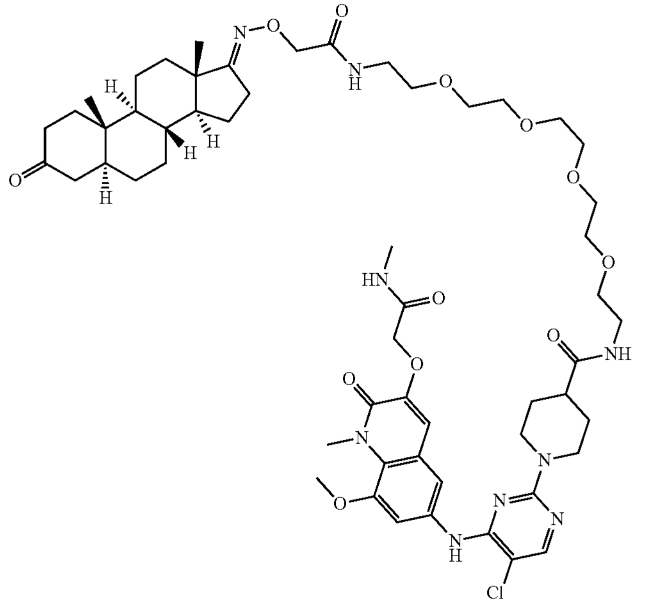
BAK-04-039
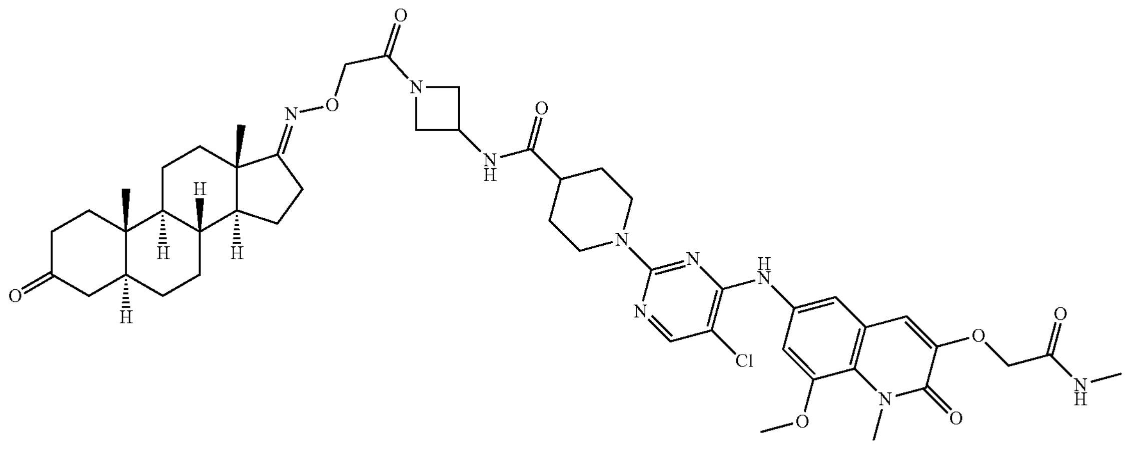

-continued
BAK-04-083
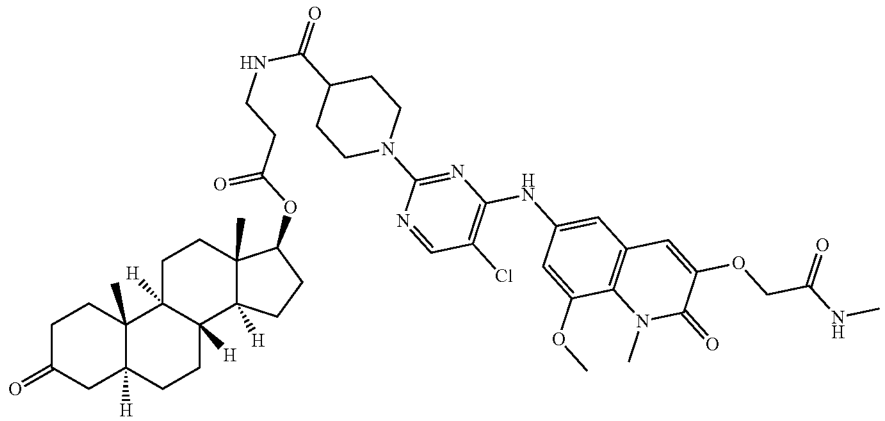
BAK-04-084
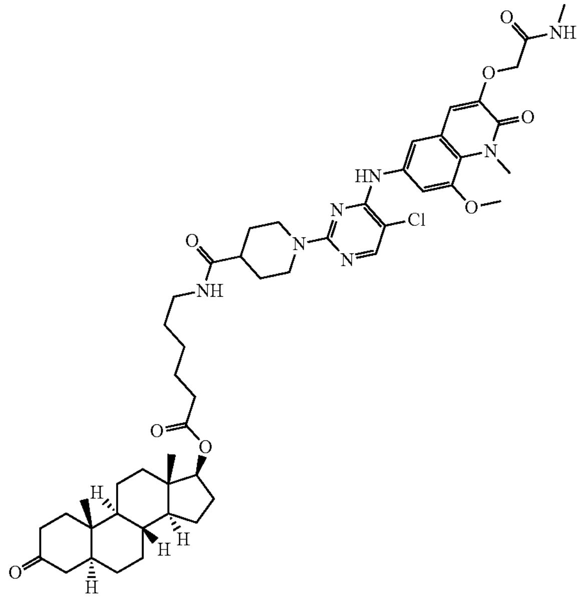
RCS-02-160
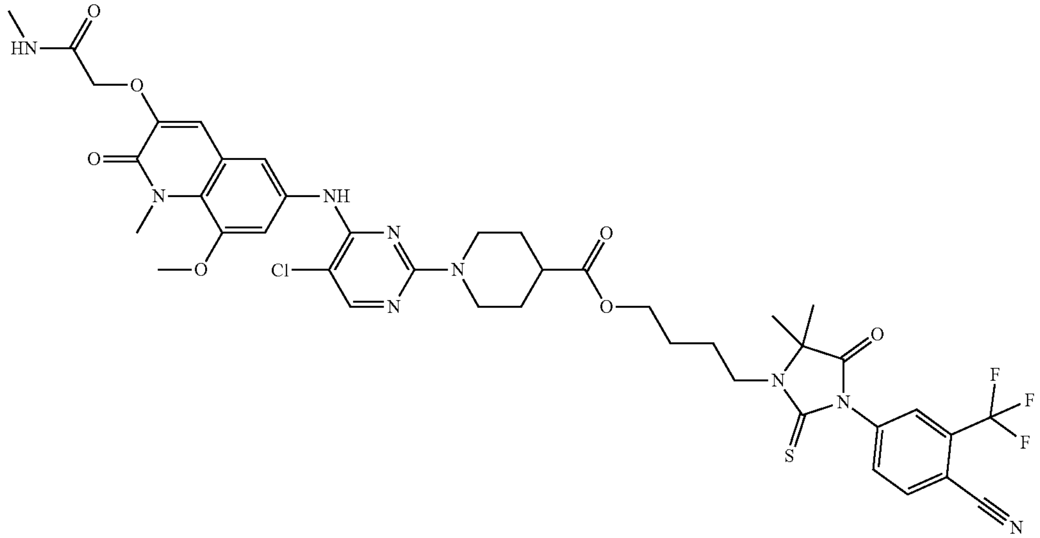

-continued

RCS-02-176

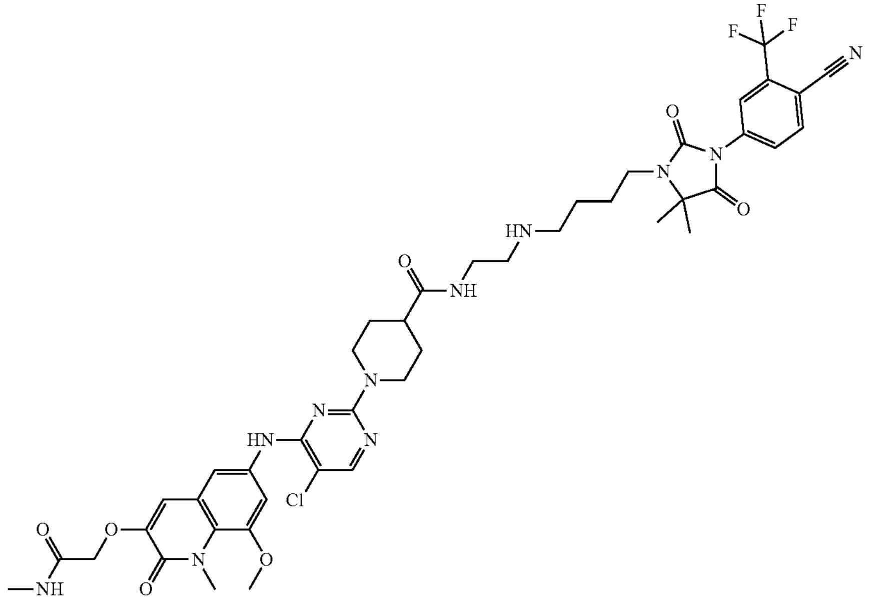

59. The pharmaceutical composition according to any of Embodiments 44 to 58, wherein the pharmaceutical composition is configured for intravenous delivery.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of modulating at least one BCL-6 target gene in a cell, the method comprising:

contacting the cell with a chemical inducer of proximity (CIP) comprising a structure of BR-L-BC, wherein the CIP has a molecular weight of 5,000 g/mol or less, wherein:

BR comprises a ligand that binds to a bromodomain of bromodomain-containing protein 4 (BRD4);

BC comprises a ligand that binds to a BTB domain of B-cell lymphoma 6 (BCL-6); wherein BC is of Formula IB:

(IB)

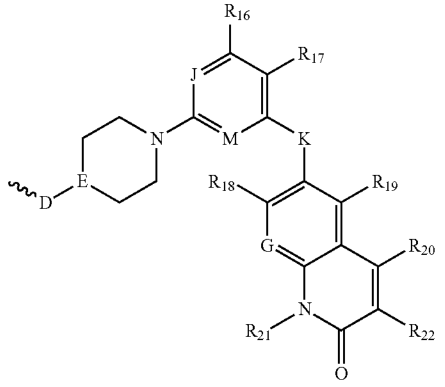

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, C(1-4) alkyl, —O—C(1-14) alkyl, —O—C (1-4) haloalkyl, C(1-4) haloalkyl and halogen;

J is —CH or nitrogen;

M is —CH or nitrogen;

K is —$CH_2$, O, S or —NH;

∿∿∿ represents a bond to the linker; and each of $R_{16}$, $R_{17}$, $R_{18}$, $R_{19}$, $R_{20}$, $R_{21}$ $R_{22}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine; or BC is of formula IB7:

(IB7)

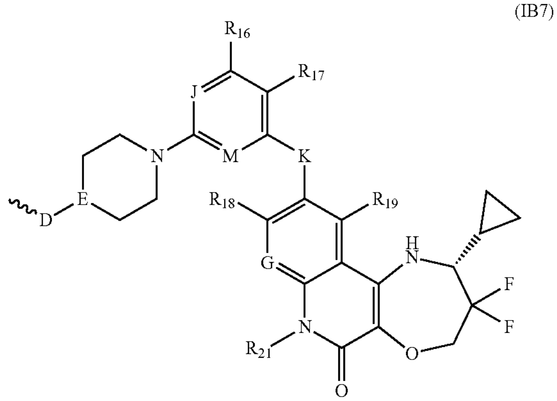

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, C(1-4) alkyl, —O-C(1-14) alkyl, —O—C (1-4) haloalkyl, C(1-4) haloalkyl and halogen;

J is —CH or nitrogen;

M is —CH or nitrogen;

K is —$CH_2$, O, S or NH;

∿∿ represents a bond to the linker; and each of $R_{16}$, $R_{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine, and L comprises a linker, wherein upon contacting the cell, BCL-6 and BRD4 are spatially complexed to each other via the CIP to yield a gain-of-function in the cell, wherein the gain-of-function is characterized by increased expression of the BCL-6 target gene in a manner dependent on presence of BRD4 bound to the CIP, thereby modulating the at least one BCL-6 target gene.

2. The method of claim 1, wherein the at least one BCL-6 target gene comprises a proapoptotic gene.

3. The method of claim 2, wherein the proapoptotic gene is selected from the group consisting of: TP53, PUMA (BBC3), BIM (BCL2L11), BID, BAX, BAK, BOK, BAD, HRK, BIK, BMF, NOXA, CASP8, and CASP10.

4. The method of claim 2, wherein the modulating the at least one BCL-6 target gene comprises increasing expression of the proapoptotic gene in the cell.

5. The method of claim 4, wherein the method results in apoptosis of the cell.

6. The method of claim 1, wherein both BCL-6 and BRD4 are endogenously expressed in the cell.

7. The method of claim 1, wherein the cell is a diseased cell.

8. The method of claim 7, wherein the diseased cell overexpresses both BCL-6 and BRD4 relative to a non-diseased cell.

9. The method of claim 7, wherein the diseased cell is a cancer cell.

10. The method of claim 1, wherein the contacting comprises administering the CIP to a subject comprising the cell.

11. The method of claim 10, wherein the subject has a disease, a disorder, or a condition.

12. The method of claim 11, wherein the administering the CIP results in treatment of the disease, disorder, or condition, or a symptom associated therewith.

13. The method of claim 11, wherein the disease, disorder, or condition is a malignancy.

14. The method of claim 13, wherein the malignancy is small cell lung cancer (SCLC), diffuse large B-cell lymphoma (DLBCL), or a malignancy with high-level expression of BCL-6 protein.

15. The method of claim 14, wherein the DLBCL is refractory DLBCL.

16. The method of claim 14, wherein the refractory DLBCL is CHOP-resistant DLBCL.

17. The method of claim 13, wherein the malignancy has a mutation in TP53.

18. The method of claim 10, wherein the subject is a human.

19. The method of claim 1, wherein BC is of formula IB:

(IB)

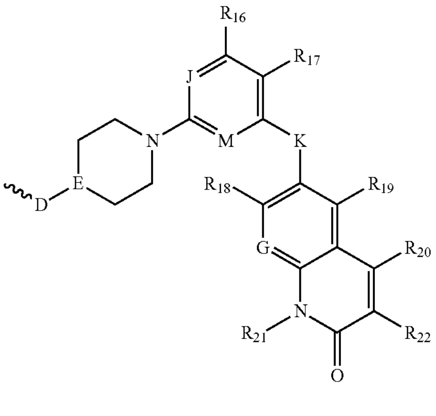

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, C(1-4) alkyl, —O—C(1-14) alkyl, —O—C (1-4) haloalkyl, C(1-4) haloalkyl and halogen;

J is —CH or nitrogen;

M is —CH or nitrogen;

K is —$CH_2$, O, S or —NH;

∿∿ represents a bond to the linker; and each of $R_{16}$, $R^{17}$, $R_{18}$, $R_{19}$, $R_{20}$, $R_{21}$ $R_{22}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

20. The method of claim 1, wherein BC is of formula IB7:

(IB7)

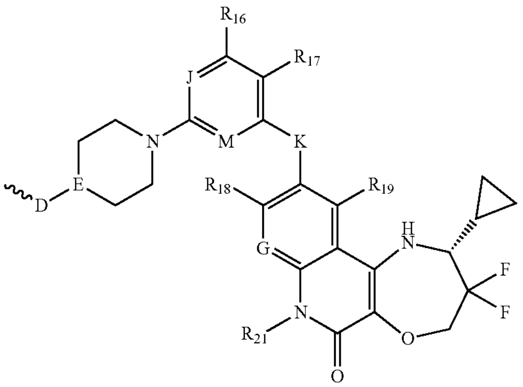

where:

D is selected from a bond, alkyl, amide, ester, carbamate, acyl, substituted acyl, carboxyl, alkoxycarbonyl, substituted alkoxycarbonyl, aminoacyl, substituted aminoacyl, amino, substituted amino, acylamino and substituted acylamino;

E is —CH or nitrogen;

G is nitrogen or $CR_{23}$, wherein $R_{23}$ is selected from hydrogen, C(1-4) alkyl, —O—C(1-14) alkyl, —O—C(1-4) haloalkyl, C(1-4) haloalkyl and halogen;

J is —CH or nitrogen;

M is —CH or nitrogen;

K is —$CH_2$, O, S or NH;

represents a bond to the linker; and each of $R_{16}$, $R^{17}$, $R_{18}$, $R_{19}$ and $R_{21}$ is independently selected from hydrogen, halogen, hydroxyl, alkoxyl, cyano, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, thiol, substituted thiol, sulfoxide, substituted sulfoxide, sulfone, substituted sulfone, sulfoximine or substituted sulfoximine.

21. The method of claim 1, wherein BC is of formula IB1:

(IB1)

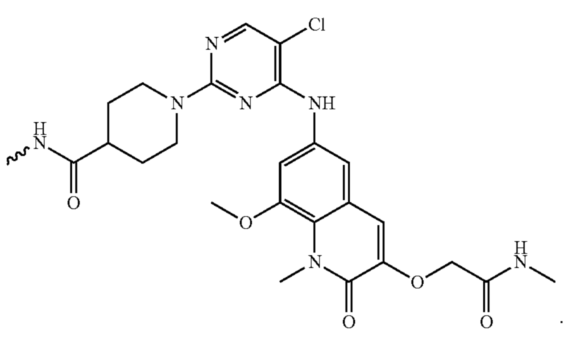

.

22. The method of claim 1, wherein the CIP has a molecular weight of 2500 Daltons or less.

23. The method of claim 1, wherein L has a structure selected from the group consisting of:

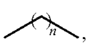,
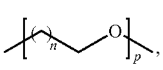,
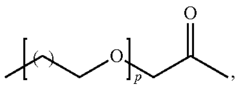,
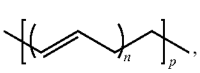,
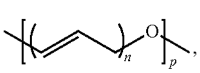,
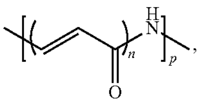,
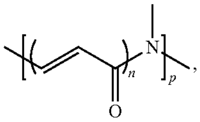,
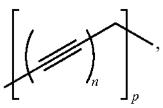,
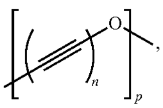,
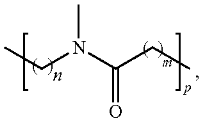,
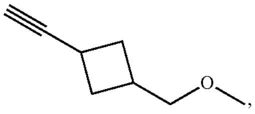,
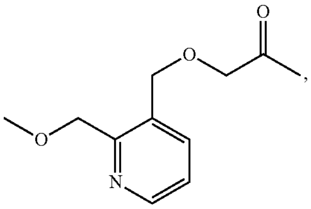,
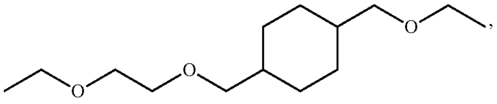,
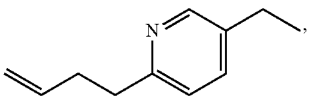,
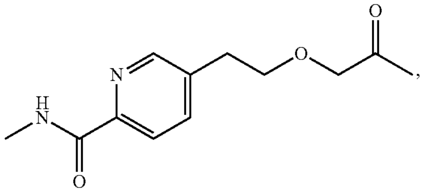,
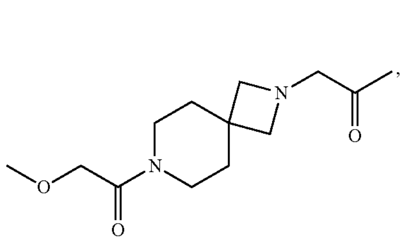,
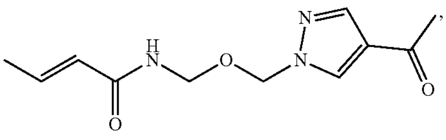,
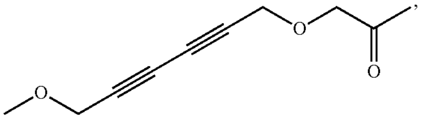,
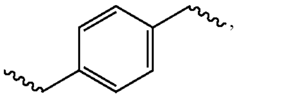,
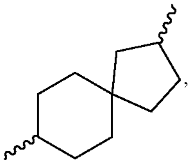,
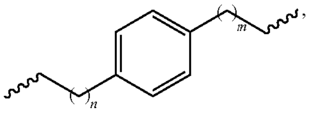,
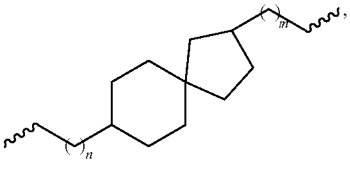,
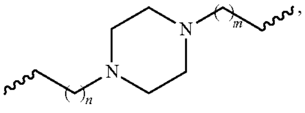, -continued
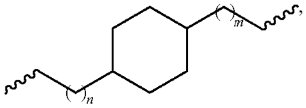,
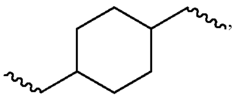,
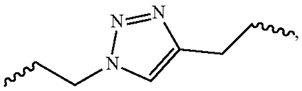,
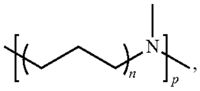,
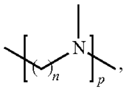,
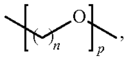,
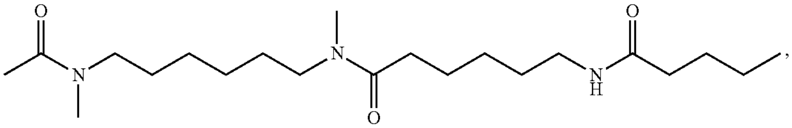,
,
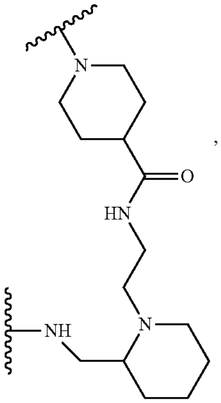,
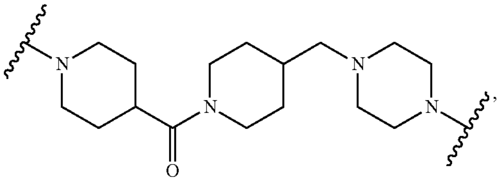,
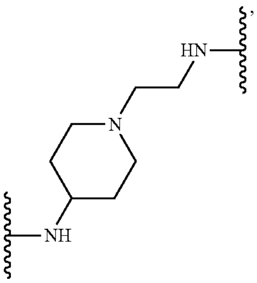,
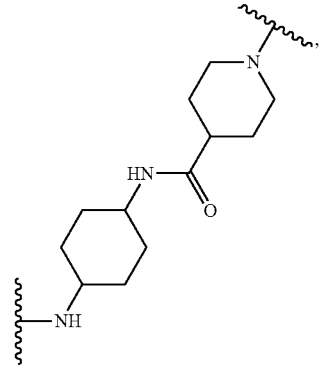,
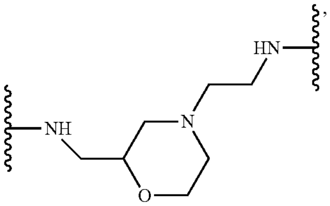,
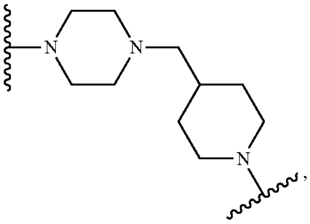,
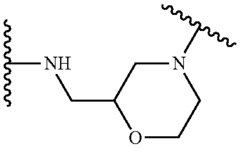,
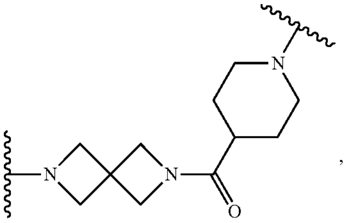,
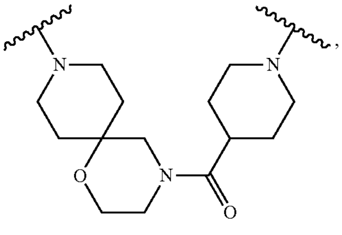,
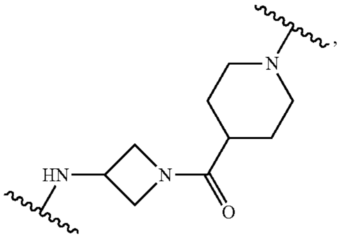,
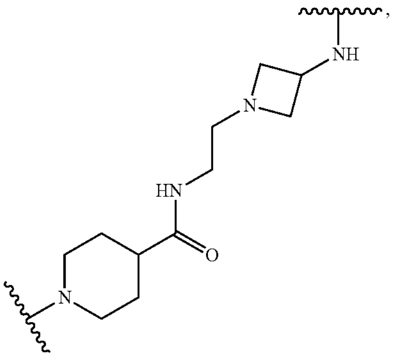, -continued
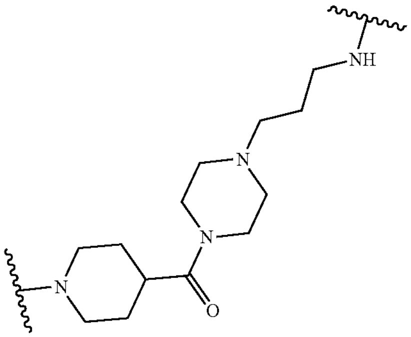,
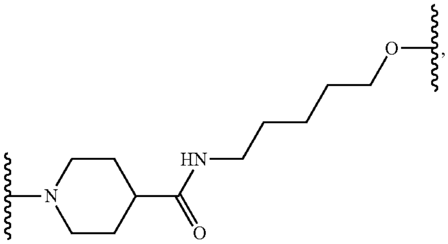,
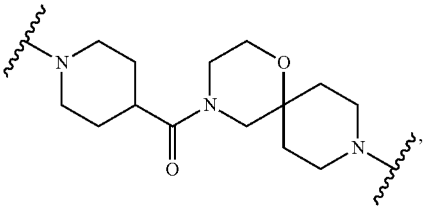,
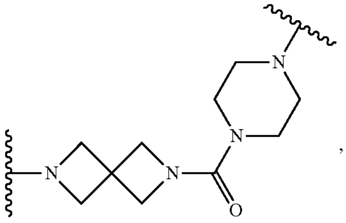,
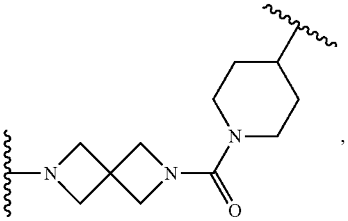,
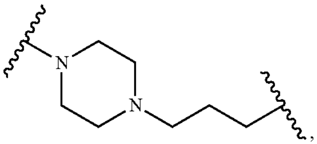,
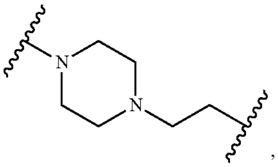,
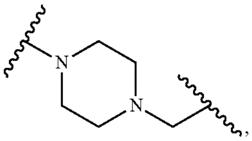,
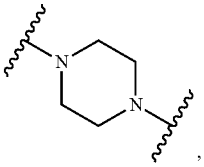,
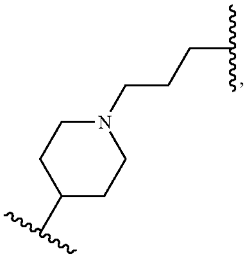,
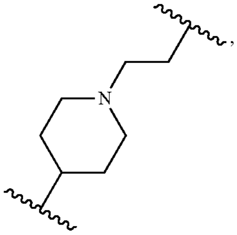,
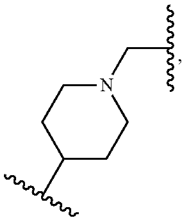, and
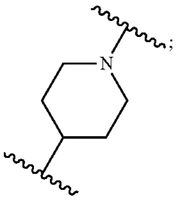;
wherein m, n and p are independently selected from 0 or an integer of from 1-12.
* * * * *